United States Patent
Abbasian et al.

(10) Patent No.: US 11,591,390 B2
(45) Date of Patent: Feb. 28, 2023

(54) SIRP-α BINDING PROTEINS AND METHODS OF USE THEREOF

(71) Applicant: Celgene Corporation, Summit, NJ (US)

(72) Inventors: Mahan Abbasian, San Diego, CA (US); Henry H. Chan, Poway, CA (US); Laure Escoubet, San Diego, CA (US); Gustavo Fenalti, San Diego, CA (US); Kandasamy Hariharan, San Diego, CA (US); Monica Wai Ling Leung, San Diego, CA (US); Konstantinos Mavrommatis, Concord, CA (US); David P. Mikolon, San Diego, CA (US); Heather K. Raymon, San Diego, CA (US); Carlo Steven Santos, San Diego, CA (US); Jeonghoon Sun, San Francisco, CA (US); Christina Valerie Trout, San Diego, CA (US)

(73) Assignee: Celgene Corporation, Summit, NJ (US)

( * ) Notice: Subject to any disclaimer, the term of this patent is extended or adjusted under 35 U.S.C. 154(b) by 244 days.

(21) Appl. No.: 16/582,813

(22) Filed: Sep. 25, 2019

(65) Prior Publication Data

US 2020/0102387 A1 Apr. 2, 2020

Related U.S. Application Data

(63) Continuation of application No. PCT/US2019/052604, filed on Sep. 24, 2019.

(60) Provisional application No. 62/853,997, filed on May 29, 2019, provisional application No. 62/737,782, filed on Sep. 27, 2018.

(51) Int. Cl.
C07K 16/28 (2006.01)

(52) U.S. Cl.
CPC ...... *C07K 16/2803* (2013.01); *C07K 16/2863* (2013.01); *C07K 16/2896* (2013.01); *C07K 2317/34* (2013.01); *C07K 2317/565* (2013.01); *C07K 2317/567* (2013.01); *C07K 2317/732* (2013.01); *C07K 2317/92* (2013.01)

(58) Field of Classification Search
CPC ............ C07K 16/2803; C07K 16/2896; C07K 2317/565; C07K 2317/567; C07K 2317/92
See application file for complete search history.

(56) References Cited

U.S. PATENT DOCUMENTS

| | | | |
|---|---|---|---|
| 7,371,826 B2 | 5/2008 | Presta | |
| 8,562,997 B2 | 10/2013 | Jaiswal et al. | |
| 9,352,037 B2 | 5/2016 | van den Berg | |
| 9,399,682 B2 | 7/2016 | Jaiswal et al. | |
| 9,493,575 B2 | 11/2016 | Jaiswal et al. | |
| 9,605,076 B2 | 3/2017 | Jaiswal et al. | |
| 9,611,329 B2 | 4/2017 | Jaiswal et al. | |
| 9,623,079 B2 | 4/2017 | Willingham et al. | |
| 9,624,305 B2 | 4/2017 | Jaiswal et al. | |
| 9,765,143 B2 | 9/2017 | Jaiswal et al. | |
| 9,771,428 B2 | 9/2017 | Weiskopf et al. | |
| 9,790,275 B2 | 10/2017 | Van Den Berg | |
| 9,920,122 B2 | 3/2018 | van den Berg | |
| 9,945,870 B2 | 4/2018 | Weiskopf et al. | |
| 10,064,925 B2 | 9/2018 | Tseng et al. | |
| 10,081,680 B2 | 9/2018 | Weiskopf et al. | |
| 10,087,255 B2 * | 10/2018 | Rosenthal | A61P 9/10 |
| 10,087,257 B2 | 10/2018 | Majeti et al. | |
| 10,184,004 B2 | 1/2019 | Weiskopf et al. | |
| 10,259,859 B2 | 4/2019 | Pons et al. | |
| 10,287,351 B2 | 5/2019 | Van Den Berg | |
| 10,301,387 B2 | 5/2019 | Willingham et al. | |
| 10,316,094 B2 | 6/2019 | Maute et al. | |
| 10,329,354 B2 | 6/2019 | Leeper et al. | |
| 10,334,094 B1 | 6/2019 | Zhidov et al. | |
| 2014/0369924 A1 | 12/2014 | Weissman et al. | |
| 2016/0257758 A1 | 9/2016 | Gray et al. | |
| 2016/0289326 A1 | 10/2016 | Chao et al. | |
| 2016/0333093 A1 | 11/2016 | Weiskopf et al. | |
| 2017/0073414 A1 | 3/2017 | Weiskopf et al. | |
| 2017/0151282 A1 | 6/2017 | Discher et al. | |
| 2017/0183412 A1 | 6/2017 | Li et al. | |
| 2017/0210803 A1 | 7/2017 | Willingham et al. | |
| 2017/0224737 A1 | 8/2017 | Shizuru et al. | |
| 2017/0247464 A1 | 8/2017 | Poirier et al. | |
| 2017/0291945 A1 | 10/2017 | Leeper et al. | |
| 2017/0320945 A1 | 11/2017 | Jaiswal et al. | |
| 2018/0000865 A1 | 1/2018 | Weissman et al. | |
| 2018/0028651 A1 | 2/2018 | Leeper et al. | |
| 2018/0037652 A1 | 2/2018 | Liu et al. | |

(Continued)

FOREIGN PATENT DOCUMENTS

WO WO 2012/059561 A1 5/2012
WO WO 2015/105995 A2 7/2015

(Continued)

OTHER PUBLICATIONS

Malia et al, Proteins, 2016, 84:427-434. (Year: 2016).*
Barthelemy et al, Journal of Biological Chemistry, 2008, 283:3639-3654. (Year: 2008).*
Beiboer et al, Journal of Molecular Biology, 2000, 296:833-849. (Year: 2000).*

(Continued)

*Primary Examiner* — Julie Wu
*Assistant Examiner* — Cheom-Gil Cheong
(74) *Attorney, Agent, or Firm* — Jones Day

(57) ABSTRACT

Provided herein are compositions, methods and uses involving antibodies that specifically bind to signal regulatory protein-α (SIRPα) and modulate the activity of SIRPα.

24 Claims, 46 Drawing Sheets

Figure 1:
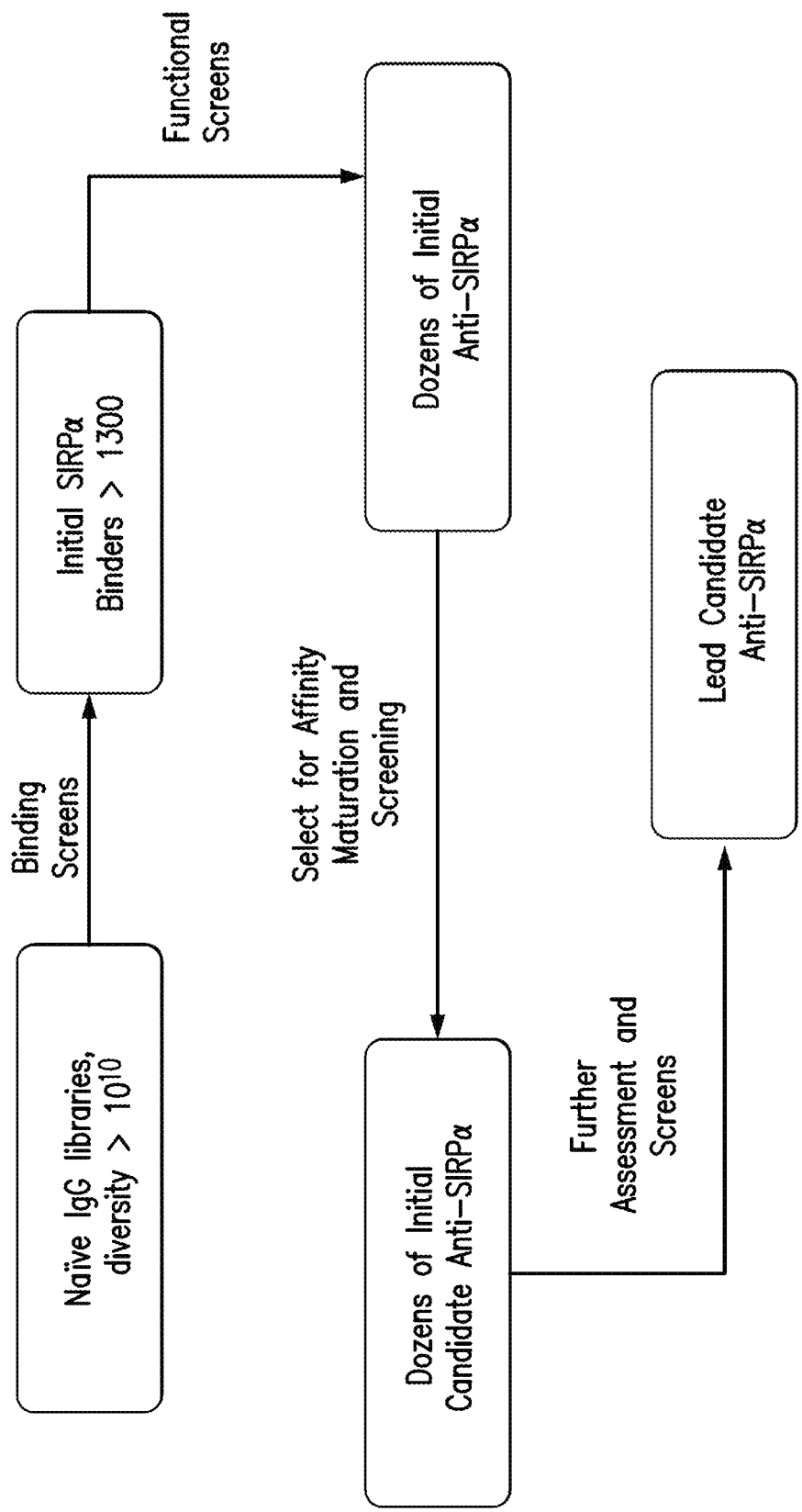

Specification includes a Sequence Listing.

(56) References Cited

U.S. PATENT DOCUMENTS

| | | |
|---|---|---|
| 2018/0105600 A1 | 4/2018 | Pons et al. |
| 2018/0155424 A1 | 6/2018 | Van Den Berg |
| 2018/0171030 A1 | 6/2018 | Weissman et al. |
| 2018/0258170 A1 | 9/2018 | Gholamin et al. |
| 2018/0311348 A1 | 11/2018 | Hopfner et al. |
| 2018/0312587 A1 | 11/2018 | Van Eenennaam et al. |
| 2018/0312600 A1 | 11/2018 | Poirier et al. |
| 2018/0319883 A1 | 11/2018 | Weiskopf et al. |
| 2018/0320137 A1 | 11/2018 | Valamehr et al. |
| 2019/0022411 A1 | 1/2019 | Parry et al. |
| 2019/0023803 A1 | 1/2019 | Spits et al. |
| 2019/0048075 A1 | 2/2019 | Weissman et al. |
| 2019/0048077 A1 | 2/2019 | Tsai et al. |
| 2019/0077856 A1 | 3/2019 | Scheinberg et al. |
| 2019/0085404 A1 | 3/2019 | Felsher et al. |
| 2019/0092873 A1 | 3/2019 | Weiskopf et al. |
| 2019/0106491 A1 | 4/2019 | Weissman et al. |
| 2019/0117741 A1 | 4/2019 | Ledford et al. |
| 2019/0119379 A1 | 4/2019 | Gottschalk et al. |
| 2019/0119396 A1 | 4/2019 | Liu et al. |
| 2019/0127467 A1 | 5/2019 | Shah et al. |
| 2019/0127477 A1 | 5/2019 | Poirier et al. |
| 2019/0134089 A1 | 5/2019 | Liu et al. |
| 2019/0135921 A1 | 5/2019 | Veillette et al. |
| 2019/0153095 A1 | 5/2019 | Matozaki et al. |
| 2019/0169266 A1 | 6/2019 | Pons et al. |
| 2019/0202917 A1 | 7/2019 | Campbell et al. |
| 2019/0218289 A1 | 7/2019 | Willingham et al. |
| 2019/0233515 A1 | 8/2019 | Jaiswal et al. |
| 2019/0233518 A1 | 8/2019 | Fayadat-Dilman et al. |
| 2019/0241664 A1 | 8/2019 | Maute et al. |
| 2019/0241668 A1 | 8/2019 | Van Rompaey |
| 2019/0248899 A1 | 8/2019 | Yan et al. |
| 2019/0255082 A1 | 8/2019 | Linderoth et al. |

FOREIGN PATENT DOCUMENTS

| | | |
|---|---|---|
| WO | WO 2015/138600 A2 | 9/2015 |
| WO | WO 2016/022971 A1 | 2/2016 |
| WO | WO 2016/033201 A1 | 3/2016 |
| WO | WO 2016/044021 A1 | 3/2016 |
| WO | WO 2016/063233 A1 | 4/2016 |
| WO | WO 2016/065329 A1 | 4/2016 |
| WO | WO 2016/092096 A1 | 6/2016 |
| WO | WO 2016/118754 A1 | 7/2016 |
| WO | WO 2016/164637 A1 | 10/2016 |
| WO | WO 2016/205042 A1 | 12/2016 |
| WO | WO 2017/119811 A1 | 1/2017 |
| WO | WO 2017/035480 A1 | 3/2017 |
| WO | WO 2017/068164 A1 | 4/2017 |
| WO | WO 2017/078807 A1 | 5/2017 |
| WO | WO 2017/152132 A1 | 9/2017 |
| WO | WO 2017/160717 A2 | 9/2017 |
| WO | WO 2017/178653 | 10/2017 |
| WO | WO 2017/180519 A1 | 10/2017 |
| WO | WO 2018/005775 A1 | 1/2018 |
| WO | WO 2018/026600 | 2/2018 |
| WO | WO 2018/037091 A1 | 3/2018 |
| WO | WO 2018/057669 | 3/2018 |
| WO | WO 2018/107058 A1 | 6/2018 |
| WO | WO 2018/149938 A1 | 8/2018 |
| WO | WO 2018/160739 A1 | 9/2018 |
| WO | WO 2018/184003 A1 | 10/2018 |
| WO | WO 2018/210793 A2 | 11/2018 |
| WO | WO 2018/210795 A1 | 11/2018 |
| WO | WO 2019/118686 A1 | 12/2018 |
| WO | WO 2019/014663 A1 | 1/2019 |
| WO | WO 2019/014664 A1 | 1/2019 |
| WO | WO 2019/014665 A1 | 1/2019 |
| WO | WO 2019/022600 A1 | 1/2019 |
| WO | WO 2019/023347 A1 | 1/2019 |
| WO | WO 2019/073080 A1 | 4/2019 |
| WO | WO 2019/084692 A1 | 5/2019 |
| WO | WO 2019/090355 A1 | 5/2019 |
| WO | WO 2019/148410 A1 | 8/2019 |
| WO | WO 2019/152571 A1 | 8/2019 |

OTHER PUBLICATIONS

Choi et al, 2011, Molecular Biosystems, 2011, 7:3327-3334. (Year: 2011).*
De Genst et al, Developmental and Comparative Immunology, 2006, 30:187-98. (Year: 2006).*
Griffiths et al, The EMBO Journal, 1993, 12:725-734. (Year: 1993).*
Klimka et al, British Journal of Cancer, 2000, 83:252-260. (Year: 2000).*
Ward et al, Nature, 1989, 341:544-546. (Year: 1989).*
Abès et al., "Activating and inhibitory Fcgamma receptors in immunotherapy: being the actor or being the target," *Expert Rev. Clin. Immunol.*, 5(6):735-747 (2009).
Desjarlais et al., "Modulation of antibody effector function," *Exp. Cell Res.*, 317(9):1278-1285 (2011).
Idusogie et al., "Mapping of the C1q binding site on rituxan, a chimeric antibody with a human IgG1 Fc," *J. Immunol.*, 164(8):4178-4184 (2000).
Jaiswal et al., "CD47 is upregulated on circulating hematopoietic stem cells and leukemia cells to avoid phagocytosis," *Cell*, 138(2):271-285 (2009).
Majeti et al., "CD47 is an adverse prognostic factor and therapeutic antibody target on human acute myeloid leukemia stem cells," *Cell*, 138(2):286-299 (2009).
Medico et al., "The molecular landscape of colorectal cancer cell lines unveils clinically actionable kinase targets," *Nat. Commun.*, 6:7002 (2015).
Nimmerjahn et al., "Fcgamma receptors: old friends and new family members," *Immunity*, 24(1):19-28 (2006).
Overdijk et al., "Crosstalk between human IgG isotypes and murine effector cells," *J. Immunol.*, 189(7):3430-3438 (2012).
Ring et al., "Anti-SIRPα antibody immunotherapy enhances neutrophil and macrophage antitumor activity," *Proc. Natl. Acad. Sci. USA*, 114(49):E10578-E10585 (2017).
Takenaka et al., "Polymorphism in Sirpa modulates engraftment of human hematopoietic stem cells," *Nat. Immunol.*, 8(12):1313-1323 (2007).
International Search Report issued on International Application No. PCT/US2019/052604 dated Jan. 13, 2020.
Yanagita, T. et al. "Anti-SIRPα Antibodies as a Potential New Tool for Cancer Immunotherapy," JCI Insight, Jan. 2017, 2(1):e89140, 15 pages.
European Search Report dated May 27, 2022 in corresponding European Application No. 19867552.2.
Blazar, Bruce R. et al. "CD47 (Integrin-associated Protein) Engagement of Dendritic Cell and Macrophate Counterreceptors is Required to Prevent the Clearance of Donor Lymphohematopoietic Cells," *J. Exp. Med.*, 194:4 (Aug. 20, 2001) 541-549.
Chen, Thomas T. et al. "Expression and Activation of Signal Regulatory Protein α on Astrocytomas," *Cancer Research*, vol. 64 (Jan. 1, 2004) 117-127.
Florian, Stefan et al. "Evaluation of Normal and Neoplastic Human Mast Cells for Expression of CD172a (SIRPα), CD47, and SHP-1," *Journal of Leukocyte Biology*, vol. 77 (Jun. 2005) 984-992.
Gül, Nuray et al. "Antibody-Dependent Phagocytosis of Tumor Cells by Macrophages: A Potent Effector Mechanism of Monoclonal Antibody Therapy of Cancer," *Cancer Research*, 75:23 (Dec. 1, 2015) 5008-5013.
Idusogie, Esohe E. et al. "Mapping of the C1q Binding Site on Rituxan, a Chimeric Antibody with a Human IgG1 Fc," *The Journal of Immunology*, vol. 164 (2000) 4178-4187.
Kapoor, Gurpreet S. et al. "Transcriptional Regulation of Signal Regulatory Protein α1 Inhibitory Receptors by Epidermal Growth Factor Receptor Signaling," *Cancer Research*, vol. 64 (Sep. 15, 2004) 6444-6452.
Manna, Partha Pratim et al. "CD47 Mediates Killing of Breast Tumor Cells via Gi-Dependent Inhibition of Protein Kinase A," *Cancer Research*, vol. 64 (Feb. 1, 2004) 1026-1036.

(56) References Cited

OTHER PUBLICATIONS

Mateo, V. et al. "CD47 Ligation Induces Caspase-Independent Cell Death in Chronic Lymphocytic Leukemia," *Nature Medicine*, 5:11 (Nov. 1999) 1277-1284.

Mateo, Véronique et al. "Mechanisms of CD47-Induced Caspase-Independent Cell Death in Normal and Leukemic Cells: Link Between Phosphatidylserine Exposure and Cytoskeleton Organization," *Blood*, 100:8 (Oct. 15, 2002) 2882-2890.

Okazawa, Hideki et al. "Negative Regulation of Phagocytosis in Macrophages by the CD47-SHPS-1 System," *The Journal of Immunology*, vol. 174 (2005) 2004-2011.

Oldenborg, Per-Arne et al. "Role of CD47 as a Marker of Self on Red Blood Cells," *Science*, vol. 288 (Jun. 16, 2000) 2051-2054.

Oldenborg, Per-Arne et al. "CD47-Signal Regulatory Protein α (SIRPα) Regulates Fcγ and Complement Receptor-Mediated Phagocytosis," *J. Exp. Med.*, 193:7 (Apr. 2, 2001) 855-861.

Oldenborg, Per-Arne "Role of CD47 in Erythroid Cells and in Autoimmunity," *Leukemia & Lymphoma*, 45:7 (Jul. 2004) 1319-1327.

Seiffert, Martina et al. "Human Signal-Regulatory Protein is Expressed on Normal, But Not on Subsets of Leukemic Myeloid Cells and Mediates Cellular Adhesion Involving Its Counterreceptor CD47," *Blood*, 94:11 (Dec. 1, 1999) 3633-3643.

Subramanian, Shyamsundar et al. "Species- and Cell Type-Specific Interactions Between CD47 and Human SIRPα," *Blood*, 107:6 (Mar. 15, 2006) 2548-2556.

\* cited by examiner

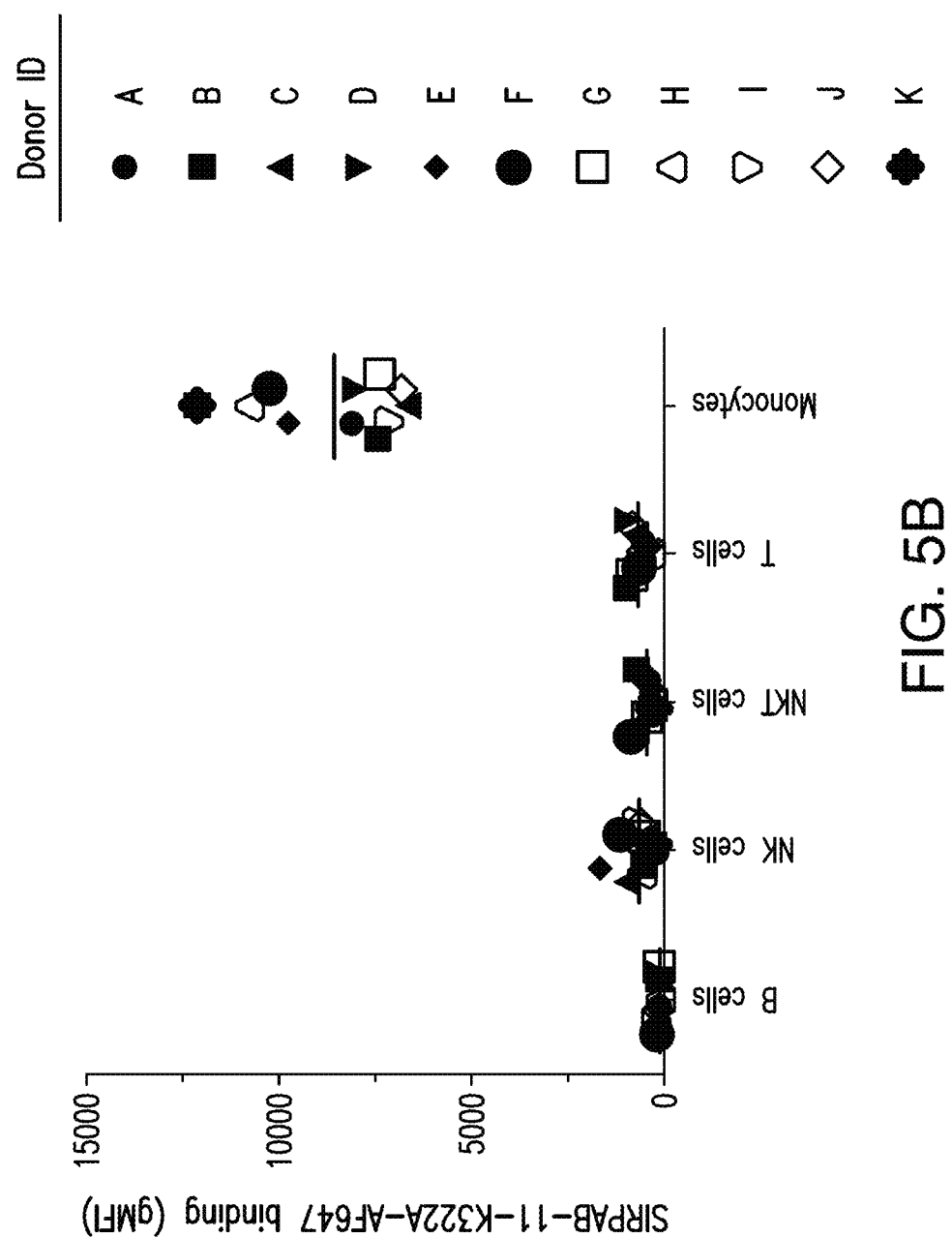

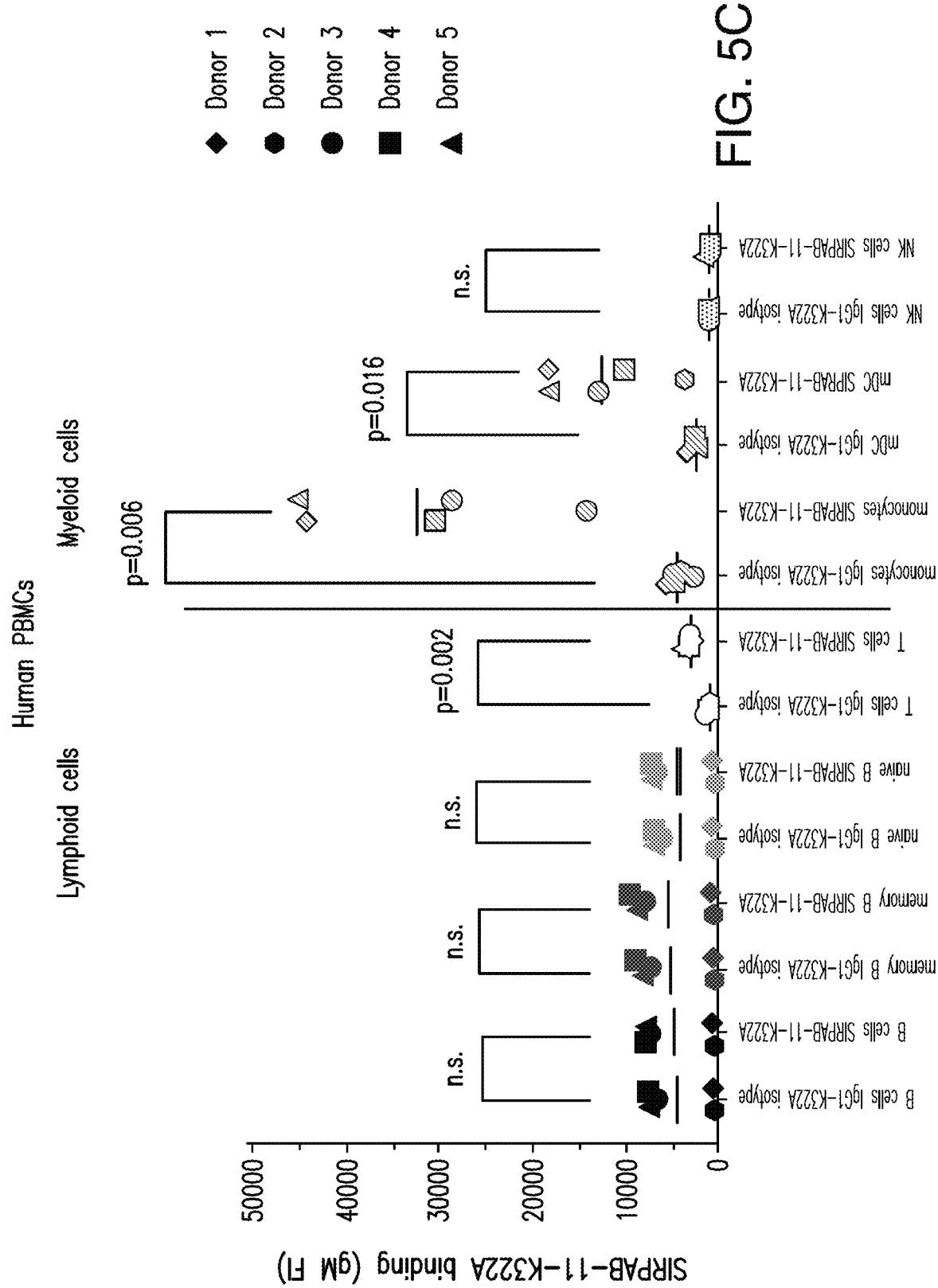

| SIRPAB-11-K322A (nM) | Response (RU) | Calculated concentration bound equilibrium (nM) | Percent CD47 Binding | Percent Inhibition |
|---|---|---|---|---|
| 0 | 307.6 | 18.56 | 100 | 0 |
| 0.4 | 298.1 | 17.55 | 96.91 | 3.09 |
| 1.2 | 275.7 | 15.36 | 89.63 | 10.37 |
| 3.7 | 239.1 | 12.23 | 77.73 | 22.27 |
| 11.11 | 167 | 7.306 | 54.29 | 45.71 |
| 33.33 | 25 | 0.8135 | 8.13 | 91.87 |
| 100 | 7.9 | 0.2523 | 2.57 | 97.43 |

Categorized Immunogenic Potentials

Optimal Antibodies (Low Effector Content – High Tregitope Content)

| Antibody | Tregitope-Adjusted EpiMatrix Protein Score[1] | Tregitope Content[2] | Predicted Ab Response | Observed Ab Response |
|---|---|---|---|---|
| Herceptin | −66.56 | 75.26 | 0.00% | 0.10% |
| SIPRAB-11-K322A | −38.19 | 41.10 | 0.17% | n.a. |
| Avastin | −31.62 | 67.57 | 0.65% | 0.00% |

Low Risk Antibodies (Low Effector Content – Low Tregitope Content)

| Antibody | Tregitope-Adjusted EpiMatrix Protein Score[1] | Tregitope Content[2] | Predicted Ab Response | Observed Ab Response |
|---|---|---|---|---|
| Tysabri | −12.71 | 15.70 | 6.16% | 7.00% |
| Humicade | −3.97 | 17.29 | 10.79% | 7.00% |

Mixed Antibodies (High Effector Content – High Tregitope Content)

| Antibody | Tregitope-Adjusted EpiMatrix Protein Score[1] | Tregitope Content[2] | Predicted Ab Response | Observed Ab Response |
|---|---|---|---|---|
| Campath | 22.94 | 21.73 | 33.27% | 45.00% |

High Risk Antibodies (High Effector Content – Low Tregitope Content)

| Antibody | Tregitope-Adjusted EpiMatrix Protein Score[1] | Tregitope Content[2] | Predicted Ab Response | Observed Ab Response |
|---|---|---|---|---|
| Remicade | 14.40 | 2.48 | 24.79% | 26.00% |
| Rituxan | 22.53 | 0.00 | 32.84% | 27.00% |

[1] Tregitope-adjusted EpiMatrix Score: Values greater than zero represent high effector epitope content.
[2] Tregitope content: Values greater than +20 represent high Tregitope content.
[3] Observed immunogenicity of Erbitux underestimated according to package insert.

FIG. 10B

Figure 11B:
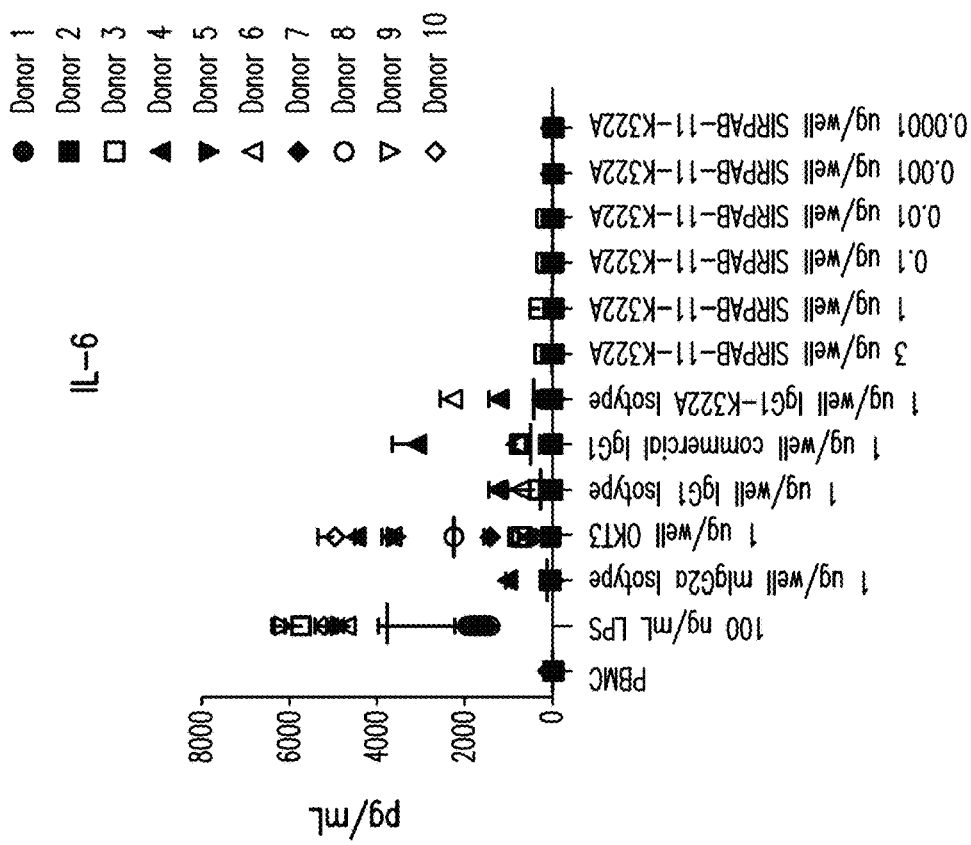
Figure 11A:
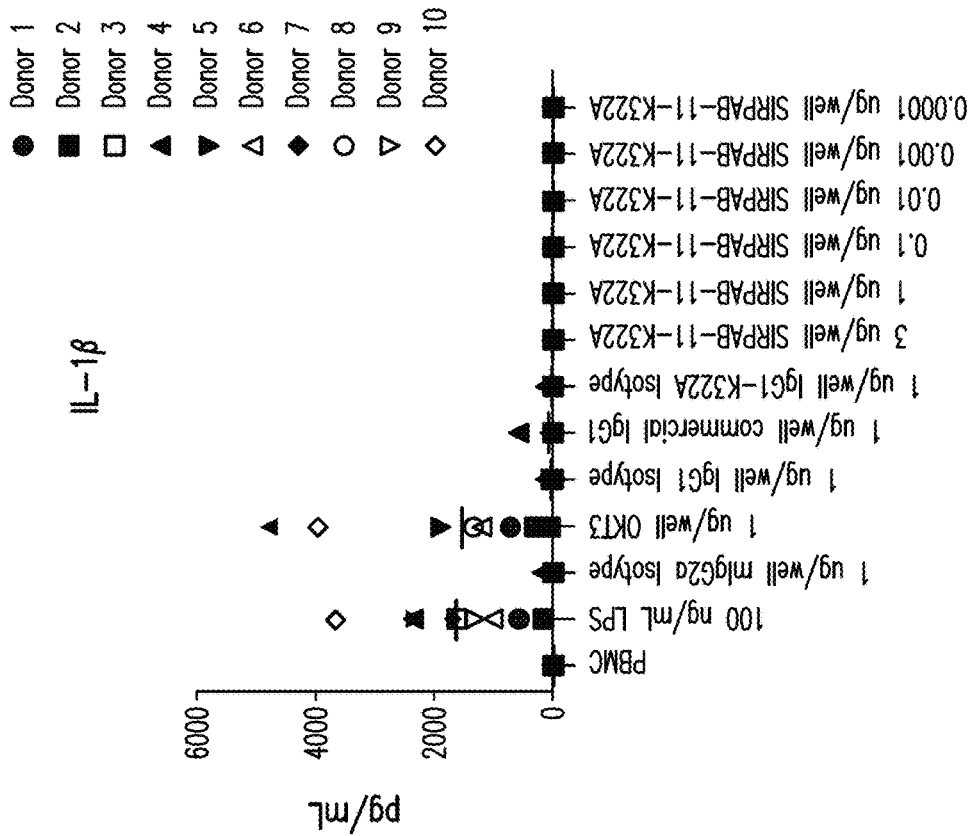
Figure 11D:
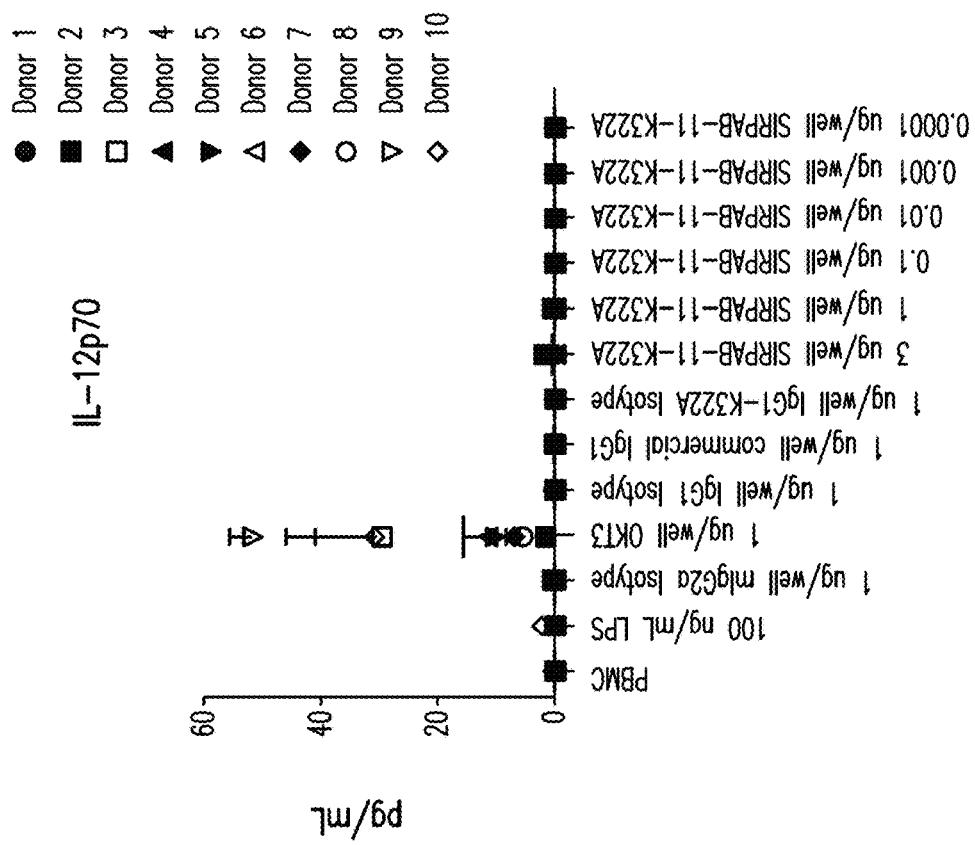
Figure 11C:
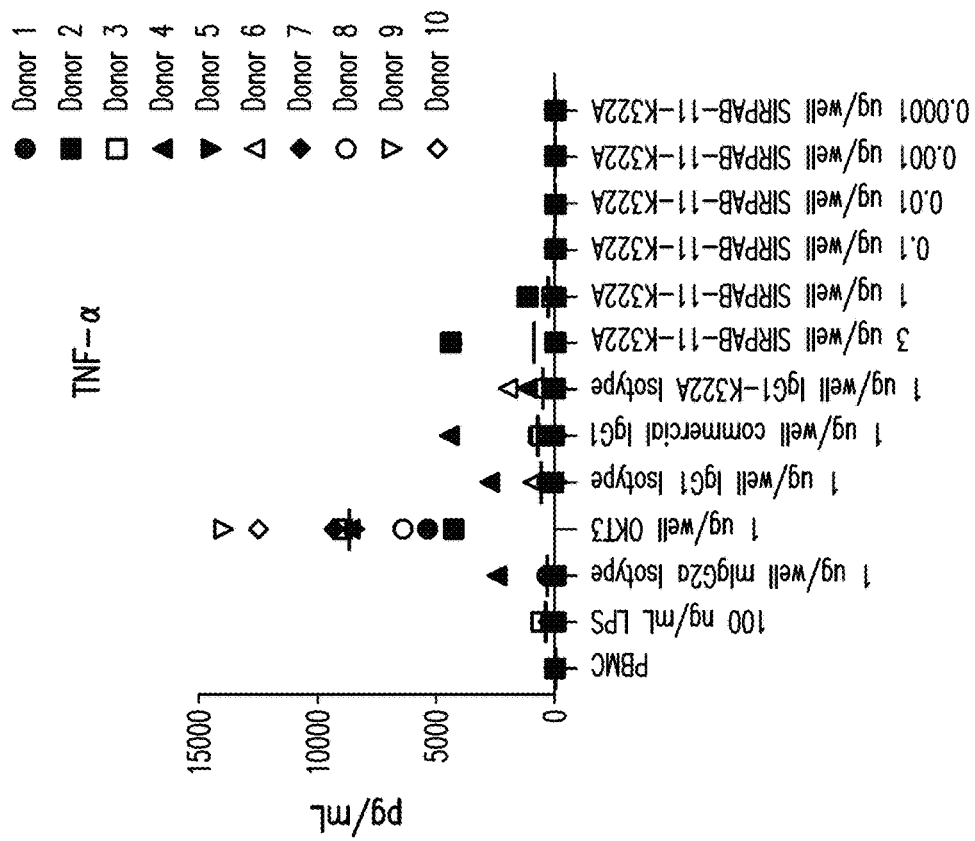
Figure 11H:
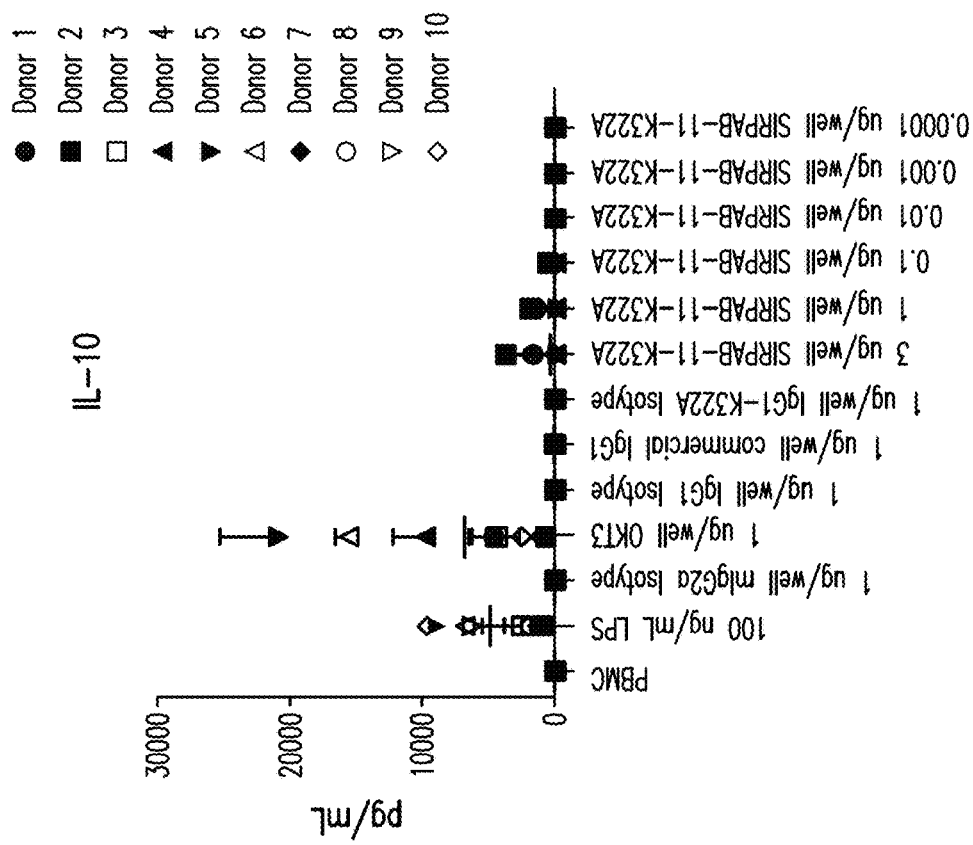
Figure 11G:
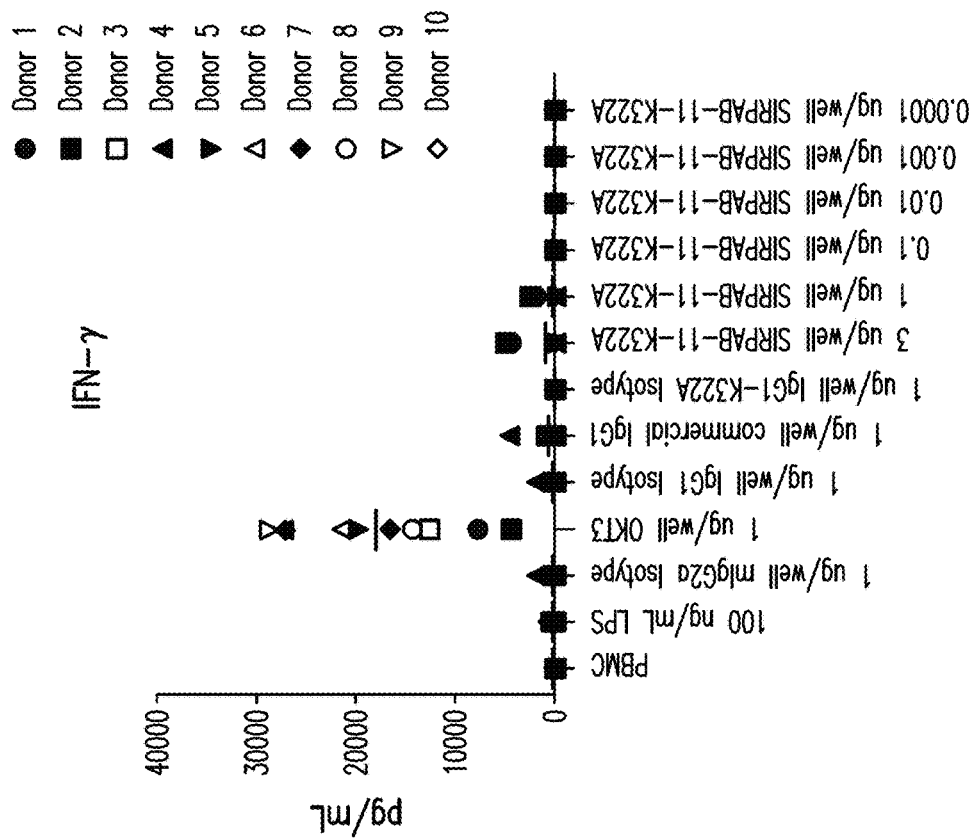
Figure 11I:
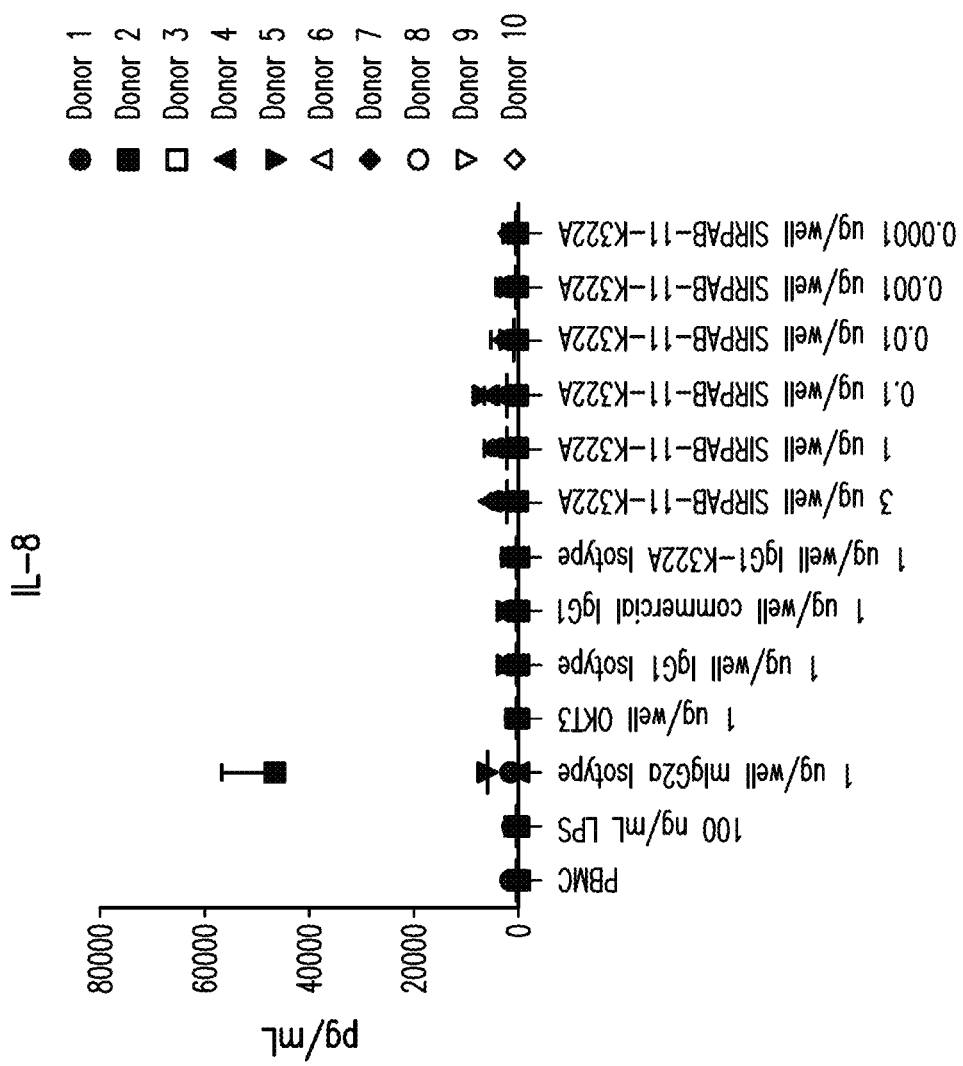

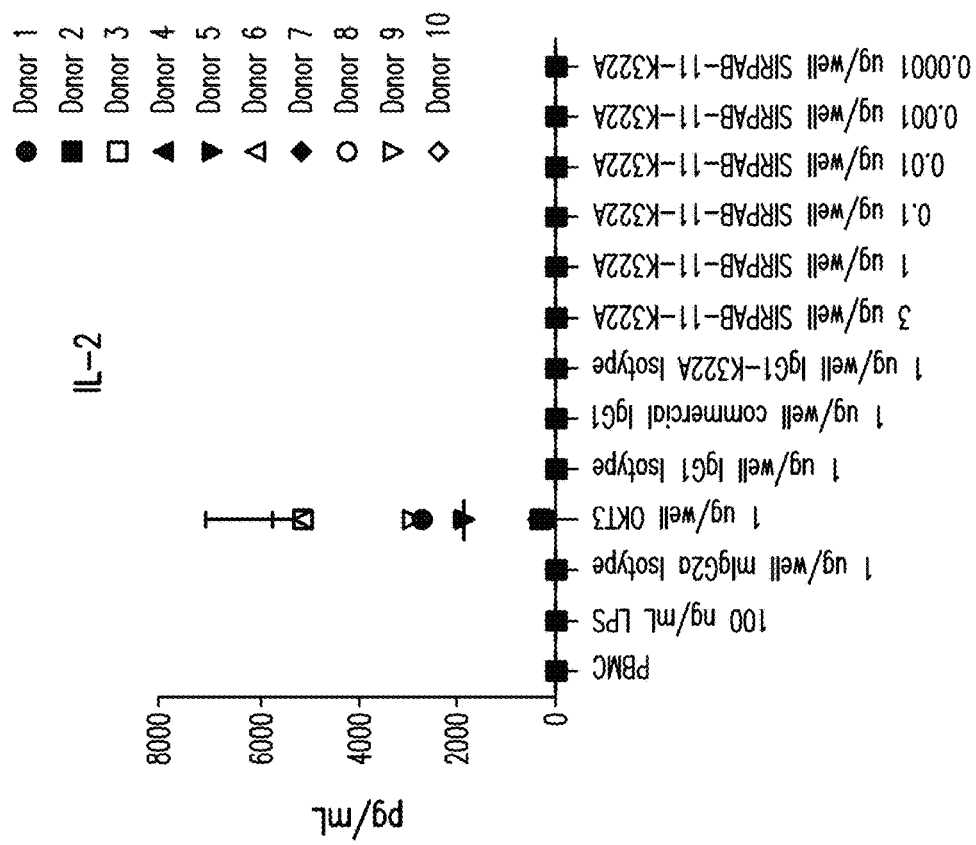
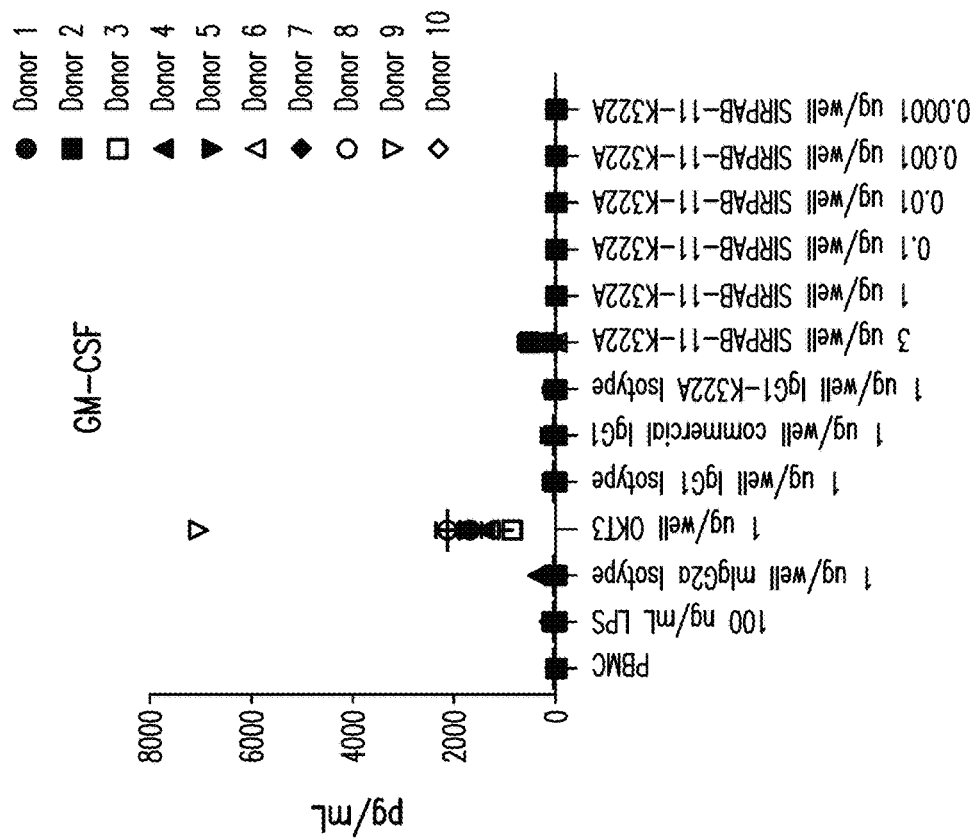
FIG. 11F
FIG. 11E

| | GM-CSF | | | IFN-γ | | | IL-10 | | | IL-12p70 | | | IL-1B | | | |
|---|---|---|---|---|---|---|---|---|---|---|---|---|---|---|---|---|
| | Mean | SD | Comparison* | Mean | SD | Comparison* | Mean | SD | Comparison* | Mean | SD | Comparison* | Mean | SD | Comparison* | N |
| PBMC | 1 | 1 | ns | 5 | 7 | ns | 3 | 3 | ns | 0 | 0 | ns | 1 | 3 | ns | 10 |
| 100 ng/mL LPS | 25 | 30 | ns | 231 | 229 | ns | 493 | 308 | ** | 0 | 1 | ns | 1381 | 967 | * | 10 |
| 1 ug/well mIgG2a Isotype | 21 | 28 | ns | 220 | 591 | ns | 0 | 20 | ns | 0 | 0 | ns | 28 | 69 | ns | 10 |
| 1 ug/well OKT3 | 2159 | 1763 | * | 17730 | 8302 | *** | 684 | 665 | ns | 16 | 16 | ns | 1539 | 1626 | ns | 10 |
| 1 ug/well commercial IgG1 | 42 | 41 | ns | 186 | 504 | ns | 0 | 1 | ns | 0 | 0 | ns | 36 | 56 | ns | 10 |
| 1 ug/well IgG1-K322A Isotype | 56 | 75 | ns | 601 | 1396 | ns | 1 | 1 | ns | 0 | 0 | ns | 77 | 184 | ns | 10 |
| 3 ug/well SRPAB-11-K322A | 42 | 42 | | 18 | 28 | | 54 | 123 | ns | 0 | 1 | ns | 45 | 49 | ns | 10 |
| 1 ug/well SRPAB-11-K322A | 79 | 166 | ns | 925 | 1946 | ns | 27 | 62 | ns | 0 | 0 | ns | 14 | 15 | ns | 10 |
| 0.1 ug/well SRPAB-11-K322A | 15 | 19 | ns | 456 | 955 | ns | 10 | 23 | ns | 0 | 0 | ns | 8 | 8 | ns | 10 |
| 0.01 ug/well SRPAB-11-K322A | 5 | 6 | ns | 105 | 214 | ns | 3 | 3 | ns | 0 | 0 | ns | 3 | 5 | ns | 10 |
| 0.001 ug/well SRPAB-11-K322A | 4 | 10 | ns | 27 | 47 | ns | 3 | 3 | ns | 0 | 0 | ns | 2 | 4 | ns | 10 |
| 0.0001 ug/well SRPAB-11-K322A | 0 | 1 | ns | 3 | 3 | ns | 3 | 3 | ns | 0 | 0 | ns | 0 | 1 | ns | 10 |

*vs. IgG1-K322A Isotype

| | IL-2 | | | IL-6 | | | IL-8 | | | TNF-α | | | |
|---|---|---|---|---|---|---|---|---|---|---|---|---|---|
| | Mean | SD | Comparison* | Mean | SD | Comparison* | Mean | SD | Comparison* | Mean | SD | Comparison* | N |
| PBMC | 9 | 6 | ns | 14 | 24 | ns | 621 | 501 | ns | 122 | 344 | ns | 10 |
| 100 ng/mL LPS | 6 | 6 | ns | 3789 | 1925 | ** | 474 | 294 | ns | 327 | 223 | ns | 10 |
| 1 ug/well mIgG2a Isotype | 5 | 5 | ns | 151 | 312 | ns | 6037 | 14379 | * | 1151 | 1894 | ns | 10 |
| 1 ug/well OKT3 | 1882 | 2019 | ns | 2247 | 1796 | ns | 265 | 114 | ns | 6082 | 3463 | * | 10 |
| 1 ug/well commercial IgG1 | 4 | 2 | ns | 305 | 412 | ns | 796 | 659 | ns | 950 | 919 | ns | 10 |
| 1 ug/well IgG1-K322A Isotype | 6 | 4 | ns | 519 | 942 | ns | 784 | 652 | ns | 1092 | 1369 | ns | 10 |
| 3 ug/well SRPAB-11-K322A | 5 | 4 | | 443 | 733 | | 640 | 470 | ns | 804 | 728 | ns | 10 |
| 1 ug/well SRPAB-11-K322A | 10 | 12 | ns | 69 | 71 | ns | 2267 | 1918 | ns | 1133 | 1758 | ns | 10 |
| 0.1 ug/well SRPAB-11-K322A | 7 | 6 | ns | 42 | 63 | ns | 2288 | 1822 | ns | 606 | 858 | ns | 10 |
| 0.01 ug/well SRPAB-11-K322A | 7 | 7 | ns | 29 | 63 | ns | 2449 | 2193 | ns | 793 | 2125 | * | 10 |
| 0.001 ug/well SRPAB-11-K322A | 8 | 6 | ns | 9 | 7 | ns | 903 | 763 | ns | 57 | 84 | * | 10 |
| 0.0001 ug/well SRPAB-11-K322A | 7 | 5 | ns | 6 | 7 | ns | 596 | 610 | ns | 20 | 38 | ns | 10 |

*vs. IgG1-K322A Isotype

One way ANOVA
Dunnett
ns = not significant

FIG. 11J

| Cytokine | Donor | GM-CSF | | | IFN-γ | | | IL-10 | | | IL-12p70 | | | IL-1β | | |
|---|---|---|---|---|---|---|---|---|---|---|---|---|---|---|---|---|
| | | p value | Max. fold value | Diff. | p value | Max. fold value | Diff. | p value | Max. fold value | Diff. | p value | Max. fold value | Diff. | p value | Max. fold value | Diff. |
| | | | | | | | Aqueous | | | | | | | | | |
| SIRPAB-11 vs Isotype control -K322A | 1 | *** | <2 | No | ** | 213 | Yes | *** | <2 | No | ns | <2 | No | **** | <2 | No |
| | 2 | ns | <2 | No | ns | <2 | No | ns | <2 | No | ns | <2 | No | * | <2 | No |
| | | | | | | | Immobilized | | | | | | | | | |
| | 1 | ns | <2 | No | ** | -6.07 | Yes | ns | <2 | No | ns | <2 | No | * | <2 | No |
| | 2 | *** | <2 | No | ns | <2 | No | *** | <2 | No | ns | <2 | No | ** | <2 | No |

| Cytokine | Donor | IL-2 | | | IL-6 | | | IL-8 | | | TNF | | |
|---|---|---|---|---|---|---|---|---|---|---|---|---|---|
| | | p value | Max. fold value | Diff. | p value | Max. fold value | Diff. | p value | Max. fold value | Diff. | p value | Max. fold value | Diff. |
| | | | | | | | Aqueous | | | | | | |
| SIRPAB-11 vs Isotype control -K322A | 1 | * | <2 | No | ns | <2 | No | ns | <2 | No | * | <2 | No |
| | 2 | ns | <2 | No | ns | <2 | No | ns | <2 | No | *** | <2 | No |
| | | | | | | | Immobilized | | | | | | |
| | 1 | ns | <2 | No | ns | <2 | No | ns | <2 | No | ns | <2 | No |
| | 2 | ns | <2 | No | ns | <2 | No | ns | <2 | No | ns | <2 | No |

FIG. 12C

| Cytokine | Donor | GM-CSF | | | IFN-γ | | | IL-10 | | | IL-12p70 | | | IL-1β | | |
|---|---|---|---|---|---|---|---|---|---|---|---|---|---|---|---|---|
| | | p value | Max. fold value | Diff. | p value | Max. fold value | Diff. | p value | Max. fold value | Diff. | p value | Max. fold value | Diff. | p value | Max. fold value | |
| | | | | | | | | Aqueous | | | | | | | | |
| SIRPAB-11 – K322A vs Isotype control –K322A | 1 | ns | <2 | No | * | <2 | No | ns | <2 | No | ns | <2 | No | ns | <2 | |
| | 2 | ns | <2 | No | ** | <2 | No | ns | <2 | No | * | <2 | No | ns | <2 | |
| | | | | | | | | Immobilized | | | | | | | | |
| | 1 | ns | <2 | No | ** | <2 | No | ns | <2 | No | * | <2 | No | ns | <2 | |
| | 2 | ns | <2 | No | ns | <2 | No | ns | <2 | No | ns | <2 | No | * | <2 | |

| Cytokine | Donor | IL-2 | | | IL-6 | | | IL-8 | | | TNF | | |
|---|---|---|---|---|---|---|---|---|---|---|---|---|---|
| | | p value | Max. fold value | Diff. | p value | Max. fold value | Diff. | p value | Max. fold value | Diff. | p value | Max. fold value | Diff. |
| | | | | | | | | Aqueous | | | | | |
| SIRPAB-11 – K322A vs Isotype control –K322A | 1 | ns | <2 | No | * | <2 | No | NA | NA | NA | ns | <2 | No |
| | 2 | ns | <2 | No | ** | <2 | No | NA | NA | NA | * | <2 | No |
| | | | | | | | | Immobilized | | | | | |
| | 1 | * | <2 | No | ns | <2 | No | NA | NA | NA | ns | <2 | No |
| | 2 | * | <2 | No | ** | <2 | No | NA | NA | NA | ns | <2 | No |

FIG. 12G

| Cytokine | | GM-CSF | | | IFN-γ | | | IL-10 | | | IL-12p70 | | | IL-1β | |
|---|---|---|---|---|---|---|---|---|---|---|---|---|---|---|---|
| | Donor | p value | Max. fold value | Diff. | p value | Max. fold value | Diff. | p value | Max. fold value | Diff. | p value | Max. fold value | Diff. | p value | Max. fold value |
| SIRPAB-11 – K322A vs Isotype control – K322A | | | | | | | Aqueous | | | | | | | | |
| | 1 | ns | <2 | No | ns | <2 | No | ns | <2 | No | ns | <2 | No | ns | <2 |
| | 2 | ns | <2 | No | ns | <2 | No | ns | <2 | No | ns | <2 | No | ns | <2 |
| | | | | | | | Immobilized | | | | | | | | |
| | 1 | * | <2 | No | ns | <2 | No | ns | <2 | No | ns | <2 | No | ns | <2 |
| | 2 | ** | <2 | No | ** | <2 | No | * | <2 | No | ns | <2 | No | * | <2 |

| Cytokine | | IL-2 | | | IL-6 | | | IL-8 | | | TNF | | |
|---|---|---|---|---|---|---|---|---|---|---|---|---|---|
| | Donor | p value | Max. fold value | Diff. | p value | Max. fold value | Diff. | p value | Max. fold value | Diff. | p value | Max. fold value | Diff. |
| SIRPAB-11 – K322A vs Isotype control – K322A | | | | | | | Aqueous | | | | | | |
| | 1 | ns | <2 | No | * | <2 | No | NA | NA | No | ns | <2 | No |
| | 2 | ** | <2 | No | ns | <2 | No | NA | NA | No | ns | <2 | No |
| | | | | | | | Immobilized | | | | | | |
| | 1 | ns | <2 | No | * | <2 | No | NA | NA | No | ns | <2 | No |
| | 2 | ** | <2 | No | ** | <2 | No | NA | NA | No | *** | <2 | No |

FIG. 12H

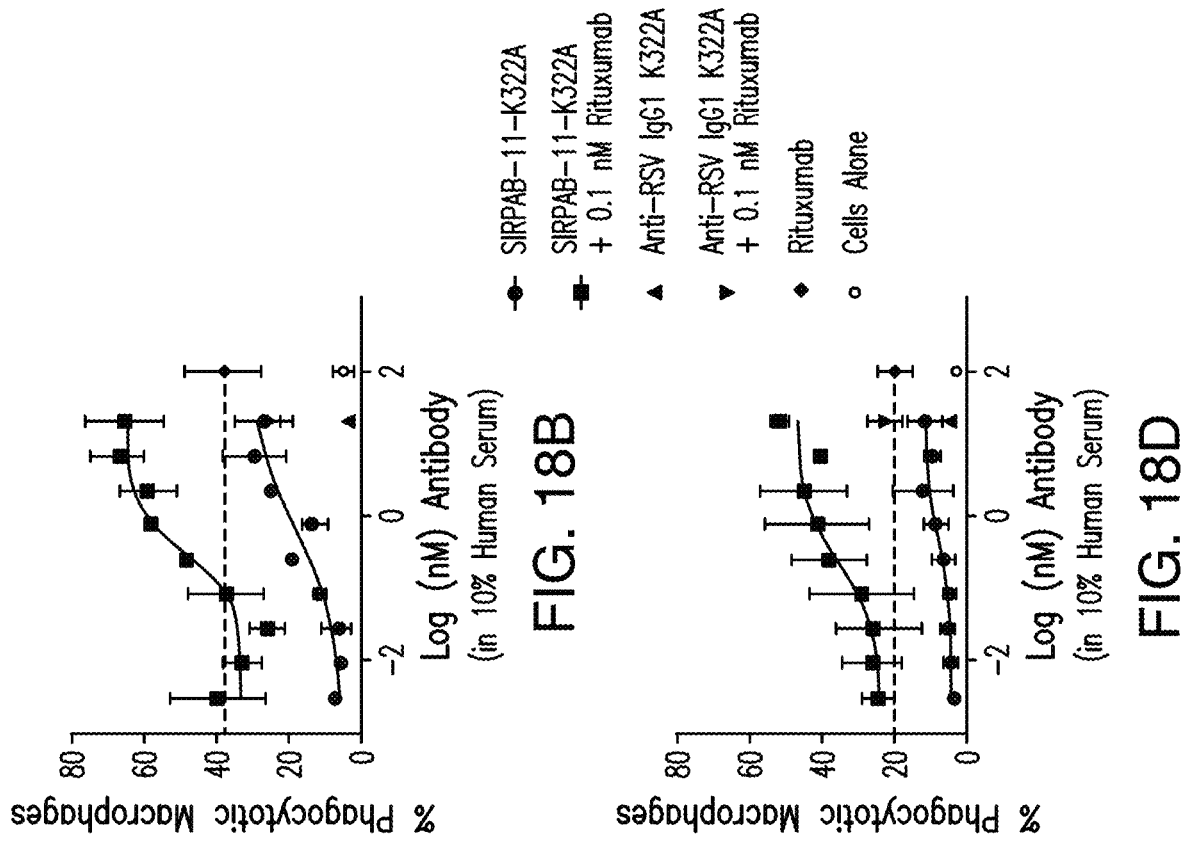
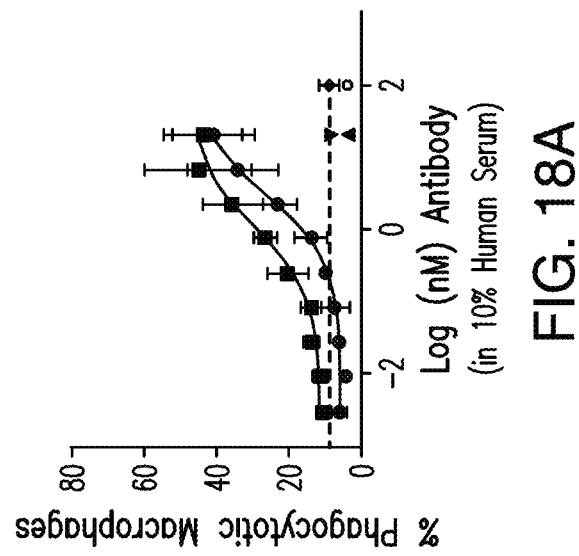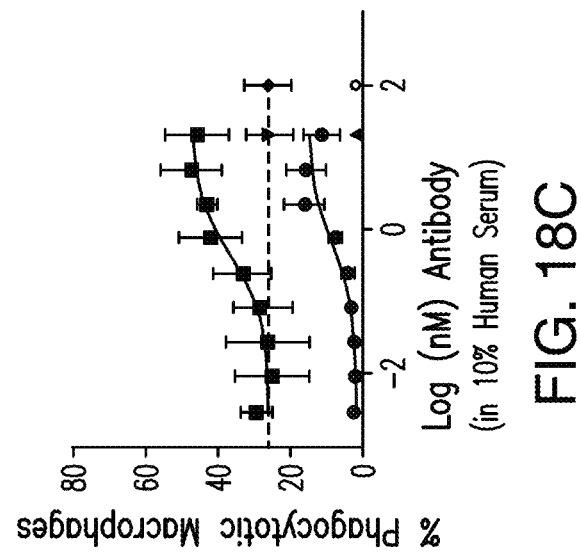
FIG. 18A  FIG. 18B  FIG. 18C  FIG. 18D

```
SEQUENCE LISTING

<160> NUMBER OF SEQ ID NOS: 225

<210> SEQ ID NO 1
<211> LENGTH: 26
<212> TYPE: PRT
<213> ORGANISM: Artificial Sequence
<220> FEATURE:
<223> OTHER INFORMATION: VH FR1 of Antibodies SIRPAB-1 to SIRPAB-7 and
      SIRPAB-17 to SIRPAB-21

<400> SEQUENCE: 1

Gln Val Gln Leu Gln Glu Ser Gly Pro Gly Leu Val Lys Pro Ser Gln
1               5                   10                  15

Thr Leu Ser Leu Thr Cys Thr Val Ser Gly
            20                  25

<210> SEQ ID NO 2
<211> LENGTH: 11
<212> TYPE: PRT
<213> ORGANISM: Artificial Sequence
<220> FEATURE:
<223> OTHER INFORMATION: VH CDR1 of Antibodies SIRPAB-1, SIRPAB-6 and
      SIRPAB-17 to SIRPAB-21

<400> SEQUENCE: 2

Gly Ser Ile Ser Ser Gly Gly Tyr Tyr Trp Ser
1               5                   10
```

```
<210> SEQ ID NO 3
<211> LENGTH: 14
<212> TYPE: PRT
<213> ORGANISM: Artificial Sequence
<220> FEATURE:
<223> OTHER INFORMATION: VH FR2 of Antibodies SIRPAB-1 to SIRPAB-7, and
      SIRPAB-17 to SIRPAB-21

<400> SEQUENCE: 3

Trp Ile Arg Gln His Pro Gly Lys Gly Leu Glu Trp Ile Gly
1               5                   10

<210> SEQ ID NO 4
<211> LENGTH: 16
<212> TYPE: PRT
<213> ORGANISM: Artificial Sequence
<220> FEATURE:
<223> OTHER INFORMATION: VH CDR2 of Antibody SIRPAB-1

<400> SEQUENCE: 4

Ser Ile Tyr Tyr Ser Gly Ser Thr Tyr Tyr Asn Pro Ser Leu Lys Ser
1               5                   10                  15

<210> SEQ ID NO 5
<211> LENGTH: 30
<212> TYPE: PRT
<213> ORGANISM: Artificial Sequence
<220> FEATURE:
<223> OTHER INFORMATION: VH FR3 of Antibodies SIRPAB-1 to SIRPAB-7, and
      SIRPAB-17 to SIRPAB-21

<400> SEQUENCE: 5

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 6
<211> LENGTH: 11
<212> TYPE: PRT
<213> ORGANISM: Artificial Sequence
<220> FEATURE:
<223> OTHER INFORMATION: VH CDR3 of Antibodies SIRPAB-1 to SIRPAB-5, and
      SIRPAB-17

<400> SEQUENCE: 6

Ala Arg Glu Gly Tyr His Ser Gly Met Asp Val
1               5                   10

<210> SEQ ID NO 7
<211> LENGTH: 11
<212> TYPE: PRT
<213> ORGANISM: Artificial Sequence
<220> FEATURE:
<223> OTHER INFORMATION: VH FR4 of Antibodies SIRPAB-1 to SIRPAB-5, and
      SIRPAB-17 to SIRPAB-21

<400> SEQUENCE: 7

Trp Gly Gln Gly Thr Thr Val Thr Val Ser Ser
1               5                   10

<210> SEQ ID NO 8
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-1
```

<400> SEQUENCE: 8

```
caggtgcagc tgcaggagtc gggcccagga ctggtgaagc cttcacagac cctgtccctc    60
acctgtactg tctctggtgg ctccatcagc agtggtggtt actactggag ctggatccgc   120
cagcacccag gaagggcct ggagtggatt gggtcaatct attacagtgg gagcacctac    180
tacaacccgt ccctcaagag tcgagttacc atatcagtag acacgtctaa gaaccagttc   240
tccctgaagc tgagttctgt gaccgccgca gacacggcgg tgtactactg cgccagagag   300
ggataccact caggaatgga cgtatggggc cagggaacaa ctgtcaccgt ctcctca      357
```

<210> SEQ ID NO 9
<211> LENGTH: 119
<212> TYPE: PRT
<213> ORGANISM: Artificial Sequence
<220> FEATURE:
<223> OTHER INFORMATION: VH Domain of Antibody SIRPAB-1

<400> SEQUENCE: 9

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Tyr His Ser Gly Met Asp Val Trp Gly Gln Gly
            100                 105                 110

Thr Thr Val Thr Val Ser Ser
        115
```

<210> SEQ ID NO 10
<211> LENGTH: 23
<212> TYPE: PRT
<213> ORGANISM: Artificial Sequence
<220> FEATURE:
<223> OTHER INFORMATION: VL FR1 of Antibodies SIRPAB-1 to SIRPAB-5 and
      SIRPAB-17 to SIRPAB-21

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 11
<211> LENGTH: 11
<212> TYPE: PRT
<213> ORGANISM: Artificial Sequence
<220> FEATURE:
<223> OTHER INFORMATION: VL CDR1 of Antibodies SIRPAB-1 to SIRPAB-7,
      SIRPAB-17, and SIRPAB-18

<400> SEQUENCE: 11

```
Gln Ala Ser Gln Asp Ile Ser Asn Tyr Leu Asn
1               5                   10
```

```
<210> SEQ ID NO 12
<211> LENGTH: 15
<212> TYPE: PRT
<213> ORGANISM: Artificial Sequence
<220> FEATURE:
<223> OTHER INFORMATION: VL FR2 of Antibodies SIRPAB-1 to SIRPAB-13 and
      SIRPAB-17 to SIRPAB-21

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: VL CDR2 of Antibodies SIRPAB-1 to SIRPAB-5,
      SIRPAB-17, and SIRPAB-18

<400> SEQUENCE: 13

Asp Ala Ser Asn Leu Ala Thr
1               5

<210> SEQ ID NO 14
<211> LENGTH: 32
<212> TYPE: PRT
<213> ORGANISM: Artificial Sequence
<220> FEATURE:
<223> OTHER INFORMATION: VL FR3 of Antibodies SIRPAB-1 to SIRPAB-7 and
      SIRPAB-17 to SIRPAB-21

<400> SEQUENCE: 14

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
                20                  25                  30

<210> SEQ ID NO 15
<211> LENGTH: 9
<212> TYPE: PRT
<213> ORGANISM: Artificial Sequence
<220> FEATURE:
<223> OTHER INFORMATION: VL CDR3 of Antibodies SIRPAB-1 to SIRPAB-5,
      SIRPAB-17 to SIRPAB-21

<400> SEQUENCE: 15

Gln Gln Phe Ala Tyr Leu Pro Trp Thr
1               5

<210> SEQ ID NO 16
<211> LENGTH: 10
<212> TYPE: PRT
<213> ORGANISM: Artificial Sequence
<220> FEATURE:
<223> OTHER INFORMATION: VL FR4 of Antibodies SIRPAB-1 to SIRPAB-13 and
      SIRPAB-17 to SIRPAB-21

<400> SEQUENCE: 16

Phe Gly Gly Gly Thr Lys Val Glu Ile Lys
1               5                   10

<210> SEQ ID NO 17
<211> LENGTH: 321
<212> TYPE: DNA
<213> ORGANISM: Artificial Sequence
```

```
<220> FEATURE:
<223> OTHER INFORMATION: VL Nucleotide Sequences of Antibody SIRPAB-1

<400> SEQUENCE: 17
gacatccaga tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggcaacagg ggtcccatca    180
aggttcagtg aagtggatc tgggacagat tttactttca ccatcagcag cctgcagcct    240
gaagatattg caacatatta ctgtcagcag ttcgcctacc tcccttggac ttttggcgga    300
gggaccaagg ttgagatcaa a                                              321

<210> SEQ ID NO 18
<211> LENGTH: 107
<212> TYPE: PRT
<213> ORGANISM: Artificial Sequence
<220> FEATURE:
<223> OTHER INFORMATION: VL Domain of Antibodies SIRPAB-1 to SIRPAB-5,
      SIRPAB-17 and SIRPAB-18

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Ala Tyr Leu Pro Trp
                85                  90                  95

Thr Phe Gly Gly Gly Thr Lys Val Glu Ile Lys
            100                 105

<210> SEQ ID NO 19
<211> LENGTH: 11
<212> TYPE: PRT
<213> ORGANISM: Artificial Sequence
<220> FEATURE:
<223> OTHER INFORMATION: VH CDR1 of Antibody SIRPAB-2

<400> SEQUENCE: 19

Gly Ser Ile Ser Ser Gly Gly Asp Tyr Trp Ala
1               5                   10

<210> SEQ ID NO 20
<211> LENGTH: 16
<212> TYPE: PRT
<213> ORGANISM: Artificial Sequence
<220> FEATURE:
<223> OTHER INFORMATION: VH CDR2 of Antibody SIRPAB-2

<400> SEQUENCE: 20

Tyr Ile Tyr Pro Ser Gly Phe Thr Tyr Tyr Asn Pro Ser Leu Lys Ser
1               5                   10                  15

<210> SEQ ID NO 21
<211> LENGTH: 357
<212> TYPE: DNA
```

<213> ORGANISM: Artificial Sequence
<220> FEATURE:
<223> OTHER INFORMATION: VH Nucleotide Sequences of Antibody SIRPAB-2

<400> SEQUENCE: 21

```
caggtgcagc tgcaggagtc gggcccagga ctggtgaagc cttcacagac cctgtccctc    60
acctgtactg tctctggtgg ctccatcagc agtggtggtg attactgggc ttggatccgc   120
cagcacccag gaagggcct ggagtggatt gggtacatct atcctagtgg gtttacctac    180
tacaacccgt ccctcaagag tcgagttacc atatcagtag acacgtctaa gaaccagttc   240
tccctgaagc tgagttctgt gaccgccgca gacacggcgg tgtactactg cgccagagag   300
ggataccact caggaatgga cgtatggggc cagggaacaa ctgtcaccgt ctcctca      357
```

<210> SEQ ID NO 22
<211> LENGTH: 119
<212> TYPE: PRT
<213> ORGANISM: Artificial Sequence
<220> FEATURE:
<223> OTHER INFORMATION: VH Domain of Antibody SIRPAB-2

<400> SEQUENCE: 22

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Asp Tyr Trp Ala Trp Ile Arg Gln His Pro Gly Lys Gly Leu Glu
        35                  40                  45

Trp Ile Gly Tyr Ile Tyr Pro Ser Gly Phe Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Tyr His Ser Gly Met Asp Val Trp Gly Gln Gly
            100                 105                 110

Thr Thr Val Thr Val Ser Ser
        115
```

<210> SEQ ID NO 23
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-2

<400> SEQUENCE: 23

```
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggcaacagg ggtcccatca   180
aggttcagtg aagtggatc tgggacagat tttactttca ccatcagcag cctgcagcct   240
gaagatattg caacatatta ctgtcagcag ttcgcctacc tcccttggac ttttggcgga   300
gggaccaagg ttgagatcaa a                                              321
```

<210> SEQ ID NO 24
<211> LENGTH: 11
<212> TYPE: PRT
<213> ORGANISM: Artificial Sequence
<220> FEATURE:
<223> OTHER INFORMATION: VH CDR1 of Antibody SIRPAB-3

<400> SEQUENCE: 24

Gly Ser Ile Ser Ser Gly Gly Trp Tyr Trp Gln
1               5                   10

<210> SEQ ID NO 25
<211> LENGTH: 16
<212> TYPE: PRT
<213> ORGANISM: Artificial Sequence
<220> FEATURE:
<223> OTHER INFORMATION: VH CDR2 of Antibodies SIRPAB-3 and SIRPAB-5

<400> SEQUENCE: 25

Thr Ile Tyr Tyr Ser Gly Ser Thr Phe Tyr Asn Pro Ser Leu Lys Ser
1               5                   10                  15

<210> SEQ ID NO 26
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-3

<400> SEQUENCE: 26
caggtgcagc tgcaggagtc gggcccagga ctggtgaagc cttcacagac cctgtccctc      60
acctgtactg tctctggtgg ctccatcagc agtggtggtt ggtactggca gtggatccgc     120
cagcacccag ggaagggcct ggagtggatt gggacgatct attacagtgg gagcaccttt     180
tacaacccgt ccctcaagag tcgagttacc atatcagtag acacgtctaa gaaccagttc     240
tccctgaagc tgagttctgt gaccgccgca gacacggcgg tgtactactg cgccagagag     300
ggataccact caggaatgga cgtatggggc cagggaacaa ctgtcaccgt ctcctca       357

<210> SEQ ID NO 27
<211> LENGTH: 119
<212> TYPE: PRT
<213> ORGANISM: Artificial Sequence
<220> FEATURE:
<223> OTHER INFORMATION: VH Domain of Antibody SIRPAB-3

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Trp Tyr Trp Gln Trp Ile Arg Gln His Pro Gly Lys Gly Leu Glu
        35                  40                  45

Trp Ile Gly Thr Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Tyr His Ser Gly Met Asp Val Trp Gly Gln Gly
            100                 105                 110

Thr Thr Val Thr Val Ser Ser
        115

<210> SEQ ID NO 28

```
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-3

<400> SEQUENCE: 28
gacatccaga tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggcaacagg ggtcccatca    180
aggttcagtg aagtggatc tgggacagat tttactttca ccatcagcag cctgcagcct    240
gaagatattg caacatatta ctgtcagcag ttcgcctacc tcccttggac ttttggcgga    300
gggaccaagg ttgagatcaa a                                              321

<210> SEQ ID NO 29
<211> LENGTH: 11
<212> TYPE: PRT
<213> ORGANISM: Artificial Sequence
<220> FEATURE:
<223> OTHER INFORMATION: VH CDR1 of Antibody SIRPAB-4

<400> SEQUENCE: 29

Gly Ser Ile Ser Ser Gly Ser Pro Tyr Trp Ser
1               5                   10

<210> SEQ ID NO 30
<211> LENGTH: 16
<212> TYPE: PRT
<213> ORGANISM: Artificial Sequence
<220> FEATURE:
<223> OTHER INFORMATION: VH CDR2 of Antibody SIRPAB-4

<400> SEQUENCE: 30

Tyr Ile Tyr Ala Ser Gly Phe Thr Tyr Tyr Asn Pro Ser Leu Lys Ser
1               5                   10                  15

<210> SEQ ID NO 31
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-4

<400> SEQUENCE: 31
caggtgcagc tgcaggagtc gggcccagga ctggtgaagc cttcacagac cctgtccctc      60
acctgtactg tctctggtgg ctccatcagc agtggtagtc cgtactggag ctggatccgc    120
cagcacccag ggaagggcct ggagtggatt gggtacatct atgctagtgg gtttacctac    180
tacaacccgt ccctcaagag tcgagttacc atatcagtag acacgtctaa gaaccagttc    240
tccctgaagc tgagttctgt gaccgccgca gacacggcgg tgtactactg cgccagagag    300
ggataccact caggaatgga cgtatggggc cagggaacaa ctgtcaccgt ctcctca      357

<210> SEQ ID NO 32
<211> LENGTH: 119
<212> TYPE: PRT
<213> ORGANISM: Artificial Sequence
<220> FEATURE:
<223> OTHER INFORMATION: VH Domain of Antibody SIRPAB-4

<400> SEQUENCE: 32

Gln Val Gln Leu Gln Glu Ser Gly Pro Gly Leu Val Lys Pro Ser Gln
```

```
1               5                  10                 15
Thr Leu Ser Leu Thr Cys Thr Val Ser Gly Gly Ser Ile Ser Ser Gly
            20                  25                  30

Ser Pro Tyr Trp Ser Trp Ile Arg Gln His Pro Gly Lys Gly Leu Glu
            35                  40                  45

Trp Ile Gly Tyr Ile Tyr Ala Ser Gly Phe Thr Tyr Tyr Asn Pro Ser
            50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Tyr His Ser Gly Met Asp Val Trp Gly Gln Gly
            100                 105                 110

Thr Thr Val Thr Val Ser Ser
            115

<210> SEQ ID NO 33
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-4

<400> SEQUENCE: 33
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggcaacagg ggtcccatca   180
aggttcagtg aagtggatc tgggacagat tttactttca ccatcagcag cctgcagcct   240
gaagatattg caacatatta ctgtcagcag ttcgcctacc tcccttggac ttttggcgga   300
gggaccaagg ttgagatcaa a                                             321

<210> SEQ ID NO 34
<211> LENGTH: 11
<212> TYPE: PRT
<213> ORGANISM: Artificial Sequence
<220> FEATURE:
<223> OTHER INFORMATION: VH CDR1 of Antibody SIRPAB-5

<400> SEQUENCE: 34

Gly Ser Ile Ser Ser Gly Pro Ala Tyr Trp Ser
1               5                  10

<210> SEQ ID NO 35
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-5

<400> SEQUENCE: 35
caggtgcagc tgcaggagtc gggcccagga ctggtgaagc cttcacagac cctgtccctc    60
acctgtactg tctctggtgg ctccatcagc agtggtccgg cttactggag ctggatccgc   120
cagcacccag ggaagggcct ggagtggatt ggactatct attacagtgg gagcaccttt   180
tacaacccgt ccctcaagag tcgagttacc atatcagtag acacgtctaa gaaccagttc   240
tccctgaagc tgagttctgt gaccgccgca gacacggcgg tgtactactg cgccagagag   300
ggataccact caggaatgga cgtatggggc cagggaacaa ctgtcaccgt ctcctca     357
```

<210> SEQ ID NO 36
<211> LENGTH: 119
<212> TYPE: PRT
<213> ORGANISM: Artificial Sequence
<220> FEATURE:
<223> OTHER INFORMATION: VH Domain of Antibody SIRPAB-5

<400> SEQUENCE: 36

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Pro Ala Tyr Trp Ser Trp Ile Arg Gln His Pro Gly Lys Gly Leu Glu
        35                  40                  45

Trp Ile Gly Thr Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Tyr His Ser Gly Met Asp Val Trp Gly Gln Gly
            100                 105                 110

Thr Thr Val Thr Val Ser Ser
        115

<210> SEQ ID NO 37
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-5

<400> SEQUENCE: 37
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggcaacagg ggtcccatca     180
aggttcagtg gaagtggatc tgggacagat tttactttca ccatcagcag cctgcagcct     240
gaagatattg caacatatta ctgtcagcag ttcgcctacc tcccttggac ttttggcgga     300
gggaccaagg ttgagatcaa a                                               321

<210> SEQ ID NO 38
<211> LENGTH: 16
<212> TYPE: PRT
<213> ORGANISM: Artificial Sequence
<220> FEATURE:
<223> OTHER INFORMATION: VH CDR2 of Antibody SIRPAB-6

<400> SEQUENCE: 38

Tyr Ile Tyr Tyr Ser Gly Ser Thr Tyr Tyr Asn Pro Ser Leu Lys Ser
1               5                   10                  15

<210> SEQ ID NO 39
<211> LENGTH: 13
<212> TYPE: PRT
<213> ORGANISM: Artificial Sequence
<220> FEATURE:
<223> OTHER INFORMATION: VH CDR3 of Antibodies SIRPAB-6 and SIRPAB-7

<400> SEQUENCE: 39

Ala Arg Glu Gly Leu Asp Gly Ser Tyr Gly Ser Ser Ala
1               5                   10

<210> SEQ ID NO 40
<211> LENGTH: 11
<212> TYPE: PRT
<213> ORGANISM: Artificial Sequence
<220> FEATURE:
<223> OTHER INFORMATION: VH FR4 of Antibodies SIRPAB-6 and SIRPAB-7

<400> SEQUENCE: 40

Trp Gly Gln Gly Thr Leu Val Thr Val Ser Ser
1               5                   10

<210> SEQ ID NO 41
<211> LENGTH: 363
<212> TYPE: DNA
<213> ORGANISM: Artificial Sequence
<220> FEATURE:
<223> OTHER INFORMATION: VH Nucleotide Sequences of Antibody SIRPAB-6

<400> SEQUENCE: 41
caggtgcagc tgcaggagtc gggcccagga ctggtgaagc cttcacagac cctgtccctc      60
acctgtactg tctctggtgg ctccatcagc agtggtggtt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagttctgt gaccgccgca gacacggcgg tgtactactg cgccagagag     300
ggcttggacg gatcctacgg ttcaagcgca tggggacagg gtacattggt caccgtctcc     360
tca                                                                   363

<210> SEQ ID NO 42
<211> LENGTH: 121
<212> TYPE: PRT
<213> ORGANISM: Artificial Sequence
<220> FEATURE:
<223> OTHER INFORMATION: VH Domain of Antibody SIRPAB-6

<400> SEQUENCE: 42

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Gly Leu Asp Gly Ser Tyr Gly Ser Ser Ala Trp Gly
        100                 105                 110

Gln Gly Thr Leu Val Thr Val Ser Ser
    115                 120

<210> SEQ ID NO 43
<211> LENGTH: 7
<212> TYPE: PRT

```
<213> ORGANISM: Artificial Sequence
<220> FEATURE:
<223> OTHER INFORMATION: VL CDR2 of Antibodies SIRPAB-6, SIRPAB-7 and
      SIRPAB-21

<400> SEQUENCE: 43

Asp Ala Ser Asn Leu Glu Thr
1               5

<210> SEQ ID NO 44
<211> LENGTH: 9
<212> TYPE: PRT
<213> ORGANISM: Artificial Sequence
<220> FEATURE:
<223> OTHER INFORMATION: VL CDR3 of Antibodies SIRPAB-6 and SIRPAB-7

<400> SEQUENCE: 44

Gln Gln Phe Ala Tyr Leu Pro Tyr Thr
1               5

<210> SEQ ID NO 45
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-6

<400> SEQUENCE: 45
gacatccagt tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg aagtggatc tgggacagat tttactttca ccatcagcag cctgcagcct    240
gaagatattg caacatatta ctgtcagcag ttcgcctacc tcccttacac ttttggcgga    300
gggaccaagg ttgagatcaa a                                              321

<210> SEQ ID NO 46
<211> LENGTH: 107
<212> TYPE: PRT
<213> ORGANISM: Artificial Sequence
<220> FEATURE:
<223> OTHER INFORMATION: VL Domain of Antibodies SIRPAB-6 and SIRPAB-7

<400> SEQUENCE: 46

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Ala Tyr Leu Pro Tyr
                85                  90                  95

Thr Phe Gly Gly Gly Thr Lys Val Glu Ile Lys
            100                 105

<210> SEQ ID NO 47
<211> LENGTH: 11
```

```
<212> TYPE: PRT
<213> ORGANISM: Artificial Sequence
<220> FEATURE:
<223> OTHER INFORMATION: VH CDR1 of Antibody SIRPAB-7

<400> SEQUENCE: 47

Gly Ser Ile Ser Ser Gly Glu Tyr Tyr Trp Glu
1               5                   10

<210> SEQ ID NO 48
<211> LENGTH: 16
<212> TYPE: PRT
<213> ORGANISM: Artificial Sequence
<220> FEATURE:
<223> OTHER INFORMATION: VH CDR2 of Antibody SIRPAB-7

<400> SEQUENCE: 48

Tyr Ile Tyr Ser Ser Gly Phe Thr Tyr Tyr Asn Pro Ser Leu Lys Ser
1               5                   10                  15

<210> SEQ ID NO 49
<211> LENGTH: 363
<212> TYPE: DNA
<213> ORGANISM: Artificial Sequence
<220> FEATURE:
<223> OTHER INFORMATION: VH Nucleotide Sequences of Antibody SIRPAB-7

<400> SEQUENCE: 49
caggtgcagc tgcaggagtc gggcccagga ctggtgaagc cttcacagac cctgtccctc      60
acctgtactg tctctggtgg ctccatcagc agtggtgagt actactggga gtggatccgc     120
cagcacccag ggaagggcct ggagtggatt gggtacatct attctagtgg gtttacctac     180
tacaacccgt ccctcaagag tcgagttacc atatcagtag acacgtctaa gaaccagttc     240
tccctgaagc tgagttctgt gaccgccgca gacacggcgg tgtactactg cgccagagag     300
ggcttggacg gatcctacgg ttcaagcgca tggggacagg gtacattggt caccgtctcc     360
tca                                                                   363

<210> SEQ ID NO 50
<211> LENGTH: 121
<212> TYPE: PRT
<213> ORGANISM: Artificial Sequence
<220> FEATURE:
<223> OTHER INFORMATION: VH Domain of Antibody SIRPAB-7

<400> SEQUENCE: 50

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Glu Tyr Tyr Trp Glu Trp Ile Arg Gln His Pro Gly Lys Gly Leu Glu
            35                  40                  45

Trp Ile Gly Tyr Ile Tyr Ser Ser Gly Phe Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Leu Asp Gly Ser Tyr Gly Ser Ser Ala Trp Gly
            100                 105                 110

Gln Gly Thr Leu Val Thr Val Ser Ser
```

<210> SEQ ID NO 51
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-7

<400> SEQUENCE: 51

```
gacatccagt tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcagcag ttcgcctacc tcccttacac ttttggcgga    300
gggaccaagg ttgagatcaa a                                              321
```

<210> SEQ ID NO 52
<211> LENGTH: 26
<212> TYPE: PRT
<213> ORGANISM: Artificial Sequence
<220> FEATURE:
<223> OTHER INFORMATION: VH FR1 of Antibodies SIRPAB-8 to SIRPAB-13

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 53
<211> LENGTH: 9
<212> TYPE: PRT
<213> ORGANISM: Artificial Sequence
<220> FEATURE:
<223> OTHER INFORMATION: VH CDR1 of Antibody SIRPAB-8

<400> SEQUENCE: 53

Tyr Thr Phe Thr Ser Tyr Gly Ile Ser
1               5

<210> SEQ ID NO 54
<211> LENGTH: 14
<212> TYPE: PRT
<213> ORGANISM: Artificial Sequence
<220> FEATURE:
<223> OTHER INFORMATION: VH FR2 of Antibodies SIRPAB-8 to SIRPAB-13

<400> SEQUENCE: 54

Trp Val Arg Gln Ala Pro Gly Gln Gly Leu Glu Trp Met Gly
1               5                   10

<210> SEQ ID NO 55
<211> LENGTH: 17
<212> TYPE: PRT
<213> ORGANISM: Artificial Sequence
<220> FEATURE:
<223> OTHER INFORMATION: VH CDR2 of Antibody SIRPAB-8

<400> SEQUENCE: 55

Trp Ile Ser Pro Tyr Asn Gly Asn Thr Asn Tyr Ala Gln Lys Leu Gln
1               5                   10                  15

<210> SEQ ID NO 56
<211> LENGTH: 30
<212> TYPE: PRT
<213> ORGANISM: Artificial Sequence
<220> FEATURE:
<223> OTHER INFORMATION: VH FR3 of Antibodies SIRPAB-8 to SIRPAB-13

<400> SEQUENCE: 56

Arg Val Thr Met Thr Thr Asp Thr Ser Thr Ser Thr Ala Tyr Met Glu
1               5                   10                  15
Leu Arg Ser Leu Arg Ser Asp Asp Thr Ala Val Tyr Tyr Cys
            20                  25                  30

<210> SEQ ID NO 57
<211> LENGTH: 13
<212> TYPE: PRT
<213> ORGANISM: Artificial Sequence
<220> FEATURE:
<223> OTHER INFORMATION: VH CDR3 of Antibodies SIRPAB-8 to SIRPAB-13

<400> SEQUENCE: 57

Ala Arg Glu Ala Gly Ser Ser Trp Tyr Asp Phe Asp Leu
1               5                   10

<210> SEQ ID NO 58
<211> LENGTH: 11
<212> TYPE: PRT
<213> ORGANISM: Artificial Sequence
<220> FEATURE:
<223> OTHER INFORMATION: VH FR4 of Antibodies SIRPAB-8 to SIRPAB-13

<400> SEQUENCE: 58

Trp Gly Arg Gly Thr Leu Val Thr Val Ser Ser
1               5                   10

<210> SEQ ID NO 59
<211> LENGTH: 360
<212> TYPE: DNA
<213> ORGANISM: Artificial Sequence
<220> FEATURE:
<223> OTHER INFORMATION: VH Nucleotide Sequences of Antibody SIRPAB-8

<400> SEQUENCE: 59
caggttcagc tggtgcagtc tggagctgag gtgaagaagc ctggggcctc agtgaaggtc      60
tcctgcaagg cttctggtta ccctttacc agctatggta tcagctgggt gcgacaggcc     120
cctggacaag ggcttgagtg gatgggatgg atcagcccctt acaatggtaa cacaaactat    180
gcacagaagc tccagggcag agtcaccatg accacagaca tccacgag cacagcctac      240 atggagctga ggagcctgag atctgacgac acggcggtgt actactgcgc cagagaagcc    300
ggaagcagct ggtacgactt cgacctatgg gggagaggta cattggtcac cgtctcctca    360

<210> SEQ ID NO 60
<211> LENGTH: 120
<212> TYPE: PRT
<213> ORGANISM: Artificial Sequence
<220> FEATURE:
<223> OTHER INFORMATION: VH Domain of Antibody SIRPAB-8

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser
        115                 120

<210> SEQ ID NO 61
<211> LENGTH: 23
<212> TYPE: PRT
<213> ORGANISM: Artificial Sequence
<220> FEATURE:
<223> OTHER INFORMATION: VL FR1 of Antibodies SIRPAB-8 to SIRPAB-13

<400> SEQUENCE: 61

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 62
<211> LENGTH: 11
<212> TYPE: PRT
<213> ORGANISM: Artificial Sequence
<220> FEATURE:
<223> OTHER INFORMATION: VL CDR1 of Antibodies SIRPAB-8 to SIRPAB-13

<400> SEQUENCE: 62

Arg Ala Ser Gln Gly Ile Ser Ser Trp Leu Ala
1               5                   10

<210> SEQ ID NO 63
<211> LENGTH: 7
<212> TYPE: PRT
<213> ORGANISM: Artificial Sequence
<220> FEATURE:
<223> OTHER INFORMATION: VL CDR2 of Antibodies SIRPAB-8 to SIRPAB-13

<400> SEQUENCE: 63

Ala Ala Ser Asn Leu Gln Ser
1               5

<210> SEQ ID NO 64
<211> LENGTH: 32
<212> TYPE: PRT
<213> ORGANISM: Artificial Sequence
<220> FEATURE:
<223> OTHER INFORMATION: VL FR3 of Antibodies SIRPAB-8 to SIRPAB-13

<400> SEQUENCE: 64

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 65
<211> LENGTH: 9
<212> TYPE: PRT
<213> ORGANISM: Artificial Sequence
<220> FEATURE:
<223> OTHER INFORMATION: VL CDR3 of Antibody SIRPAB-8 to SIRPAB-13

<400> SEQUENCE: 65

Gln Gln Gly Ala Ser Phe Pro Ile Thr
1               5

<210> SEQ ID NO 66
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-8

<400> SEQUENCE: 66
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccaatt tgcaaagtgg ggtcccatca   180
aggttcagcg gcagtggatc tgggacagat tcactctca ccatcagcag cctgcagcct   240
gaagattttg caactyatta ctgtcagcag ggagccagtt ccctatcac ttttggcgga   300 gggaccaagg ttgagatcaa a                                             321

<210> SEQ ID NO 67
<211> LENGTH: 107
<212> TYPE: PRT
<213> ORGANISM: Artificial Sequence
<220> FEATURE:
<223> OTHER INFORMATION: VL Domain of Antibodies SIRPAB-8 to SIRPAB-13

<400> SEQUENCE: 67

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Ser Phe Pro Ile
                85                  90                  95

Thr Phe Gly Gly Gly Thr Lys Val Glu Ile Lys
            100                 105

<210> SEQ ID NO 68
<211> LENGTH: 9
<212> TYPE: PRT
<213> ORGANISM: Artificial Sequence
<220> FEATURE:
<223> OTHER INFORMATION: VH CDR1 of Antibody SIRPAB-9

<400> SEQUENCE: 68

Tyr Thr Phe Gly Gly Tyr Gly Ile Ser
1               5

<210> SEQ ID NO 69
<211> LENGTH: 17
<212> TYPE: PRT
<213> ORGANISM: Artificial Sequence
<220> FEATURE:
<223> OTHER INFORMATION: VH CDR2 of Antibodies SIRPAB-9 and SIRPAB-11

<400> SEQUENCE: 69

Trp Ile Ser Ala Tyr Gly Gly Glu Thr Asn Tyr Ala Gln Lys Leu Gln
1               5                   10                  15

Gly

<210> SEQ ID NO 70
<211> LENGTH: 360
<212> TYPE: DNA
<213> ORGANISM: Artificial Sequence
<220> FEATURE:
<223> OTHER INFORMATION: VH Nucleotide Sequences of Antibody SIRPAB-9

<400> SEQUENCE: 70
caggttcagc tggtgcagtc tggagctgag gtgaagaagc ctggggcctc agtgaaggtc      60
tcctgcaagg cttctggtta cacctttggg ggttatggta tcagctgggt gcgacaggcc     120
cctggacaag gcttgagtg gatgggatgg atcagcgctt acggggtga cacaaactat        180 gcacagaagc tccagggcag agtcaccatg accacagaca catccacgag cacagcctac     240
atggagctga ggagcctgag atctgacgac acggcggtgt actactgcgc cagagaagcc     300
ggaagcagct ggtacgactt cgacctatgg gggagaggta cattggtcac cgtctcctca     360

<210> SEQ ID NO 71
<211> LENGTH: 120
<212> TYPE: PRT
<213> ORGANISM: Artificial Sequence
<220> FEATURE:
<223> OTHER INFORMATION: VH Domain of Antibody SIRPAB-9

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Gly Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Gly Gly Glu Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser
        115                 120

<210> SEQ ID NO 72
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-9

<400> SEQUENCE: 72

```
gacatccaga tgacccagtc tccatcttcc gtgtctgcat ctgtaggaga cagagtcacc      60
atcacttgtc gggcgagtca gggtattagc agctggttag cctggtatca gcagaaacca    120
gggaaagccc ctaagctcct gatctatgct gcatccaatt tgcaaagtgg ggtcccatca    180
aggttcagcg gcagtggatc tgggacagat tcactctca ccatcagcag cctgcagcct    240
gaagattttg caacttatta ctgtcagcag ggagccagtt tccctatcac ttttggcgga    300
gggaccaagg ttgagatcaa a                                              321
```

<210> SEQ ID NO 73
<211> LENGTH: 9
<212> TYPE: PRT
<213> ORGANISM: Artificial Sequence
<220> FEATURE:
<223> OTHER INFORMATION: VH CDR1 of Antibody SIRPAB-10

<400> SEQUENCE: 73

Tyr Thr Phe Thr Gly Tyr Pro Ile Ser
1               5

<210> SEQ ID NO 74
<211> LENGTH: 17
<212> TYPE: PRT
<213> ORGANISM: Artificial Sequence
<220> FEATURE:
<223> OTHER INFORMATION: VH CDR2 of Antibody SIRPAB-10

<400> SEQUENCE: 74

Trp Ile Tyr Ala Tyr Gly Gly Asn Thr Asn Tyr Ala Gln Lys Leu Gln
1               5                   10                  15
Gly

<210> SEQ ID NO 75
<211> LENGTH: 360
<212> TYPE: DNA
<213> ORGANISM: Artificial Sequence
<220> FEATURE:
<223> OTHER INFORMATION: VH Nucleotide Sequences of Antibody SIRPAB-10

<400> SEQUENCE: 75

```
caggttcagc tggtgcagtc tggagctgag gtgaagaagc ctggggcctc agtgaaggtc     60
tcctgcaagg cttctggtta cacctttacc ggttatccta tcagctgggt gcgacaggcc   120
cctggacaag gcttgagtg gatgggatgg atctatgctt acgggggtaa cacaaactat    180
gcacagaagc tccagggcag agtcaccatg accacagaca tccacgag cacagcctac     240
atggagctga ggagcctgag atctgacgac acggcggtgt actactgcgc cagagaagcc   300
ggaagcagct ggtacgactt cgacctatgg gggagaggta cattggtcac cgtctcctca   360
```

<210> SEQ ID NO 76
<211> LENGTH: 120
<212> TYPE: PRT
<213> ORGANISM: Artificial Sequence
<220> FEATURE:
<223> OTHER INFORMATION: VH Domain of Antibody SIRPAB-10

<400> SEQUENCE: 76

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30

```
Pro Ile Ser Trp Val Arg Gln Ala Pro Gly Gln Gly Leu Glu Trp Met
            35                  40                  45
Gly Trp Ile Tyr Ala Tyr Gly Gly Asn Thr Asn Tyr Ala Gln Lys Leu
        50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                85                  90                  95
Ala Arg Glu Ala Gly Ser Ser Trp Tyr Asp Phe Asp Leu Trp Gly Arg
            100                 105                 110
Gly Thr Leu Val Thr Val Ser Ser
        115                 120
```

<210> SEQ ID NO 77
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-10

<400> SEQUENCE: 77

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccaatt tgcaaagtgg ggtcccatca   180
aggttcagcg gcagtggatc tgggacagat tcactctca ccatcagcag cctgcagcct    240
gaagattttg caacttatta ctgtcagcag ggagccagtt ccctatcac ttttggcgga    300
gggaccaagg ttgagatcaa a                                             321
```

<210> SEQ ID NO 78
<211> LENGTH: 9
<212> TYPE: PRT
<213> ORGANISM: Artificial Sequence
<220> FEATURE:
<223> OTHER INFORMATION: VH CDR1 of Antibody SIRPAB-11

<400> SEQUENCE: 78

```
Tyr Thr Phe Arg Gly Tyr Gly Ile Ser
1               5
```

<210> SEQ ID NO 79
<211> LENGTH: 360
<212> TYPE: DNA
<213> ORGANISM: Artificial Sequence
<220> FEATURE:
<223> OTHER INFORMATION: VH Nucleotide Sequences of Antibody SIRPAB-11

<400> SEQUENCE: 79

```
caggttcagc tggtgcagtc tggagctgag gtgaagaagc ctggggcctc agtgaaggtc    60
tcctgcaagg cttctggtta cacctttagg gggtatggta tcagctgggt gcgacaggcc   120
cctggacaag gcttgagtg gatgggatgg atcagcgctt acgggggtga caaactat     180
gcacagaagc tccagggcag agtcaccatg accacagaca catccacgag cacagcctac   240
atggagctga ggagcctgag atctgacgac acggcggtgt actactgcgc cagagaagcc   300
ggaagcagct ggtacgactt cgacctatgg gggagaggta cattggtcac cgtctcctca   360
```

<210> SEQ ID NO 80
<211> LENGTH: 120

```
<212> TYPE: PRT
<213> ORGANISM: Artificial Sequence
<220> FEATURE:
<223> OTHER INFORMATION: VH Domain of Antibody SIRPAB-11

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Gly Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser
        115                 120

<210> SEQ ID NO 81
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-11

<400> SEQUENCE: 81
gacatccaga tgacccagtc tccatcttcc gtgtctgcat ctgtaggaga cagagtcacc    60
atcacttgtc gggcgagtca gggtattagc agctggttag cctggtatca gcagaaacca    120
gggaaagccc ctaagctcct gatctatgct gcatccaatt tgcaaagtgg ggtcccatca    180
aggttcagcg gcagtggatc tgggacagat ttcactctca ccatcagcag cctgcagcct    240
gaagattttg caacttatta ctgtcagcag ggagccagtt ccctatcac ttttggcgga    300 gggaccaagg ttgagatcaa a                                              321

<210> SEQ ID NO 82
<211> LENGTH: 9
<212> TYPE: PRT
<213> ORGANISM: Artificial Sequence
<220> FEATURE:
<223> OTHER INFORMATION: VH CDR1 of Antibody SIRPAB-12

<400> SEQUENCE: 82

Tyr Thr Phe Thr Gly Tyr Gly Ile Val
1               5

<210> SEQ ID NO 83
<211> LENGTH: 17
<212> TYPE: PRT
<213> ORGANISM: Artificial Sequence
<220> FEATURE:
<223> OTHER INFORMATION: VH CDR2 of Antibody SIRPAB-12

<400> SEQUENCE: 83

Trp Ile Ser Ala Tyr Ala Gly Glu Thr Asn Tyr Ala Gln Lys Leu Gln
1               5                   10                  15
```

Gly

<210> SEQ ID NO 84
<211> LENGTH: 360
<212> TYPE: DNA
<213> ORGANISM: Artificial Sequence
<220> FEATURE:
<223> OTHER INFORMATION: VH Nucleotide Sequences of Antibody SIRPAB-12

<400> SEQUENCE: 84

```
caggttcagc tggtgcagtc tggagctgag gtgaagaagc ctggggcctc agtgaaggtc      60
tcctgcaagg cttctggtta ccctttacc gggtatggta tcgtttgggt gcgacaggcc     120
cctggacaag ggcttgagtg gatgggatgg atcagcgctt acgctggtga gacaaactat    180
gcacagaagc tccagggcag agtcaccatg accacagaca catccacgag cacagcctac    240
atggagctga ggagcctgag atctgacgac acggcggtgt actactgcgc cagagaagcc    300
ggaagcagct ggtacgactt cgacctatgg gggagaggta cattggtcac cgtctcctca    360
```

<210> SEQ ID NO 85
<211> LENGTH: 120
<212> TYPE: PRT
<213> ORGANISM: Artificial Sequence
<220> FEATURE:
<223> OTHER INFORMATION: VH Domain of Antibody SIRPAB-12

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Gly Ile Val Trp Val Arg Gln Ala Pro Gly Gln Gly Leu Glu Trp Met
        35                  40                  45

Gly Trp Ile Ser Ala Tyr Ala Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser
        115                 120

<210> SEQ ID NO 86
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-12

<400> SEQUENCE: 86

```
gacatccaga tgacccagtc tccatcttcc gtgtctgcat ctgtaggaga cagagtcacc      60
atcacttgtc gggcgagtca gggtattagc agctggttag cctggtatca gcagaaacca    120
gggaaagccc ctaagctcct gatctatgct gcatccaatt tgcaaagtgg ggtcccatca    180
aggttcagcg gcagtggatc tgggacagat ttcactctca ccatcagcag cctgcagcct    240
gaagattttg caacttatta ctgtcagcag ggagccagtt tccctatcac ttttggcgga    300
gggaccaagg ttgagatcaa a                                              321
```

<210> SEQ ID NO 87
<211> LENGTH: 9
<212> TYPE: PRT
<213> ORGANISM: Artificial Sequence
<220> FEATURE:
<223> OTHER INFORMATION: VH CDR1 of Antibody SIRPAB-13

<400> SEQUENCE: 87

Tyr Thr Phe His Gly Tyr Gly Ile Ser
1               5

<210> SEQ ID NO 88
<211> LENGTH: 17
<212> TYPE: PRT
<213> ORGANISM: Artificial Sequence
<220> FEATURE:
<223> OTHER INFORMATION: VH CDR2 of Antibody SIRPAB-13

<400> SEQUENCE: 88

Trp Ile Ser Ala Tyr Ser Gly Glu Thr Asn Tyr Ala Gln Lys Leu Gln
1               5                   10                  15

Gly

<210> SEQ ID NO 89
<211> LENGTH: 360
<212> TYPE: DNA
<213> ORGANISM: Artificial Sequence
<220> FEATURE:
<223> OTHER INFORMATION: VH Nucleotide Sequences of Antibody SIRPAB-13

<400> SEQUENCE: 89
caggttcagc tggtgcagtc tggagctgag gtgaagaagc ctggggcctc agtgaaggtc        60
tcctgcaagg cttctggtta cacctttcat gggtatggta tcagctgggt gcgacaggcc       120
cctggacaag gcttgagtg gatgggatgg atcagcgctt actcgggtga gacaaactat        180
gcacagaagc tccagggcag agtcaccatg accacagaca catccacgag cacagcctac       240
atggagctga ggagcctgag atctgacgac acggcggtgt actactgcgc cagagaagcc       300
ggaagcagct ggtacgactt cgacctatgg gggagaggta cattggtcac cgtctcctca       360

<210> SEQ ID NO 90
<211> LENGTH: 120
<212> TYPE: PRT
<213> ORGANISM: Artificial Sequence
<220> FEATURE:
<223> OTHER INFORMATION: VH Domain of Antibody SIRPAB-13

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe His Gly Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser
        115                 120

<210> SEQ ID NO 91
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-13

<400> SEQUENCE: 91

```
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccaatt tgcaaagtgg ggtcccatca     180
aggttcagcg gcagtggatc tgggacagat tcactctca ccatcagcag cctgcagcct     240
gaagattttg caacttatta ctgtcagcag ggagccagtt tccctatcac ttttggcgga     300
gggaccaagg ttgagatcaa a                                               321
```

<210> SEQ ID NO 92
<211> LENGTH: 600
<212> TYPE: PRT
<213> ORGANISM: Homo sapiens
<220> FEATURE:
<223> OTHER INFORMATION: human SIRPbeta-Fc

<400> SEQUENCE: 92

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
        35                  40                  45

Ser Ala Thr Leu Cys Cys Ala Met Thr Ser Leu Ile Pro Val Gly Pro
    50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Thr Val Ser Glu Leu Thr
                85                  90                  95

Lys Arg Asn Asn Leu Asp Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
        195                 200                 205

His Ser Thr Ala Arg Val Val Leu Thr Arg Gly Asp Val His Ser Gln
    210                 215                 220

```
Val Ile Cys Glu Met Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
            245                 250                 255

Val Thr Gln Gln Pro Met Arg Ala Glu Asn Gln Ala Asn Val Thr Cys
        260                 265                 270

Gln Val Ser Asn Phe Tyr Pro Arg Gly Leu Gln Leu Thr Trp Leu Glu
    275                 280                 285

Asn Gly Asn Val Ser Arg Thr Glu Thr Ala Ser Thr Leu Ile Glu Asn
290                 295                 300

Lys Asp Gly Thr Tyr Asn Trp Met Ser Trp Leu Leu Val Asn Thr Cys
305                 310                 315                 320

Ala His Arg Asp Val Val Leu Thr Cys Gln Val Glu His Asp Gly
            325                 330                 335

Gln Gln Ala Val Ser Lys Ser Tyr Ala Leu Glu Ile Ser Ala His Gln
        340                 345                 350

Lys Glu His Gly Ser Asp Ile Thr His Glu Pro Ala Leu Ala Pro Thr
    355                 360                 365

Ala Pro Leu Gly Ser Asp Lys Thr His Thr Cys Pro Pro Cys Pro Ala
370                 375                 380

Pro Glu Leu Leu Gly Gly Pro Ser Val Phe Leu Phe Pro Pro Lys Pro
385                 390                 395                 400

Lys Asp Thr Leu Met Ile Ser Arg Thr Pro Glu Val Thr Cys Val Val
            405                 410                 415

Val Asp Val Ser His Glu Asp Pro Glu Val Lys Phe Asn Trp Tyr Val
        420                 425                 430

Asp Gly Val Glu Val His Asn Ala Lys Thr Lys Pro Arg Glu Glu Gln
    435                 440                 445

Tyr Ala Ser Thr Tyr Arg Val Val Ser Val Leu Thr Val Leu His Gln
450                 455                 460

Asp Trp Leu Asn Gly Lys Glu Tyr Lys Cys Lys Val Ser Asn Lys Ala
465                 470                 475                 480

Leu Pro Ala Pro Ile Glu Lys Thr Ile Ser Lys Ala Lys Gly Gln Pro
            485                 490                 495

Arg Glu Pro Gln Val Tyr Thr Leu Pro Pro Ser Arg Asp Glu Leu Thr
        500                 505                 510

Lys Asn Gln Val Ser Leu Thr Cys Leu Val Lys Gly Phe Tyr Pro Ser
    515                 520                 525

Asp Ile Ala Val Glu Trp Glu Ser Asn Gly Gln Pro Glu Asn Asn Tyr
530                 535                 540

Lys Thr Thr Pro Pro Val Leu Asp Ser Asp Gly Ser Phe Phe Leu Tyr
545                 550                 555                 560

Ser Lys Leu Thr Val Asp Lys Ser Arg Trp Gln Gln Gly Asn Val Phe
            565                 570                 575

Ser Cys Ser Val Met His Glu Ala Leu His Asn His Tyr Thr Gln Lys
        580                 585                 590

Ser Leu Ser Leu Ser Pro Gly Lys
    595                 600
```

<210> SEQ ID NO 93
<211> LENGTH: 373
<212> TYPE: PRT
<213> ORGANISM: Artificial Sequence
<220> FEATURE:

<223> OTHER INFORMATION: SIRPalpha4 ECD Sequences

<400> SEQUENCE: 93

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Lys Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr
    370
```

<210> SEQ ID NO 94
<211> LENGTH: 600

```
<212> TYPE: PRT
<213> ORGANISM: Mus musculus
<220> FEATURE:
<223> OTHER INFORMATION: NOD/SCID Mouse SIRPalpha-Fc

<400> SEQUENCE: 94

Met Glu Pro Ala Gly Pro Ala Pro Gly Arg Leu Gly Pro Leu Leu Leu
1               5                   10                  15

Cys Leu Leu Ser Ala Ser Cys Phe Cys Thr Gly Ala Thr Arg Thr
            20                  25                  30

Glu Val Lys Val Ile Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Gln Ser Arg Gln Leu Ile Tyr
65                  70                  75                  80

Ser Phe Thr Thr Glu His Phe Pro Arg Val Thr Asn Val Ser Asp Ala
                85                  90                  95

Thr Lys Arg Ser Asn Leu Asp Phe Ser Ile Arg Ile Ser Asn Val Thr
            100                 105                 110

Pro Glu Asp Ala Gly Thr Tyr Tyr Cys Val Lys Phe Gln Arg Gly Ser
        115                 120                 125

Pro Asp Thr Glu Ile Gln Ser Gly Gly Thr Glu Val Tyr Val Leu
    130                 135                 140

Ala Lys Pro Ser Pro Pro Glu Val Ser Gly Pro Ala Asp Arg Gly Ile
145                 150                 155                 160

Pro Asp Gln Lys Val Asn Phe Thr Cys Lys Ser His Gly Phe Ser Pro
                165                 170                 175

Arg Asn Ile Thr Leu Lys Trp Phe Lys Asp Gly Gln Glu Leu His Pro
            180                 185                 190

Leu Glu Thr Thr Val Asn Pro Ser Gly Lys Asn Val Ser Tyr Asn Ile
        195                 200                 205

Ser Ser Thr Val Arg Val Val Leu Asn Ser Met Asp Val Asn Ser Lys
    210                 215                 220

Val Ile Cys Glu Val Ala His Ile Thr Leu Asp Arg Ser Pro Leu Arg
225                 230                 235                 240

Gly Ile Ala Asn Leu Ser Asn Phe Ile Arg Val Ser Pro Thr Val Lys
                245                 250                 255

Val Thr Gln Gln Ser Pro Thr Ser Met Asn Gln Val Asn Leu Thr Cys
            260                 265                 270

Arg Ala Glu Arg Phe Tyr Pro Glu Asp Leu Gln Leu Ile Trp Leu Glu
        275                 280                 285

Asn Gly Asn Val Ser Arg Asn Asp Thr Pro Lys Asn Leu Thr Lys Asn
    290                 295                 300

Thr Asp Gly Thr Tyr Asn Tyr Thr Ser Leu Phe Leu Val Asn Ser Ser
305                 310                 315                 320

Ala His Arg Glu Asp Val Val Phe Thr Cys Gln Val Lys His Asp Gln
                325                 330                 335

Gln Pro Ala Ile Thr Arg Asn His Thr Val Leu Gly Phe Ala His Ser
            340                 345                 350

Ser Asp Gln Gly Ser Met Gln Thr Phe Pro Asp Asn Asn Ala Thr His
        355                 360                 365

Asn Trp Asn Gly Ser Asp Lys Thr His Thr Cys Pro Pro Cys Pro Ala
    370                 375                 380
```

```
Pro Glu Leu Leu Gly Gly Pro Ser Val Phe Leu Phe Pro Pro Lys Pro
385                 390                 395                 400

Lys Asp Thr Leu Met Ile Ser Arg Thr Pro Glu Val Thr Cys Val Val
            405                 410                 415

Val Asp Val Ser His Glu Asp Pro Glu Val Lys Phe Asn Trp Tyr Val
            420                 425                 430

Asp Gly Val Glu Val His Asn Ala Lys Thr Lys Pro Arg Glu Glu Gln
            435                 440                 445

Tyr Ala Ser Thr Tyr Arg Val Val Ser Val Leu Thr Val Leu His Gln
    450                 455                 460

Asp Trp Leu Asn Gly Lys Glu Tyr Lys Cys Lys Val Ser Asn Lys Ala
465                 470                 475                 480

Leu Pro Ala Pro Ile Glu Lys Thr Ile Ser Lys Ala Lys Gly Gln Pro
                485                 490                 495

Arg Glu Pro Gln Val Tyr Thr Leu Pro Pro Ser Arg Asp Glu Leu Thr
                500                 505                 510

Lys Asn Gln Val Ser Leu Thr Cys Leu Val Lys Gly Phe Tyr Pro Ser
            515                 520                 525

Asp Ile Ala Val Glu Trp Glu Ser Asn Gly Gln Pro Glu Asn Asn Tyr
530                 535                 540

Lys Thr Thr Pro Pro Val Leu Asp Ser Asp Gly Ser Phe Phe Leu Tyr
545                 550                 555                 560

Ser Lys Leu Thr Val Asp Lys Ser Arg Trp Gln Gln Gly Asn Val Phe
                565                 570                 575

Ser Cys Ser Val Met His Glu Ala Leu His Asn His Tyr Thr Gln Lys
            580                 585                 590

Ser Leu Ser Leu Ser Pro Gly Lys
        595                 600

<210> SEQ ID NO 95
<211> LENGTH: 373
<212> TYPE: PRT
<213> ORGANISM: Artificial Sequence
<220> FEATURE:
<223> OTHER INFORMATION: SIRPalpha5 ECD Sequences

<400> SEQUENCE: 95

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Glu Pro
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140
```

-continued

```
Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
                260                 265                 270

Cys Gln Val Arg Lys Phe Tyr Pro Gln Arg Leu Gln Leu Thr Trp Leu
            275                 280                 285

Glu Asn Gly Asn Val Ser Arg Thr Glu Thr Ala Ser Thr Val Thr Glu
        290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
                340                 345                 350

Pro Lys Glu Gln Gly Ser Asn Thr Ala Ala Glu Asn Thr Gly Ser Asn
            355                 360                 365

Glu Arg Asn Ile Tyr
            370
```

<210> SEQ ID NO 96
<211> LENGTH: 602
<212> TYPE: PRT
<213> ORGANISM: Mus musculus
<220> FEATURE:
<223> OTHER INFORMATION: mouse SIRPalpha-Fc

<400> SEQUENCE: 96

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
                20                  25                  30

Glu Leu Lys Val Thr Gln Pro Glu Lys Ser Val Ser Val Ala Ala Gly
            35                  40                  45

Asp Ser Thr Val Leu Asn Cys Thr Leu Thr Ser Leu Leu Pro Val Gly
        50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125
```

-continued

```
Ser Glu Pro Asp Thr Glu Ile Gln Ser Gly Gly Thr Glu Val Tyr
    130                 135                 140

Val Leu Ala Lys Pro Ser Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Gly Ser Asp Lys Thr His Thr Cys Pro Pro Cys
370                 375                 380

Pro Ala Pro Glu Leu Leu Gly Gly Pro Ser Val Phe Leu Phe Pro Pro
385                 390                 395                 400

Lys Pro Lys Asp Thr Leu Met Ile Ser Arg Thr Pro Glu Val Thr Cys
                405                 410                 415

Val Val Val Asp Val Ser His Glu Asp Pro Glu Val Lys Phe Asn Trp
            420                 425                 430

Tyr Val Asp Gly Val Glu Val His Asn Ala Lys Thr Lys Pro Arg Glu
        435                 440                 445

Glu Gln Tyr Ala Ser Thr Tyr Arg Val Val Ser Val Leu Thr Val Leu
450                 455                 460

His Gln Asp Trp Leu Asn Gly Lys Glu Tyr Lys Cys Lys Val Ser Asn
465                 470                 475                 480

Lys Ala Leu Pro Ala Pro Ile Glu Lys Thr Ile Ser Lys Ala Lys Gly
                485                 490                 495

Gln Pro Arg Glu Pro Gln Val Tyr Thr Leu Pro Pro Ser Arg Asp Glu
            500                 505                 510

Leu Thr Lys Asn Gln Val Ser Leu Thr Cys Leu Val Lys Gly Phe Tyr
        515                 520                 525

Pro Ser Asp Ile Ala Val Glu Trp Glu Ser Asn Gly Gln Pro Glu Asn
530                 535                 540

Asn Tyr Lys Thr Thr Pro Pro Val Leu Asp Ser Asp Gly Ser Phe Phe
```

```
                545                 550                 555                 560
Leu Tyr Ser Lys Leu Thr Val Asp Lys Ser Arg Trp Gln Gln Gly Asn
                    565                 570                 575

Val Phe Ser Cys Ser Val Met His Glu Ala Leu His Asn His Tyr Thr
                580                 585                 590

Gln Lys Ser Leu Ser Leu Ser Pro Gly Lys
            595                 600

<210> SEQ ID NO 97
<211> LENGTH: 373
<212> TYPE: PRT
<213> ORGANISM: Artificial Sequence
<220> FEATURE:
<223> OTHER INFORMATION: SIRPalpha6 ECD Sequences

<400> SEQUENCE: 97

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Glu Leu
                85                  90                  95

Thr Lys Arg Glu Asn Met Asp Phe Ser Ile Arg Ile Gly Asn Ile Thr
                100                 105                 110

Pro Ala Asp Ala Gly Thr Tyr Tyr Cys Val Lys Phe Arg Lys Gly Ser
            115                 120                 125

Pro Asp Asp Val Glu Phe Lys Ser Gly Ala Gly Thr Glu Leu Ser Val
        130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
```

Ser Ala His Arg Asp Asp Val Lys Leu Thr Cys Gln Val Glu His Asp
305                 310                 315                 320

Gly Gln Pro Ala Val Ser Lys Ser His Asp Leu Lys Val Ser Ala His
            325                 330                 335

Pro Lys Glu Gln Gly Ser Asn Thr Ala Ala Glu Asn Thr Gly Ser Asn
            340                 345                 350

Glu Arg Asn Ile Tyr
    370

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr
    370

<210> SEQ ID NO 98
<211> LENGTH: 450
<212> TYPE: PRT
<213> ORGANISM: Artificial Sequence
<220> FEATURE:
<223> OTHER INFORMATION: Heavy Chain Sequence for SIRPAB-11-AAS

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Gly Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg

```
                    290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 99
<211> LENGTH: 161
<212> TYPE: PRT
<213> ORGANISM: Artificial Sequence
<220> FEATURE:
<223> OTHER INFORMATION: CD47-ECD with His Tag

<400> SEQUENCE: 99

Met Tyr Arg Met Gln Leu Leu Ser Cys Ile Ala Leu Ser Leu Ala Leu
1               5                   10                  15

Val Thr Asn Ser Gln Leu Leu Phe Asn Lys Thr Lys Ser Val Glu Phe
            20                  25                  30

Thr Phe Cys Asn Asp Thr Val Val Ile Pro Cys Phe Val Thr Asn Met
        35                  40                  45

Glu Ala Gln Asn Thr Thr Glu Val Tyr Val Lys Trp Lys Phe Lys Gly
    50                  55                  60

Arg Asp Ile Tyr Thr Phe Asp Gly Ala Leu Asn Lys Ser Thr Val Pro
65                  70                  75                  80

Thr Asp Phe Ser Ser Ala Lys Ile Glu Val Ser Gln Leu Leu Lys Gly
                85                  90                  95

Asp Ala Ser Leu Lys Met Asp Lys Ser Asp Ala Val Ser His Thr Gly
            100                 105                 110

Asn Tyr Thr Cys Glu Val Thr Glu Leu Thr Arg Glu Gly Glu Thr Ile
        115                 120                 125

Ile Glu Leu Lys Tyr Arg Val Val Arg Ser Gly Gly Gly Leu Asn Asp
    130                 135                 140

Ile Phe Glu Ala Gln Lys Ile Glu Trp His Glu His His His His
145                 150                 155                 160

His

<210> SEQ ID NO 100
<211> LENGTH: 371
<212> TYPE: PRT
<213> ORGANISM: Mus musculus
```

<220> FEATURE:
<223> OTHER INFORMATION: NOD/SCID Mouse SIRPalpha

<400> SEQUENCE: 100

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Arg Thr
            20                  25                  30

Glu Val Lys Val Ile Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Gln Ser Arg Gln Leu Ile Tyr
65                  70                  75                  80

Ser Phe Thr Thr Glu His Phe Pro Arg Val Thr Asn Val Ser Asp Ala
                85                  90                  95

Thr Lys Arg Ser Asn Leu Asp Phe Ser Ile Arg Ile Ser Asn Val Thr
            100                 105                 110

Pro Glu Asp Ala Gly Thr Tyr Tyr Cys Val Lys Phe Gln Arg Gly Ser
        115                 120                 125

Pro Asp Thr Glu Ile Gln Ser Gly Gly Gly Thr Glu Val Tyr Val Leu
    130                 135                 140

Ala Lys Pro Ser Pro Glu Val Ser Gly Pro Ala Asp Arg Gly Ile
145                 150                 155                 160

Pro Asp Gln Lys Val Asn Phe Thr Cys Lys Ser His Gly Phe Ser Pro
                165                 170                 175

Arg Asn Ile Thr Leu Lys Trp Phe Lys Asp Gly Gln Glu Leu His Pro
            180                 185                 190

Leu Glu Thr Thr Val Asn Pro Ser Gly Lys Asn Val Ser Tyr Asn Ile
        195                 200                 205

Ser Ser Thr Val Arg Val Val Leu Asn Ser Met Asp Val Asn Ser Lys
    210                 215                 220

Val Ile Cys Glu Val Ala His Ile Thr Leu Asp Arg Ser Pro Leu Arg
225                 230                 235                 240

Gly Ile Ala Asn Leu Ser Asn Phe Ile Arg Val Ser Pro Thr Val Lys
                245                 250                 255

Val Thr Gln Gln Ser Pro Thr Ser Met Asn Gln Val Asn Leu Thr Cys
            260                 265                 270

Arg Ala Glu Arg Phe Tyr Pro Glu Asp Leu Gln Leu Ile Trp Leu Glu
        275                 280                 285

Asn Gly Asn Val Ser Arg Asn Asp Thr Pro Lys Asn Leu Thr Lys Asn
    290                 295                 300

Thr Asp Gly Thr Tyr Asn Tyr Thr Ser Leu Phe Leu Val Asn Ser Ser
305                 310                 315                 320

Ala His Arg Glu Asp Val Val Phe Thr Cys Gln Val Lys His Asp Gln
                325                 330                 335

Gln Pro Ala Ile Thr Arg Asn His Thr Val Leu Gly Phe Ala His Ser
            340                 345                 350

Ser Asp Gln Gly Ser Met Gln Thr Phe Pro Asp Asn Asn Ala Thr His
        355                 360                 365

Asn Trp Asn
    370

<210> SEQ ID NO 101

<211> LENGTH: 373
<212> TYPE: PRT
<213> ORGANISM: Artificial Sequence
<220> FEATURE:
<223> OTHER INFORMATION: SIRPalpha1 ECD Sequences

<400> SEQUENCE: 101

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr
    370

<210> SEQ ID NO 102
<211> LENGTH: 373
<212> TYPE: PRT
<213> ORGANISM: Mus musculus
<220> FEATURE:
<223> OTHER INFORMATION: mouse SIRPalpha

<400> SEQUENCE: 102

```
Met Glu Pro Ala Gly Pro Ala Pro Gly Arg Leu Gly Pro Leu Leu Leu
1               5                   10                  15

Cys Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
            35                  40                  45

Asp Ser Thr Val Leu Asn Cys Thr Leu Thr Ser Leu Leu Pro Val Gly
        50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365
```

Thr His Asn Trp Asn
    370

<210> SEQ ID NO 103
<211> LENGTH: 372
<212> TYPE: PRT
<213> ORGANISM: Artificial Sequence
<220> FEATURE:
<223> OTHER INFORMATION: SIRPalpha2 ECD Sequences

<400> SEQUENCE: 103

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Val Thr Glu Asn
    290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
            355                 360                 365

Arg Asn Ile Tyr
    370

<210> SEQ ID NO 104
<211> LENGTH: 601
<212> TYPE: PRT
<213> ORGANISM: Cynomolgus
<220> FEATURE:
<223> OTHER INFORMATION: Cynomolgus SIRPalpha-Fc

<400> SEQUENCE: 104

Met Glu Pro Ala Gly Pro Ala Pro Gly Arg Leu Gly Pro Leu Leu Cys
1               5                   10                  15

Leu Leu Leu Thr Ala Ser Cys Ala Trp Ser Gly Val Leu Gly Glu Glu
            20                  25                  30

Glu Leu Gln Val Ile Gln Pro Glu Lys Ser Val Ser Val Ala Ala Gly
        35                  40                  45

Glu Ser Ala Thr Leu Asn Cys Thr Ala Thr Ser Leu Ile Pro Val Gly
    50                  55                  60

Pro Ile Gln Trp Phe Arg Gly Val Gly Pro Gly Arg Glu Leu Ile Tyr
65                  70                  75                  80

Ser Gln Lys Glu Gly His Phe Pro Arg Val Thr Pro Val Ser Asp Pro
                85                  90                  95

Thr Lys Arg Asn Asn Met Asp Phe Ser Ile Arg Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Val Glu Leu Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Ala Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Lys Ser Val Ser Tyr Ser Ile
        195                 200                 205

Arg Ser Thr Ala Arg Val Val Leu Thr Arg Arg Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Ala Ile Arg Val Pro Pro Phe Leu Glu
                245                 250                 255

Val Thr Gln Gln Ser Met Arg Ala Asp Asn Gln Val Asn Val Thr Cys
            260                 265                 270

Gln Val Thr Lys Phe Tyr Pro Gln Arg Leu Gln Leu Thr Trp Leu Glu
        275                 280                 285

Asn Gly Asn Val Ser Arg Thr Glu Met Ala Ser Ala Leu Pro Glu Asn
    290                 295                 300

Lys Asp Gly Thr Tyr Asn Trp Thr Ser Trp Leu Leu Val Asn Val Ser
305                 310                 315                 320

Ala His Arg Asp Asp Val Lys Leu Thr Cys Gln Val Glu His Asp Gly
                325                 330                 335

-continued

```
Gln Pro Ala Val Asn Lys Ser Phe Ser Val Lys Val Ser Ala His Pro
                340                 345                 350

Lys Glu Gln Gly Ser Asn Thr Ala Glu Asn Thr Gly Thr Asn Glu
            355                 360                 365

Arg Asn Ile Tyr Gly Ser Asp Lys Thr His Thr Cys Pro Pro Cys Pro
370                 375                 380

Ala Pro Glu Leu Leu Gly Gly Pro Ser Val Phe Leu Phe Pro Pro Lys
385                 390                 395                 400

Pro Lys Asp Thr Leu Met Ile Ser Arg Thr Pro Glu Val Thr Cys Val
                405                 410                 415

Val Val Asp Val Ser His Glu Asp Pro Glu Val Lys Phe Asn Trp Tyr
            420                 425                 430

Val Asp Gly Val Glu Val His Asn Ala Lys Thr Lys Pro Arg Glu Glu
        435                 440                 445

Gln Tyr Ala Ser Thr Tyr Arg Val Val Ser Val Leu Thr Val Leu His
    450                 455                 460

Gln Asp Trp Leu Asn Gly Lys Glu Tyr Lys Cys Lys Val Ser Asn Lys
465                 470                 475                 480

Ala Leu Pro Ala Pro Ile Glu Lys Thr Ile Ser Lys Ala Lys Gly Gln
                485                 490                 495

Pro Arg Glu Pro Gln Val Tyr Thr Leu Pro Pro Ser Arg Asp Glu Leu
            500                 505                 510

Thr Lys Asn Gln Val Ser Leu Thr Cys Leu Val Lys Gly Phe Tyr Pro
        515                 520                 525

Ser Asp Ile Ala Val Glu Trp Glu Ser Asn Gly Gln Pro Glu Asn Asn
    530                 535                 540

Tyr Lys Thr Thr Pro Pro Val Leu Asp Ser Asp Gly Ser Phe Phe Leu
545                 550                 555                 560

Tyr Ser Lys Leu Thr Val Asp Lys Ser Arg Trp Gln Gln Gly Asn Val
                565                 570                 575

Phe Ser Cys Ser Val Met His Glu Ala Leu His Asn His Tyr Thr Gln
            580                 585                 590

Lys Ser Leu Ser Leu Ser Pro Gly Lys
        595                 600

<210> SEQ ID NO 105
<211> LENGTH: 373
<212> TYPE: PRT
<213> ORGANISM: Artificial Sequence
<220> FEATURE:
<223> OTHER INFORMATION: SIRPalpha3 ECD Sequences

<400> SEQUENCE: 105

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95
```

Thr Lys Arg Glu Asn Met Asp Phe Ser Ile Arg Ile Gly Asn Ile Thr
                100                 105                 110

Pro Ala Asp Ala Gly Thr Tyr Tyr Cys Val Lys Phe Arg Lys Gly Ser
            115                 120                 125

Pro Asp Asp Val Glu Phe Lys Ser Gly Ala Gly Thr Glu Leu Ser Val
        130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr
    370

<210> SEQ ID NO 106
<211> LENGTH: 450
<212> TYPE: PRT
<213> ORGANISM: Artificial Sequence
<220> FEATURE:
<223> OTHER INFORMATION: Heavy Chain Sequence for SIRPAB-12-AAS

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Gly Ile Val Trp Val Arg Gln Ala Pro Gly Gln Gly Leu Glu Trp Met
        35                  40                  45

Gly Trp Ile Ser Ala Tyr Ala Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 107
<211> LENGTH: 25
<212> TYPE: PRT
<213> ORGANISM: Artificial Sequence
<220> FEATURE:

<223> OTHER INFORMATION: Avi-HIS Tagg

<400> SEQUENCE: 107

```
Arg Ser Gly Gly Gly Leu Asn Asp Ile Phe Glu Ala Gln Lys Ile Glu
1               5                   10                  15

Trp His Glu His His His His His His
            20                  25
```

<210> SEQ ID NO 108
<211> LENGTH: 371
<212> TYPE: PRT
<213> ORGANISM: Homo sapiens
<220> FEATURE:
<223> OTHER INFORMATION: human SIRPbeta

<400> SEQUENCE: 108

```
Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
        35                  40                  45

Ser Ala Thr Leu Cys Cys Ala Met Thr Ser Leu Ile Pro Val Gly Pro
    50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Thr Val Ser Glu Leu Thr
                85                  90                  95

Lys Arg Asn Asn Leu Asp Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
        195                 200                 205

His Ser Thr Ala Arg Val Val Leu Thr Arg Gly Asp Val His Ser Gln
    210                 215                 220

Val Ile Cys Glu Met Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
                245                 250                 255

Val Thr Gln Gln Pro Met Arg Ala Glu Asn Gln Ala Asn Val Thr Cys
            260                 265                 270

Gln Val Ser Asn Phe Tyr Pro Arg Gly Leu Gln Leu Thr Trp Leu Glu
        275                 280                 285

Asn Gly Asn Val Ser Arg Thr Glu Thr Ala Ser Thr Leu Ile Glu Asn
    290                 295                 300

Lys Asp Gly Thr Tyr Asn Trp Met Ser Trp Leu Leu Val Asn Thr Cys
305                 310                 315                 320
```

Ala His Arg Asp Asp Val Val Leu Thr Cys Gln Val Glu His Asp Gly
            325                 330                 335

Gln Gln Ala Val Ser Lys Ser Tyr Ala Leu Glu Ile Ser Ala His Gln
            340                 345                 350

Lys Glu His Gly Ser Asp Ile Thr His Glu Pro Ala Leu Ala Pro Thr
            355                 360                 365

Ala Pro Leu
    370

<210> SEQ ID NO 109
<211> LENGTH: 227
<212> TYPE: PRT
<213> ORGANISM: Homo sapiens
<220> FEATURE:
<223> OTHER INFORMATION: human IGHG1_Fc

<400> SEQUENCE: 109

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 110
<211> LENGTH: 449
<212> TYPE: PRT
<213> ORGANISM: Artificial Sequence
<220> FEATURE:
<223> OTHER INFORMATION: Heavy Chain Sequence for SIRPAB-20

<400> SEQUENCE: 110

Gln Val Gln Leu Gln Glu Ser Gly Pro Gly Leu Val Lys Pro Ser Gln

```
1               5                   10                  15
Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
                35                  40                  45

Trp Ile Gly Ala Ile Tyr Tyr Ser Gly Pro Ile Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ser Lys Glu Gly Tyr His Ser Gly Met Asp Val Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430
```

```
Ala Leu His Asn His Tyr Thr Gln Lys Ser Leu Ser Leu Ser Pro Gly
        435                 440                 445

Lys

<210> SEQ ID NO 111
<211> LENGTH: 447
<212> TYPE: PRT
<213> ORGANISM: Artificial Sequence
<220> FEATURE:
<223> OTHER INFORMATION: Heavy Chain Sequence for SIRPAB-12-4P

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Gly Ile Val Trp Val Arg Gln Ala Pro Gly Gln Gly Leu Glu Trp Met
        35                  40                  45

Gly Trp Ile Ser Ala Tyr Ala Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 112
<211> LENGTH: 447
<212> TYPE: PRT
<213> ORGANISM: Artificial Sequence
<220> FEATURE:
<223> OTHER INFORMATION: Heavy Chain Sequence for SIRPAB-11-4P

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Gly Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 113
<211> LENGTH: 589
<212> TYPE: PRT
<213> ORGANISM: Homo sapiens
<220> FEATURE:
<223> OTHER INFORMATION: human SIRPgamma-Fc

<400> SEQUENCE: 113

Met Pro Val Pro Ala Ser Trp Pro His Pro Gly Pro Phe Leu Leu
1               5                   10                  15

Leu Thr Leu Leu Leu Gly Leu Thr Glu Val Ala Gly Glu Glu Leu
            20                  25                  30

Gln Met Ile Gln Pro Glu Lys Leu Leu Leu Val Thr Val Gly Lys Thr
        35                  40                  45

Ala Thr Leu His Cys Thr Val Thr Ser Leu Leu Pro Val Gly Pro Val
    50                  55                  60

Leu Trp Phe Arg Gly Val Gly Pro Gly Arg Glu Leu Ile Tyr Asn Gln
65                  70                  75                  80

Lys Glu Gly His Phe Pro Arg Val Thr Thr Val Ser Asp Leu Thr Lys
                85                  90                  95

Arg Asn Asn Met Asp Phe Ser Ile Arg Ile Ser Ser Ile Thr Pro Ala
            100                 105                 110

Asp Val Gly Thr Tyr Tyr Cys Val Lys Phe Arg Lys Gly Ser Pro Glu
        115                 120                 125

Asn Val Glu Phe Lys Ser Gly Pro Gly Thr Glu Met Ala Leu Gly Ala
    130                 135                 140

Lys Pro Ser Ala Pro Val Val Leu Gly Pro Ala Ala Arg Thr Thr Pro
145                 150                 155                 160

Glu His Thr Val Ser Phe Thr Cys Glu Ser His Gly Phe Ser Pro Arg
                165                 170                 175
```

```
Asp Ile Thr Leu Lys Trp Phe Lys Asn Gly Asn Glu Leu Ser Asp Phe
            180                 185                 190

Gln Thr Asn Val Asp Pro Thr Gly Gln Ser Val Ala Tyr Ser Ile Arg
        195                 200                 205

Ser Thr Ala Arg Val Val Leu Asp Pro Trp Asp Val Arg Ser Gln Val
    210                 215                 220

Ile Cys Glu Val Ala His Val Thr Leu Gln Gly Asp Pro Leu Arg Gly
225                 230                 235                 240

Thr Ala Asn Leu Ser Glu Ala Ile Arg Val Pro Pro Thr Leu Glu Val
                245                 250                 255

Thr Gln Gln Pro Met Arg Val Gly Asn Gln Val Asn Val Thr Cys Gln
            260                 265                 270

Val Arg Lys Phe Tyr Pro Gln Ser Leu Gln Leu Thr Trp Ser Glu Asn
        275                 280                 285

Gly Asn Val Cys Gln Arg Glu Thr Ala Ser Thr Leu Thr Glu Asn Lys
    290                 295                 300

Asp Gly Thr Tyr Asn Trp Thr Ser Trp Phe Leu Val Asn Ile Ser Asp
305                 310                 315                 320

Gln Arg Asp Asp Val Val Leu Thr Cys Gln Val Lys His Asp Gly Gln
                325                 330                 335

Leu Ala Val Ser Lys Arg Leu Ala Leu Glu Val Thr Val His Gln Lys
            340                 345                 350

Asp Gln Ser Ser Asp Ala Thr Pro Gly Ser Asp Lys Thr His Thr Cys
        355                 360                 365

Pro Pro Cys Pro Ala Pro Glu Leu Leu Gly Gly Pro Ser Val Phe Leu
    370                 375                 380

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
                405                 410                 415

Phe Asn Trp Tyr Val Asp Gly Val Glu Val His Asn Ala Lys Thr Lys
            420                 425                 430

Pro Arg Glu Glu Gln Tyr Ala Ser Thr Tyr Arg Val Val Ser Val Leu
        435                 440                 445

Thr Val Leu His Gln Asp Trp Leu Asn Gly Lys Glu Tyr Lys Cys Lys
    450                 455                 460

Val Ser Asn Lys Ala Leu Pro Ala Pro Ile Glu Lys Thr Ile Ser Lys
465                 470                 475                 480

Ala Lys Gly Gln Pro Arg Glu Pro Gln Val Tyr Thr Leu Pro Pro Ser
                485                 490                 495

Arg Asp Glu Leu Thr Lys Asn Gln Val Ser Leu Thr Cys Leu Val Lys
            500                 505                 510

Gly Phe Tyr Pro Ser Asp Ile Ala Val Glu Trp Glu Ser Asn Gly Gln
        515                 520                 525

Pro Glu Asn Asn Tyr Lys Thr Thr Pro Pro Val Leu Asp Ser Asp Gly
    530                 535                 540

Ser Phe Phe Leu Tyr Ser Lys Leu Thr Val Asp Lys Ser Arg Trp Gln
545                 550                 555                 560

Gln Gly Asn Val Phe Ser Cys Ser Val Met His Glu Ala Leu His Asn
                565                 570                 575

His Tyr Thr Gln Lys Ser Leu Ser Leu Ser Pro Gly Lys
            580                 585
```

```
<210> SEQ ID NO 114
<211> LENGTH: 360
<212> TYPE: PRT
<213> ORGANISM: Homo sapiens
<220> FEATURE:
<223> OTHER INFORMATION: human SIRPgamma

<400> SEQUENCE: 114
```

| | | | | | | | | | | | | | | | |
|---|---|---|---|---|---|---|---|---|---|---|---|---|---|---|---|
| Met | Pro | Val | Pro | Ala | Ser | Trp | Pro | His | Pro | Gly | Pro | Phe | Leu | Leu | |
| 1 | | | | 5 | | | | | 10 | | | | | 15 | |
| Leu | Thr | Leu | Leu | Leu | Gly | Leu | Thr | Glu | Val | Ala | Gly | Glu | Glu | Glu | Leu |
| | | | 20 | | | | | 25 | | | | | 30 | | |
| Gln | Met | Ile | Gln | Pro | Glu | Lys | Leu | Leu | Leu | Val | Thr | Val | Gly | Lys | Thr |
| | | | 35 | | | | | 40 | | | | | 45 | | |
| Ala | Thr | Leu | His | Cys | Thr | Val | Thr | Ser | Leu | Leu | Pro | Val | Gly | Pro | Val |
| | 50 | | | | | 55 | | | | | 60 | | | | |
| Leu | Trp | Phe | Arg | Gly | Val | Gly | Pro | Gly | Arg | Glu | Leu | Ile | Tyr | Asn | Gln |
| 65 | | | | | 70 | | | | | 75 | | | | | 80 |
| Lys | Glu | Gly | His | Phe | Pro | Arg | Val | Thr | Thr | Val | Ser | Asp | Leu | Thr | Lys |
| | | | | 85 | | | | | 90 | | | | | 95 | |
| Arg | Asn | Asn | Met | Asp | Phe | Ser | Ile | Arg | Ile | Ser | Ser | Ile | Thr | Pro | Ala |
| | | | 100 | | | | | 105 | | | | | 110 | | |
| Asp | Val | Gly | Thr | Tyr | Tyr | Cys | Val | Lys | Phe | Arg | Lys | Gly | Ser | Pro | Glu |
| | | | 115 | | | | | 120 | | | | | 125 | | |
| Asn | Val | Glu | Phe | Lys | Ser | Gly | Pro | Gly | Thr | Glu | Met | Ala | Leu | Gly | Ala |
| | 130 | | | | | 135 | | | | | 140 | | | | |
| Lys | Pro | Ser | Ala | Pro | Val | Val | Leu | Gly | Pro | Ala | Ala | Arg | Thr | Thr | Pro |
| 145 | | | | | 150 | | | | | 155 | | | | | 160 |
| Glu | His | Thr | Val | Ser | Phe | Thr | Cys | Glu | Ser | His | Gly | Phe | Ser | Pro | Arg |
| | | | | 165 | | | | | 170 | | | | | 175 | |
| Asp | Ile | Thr | Leu | Lys | Trp | Phe | Lys | Asn | Gly | Asn | Glu | Leu | Ser | Asp | Phe |
| | | | 180 | | | | | 185 | | | | | 190 | | |
| Gln | Thr | Asn | Val | Asp | Pro | Thr | Gly | Gln | Ser | Val | Ala | Tyr | Ser | Ile | Arg |
| | | | 195 | | | | | 200 | | | | | 205 | | |
| Ser | Thr | Ala | Arg | Val | Val | Leu | Asp | Pro | Trp | Asp | Val | Arg | Ser | Gln | Val |
| | 210 | | | | | 215 | | | | | 220 | | | | |
| Ile | Cys | Glu | Val | Ala | His | Val | Thr | Leu | Gln | Gly | Asp | Pro | Leu | Arg | Gly |
| 225 | | | | | 230 | | | | | 235 | | | | | 240 |
| Thr | Ala | Asn | Leu | Ser | Glu | Ala | Ile | Arg | Val | Pro | Pro | Thr | Leu | Glu | Val |
| | | | | 245 | | | | | 250 | | | | | 255 | |
| Thr | Gln | Gln | Pro | Met | Arg | Val | Gly | Asn | Gln | Val | Asn | Val | Thr | Cys | Gln |
| | | | 260 | | | | | 265 | | | | | 270 | | |
| Val | Arg | Lys | Phe | Tyr | Pro | Gln | Ser | Leu | Gln | Leu | Thr | Trp | Ser | Glu | Asn |
| | | | 275 | | | | | 280 | | | | | 285 | | |
| Gly | Asn | Val | Cys | Gln | Arg | Glu | Thr | Ala | Ser | Thr | Leu | Thr | Glu | Asn | Lys |
| | 290 | | | | | 295 | | | | | 300 | | | | |
| Asp | Gly | Thr | Tyr | Asn | Trp | Thr | Ser | Trp | Phe | Leu | Val | Asn | Ile | Ser | Asp |
| 305 | | | | | 310 | | | | | 315 | | | | | 320 |
| Gln | Arg | Asp | Asp | Val | Val | Leu | Thr | Cys | Gln | Val | Lys | His | Asp | Gly | Gln |
| | | | | 325 | | | | | 330 | | | | | 335 | |
| Leu | Ala | Val | Ser | Lys | Arg | Leu | Ala | Leu | Glu | Val | Thr | Val | His | Gln | Lys |
| | | | 340 | | | | | 345 | | | | | 350 | | |
| Asp | Gln | Ser | Ser | Asp | Ala | Thr | Pro | | | | | | | | |
| | | | 355 | | | | | 360 | | | | | | | |

```
<210> SEQ ID NO 115
<211> LENGTH: 372
<212> TYPE: PRT
<213> ORGANISM: Cynomolgus
<220> FEATURE:
<223> OTHER INFORMATION: Cynomolgus SIRPa

<400> SEQUENCE: 115

Met Glu Pro Ala Gly Pro Ala Pro Gly Arg Leu Gly Pro Leu Leu Cys
1               5                   10                  15

Leu Leu Leu Thr Ala Ser Cys Ala Trp Ser Gly Val Leu Gly Glu Glu
                20                  25                  30

Glu Leu Gln Val Ile Gln Pro Glu Lys Ser Val Ser Val Ala Ala Gly
            35                  40                  45

Glu Ser Ala Thr Leu Asn Cys Thr Ala Thr Ser Leu Ile Pro Val Gly
    50                  55                  60

Pro Ile Gln Trp Phe Arg Gly Val Gly Pro Gly Arg Glu Leu Ile Tyr
65                  70                  75                  80

Ser Gln Lys Glu Gly His Phe Pro Arg Val Thr Pro Val Ser Asp Pro
                85                  90                  95

Thr Lys Arg Asn Asn Met Asp Phe Ser Ile Arg Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Val Glu Leu Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Ala Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Lys Ser Val Ser Tyr Ser Ile
        195                 200                 205

Arg Ser Thr Ala Arg Val Val Leu Thr Arg Arg Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Ala Ile Arg Val Pro Pro Phe Leu Glu
                245                 250                 255

Val Thr Gln Gln Ser Met Arg Ala Asp Asn Gln Val Asn Val Thr Cys
            260                 265                 270

Gln Val Thr Lys Phe Tyr Pro Gln Arg Leu Gln Leu Thr Trp Leu Glu
        275                 280                 285

Asn Gly Asn Val Ser Arg Thr Glu Met Ala Ser Ala Leu Pro Glu Asn
    290                 295                 300

Lys Asp Gly Thr Tyr Asn Trp Thr Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Asn Lys Ser Phe Ser Val Lys Val Ser Ala His Pro
            340                 345                 350

Lys Glu Gln Gly Ser Asn Thr Ala Ala Glu Asn Thr Gly Thr Asn Glu
        355                 360                 365

Arg Asn Ile Tyr
```

<210> SEQ ID NO 116
<211> LENGTH: 136
<212> TYPE: PRT
<213> ORGANISM: Artificial Sequence
<220> FEATURE:
<223> OTHER INFORMATION: CD47-ECD

<400> SEQUENCE: 116

Met Tyr Arg Met Gln Leu Leu Ser Cys Ile Ala Leu Ser Leu Ala Leu
1               5                   10                  15

Val Thr Asn Ser Gln Leu Leu Phe Asn Lys Thr Lys Ser Val Glu Phe
            20                  25                  30

Thr Phe Cys Asn Asp Thr Val Val Ile Pro Cys Phe Val Thr Asn Met
        35                  40                  45

Glu Ala Gln Asn Thr Thr Glu Val Tyr Val Lys Trp Lys Phe Lys Gly
    50                  55                  60

Arg Asp Ile Tyr Thr Phe Asp Gly Ala Leu Asn Lys Ser Thr Val Pro
65                  70                  75                  80

Thr Asp Phe Ser Ser Ala Lys Ile Glu Val Ser Gln Leu Leu Lys Gly
                85                  90                  95

Asp Ala Ser Leu Lys Met Asp Lys Ser Asp Ala Val Ser His Thr Gly
            100                 105                 110

Asn Tyr Thr Cys Glu Val Thr Glu Leu Thr Arg Glu Gly Glu Thr Ile
        115                 120                 125

Ile Glu Leu Lys Tyr Arg Val Val
    130                 135

<210> SEQ ID NO 117
<211> LENGTH: 449
<212> TYPE: PRT
<213> ORGANISM: Artificial Sequence
<220> FEATURE:
<223> OTHER INFORMATION: Heavy Chain Sequence for SIRPAB-19

<400> SEQUENCE: 117

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Ala Ile Tyr Tyr Ser Gly Pro Ile Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ser Lys Glu Gly Tyr His Ser Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 118
<211> LENGTH: 447
<212> TYPE: PRT
<213> ORGANISM: Artificial Sequence
<220> FEATURE:
<223> OTHER INFORMATION: Heavy Chain Sequence for SIRPAB-12-4PE

<400> SEQUENCE: 118

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Gly Ile Val Trp Val Arg Gln Ala Pro Gly Gln Gly Leu Glu Trp Met
            35                  40                  45
Gly Trp Ile Ser Ala Tyr Ala Gly Glu Thr Asn Tyr Ala Gln Lys Leu
            50                  55                  60
Gln Gly Arg Val Thr Met Thr Thr Asp Thr Ser Thr Ser Thr Ala Tyr
```

```
                65                  70                  75                  80
Met Glu Leu Arg Ser Leu Arg Ser Asp Asp Thr Ala Val Tyr Tyr Cys
                    85                  90                  95

Ala Arg Glu Ala Gly Ser Ser Trp Tyr Asp Phe Asp Leu Trp Gly Arg
                100                 105                 110

Gly Thr Leu Val Thr Val Ser Ala Ser Thr Lys Gly Pro Ser Val
                115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 119
<211> LENGTH: 450
<212> TYPE: PRT
<213> ORGANISM: Artificial Sequence
<220> FEATURE:
<223> OTHER INFORMATION: Heavy Chain Sequence for SIRPAB-11-K322A
```

<400> SEQUENCE: 119

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Arg Gly Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Gly Gly Glu Thr Asn Tyr Ala Gln Lys Leu
50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Glu Ala Gly Ser Ser Trp Tyr Asp Phe Asp Leu Trp Gly Arg
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Ala Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
```

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 120
<211> LENGTH: 447
<212> TYPE: PRT
<213> ORGANISM: Artificial Sequence
<220> FEATURE:
<223> OTHER INFORMATION: Heavy Chain Sequence for SIRPAB-11-4PE

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Gly Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

```
Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 121
<211> LENGTH: 16
<212> TYPE: PRT
<213> ORGANISM: Artificial Sequence
<220> FEATURE:
<223> OTHER INFORMATION: VH CDR2 of Antibodies SIRPAB-17 to SIRPAB-21

<400> SEQUENCE: 121

Ala Ile Tyr Tyr Ser Gly Pro Ile Tyr Tyr Asn Pro Ser Leu Lys Ser
1               5                   10                  15

<210> SEQ ID NO 122
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-17

<400> SEQUENCE: 122
caggtgcagc tgcaggagtc gggcccagga ctggtgaagc cttcacagac cctgtccctc       60
acctgtactg tctctggtgg ctccatcagc agtggtggtt actactggag ctggatccgc      120
cagcacccag ggaagggcct ggagtggatt ggggctatct attacagtgg gccgatctac      180
tacaacccgt ccctcaagag tcgagttacc atatcagtag acacgtctaa gaaccagttc      240
tccctgaagc tgagttctgt gaccgccgca gacacggcgg tgtactactg cgccagagag      300
ggataccact caggaatgga cgtatggggc cagggaacaa ctgtcaccgt ctcctca         357

<210> SEQ ID NO 123
<211> LENGTH: 119
<212> TYPE: PRT
<213> ORGANISM: Artificial Sequence
<220> FEATURE:
<223> OTHER INFORMATION: VH Domain of Antibody SIRPAB-17

<400> SEQUENCE: 123

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45
```

```
Trp Ile Gly Ala Ile Tyr Tyr Ser Gly Pro Ile Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Gly Tyr His Ser Gly Met Asp Val Trp Gly Gln Gly
            100                 105                 110

Thr Thr Val Thr Val Ser Ser
        115

<210> SEQ ID NO 124
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-17

<400> SEQUENCE: 124
gacatccaga tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggcaacagg ggtcccatca    180
aggttcagtg gaagtggatc tgggacagat tttactttca ccatcagcag cctgcagcct    240
gaagatattg caacatatta ctgtcagcag ttcgcctacc tcccttggac ttttggcgga    300
gggaccaagg ttgagatcaa a                                              321

<210> SEQ ID NO 125
<211> LENGTH: 11
<212> TYPE: PRT
<213> ORGANISM: Artificial Sequence
<220> FEATURE:
<223> OTHER INFORMATION: VH CDR3 of Antibodies SIRPAB-18 to SIRPAB-21

<400> SEQUENCE: 125

Ser Lys Glu Gly Tyr His Ser Gly Met Asp Val
1               5                   10

<210> SEQ ID NO 126
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-18

<400> SEQUENCE: 126
caggtgcagc tgcaggagtc gggcccagga ctggtgaagc cttcacagac cctgtccctc      60
acctgtactg tctctggtgg ctccatcagc agtggtggtt actactggag ctggatccgc    120
cagcacccag ggaagggcct ggagtggatt gggctatct attacagtgg gccgatctac    180
tacaacccgt ccctcaagag tcgagttacc atatcagtag acacgtctaa gaaccagttc    240
tccctgaagc tgagttctgt gaccgccgca gacacggcgg tgtactactg cagtaaggag    300
ggataccact caggaatgga cgtatggggg caagggacca cggtcaccgt ctcctca      357

<210> SEQ ID NO 127
<211> LENGTH: 119
<212> TYPE: PRT
<213> ORGANISM: Artificial Sequence
<220> FEATURE:
<223> OTHER INFORMATION: VH Domain of Antibodies SIRPAB-18 to SIRPAB-21
```

<400> SEQUENCE: 127

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Ala Ile Tyr Tyr Ser Gly Pro Ile Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ser Lys Glu Gly Tyr His Ser Gly Met Asp Val Trp Gly Gln Gly
            100                 105                 110

Thr Thr Val Thr Val Ser Ser
            115

<210> SEQ ID NO 128
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-18

<400> SEQUENCE: 128
gacatccaga tgacccagtc tccatcctcc ctgtctgcat ctgtaggaga cagagtcacc        60
atcacttgcc aggcgagtca ggacattagc aactatttaa attggtatca gcagaaacca       120
gggaaagccc ctaagctcct gatctacgat gcatccaatt tggcaacagg ggtcccatca       180
aggttcagtg gaagtggatc tgggacagat tttactttca ccatcagcag cctgcagcct       240
gaagatattg caacatatta ctgtcagcag ttcgcctacc tcccttggac ttttggcgga       300
gggaccaagg ttgagatcaa a                                                 321

<210> SEQ ID NO 129
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-19

<400> SEQUENCE: 129
caggtgcagc tgcaggagtc gggcccagga ctggtgaagc cttcacagac cctgtccctc        60
acctgtactg tctctggtgg ctccatcagc agtggtggtt actactggag ctggatccgc       120
cagcacccag ggaagggcct ggagtggatt ggggctatct attacagtgg gccgatctac       180
tacaacccgt ccctcaagag tcgagttacc atatcagtag acacgtctaa gaaccagttc       240
tccctgaagc tgagttctgt gaccgccgca gacacggcgg tgtactactg cagtaaggag       300
ggataccact caggaatgga cgtatggggg caagggacca cggtcaccgt ctcctca         357

<210> SEQ ID NO 130
<211> LENGTH: 11
<212> TYPE: PRT
<213> ORGANISM: Artificial Sequence
<220> FEATURE:
<223> OTHER INFORMATION: VL CDR1 of Antibodies SIRPAB-19 and SIRPAB-21

<400> SEQUENCE: 130

Gln Ala Ser Asp Asp Ile Ser Asp Tyr Leu Asn
1               5                   10

<210> SEQ ID NO 131
<211> LENGTH: 7
<212> TYPE: PRT
<213> ORGANISM: Artificial Sequence
<220> FEATURE:
<223> OTHER INFORMATION: VL CDR2 of Antibody SIRPAB-19

<400> SEQUENCE: 131

Asp Ala Ser Asn Ile Glu Asp
1               5

<210> SEQ ID NO 132
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-19

<400> SEQUENCE: 132
gacatccaga tgacccagtc tccatcctcc ctgtctgcat ctgtaggaga cagagtcacc    60
atcacttgcc aggcgagtga cgacattagc gactatttaa attggtatca gcagaaacca   120
gggaaagccc ctaagctcct gatctacgat gcatccaata tcgaagacgg ggtcccatca   180
aggttcagtg gaagtggatc tgggacagat tttactttca ccatcagcag cctgcagcct   240
gaagatattg caacatatta ctgtcagcag ttcgcctacc tcccttggac ttttggcgga   300
gggaccaagg ttgagatcaa a                                              321

<210> SEQ ID NO 133
<211> LENGTH: 107
<212> TYPE: PRT
<213> ORGANISM: Artificial Sequence
<220> FEATURE:
<223> OTHER INFORMATION: VL Domain of Antibody SIRPAB-19

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Gln Ala Ser Asp Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Ile Glu Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Ala Tyr Leu Pro Trp
                85                  90                  95

Thr Phe Gly Gly Gly Thr Lys Val Glu Ile Lys
            100                 105

<210> SEQ ID NO 134
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-20

<400> SEQUENCE: 134

```
caggtgcagc tgcaggagtc gggcccagga ctggtgaagc cttcacagac cctgtccctc    60
acctgtactg tctctggtgg ctccatcagc agtggtggtt actactggag ctggatccgc   120
cagcacccag gaagggcct ggagtggatt ggggctatct attacagtgg gccgatctac    180
tacaacccgt ccctcaagag tcgagttacc atatcagtag acacgtctaa gaaccagttc   240
tccctgaagc tgagttctgt gaccgccgca gacacggcgg tgtactactg cagtaaggag   300
ggataccact caggaatgga cgtatggggg caagggacca cggtcaccgt ctcctca      357
```

<210> SEQ ID NO 135
<211> LENGTH: 11
<212> TYPE: PRT
<213> ORGANISM: Artificial Sequence
<220> FEATURE:
<223> OTHER INFORMATION: VL CDR1 of Antibody SIRPAB-20

<400> SEQUENCE: 135

Gln Ala Ser Gln Asp Ile Ser Asp Tyr Leu Asn
1               5                   10

<210> SEQ ID NO 136
<211> LENGTH: 7
<212> TYPE: PRT
<213> ORGANISM: Artificial Sequence
<220> FEATURE:
<223> OTHER INFORMATION: VL CDR2 of Antibody SIRPAB-20

<400> SEQUENCE: 136

Asp Ala Asp Asn Leu Glu Thr
1               5

<210> SEQ ID NO 137
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-20

<400> SEQUENCE: 137

```
gacatccaga tgacccagtc tccatcctcc ctgtctgcat ctgtaggaga cagagtcacc    60
atcacttgcc aggcgagtca ggacatttcc gactatttaa attggtatca gcagaaacca   120
gggaaagccc ctaagctcct gatctacgac gcagacaatt tggaaacagg ggtcccatca   180
aggttcagtg aagtggatc tgggacagat tttactttca ccatcagcag cctgcagcct   240
gaagatattg caacatatta ctgtcagcag ttcgcctacc tcccttggac ttttggcgga   300
gggaccaagg ttgagatcaa a                                              321
```

<210> SEQ ID NO 138
<211> LENGTH: 107
<212> TYPE: PRT
<213> ORGANISM: Artificial Sequence
<220> FEATURE:
<223> OTHER INFORMATION: VL Domain of Antibody SIRPAB-20

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asp Tyr
            20                  25                  30

Leu Asn Trp Tyr Gln Gln Lys Pro Gly Lys Ala Pro Lys Leu Leu Ile

```
                    35                  40                  45

Tyr Asp Ala Asp Asn Leu Glu Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Ala Tyr Leu Pro Trp
                 85                  90                  95

Thr Phe Gly Gly Gly Thr Lys Val Glu Ile Lys
            100                 105
```

<210> SEQ ID NO 139
<211> LENGTH: 357
<212> TYPE: DNA
<213> ORGANISM: Artificial Sequence
<220> FEATURE:
<223> OTHER INFORMATION: VH Nucleotide Sequences of Antibody SIRPAB-21

<400> SEQUENCE: 139

```
caggtgcagc tgcaggagtc gggcccagga ctggtgaagc cttcacagac cctgtccctc      60
acctgtactg tctctggtgg ctccatcagc agtggtggtt actactggag ctggatccgc     120
cagcacccag gaagggcct ggagtggatt ggggctatct attacagtgg gccgatctac      180
tacaacccgt ccctcaagag tcgagttacc atatcagtag acacgtctaa gaaccagttc     240
tccctgaagc tgagttctgt gaccgccgca gacacggcgg tgtactactg cagtaaggag     300
ggataccact caggaatgga cgtatggggg caagggacca cggtcaccgt ctcctca       357
```

<210> SEQ ID NO 140
<211> LENGTH: 321
<212> TYPE: DNA
<213> ORGANISM: Artificial Sequence
<220> FEATURE:
<223> OTHER INFORMATION: VL Nucleotide Sequences of Antibody SIRPAB-21

<400> SEQUENCE: 140

```
gacatccaga tgacccagtc tccatcctcc ctgtctgcat ctgtaggaga cagagtcacc      60
atcacttgcc aggcgagtga cgacattagc gactatttaa attggtatca gcagaaacca     120
gggaaagccc ctaagctcct gatctacgac gcatccaatt tggaaacagg ggtcccatca     180
aggttcagtg gaagtggatc tgggacagat tttactttca ccatcagcag cctgcagcct     240
gaagatattg caacatatta ctgtcagcag ttcgcctacc tcccttggac ttttggcgga     300
gggaccaagg ttgagatcaa a                                              321
```

<210> SEQ ID NO 141
<211> LENGTH: 107
<212> TYPE: PRT
<213> ORGANISM: Artificial Sequence
<220> FEATURE:
<223> OTHER INFORMATION: VL Domain of Antibody SIRPAB-21

<400> SEQUENCE: 141

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Asp Asp Ile Ser Asp Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Ala Tyr Leu Pro Trp
                 85                  90                  95

Thr Phe Gly Gly Gly Thr Lys Val Glu Ile Lys
            100                 105

<210> SEQ ID NO 142
<211> LENGTH: 450
<212> TYPE: PRT
<213> ORGANISM: Artificial Sequence
<220> FEATURE:
<223> OTHER INFORMATION: Heavy Chain Sequence for SIRPAB-11

<400> SEQUENCE: 142

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Arg Gly Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Gly Gly Glu Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Ala Gly Ser Ser Trp Tyr Asp Phe Asp Leu Trp Gly Arg
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 143
<211> LENGTH: 214
<212> TYPE: PRT
<213> ORGANISM: Artificial Sequence
<220> FEATURE:
<223> OTHER INFORMATION: Light Chain Sequence of anti-SIRPAB-8 to
      SIRPAB-13, also SIRPAB-11 and SIRPAB-12 variants K332A, AAS, 4PE
      and 4P

<400> SEQUENCE: 143

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Ser Phe Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
210

<210> SEQ ID NO 144
<211> LENGTH: 330
<212> TYPE: PRT
<213> ORGANISM: Homo sapiens
<220> FEATURE:
<223> OTHER INFORMATION: human IgG1-AAS Fc Region

<400> SEQUENCE: 144

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 145
<211> LENGTH: 504

```
<212> TYPE: PRT
<213> ORGANISM: Artificial Sequence
<220> FEATURE:
<223> OTHER INFORMATION: SIRP-alpha Sequence with Signal Peptide (1-30)

<400> SEQUENCE: 145
```

| | | | | | | | | | | | | | | |
|---|---|---|---|---|---|---|---|---|---|---|---|---|---|---|
| Met | Glu | Pro | Ala | Gly | Pro | Ala | Pro | Gly | Arg | Leu | Gly | Pro | Leu | Cys |
| 1 | | | | 5 | | | | | 10 | | | | | 15 |
| Leu | Leu | Leu | Ala | Ala | Ser | Cys | Ala | Trp | Ser | Gly | Val | Ala | Gly | Glu | Glu |
| | | | | 20 | | | | | 25 | | | | | 30 | |
| Glu | Leu | Gln | Val | Ile | Gln | Pro | Asp | Lys | Ser | Val | Leu | Val | Ala | Ala | Gly |
| | | | | 35 | | | | | 40 | | | | | 45 | |
| Glu | Thr | Ala | Thr | Leu | Arg | Cys | Thr | Ala | Thr | Ser | Leu | Ile | Pro | Val | Gly |
| | 50 | | | | | 55 | | | | | 60 | | | | |
| Pro | Ile | Gln | Trp | Phe | Arg | Gly | Ala | Gly | Pro | Gly | Arg | Glu | Leu | Ile | Tyr |
| 65 | | | | | 70 | | | | | 75 | | | | | 80 |
| Asn | Gln | Lys | Glu | Gly | His | Phe | Pro | Arg | Val | Thr | Thr | Val | Ser | Asp | Leu |
| | | | | 85 | | | | | 90 | | | | | 95 | |
| Thr | Lys | Arg | Asn | Asn | Met | Asp | Phe | Ser | Ile | Arg | Ile | Gly | Asn | Ile | Thr |
| | | | | 100 | | | | | 105 | | | | | 110 | |
| Pro | Ala | Asp | Ala | Gly | Thr | Tyr | Tyr | Cys | Val | Lys | Phe | Arg | Lys | Gly | Ser |
| | | | | 115 | | | | | 120 | | | | | 125 | |
| Pro | Asp | Asp | Val | Glu | Phe | Lys | Ser | Gly | Ala | Gly | Thr | Glu | Leu | Ser | Val |
| | | 130 | | | | | 135 | | | | | 140 | | | |
| Arg | Ala | Lys | Pro | Ser | Ala | Pro | Val | Val | Ser | Gly | Pro | Ala | Ala | Arg | Ala |
| 145 | | | | | 150 | | | | | 155 | | | | | 160 |
| Thr | Pro | Gln | His | Thr | Val | Ser | Phe | Thr | Cys | Glu | Ser | His | Gly | Phe | Ser |
| | | | | 165 | | | | | 170 | | | | | 175 | |
| Pro | Arg | Asp | Ile | Thr | Leu | Lys | Trp | Phe | Lys | Asn | Gly | Asn | Glu | Leu | Ser |
| | | | | 180 | | | | | 185 | | | | | 190 | |
| Asp | Phe | Gln | Thr | Asn | Val | Asp | Pro | Val | Gly | Glu | Ser | Val | Ser | Tyr | Ser |
| | | | | 195 | | | | | 200 | | | | | 205 | |
| Ile | His | Ser | Thr | Ala | Lys | Val | Val | Leu | Thr | Arg | Glu | Asp | Val | His | Ser |
| | | 210 | | | | | 215 | | | | | 220 | | | |
| Gln | Val | Ile | Cys | Glu | Val | Ala | His | Val | Thr | Leu | Gln | Gly | Asp | Pro | Leu |
| 225 | | | | | 230 | | | | | 235 | | | | | 240 |
| Arg | Gly | Thr | Ala | Asn | Leu | Ser | Glu | Thr | Ile | Arg | Val | Pro | Pro | Thr | Leu |
| | | | | 245 | | | | | 250 | | | | | 255 | |
| Glu | Val | Thr | Gln | Gln | Pro | Val | Arg | Ala | Glu | Asn | Gln | Val | Asn | Val | Thr |
| | | | | 260 | | | | | 265 | | | | | 270 | |
| Cys | Gln | Val | Arg | Lys | Phe | Tyr | Pro | Gln | Arg | Leu | Gln | Leu | Thr | Trp | Leu |
| | | 275 | | | | | 280 | | | | | 285 | | | |
| Glu | Asn | Gly | Asn | Val | Ser | Arg | Thr | Glu | Thr | Ala | Ser | Thr | Val | Thr | Glu |
| | 290 | | | | | 295 | | | | | 300 | | | | |
| Asn | Lys | Asp | Gly | Thr | Tyr | Asn | Trp | Met | Ser | Trp | Leu | Leu | Val | Asn | Val |
| 305 | | | | | 310 | | | | | 315 | | | | | 320 |
| Ser | Ala | His | Arg | Asp | Asp | Val | Lys | Leu | Thr | Cys | Gln | Val | Glu | His | Asp |
| | | | | 325 | | | | | 330 | | | | | 335 | |
| Gly | Gln | Pro | Ala | Val | Ser | Lys | Ser | His | Asp | Leu | Lys | Val | Ser | Ala | His |
| | | | | 340 | | | | | 345 | | | | | 350 | |
| Pro | Lys | Glu | Gln | Gly | Ser | Asn | Thr | Ala | Ala | Glu | Asn | Thr | Gly | Ser | Asn |
| | | | | 355 | | | | | 360 | | | | | 365 | |
| Glu | Arg | Asn | Ile | Tyr | Ile | Val | Val | Gly | Val | Val | Cys | Thr | Leu | Leu | Val |
| | 370 | | | | | 375 | | | | | 380 | | | | |

```
Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
            405                 410                 415

Ala Arg Glu Ile Thr Gln Asp Thr Asn Asp Ile Thr Tyr Ala Asp Leu
        420                 425                 430

Asn Leu Pro Lys Gly Lys Lys Pro Ala Pro Gln Ala Ala Glu Pro Asn
    435                 440                 445

Asn His Thr Glu Tyr Ala Ser Ile Gln Thr Ser Pro Gln Pro Ala Ser
450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
                500

<210> SEQ ID NO 146
<211> LENGTH: 474
<212> TYPE: PRT
<213> ORGANISM: Artificial Sequence
<220> FEATURE:
<223> OTHER INFORMATION: SIRP-alpha Sequence without Signal Peptide

<400> SEQUENCE: 146

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240
```

```
Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ile Val Val Gly Val Val Cys Thr Leu
            340                 345                 350

Leu Val Ala Leu Leu Met Ala Ala Leu Tyr Leu Val Arg Ile Arg Gln
        355                 360                 365

Lys Lys Ala Gln Gly Ser Thr Ser Ser Thr Arg Leu His Glu Pro Glu
    370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
                405                 410                 415

Pro Asn Asn His Thr Glu Tyr Ala Ser Ile Gln Thr Ser Pro Gln Pro
            420                 425                 430

Ala Ser Glu Asp Thr Leu Thr Tyr Ala Asp Leu Asp Met Val His Leu
        435                 440                 445

Asn Arg Thr Pro Lys Gln Pro Ala Pro Lys Pro Glu Pro Ser Phe Ser
    450                 455                 460

Glu Tyr Ala Ser Val Gln Val Pro Arg Lys
465                 470

<210> SEQ ID NO 147
<211> LENGTH: 7
<212> TYPE: PRT
<213> ORGANISM: Artificial Sequence
<220> FEATURE:
<223> OTHER INFORMATION: SIRP-alpha Epitope 1, 30-36 of SIRP-alpha
      without Signal Peptide

<400> SEQUENCE: 147

Leu Ile Pro Val Gly Pro Ile
1               5

<210> SEQ ID NO 148
<211> LENGTH: 449
<212> TYPE: PRT
<213> ORGANISM: Artificial Sequence
<220> FEATURE:
<223> OTHER INFORMATION: Heavy Chain Sequence for SIRPAB-21

<400> SEQUENCE: 148

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Ala Ile Tyr Tyr Ser Gly Pro Ile Tyr Tyr Asn Pro Ser
```

```
                50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ser Lys Glu Gly Tyr His Ser Gly Met Asp Val Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 149
<211> LENGTH: 31
```

```
<212> TYPE: PRT
<213> ORGANISM: Artificial Sequence
<220> FEATURE:
<223> OTHER INFORMATION: SIRPalpha v1 (SIRPalpha/CD47 binding interface
      in IgV domain)

<400> SEQUENCE: 149

Arg Glu Leu Ile Tyr Asn Gln Lys Glu Gly His Phe Pro Arg Val Thr
1               5                   10                  15

Thr Val Ser Asp Leu Thr Lys Arg Asn Asn Met Asp Phe Ser Ile
            20                  25                  30

<210> SEQ ID NO 150
<211> LENGTH: 31
<212> TYPE: PRT
<213> ORGANISM: Artificial Sequence
<220> FEATURE:
<223> OTHER INFORMATION: SIRPalpha v2 (SIRPalpha/CD47 binding interface
      in IgV domain)

<400> SEQUENCE: 150

Arg Glu Leu Ile Tyr Asn Gln Lys Glu Gly His Phe Pro Arg Val Thr
1               5                   10                  15

Thr Val Ser Glu Ser Thr Lys Arg Glu Asn Met Asp Phe Ser Ile
            20                  25                  30

<210> SEQ ID NO 151
<211> LENGTH: 31
<212> TYPE: PRT
<213> ORGANISM: Artificial Sequence
<220> FEATURE:
<223> OTHER INFORMATION: SIRPalpha v3 (SIRPalpha/CD47 binding interface
      in IgV domain)

<400> SEQUENCE: 151

Arg Glu Leu Ile Tyr Asn Gln Lys Glu Gly His Phe Pro Arg Val Thr
1               5                   10                  15

Thr Val Ser Asp Leu Thr Lys Arg Glu Asn Met Asp Phe Ser Ile
            20                  25                  30

<210> SEQ ID NO 152
<211> LENGTH: 31
<212> TYPE: PRT
<213> ORGANISM: Artificial Sequence
<220> FEATURE:
<223> OTHER INFORMATION: SIRPalpha v4 (SIRPalpha/CD47 binding interface
      in IgV domain)

<400> SEQUENCE: 152

Arg Glu Leu Ile Tyr Asn Gln Lys Glu Gly His Phe Pro Arg Val Thr
1               5                   10                  15

Thr Val Ser Glu Ser Thr Lys Arg Lys Asn Met Asp Phe Ser Ile
            20                  25                  30

<210> SEQ ID NO 153
<211> LENGTH: 31
<212> TYPE: PRT
<213> ORGANISM: Artificial Sequence
<220> FEATURE:
<223> OTHER INFORMATION: SIRPalpha v5 (SIRPalpha/CD47 binding interface
      in IgV domain)

<400> SEQUENCE: 153

Arg Glu Leu Ile Tyr Asn Gln Lys Glu Gly His Phe Pro Arg Val Thr
1               5                   10                  15
```

```
Thr Val Ser Glu Pro Thr Lys Arg Asn Asn Met Asp Phe Ser Ile
            20                  25                  30
```

<210> SEQ ID NO 154
<211> LENGTH: 31
<212> TYPE: PRT
<213> ORGANISM: Artificial Sequence
<220> FEATURE:
<223> OTHER INFORMATION: SIRPalpha v6 (SIRPalpha/CD47 binding interface
      in IgV domain)

<400> SEQUENCE: 154

```
Arg Glu Leu Ile Tyr Asn Gln Lys Glu Gly His Phe Pro Arg Val Thr
1               5                   10                  15

Thr Val Ser Glu Leu Thr Lys Arg Glu Asn Met Asp Phe Ser Ile
            20                  25                  30
```

<210> SEQ ID NO 155
<211> LENGTH: 330
<212> TYPE: PRT
<213> ORGANISM: Homo sapiens
<220> FEATURE:
<223> OTHER INFORMATION: Human IgG1 Fc Region

<400> SEQUENCE: 155

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 156
<211> LENGTH: 327
<212> TYPE: PRT
<213> ORGANISM: Homo sapiens
<220> FEATURE:
<223> OTHER INFORMATION: Human IgG4 Fc Region

<400> SEQUENCE: 156

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
```

```
                290                 295                 300
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 157
<211> LENGTH: 330
<212> TYPE: PRT
<213> ORGANISM: Homo sapiens
<220> FEATURE:
<223> OTHER INFORMATION: human IgG1 K322A Fc Region

<400> SEQUENCE: 157

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

325                 330

<210> SEQ ID NO 158
<211> LENGTH: 327
<212> TYPE: PRT
<213> ORGANISM: Homo sapiens
<220> FEATURE:
<223> OTHER INFORMATION: Human IgG4P Fc Region

<400> SEQUENCE: 158

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 159
<211> LENGTH: 327
<212> TYPE: PRT

<213> ORGANISM: Homo sapiens
<220> FEATURE:
<223> OTHER INFORMATION: Human IgG4PE Fc Region

<400> SEQUENCE: 159

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 160
<211> LENGTH: 23
<212> TYPE: PRT
<213> ORGANISM: Artificial Sequence
<220> FEATURE:
<223> OTHER INFORMATION: SIRPalpha epitope 2, 30-52 of SIRPalpha without signal peptide

<400> SEQUENCE: 160

Leu Ile Pro Val Gly Pro Ile Gln Trp Phe Arg Gly Ala Gly Pro Gly
1               5                   10                  15

Arg Glu Leu Ile Tyr Asn Gln
            20

<210> SEQ ID NO 161
<211> LENGTH: 38
<212> TYPE: PRT
<213> ORGANISM: Artificial Sequence
<220> FEATURE:
<223> OTHER INFORMATION: SIRPalpha epitope 3, 30-67 of SIRPalpha without
      signal peptide

<400> SEQUENCE: 161

Leu Ile Pro Val Gly Pro Ile Gln Trp Phe Arg Gly Ala Gly Pro Gly
1               5                   10                  15

Arg Glu Leu Ile Tyr Asn Gln Lys Glu Gly His Phe Pro Arg Val Thr
            20                  25                  30

Thr Val Ser Asp Leu Thr
        35

<210> SEQ ID NO 162
<211> LENGTH: 40
<212> TYPE: PRT
<213> ORGANISM: Artificial Sequence
<220> FEATURE:
<223> OTHER INFORMATION: SIRPalpha epitope 4, 30-69 of SIRPalpha without
      signal peptide

<400> SEQUENCE: 162

Leu Ile Pro Val Gly Pro Ile Gln Trp Phe Arg Gly Ala Gly Pro Gly
1               5                   10                  15

Arg Glu Leu Ile Tyr Asn Gln Lys Glu Gly His Phe Pro Arg Val Thr
            20                  25                  30

Thr Val Ser Asp Leu Thr Lys Arg
        35                  40

<210> SEQ ID NO 163
<211> LENGTH: 45
<212> TYPE: PRT
<213> ORGANISM: Artificial Sequence
<220> FEATURE:
<223> OTHER INFORMATION: SIRPalpha epitope 5, 30-74 of SIRPalpha without
      signal peptide

<400> SEQUENCE: 163

Leu Ile Pro Val Gly Pro Ile Gln Trp Phe Arg Gly Ala Gly Pro Gly
1               5                   10                  15

Arg Glu Leu Ile Tyr Asn Gln Lys Glu Gly His Phe Pro Arg Val Thr
            20                  25                  30

Thr Val Ser Asp Leu Thr Lys Arg Asn Asn Met Asp Phe
        35                  40                  45

<210> SEQ ID NO 164
<211> LENGTH: 64
<212> TYPE: PRT
<213> ORGANISM: Artificial Sequence
<220> FEATURE:
<223> OTHER INFORMATION: SIRPalpha epitope 6, 30-93 of SIRPalpha without
      signal peptide

<400> SEQUENCE: 164

Leu Ile Pro Val Gly Pro Ile Gln Trp Phe Arg Gly Ala Gly Pro Gly

```
                1               5                  10                  15
Arg Glu Leu Ile Tyr Asn Gln Lys Glu Gly His Phe Pro Arg Val Thr
                        20                  25                  30

Thr Val Ser Asp Leu Thr Lys Arg Asn Asn Met Asp Phe Ser Ile Arg
            35                  40                  45

Ile Gly Asn Ile Thr Pro Ala Asp Ala Gly Thr Tyr Tyr Cys Val Lys
        50                  55                  60

<210> SEQ ID NO 165
<211> LENGTH: 66
<212> TYPE: PRT
<213> ORGANISM: Artificial Sequence
<220> FEATURE:
<223> OTHER INFORMATION: SIRPalpha epitope 7, 30-95 of SIRPalpha without
      signal peptide

<400> SEQUENCE: 165

Leu Ile Pro Val Gly Pro Ile Gln Trp Phe Arg Gly Ala Gly Pro Gly
1               5                   10                  15

Arg Glu Leu Ile Tyr Asn Gln Lys Glu Gly His Phe Pro Arg Val Thr
                    20                  25                  30

Thr Val Ser Asp Leu Thr Lys Arg Asn Asn Met Asp Phe Ser Ile Arg
            35                  40                  45

Ile Gly Asn Ile Thr Pro Ala Asp Ala Gly Thr Tyr Tyr Cys Val Lys
        50                  55                  60

Phe Arg
65

<210> SEQ ID NO 166
<211> LENGTH: 67
<212> TYPE: PRT
<213> ORGANISM: Artificial Sequence
<220> FEATURE:
<223> OTHER INFORMATION: SIRPalpha epitope 8, 30-96 of SIRPalpha without
      signal peptide

<400> SEQUENCE: 166

Leu Ile Pro Val Gly Pro Ile Gln Trp Phe Arg Gly Ala Gly Pro Gly
1               5                   10                  15

Arg Glu Leu Ile Tyr Asn Gln Lys Glu Gly His Phe Pro Arg Val Thr
                    20                  25                  30

Thr Val Ser Asp Leu Thr Lys Arg Asn Asn Met Asp Phe Ser Ile Arg
            35                  40                  45

Ile Gly Asn Ile Thr Pro Ala Asp Ala Gly Thr Tyr Tyr Cys Val Lys
        50                  55                  60

Phe Arg Lys
65

<210> SEQ ID NO 167
<211> LENGTH: 69
<212> TYPE: PRT
<213> ORGANISM: Artificial Sequence
<220> FEATURE:
<223> OTHER INFORMATION: SIRPalpha epitope 9, 30-98 of SIRPalpha without
      signal peptide

<400> SEQUENCE: 167

Leu Ile Pro Val Gly Pro Ile Gln Trp Phe Arg Gly Ala Gly Pro Gly
1               5                   10                  15

Arg Glu Leu Ile Tyr Asn Gln Lys Glu Gly His Phe Pro Arg Val Thr
                    20                  25                  30
```

```
Thr Val Ser Asp Leu Thr Lys Arg Asn Asn Met Asp Phe Ser Ile Arg
        35                  40                  45

Ile Gly Asn Ile Thr Pro Ala Asp Ala Gly Thr Tyr Tyr Cys Val Lys
    50                  55                  60

Phe Arg Lys Gly Ser
65

<210> SEQ ID NO 168
<211> LENGTH: 17
<212> TYPE: PRT
<213> ORGANISM: Artificial Sequence
<220> FEATURE:
<223> OTHER INFORMATION: SIRPalpha epitope 10, 36-52 of SIRPalpha
      without signal peptide

<400> SEQUENCE: 168

Ile Gln Trp Phe Arg Gly Ala Gly Pro Gly Arg Glu Leu Ile Tyr Asn
1               5                   10                  15

Gln

<210> SEQ ID NO 169
<211> LENGTH: 32
<212> TYPE: PRT
<213> ORGANISM: Artificial Sequence
<220> FEATURE:
<223> OTHER INFORMATION: SIRPalpha epitope 11, 36-67 of SIRPalpha
      without signal peptide

<400> SEQUENCE: 169

Ile Gln Trp Phe Arg Gly Ala Gly Pro Gly Arg Glu Leu Ile Tyr Asn
1               5                   10                  15

Gln Lys Glu Gly His Phe Pro Arg Val Thr Thr Val Ser Asp Leu Thr
            20                  25                  30

<210> SEQ ID NO 170
<211> LENGTH: 34
<212> TYPE: PRT
<213> ORGANISM: Artificial Sequence
<220> FEATURE:
<223> OTHER INFORMATION: SIRPalpha epitope 12, 36-69 of SIRPalpha
      without signal peptide

<400> SEQUENCE: 170

Ile Gln Trp Phe Arg Gly Ala Gly Pro Gly Arg Glu Leu Ile Tyr Asn
1               5                   10                  15

Gln Lys Glu Gly His Phe Pro Arg Val Thr Thr Val Ser Asp Leu Thr
            20                  25                  30

Lys Arg

<210> SEQ ID NO 171
<211> LENGTH: 39
<212> TYPE: PRT
<213> ORGANISM: Artificial Sequence
<220> FEATURE:
<223> OTHER INFORMATION: SIRPalpha epitope 13, 36-74 of SIRPalpha
      without signal peptide

<400> SEQUENCE: 171

Ile Gln Trp Phe Arg Gly Ala Gly Pro Gly Arg Glu Leu Ile Tyr Asn
1               5                   10                  15

Gln Lys Glu Gly His Phe Pro Arg Val Thr Thr Val Ser Asp Leu Thr
            20                  25                  30
```

-continued

Lys Arg Asn Asn Met Asp Phe
        35

<210> SEQ ID NO 172
<211> LENGTH: 58
<212> TYPE: PRT
<213> ORGANISM: Artificial Sequence
<220> FEATURE:
<223> OTHER INFORMATION: SIRPalpha epitope 14, 36-93 of SIRPalpha
      without signal peptide

<400> SEQUENCE: 172

Ile Gln Trp Phe Arg Gly Ala Gly Pro Gly Arg Glu Leu Ile Tyr Asn
1               5                   10                  15

Gln Lys Glu Gly His Phe Pro Arg Val Thr Thr Val Ser Asp Leu Thr
            20                  25                  30

Lys Arg Asn Asn Met Asp Phe Ser Ile Arg Ile Gly Asn Ile Thr Pro
        35                  40                  45

Ala Asp Ala Gly Thr Tyr Tyr Cys Val Lys
    50                  55

<210> SEQ ID NO 173
<211> LENGTH: 60
<212> TYPE: PRT
<213> ORGANISM: Artificial Sequence
<220> FEATURE:
<223> OTHER INFORMATION: SIRPalpha epitope 15, 36-95 of SIRPalpha
      without signal peptide

<400> SEQUENCE: 173

Ile Gln Trp Phe Arg Gly Ala Gly Pro Gly Arg Glu Leu Ile Tyr Asn
1               5                   10                  15

Gln Lys Glu Gly His Phe Pro Arg Val Thr Thr Val Ser Asp Leu Thr
            20                  25                  30

Lys Arg Asn Asn Met Asp Phe Ser Ile Arg Ile Gly Asn Ile Thr Pro
        35                  40                  45

Ala Asp Ala Gly Thr Tyr Tyr Cys Val Lys Phe Arg
    50                  55                  60

<210> SEQ ID NO 174
<211> LENGTH: 61
<212> TYPE: PRT
<213> ORGANISM: Artificial Sequence
<220> FEATURE:
<223> OTHER INFORMATION: SIRPalpha epitope 16, 36-96 of SIRPalpha
      without signal peptide

<400> SEQUENCE: 174

Ile Gln Trp Phe Arg Gly Ala Gly Pro Gly Arg Glu Leu Ile Tyr Asn
1               5                   10                  15

Gln Lys Glu Gly His Phe Pro Arg Val Thr Thr Val Ser Asp Leu Thr
            20                  25                  30

Lys Arg Asn Asn Met Asp Phe Ser Ile Arg Ile Gly Asn Ile Thr Pro
        35                  40                  45

Ala Asp Ala Gly Thr Tyr Tyr Cys Val Lys Phe Arg Lys
    50                  55                  60

<210> SEQ ID NO 175
<211> LENGTH: 63
<212> TYPE: PRT
<213> ORGANISM: Artificial Sequence
<220> FEATURE:
<223> OTHER INFORMATION: SIRPalpha epitope 17, 36-98 of SIRPalpha without signal peptide

<400> SEQUENCE: 175

Ile Gln Trp Phe Arg Gly Ala Gly Pro Gly Arg Glu Leu Ile Tyr Asn
1               5                   10                  15

Gln Lys Glu Gly His Phe Pro Arg Val Thr Thr Val Ser Asp Leu Thr
            20                  25                  30

Lys Arg Asn Asn Met Asp Phe Ser Ile Arg Ile Gly Asn Ile Thr Pro
        35                  40                  45

Ala Asp Ala Gly Thr Tyr Tyr Cys Val Lys Phe Arg Lys Gly Ser
    50                  55                  60

<210> SEQ ID NO 176
<211> LENGTH: 16
<212> TYPE: PRT
<213> ORGANISM: Artificial Sequence
<220> FEATURE:
<223> OTHER INFORMATION: SIRPalpha epitope 18, 52-67 of SIRPalpha
      without signal peptide

<400> SEQUENCE: 176

Gln Lys Glu Gly His Phe Pro Arg Val Thr Thr Val Ser Asp Leu Thr
1               5                   10                  15

<210> SEQ ID NO 177
<211> LENGTH: 18
<212> TYPE: PRT
<213> ORGANISM: Artificial Sequence
<220> FEATURE:
<223> OTHER INFORMATION: SIRPalpha epitope 19, 52-69 of SIRPalpha
      without signal peptide

<400> SEQUENCE: 177

Gln Lys Glu Gly His Phe Pro Arg Val Thr Thr Val Ser Asp Leu Thr
1               5                   10                  15

Lys Arg

<210> SEQ ID NO 178
<211> LENGTH: 23
<212> TYPE: PRT
<213> ORGANISM: Artificial Sequence
<220> FEATURE:
<223> OTHER INFORMATION: SIRPalpha epitope 20, 52-74 of SIRPalpha
      without signal peptide

<400> SEQUENCE: 178

Gln Lys Glu Gly His Phe Pro Arg Val Thr Thr Val Ser Asp Leu Thr
1               5                   10                  15

Lys Arg Asn Asn Met Asp Phe
            20

<210> SEQ ID NO 179
<211> LENGTH: 42
<212> TYPE: PRT
<213> ORGANISM: Artificial Sequence
<220> FEATURE:
<223> OTHER INFORMATION: SIRPalpha epitope 21, 52-93 of SIRPalpha
      without signal peptide

<400> SEQUENCE: 179

Gln Lys Glu Gly His Phe Pro Arg Val Thr Thr Val Ser Asp Leu Thr
1               5                   10                  15

Lys Arg Asn Asn Met Asp Phe Ser Ile Arg Ile Gly Asn Ile Thr Pro
            20                  25                  30

```
Ala Asp Ala Gly Thr Tyr Tyr Cys Val Lys
        35                  40

<210> SEQ ID NO 180
<211> LENGTH: 44
<212> TYPE: PRT
<213> ORGANISM: Artificial Sequence
<220> FEATURE:
<223> OTHER INFORMATION: SIRPalpha epitope 22, 52-95 of SIRPalpha
      without signal peptide

<400> SEQUENCE: 180

Gln Lys Glu Gly His Phe Pro Arg Val Thr Thr Val Ser Asp Leu Thr
1               5                   10                  15

Lys Arg Asn Asn Met Asp Phe Ser Ile Arg Ile Gly Asn Ile Thr Pro
            20                  25                  30

Ala Asp Ala Gly Thr Tyr Tyr Cys Val Lys Phe Arg
        35                  40

<210> SEQ ID NO 181
<211> LENGTH: 45
<212> TYPE: PRT
<213> ORGANISM: Artificial Sequence
<220> FEATURE:
<223> OTHER INFORMATION: SIRPalpha epitope 23, 52-96 of SIRPalpha
      without signal peptide

<400> SEQUENCE: 181

Gln Lys Glu Gly His Phe Pro Arg Val Thr Thr Val Ser Asp Leu Thr
1               5                   10                  15

Lys Arg Asn Asn Met Asp Phe Ser Ile Arg Ile Gly Asn Ile Thr Pro
            20                  25                  30

Ala Asp Ala Gly Thr Tyr Tyr Cys Val Lys Phe Arg Lys
        35                  40                  45

<210> SEQ ID NO 182
<211> LENGTH: 47
<212> TYPE: PRT
<213> ORGANISM: Artificial Sequence
<220> FEATURE:
<223> OTHER INFORMATION: SIRPalpha epitope 24, 52-98 of SIRPalpha
      without signal peptide

<400> SEQUENCE: 182

Gln Lys Glu Gly His Phe Pro Arg Val Thr Thr Val Ser Asp Leu Thr
1               5                   10                  15

Lys Arg Asn Asn Met Asp Phe Ser Ile Arg Ile Gly Asn Ile Thr Pro
            20                  25                  30

Ala Asp Ala Gly Thr Tyr Tyr Cys Val Lys Phe Arg Lys Gly Ser
        35                  40                  45

<210> SEQ ID NO 183
<211> LENGTH: 8
<212> TYPE: PRT
<213> ORGANISM: Artificial Sequence
<220> FEATURE:
<223> OTHER INFORMATION: SIRPalpha epitope 26, 67-74 of SIRPalpha
      without signal peptide

<400> SEQUENCE: 183

Thr Lys Arg Asn Asn Met Asp Phe
1               5
```

```
<210> SEQ ID NO 184
<211> LENGTH: 27
<212> TYPE: PRT
<213> ORGANISM: Artificial Sequence
<220> FEATURE:
<223> OTHER INFORMATION: SIRPalpha epitope 27, 67-93 of SIRPalpha
      without signal peptide

<400> SEQUENCE: 184

Thr Lys Arg Asn Asn Met Asp Phe Ser Ile Arg Ile Gly Asn Ile Thr
1               5                   10                  15

Pro Ala Asp Ala Gly Thr Tyr Tyr Cys Val Lys
            20                  25

<210> SEQ ID NO 185
<211> LENGTH: 29
<212> TYPE: PRT
<213> ORGANISM: Artificial Sequence
<220> FEATURE:
<223> OTHER INFORMATION: SIRPalpha epitope 28, 67-95 of SIRPalpha
      without signal peptide

<400> SEQUENCE: 185

Thr Lys Arg Asn Asn Met Asp Phe Ser Ile Arg Ile Gly Asn Ile Thr
1               5                   10                  15

Pro Ala Asp Ala Gly Thr Tyr Tyr Cys Val Lys Phe Arg
            20                  25

<210> SEQ ID NO 186
<211> LENGTH: 30
<212> TYPE: PRT
<213> ORGANISM: Artificial Sequence
<220> FEATURE:
<223> OTHER INFORMATION: SIRPalpha epitope 29, 67-96 of SIRPalpha
      without signal peptide

<400> SEQUENCE: 186

Thr Lys Arg Asn Asn Met Asp Phe Ser Ile Arg Ile Gly Asn Ile Thr
1               5                   10                  15

Pro Ala Asp Ala Gly Thr Tyr Tyr Cys Val Lys Phe Arg Lys
            20                  25                  30

<210> SEQ ID NO 187
<211> LENGTH: 32
<212> TYPE: PRT
<213> ORGANISM: Artificial Sequence
<220> FEATURE:
<223> OTHER INFORMATION: SIRPalpha epitope 30, 67-98 of SIRPalpha
      without signal peptide

<400> SEQUENCE: 187

Thr Lys Arg Asn Asn Met Asp Phe Ser Ile Arg Ile Gly Asn Ile Thr
1               5                   10                  15

Pro Ala Asp Ala Gly Thr Tyr Tyr Cys Val Lys Phe Arg Lys Gly Ser
            20                  25                  30

<210> SEQ ID NO 188
<211> LENGTH: 6
<212> TYPE: PRT
<213> ORGANISM: Artificial Sequence
<220> FEATURE:
<223> OTHER INFORMATION: SIRPalpha epitope 31, 69-74 of SIRPalpha
      without signal peptide

<400> SEQUENCE: 188

Arg Asn Asn Met Asp Phe
```

<210> SEQ ID NO 189
<211> LENGTH: 25
<212> TYPE: PRT
<213> ORGANISM: Artificial Sequence
<220> FEATURE:
<223> OTHER INFORMATION: SIRPalpha epitope 32, 69-93 of SIRPalpha
      without signal peptide

<400> SEQUENCE: 189

Arg Asn Asn Met Asp Phe Ser Ile Arg Ile Gly Asn Ile Thr Pro Ala
1               5                   10                  15

Asp Ala Gly Thr Tyr Tyr Cys Val Lys
            20                  25

<210> SEQ ID NO 190
<211> LENGTH: 27
<212> TYPE: PRT
<213> ORGANISM: Artificial Sequence
<220> FEATURE:
<223> OTHER INFORMATION: SIRPalpha epitope 33, 69-95 of SIRPalpha
      without signal peptide

<400> SEQUENCE: 190

Arg Asn Asn Met Asp Phe Ser Ile Arg Ile Gly Asn Ile Thr Pro Ala
1               5                   10                  15

Asp Ala Gly Thr Tyr Tyr Cys Val Lys Phe Arg
            20                  25

<210> SEQ ID NO 191
<211> LENGTH: 28
<212> TYPE: PRT
<213> ORGANISM: Artificial Sequence
<220> FEATURE:
<223> OTHER INFORMATION: SIRPalpha epitope 34, 69-96 of SIRPalpha
      without signal peptide

<400> SEQUENCE: 191

Arg Asn Asn Met Asp Phe Ser Ile Arg Ile Gly Asn Ile Thr Pro Ala
1               5                   10                  15

Asp Ala Gly Thr Tyr Tyr Cys Val Lys Phe Arg Lys
            20                  25

<210> SEQ ID NO 192
<211> LENGTH: 30
<212> TYPE: PRT
<213> ORGANISM: Artificial Sequence
<220> FEATURE:
<223> OTHER INFORMATION: SIRPalpha epitope 35, 69-98 of SIRPalpha
      without signal peptide

<400> SEQUENCE: 192

Arg Asn Asn Met Asp Phe Ser Ile Arg Ile Gly Asn Ile Thr Pro Ala
1               5                   10                  15

Asp Ala Gly Thr Tyr Tyr Cys Val Lys Phe Arg Lys Gly Ser
            20                  25                  30

<210> SEQ ID NO 193
<211> LENGTH: 20
<212> TYPE: PRT
<213> ORGANISM: Artificial Sequence
<220> FEATURE:
<223> OTHER INFORMATION: SIRPalpha epitope 36, 74-93 of SIRPalpha
      without signal peptide -continued

```
<400> SEQUENCE: 193

Phe Ser Ile Arg Ile Gly Asn Ile Thr Pro Ala Asp Ala Gly Thr Tyr
1               5                   10                  15

Tyr Cys Val Lys
            20

<210> SEQ ID NO 194
<211> LENGTH: 22
<212> TYPE: PRT
<213> ORGANISM: Artificial Sequence
<220> FEATURE:
<223> OTHER INFORMATION: SIRPalpha epitope 37, 74-95 of SIRPalpha
      without signal peptide

<400> SEQUENCE: 194

Phe Ser Ile Arg Ile Gly Asn Ile Thr Pro Ala Asp Ala Gly Thr Tyr
1               5                   10                  15

Tyr Cys Val Lys Phe Arg
            20

<210> SEQ ID NO 195
<211> LENGTH: 23
<212> TYPE: PRT
<213> ORGANISM: Artificial Sequence
<220> FEATURE:
<223> OTHER INFORMATION: SIRPalpha epitope 38, 74-96 of SIRPalpha
      without signal peptide

<400> SEQUENCE: 195

Phe Ser Ile Arg Ile Gly Asn Ile Thr Pro Ala Asp Ala Gly Thr Tyr
1               5                   10                  15

Tyr Cys Val Lys Phe Arg Lys
            20

<210> SEQ ID NO 196
<211> LENGTH: 25
<212> TYPE: PRT
<213> ORGANISM: Artificial Sequence
<220> FEATURE:
<223> OTHER INFORMATION: SIRPalpha epitope 39, 74-98 of SIRPalpha
      without signal peptide

<400> SEQUENCE: 196

Phe Ser Ile Arg Ile Gly Asn Ile Thr Pro Ala Asp Ala Gly Thr Tyr
1               5                   10                  15

Tyr Cys Val Lys Phe Arg Lys Gly Ser
            20                  25

<210> SEQ ID NO 197
<211> LENGTH: 23
<212> TYPE: PRT
<213> ORGANISM: Artificial Sequence
<220> FEATURE:
<223> OTHER INFORMATION: VL FR1 of Antibodies SIRPAB-6 and SIRPAB-7

<400> SEQUENCE: 197

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 198
<211> LENGTH: 4
<212> TYPE: PRT
```

<213> ORGANISM: Artificial Sequence
<220> FEATURE:
<223> OTHER INFORMATION: SIRPalpha epitope 41, 93-96 of SIRPalpha without signal peptide

<400> SEQUENCE: 198

Lys Phe Arg Lys
1

<210> SEQ ID NO 199
<211> LENGTH: 6
<212> TYPE: PRT
<213> ORGANISM: Artificial Sequence
<220> FEATURE:
<223> OTHER INFORMATION: SIRPalpha epitope 42, 93-98 of SIRPalpha without signal peptide

<400> SEQUENCE: 199

Lys Phe Arg Lys Gly Ser
1               5

<210> SEQ ID NO 200
<211> LENGTH: 214
<212> TYPE: PRT
<213> ORGANISM: Artificial Sequence
<220> FEATURE:
<223> OTHER INFORMATION: Light Chain Sequence for SIRPAB-1 to SIRPAB-5, SIRPAB-17 and SIRPAB-18

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Ala Tyr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 201

-continued

<211> LENGTH: 4
<212> TYPE: PRT
<213> ORGANISM: Artificial Sequence
<220> FEATURE:
<223> OTHER INFORMATION: SIRPalpha epitope 44, 95-98 of SIRPalpha
      without signal peptide

<400> SEQUENCE: 201

Arg Lys Gly Ser
1

<210> SEQ ID NO 202
<211> LENGTH: 214
<212> TYPE: PRT
<213> ORGANISM: Artificial Sequence
<220> FEATURE:
<223> OTHER INFORMATION: Light Chain Sequence for SIRPAB-6 and SIRPAB-7

<400> SEQUENCE: 202

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Ala Tyr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 203
<211> LENGTH: 107
<212> TYPE: PRT
<213> ORGANISM: Artificial Sequence
<220> FEATURE:
<223> OTHER INFORMATION: SIRPalpha IgV domain

<400> SEQUENCE: 203

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
        50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly
            100                 105

<210> SEQ ID NO 204
<211> LENGTH: 450
<212> TYPE: PRT
<213> ORGANISM: Artificial Sequence
<220> FEATURE:
<223> OTHER INFORMATION: Heavy Chain Sequence for SIRPAB-12

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Gly Ile Val Trp Val Arg Gln Ala Pro Gly Gln Gly Leu Glu Trp Met
        35                  40                  45

Gly Trp Ile Ser Ala Tyr Ala Gly Glu Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

```
Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 205
<211> LENGTH: 450
<212> TYPE: PRT
<213> ORGANISM: Artificial Sequence
<220> FEATURE:
<223> OTHER INFORMATION: Heavy Chain Sequence for SIRPAB-12-K322A

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Gly Ile Val Trp Val Arg Gln Ala Pro Gly Gln Gly Leu Glu Trp Met
            35                  40                  45

Gly Trp Ile Ser Ala Tyr Ala Gly Glu Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 206
<211> LENGTH: 38
<212> TYPE: PRT
<213> ORGANISM: Artificial Sequence
<220> FEATURE:
<223> OTHER INFORMATION: Signal peptide sequence used for expression of
      SIRPalpha

<400> SEQUENCE: 206

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala
        35

<210> SEQ ID NO 207
<211> LENGTH: 449
<212> TYPE: PRT
<213> ORGANISM: Artificial Sequence
<220> FEATURE:
<223> OTHER INFORMATION: Heavy Chain Sequence for SIRPAB-18

<400> SEQUENCE: 207

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Ala Ile Tyr Tyr Ser Gly Pro Ile Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ser Lys Glu Gly Tyr His Ser Gly Met Asp Val Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys

```
                    405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 208
<211> LENGTH: 214
<212> TYPE: PRT
<213> ORGANISM: Artificial Sequence
<220> FEATURE:
<223> OTHER INFORMATION: Light Chain Sequence for SIRPAB-19

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Gln Ala Ser Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Ile Glu Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Ala Tyr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 209
<211> LENGTH: 214
<212> TYPE: PRT
<213> ORGANISM: Artificial Sequence
<220> FEATURE:
<223> OTHER INFORMATION: Light Chain Sequence for SIRPAB-20

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asp Tyr
            20                  25                  30

Leu Asn Trp Tyr Gln Gln Lys Pro Gly Lys Ala Pro Lys Leu Leu Ile
```

```
            35                  40                  45

Tyr Asp Ala Asp Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Ala Tyr Leu Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 210
<211> LENGTH: 214
<212> TYPE: PRT
<213> ORGANISM: Artificial Sequence
<220> FEATURE:
<223> OTHER INFORMATION: Light Chain Sequence for SIRPAB-21

<400> SEQUENCE: 210

Asp Ile Gln Met Thr Gln Ser Pro Ser Ser Leu Ser Ala Ser Val Gly
 1               5                  10                  15

Asp Arg Val Thr Ile Thr Cys Gln Ala Ser Asp Ile Ser Asp Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Ala Tyr Leu Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190
Ala Cys Glu Val Thr His Gln Gly Leu Ser Ser Pro Val Thr Lys Ser
                195                 200                 205

Phe Asn Arg Gly Glu Cys
            210

<210> SEQ ID NO 211
<211> LENGTH: 107
<212> TYPE: PRT
<213> ORGANISM: Artificial Sequence
<220> FEATURE:
<223> OTHER INFORMATION: LC constance region sequences after VL

<400> SEQUENCE: 211

Arg Thr Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 212
<211> LENGTH: 449
<212> TYPE: PRT
<213> ORGANISM: Artificial Sequence
<220> FEATURE:
<223> OTHER INFORMATION: Heavy Chain Sequence for SIRPAB-1

<400> SEQUENCE: 212

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Tyr His Ser Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 213
<211> LENGTH: 449
<212> TYPE: PRT
<213> ORGANISM: Artificial Sequence
<220> FEATURE:
<223> OTHER INFORMATION: Heavy Chain Sequence for SIRPAB-2

<400> SEQUENCE: 213

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Asp Tyr Trp Ala Trp Ile Arg Gln His Pro Gly Lys Gly Leu Glu
        35                  40                  45

Trp Ile Gly Tyr Ile Tyr Pro Ser Gly Phe Thr Tyr Tyr Asn Pro Ser
    50                  55                  60

Leu Lys Ser Arg Val Thr Ile Ser Val Asp Thr Ser Lys Asn Gln Phe

```
                65                  70                  75                  80
Ser Leu Lys Leu Ser Ser Val Thr Ala Ala Asp Thr Ala Val Tyr Tyr
                    85                  90                  95

Cys Ala Arg Glu Gly Tyr His Ser Gly Met Asp Val Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 214
<211> LENGTH: 449
<212> TYPE: PRT
<213> ORGANISM: Artificial Sequence
<220> FEATURE:
```

<223> OTHER INFORMATION: Heavy Chain Sequence for SIRPAB-3

<400> SEQUENCE: 214

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Gly Trp Tyr Trp Gln Trp Ile Arg Gln His Pro Gly Lys Gly Leu Glu
         35                  40                  45

Trp Ile Gly Thr Ile Tyr Tyr Ser Gly Ser Thr Phe Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Gly Tyr His Ser Gly Met Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 215
<211> LENGTH: 449
<212> TYPE: PRT
<213> ORGANISM: Artificial Sequence
<220> FEATURE:
<223> OTHER INFORMATION: Heavy Chain Sequence for SIRPAB-4

<400> SEQUENCE: 215

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Pro Tyr Trp Ser Trp Ile Arg Gln His Pro Gly Lys Gly Leu Glu
        35                  40                  45

Trp Ile Gly Tyr Ile Tyr Ala Ser Gly Phe Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Gly Tyr His Ser Gly Met Asp Val Trp Gly Gln Gly
        100                 105                 110

Thr Thr Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
```

```
                    305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Arg Glu Glu Met Thr Lys Asn Gln Val Ser Leu Thr
                    355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

Lys

<210> SEQ ID NO 216
<211> LENGTH: 449
<212> TYPE: PRT
<213> ORGANISM: Artificial Sequence
<220> FEATURE:
<223> OTHER INFORMATION: Heavy Chain Sequence for SIRPAB-5

<400> SEQUENCE: 216

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                    20                  25                  30

Pro Ala Tyr Trp Ser Trp Ile Arg Gln His Pro Gly Lys Gly Leu Glu
                35                  40                  45

Trp Ile Gly Thr Ile Tyr Tyr Ser Gly Ser Thr Phe Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                    85                  90                  95

Cys Ala Arg Glu Gly Tyr His Ser Gly Met Asp Val Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 217
<211> LENGTH: 451
<212> TYPE: PRT
<213> ORGANISM: Artificial Sequence
<220> FEATURE:
<223> OTHER INFORMATION: Heavy Chain Sequence for SIRPAB-6

<400> SEQUENCE: 217

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Leu Asp Gly Ser Tyr Gly Ser Ser Ala Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 218
<211> LENGTH: 451
<212> TYPE: PRT
<213> ORGANISM: Artificial Sequence
<220> FEATURE:
<223> OTHER INFORMATION: Heavy Chain Sequence for SIRPAB-7

<400> SEQUENCE: 218

Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Gly
            20                  25                  30
```

```
Glu Tyr Tyr Trp Glu Trp Ile Arg Gln His Pro Gly Lys Gly Leu Glu
         35                  40                  45

Trp Ile Gly Tyr Ile Tyr Ser Ser Gly Phe Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Gly Leu Asp Gly Ser Tyr Gly Ser Ser Ala Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
```

-continued

```
            450
```

<210> SEQ ID NO 219
<211> LENGTH: 450
<212> TYPE: PRT
<213> ORGANISM: Artificial Sequence
<220> FEATURE:
<223> OTHER INFORMATION: Heavy Chain Sequence for SIRPAB-8

<400> SEQUENCE: 219

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gly Ser Ser Trp Tyr Asp Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 220
<211> LENGTH: 450
<212> TYPE: PRT
<213> ORGANISM: Artificial Sequence
<220> FEATURE:
<223> OTHER INFORMATION: Heavy Chain Sequence for SIRPAB-9

<400> SEQUENCE: 220

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Gly Gly Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Gly Gly Glu Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Glu Ala Gly Ser Ser Trp Tyr Asp Phe Asp Leu Trp Gly Arg
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
```

-continued

```
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
    450

<210> SEQ ID NO 221
<211> LENGTH: 450
<212> TYPE: PRT
<213> ORGANISM: Artificial Sequence
<220> FEATURE:
<223> OTHER INFORMATION: Heavy Chain Sequence for SIRPAB-10

<400> SEQUENCE: 221

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Pro Ile Ser Trp Val Arg Gln Ala Pro Gly Gln Gly Leu Glu Trp Met
        35                  40                  45
Gly Trp Ile Tyr Ala Tyr Gly Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Glu Ala Gly Ser Ser Trp Tyr Asp Phe Asp Leu Trp Gly Arg
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
```

```
                    165                 170                 175
Leu Gln Ser Ser Gly Leu Tyr Ser Leu Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 222
<211> LENGTH: 450
<212> TYPE: PRT
<213> ORGANISM: Artificial Sequence
<220> FEATURE:
<223> OTHER INFORMATION: Heavy Chain Sequence for SIRPAB-13

<400> SEQUENCE: 222

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe His Gly Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Glu Thr Asn Tyr Ala Gln Lys Leu
    50                  55                  60

Gln Gly Arg Val Thr Met Thr Thr Asp Thr Ser Thr Ser Thr Ala Tyr
```

```
              65                  70                  75                  80
        Met Glu Leu Arg Ser Leu Arg Ser Asp Asp Thr Ala Val Tyr Tyr Cys
                            85                  90                  95

Ala Arg Glu Ala Gly Ser Ser Trp Tyr Asp Phe Asp Leu Trp Gly Arg
                           100                 105                 110

Gly Thr Leu Val Thr Val Ser Ser Ala Ser Thr Lys Gly Pro Ser Val
                           115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                            165                 170                 175

Leu Gln Ser Ser Gly Leu Tyr Ser Leu Ser Ser Val Val Thr Val Pro
                            180                 185                 190

Ser Ser Ser Leu Gly Thr Gln Thr Tyr Ile Cys Asn Val Asn His Lys
                        195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
        225                 230                 235                 240

Pro Ser Val Phe Leu Phe Pro Pro Lys Pro Lys Asp Thr Leu Met Ile
                            245                 250                 255

Ser Arg Thr Pro Glu Val Thr Cys Val Val Val Asp Val Ser His Glu
                            260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                            325                 330                 335

Lys Thr Ile Ser Lys Ala Lys Gly Gln Pro Arg Glu Pro Gln Val Tyr
                            340                 345                 350

Thr Leu Pro Pro Ser Arg Glu Glu Met Thr Lys Asn Gln Val Ser Leu
                        355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                            405                 410                 415

Lys Ser Arg Trp Gln Gln Gly Asn Val Phe Ser Cys Ser Val Met His
                            420                 425                 430

Glu Ala Leu His Asn His Tyr Thr Gln Lys Ser Leu Ser Leu Ser Pro
                        435                 440                 445

Gly Lys
            450

<210> SEQ ID NO 223
<211> LENGTH: 449
<212> TYPE: PRT
<213> ORGANISM: Artificial Sequence
```

<220> FEATURE:
<223> OTHER INFORMATION: Heavy Chain Sequence for SIRPAB-17

<400> SEQUENCE: 223

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Ala Ile Tyr Tyr Ser Gly Pro Ile Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Gly Tyr His Ser Gly Met Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 224
<211> LENGTH: 215
<212> TYPE: PRT
<213> ORGANISM: Artificial Sequence
<220> FEATURE:
<223> OTHER INFORMATION: Reference Anti-SIRPalpha light chain (215 AA)

<400> SEQUENCE: 224

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Arg Thr Phe Gly Ala Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 225
<211> LENGTH: 443
<212> TYPE: PRT
<213> ORGANISM: Artificial Sequence
<220> FEATURE:
<223> OTHER INFORMATION: Reference Anti-SIRPalpha heavy chain (442 AA)

<400> SEQUENCE: 225

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30
```

-continued

Tyr Ile His Trp Val Gln Gln Arg Thr Glu Gln Gly Leu Glu Trp Ile
           35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Ala Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
    275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Ala Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

SIRP-α BINDING PROTEINS AND METHODS OF USE THEREOF

CROSS-REFERENCE TO RELATED APPLICATIONS

This application is a continuation of International Patent Application No. PCT/US19/52604 filed Sep. 24, 2019, which claims the benefit of priority to U.S. Provisional Patent Application No. 62/737,782, filed Sep. 27, 2018, and U.S. Provisional Patent Application No. 62/853,997, filed May 29, 2019, the disclosures of each of which are incorporated by reference herein in their entirety.

1. FIELD

Provided herein are compositions, methods, and uses involving antibodies that specifically bind to signal regulatory protein-α (SIRPα) and modulate the activity of SIRPα.

2. SUMMARY

The present disclosure provides proteins that bind to SIRPα (e.g., human SIRPα, SEQ ID NO:146), including binding proteins such as antibodies that bind to SIRPα. Such binding proteins, including antibodies, may bind to a SIRPα polypeptide, a SIRPα fragment, and/or a SIRPα epitope. Such binding proteins, including antibodies, can be antagonists or a SIRPα blocking antibody that competes with SIRPα ligand (e.g., CD47) for the interaction with SIRPα. In some embodiments, provided herein is an antibody. In other embodiments, provided herein is an antigen-binding fragment of the antibody.

In one aspect, provided herein is an antibody or antigen-binding fragment thereof that (a) binds to an epitope of human SIRPα recognized by an antibody comprising a light chain variable region having an amino acid sequence of SEQ ID NO:67 and a heavy chain variable region having an amino acid sequence of SEQ ID NO:80; or (b) competes for the binding to human SIRPα with an antibody comprising a light chain variable region having an amino acid sequence of SEQ ID NO:67 and a heavy chain variable region having an amino acid sequence of SEQ ID NO:80.

In another aspect, provided herein is an antibody or antigen-binding fragment thereof that binds to SIRPα, wherein the antibody or antigen-binding fragment thereof comprises: (a) a light chain variable region (VL) comprising VL complementarity determining region 1 (CDR1), VL CDR2, and VL CDR3 of any one of antibodies SIRPAB-11, SIRPAB-12, SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, or SIRPAB-13 as set forth in Table 1; and/or (b) a heavy chain variable region (VH) comprising VH complementarity determining region 1 (CDR1), VH CDR2, and VH CDR3 of any one of antibodies SIRPAB-11, SIRPAB-12, SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, or SIRPAB-13 as set forth in Table 2.

In some embodiments, the antibody or antigen-binding fragment thereof provided herein comprises: (a) a light chain variable region (VL) further comprising VL framework 1 (FR1), VL FR2, VL FR3, and VL FR4 of any one of antibodies SIRPAB-11, SIRPAB-12, SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, or SIRPAB-13 as set forth in Table 3; and/or (b) a heavy chain variable region (VH) further comprising VH framework 1 (FR1), VH FR2, VH FR3, and VH FR4 of any one of antibodies SIRPAB-11, SIRPAB-12, SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, or SIRPAB-13 as set forth in Table 4.

In certain embodiments, the antibody or antigen-binding fragment thereof provided herein comprises VL CDR1, VL CDR2, and VL CDR3 comprising amino acid sequences of SEQ ID NOS:62, 63, and 65, respectively, and the VH CDR1, VH CDR2, and VH CDR3 comprising amino acid sequences of SEQ ID NOS:78, 69, and 57, respectively.

In some embodiments, the antibody or antigen-binding fragment thereof provided herein comprises the VL CDR1, VL CDR2, and VL CDR3 comprising amino acid sequences of SEQ ID NOS:62, 63, and 65, respectively, and the VH CDR1, VH CDR2, and VH CDR3 comprising amino acid sequences of SEQ ID NOS:82, 83, and 57, respectively.

In certain embodiments, the antibody or antigen-binding fragment thereof comprises a VL comprising an amino acid sequence of SEQ ID NO:18. In some embodiments, the antibody or antigen-binding fragment thereof comprises a VL comprising an amino acid sequence of SEQ ID NO:46. In certain embodiments, the antibody or antigen-binding fragment thereof comprises a VL comprising an amino acid sequence of SEQ ID NO:67.

In some embodiments, the antibody or antigen-binding fragment thereof comprises a VH comprising an amino acid sequence of SEQ ID NO:9. In certain embodiments, the antibody or antigen-binding fragment thereof comprises a VH comprising an amino acid sequence of SEQ ID NO:22. In some embodiments, the antibody or antigen-binding fragment thereof comprises a VH comprising an amino acid sequence of SEQ ID NO:27. In certain embodiments, the antibody or antigen-binding fragment thereof comprises a VH comprising an amino acid sequence of SEQ ID NO:32. In some embodiments, the antibody or antigen-binding fragment thereof comprises a VH comprising an amino acid sequence of SEQ ID NO:36. In certain embodiments, the antibody or antigen-binding fragment thereof comprises a VH comprising an amino acid sequence of SEQ ID NO:42. In some embodiments, the antibody or antigen-binding fragment thereof comprises a VH comprising an amino acid sequence of SEQ ID NO:50. In some embodiments, the antibody or antigen-binding fragment thereof comprises a VH comprising an amino acid sequence of SEQ ID NO:60. In certain embodiments, the antibody or antigen-binding fragment thereof comprises a VH comprising an amino acid sequence of SEQ ID NO:71. In some embodiments, the antibody or antigen-binding fragment thereof comprises a VH comprising an amino acid sequence of SEQ ID NO:76. In certain embodiments, the antibody or antigen-binding fragment thereof comprises a VH comprising an amino acid sequence of SEQ ID NO:80. In some embodiments, the antibody or antigen-binding fragment thereof comprises a VH comprising an amino acid sequence of SEQ ID NO:85. In certain embodiments, the antibody or antigen-binding fragment thereof comprises a VH comprising an amino acid sequence of SEQ ID NO:90.

In other embodiments, the antibody or antigen-binding fragment thereof comprises: (a) a VL comprising an amino acid sequence of SEQ ID NO:18; and (b) a VH comprising an amino acid sequence of SEQ ID NO:9. In certain embodiments, the antibody or antigen-binding fragment thereof comprises: (a) a VL comprising an amino acid sequence of SEQ ID NO:18; and (b) a VH comprising an amino acid sequence of SEQ ID NO:22. In another embodiment, the antibody or antigen-binding fragment thereof comprises: (a) a VL comprising an amino acid sequence of SEQ ID NO:18;

and (b) a VH comprising an amino acid sequence of SEQ ID NO:27. In some embodiments, the antibody or antigen-binding fragment thereof comprises: (a) a VL comprising an amino acid sequence of SEQ ID NO:18; and (b) a VH comprising an amino acid sequence of SEQ ID NO:32. In certain embodiments, the antibody or antigen-binding fragment thereof comprises: (a) a VL comprising an amino acid sequence of SEQ ID NO:18; and (b) a VH comprising an amino acid sequence of SEQ ID NO:36. In other embodiments, the antibody or antigen-binding fragment thereof comprises: (a) a VL comprising an amino acid sequence of SEQ ID NO:46; and (b) a VH comprising an amino acid sequence of SEQ ID NO:42. In another embodiment, the antibody or antigen-binding fragment thereof comprises: (a) a VL comprising an amino acid sequence of SEQ ID NO:46; and (b) a VH comprising an amino acid sequence of SEQ ID NO:50. In some embodiments, the antibody or antigen-binding fragment thereof comprises: (a) a VL comprising an amino acid sequence of SEQ ID NO:67; and (b) a VH comprising an amino acid sequence of SEQ ID NO:60. In certain embodiments, the antibody or antigen-binding fragment thereof comprises: (a) a VL comprising an amino acid sequence of SEQ ID NO:67; and (b) a VH comprising an amino acid sequence of SEQ ID NO:71. In other embodiments, the antibody or antigen-binding fragment thereof comprises: (a) a VL comprising an amino acid sequence of SEQ ID NO:67; and (b) a VH comprising an amino acid sequence of SEQ ID NO:76. In another embodiment, the antibody or antigen-binding fragment thereof comprises: (a) a VL comprising an amino acid sequence of SEQ ID NO:67; and (b) a VH comprising an amino acid sequence of SEQ ID NO:80. In some embodiments, the antibody or antigen-binding fragment thereof comprises: (a) a VL comprising an amino acid sequence of SEQ ID NO:67; and (b) a VH comprising an amino acid sequence of SEQ ID NO:85. In certain embodiments, the antibody or antigen-binding fragment thereof comprises: (a) a VL comprising an amino acid sequence of SEQ ID NO:67; and (b) a VH comprising an amino acid sequence of SEQ ID NO:90.

In certain embodiments, the antibody or antigen-binding fragment thereof comprises: (a) a VL comprising an amino acid sequence selected from the group consisting of SEQ ID NOS:18, 46, and 67; and (b) a VH comprising an amino acid sequence selected from the group consisting of SEQ ID NOS:9, 22, 27, 32, 36, 42, 50, 60, 71, 76, 80, 85, and 90.

In other embodiments, the antibody or antigen-binding fragment thereof comprises a human IgG1 Fc region or a mutant thereof. In another embodiment, the antibody or antigen-binding fragment thereof comprises a human IgG1-K322A Fc region. In some embodiments, the antibody or antigen-binding fragment thereof comprises a human IgG1-AAS Fc region.

In some embodiments, the antibody or antigen-binding fragment thereof comprises a human IgG4 Fc region or a mutant thereof. In certain embodiments, the antibody or antigen-binding fragment thereof comprises a human IgG4P Fc region. In other embodiments, the antibody or antigen-binding fragment thereof comprises a human IgG4PE Fc region. In another embodiment, the antibody or antigen-binding fragment thereof comprises a heavy chain Fc region comprising an amino add sequence selected from the group consisting of SEQ ID NOS:144, 155-159.

In some embodiments, the antibody or antigen-binding fragment thereof comprises a light chain constant region comprising an amino acid sequence of SEQ ID NO:211.

In some embodiments, the antibody or antigen-binding fragment thereof comprises: (a) a light chain constant region comprising an amino acid sequence of SEQ ID NO:211; and (b) a heavy chain Fc region comprising an amino acid sequence selected from the group consisting of SEQ ID NOS:144, 155-159.

In some embodiments, the antibody or antigen-binding fragment thereof comprises a light chain comprising an amino acid sequence of SEQ ID NO:143. In certain embodiments, the antibody or antigen-binding fragment thereof comprises a heavy chain comprising an amino acid sequence of SEQ ID NO:142. In other embodiments, the antibody or antigen-binding fragment thereof comprises: (a) a light chain comprising an amino acid sequence of SEQ ID NO:143; and (b) a heavy chain comprising an amino acid sequence of SEQ ID NO:142.

In some embodiments, the antibody or antigen-binding fragment thereof comprises a light chain comprising an amino acid sequence of SEQ ID NO:200. In some embodiments, the antibody or antigen-binding fragment thereof comprises a light chain comprising an amino acid sequence of SEQ ID NO:202. In some embodiments, the antibody or antigen-binding fragment thereof comprises a light chain comprising an amino acid sequence of SEQ ID NO:143. In some embodiments, the antibody or antigen-binding fragment thereof comprises a light chain comprising an amino acid sequence of SEQ ID NO:208. In some embodiments, the antibody or antigen-binding fragment thereof comprises a light chain comprising an amino acid sequence of SEQ ID NO:209. In some embodiments, the antibody or antigen-binding fragment thereof comprises a light chain comprising an amino acid sequence of SEQ ID NO:210. In certain embodiments, the antibody or antigen-binding fragment thereof comprises a heavy chain comprising an amino acid sequence of SEQ ID NO:212. In certain embodiments, the antibody or antigen-binding fragment thereof comprises a heavy chain comprising an amino acid sequence of SEQ ID NO:213. In certain embodiments, the antibody or antigen-binding fragment thereof comprises a heavy chain comprising an amino acid sequence of SEQ ID NO:214. In certain embodiments, the antibody or antigen-binding fragment thereof comprises a heavy chain comprising an amino acid sequence of SEQ ID NO:215. In certain embodiments, the antibody or antigen-binding fragment thereof comprises a heavy chain comprising an amino acid sequence of SEQ ID NO:216. In certain embodiments, the antibody or antigen-binding fragment thereof comprises a heavy chain comprising an amino acid sequence of SEQ ID NO:217. In certain embodiments, the antibody or antigen-binding fragment thereof comprises a heavy chain comprising an amino acid sequence of SEQ ID NO:218. In certain embodiments, the antibody or antigen-binding fragment thereof comprises a heavy chain comprising an amino acid sequence of SEQ ID NO:219. In certain embodiments, the antibody or antigen-binding fragment thereof comprises a heavy chain comprising an amino acid sequence of SEQ ID NO:220. In certain embodiments, the antibody or antigen-binding fragment thereof comprises a heavy chain comprising an amino acid sequence of SEQ ID NO:221. In certain embodiments, the antibody or antigen-binding fragment thereof comprises a heavy chain comprising an amino acid sequence of SEQ ID NO:142. In certain embodiments, the antibody or antigen-binding fragment thereof comprises a heavy chain comprising an amino acid sequence of SEQ ID NO:204. In certain embodiments, the antibody or antigen-binding fragment thereof comprises a heavy chain comprising an amino acid sequence of SEQ ID NO:222. In certain embodiments, the antibody or antigen-binding fragment thereof comprises a heavy chain comprising an amino acid sequence of SEQ ID NO:223. In certain embodiments, the antibody or antigen-binding fragment thereof comprises a heavy chain comprising an amino acid sequence of SEQ ID NO:207. In certain embodiments, the antibody or antigen-binding fragment thereof comprises a heavy chain comprising an amino acid sequence of SEQ ID NO:117. In certain embodiments, the antibody or antigen-binding fragment thereof comprises a heavy chain comprising an amino acid sequence of SEQ ID NO:110. In certain embodiments, the antibody or antigen-binding fragment thereof comprises a heavy chain comprising an amino acid sequence of SEQ ID NO:148.

In other embodiments, the antibody or antigen-binding fragment thereof comprises: (a) a light chain comprising an amino acid sequence of SEQ ID NO:200; and (b) a heavy chain comprising an amino acid sequence of SEQ ID NO:212. In some embodiments, the antibody or antigen-binding fragment thereof comprises: (a) a light chain comprising an amino acid sequence of SEQ ID NO:200; and (b) a heavy chain comprising an amino acid sequence of SEQ ID NO:213. In some embodiments, the antibody or antigen-binding fragment thereof comprises: (a) a light chain comprising an amino acid sequence of SEQ ID NO:200; and (b) a heavy chain comprising an amino acid sequence of SEQ ID NO:214. In some embodiments, the antibody or antigen-binding fragment thereof comprises: (a) a light chain comprising an amino acid sequence of SEQ ID NO:200; and (b) a heavy chain comprising an amino acid sequence of SEQ ID NO:215. In some embodiments, the antibody or antigen-binding fragment thereof comprises: (a) a light chain comprising an amino acid sequence of SEQ ID NO:200; and (b) a heavy chain comprising an amino acid sequence of SEQ ID NO:216. In some embodiments, the antibody or antigen-binding fragment thereof comprises: (a) a light chain comprising an amino acid sequence of SEQ ID NO:202; and (b) a heavy chain comprising an amino acid sequence of SEQ ID NO:217. In some embodiments, the antibody or antigen-binding fragment thereof comprises: (a) a light chain comprising an amino acid sequence of SEQ ID NO:202; and (b) a heavy chain comprising an amino acid sequence of SEQ ID NO:218. In some embodiments, the antibody or antigen-binding fragment thereof comprises: (a) a light chain comprising an amino acid sequence of SEQ ID NO:143; and (b) a heavy chain comprising an amino acid sequence of SEQ ID NO:219. In some embodiments, the antibody or antigen-binding fragment thereof comprises: (a) a light chain comprising an amino acid sequence of SEQ ID NO:143; and (b) a heavy chain comprising an amino acid sequence of SEQ ID NO:220. In some embodiments, the antibody or antigen-binding fragment thereof comprises: (a) a light chain comprising an amino acid sequence of SEQ ID NO:143; and (b) a heavy chain comprising an amino acid sequence of SEQ ID NO:221. In some embodiments, the antibody or antigen-binding fragment thereof comprises: (a) a light chain comprising an amino acid sequence of SEQ ID NO:143; and (b) a heavy chain comprising an amino acid sequence of SEQ ID NO:142. In some embodiments, the antibody or antigen-binding fragment thereof comprises: (a) a light chain comprising an amino acid sequence of SEQ ID NO:143; and (b) a heavy chain comprising an amino acid sequence of SEQ ID NO:204. In some embodiments, the antibody or antigen-binding fragment thereof comprises: (a) a light chain comprising an amino acid sequence of SEQ ID NO:143; and (b) a heavy chain comprising an amino acid sequence of SEQ ID NO:222. In some embodiments, the antibody or antigen-binding fragment thereof comprises: (a) a light chain comprising an amino acid sequence of SEQ ID NO:200; and (b) a heavy chain comprising an amino acid sequence of SEQ ID NO:223. In some embodiments, the antibody or antigen-binding fragment thereof comprises: (a) a light chain comprising an amino acid sequence of SEQ ID NO:200; and (b) a heavy chain comprising an amino acid sequence of SEQ ID NO:207. In some embodiments, the antibody or antigen-binding fragment thereof comprises: (a) a light chain comprising an amino acid sequence of SEQ ID NO:208; and (b) a heavy chain comprising an amino acid sequence of SEQ ID NO:117. In some embodiments, the antibody or antigen-binding fragment thereof comprises: (a) a light chain comprising an amino acid sequence of SEQ ID NO:209; and (b) a heavy chain comprising an amino acid sequence of SEQ ID NO:110. In some embodiments, the antibody or antigen-binding fragment thereof comprises: (a) a light chain comprising an amino acid sequence of SEQ ID NO:210; and (b) a heavy chain comprising an amino acid sequence of SEQ ID NO:148.

In certain embodiments, the antibody or antigen-binding fragment thereof comprises: (a) a light chain comprising an amino acid sequence selected from the group consisting of SEQ ID NOS:143, 200, 202, 208, 209, and 210; and (b) a heavy chain comprising an amino acid sequence selected from the group consisting of SEQ ID NOS:212, 213, 214, 215, 216, 217, 218, 219, 220, 221, 142, 204, 222, 223, 207, 117, 110, 148, 119, 98, 120, 112, 205, 106, 118, and 111.

In some embodiments, the antibody or antigen-binding fragment thereof, when bound to SIRPα, binds to at least one of residues 67-98 within an amino acid sequence of SEQ ID NO:146. In certain embodiments, the antibody or antigen-binding fragment thereof, when bound to SIRPα, binds to at least one of residues 67-74 within an amino acid sequence of SEQ ID NO:146. In some embodiments, the antibody or antigen-binding fragment thereof, when bound to SIRPα, binds to at least one of residues 93-98 within an amino acid sequence of SEQ ID NO:146. In some embodiments, the antibody or antigen-binding fragment thereof, when bound to SIRPα, binds to at least one of residues 30-93 within an amino acid sequence of SEQ ID NO:146.

In some embodiments, the antibody or antigen-binding fragment thereof, when bound to SIRPα, binds to at least one residue selected from the group consisting of L30, I36, Q52, T67, R69, F74, K93, R95, K96, and S98 within an amino acid sequence of SEQ ID NO:146. In some embodiments, the antibody or antigen-binding fragment thereof, when bound to SIRPα, binds to L30 within an amino acid sequence of SEQ ID NO:146. In some embodiments, the antibody or antigen-binding fragment thereof, when bound to SIRPα, binds to I36 within an amino acid sequence of SEQ ID NO:146. In some embodiments, the antibody or antigen-binding fragment thereof, when bound to SIRPα, binds to Q52 within an amino acid sequence of SEQ ID NO:146. In some embodiments, the antibody or antigen-binding fragment thereof, when bound to SIRPα, binds to T67 within an amino acid sequence of SEQ ID NO:146. In some embodiments, the antibody or antigen-binding fragment thereof, when bound to SIRPα, binds to R69 within an amino acid sequence of SEQ ID NO:146. In some embodiments, the antibody or antigen-binding fragment thereof, when bound to SIRPα, binds to F74 within an amino acid sequence of SEQ ID NO:146. In some embodiments, the antibody or antigen-binding fragment thereof, when bound to SIRPα, binds to K93 within an amino acid sequence of SEQ ID NO:146. In some embodiments, the antibody or antigen-binding fragment thereof, when bound to SIRPα, binds to R95 within an amino acid sequence of SEQ ID NO:146. In some embodiments, the antibody or antigen-binding fragment thereof, when bound to SIRPα, binds to K96 within an amino acid sequence of SEQ ID NO:146. In some embodiments, the antibody or antigen-binding fragment thereof, when bound to SIRPα, binds to S98 within an amino acid sequence of SEQ ID NO:146. In some embodiments, the antibody or antigen-binding fragment thereof, when bound to SIRPα, binds to T67, R69, R95, K96, and S98 within an amino acid sequence of SEQ ID NO:146.

In certain embodiments, the antibody or antigen-binding fragment thereof reduces binding between SIRPα and CD47. In some embodiments, the antibody or antigen-binding fragment thereof reduces binding between SIRPα and CD47, wherein the SIRPα comprises a haplotype in the IgV domain selected from the group consists of SEQ ID NOS:149, 150, 151, 152, 153, and 154. In some embodiments, the antibody or antigen-binding fragment thereof reduces CD47 binding to each of 6 SIRPα haplotypes, wherein the 6 SIRPα haplotypes consist of SIRPα v1, SIRPα v2, SIRPα v3, SIRPα v4, SIRPα v5, and SIRPα v6, and wherein SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, the antibody or antigen-binding fragment thereof reduces binding between SIRPα and CD47, wherein the reduction in CD47-SIRPα binding is 50%, 60%, 70%, 80%, 90%, 95%, or 99%.

In certain embodiments, the antibody or antigen-binding fragment thereof reduces binding between SIRPα and CD47, wherein the $EC_{50}$ of the antibody or antigen-binding fragment thereof for reducing CD47-SIRPα binding is from about 1 pM to about 10 pM, from about 10 pM to about 100 pM, from about 100 pM to about 1 nM, from about 1 nM to about 10 nM, or from about 10 nM to about 100 nM. In other embodiments, the antibody or antigen-binding fragment thereof reduces binding between SIRPα and CD47, wherein the $EC_{50}$ of the antibody or antigen-binding fragment thereof for reducing CD47-SIRPα binding is about 2 nM, about 2.1 nM, about 2.2 nM, about 2.3 nM, about 2.4 nM, about 2.5 nM, about 2.6 nM, about 2.7 nM, about 2.8 nM, about 2.9 nM, about 3 nM, about 3.1 nM, about 3.2 nM, about 3.3 nM, about 3.4 nM, about 3.5 nM, about 3.6 nM, about 3.7 nM, about 3.8 nM, about 3.9 nM, about 4.0 nM, about 4.1 nM, about 4.2 nM, about 4.3 nM, about 4.4 nM, about 4.5 nM, about 4.6 nM, about 4.7 nM, about 4.8 nM, about 4.9 nM, about 5.0 nM, about 5.1 nM, about 5.2 nM, about 5.3 nM, about 5.4 nM, about 5.5 nM, about 5.6 nM, about 5.7 nM, about 5.8 nM, about 5.9 nM, or about 6.0 nM.

In some embodiments, the anti-SIRPα antibody or antigen-binding fragment thereof provided herein achieves about 100% or about or at least 95%, 90%, 85%, 80%, or 75% SIRPα receptor occupancy in about 24 hours after administration into a patient. In some embodiments, the anti-SIRPα antibody or antigen-binding fragment thereof provided herein achieves about or at least 95% SIRPα receptor occupancy in about 6, 12, 24, 36, 48, 60, or 72 hours after administration into a patient. In some embodiments, the anti-SIRPα antibody or antigen-binding fragment thereof provided herein achieves about or at least 90% SIRPα receptor occupancy in about 6, 12, 24, 36, 48, 60, or 72 hours after administration into a patient. In some embodiments, the anti-SIRPα antibody or antigen-binding fragment thereof provided herein achieves about or at least 85% SIRPα receptor occupancy in about 6, 12, 24, 36, 48, 60, or 72 hours after administration into a patient. In some embodiments, the anti-SIRPα antibody or antigen-binding fragment thereof provided herein achieves about or at least 80% SIRPα receptor occupancy in about 6, 12, 24, 36, 48, 60, or 72 hours after administration into a patient. In some embodiments, the anti-SIRPα antibody or antigen-binding fragment thereof provided herein achieves about or at least 75% SIRPα receptor occupancy in about 6, 12, 24, 36, 48, 60, or 72 hours after administration into a patient. In some embodiments, the anti-SIRPα antibody or antigen-binding fragment thereof provided herein achieves about 100% SIRPα receptor occupancy in about 24 hours after administration into a patient and maintains about 100% occupancy for about or at least 6, 12, 24. 36, 48, 60, 72, 84, or 96 more hours. In some embodiments, the anti-SIRPα antibody or antigen-binding fragment thereof provided herein achieves about or at least 95% SIRPα receptor occupancy in about 24 hours after administration into a patient and maintains about or at least 95% occupancy for about or at least 6, 12, 24, 36, 48, 60, 72, 84, or 96 more hours. In some embodiments, the anti-SIRPα antibody or antigen-binding fragment thereof provided herein achieves about or at least 90% SIRPα receptor occupancy in 24 hours after administration into a patient and maintains about or at least 90% occupancy for about or at least 6, 12, 24, 36. 48, 60, 72, 84, or 96 more hours. In some embodiments, the anti-SIRPα antibody or antigen-binding fragment thereof provided herein achieves about or at least 85% SIRPα receptor occupancy in about 24 hours after administration into a patient and maintains about or at least 85% occupancy for about or at least 6, 12, 24, 36, 48, 60, 72, 84, or 96 more hours. In some embodiments, the anti-SIRPα antibody or antigen-binding fragment thereof provided herein achieves about or at least 80% SIRPα receptor occupancy in about 24 after administration into a patient and maintains about or at least 80% occupancy for about or at least 6, 12, 24, 36, 48, 60, 72, 84, or 96 more hours. In some embodiments, the anti-SIRPα antibody or antigen-binding fragment thereof provided herein achieves about 100%, about or at least 95%, about or at least 90%, about or at least 85%, or about or at least 80% SIRPα receptor occupancy in about 24 after administration into a patient and maintains about or at least 80% occupancy for about or at least 6, 12, 24, 36, 48, 60, 72, 84, or 96 more hours. In some embodiments, the anti-SIRPα antibody or antigen-binding fragment thereof provided herein achieves about 100%, about or at least 95%, about or at least 90%, about or at least 85%, or about or at least 80% SIRPα receptor occupancy in about 24 after administration into a patient and maintains about or at least 95%, about or at least 90%, about or at least 85%, or about or at least 80% occupancy for about or at least 6, 12, 24, 36, 48, 60, 72, 84, or 96 more hours. In some embodiments, the anti-SIRPα antibody or antigen-binding fragment thereof provided herein achieves about 100%, about or at least 95%, about or at least 90%, about or at least 85%, or about or at least 80% SIRPα receptor occupancy in about 24 after administration into a patient and maintains about or at least 95%, about or at least 90%, about or at least 85%, or about or at least 80% occupancy for about or at least 24 more hours. In some embodiments, the anti-SIRPα antibody or antigen-binding fragment thereof provided herein achieves about 100%, about or at least 95%, about or at least 90%, about or at least 85%, or about or at least 80% SIRPα receptor occupancy in about 24 after administration into a patient and maintains about or at least 80% occupancy for another 24 hours. In some embodiments, the anti-SIRPα antibody or antigen-binding fragment thereof provided herein achieves about 100% SIRPα receptor occupancy in about 24 hours after administration into a patient and maintains about 80% occupancy for about or at least 24 more hours. In some embodiments, the anti-SIRPα antibody or antigen-binding fragment thereof provided herein achieves about or at least 95% SIRPα receptor occupancy in about 24 hours after administration into a patient and maintains about or at least 80% occupancy for about or at least 24 more hours. In some embodiments, the anti-SIRPα antibody or antigen-binding fragment thereof provided herein achieves about or at least 90% SIRPα receptor occupancy in 24 hours after administration into a patient and maintains about or at least 80% occupancy for about or at least 24 more hours. In some embodiments, the anti-SIRPα antibody or antigen-binding fragment thereof provided herein achieves about or at least 85% SIRPα receptor occupancy in about 24 hours after administration into a patient and maintains about or at least 80% occupancy for about or at least 24 more hours. In some embodiments, the anti-SIRPα antibody or antigen-binding fragment thereof provided herein achieves about or at least 80% SIRPα receptor occupancy in about 24 after administration into a patient and maintains about or at least 80% occupancy for about or at least 24 more hours. In some embodiments, the receptor occupancy provided in this paragraph can be achieved and/or maintained as provided in this paragraph with a single dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, or 3.0 mg/kg of an anti-SIRPα antibody or antigen-binding fragment thereof provided herein. In some embodiments, the receptor occupancy provided in this paragraph can be achieved and/or maintained as provided in this paragraph with a single dose of 25 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, or 4000 mg of an anti-SIRPα antibody or antigen-binding fragment thereof provided herein.

In another embodiment, the antibody or antigen-binding fragment thereof specifically binds to one or more of 6 SIRPα haplotypes, wherein the 6 SIRPα haplotypes consist of SIRPα v1, SIRPα v2, SIRPα v3, SIRPα v4, SIRPα v5, and SIRPα v6, and wherein SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain. In some embodiments, the antibody or antigen-binding fragment thereof binds to each of the 6 SIRPα haplotypes. In other embodiments, the antibody or antigen-binding fragment thereof binds to each of the 6 SIRPα haplotypes with a dissociation constant ($K_D$) of no more than 5 nM.

In certain embodiments, the antibody or antigen-binding fragment thereof binds to purified SIRPα v1 with a $K_D$ of no more than 0.2 nM. In some embodiments, the antibody or antigen-binding fragment thereof binds to purified SIRPα v1 with a dissociation constant ($K_D$) about 0.13 nM. In certain embodiments, the antibody or antigen-binding fragment thereof binds to purified SIRPα v2 with a $K_D$ of no more than 5 nM. In some embodiments, the antibody or antigen-binding fragment thereof binds to purified SIRPα v2 with a $K_D$ of about 4.4 nM. In certain embodiments, the antibody or antigen-binding fragment thereof binds to purified SIRPα v3 with a $K_D$ of no more than 0.2 nM. In some embodiments, the antibody or antigen-binding fragment thereof binds to purified SIRPα v3 with a $K_D$ of about 0.15 nM. In certain embodiments, the antibody or antigen-binding fragment thereof binds to purified SIRPα v4 with a $K_D$ of no more than 2 nM. In some embodiments, the antibody or antigen-binding fragment thereof binds to purified SIRPα v4 with a $K_D$ of about 1.5 nM. In certain embodiments, the antibody or antigen-binding fragment thereof binds to purified SIRPα v5 with a $K_D$ of no more than 0.7 nM. In some embodiments, the antibody or antigen-binding fragment thereof binds to purified SIRPα v5 with a $K_D$ of about 0.6 nM. In certain embodiments, the antibody or antigen-binding fragment thereof binds to purified SIRPα v6 with a $K_D$ of no more than 0.2 nM. In some embodiments, the antibody or antigen-binding fragment thereof binds to purified SIRPα v6 with a $K_D$ of about 0.18 nM.

In other embodiments, the antibody or antigen-binding fragment thereof binds to human SIRPα expressed on a cell with an $EC_{50}$ from about 1 pM to about 10 pM, from about 10 pM to about 100 pM, from about 100 pM to about 1 nM, from about 1 nM to about 10 nM, or from about 10 nM to about 100 nM. In certain embodiments, the antibody or antigen-binding fragment thereof binds to human SIRPα expressed on a cell with an $EC_{50}$ of about 2 nM, about 2.1 nM, about 2.2 nM, about 2.3 nM, about 2.4 nM, about 2.5 nM, about 2.6 nM, about 2.7 nM, about 2.8 nM, about 2.9 nM, about 3 nM, about 3.1 nM, about 3.2 nM, about 3.3 nM, about 3.4 nM, about 3.5 nM, about 3.6 nM, about 3.7 nM, about 3.8 nM, about 3.9 nM, about 4.0 nM, about 4.1 nM, about 4.2 nM, about 4.3 nM, about 4.4 nM, about 4.5 nM, about 4.6 nM, about 4.7 nM, about 4.8 nM, about 4.9 nM, about 5.0 nM, about 5.1 nM, about 5.2 nM, about 5.3 nM, about 5.4 nM, about 5.5 nM, about 5.6 nM, about 5.7 nM, about 5.8 nM, about 5.9 nM, or about 6.0 nM.

In some embodiments, the antibody or antigen-binding fragment thereof specifically binds to human SIRPα and/or monkey SIRPα, but not rodent SIRPα. In certain embodiments, the antibody or antigen-binding fragment thereof binds to cynomolgus (cyno) SIRPα expressed on a cell with an $EC_{50}$ from about 1 pM to about 10 pM, from about 10 pM to about 100 pM, from about 100 pM to about 1 nM, from about 1 nM to about 10 nM, or from about 10 nM to about 100 nM. In some embodiments, the antibody or antigen-binding fragment thereof binds to binds to cyno SIRPα expressed on a cell with an $EC_{50}$ of about 2 nM, about 2.1 nM, about 2.2 nM, about 2.3 nM, about 2.4 nM, about 2,5 nM, about 2.6 nM, about 2.7 nM, about 2.8 nM, about 2.9 nM, about 3 nM, about 3.1 nM, about 3.2 nM, about 3.3 nM, about 3.4 nM, about 3.5 nM, about 3.6 nM, about 3.7 nM, about 3.8 nM, about 3.9 nM, about 4.0 nM, about 4.1 nM, about 4.2 nM, about 4.3 nM, about 4.4 nM, about 4.5 nM, about 4.6 nM, about 4.7 nM, about 4.8 nM, about 4.9 nM, about 5.0 nM, about 5.1 nM, about 5.2 nM, about 5.3 nM, about 5.4 nM, about 5.5 nM, about 5.6 nM, about 5.7 nM, about 5.8 nM, about 5.9 nM, or about 6.0 nM.

In some embodiments, the antibody or antigen-binding fragment thereof increases phagocytosis of cancer cells by co-cultured macrophages as compared to that by untreated macrophages or by macrophages treated with a control isotype antibody. In some embodiments, the antibody or antigen-binding fragment thereof increases phagocytosis of cancer cells by co-cultured macrophages as compared to that by untreated macrophages or by macrophages treated with a control isotype antibody, wherein the antibody or antigen-binding fragment thereof is used as a single therapeutic agent.

In certain embodiments, the antibody or antigen-binding fragment thereof increases phagocytosis of cancer cells by co-cultured macrophages as compared to that by untreated macrophages or by macrophages treated with a control isotype antibody, wherein the antibody or antigen-binding fragment thereof is used in combination with a second therapeutic agent. In some embodiments, the second therapeutic agent is cetuximab or rituximab. In one embodiment, the second therapeutic agent is cetuximab. In another embodiment, the second. therapeutic agent is rituximab.

In certain embodiments, the antibody or antigen-binding fragment thereof increases phagocytosis of cancer cells by co-cultured macrophages as compared to that by untreated macrophages or by macrophages treated with a control isotype antibody, wherein SIRPα is expressed on the macrophage, the cancer cells, or both the macrophage and the cancer cells. In some embodiments, the SIRPα on the macrophage and/or the cancer cells is one or more of 6 SIRPα haplotypes, wherein the 6 SIRPα haplotypes consist of SIRPα v1, SIRPα v2, SIRPα v3, SIRPα v4, SIRPα v5, and SIRPα v6, and wherein SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, the antibody or antigen-binding fragment thereof increases a minimal percentage of phagocytotic macrophages in a population of macrophages to about 10%, 70%, 30%, 40%, 45%, 50%, 55%, 60%, 65%, 70%, 75%, 80%, 85%, 90%, 95%, or 99%. In other embodiments, the antibody or antigen-binding fragment thereof increases phagocytosis of the macrophage by about 10%, 20%, 30%, 40%, 45%, 50%, 55%, 60%, 65%, 70%, 75%, 80%, 85%, 90%, 95%, 100%, 125%, 150%, 175%, 200%, 250%, 300%, 400%, 500%, 600%, 700%, 800%, 900% or 1000%, as compared to untreated macrophages or macrophages treated with a control isotype antibody.

In certain embodiments, the antibody or antigen-binding fragment thereof increases phagocytosis of cancer cells by co-cultured macrophages as compared to that by untreated macrophages or by macrophages treated with a control isotype antibody, wherein the cancer cells are from colorectal cancer, head and neck squamous cell carcinoma, acute myeloid leukemia, or diffuse large B-cell lymphoma (DLBCL). In some embodiments, the antibody or antigen-binding fragment thereof increases phagocytosis of cancer cells by co-cultured macrophages as compared to that by untreated macrophages or by macrophages treated with a control isotype antibody, wherein the cancer cells are from non-Hodgkin's lymphoma (NHL) such as DLBCL, follicular lymphoma, marginal zone lymphoma, and mantle cell lymphoma. In other embodiments, the antibody or antigen-binding fragment thereof increases phagocytosis of cancer cells by co-cultured macrophages as compared to that by untreated macrophages or by macrophages treated with a control isotype antibody, wherein the cancer cells are from Grade 1 follicular lymphoma, Grade 2 follicular lymphoma, Grade 3a follicular lymphoma, Grade 3b follicular lymphoma, relapsed follicular lymphoma (including e.g. Grade 1, 2, 3a and 3b), refractory follicular lymphoma (including e.g. Grade 1, 2, 3a and 3b), relapsed DLBCL, or refractory DLBCL.

In certain embodiments, the antibody or antigen-binding fragment thereof synergizes with a second therapeutic agent in increasing phagocytosis of cancer cells by co-cultured macrophages as compared to that by untreated macrophages or by macrophages treated with a control isotype antibody. In some embodiments, the second therapeutic agent is cetuximab or rituximab. In one embodiment, the second therapeutic agent is cetuximab. In another embodiment, the second therapeutic agent is rituximab.

In some embodiments, the antibody or antigen-binding fragment thereof synergizes with a second therapeutic agent in increasing phagocytosis of cancer cells by co-cultured macrophages as compared to that by untreated macrophages or by macrophages treated with a control isotype antibody, wherein SIRPα is expressed on the macrophage, the cancer cells, or both the macrophage and the cancer cells. In some embodiments, the SIRPα on the macrophage and/or the cancer cells is one or more of 6 SIRPα haplotypes, wherein the 6 SIRPα haplotypes consist of SIRPα v1, SIRPα v2, SIRPα v3, SIRPα v4, SIRPα v5, and SIRPα v6, and wherein SIRPα V1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In certain embodiments, the difference between the percentage of the phagocytotic macrophages synergistically induced and the sum of the phagocytotic percentage induced by the antibody or antigen-binding fragment and the second therapeutic agent separately is about 10%, 15%, 20%, 25%, 30%, 35%, 40%, 45%, 50%, 55%, 60%, 65%, or 70%. In other embodiments, the antibody or antigen-binding fragment and the second therapeutic agent synergistically increase the percentage of the phagocytotic macrophages over the sum of the phagocytotic percentage induced by the antibody or antigen-binding fragment and the second therapeutic agent separately by about 10%, 20%, 30%, 40%, 45%, 50%, 55%, 60%, 65%, 70%, 75%, 80%, 85%, 90%, 95%, 100%, 125%, 150%, 175%, 2 00%, 250%, 300%, or 400%.

In some embodiments, the antibody or antigen-binding fragment and the second therapeutic agent synergistically increase phagocytosis of cancer cells, wherein the cancer cells are from colorectal cancer, head and neck squamous cell carcinoma, acute myeloid leukemia, or DLBCL. In some embodiments, the antibody or antigen-binding fragment and the second therapeutic agent synergistically increase phagocytosis of cancer cells, wherein the cancer cells are from NHL such as DLBCL, follicular lymphoma, marginal zone lymphoma, and mantle cell lymphoma. In other embodiments, the antibody or antigen-binding fragment and the second therapeutic agent synergistically increase phagocytosis of cancer cells, wherein the cancer cells are from Grade 1 follicular lymphoma, Grade 2 follicular lymphoma, Grade 3a follicular lymphoma, Grade 3b follicular lymphoma, relapsed follicular lymphoma (including e.g. Grade 1, 2, 3a and 3b), refractory follicular lymphoma (including e.g. Grade 1, 2, 3a and 3b), relapsed DLBCL, or refractory DLBCL.

In some embodiments, the antibody or antigen-binding fragment thereof has attenuated ADCC activity as compared to an isotype control antibody, attenuated ADCP activity as compared to an isotype control antibody, and/or attenuated CDC activity as compared to an isotype control antibody. In some embodiments, the antibody or antigen-binding fragment thereof has attenuated ADCC activity as compared to an isotype control antibody. In certain embodiments, the maximal ADCC activity of the antibody or antigen-binding fragment thereof is no more than about 5%, 10%, 20%, 30%, or 40% cytotoxicity as measured by the percentage of target cells killed. In some embodiments, the antibody or antigen-binding fragment thereof has attenuated ADCP activity as compared to an isotype control antibody. In other embodiments, the maximal ADCP activity of the antibody or antigen-binding fragment thereof is no more than about 5%, 10%, 20%, or 30% of phagocytotic macrophages targeting autologous T cells and/or monocytes. In some embodiments, antibody or antigen-binding fragment thereof has attenuated CDC activity as compared to an isotype control antibody. In another embodiment, the $EC_{50}$ of the antibody or antigen-binding fragment thereof in a CDC assay is at least 100 µM.

In some embodiments, the antibody or antigen-binding fragment thereof does not induce cytokine release more than a level of cytokine release induced by an isotype control antibody.

In some embodiments, provided herein is an antibody. In other embodiments, provided herein is an antigen-binding fragment of the antibody.

In some embodiments, the antibody or antigen-binding fragment thereof is a monoclonal antibody. In certain embodiments, the antibody or antigen-binding fragment thereof is a humanized, human, or chimeric antibody. In some embodiments, the antibody or antigen-binding fragment thereof is a deimmunized antibody or a composite human antibody. In other embodiments, the antibody or antigen-binding fragment thereof is a Fab, a Fab', a $F(ab')_2$, a Fv, a scFv, a dsFv, a diabody, a triabody, a tetrabody, or a multispecific antibody formed from antibody fragments.

In certain embodiments, the antibody or antigen-binding fragment thereof is conjugated to an agent. In some embodiments, the agent conjugated to the antibody or antigen-binding fragment thereof is selected from the group consisting of a radioisotope, a metal chelator, an enzyme, a fluorescent compound, a bioluminescent compound, and a chemiluminescent compound.

In another aspect, provided herein is a composition comprising an antibody or antigen-binding fragment thereof provided herein, and a pharmaceutically acceptable carrier.

In one aspect, provided herein is a polynucleotide comprising nucleic acid sequences encoding an antibody provided herein. In some embodiments, provided herein is a polynucleotide comprising nucleic acid sequences encoding an antigen binding fragment of an antibody provided herein.

In another aspect, provided herein is a polynucleotide comprising nucleic acid sequences encoding an antibody or antigen-binding fragment thereof that binds to SIRPα, wherein the antibody or antigen-binding fragment thereof comprises: (a) VL CDR1, VL CDR2, and VL CDR3 of any one of antibodies SIRPAB-11, SIRPAB-12, SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, or SIRPAB-13 as set forth in Table 1; and/or (b) VH CDR1, VH CDR2, and VH CDR3 of any one of antibodies SIRPAB-11, SIRPAB-12, SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, SIRPAB-12, or SIRPAB-13 as set forth in Table 2. In some embodiments, provided herein is a polynucleotide comprising nucleic acid sequences encoding an antibody or antigen-binding fragment thereof that binds to SIRPα, wherein the antibody or antigen-binding fragment thereof comprises: (a) a VL further comprising a VL FR1, VL FR2, VL FR3, and VL FR4 of any one of antibodies SIRPAB-11, SIRPAB-12, SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, or SIRPAB-13 as set forth in Table 3; and/or (b) a VH FR1, VH FR2, VH FR3, and VH FR4 of any one of antibodies SIRPAB-11, SIRPAB-12, SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, or SIRPAB-13 as set forth in Table 4.

In yet another aspect, provided herein is a polynucleotide comprising nucleotide sequences encoding a VH, a VL, or both a VH and a VL of the antibody or antigen-binding fragment thereof provided herein. In some embodiments, the polynucleotide comprising nucleotide sequences encoding a heavy chain, a light chain, or both a heavy chain and a light chain of an antibody provided herein, In certain embodiments, the polynucleotide is operably linked to a promoter.

In some aspects, provide herein is a vector comprising the polynucleotide disclosed herein.

In other aspects, provided herein is a cell comprising the polynucleotide disclosed herein. In another aspect, provided herein is a cell comprising a vector disclosed herein. In other embodiments, the disclosure provides an isolated cell producing the antibody or antigen-binding fragment thereof provided herein.

In some aspect, the disclosure also provides a kit comprising the antibody or antigen-binding fragment thereof provided herein.

In one aspect, provided herein is a method of making an antibody or antigen-binding fragment thereof provided herein that specifically binds to an epitope of human SIRPα, comprising culturing a cell provided herein to express the antibody or antigen-binding fragment thereof. In some embodiments, the method of making an antibody or antigen-binding fragment thereof comprises expressing the polynucleotide provided herein.

In another aspect, provided herein is a method of increasing phagocytosis by a macrophage, wherein the method comprises contacting the macrophage with an effective amount of an antibody or antigen binding fragment thereof provided herein, whereby the phagocytosis by a macrophage is increased as compared to that by untreated macrophages or by macrophages treated with a control isotype antibody. In certain embodiments of the methods, the phagocytotic activity by the macrophage is increased by about 10%, 20%, 30%, 40%, 45%, 50%, 55%, 60%, 65%, 70%, 75%, 80%, 85%, 90%, 95%, 100%, 125%, 150%, 175%, 200%, 250%, 300%, 400%, 500%, 600%, 700%, 800%, 900% or 1000%.

In other aspect, provided herein is a method of increasing a percentage of phagocytotic macrophages in a population of macrophages, wherein the method comprises contacting the macrophages with an effective amount of an antibody or antigen binding fragment thereof described herein, whereby the percentage of phagocytotic macrophages in a population of macrophages is increased as compared to that by untreated macrophages or by macrophages treated with a control isotype antibody. In some embodiments of the method, the minimal percentage of phagocytotic macrophages in the population of macrophages is increased to about 10%, 20%, 30%, 40%, 45%, 50%, 55%, 60%, 65%, 70%, 75%, 80%, 85%, 90%, 95%, or 99%.

In one aspect, provided herein is a method of increasing phagocytosis of cancer cells by a population of macrophages, wherein the method comprises contacting the cancer cells, the macrophages, or both the cancer cells and the macrophages with an effective amount of an antibody or antigen binding fragment thereof provided herein, whereby the phagocytosis of cancer cells by a population of macrophages is increased as compared to that by untreated macrophages or by macrophages treated with a control isotype antibody. In certain embodiments of the methods of increasing phagocytosis of cancer cells by a population of macrophages, the minimal percentage of phagocytotic macrophages in the population of macrophages is increased to about 10%, 20%, 30%, 40%, 45%, 50%, 55%, 60%, 65%, 70%, 75%, 80%, 85%, 90%, 95%, or 99%.

In some embodiments of the methods, the phagocytosis by macrophages is measured by co-culturing macrophages labeled with a first fluorescent dye and cancer cells labeled with a second fluorescent dye, wherein the first fluorescent dye and the second fluorescent dye are different. In certain embodiments of the methods, the percentage of phagocytotic macrophages is measured by determining the percentage of macrophages comprising cancer cells.

In another aspect, provided herein is a method of increasing phagocytosis of cancer cells in a subject, wherein the method comprises administering an effective amount of an antibody or antigen binding fragment thereof provided herein to the subject, whereby the phagocytosis of cancer cells in a subject is increased as compared to that in an untreated subject or in subject treated with an isotype control antibody.

In certain aspect, provided herein is a method of increasing elimination of cancer cells by phagocytosis in a subject, wherein the method comprises administering an effective amount of an antibody or antigen binding fragment thereof provided herein to the subject.

In some aspect, the disclosure also provides a method of targeting cancer cells for immunodepletion in a subject, wherein the method comprises administering an effective amount of an antibody or antigen binding fragment thereof provided herein to the subject.

In one additional aspect, the disclosure also provides a method of treating a cancer in a subject, wherein the method comprises administering an effective amount of an antibody or antigen binding fragment thereof provided herein to the subject.

In some embodiments of the various methods provided herein, the cancer is selected from the group consisting of colorectal cancer, head and neck squamous cell carcinoma, acute myeloid leukemia, and DLBCL. In some embodiments of the various methods provided herein, the cancer is NHL such as DLBCL, follicular lymphoma, marginal zone lymphoma, and mantle cell lymphoma. In certain embodiments of the various methods provided herein, the cancer is selected from the group consisting of Grade 1 follicular lymphoma, Grade 2 follicular lymphoma, Grade 3a follicular lymphoma, Grade 3b follicular lymphoma, relapsed follicular lymphoma (including e.g. Grade 1, 2, 3a and 3b), refractory follicular lymphoma (including e.g. Grade 1, 2, 3a and 3b), relapsed DLBCL, or refractory DLBCL. In other embodiments of the methods, the cancer cells, the macrophages, or both the cancer cells and the macrophages in the methods expresses SIRPα.

In certain embodiments of the various methods provided herein, the cancer cells, the macrophages, or both the cancer cells and the macrophages express SIRPα, wherein SIRPα is one or more of 6 SIRPα haplotypes selected from the group consisting of SIRPα v1, SIRPα v2, SIRPα v3, SIRPα v4, SIRPα v5, and SIRPα v6. In certain embodiments, the SIRPα v1 comprises SEQ ID NO:149 in the IgV-domain. In some embodiments, the SIRPα v2 comprises SEQ ID NO:150 in the IgV-domain. In one embodiment, the SIRPα v3 comprised SEQ ID NO:151 in the IgV-domain. In other embodiments, the SIRPα v4 comprises SEQ ID NO:152 in the IgV-domain. In some embodiments, the SIRPα v5 comprises SEQ ID NO:153 in the IgV-domain. In other embodiments, the SIRPα v6 comprises SEQ ID NO:154 in the IgV-domain.

In other embodiments of the methods provided herein, the antibody or antigen-binding fragment thereof is coadministered with a second therapeutic agent. In some embodiments of the methods, the second therapeutic agent is cetuximab or rituximab. In one embodiment, the second therapeutic agent is cetuximab. In another embodiment, the second therapeutic agent is rituximab.

In certain embodiments of the methods provided herein, the subject is selected from the group consisting of a human, a monkey, a mouse, a dog, and a rat. In a specific embodiment, the subject is a human.

3. BRIEF DESCRIPTION OF THE FIGURES

FIG. 1 shows a summary of an anti-SIRPα antibody generation, screening, identification, and affinity maturation scheme.

Figure 2:
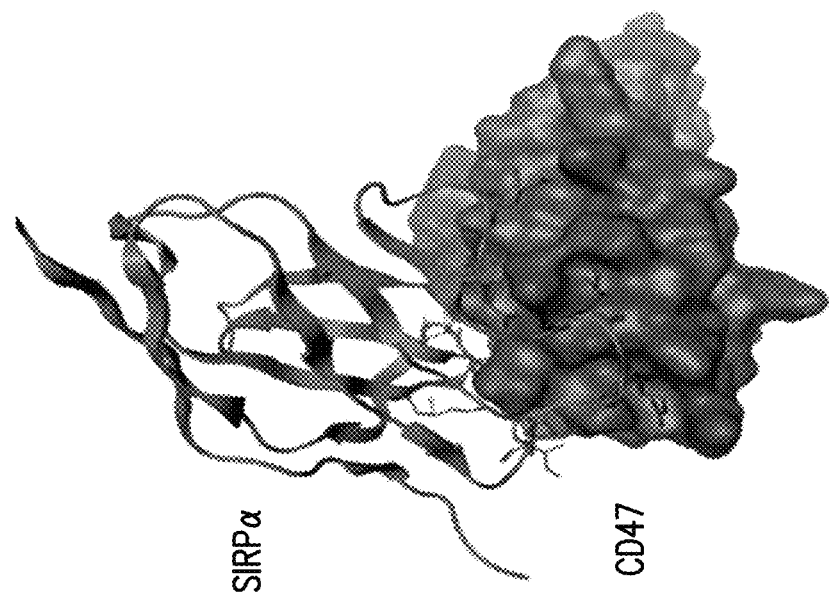
Figure 2:
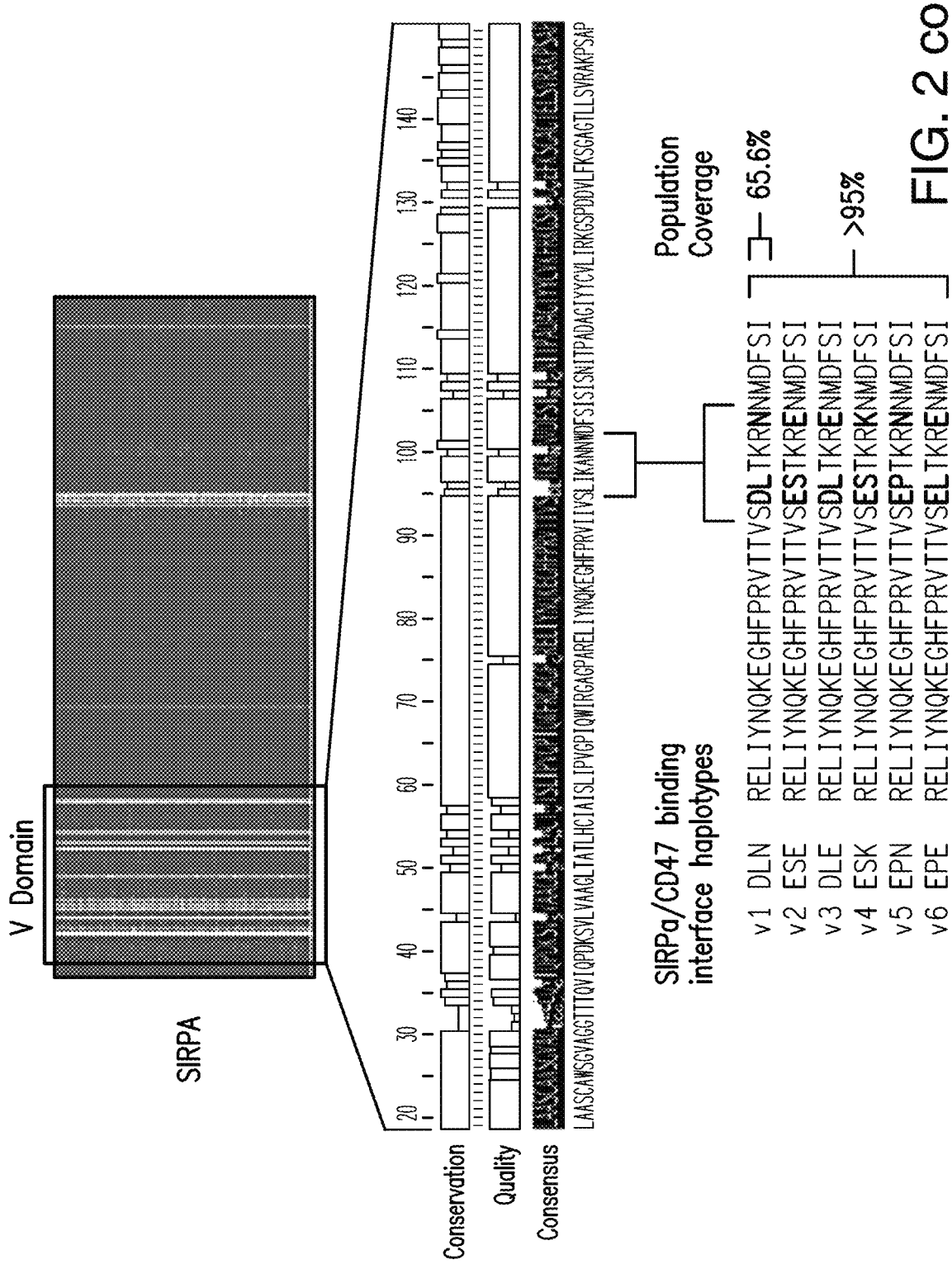

FIG. 2 shows identification of the most prevalent SIRPα polymorphisms surrounding the CD47:SIRPα Interface. DLN=the most prevalent SIRPα polymorphisms surrounding the CD47:SIRPα interface. Amino acid residues in red correspond to differences identified covering approximately 95% of the SIRPα polymorphisms in the CD47-SIRPα binding interface in human population. Particularly, the depicted sequences are v1 DLN (SEQ ID NO:149), v2 ESE (SEQ ID NO:150), v3 DLE (SEQ ID NO:151), v4 ESK (SEQ ID NO:152), v5 EPN (SEQ ID NO:153), and v6 ELE (SEQ ID NO:154), respectively.

Figure 3:
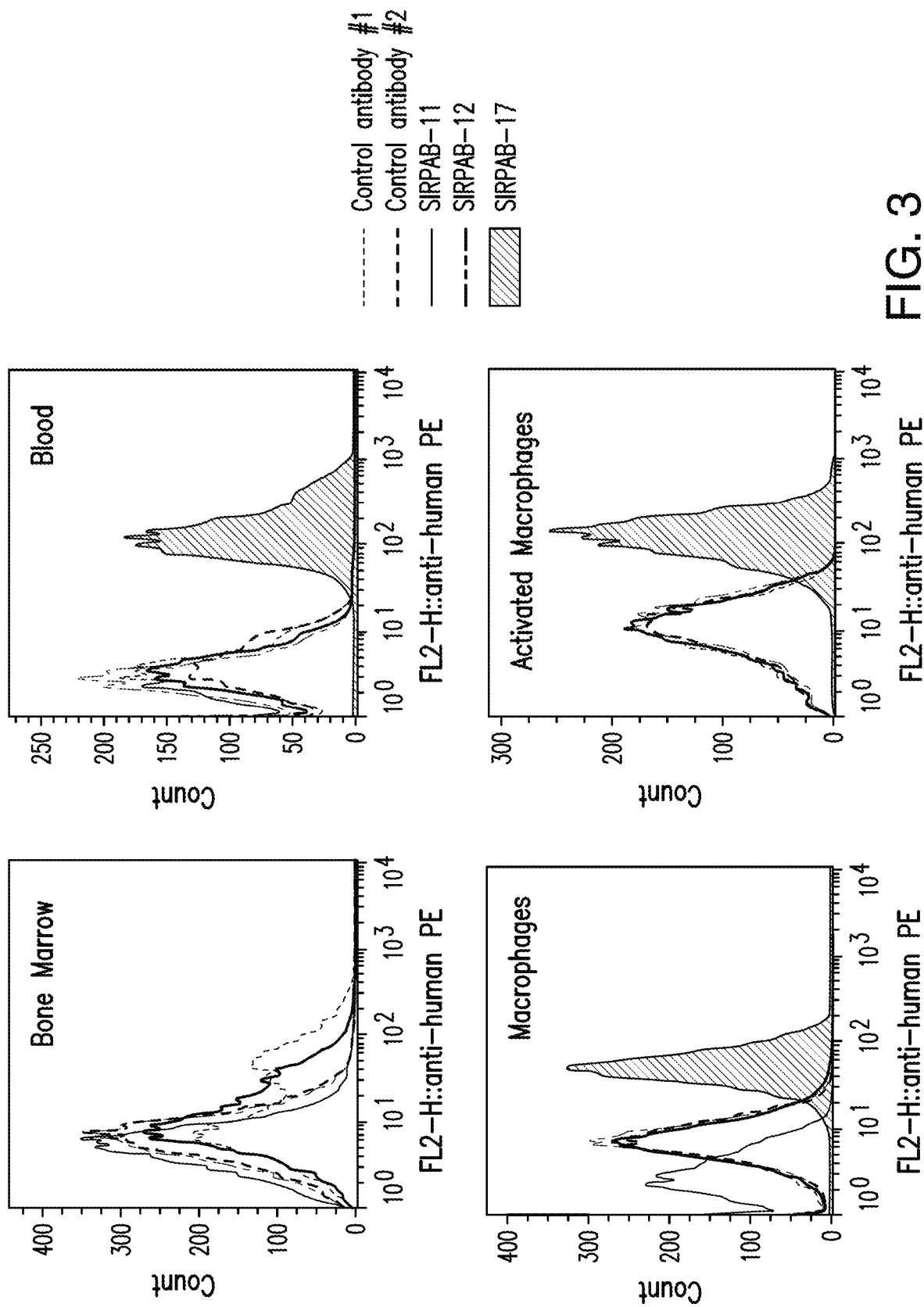
Figure 4A:
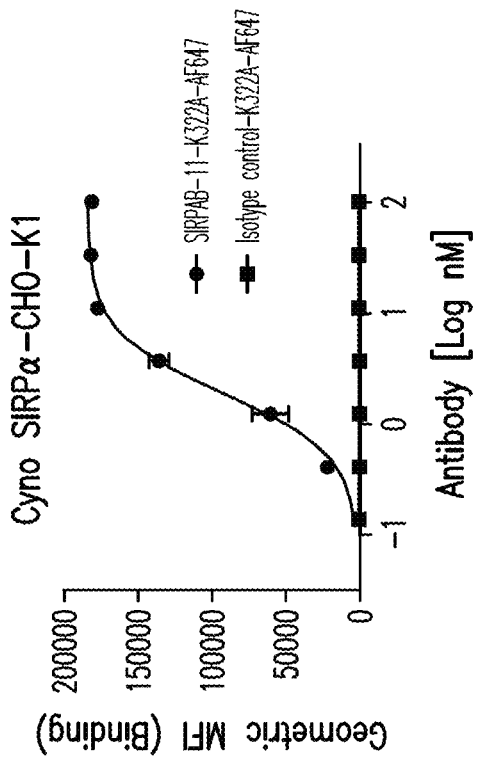
Figure 4B:
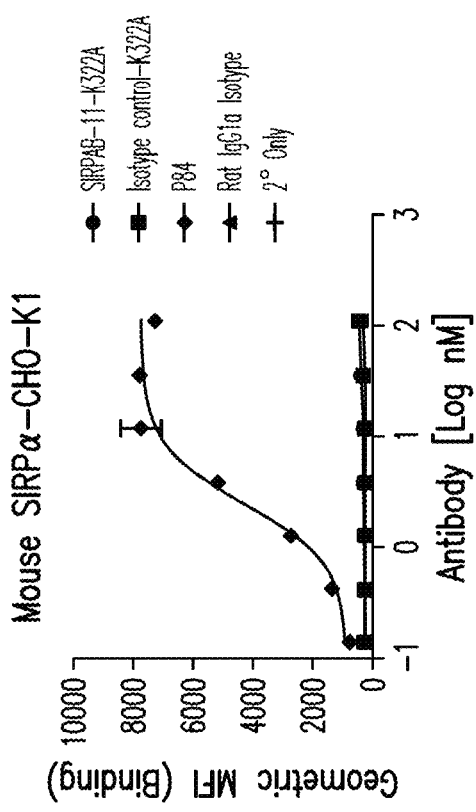
Figure 4C:
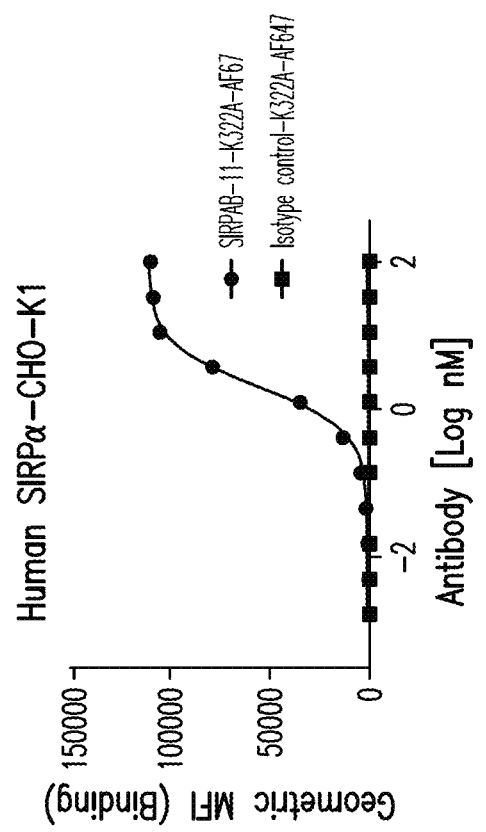
Figure 4D:
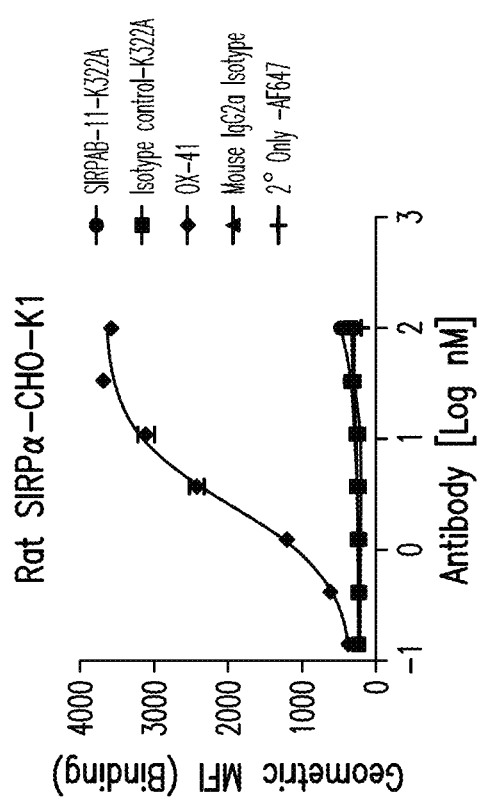

FIG. 3 shows binding of mouse CD11b positive cell with several SIRPα antibodies, demonstrating that antibodies SIRPAB-11 and SIRPAB-12 do not bind to mouse SIRPα; whereas SIRPAB-17 binds to mouse SIRPα.

FIGS. 4A-4D show SIRPAB-11 binding to human and cynomolgus macaque SIRPα-overexpressing Chinese Hamster Ovary K1 cells, but not to rodent SIRPα-overexpressing cells, and the determination of SIRPAB-11 binding $EC_{50}$. (4A) $EC_{50}$ of SIRPAB-11-K322A binding to human SIRPα ectopically expressed on CHO cells is 2.06 nM. (4B) $EC_{50}$ of SIRPAB-11-K322A binding to cyno SIRPα ectopically expressed on CHO cells is 1.9 nM. (4C) SIRPAB-11 does not bind to rat SIRPα-CHO-K1, as binding of SIRPAB-11 to rat SIRPα-CHO-K1 is only at a level comparable to that of an isotype control IgG; whereas the positive control, anti-rat-SIRPα antibody OX-41, demonstrates robust binding in the same assay. (4D) SIRPAB-11 does not bind to mouse SIRPα-CHO-K1, as binding of SIRPAB-11 to mouse SIRPα-CHO-K1 is only at a level comparable to that of an isotype control-IgG; whereas the positive control, anti-mouse-SIRPα antibody P84, demonstrates robust binding in the same assay. AF647=Alexa Fluor 647 nm; CHO=Chinese hamster ovary; cyno=cynomolgus macaque; Geometric MFI=geometric mean fluorescence intensity; K322A=immunoglobulin G1 with Lys322Ala.

FIGS. 5A-5F show the binding of anti-SIRPα antibodies to SIRPα expressing cells. (5A) Binding (manifested as co-staining) of primary human (left) and cynomolgus (right) CD14 positive population with SIRPAB-11-K322A. (5B) Binding profile of SIRPAB-11-K322A on human immune cell subsets in human peripheral blood mononuclear cells shown as level of SIRPAB-11-K322A binding to various immune cells as indicated. AF647=Alexa Fluor 647 nM; gMFI=geometric mean fluorescence intensity; ID=identification; NK cells=natural killer cells; NKT cells=natural killer T cells. (5C) Additional binding assays of primary human immune cell subsets with SIRPAB-11-K322A. (5D) Binding assays of primary cynomolgus immune cell subsets with SIRPAB-11-K322A. In (5C) and (5D), gMFI=geometric mean fluorescent intensity; mDC=myeloid dendritic cells; NK=natural killer; n.s=not significant; PBMC=peripheral blood mononuclear cell. (5E) Binding of SIRPAB-11-4PE antibody with two cynomolgus donors and the $EC_{50}$ of SIRPAB-11-4PE for binding to the two cynomolgus donors. (5F) Binding and affinity of SIRPAB-17, SIRPAB-19, SIRPAB-20, SIRPAB-21, and SIRPAB-18 to SIRPα expressing cells. SIRPAB-19, SIRPAB-20, and SIRPAB-21 bind to mouse SIRPα with the highest affinity. Binding of isotype antibody controls was also performed as a negative control.

Figure 6A:
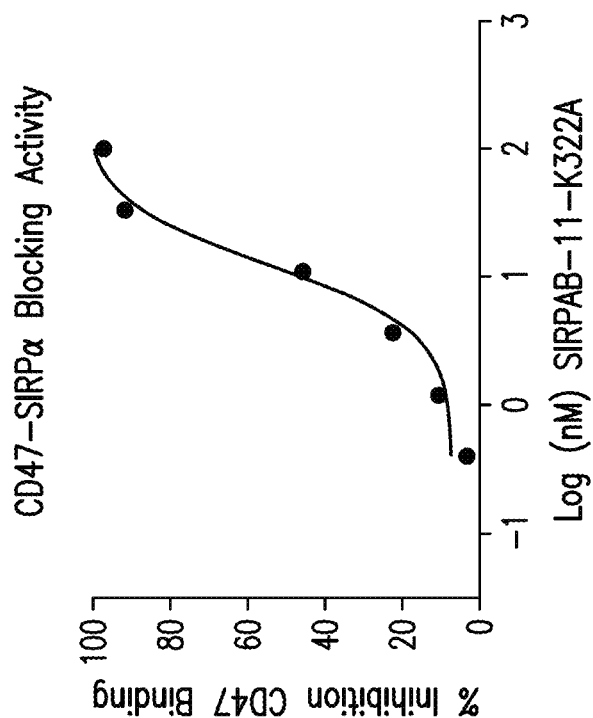
Figure 6B:
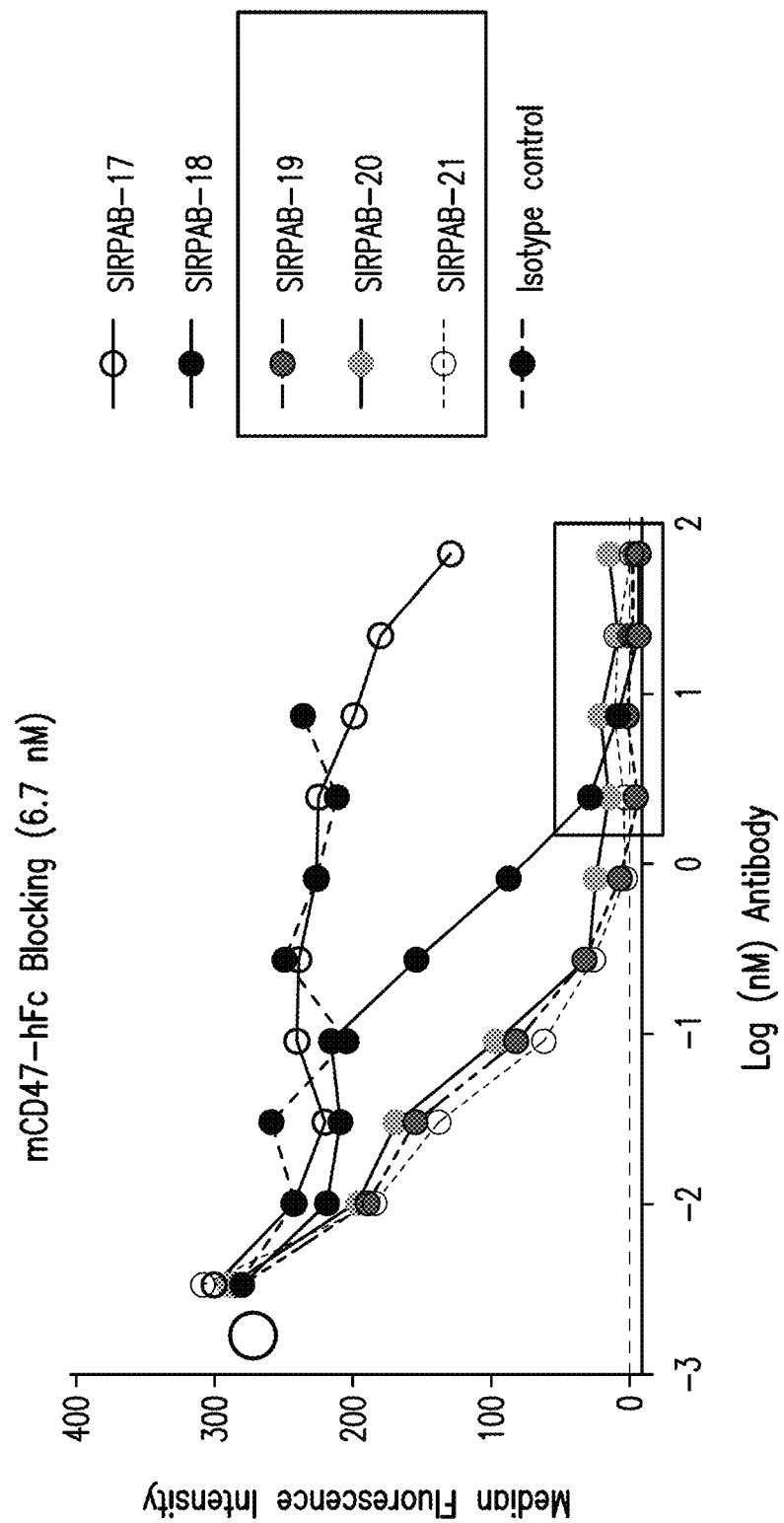

FIGS. 6A-6B show that anti-SIRPα antibody blocks binding between SIRPα and CD47. (6A) The $EC_{50}$ value of SIRPAB-11-K322A in blocking the interaction between CD47-extracellular domain and SIRPα as determined in Biacore. CD=cluster of differentiation; nM=nanomolar; RU=refractive unit. (6B) Blocking activity of anti-mouse-SIRPα antibodies against the binding between recombinant mouse CD47 and C57/BL6 macrophages.

Figure 7A:
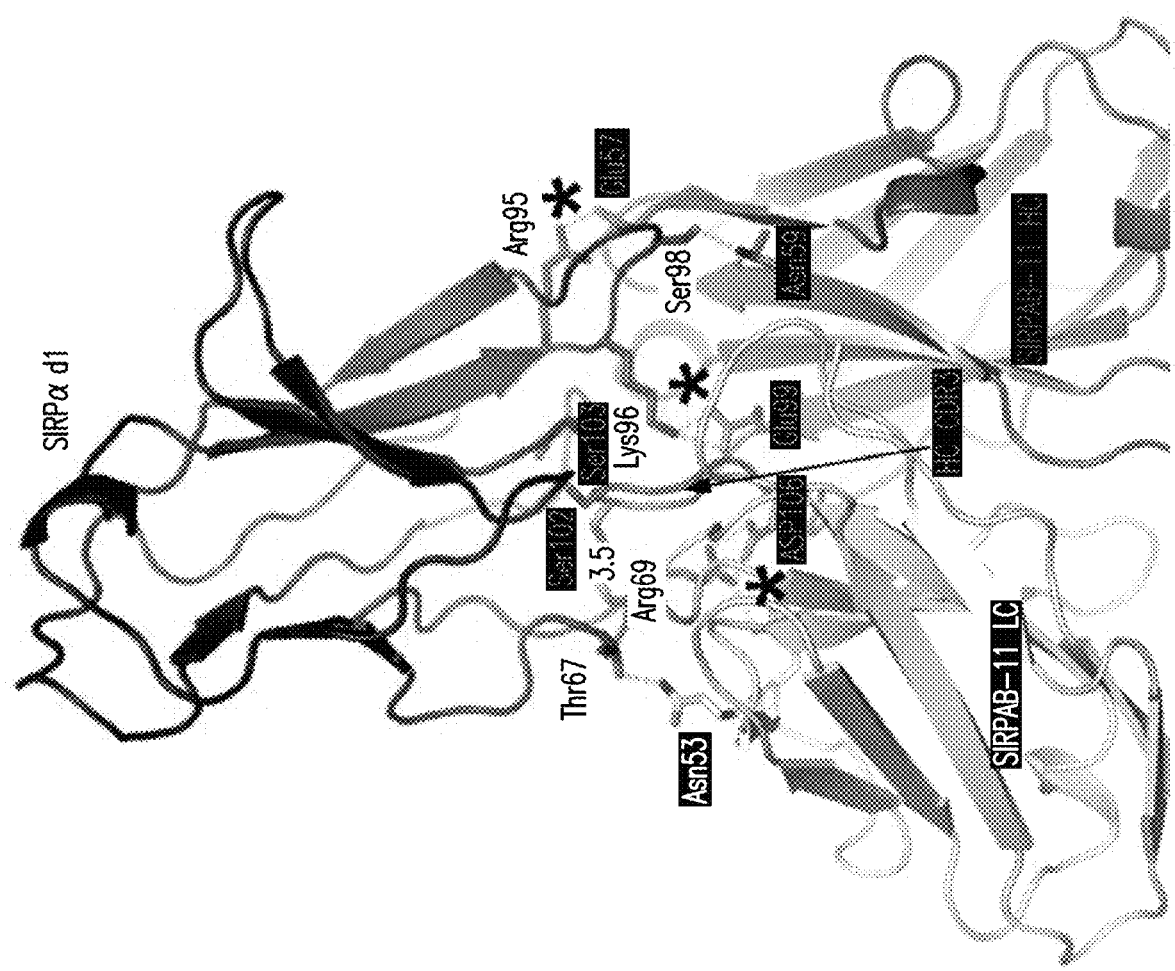
Figure 7B:
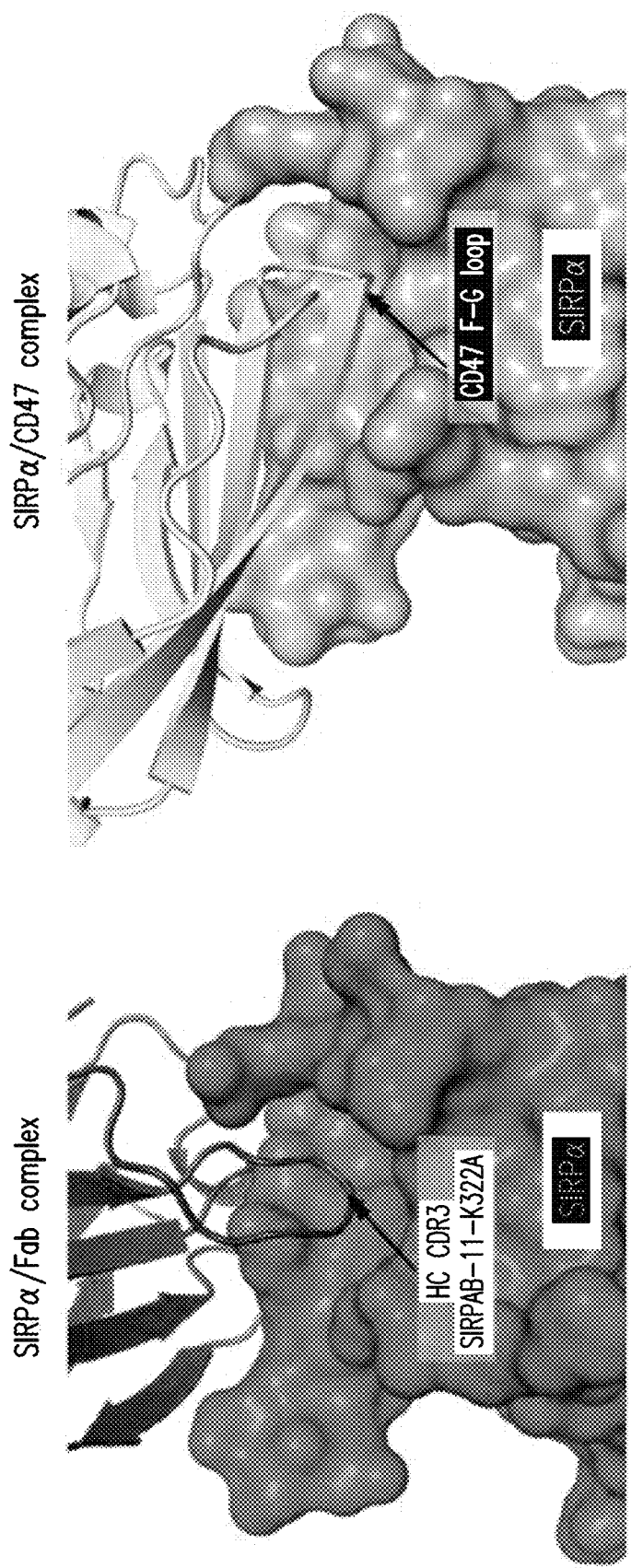

FIGS. 7A-7B show the crystal structure of SIRPAB-11-Fab bound to SIRPα domain 1. (7A) The crystal structure of SIRPAB-11-Fab bound to SIRPα domain 1 and the residues in SIRPα that interacts with SIRPAB-11-Fab. HC=heavy chain; LC=light chain. The SIRPAB-11-Fab HC (colored blue) from SIRPAB-11-Fab mediates most of the interactions (yellow dotted lines) with SIRPα (colored magenta), and displays a centrally located HC CDR3 (black arrow) that protrudes from the fragment antigen-binding surface and inserts into the SIRPα large pocket. Three key electrostatic interactions are observed and indicated by black asterisks. Additional interactions are also observed between SIRPAB-11-Fab LC (colored grey) and SIRPα. (7B) Comparison of the SIRPAB-11-Fab and CD47 interaction sites on SIRPα. Fab=fragment antigen-binding; HC=heavy chain. The HC CDR3 of SIRPAB-11-Fab (blue cartoon) occupies the same major pocket on SIRPα (magenta and orange surfaces) recognized by CD47 F-G loop (yellow cartoon). The LC of SIRPAB-11-Fab is omitted for clarity.

Figure 8:
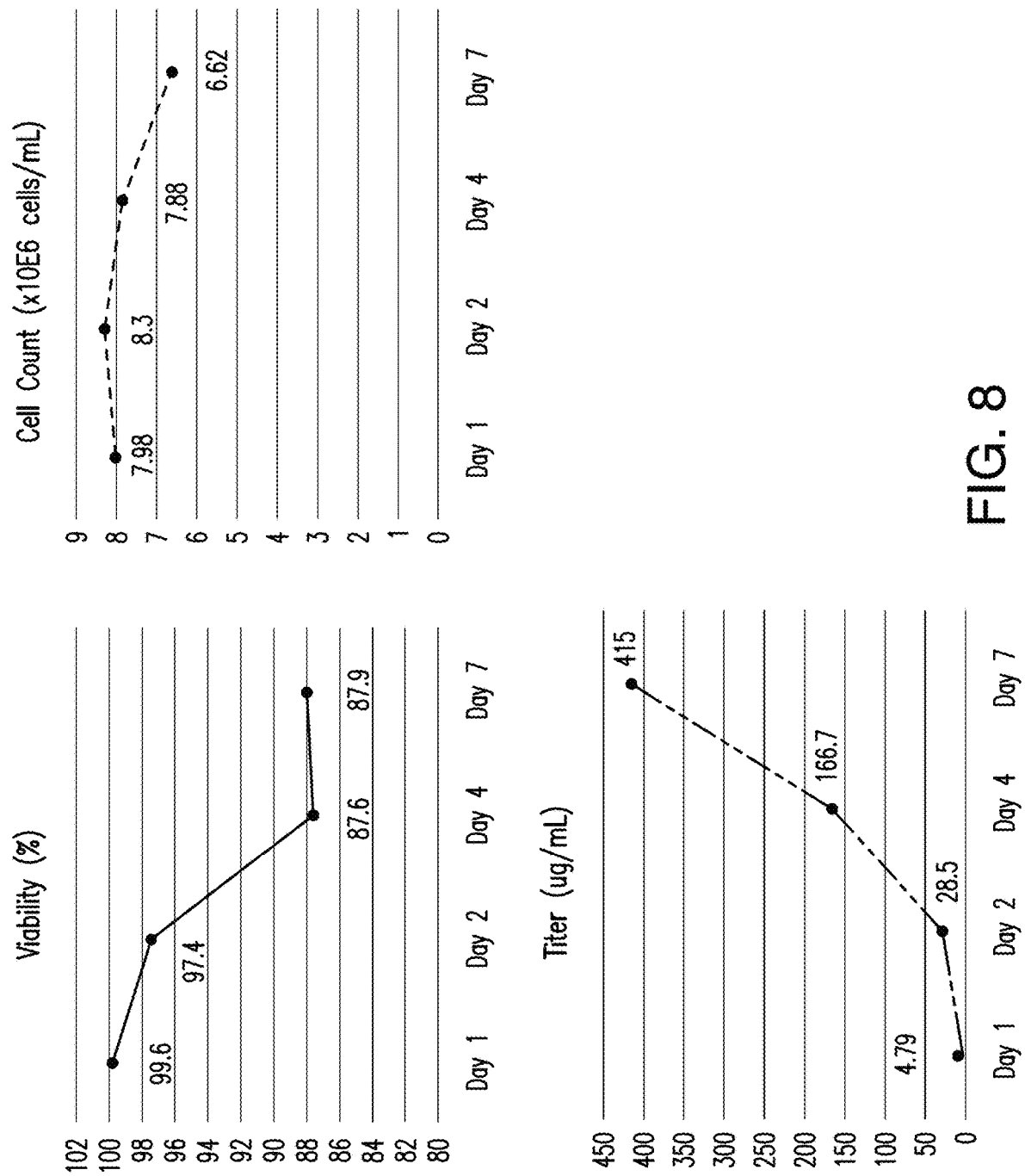

FIG. 8 shows cell growth and titer for production of SIRPAB-11-K322A in Expi Chinese Hamster Ovary cells.

FIGS. 9A-9K show antibody-dependent cellular cytotoxicity activity, complement-dependent activity, and antibody-dependent cellular phagocytosis activity of SIRPAB-11-K322A. (9A) SIRPAB-11 did not induce antibody-dependent cellular cytotoxicity of human MOLM-13 cell line expressing SIRPα. ADCC=antibody-dependent cellular cytotoxicity; G&P=G & P Biosciences; HuMy 9.6=humanized monoclonal antibody 9.6; IgG1=immunoglobulin G1; K322A=immunoglobulin G1 with Lys322Ala, MOLM-13=acute myeloid leukemia cell line. (9B) SIRPAB-11-K322A treatment did not induce antibody-dependent cellular cytotoxicity against autologous CD4 positive T cells in unactivated state. (9C) SIRPAB-11-K322A treatment did not induce antibody-dependent cellular cytotoxicity against autologous CD4 positive T cells in activated state. (9D) SIRPAB-11-K322A treatment did not induce antibody-dependent cellular cytotoxicity against autologous CD8 positive T cells in unactivated state. (9E) SIRPAB-11-K322A treatment did not cause antibody-dependent cellular cytotoxicity against autologous CD8 positive T cells in activated state. (9F) and (9G) SIRPAB-11-K322A treatment did not induce antibody-dependent cellular cytotoxicity against autologous monocytes as measured by flow cytometry (9F) and by Mirrorball fluorescent cytometry (9G). In (9B) to (9G), Ab=antibody; ADCC=antibody-dependent cellular cytotoxicity; CD=cluster of differentiation; Fc=fragment crystallizable; IgG=immunoglobulin; K322A=immunoglobulin G1 with Lys322Ala; Max=maximum; NK=natural killer cells. (9H) and (9I) Lack of complement-dependent activity mediated by SIRPAB-11 fragment crystallizable variants in the presence of rabbit complement serum. IgG1=immunoglobulin G1; 4PE=immunoglobulin G4 with Ser228Pro and Leu235Glu mutations; mAb=monoclonal antibody; RLU=relative light unit; SIRPα=signal regulatory protein alpha. (9J) Macrophage phagocytosis of autologous T cells from Donor 224. (9K) Macrophage phagocytosis of autologous T cells from Donor 224. In (9J) and (9K), CD=cluster of differentiation; IgG1=immunoglobulin G1; K322A=immunoglobulin G1 with Lys322Ala; 4PE=immunoglobulin G4 with Ser228Pro and Leu235Glu mutations; SIRPα=signal regulatory protein alpha.

Figure 10A:
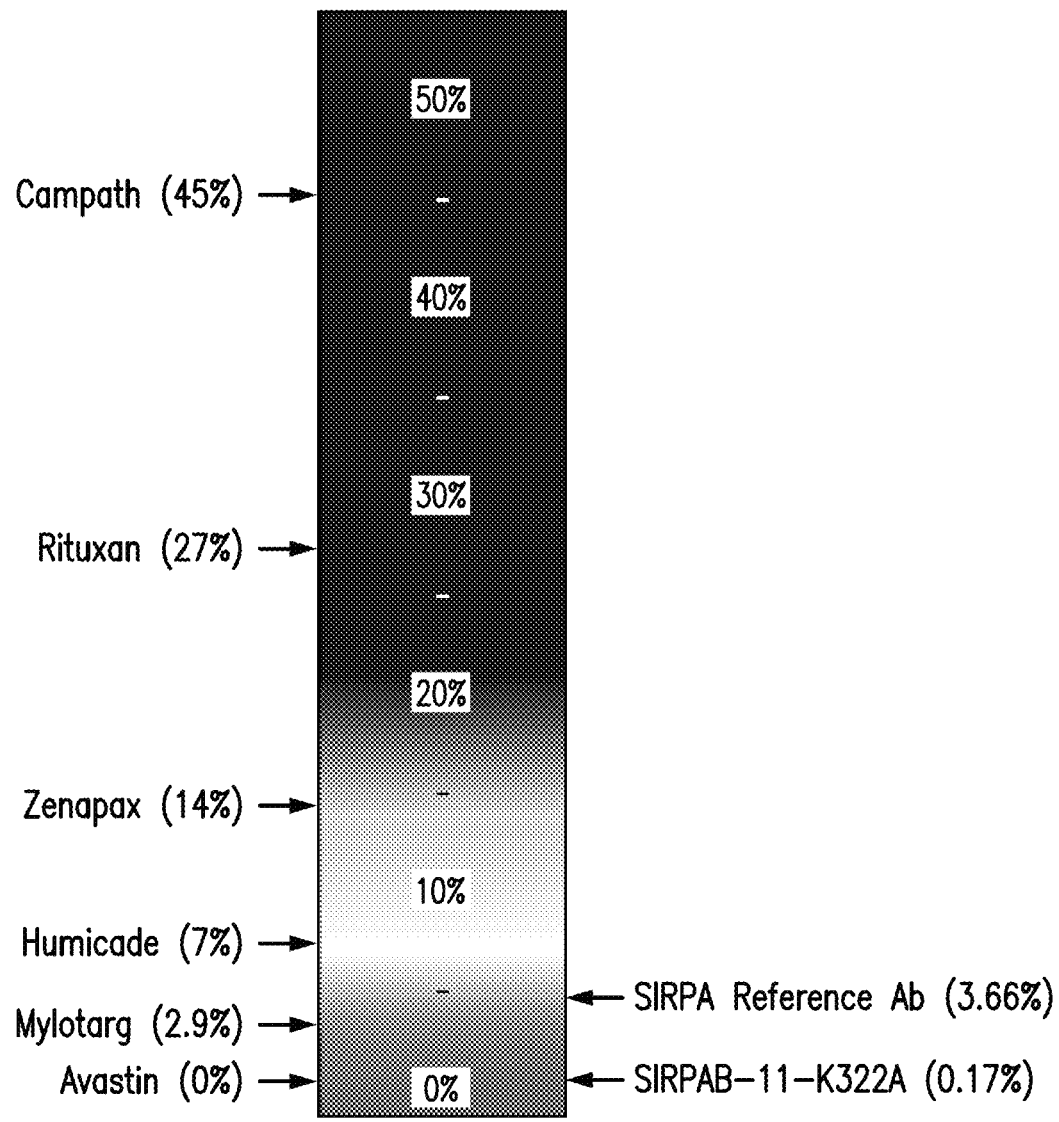

FIGS. 10A-10B show analysis of antibody immunogenicity. (10A) EpiMatrix Antibody Immunogenicity Scale, observed ADA responses in known antibodies, and predicted ADA responses in submitted VH/VL pairs of SIRPAB-11-K322A and a SIRPα reference antibody that has a light chain of an amino acid sequence of SEQ ID NO:224 and a heavy chain of an amino acid sequence of SEQ NO:225. All predictions are adjusted for the presence of Tregitopes. (10B) Antibody Immunogenicity Prediction SIRPAB-11-K322A.

FIGS. 11A-11J show the profile of cytokine release of human immune cells treated with SIRPAB-11. (11A) to (11I) Sample cytokine release assay data for cells treated with SIRPAB-11-K322A, including interleukin 1β (11A), interleukin 6 (11B), and tumor necrosis factor alpha (TNFα) (11C), interleukin 12p70 (11D), granulocyte macrophage colony-stimulating factor (GM-CSF) (11E), interleukin 2 (11F), interferon gamma (IFN-γ) (11G), interleukin 10 (11H), and interleukin 8 (11I). In (11A) to (11I), IgG1=immunoglobulin G1; IL=interleukin; PBMC=peripheral blood mononuclear cell. (11J) Summary of the cytokine release data from cells treated with SIRPAB-11-K322A and the related statistical analysis.

FIGS. 12A-12H show profile of cytokine release in SIRPAB-11-treated PBMC with or without additional stimulation. (12A) and (12B) SIRPAB-11-K322A did not induce interleukin-1β in peripheral blood mononuclear cells with (12B) or without (12A) lipopolysaccharide stimulation. In (12A) and (12B), IgG1=immunoglobulin G1; 1L-1β=Interleukin 1β; LPS=lipopolysaccharide; K322A=immunoglobulin G1 with Lys322Ala. (12C) Detailed results from (12A) and (12B). (12D), (12E) and (12F) Treatment of SIRPAB-11-K322A did not change the level of interferon in peripheral blood mononuclear cells with 1 ng/ml (12E), with 100 ng/ml (12F), or without (12D) staphylococcal enterotoxin b stimulation. In (12D), (12E) and (12F), IgG1=immunoglobulin G1; IFNγ=interferon gamma; K322A=immunoglobulin G1 with Lys322Ala; SEB=Staphylococcal Enterotoxin B. (12G) and (12H) Detailed results from (12E) and (12F), respectively.

FIGS. 13A-13I show the activity of SIRPAB-11 in increasing tumor phagocytosis either alone or in combination with a second antibody. (13A) to (13C) Surface levels of SIRPα (13A), CD47 (13B), and EGFR (13C) of the four cetuximab-resistant, KRAS mutant colorectal cancer cell lines by staining with SIRPAB-11-IgG4PE, anti-CD47, and anti-EGFR. (13D) to (13F) Evaluation of tumor phagocytosis mediated by SIRPAB-11-K322A alone or in combination with cetuximab in four KRAS mutant colorectal cancer cell lines, including GP5d (13D), GP2d (13E), and SW480 (13F). In (13D) to (13F), CD=cluster of differentiation; IgG1=immunoglobulin G1; K322A=immunoglobulin G1 with a lysine to alanine mutation at position 322. (13G) and (13H) Effect of cetuximab concentration on phagocytosis of KRAS mutant colorectal cancer cell lines GP2d (13G) and GP5d (13H). (13I) Evaluation of FaDu head and neck squamous cell carcinoma phagocytosis mediated by SIRPAB-11-K322A in combination with cetuximab. CD=cluster of differentiation; FaDu=head and neck squamous cell carcinoma cell line; IgG1=immunoglobulin G1.

Figure 14:
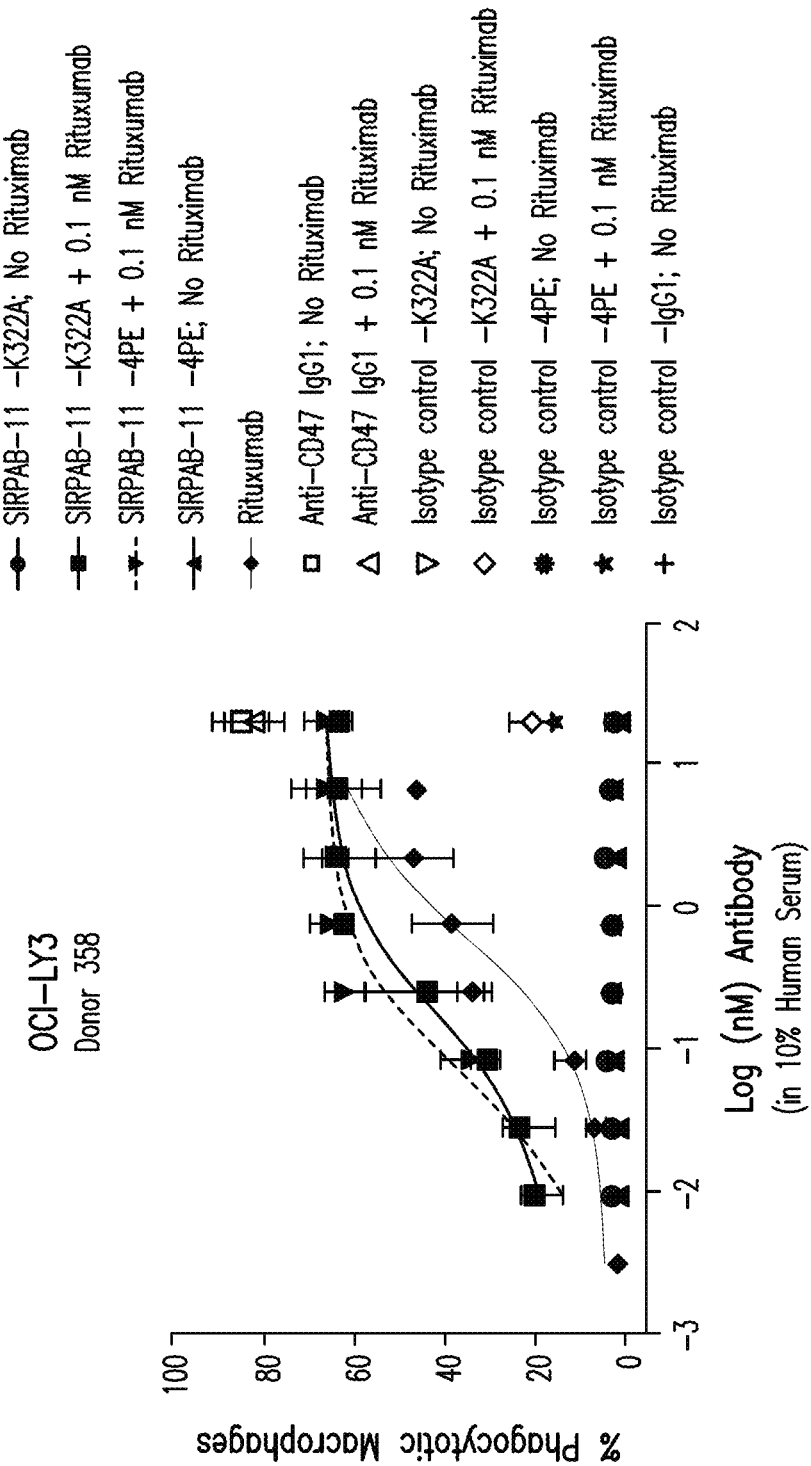

FIG. 14 shows evaluation of phagocytosis of DLBCL cells mediated by SIRPAB-11-K322A in combination with rituximab or SIRPAB-11-4PE in combination with rituximab. IgG1=immunoglobulin G1; K322A=immunoglobulin G1 with Lys322Ala.; OCI-LY3=DLBCL cell line.

FIGS. 15A-15F show the effect of SIRPAB-11 Fc variants as a single agent on phagocytosis of human cells and the effect of SIRPAB-11 Fc variants on mouse or cynomolgus macrophage phagocytosis. (15A) Effect of SIRPAB-11-K322A and SIRPAB-11-IgG4PE as a single agent in promoting phagocytosis activity targeting acute myeloid leukemia cell line MOLM-13. (15B) Effect of SIRPAB-11-K322A and SIRPAB-11-IgG4PE as a single agent in promoting phagocytosis activity targeting acute myeloid leukemia cell line OCI-AML2. (15C) Effect of SIRPAB-11-K322A and SIRPAB-11-IgG4PE as a single agent in promoting phagocytosis activity targeting acute myeloid leukemia cell Line MV-4-11. (15D) Effect of SIRPAB-11-K322A and SIRPAB-11-IgG4PE as a single agent in promoting phagocytosis activity targeting acute myeloid leukemia patient-derived xenograft P1202. (15E) Effect of SIRPAB-11-K322A and SIRPAB-11-IgG4PE as a single agent in promoting phagocytosis activity targeting acute myeloid leukemia patient-derived xenograft P5478. In (15A) to (15E), CD=cluster of differentiation; IgG=immunoglobulin G1; K322A=immunoglobulin G1 with Lys322Ala; 4PE=immunoglobulin G4 with Ser228Pro and Leu235Glu mutations; OCI-AML2=acute myeloid leukemia (AML) cell line. (15F) Effect of SIRPAB-11-K322A as a single agent in promoting phagocytosis activity of cynomolgus macrophages targeting acute myeloid leukemia cell line OCI-AML2. CD=cluster of differentiation; Hr=hour; IgG=immunoglobulin G1; K322A=immunoglobulin G1 with Lys322Ala; NS=not significant.

Figure 16A:
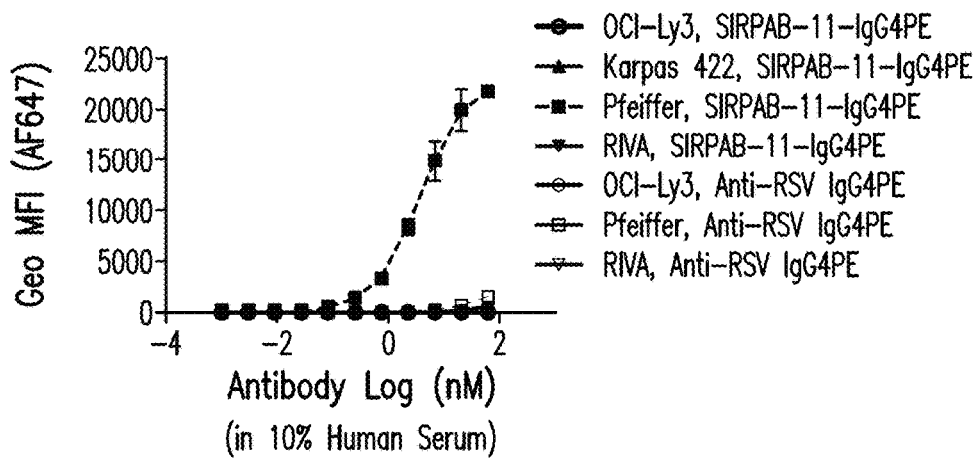
Figure 16B:
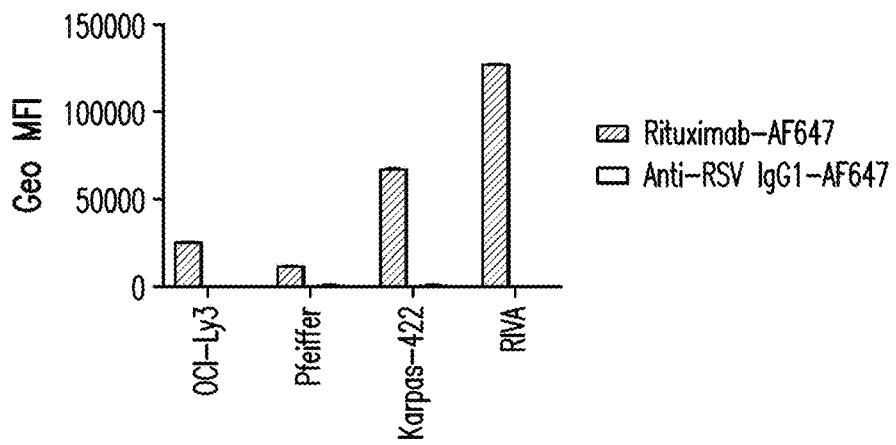
Figure 16C:
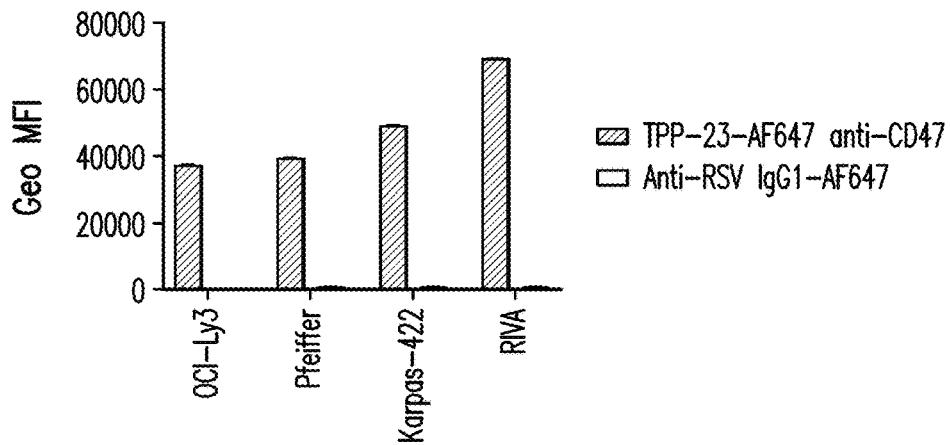

FIGS. 16A-16C show surface expression of (16A) SIRPα, (16B) CD20, and (16C) CD47 in OCI-LY3, RIVA, Karpas 422, and Pfeiffer cells. In FIGS. 16A-16C, AF647=Alexa Fluor 647; Geo MFI=geometric mean fluorescence intensity; IgG1=immunoglobulin G1; and RSV=respiratory syncytial virus.

Figure 17A:
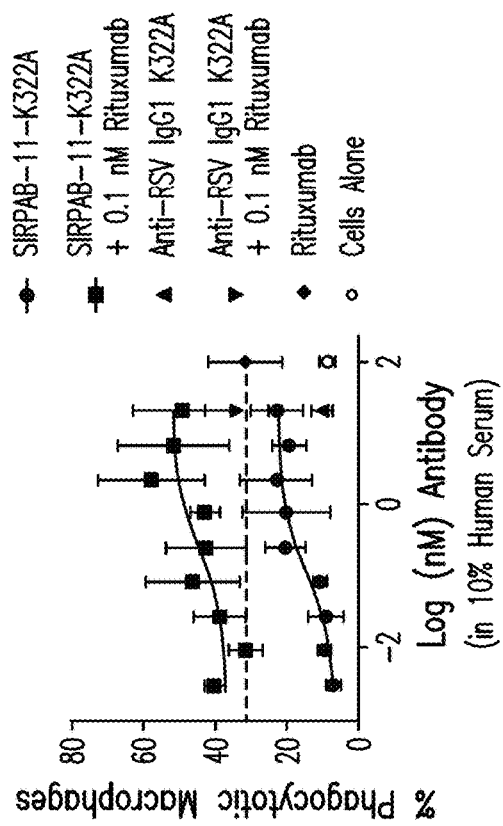
Figure 17B:
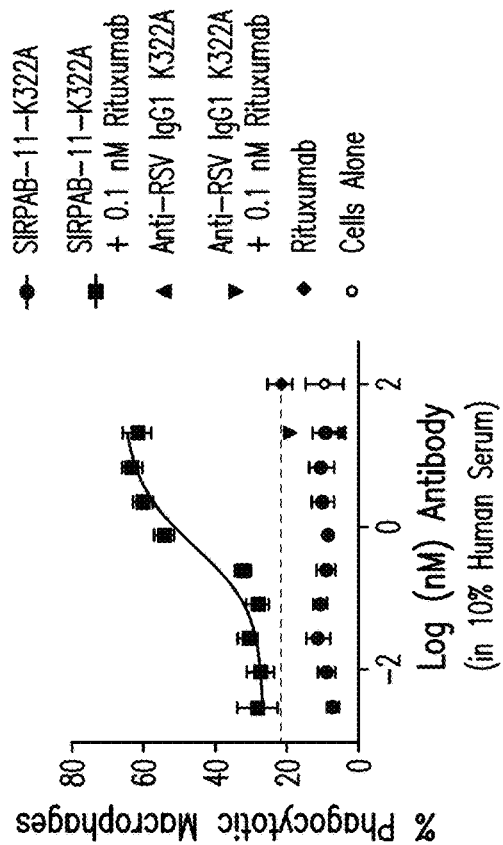
Figure 17C:
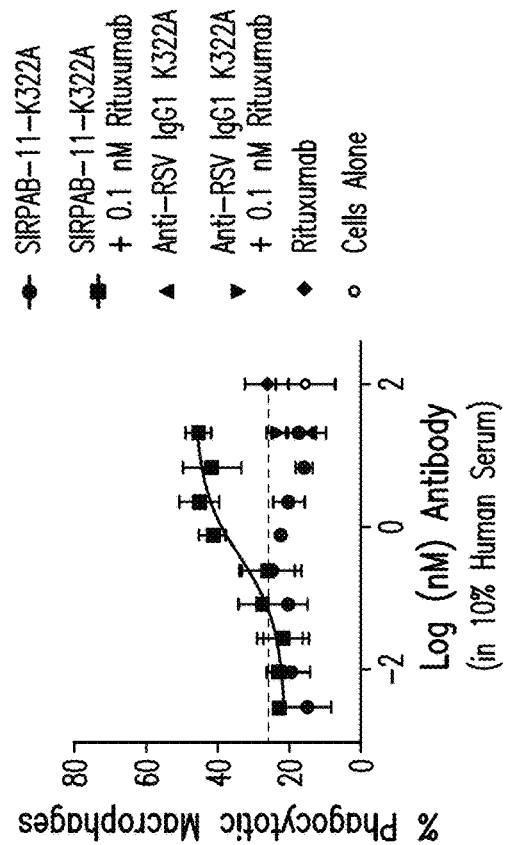

FIGS. 17A-17C show additional studies of phagocytosis of 3 DLBCL cells mediated by SIRPAB-11-K322A in combination with rituximab. Depicted are effects of SIRPAB-11-K322A as a single agent or in combination with rituximab in promoting phagocytosis activity targeting (17A) OCI-LY3 cells, (17B) RIVA cells, and (17C) Karpas 422 cells. IgG1 K322A=immunoglobulin G1 with Lys322Ala; nM=nanomolar; RSV=respiratory syncytial virus.

FIGS. 18A-18D show additional studies of phagocytosis of Pfeiffer cells mediated by SIRPAB-11-K322A in combination with rituximab. Depicted are effects of SIRPAB-11-K322A as a single agent or in combination with rituximab in promoting phagocytosis activity targeting Pfeiffer cells using macrophages from (18A) donor 1, (18B) donor 2, (18C) donor 3, and (18D) donor 4. IgG1 K322A=immunoglobulin G1 with Lys322Ala; nM=nanomolar; RSV=respiratory syncytial virus.

Figure 19B:
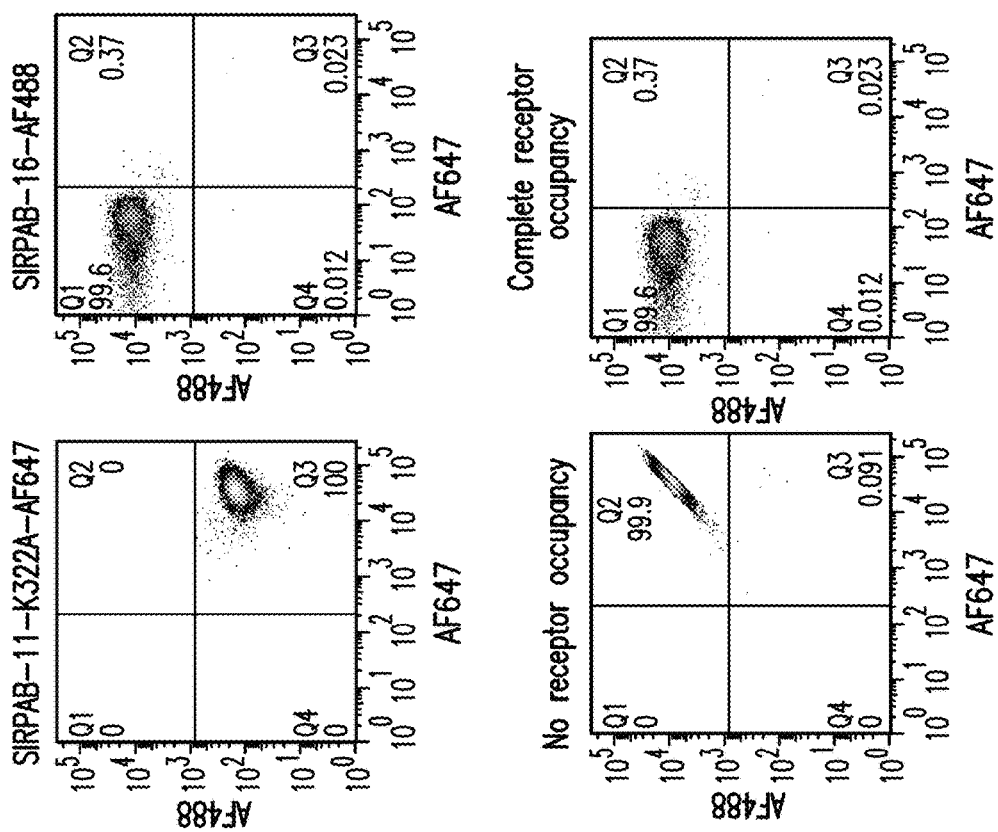
Figure 19A:
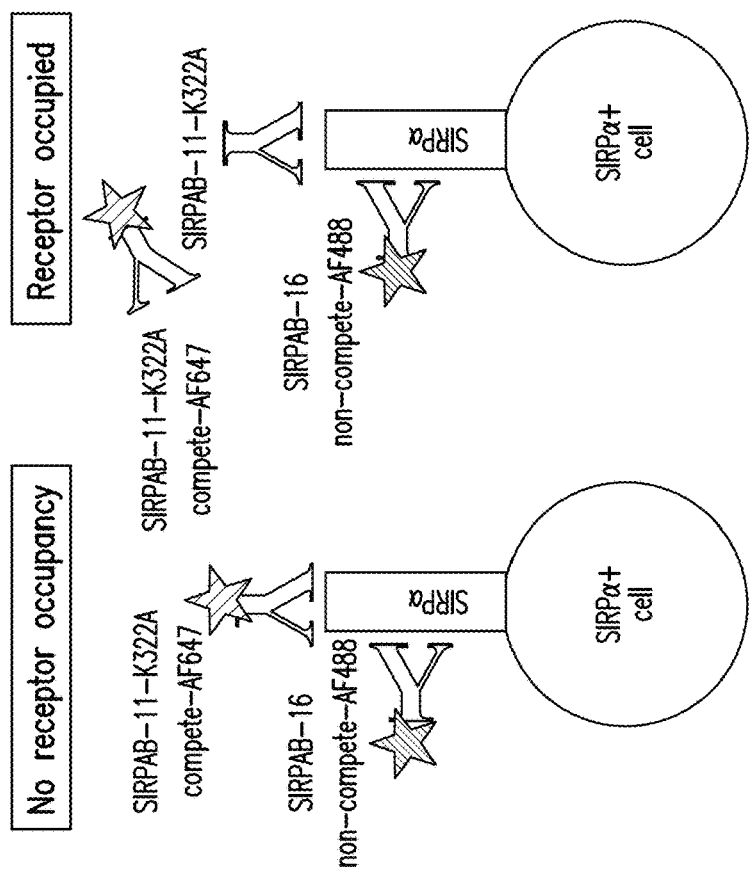

FIGS. 19A-19B show the design and validation of SIRPα receptor occupancy assay. (19A) Schematic representation of the SIRPα receptor occupancy assay, as described in Section 5.13. (19B) FACS dot plots showing validation of the assay, with SIRPAB-11-K322A staining shown in upper left panel, anti-SIRPα-29 staining shown in upper right panel, an exemplary dot plot of no receptor occupancy shown in lower left panel, and an exemplary dot plot of complete receptor occupancy shown in lower right panel.

4. DETAILED DESCRIPTION

Binding proteins, such as antibodies that bind to SIRPα, including human and/or cyno SIRPα, are provided herein. In some embodiments, the binding proteins provided herein, such as antibodies that bind to human and/or cynomolgus (cyno) SIRPα, do not bind to rodent SIRPα. In certain embodiments, the SIRPα binding proteins, including antibodies disclosed herein, are antagonist (e.g., can block the binding of SIRPα ligand and block ligand-induced SIRPα signaling). In some embodiments, the binding proteins such as antibodies to SIRPα provided herein (i) bind to human and/or cyno SIRPα, (ii) compete for binding with SIRPα ligand (e.g., CD47), and/or (iii) block SIRPα signaling. In one embodiment, the SIRPα antibodies bind to human SIRPα. In one embodiment, the SIRPα antibodies bind to cyno SIRPα. In one embodiment, the SIRPα antibodies bind to both human SIRPα and cyno SIRPα. In some embodiments, the SIRPα antibodies compete with CD47 for binding to SIRPα. In other embodiments, the SIRPα antibodies block SIRPα signaling. In yet another embodiment, the SIRPα antibodies block SIRPα signaling that is induced by CD47.

In some embodiments, the SIRPα antibodies provided herein bind to both human SIRPα and cyno SIRPα. In specific embodiments, the SIRPα antibodies provided herein bind to each of at least 6 SIRPα haplotypes including SIRPα v1, SIRPα v2, SIRPα v3, SIRPα v4, SIRPα v5, and SIRPα v6. In other specific embodiments, the SIRPα antibodies provided herein bind to at least one of the 6 SIRPα haplotypes including SIRPα v1, SIRPα v2, SIRPα v3, SIRPα v4, SIRPα v5, and SIRPα v6. In another specific embodiment, the SIRPα antibodies provided herein bind to SIRPα haplotypes in the IgV-domain covering no less than 95% of SIRPα polymorphism of human population. In some embodiments, the binding, competition, and/or signaling is assayed in vitro, e.g., in a cell-based assay. In other embodiments, the binding, competition, and/or signaling is assayed ex vivo, e.g., in a macrophage phagocytosis assay. In other embodiments, the binding, competition, and/or signaling is assayed using a sample from a subject (e.g., a human subject). In certain embodiments, assays include (1) a human or cyno macrophage phagocytosis assay (see, e.g., Example 9); (2) a cell based competitive binding assay (see, e.g., Example 2); (3) a surface plasmon resonance (SPR) competitive binding assay (see, e.g. Example 2). In certain embodiments, binding proteins, such as anti-SIRPα antibodies, as described herein, block activities of CD47 that are consistent with the natural biological function of CD47, including the activities induced by CD47 and SIRPα binding. In some embodiments, the blocking activities of anti-SIRPα antibodies are exhibited in vitro. In other embodiments, the blocking activities anti-SIRPα antibodies are exhibited ex vivo.

In some embodiments of the present disclosure, an anti-SIRPα antibody induces no more than or induces comparable level of cytokines (e.g. IL-2, IL-6, IL-8, IL-10, IL-12p70, TNFα, interferon gamma, and granulocyte macrophage colony-stimulating factor) as compared to a negative isotype antibody control. In some specific embodiments, the levels of cytokines (e.g. 1L-1β, IL-2, IL-6, IL-8, IL-10, IL-12p70, TNFα, interferon gamma, and granulocyte macrophage colony-stimulating factor) induced by anti-SIRPα antibodies provided herein are within 2, 3, 4, 5, 6, 7, 8, 9, or 10 fold of the levels of cytokines of those induced by a negative isotype antibody control. In certain embodiments, the negative isotype control antibody is cetuximab.

In some embodiments, the binding proteins, such as antibodies that bind to SIRPα, provided herein increase phagocytosis of cancer cells by co-cultured macrophages, and/or increase the percentage of phagocytotic macrophages in a population of macrophages co-cultured with cancer cells. In other embodiments, the binding proteins, such as antibodies that bind to SIRPα, provided herein increase phagocytosis of cancer cells by macrophages in a subject, and/or increase the percentage of phagocytotic macrophages in a population of macrophages in a subject having cancer.

In specific embodiments, the binding proteins, such as antibodies that bind to SIRPα, provided herein share the common feature of competing with each other for the binding of SIRPα. This competitive inhibition can indicate that each antibody binds to the same region of SIRPα (e.g., the same epitope), thereby asserting similar effects. In certain embodiments, anti-SIRPα antibodies provided herein include human anti-SIRPα antibodies, such as SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, SIRPAB-11, SIRPAB-12, or SIRPAB-13, or those derived from or based on these antibodies. In other embodiments, anti-SIRPα antibodies provided herein compete for binding with an antibody that is, or derived from, or based on SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, SIRPAB-11, SIRPAB-12, or SIRPAB-13. In some embodiments, the anti-SIRPα antibodies have CDR sequences as described in Tables 1-2. In certain embodiments, the anti-SIRPα antibodies bind to a specific domain or epitope of human SIRPα (e.g., residues 67-98, 67-74, 93-98, or 30-93 of SEQ ID NO:146; see Example 3). Moreover, such binding can be largely attributed to particular amino acid residues within the region (e.g., T67, R69, R95, K96, and S98; see Example 3), which comprise the epitope recognized by the anti-SIRPα antibodies described herein. Taken together, the results described herein demonstrate that the effects observed for an anti-SIRPα antibody that is, is derived from, or is based on SIRPAB-11, including an antibody having one or more CDRs described in Tables 1-2, can be extrapolated to other anti-SIRPα antibodies described herein having the same or similar epitope specificity (e.g., the same or similar CDRs). For example, the activities of antibodies as shown in Examples 2, 3, 9, 10, 11, and 12, for an exemplary humanized anti-SIRPα antibody, are representative of the activities and effects of the anti-SIRPα antibodies described herein.

In some embodiments of the present disclosure, the binding proteins such as anti-SIRPα antibodies may comprise immunoglobulin variable regions which comprise one or more CDRs as described in Tables 1-2. In such binding proteins (e.g., anti-SIRPα antibodies), the CDRs may be joined with one or more scaffold regions or framework regions (FRs), which orient(s) the CDR(s) such that the proper antigen binding properties of the CDR(s) is achieved. Such binding proteins, including anti-SIRPα antibodies as described herein, can block or inhibit CD47 binding to SIRPα and CD47-induced SIRPα signaling.

4.1 General Techniques

Techniques and procedures described or referenced herein include those that are generally well understood and/or commonly employed using conventional methodology by those skilled in the art, such as, for example, the widely utilized methodologies described in Sambrook et al., *Molecular Cloning: A Laboratory Manual* (3d ed. 2001); *Current Protocols in Molecular Biology* (Ausubel et al. eds., 2003); *Therapeutic Monoclonal Antibodies: From Bench to Clinic* (An ed. 2009); *Monoclonal Antibodies: Methods and Protocols* (Albitar ed. 2010); and *Antibody Engineering* Vols 1 and 2 (Kontermann and Dübel eds., 2d ed. 2010).

4.2 Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

The terms "SIRPα" "SIRPα" "Protein SIRPα," "SIRPα polypeptide," "SIRPA," "SIRP-A," "SIRP-alpha," or "SIRPalpha" (also known as BIT, MFR, MYD1, P84, PTPNS1, SHPS1, CD172a) is intended to mean a polypeptide ("polypeptide" and "protein" are used interchangeably herein), that is an immunoglobulin-like (Ig-like) family member and that in humans is encoded by signal regulatory protein alpha gene on human chromosome 20p13. Examples of SIRPα encompasses any such native polypeptide from any vertebrate source, including mammals such as primates humans and cynomolgus monkeys (cynos)), dogs, and rodents (e.g., mice and rats), unless otherwise indicated. In certain embodiments, the terms include "related SIRPα polypeptides," including SNP variants thereof. The term "SIRPα" also encompasses "full-length," unprocessed SIRPα as well as any form of SIRPα that results from processing in the cell. In some embodiments, the human SIRPα has an amino acid sequence of EEELQVIQPDKSVLVAAGETATLRC-TATSLIPVGPIQWFRGAGPGRELIYNQKEGHFPRV TTVSDLTKRNNMDFSIRIGNIT-PADAGTYYCVKFRKGSPDDVEFKSGAGTELSVRAK-PSA PVVSGPAARATPQHTVSFTCESHGFSPRDITLKW-KNGNELSDFQTNVDPVGESVSYSIH STAKVVLTREDVHSQVICEVAHVTLQGDPLRGTANL-SETIRVPPTLEVTQQPVRAENQV NVTCQVRKFYPQRLQLTWLENGNVSRTE-TASTVTENKDGTYNWMSWLLVNVSAHRD DVKLTQVEHDGQPAVSKSHDLKVSAHPKEQGSN-TAAENTGSNERNIYIVVGVVCTLL VALLMAALYL-VRIRQKKAQGSTSSTRLHEPEKNAREITQDTNDITY-ADLNLPKGKKPAP QAAEPNNHTEYASIQTSPQPASEDTLTY- ADLDMVHLNRITPKQPAPKPEPSFSEYASVQVP RK (SEQ ID NO:146). In other embodiments, the SIRPα has an amino acid sequence of SEQ ID NO:145, which is the SEQ ID NO:146 with an exemplary signal peptide. NCBI Reference Sequences NP_001035111.1, NP_001035112.1, NP_001317657.1, NP_542970.1, XP_005260727.1, XP_024307604.1, XP_006723608.1, and XP_011527475.1, and UniProtKB: P78324 provides other exemplary amino acid sequences of SIRPα. GENBANK accession number 140885, NCBI Reference Sequences NM_001040022.1, NM_001040023.1, NM_001330728.1, NM_080792.2, XM_005260670.3, NM_024451836.1, NM_006723545.4 and XM_011529173.2 provide exemplary human SIRPα nucleic acid sequence. In some embodiments, the cynomolgus SIRPα includes or has of the sequence of MEPAGPAPGRLGPLLCLLLTASCAWSGVLGEEELQVIQPEKSVSVAAGESATLNCTATSLIPVGPIQWFRGVGPGRELIYSQKEGHFPRVTPVSDPTKRNNMDFSTRISNITPADAGTYYCVKFNKGS PDVELKSGAGTELSVRAKPSAPVVSGPAVRATAEHTVSFTCESHGFSPRDITLKWFKNGNELSD FQTNVDPAGKSVSYSIRSTAPVVLTRRDVHSQVICEVAHVTLQGDPLRGTANLSEAIRVPPFLE VTQQSMRADNQVNNVTCQVTKFYPQRLQLTWLENGNVSRTE MASALPENKDGTYNWTSWLLVNVS AHRDDVKLTCQVEHDGQPAVNKSFSVKVSAHPKEQGSNTAAENTGTNERNIY (SEQ ID NO:115). In certain embodiments, the mouse SIRPα include or has the sequence of MEPAGPAPGRLGPLLLCLLLSASCFCTGATGKELKVTQPEKSVSVAAGDSTVLNCTLTSLLPVG PIRWYRGVGPSRLLIYSFAGEYVPRIRNVSDTTKRNNMDFSIRISNVTPADAGIYYCVKFQKGS SEPDTEIQSGGGTEVYVLAKPSPPEVSGPADRGIPDQKVNFTCKSHGFSPRNITLKW FKDGQEL HPLETTVNPSGKNVSYNISSTVRVVLNSMDVNSKVICEVAHITLDRSPLRGIANLSNFIRVSPT VKVTQQSPTSMNQVNLTCRAERFYPEDLQLIWLENGNVSRNDTPKNLTKNTDGTYNYI SLFLVN SSAHREDVVFTCQVKHDQQFAITRNHTVLGFAHSSDQGSM QTFPDNNATHNWN (SEQ ID NO:102). In other embodiments, the mouse SIRPα is the NOD/SCID Mouse SIRPα, which include or has the sequence of MEPAGPAPGRLGPLLLCLLLSASCFCTGATRTEVKVIQPEKSVSVAAGDSTVLNCTLTSLLPVG PIRWYRGVGQSRQLIYSFTTEHFPRVTNVSDATKRSNLDFSIRISNVTPEDAGTYYCVKFQRGS PDTEIQSGGGTEVYVLAKPSPPEVSGPADRGIPDQKVNFTCKSHGFSPRNITLKWFKDGQELHP LETTVNPSGKNVSYNISSTVRVVLNSMDVNSKVICEVAHITLDRSPLRGIANLSNFIRVSPTVK VTQQSPTSMNQVNLTCRAERFYPEDLQLTWLENGNVSRNDTPKNLTKNTDGTYNYTSLFLVNSS AHREDVVFTCQVKHDQQPAITRNHTVLGFAHSSDQG SMQTFPDNNATHNWN (SEQ ID NO:100).

As used herein, the term "IgV domain", also known as "Ig-like V-type domain," "V domain," "N-terminal IgSF domain," "SIRPα domain 1" or "N-terminal V domain," when used in reference to SIRPα, is intended to mean a polypeptide that in one human polymorphism has the amino acid residues of 1 to 107 (EEELQVIQPDKSVLVAAGETATLRCTATSLIPVGPIQWFRGAGPGRELIYNQKEGHFPRVTTVS DLTKRNNMDFSIRIGNITPADAGTYYCVKFRKGSPDDVEFKSG SEQ ID NO:203) of human SIRPα having SEQ ID NO:146 and that has the V-type Ig fold, and its equivalent in other human SIRPα polymorphisms and other SIRPα from any vertebrate source, including mammals such as primates (e.g., humans and cynomolgus monkeys (cynos)), dogs, and rodents (e.g., mice and rats), unless otherwise indicated.

As used herein, the term "SIRPα variant" is intended to mean a SIRPα protein comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. For example, a SIRPα variant may result from one or more (such as, for example, about 1 to about 25, about 1 to about 20, about 1 to about 15, about 1 to about 10, or about 1 to about 5) changes to an amino acid sequence of a native SIRPα. SIRPα variants include naturally-occurring variants of SIRPα, including allelic variants (e.g., SNP variants); splice variants; fragments; and interspecies homologs, which retain SIRPα activity. As such, SIRPα variants also encompass SIRPα encoded by SIRPα gene including one or more single nucleotide polymorphisms (SNPs), in human or other species, and "SIRPα haplotype." A "SIRPα haplotype" refers to a SIRPα variant having SNPs that tend to be inherited together. Thus a "SIRPα haplotype" is a type SIRPα polymorphism and can include a combination of any set of single nucleotide polymorphisms (SNPs) found in SIRPα gene, wherein the set of SNPs tend to be inherited together. As those skilled in the art will appreciate, an anti-SIRPα antibody provided herein can bind to a SIRPα variant, including a SIRPα haplotype. As described further below, 6 SIRPα haplotypes in the IgV domain of SIRPα, including SIRPα v1, SIRPα v2, SIRPα v3, SIRPα v4, SIRPα v5, and SIRPα v6, account for 95% of polymorphisms in the CD47 binding regions of SIRPα in human population. These 6 SIRPα haplotypes, SIRPα v1, SIRPα v2, SIRPα v3, SIRPα v4, SIRPα v5, and SIRPα v6, in the IgV domain comprises amino acid sequence of SEQ ID NOS: 149, 150, 151, 152, 153, and 154, respectively, as shown in Table 5.

TABLE 5

Haplotypes in SIRPα IgV domain in the SIRPα/CD47 binding interface

| Haplotypes in SIRPα IgV domain in the SIRPα/CD47 binding interface | Sequences |
| --- | --- |
| SIRPα v1 | RELIYNQKEGHFPRVTTVSDLTKRNNMDFSI (SEQ ID NO: 149) |
| SIRPα v2 | RELIYNQKEGHFPRVTTVSESTKRENMDFSI (SEQ ID NO: 150) |
| SIRPα v3 | RELIYNQKEGHFPRVTTVSDLTKRENMDFSI (SEQ ID NO: 151) |
| SIRPα v4 | RELIYNQKEGHFPRVTTVSESTKRKNMDFSI (SEQ ID NO: 152) |
| SIRPα v5 | RELIYNQKEGHFPRVTTVSEPTKRNNMDFSI (SEQ ID NO: 153) |
| SIRPα v6 | RELIYNQKEGHFPRVTTVSELTKRENMDFSI (SEQ ID NO: 154) |

"Related SIRPα polypeptides" include allelic variants (e.g., SNP variants); splice variants; fragments; derivatives; substitution, deletion, and insertion variants; fusion polypeptides; and interspecies homologs, which can retain SIRPα activity. As those skilled in the art will appreciate, an anti-SIRPα antibody provided herein can bind to a SIRPα polypeptide, a SIRPα polypeptide fragment, a SIRPα antigen, and/or a SIRPα epitope. An "epitope" may be part of a larger SIRPα antigen, which may be part of a larger SIRPα polypeptide fragment, which, in turn, may be part of a larger SIRPα polypeptide. SIRPα may exist in a native or denatured form. SIRPα polypeptides described herein may be isolated from a variety of sources, such as from human tissue types or from another source, or prepared by recombinant or synthetic methods. Orthologs to the SIRPα polypeptide are also well known in the art.

Exemplary SIRPα extracellular domain sequences that comprise one the 6 SIRPα haplotypes (SIRPα v1, SIRPα v2, SIRPα v3, SIRPα v4, SIRPα v5, or SIRPα v6) are shown in Table 6 below.

TABLE 6

Exemplary SIRPα extracellular domain sequences comprising one the 6 SIRPα haplotypes.

| SIRPα Extracellular Domain Sequences | Sequences |
| --- | --- |
| SIRPα1 | MEPAGPAPGRLGPLLCLLLAASCAWSGVAGEEELQVIQPDKSVLVAAGETATLRC TATSLIPVGPIQWFRGAGPGRELIYNQKEGHFPRVTTVSDLTKRNNMDFSIRIGN ITPADAGTYYCVKFRKGSPDDVEFKSGAGTELSVRAKPSAPVVSGPAARATPQHT VSFTCESHGFSPRDITLKWFKNGNELSDFQTNVDPVGESVSYSIHSTAKVVLTRE DVHSQVICEVAHVTLQGDPLRGTANLSETIRVPPTLEVTQQPVRAENQVNVTCQV RKFYPQRLQLTWLENGNVSRTETASTVTENKDGTYNWMSWLLVNVSAHRDDVKLT CQVEHDGQPAVSKSHDLKVSAHPKEQGSNTAAENTGSNERNIY (SEQ ID NO: 101) |
| SIRPα2 | MEPAGPAPGRLGPLLCLLLAASCAWSGVAGEEELQVIQPDKSVSVAAGESAILHC TVTSLIPVGPIQWFRGAGPARELIYNQKEGHFPRVTTVSESTKRENMDFSISISN ITPADAGTYYCVKFRKGSPDTEFKSGAGTELSVRAKPSAPVVSGPAARATPQHTV SFTCESHGFSPRDITLKWFKNGNELSDFQTNVDPVGESVSYSIHSTAKVVLTRED VHSQVICEVAHVTLQGDPLRGTANLSETIRVPPTLEVTQQPVRAENQVNVTCQVR KFYPQRLQLTWLENGNVSRTETASTVTENKDGTYNWMSWLLVNVSAHRDDVKLTC QVEHDGQPAVSKSHDLKVSAHPKEQGSNTAAENTGSNERNIY (SEQ ID NO: 103) |
| SIRPα3 | MEPAGPAPGRLGPLLCLLLAASCAWSGVAGEEELQVIQPDKSVLVAAGETATLRC TATSLIPVGPIQWFRGAGPGRELIYNQKEGHFPRVTTVSDLTKRENMDFSIRIGN ITPADAGTYYCVKFRKGSPDDVEFKSGAGTELSVRAKPSAPVVSGPAARATPQHT VSFTCESHGFSPRDITLKWFKNGNELSDFQTNVDPVGESVSYSIHSTAKVVLTRE DVHSQVICEVAHVTLQGDPLRGTANLSETIRVPPTLEVTQQPVRAENQVNVTCQV RKFYPQRLQLTWLENGNVSRTETASTVTENKDGTYNWMSWLLVNVSAHRDDVKLT CQVEHDGQPAVSKSHDLKVSAHPKEQGSNTAAENTGSNERNIY (SEQ ID NO: 105) |
| SIRPα4 | MEPAGPAPGRLGPLLCLLLAASCAWSGVAGEEELQVIQPDKSVLVAAGETATLRC TATSLIPVGPIQWFRGAGPGRELIYNQKEGHFPRVTTVSESTKRKNMDFSIRIGN ITPADAGTYYCVKFRKGSPDDVEFKSGAGTELSVRAKPSAPVVSGPAARATPQHT VSFTCESHGFSPRDITLKWFKNGNELSDFQTNVDPVGESVSYSIHSTAKVVLTRE DVHSQVICEVAHVTLQGDPLRGTANLSETIRVPPTLEVTQQPVRAENQVNVTCQV RKFYPQRLQLTWLENGNVSRTETASTVTENKDGTYNWMSWLLVNVSAHRDDVKLT CQVEHDGQPAVSKSHDLKVSAHPKEQGSNTAAENTGSNERNIY (SEQ ID NO: 93) |
| SIRPα5 | MEPAGPAPGRLGPLLCLLLAASCAWSGVAGEEELQVIQPDKSVLVAAGETATLRC TATSLIPVGPIQWFRGAGPGRELIYNQKEGHFPRVTTVSEPTKRNNMDFSIRIGN ITPADAGTYYCVKFRKGSPDDVEFKSGAGTELSVRAKPSAPVVSGPAARATPQHT VSFTCESHGFSPRDITLKWFKNGNELSDFQTNVDPVGESVSYSIHSTAKVVLTRE DVHSQVICEVAHVTLQGDPLRGTANLSETIRVPPTLEVTQQPVRAENQVNVTCQV RKFYPQRLQLTWLENGNVSRTETASTVTENKDGTYNWMSWLLVNVSAHRDDVKLT CQVEHDGQPAVSKSHDLKVSAHPKEQGSNTAAENTGSNERNIY (SEQ ID NO: 95) |
| SIRPα6 | MEPAGPAPGRLGPLLCLLLAASCAWSGVAGEEELQVIQPDKSVLVAAGETATLRC TATSLIPVGPIQWFRGAGPGRELIYNQKEGHFPRVTTVSELTKRENMDFSIRIGN ITPADAGTYYCVKFRKGSPDDVEFKSGAGTELSVRAKPSAPVVSGPAARATPQHT VSFTCESHGFSPRDITLKWFKNGNELSDFQTNVDPVGESVSYSIHSTAKVVLTRE DVHSQVICEVAHVTLQGDPLRGTANLSETIRVPPTLEVTQQPVRAENQVNVTCQV RKFYPQRLQLTWLENGNVSRTETASTVTENKDGTYNWMSWLLVNVSAHRDDVKLT CQVEHDGQPAVSKSHDLKVSAHPKEQGSNTAAENTGSNERNIY (SEQ ID NO: 97) |

The term "SIRPAB-11-K322A," refers to the SIRPAB-11 variant having a K322A substitution in the IgG1 Fc region. In certain embodiments, the SIRPα-K322A variant has a heavy chain amino acid sequence of HC_SIRPα-K322A (SEQ ID NO:119).

The term "SIRPAB-11-AAS," refers to the SIRPAB-11 variant having an IgG1 AAS Fc region. In certain embodiments, the anti-SIRPα antibody variant has a heavy chain amino acid sequence of HC_SIRPAB-11-IgG1-AAS (SEQ ID NO:98).

The term "SIRPAB-11-4PE," refers to the SIRPAB-11 variant having an IgG4PE heavy chain amino acid sequence as HC_SIRPAB-11-IgG4PE (SEQ ID NO:120).

The term "SIRPα ligand" refers to a molecule that binds to SIRPα, e.g., in vivo or in vitro. Non-limiting examples of SIRPα ligand include naturally occurring ligands, e.g., CD47, and artificially generated ligands.

The term "CD47," also known as "integrin associated protein," "IAP" or "Cluster of Differentiation 47" is intended to mean a transmembrane protein that belongs to the immunoglobulin superfamily and that in humans is encoded by the CD47 gene on human chromosome 3. Examples of CD47 encompasses any such native polypeptide from any vertebrate source, including mammals such as primates (e.g., humans and cynomolgus monkeys (cynos)), dogs, and rodents (e.g., mice and rats), unless otherwise indicated. In certain embodiments, the term includes all natural variants of CD47, including allelic variants (e.g., SNP variants); splice variants; fragments; and derivatives. The term "CD47" also encompasses "full-length," unprocessed CD47 as well as any form of CD47 that results from processing in the cell. In some embodiments, the CD47 extracellular domain has an amino acid sequence of MLYRMQLLSCIALSLALVTNSQLLFNKTKS-VEFTFCNDTVVIPCFVTNMEAQNTTEVYVKWKFKG RDIYTFDGALNKSTVPTDFSSAKTEVSQLLKG-DASLKMDKSDAVSHTGNYTCEVTELTREGETI IELKYRVV (SEQ ID NO:116). NCBI Reference Sequences NP_001768.1, NP_942088.1, XP_005247966.1, XP_005247965.1, and XP_016863025.1, and Uniprot database UniProtKB-Q08722 provides other exemplary amino acid sequences of CD47. GenBank™ ID number 961, NCBI Reference Sequences NM_001777.3, NM_198793.2, XM_005247909.2, XM_005247908.2, and XM_017007536.1 provide exemplary human CD47 nucleic acid sequence.

As used herein, the term "antagonist," when used in reference to SIRPα or a SIRPα function, is intended to mean a molecule that is capable of inhibiting, decreasing, attenuating, reducing, or otherwise completely blocking one or more of the biological activities or functions of SIRPα. An antagonist of a SIRPα function includes a molecule that can block, inhibit, attenuate, or reduce SIRPα-mediated or SIRPα-dependent signaling in a cell expressing a SIRPα. An antagonist of a SIRPα function also includes a molecule that can block, inhibit, attenuate, or reduce SIRPα signaling, including downstream signaling induced by ligation or engagement between SIRPα and CD47. In some examples, an antagonist of SIRPα further includes molecules that can block, inhibit, attenuate, or reduce SIRPα binding to a natural SIRPα-binding molecule. In other examples, an antagonist of SIRPα additionally includes molecules that can block, inhibit, or reduce SIRPα binding to a SIRPα ligand such as CD47. An "antagonist" of SIRPα is "antagonistic" to SIRPα or SIRPα function. In some embodiments, provided herein are antagonistic anti-SIRPα antibodies or fragments thereof.

A "blocking" antibody, a "neutralizing" antibody, or an "antagonist" antibody when used in reference to SIRPα or a SIRPα function, is intended to mean an antibody that binds to the SIRPα and act as an antagonist to SIRPα or the SIRPα activities or functions. For example, blocking antibodies or antagonist antibodies may substantially or completely inhibit the biological activity of SIRPα or the binding of CD47 to SIRPα. In some embodiments, provided herein are anti-SIRPα blocking antibodies or fragments thereof.

The term "binding protein" refers to a protein comprising a portion (e.g., one or more binding regions such as CDRs) that binds to SIRPα, including human and/or cyno SIRPα and, optionally, a scaffold or framework portion (e.g., one or more scaffold or framework regions) that allows the binding portion to adopt a conformation that promotes binding of the binding protein to a SIRPα polypeptide, fragment, or epitope. Examples of such binding proteins include antibodies, such as a human antibody, a humanized antibody, a chimeric antibody, a recombinant antibody, a single chain antibody, a diabody, a triabody, a tetrabody, a Fab fragment, a F(ab')$_2$ fragment, an IgD antibody, an IgE antibody, an IgM antibody, an IgG1 antibody, an IgG2 antibody, an IgG3 antibody, or an IgG4 antibody, and fragments thereof. The binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, Proteins: Structure, Function, and Bioinformatics 53(1):121-29; and Roque et al., 2004, Biotechnol. Prog. 20:639-54. In addition, peptide antibody mimetics ("PAMs") can be used, as well as scaffolds based on antibody mimetics utilizing fibronectin components as a scaffold. In the context of the present disclosure, a binding protein is said to specifically bind or selectively bind to SIRPα, for example, when the dissociation constant ($K_D$) is ≤$10^{-9}$ M. In some embodiments, the binding proteins (e.g., antibodies) may specifically bind to SIRPα with a $K_D$ of from about $10^{-7}$ M to about $10^{-12}$ M. In certain embodiments, the binding protein (e.g., antibody) may specifically bind to SIRPα with high affinity when the $K_D$ is ≤$10^{-8}$ M or $K_D$ is ≤$10^{-9}$ M. In one embodiment, the binding proteins (e.g., antibodies) may specifically bind to purified human SIRPα with a $K_D$ of from $1\times10^{-9}$ M to $10\times10^{-9}$ M as measured by Biacore®. In another embodiment, the binding proteins (e.g., antibodies) may specifically bind to purified human SIRPα with a $K_D$ of from $0.1\times10^{-9}$ M to $1\times10^{-9}$ M as measured by KinExA™ (Sapidyne, Boise, Id.). In yet another embodiment, the binding proteins (e.g., antibodies) specifically bind to human SIRPα expressed on cells with a $K_D$ of from $0.1\times10^{-9}$ M to $10\times10^{-9}$ M. In certain embodiments, the binding proteins (e.g., antibodies) specifically bind to human SIRPα expressed on cells with a $K_D$ of from $0.1\times10^{-9}$ M to $1\times10^{-9}$ M. In some embodiments, the binding proteins (e.g., antibodies) specifically bind to human SIRPα expressed on cells with a $K_D$ of $1\times10^{-9}$ M to $10\times10^{-9}$ M. In certain embodiments, the binding proteins (e.g., antibodies) specifically bind to human SIRPα expressed on cells with a $K_D$ of about $0.1\times10^{-9}$ M, about $0.5\times10^{-9}$ M, about $1\times10^{-9}$ M, about $5\times10^{-9}$ M, about $10\times10^{-9}$ M, or any range or interval thereof. In still another embodiment, the binding proteins (e.g., antibodies) may specifically bind to cyno SIRPα expressed on cells with a $K_D$ of $0.1\times10^{-9}$ M to $10\times10^{-9}$ M. In certain embodiments, the binding proteins (e.g., antibodies) specifically bind to cyno SIRPα expressed on cells with a $K_D$ of from $0.1\times10^{-9}$ M to $1\times10^{-9}$ M. In some embodiments, the binding proteins (e.g., antibodies) specifically bind to cyno SIRPα expressed on cells with a $K_D$ of $1\times10^{-9}$ M to $10\times10^{-9}$ M. In certain embodiments, the binding proteins (e.g., antibodies) specifically bind to cyno SIRPα expressed on cells with a $K_D$ of about $0.1 \times 10^{-9}$ M, about $0.5 \times 10^{-9}$ M, about $1 \times 10^{-9}$ M, about $5 \times 10^{-9}$ M, about $10 \times 10^{-9}$ M, or any range or interval thereof.

The term "antibody," "immunoglobulin," or "Ig" is used interchangeably herein, and is used in the broadest sense and specifically covers, for example, individual anti-SIRPα monoclonal antibodies (including agonist, antagonist, neutralizing antibodies, full length or intact monoclonal antibodies), anti-SIRPα antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-SIRPα antibodies, and fragments of anti-SIRPα antibodies, as described below. An antibody can be human, humanized, chimeric and/or affinity matured, as well as an antibody from other species, for example, mouse and rabbit, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., Antibody Engineering (Borrebaeck ed., 2d ed. 1995); and Kuby, Immunology (3d ed. 1997). In specific embodiments, the specific molecular antigen can be bound by an antibody provided herein, including a SIRPα polypeptide, a SIRPα fragment, or a SIRPα. epitope. Antibodies also include, but are not limited to, synthetic antibodies, recombinantly produced antibodies, camelized antibodies, intrabodies, anti-idiotypic (anti-Id) antibodies, and functional fragments (e.g., antigen-binding fragments such as SIRPα-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments such as SIRPα-binding fragments) include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to a SIRPα antigen (e.g., one or more CDRs of an anti-SIRPα antibody). Such antibody fragments can be found in, for example, Harlow and Lane, Antibodies: A Laboratory Manual (1989); Mol. Biology and Biotechnology: A Comprehensive Desk Reference (Myers ed., 1995); Huston et al., 1993, Cell Biophysics 22:189-224; Plückthun and Skerra, 1989, Meth. Enzymol. 178:497-515; and Day, Advanced Immunochemistry (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Anti-SIRPα antibodies may be agonistic antibodies or antagonistic antibodies. Provided herein are antagonistic antibodies to SIRPα, including antibodies that reduce or block SIRPα signaling, and/or block or reduce binding between CD47 and SIRPα.

An "antigen" is a predetermined antigen to which an antibody can selectively bind. A target antigen may be a polypeptide, carbohydrate, nucleic acid, lipid, hapten, or other naturally occurring or synthetic compound. In some embodiments, the target antigen is a polypeptide.

The terms "antigen-binding fragment," "antigen-binding domain," "antigen-binding region," and similar terms refer to that portion of an antibody, which comprises the amino acid residues that interact with an antigen and confer on the binding agent its specificity and affinity for the antigen (e.g., the CDRs).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as SIRPα, is the affinity of the antibody or functional fragment for that epitope. The ratio of dissociation rate ($k_{off}$) to association rate ($k_{on}$) of an antibody to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent SIRPα, come in contact with antibodies containing multiple binding sites, the interaction of antibody with antigen at one site will increase the probability of a reaction at a second site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The terms "antibodies that specifically bind to SIRPα," "antibodies that specifically bind to a SIRPα epitope," and analogous terms are also used interchangeably herein and refer to antibodies that specifically bind to a SIRPα polypeptide, such as a SIRPα antigen, or fragment, or epitope (e.g., human SIRPα such as a human SIRPα polypeptide, antigen, or epitope). An antibody that specifically binds to SIRPα (e.g., human SIRPα may bind to the extracellular domain or peptide derived from the extracellular domain of SIRPα. An antibody that specifically binds to a SIRPα antigen (e.g., human SIRPα) may be cross-reactive with related antigens (e.g., cyno SIRPα). In certain embodiments, an antibody that specifically binds to a SIRPα antigen does not cross-react with other antigens. An antibody that specifically binds to a SIRPα antigen can be identified, for example, by immunoassays, Biacore®, or other techniques known to those of skill in the art. An antibody binds specifically to a SIRPα antigen when it binds to a SIRPα antigen with higher affinity than to any cross-reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., *Fundamental Immunology* 332-36 (Paul ed., 2d ed. 1989) for a discussion regarding antibody specificity. An antibody which "binds an antigen of interest" (e.g., a target antigen such as SIRPα) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein, for example, as determined by fluorescence activated cell sorting (FACS) analysis or RIA. With regard to the binding of an antibody to a target molecule, the term "specific binding," "specifically binds to," or "is specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "anti-SIRPα antibody" or "an antibody that binds to SIRPα" includes an antibody that is capable of binding SIRPα with sufficient affinity such that the antibody is useful, for example, as an agent in targeting SIRPα. The term "specific binding," "specifically binds to," or "is specific for" a particular polypeptide or an epitope on a particular polypeptide target as used herein refers to binding where a molecule binds to a particular polypeptide or epitope on a particular polypeptide without substantially binding to any other polypeptide or polypeptide epitope. In certain embodiments, an antibody that binds to SIRPα has a dissociation constant ($K_D$) of less than or equal to 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, an anti-SIRPα antibody binds to an epitope of SIRPα that is conserved among SIRPα from different species (e.g., between human and cyno SIRPα). In some embodiments, an anti-SIRPα antibody binds to an epitope of SIRPα that is the region that contacts with CD47 when CD47 is bound to SIRPα.

The term "compete" when used in the context of anti-SIRPα antibodies (e.g., antagonistic antibodies and binding proteins that bind to SIRPα and compete for the same epitope or binding site on a target) means competition as determined by an assay in which the antibody (or binding fragment) thereof under study prevents or inhibits the specific binding of a reference molecule (e.g., a reference ligand or reference antigen-binding protein, such as a reference antibody) to a common antigen (e.g., SIRPα or a fragment thereof). Numerous types of competitive binding assays can be used to determine if a test antibody competes with a reference antibody for binding to SIRPα (e.g., human SIRPα). Examples of assays that can be employed include solid phase direct or indirect RIA, solid phase direct or indirect enzyme immunoassay (EIA), sandwich competition assay (see, e.g., Stahli et al., 1983, Methods in Enzymology 9:242-53), solid phase direct biotin-avidin EIA (see, e.g., Kirkland et al., 1986, J. Immunol. 137:3614-19), solid phase direct labeled assay, solid phase direct labeled sandwich assay (see, e.g., Harlow and Lane, *Antibodies, A Laboratory Manual* (1988)), solid phase direct label RIA using 1-125 label (see, e.g., Morel et al., 1988, Mol. Immunol. 25:7-15), and direct labeled RIA (Moldenhauer et al., 1990, Scand. J. Immunol. 32:77-82). Typically, such an assay involves the use of a purified antigen (e.g., SIRPα such as human SIRPα) bound to a solid surface, or cells bearing either of an unlabelled test antigen-binding protein (e.g., test anti-SIRPα antibody) or a labeled reference antigen-binding protein (e.g., reference anti-SIRPα antibody). Competitive inhibition may be measured by determining the amount of label bound to the solid surface or cells in the presence of the test antigen-binding protein. Usually the test antigen-binding protein is present in excess. Antibodies identified by competition assay (competing antibodies) include antibodies binding to the same epitope as the reference antibody and/or antibodies binding to an adjacent epitope sufficiently proximal to the epitope bound by the reference for antibodies steric hindrance to occur. Additional details regarding methods for determining competitive binding are described herein. Usually, when a competing antibody protein is present in excess, it will inhibit specific binding of a reference antibody to a common antigen by at least 30%, for example 40%, 45%, 50%, 55%, 60%, 65%, 70%, or 75%. In some instance, binding is inhibited by at least 80%, 85%, 90%, 95%, 96%, 97%, 98%, 99%, or more.

An "isolated" antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 25%, 20%, 15%, 10%, 5%, or 1% (by dry weight) of heterologous protein (also referred to herein as a "contaminating protein"). In certain embodiments, when the antibody is recombinantly produced, it is substantially free of culture medium, e.g., culture medium represents less than about 20%, 15%, 10%, 5%, or 1% of the volume of the protein preparation. In certain embodiments, when the antibody is produced by chemical synthesis, it is substantially free of chemical precursors or other chemicals, for example, it is separated from chemical precursors or other chemicals that are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al., 1951, J. Bio. Chem. 193: 265-75, such as 96%, 97%, 98%, or 99%, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step. In specific embodiments, antibodies provided herein are isolated.

A 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites el al. eds., 8th ed. 1994).

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering as in Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Other numbering systems have been described, for example, by AbM, Chothia, Contact, IMGT, and AHon.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

"Antibody fragments" comprise a portion of an intact antibody, such as the antigen-binding or variable region of the intact antibody. Examples of antibody fragments include, without limitation, Fab, Fab', F(ab')₂, and Fv fragments; diabodies and di-diabodies (see, e.g., Holliger et al., 1993, Proc. Natl. Acad. Sci. 90:6444-48; Lu et al., 2005, J. Biol. Chem. 280:19665-72; Hudson et al., 2003, Nat. Med. 9:129-34; WO 93/11161; and U.S. Pat. Nos. 5,837,242 and 6,492,123); single-chain antibody molecules (see, e.g., U.S. Pat. Nos. 4,946,778; 5,260,203; 5,482,858; and 5,476,786); dual variable domain antibodies (see, e.g., U.S. Pat. No. 7,612,181); single variable domain antibodies (sdAbs) (see, e.g., Woolven et al., 1999, Immunogenetics 50: 98-101; and Streltsov et al., 2004, Proc Natl Acad Sci USA. 101:12444-49); and multispecific antibodies formed from antibody fragments.

A "functional fragment," "binding fragment," or "antigen-binding fragment" of a therapeutic antibody will exhibit at least one if not some or all of the biological functions attributed to the intact antibody, the function comprising at least binding to the target antigen (e.g., a SIRPα binding fragment or fragment that binds to SIRPα).

The term "fusion protein" as used herein refers to a polypeptide that comprises an amino acid sequence of an antibody and an amino acid sequence of a heterologous polypeptide or protein (e.g., a polypeptide or protein not normally a part of the antibody (e.g., a non-anti-SIRPα antigen-binding antibody)). The term "fusion" when used in relation to SIRPα or to an anti-SIRPα antibody refers to the joining of a peptide or polypeptide, or fragment, variant, and/or derivative thereof, with a heterologous peptide or polypeptide. In certain embodiments, the fusion protein retains the biological activity of the SIRPα or anti-SIRPα antibody. In certain embodiments, the fusion protein comprises an anti-SIRPα antibody VH region, VL region, VH CDR (one, two, or three VH CDRs), and/or VL CDR (one, two, or three VL CDRs), wherein the fusion protein binds to a SIRPα epitope, a SIRPα fragment, and/or a SIRPα polypeptide.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains. Light chain amino acid sequences are well known in the art. A light chain can be a human light chain.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "monoclonal antibody" as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell, wherein the antibody binds to only a SIRPα epitope as determined, for example, by ELISA or other antigen-binding or competitive binding assay known in the art. The term "monoclonal" is not limited to any particular method for making the antibody. For example, the monoclonal antibodies useful in the present disclosure may be prepared by the hybridoma methodology first described by Kohler et al., 1975, Nature 256:495, or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., 1991, Nature 352:624-28 and Marks et al., 1991, J. Mol. Biol. 222:581-97, for example. Other methods for the preparation of clonal cell lines and of monoclonal antibodies expressed thereby are well known in the art. See, e.g., *Short Protocols in Molecular Biology* (Ausubel et al. eds., 5th ed. 2002). Exemplary methods of producing monoclonal antibodies are provided in the :Examples herein.

The term "native" when used in connection with biological materials such as nucleic acid molecules, polypeptides, host cells, and the like, refers to those which are found in nature and not manipulated, modified, and/or changed (e.g., isolated, purified, selected) by a human being.

The antibodies provided herein can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No, 4,816,567; and Morrison et al., 1984, Proc. Natl. Acad. Sci. USA 81:6851-55).

"Humanized" forms of nonhuman (e.g., murine) antibodies are chimeric antibodies that include human immunoglobulins (e.g., recipient antibody) in which the native CDR residues are replaced by residues from the corresponding CDR of a nonhuman species (e.g., donor antibody) such as mouse, rat, rabbit, or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones el al., 1986, Nature 321:522-25; Riechmann et al., 1988, Nature 332:323-29; Presta, 1992, Curr. Op. Strict. Biol. 2:593-96; Carter et al., 1992, Proc. Natl. Acad. Sci. USA 89:4285-89; U.S. Pat. Nos: 6,800,738; 6,719,971; 6,639,055; 6,407,213; and 6,054,297.

A "human antibody" is one that possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (Hoogenboom and Winter, 1991, Mol. Biol. 227:381; Marks et al., 1991, J. Mol. Biol. 222:581) and yeast display libraries (Chao et al., 2006, Nature Protocols 1: 755-68). Also available for the preparation of human monoclonal antibodies are methods described in Cole et al., *Monoclonal Antibodies and Cancer Therapy* 77 (1985); Boerner et al., 1991, J. Immunol. 147(1):86-95; and van Dijk and van de Winkel, 2001, Curr. Opin. Pharmacol. 5: 368-74. Human antibodies can be prepared by administering the antigen to a transgenic animal that has been modified to produce such antibodies in response to antigenic challenge, but whose endogenous loci have been disabled, e.g., mice (see, e.g., Jakobovits, 1995, Curr. Opin. Biotechnol. 6(5): 561-66; Bruggemann and Taussing, 1997, Curr. Opin. Biotechnol. 8(4):455-58; and U.S. Pat. Nos. 6,075,181 and 6,150,584 regarding XENOMOUSE™ technology). See also, for example, Li et al., 2006, Proc. Natl. Acad. Sci. USA 103:3557-62 regarding human antibodies generated via a human B-cell hybridoma technology.

A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., 1997, J. Biol. Chem. 252:6609-16; Kabat, 1978, Adv. Prot. Chem. 32:1-75). CDR region sequences also have been defined structurally by Chothia as those residues that are not part of the conserved β-sheet framework, and thus are able to adapt different conformations (Chothia and Lesk, 1987, J. Mol. Biol. 196:901-17). Both terminologies are well recognized in the art. CDR region sequences have also been defined by AbM, Contact, and IMGT. The positions of CDRs within a canonical antibody variable region have been determined by comparison of numerous structures (Al-Lazikani et al., 1997, J. Mol. Biol. 273:927-48; Morea et al., 2000, Methods 20:267-79). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra). Such nomenclature is similarly well known to those skilled in the art.

The term "hypervariable region," "HVR," or "HV," when used herein refers to the regions of an antibody variable region that are hypervariable in sequence and/or form structurally defined loops. Generally, antibodies comprise six hypervariable regions, three in the VH (H1, H2, H3) and three in the VL (L1, L2, L3). A number of hypervariable region delineations are in use and are encompassed herein. The Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Antibody Engineering Vol. 2 (Kontermann and Dübel eds., 2d ed. 2010)). The "contact" hypervariable regions are based on an analysis of the available complex crystal structures. The residues from each of these hypervariable regions or CDRs are noted below.

Recently, a universal numbering system has been developed and widely adopted, ImMunoGeneTics (IMGT) Information System® (Lafranc et al., 2003, Dev. Comp. Immunol. 27(1):55-77). IMGT is an integrated information system specializing in immunoglobulins (IG), T-cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, 2001, J. Mol. Biol. 309: 657-70. Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra).

|  | IMGT | Kabat | AbM | Chothia | Contact |
|---|---|---|---|---|---|
| $V_H$ CDR1 | 27-38 | 31-35 | 26-35 | 26-32 | 30-35 |
| $V_H$ CDR2 | 56-65 | 50-65 | 50-58 | 53-55 | 47-58 |
| $V_H$ CDR3 | 105-117 | 95-102 | 95-102 | 96-101 | 93-101 |
| $V_L$ CDR1 | 27-38 | 24-34 | 24-34 | 26-32 | 30-36 |
| $V_L$ CDR2 | 56-65 | 50-56 | 50-56 | 50-52 | 46-55 |
| $V_L$ CDR3 | 105-117 | 89-97 | 89-97 | 91-96 | 89-96 |

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH. As used herein, the terms "HVR" and "CDR" are used interchangeably.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

An "affinity matured" antibody is one with one or more alterations (e.g., amino acid sequence variations, including changes, additions, and/or deletions) in one or more HVRs thereof which result in an improvement in the affinity of the antibody for antigen, compared to a parent antibody which does not possess those alteration(s). Affinity matured antibodies can have nanomolar or even picomolar affinities for the target antigen. Affinity matured antibodies are produced by procedures known in the art. For review, see Hudson and Souriau, 2003, Nature Medicine 9:129-34; Hoogenboom, 2005, Nature Biotechnol. 23:1105-16; Quiroz and Sinclair, 2010, Revista Ingeneria Biomedia 4:39-51.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ or $K_D$ value may also be measured by using surface plasmon resonance assays by Biacore®, using, for example, a Biacore®TM-2000 or a Biacore®TM-3000, or by biolayer interferometry using, for example, the Octet®QK384 system. An "on-rate" or "rate of association" or "association rate" or "$k_{on}$" may also be determined with the same surface plasmon resonance or biolayer interferometry techniques described above using, for example, a Biacore®TM-2000 or a Biacore®TM-3000, or the Octet®QK384 system.

The phrase "substantially similar" or "substantially the same" denotes a sufficiently high degree of similarity between two numeric values (e.g., one associated with an antibody of the present disclosure and the other associated with a reference antibody) such that one of skill in the art would consider the difference between the two values to be of little or no biological and/or statistical significance within the context of the biological characteristic measured by the values (e.g., $K_D$ values). For example, the difference between the two values may be less than about 50%, less than about 40%, less than about 30%, less than about 20%, less than about 10%, or less than about 5%, as a function of the value for the reference antibody.

The phrase "substantially increased," "substantially reduced," or "substantially different," as used herein, denotes a sufficiently high degree of difference between two numeric values (e.g., one associated with an antibody of the present disclosure and the other associated with a reference antibody) such that one of skill in the art would consider the difference between the two values to be of statistical significance within the context of the biological characteristic measured by the values. For example, the difference between said two values can be greater than about 10%, greater than about 20%, greater than about 30%, greater than about 40%, or greater than about 50%, as a function of the value for the reference antibody.

Antibody "effector functions" refer to those biological activities attributable to the Fc region (e.g., a native sequence Fc region or amino acid sequence variant Fc region) of an antibody, and vary with the antibody isotype. Examples of antibody effector functions include: C1q binding; CDC; Fc receptor binding; and ADCC.

The term "effective amount" as used herein refers to the amount of an antibody or pharmaceutical composition provided herein which is sufficient to result in the desired outcome.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays as disclosed.

A "native sequence Fc region" comprises an amino acid sequence identical to the amino acid sequence of an Fc region found in nature, and not manipulated, modified, and/or changed (e.g., isolated, purified, selected, including or combining with other sequences such as variable region sequences) by a human. Native sequence human IgG1 Fc regions include a native sequence human IgG1 Fc region (non-A and A allotypes), native sequence human IgG2 Fc region; native sequence human IgG3 Fc region; and native sequence human IgG4 Fc region as well as naturally occurring variants thereof. For example, a native human IgG1 Fc region amino acid sequence is provided below:

```
                    (SEQ ID NO: 155, K322 emphasized)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

An exemplary native human IgG4 Fc region sequence is provided below:

```
                    (SEQ ID NO: 156, S228 and L235 emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK.
```

A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith. For example, a variant with one amino acid K change to A at 322 position in the human IgG1 Fc amino acid sequence, IgG1-K322A Fc region, is provided below:

(SEQ ID NO: 157, K322A substitution emphasized)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCAVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

An exemplary variant with two amino acids LL change to AA at 234-235 positions, and one amino acid D change to S at 265 position in the human IgG1 Fc amino acid sequence, IgG1-AAS Fc region, is provided below:

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVSVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK. (SEQ ID NO: 144,

LL to AA and D to S substitutions emphasized)

An exemplary variant with one amino acid S change to P at 228 position in the human IgG4 Fc amino acid sequence, IgG4P Fc region, is provided below:

(SEQ ID NO: 158, S228P substitution emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK.

An exemplary variant with two amino acid changes at 228 and 235 positions in the human IgG4 Fc amino acid sequence, IgG4PE Fc region, is provided below:

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK. (SEQ ID NO: 159,

S228P and L235E substitutions emphasized)

The term "variant" when used in relation to an anti-SIRPα antibody refers to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. For example, a variant of an anti-SIRPα antibody may result from one or more (such as, for example, about 1 to about 25, about 1 to about 20, about 1 to about 15, about 1 to about 10, or about 1 to about 5) changes to an amino acid sequence of a native or previously unmodified anti-SIRPα antibody. Anti-SIRPα antibody variants may be naturally occurring, such as allelic or splice variants, or may be artificially constructed. Anti-SIRPα antibody variants may be prepared from the corresponding nucleic acid molecules encoding the variants. In specific embodiments, the anti-SIRPα antibody variant at least retains anti-SIRPα antibody functional activity (e.g. antagonistic activities to CD47 binding and/or CD47-induced SIRPα signaling). In specific embodiments, an anti-SIRPα antibody variant binds SIRPα and/or is antagonistic to CD47 binding to SIRPα and/or SIRPα activity. In certain embodiments, the variant is encoded by a single nucleotide polymorphism (SNP) variant of a nucleic acid molecule that encodes anti-SIRPα antibody VH or VL regions or subregions, such as one or more CDRs.

The term "vector" refers to a substance that is used to carry or include a nucleic acid sequence, including for example, a nucleic acid sequence encoding an anti-SIRPα antibody as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g., an anti-SIRPα antibody as described herein), and it is further understood that expression levels can be optimized to obtain sufficient expression using methods well known in the art.

"Antibody-dependent cell-mediated cytotoxicity" or "ADCC" refers to a form of cytotoxicity in which secreted immunoglobulin bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. NK cells, the primary cells for mediating ADCC, express FcγRIII only, whereas monocytes express FcγRI, FcγRII, and FcγRIII. FcR expression on hematopoietic cells is known (see, e.g., Ravetch and Kinet, 1991, Annu. Rev. Immunol. 9:457-92). To assess ADCC activity of a molecule of interest, an in vitro ADCC assay (see, e.g., U.S. Pat. Nos. 5,500,362 and 5,821,337) can be performed. Useful effector cells for such assays include peripheral blood mononuclear cells (PBMC) and Natural Killer (NK) cells. Alternatively or additionally, ADCC activity of the molecule of interest may be assessed in vivo, for example, in an animal model (see, e.g., Clynes et al., 1998, Proc. Natl. Acad. Sci. USA 95:652-56). Antibodies with little or no ADCC activity may be selected for use.

"Antibody-dependent cellular phagocytosis" or "ADCP" refers to the destruction of target cells via monocyte or macrophage-mediated phagocytosis when immunoglobulin bound onto Fc receptors (FcRs) present on certain phagocytotic cells (e.g., neutrophils, monocytes, and macrophages) enable these phagocytotic cells to bind specifically to an antigen-bearing target cell and subsequently kill the target cell. To assess ADCP activity of a molecule of interest, an in vitro ADCP assay (see, e.g., Bracher et al., 2007, J. Immunol. Methods 323:160-71) can be performed. Useful phagocytotic cells for such assays include peripheral blood mononuclear cells (PBMC), purified monocytes from PBMC, or U937 cells differentiated to the mononuclear type. Alternatively or additionally, ADCP activity of the molecule of interest may be assessed in vivo, for example, in an animal model (see, e.g., Wallace et al., 2001, J. Immunol. Methods 248:167-82). Antibodies with little or no ADCP activity may be selected for use.

"Fc receptor" or "FcR" describes a receptor that binds to the Fc region of an antibody. An exemplary FcR is a native sequence human FcR. Moreover, an exemplary FcR is one that binds an IgG antibody (e.g., a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof (see, e.g., Daëron, 1997, Annu. Rev. Immunol. 15:203-34). Various FcRs are known (see, e.g., Ravetch and Kinet, 1991, Annu. Rev. Immunol. 9:457-92; Capel et al., 1994, Immunomethods 4:25-34; and de Haas et al., 1995, J. Lab. Clin. Med. 126:330-41). Other FcRs, including those to be identified in the future, are encompassed by the term "FcR" herein. The term also includes the neonatal receptor, FcRn, which is responsible for the transfer of maternal IgGs to the fetus (see, e.g., Guyer et al., 1976, J. Immunol. 117:587-93; and Kim et al., 1994, Eu. J. Immunol. 24:2429-34). Antibody variants with improved or diminished binding to FcRs have been described (see, e.g., WO 2000/42072; U.S. Pat. Nos. 7,183,387; 7,332,581; and 7,335,742; Shields et al. 2001, J. Biol. Chem. 9(2):6591-604).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay (see, e.g., Gazzano-Santoro et al., 1996, J. Immunol. Methods 202:163) may be performed. Polypeptide variants with altered Fc region amino acid sequences (polypeptides with a variant Fc region) and increased or decreased C1q binding capability have been described (see, e.g., U.S. Pat. No. 6,194,551; WO 1999/51642; Idusogie et al., 2000, J. Immunol. 164: 4178-84). Antibodies with little or no CDC activity may be selected for use.

A SIRPα polypeptide "extracellular domain" or "ECD" refers to a form of the SIRPα polypeptide that is essentially free of the transmembrane and cytoplasmic domains. For example, a SIRPα polypeptide ECD may have less than 1% of such transmembrane and/or cytoplasmic domains and can have less than 0.5% of such domains.

The term "identity" refers to a relationship between the sequences of two or more polypeptide molecules or two or more nucleic acid molecules, as determined by aligning and comparing the sequences. "Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALIGN (DNAStar, Inc.) software. Those skilled in the art can determine appropriate parameters for aligning sequences, including any algorithms needed to achieve maximal alignment over the full length of the sequences being compared.

A "modification" of an amino acid residue/position refers to a change of a primary amino acid sequence as compared to a starting amino acid sequence, wherein the change results from a sequence alteration involving said amino acid residue/position. For example, typical modifications include substitution of the residue with another amino acid (e.g., a conservative or non-conservative substitution), insertion of one or more (e.g., generally fewer than 5, 4, or 3) amino acids adjacent to said residue/position, and/or deletion of said residue/position.

An "epitope" is the site on the surface of an antigen molecule to which a single antibody molecule binds, such as a localized region on the surface of an antigen, such as a SIRPα polypeptide, a SIRPα polypeptide fragment, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three dimensional structure of the protein is in an altered conformation, such as following activation or binding of another protein or ligand. In certain embodiments, a SIRPα epitope is a three-dimensional surface feature of a SIRPα polypeptide. In other embodiments, a SIRPα epitope is linear feature of a SIRPα polypeptide. Generally an antigen has several or many different epitopes and may react with many different antibodies.

An antibody binds "an epitope," "essentially the same epitope," or "the same epitope" as a reference antibody, when the two antibodies recognize identical, overlapping, or adjacent epitopes in a three-dimensional space. The most widely used and rapid methods for determining whether two antibodies bind to identical, overlapping, or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies is measured using radioactive, fluorescent, or enzyme labels.

"Epitope mapping" is the process of identifying the binding sites, or epitopes, of antibodies on their target antigens. "Epitope binning" is the process of grouping antibodies based on the epitopes they recognize. More particularly, epitope binning comprises methods and systems for discriminating the epitope recognition properties of different antibodies, using competition assays combined with computational processes for clustering antibodies based on their epitope recognition properties and identifying antibodies having distinct binding specificities.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. The term "carrier" can also refer to a diluent, adjuvant (e.g., Freund's adjuvant (complete or incomplete)), excipient, or vehicle. Such carriers, including pharmaceutical carriers, can be sterile liquids, such as water and oils, including those of petroleum, animal, vegetable, or synthetic origin, such as peanut oil, soybean oil, mineral oil, sesame oil, and the like. Water is an exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard carriers such as pharmaceutical grades of mannitol, lactose, starch, magnesium stearate, sodium saccharine, cellulose, magnesium carbonate, etc. Examples of suitable pharmaceutical carriers are described in Remington and Gennaro, *Remington's Pharmaceutical Sciences* (18th ed. 1990). Compositions, including pharmaceutical compounds, may contain an anti-SIRPα antibody, for example, in isolated or purified form, together with a suitable amount of carriers.

The term "pharmaceutically acceptable" as used herein means being approved by a regulatory agency of the Federal or a state government, or listed in United States Pharmacopeia, European Pharmacopeia, or other generally recognized Pharmacopeia for use in animals, and more particularly in humans.

"Polyclonal antibodies" as used herein refer to an antibody population generated in an immunogenic response to a protein having many epitopes and thus includes a variety of different antibodies directed to the same or different epitopes within the protein. Methods for producing polyclonal antibodies are known in the art (See, e.g., Short Protocols in Molecular Biology (Ausubel et al. eds., 5th ed. 2002)).

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces an anti-SIRPα antibody of the present disclosure may include a parent hybridoma cell, as well as bacterial and eukaryotic host cells into which nucleic acids encoding the antibodies have been introduced. Suitable host cells are disclosed below.

Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

The term "recombinant antibody" refers to an antibody that is prepared, expressed, created, or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor et al., 1992, Nucl. Acids Res. 20:6287-95), or antibodies prepared, expressed, created, or isolated by any other means that involves splicing of immunoglobulin gene sequences to other DNA sequences. Such recombinant antibodies can have variable and constant regions, including those derived from human germline immunoglobulin sequences (See Kabat et al., supra). In certain embodiments, however, such recombinant antibodies may be subjected to in vitro mutagenesis (or, when an animal transgenic for human Ig sequences is used, in vivo somatic mutagenesis), thus the amino acid sequences of the VH and VL regions of the recombinant antibodies are sequences that, while derived from and related to human germline VH and VL sequences, may not naturally exist within the human antibody germline repertoire in vivo.

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human.

"Substantially all" refers to at least about 60%, at least about 65%, at least about 70%, at least about 75%, at least about 80%, at least about 85%, at least about 90%, at least about 95%, at least about 98%, at least about 99%, or about 100%.

The terms "detectable agent" or "detectable molecule" are used interchangeably herein and refers to a substance that can be used to ascertain the existence or presence of a desired molecule, such as an anti-SIRPα antibody as described herein, in a sample or subject. A detectable agent can be a substance that is capable of being visualized or a substance that is otherwise able to be determined and/or measured (e.g., by quantitation).

The term "elevated" or "upregulated" when used in reference to SIRPα or a cytokine is intended to mean that the level of SIRPα or the cytokine is higher than that of a normal reference range or a corresponding control subject. Such "elevated" or "upregulated" SIRPα or cytokines can be 110%, 120%, 130%, 140%, 150%, 160%, 170%, 180%, 190%, 200%, 250%, 300%, 400%, 500%, 600%, 700%, 800%, 900%, 10 fold, 20 fold, 30 fold, 40 fold, 50 fold, 100 fold, 200 fold, 300 fold, 400 fold, 500 fold, 600 fold, 700 fold, 800 fold, 1000 fold, or higher of that in a control subject or that of the normal reference range.

The term "encoding nucleic acid" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The term "excipient" refers to an inert substance which is commonly used as a diluent, vehicle, preservative, binder, or stabilizing agent, and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.), and polyols (e.g., mannitol, sorbitol, etc.), See, also, Remington and Gennaro, *Remington's Pharmaceutical Sciences* (18th ed. 1990), which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, SIRPα fragments or anti-SIRPα antibody fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250, at least 300, at least 350, at least 400, at least 450, at least 500, at least 550, at least 600, at least 650, at least 700, at least 750, at least 800, at least 850, at least 900, or at least 950 contiguous amino acid residues of the amino acid sequence of a SIRPα polypeptide or an anti-SIRPα antibody. In a specific embodiment, a fragment of a SIRPα polypeptide or an anti-SIRPα antibody retains at least 1, at least 2, at least 3, or more functions of the polypeptide or antibody.

The terms "about" and "approximately" mean within 20%, within 15%, within 10%, within 9%, within 8%, within 7%, within 6%, within 5%, within 4%, within 3%, within 2%, within 1%, or less of a given value or range.

"Administer" or "administration" refers to the act of injecting or otherwise physically delivering a substance as it exists outside the body (e.g., an anti-SIRPα antibody as described herein) into a patient, such as by mucosal, intradermal, intravenous, intramuscular delivery, and/or any other method of physical delivery described herein or known in the art.

In the context of solid tumors, "inhibition" may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from randomization (for example, first dose date) until death from any cause, and is measured in the intent-to-treat population. TTP as used herein means the time from randomization (for example, first dose date) until objective tumor progression; TTP does not include deaths. As used herein, PFS means the time from randomization (for example, first dose date) until objective tumor progression or death. In one embodiment, PFS rates are computed using the Kaplan-Meier estimates.

In certain embodiments, the treatment of solid tumors may be assessed by Response Evaluation Criteria in Solid Tumors (RECIST 1.1) see Eisenhauer E A, et al. Eur J Cancer 2009;45(2):228-247. Assessment by RECIST 1.1 is summarized below.

Overall response should be assessed according to Table 7 for subjects with target lesions, and Table 8 for subjects with only non-target lesions.

TABLE 7

Time Point Response: Subjects With Target (±Non-target) Disease

| Target Lesions Response | Non-target Lesion Response | New Lesions | Overall Response |
|---|---|---|---|
| CR | CR | No | CR |
| CR | Non-CR/non-PD | No | PR |
| CR | Not evaluated | No | PR |
| PR | Non-PD or not all evaluated | No | PR |
| SD | Non-PD or not all evaluated | No | SD |
| Not all evaluated | Non-PD | No | NE |
| PD | Any | Yes or No | PD |
| Any | PD | Yes or No | PD |
| Any | Any | Yes | PD |

CR = complete response, PR = partial response, SD = stable disease, PD = progressive disease, NE = inevaluable.

TABLE 8

Time Point Response: Subjects With Non-target Disease Only

| Nontarget Lesions Response | New Lesions | Overall Response |
|---|---|---|
| CR | No | CR |
| Non-CR/non-PD | No | Non-CR/non-PD[a] |
| Not all evaluated | No | NE |
| Unequivocal PD | Yes or No | PD |
| Any | Yes | PD |

CR = complete response, SD = stable disease, PD = progressive disease, NE = inevaluable.
[a]"Non-CR/non-PD" is preferred over "stable disease" for non-target disease With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions, and stable disease (SD) is neither sufficient shrinkage to qualify for partial response nor sufficient increase to qualify for progressive disease, taking as reference the smallest sum longest diameter since the treatment started.

With respect to the evaluation of non-target lesions, CR is the disappearance of all non-target lesions and normalization of tumor marker level, incomplete response/non-CR/non-PD is the persistence of one or more non-target lesion(s) and/or the maintenance of tumor marker level above the normal limits, and PD is the appearance of one or more new lesions and/or unequivocal progression of existing non-target lesions.

Guidelines for response criteria for use in trials testing immunotherapeutics (Seymour et al. Lancet Oncol. 2017; 18:e143-e152) can be accessed online at: www.thelancet.com/journals/lanonc/article/PIIS1470-2045(17)30074-8

In certain embodiments, the treatment of solid tumors may be assessed by changes in Eastern Cooperative Oncology Group (ECOG) performance status (also referred to as ECOG PS) (Olen et al. Am J Clin Oncol. 1982;5(6):649-55). As used herein ECOG PS is defined as follows.

| ECOG PS Score | Description |
|---|---|
| 0 | Fully active, able to carry on all pre-disease performance without restriction |
| 1 | Restricted in physically strenuous activity but ambulatory and able to carry out work of a light or sedentary nature, e.g., light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

In certain embodiments, the efficacy for the treatment of NHL is assessed according to the "Lugano Criteria", which incorporate International Working Group (IWG) Response Criteria for NHL (Cheson B D, et al., J Clin Oncol. 32(27): 3059-3068 (2014)) and Deauville Criteria for fluorodeoxyglucose-positron emission tomography (FDG PET) scan interpretation (Itti E, et al., Eur J Nucl Med Mol Imaging. 40(9):1312-20 (2013)). As used herein, Lugano Criteria includes an the initial evaluation criteria for the involvement of site, and the criteria for response assessment, both of which are described in further detail in the two paragraphs below.

Criteria for Involvement of Site

| Tissue Site | Clinical | FDG Avidity | Test | Positive Finding |
|---|---|---|---|---|
| Lymph nodes | Palpable | FDG-avid histologies | PET-CT | Increase FDG uptake |
| | | Nonavid disease | CT | Unexplained node enlargement |
| Spleen | Palpable | FDG-avid histologies | PET-CT | Diffuse uptake, solitary mass, miliary lesions, nodules > 13 cm in vertical length, mass, |
| | | Nonavid disease | CT | |
| Liver | Palpable | FDG-avid histologies | PET-CT | Diffuse uptake, mass |
| | | Nonavid disease | CT | Nodules |
| CNS | Signs, symptoms | | CT | Mass lesion(s) |
| | | | MRI | Leptomeningeal infiltration, mass lesions |
| | | | CSF assessment | Cytology, flow cytometry |
| Other (e.g., skin, lung, GI tract, bone, bone marrow) | Site dependent | | PET-CT[a], biopsy | Lymphoma involvement |

CNS = central nervous system; CSF = cerebrospinal fluid; CT = computed tomography; FDG = fluorodeoxyglucose; GI = gastrointestinal; MRI = magnetic resonance imaging; PET = positron emission tomography.
[a]PET-CT is adequate for determination of bone marrow involvement and can be considered highly suggestive for involvement of other extralymphatic sites. Biopsy confirmation of those sites can be considered if necessary.

Criteria for Response Assessment

| RESPONSE AND SITE | PET-CT BASED RESPONSE | CT-BASED RESPONSE |
|---|---|---|
| Complete | Complete metabolic response | Complete radiologic response (all of the following) |
| Lymph nodes and extralymphatic sites | Score 1, 2, or 3[a] with or without a residual mass on 5PS[b] It is recognized that in Waldeyer's ring or extranodal sites with high physiologic uptake or with activation within spleen or marrow (eg, with chemotherapy or myeloid colony- stimulating factors), uptake may be greater than normal mediastinum and/or liver. In this circumstance, complete metabolic response may be inferred if uptake at sites of initial involvement is no greater than surrounding normal tissue even if the tissue has high physiologic uptake | Target nodes/nodal masses must regress to ≤1.5 cm in LDi No extralymphatic sites of disease |
| Nonmeasured lesion | Not applicable | Absent |
| Organ enlargement | Not applicable | Regress to normal |
| New lesions | None | None |
| Bone marrow | No evidence of FDG-avid disease in marrow | Normal by morphology; if indeterminate, IHC negative |
| Partial | Partial metabolic response | Partial remission (all of the following) |
| Lymph nodes and extralymphatic sites | Score 4 or 5[b] with reduced uptake compared with baseline and residual mass(es) of any size At interim, these findings suggest responding disease At end of treatment, these findings indicate residual disease | ≥50% decrease in sum of perpendicular diameters (SPD) of up to 6 target measurable nodes and extranodal sites When a lesion is too small to measure on CT, assign 5 mm × 5 mm as the default value When no longer visible, 0 × 0 mm For a node > 5 mm × 5 mm, but smaller than normal, use actual measurement for calculation |
| Nonmeasured lesion | Not applicable | Absent/normal, regressed, but no increase |
| Organ enlargement | Not applicable | Spleen must have regressed > 50% in length beyond normal |
| New lesions | None | None |
| Bone marrow | Residual uptake higher than uptake in normal marrow but reduced compared with baseline (diffuse uptake compatible with reactive changes from chemotherapy allowed). If there are persistent focal changes in the marrow in the context of a nodal response, consideration should be given to further evaluation with MRI or biopsy or an interval scan | Not applicable |

-continued

| RESPONSE AND SITE | PET-CT BASED RESPONSE | CT-BASED RESPONSE |
|---|---|---|
| No response or stable disease | No metabolic response | Stable disease |
| Target nodes/nodal masses, extranodal lesions | Score 4 or 5$^b$ with no significant change in FDG uptake from baseline at interim or end of treatment | <50% decrease from baseline in SPD of up to 6 dominant measurable nodes and extranodal sites; no criteria for progressive disease are met |
| Nonmeasured lesion | Not applicable | No increase consistent with progression |
| Organ enlargement | Not applicable | No increase consistent with progression |
| New lesions | None | None |
| Bone marrow | No change from baseline | Not applicable |
| Progressive disease | Progressive metabolic response | Progressive disease requires at least 1 of the following |
| Individual target nodes/nodal masses Extranodal lesions | Score 4 or 5$^b$ with an increase in intensity of uptake from baseline and/or New FDG-avid foci consistent with lymphoma at interim or end-of-treatment assessment | PPD progression: An individual node/lesion must be abnormal with: LDi > 1.5 cm and Increase by ≥ 50% from PPD nadir and An increase in LDi or SDi from nadir 0.5 cm for lesions ≤ 2 cm 1.0 cm for lesions > 2 cm In the setting of splenomegaly, the splenic length must increase by > 50% of the extent of its prior increase beyond baseline (eg, a 15 cm spleen must increase to > 16 cm). If no prior splenomegaly, must increase by at least 2 cm from baseline New or recurrent splenomegaly |
| Nonmeasured lesions | None | New or clear progression of preexisting nonmeasured lesions |
| New lesions | New FDG-avid foci consistent with lymphoma rather than another etiology (eg, infection, inflammation). If uncertain regarding etiology of new lesions, biopsy or interval scan may be considered | Regrowth of previously resolved lesions A new node > 1.5 cm in any axis A new extranodal site > 1.0 cm in any axis, if < 1.0 cm in any axis, its presence must be unequivocal and must be attributable to lymphoma Assessable disease of any size unequivocally attributable to lymphoma |
| Bone marrow | New or recurrent FDG-avid foci | New or recurrent involvement |

5PS = 5-point scale; CT = computed tomography; FDG = fluorodeoxyglucose; GI = gastrointestinal; IHC = immunohistochemistry; LDi = longest transverse diameter of a lesion; MRI = magnetic resonance imaging; PET = positron emission tomography; PPD = cross product of the LDi and perpendicular diameter; SDi = shortest axis perpendicular to the LDi; SPD = sum of the product of the perpendicular diameters for multiple lesions.
$^a$A score of 3 in many Subjects indicates a good prognosis with standard treatment, especially if at the time of an interim scan. However, in trials involving PET where de-escalation is investigated, it may be preferable to consider a score of 3 as inadequate response (to avoid undertreatment).
Measured dominant lesions: Up to six of the largest dominant nodes, nodal masses, and extranodal lesions selected to be clearly measurable in two diameters. Nodes should preferably be from disparate regions of the body and should include, where applicable, mediastinal and retroperitoneal areas. Non-nodal lesions include those in solid organs (eg, liver, spleen, kidneys, and lungs), GI involvement, cutaneous lesions, or those noted on palpation.
Nonmeasured lesions: Any disease not selected as measured, dominant disease and truly assessable disease should be considered not measured. These sites include any nodes, nodal masses, and extranodal sites not selected as dominant or measurable or that do not meet the requirements for measurability but are still considered abnormal, as well as truly assessable disease, which is any site of suspected disease that would be difficult to follow quantitatively with measurement, including pleural effusions, ascites, bone lesions, leptomeningeal disease, abdominal masses, and other lesions that cannot be confirmed and followed by imaging. In Waldeyer's ring or in extranodal sites (eg, GI tract, liver, bone marrow), FDG uptake may be greater than in the mediastinum with complete metabolic response, but should be no higher than surrounding normal physiologic uptake (eg, with marrow activation as a result of chemotherapy or myeloid growth factors).
$^b$PET 5PS: 1, no uptake above background; 2, uptake < mediastinum; 3, uptake > mediastinum but < liver; 4, uptake moderately > liver; 5, uptake markedly higher than liver and/or new lesions; X, new areas of uptake unlikely to be related to lymphoma.

The Deauville five-point scale (5PS) is an internationally recommended scale for clinical routine and clinical trials using FDG-PET/CT in the initial staging and assessment of treatment response in Hodgkin's lymphoma (HL) and certain types of NHL (See Itti E, et al., Eur J Nucl Med Mol Imaging. 40(9):1312-20 (2013); Meignan M, et al., Leuk Lymphoma. 55(1):31-7 (2014)).

The Deauville five-point scale is a simple tool based on visual interpretation of FDG-uptake. It takes advantage of two reference points of the individual patient, which have demonstrated relatively constant uptake on serial imaging. The two reference organs are the mediastinum (aka blood pool) and the liver. The scale ranges from 1 to 5, where 1 is best and 5 is the worst, as listed below. Each FDG-avid (or previously FDG-avid) lesion is rated independently.
1. no uptake or no residual uptake (when used interim)
2. slight uptake, but below blood pool (mediastinum)
3. uptake above mediastinal, but below or equal to uptake in the liver
4. uptake slightly to moderately higher than liver
5. markedly increases uptake or any new lesion (on response evaluation)

In some embodiments, the treatment response according to the Deauville five-point scale is assessed as follows:
complete response (CR): scores 1, 2 or 3 together with the absence of FDG-avid bone marrow lesion(s) are interpreted as complete metabolic response (CR), irrespective of a persistent mass on CT partial response (PR): a Deauville score of 4 or 5, provided:
uptake is decreased compared with baseline and
absence of structural progression development on CT stable disease (SD), also called no metabolic response: a Deauville score of 4 or 5 without significant change in FDG uptake from baseline.

progressive disease (PD): a Deauville score of 4 to 5 with increasing intensity compared to baseline or any interim scan and/or any new FDG-avid focus consistent with malignant lymphoma.

In the context of cancer, a "refractory" cancer, for example refractory NHL, refractory follicular lymphoma, or refractory DLBCL, is a cancer that has not responded to initial treatment. The term refractory cancer thus includes cancers in which the expected effects of the initial treatment are not observed. A refractory cancer can be a cancer that is getting worse or staying the same. A "relapsed" cancer, for example relapsed NHL, relapsed follicular lymphoma, or relapsed DLBCL is a cancer that responded to a treatment, for example, stopped progressing, progressed slower than when left untreated, regressed, or even mostly or completely disappeared, but then stops responding or returns.

In the context of a polypeptide, the term "analog" as used herein refers to a polypeptide that possesses a similar or identical function as a SIRPα polypeptide, a fragment of a SIRPα polypeptide, or an anti-SIRPα antibody but does not necessarily comprise a similar or identical amino acid sequence of a SIRPα polypeptide, a fragment of a SIRPα polypeptide, or an anti-SIRPα antibody, or possess a similar or identical structure of a SIRPα polypeptide, a fragment of a SIRPα polypeptide, or an anti-SIRPα antibody. A polypeptide that has a similar amino acid sequence refers to a polypeptide that satisfies at least one of the followings: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a SIRPα polypeptide, a fragment of a SIRPα polypeptide, or an anti-SIRPα antibody described herein; (b) a polypeptide encoded by a nucleotide sequence that hybridizes under stringent conditions to a nucleotide sequence encoding a SIRPα polypeptide, a fragment of a SIRPα polypeptide, or an anti-SIRPα antibody (or VH or VL region thereof) described herein at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al., *Molecular Cloning: A Laboratory Manual* (2001); and Maniatis et al., *Molecular Cloning: A Laboratory Manual* (1982)); or (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a SIRPα polypeptide, a fragment of a SIRPα polypeptide, or an anti-SIRPα antibody (or VH or VL region thereof) described herein. A polypeptide with similar structure to a SIRPα polypeptide, a fragment of a SIRPα polypeptide, or an anti-SIRPα antibody described herein refers to a polypeptide that has a similar secondary, tertiary, or quaternary structure of a SIRPα polypeptide, a fragment of a SIRPα polypeptide, or an anti-SIRPα antibody described herein. The structure of a polypeptide can be determined by methods known to those skilled in the art, including but not limited to, X-ray crystallography, nuclear magnetic resonance, and crystallographic electron microscopy.

In the context of a polypeptide, the term "derivative" as used herein refers to a polypeptide that comprises an amino acid sequence of a SIRPα polypeptide, a fragment of a SIRPα polypeptide, or an antibody that binds to a SIRPα polypeptide which has been altered by the introduction of amino acid residue substitutions, deletions, or additions. The term "derivative" as used herein also refers to a SIRPα polypeptide, a fragment of a SIRPα polypeptide, or an antibody that binds to a SIRPα polypeptide which has been chemically modified, e.g., by the covalent attachment of any type of molecule to the polypeptide. For example, but not by way of limitation, a SIRPα polypeptide, a fragment of a SIRPα polypeptide, or an anti-SIRPα antibody may be chemically modified, e.g., by glycosylation, acetylation, pegylation, phosphorylation, amidation, derivatization by known protecting/blocking groups, proteolytic cleavage, chemical cleavage, formulation, metabolic synthesis of tunicamycin, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. Further, a derivative of a SIRPα polypeptide, a fragment of a SIRPα polypeptide, or an anti-SIRPα antibody may contain one or more non-classical amino acids. A polypeptide derivative possesses a similar or identical function as a SIRPα polypeptide, a fragment of a SIRPα polypeptide, or an anti-SIRPα antibody described herein.

The term "composition" is intended to encompass a product containing the specified ingredients (e.g., an antibody provided herein) in, optionally, the specified amounts.

4.3 Compositions and Methods of Making the Same

Provided herein are antibodies that bind to a SIRPα polypeptide, a SIRPα polypeptide fragment, a SIRPα peptide, or a SIRPα epitope.

In certain embodiments, the antibodies provided herein bind to human and/or cyno SIRPα. In one embodiment, the SIRPα antibodies bind to human SIRPα. In one embodiment, the SIRPα antibodies bind to cyno SIRPα. In one embodiment, the SIRPα antibodies bind to both human SIRPα and cyno SIRPα. In other embodiments, the antibodies provided herein do not bind to rodent SIRPα.

In some embodiments, the anti-SIRPα antibodies bind to the extracellular domain (ECD) of SIRPα. In certain embodiments, the anti-SIRPα antibodies bind to an epitope in the ECD of SIRPα, which overlaps with the CD47 binding site. In certain embodiments, the anti-SIRPα antibodies bind to an epitope in the ECD of SIRPα, which is the same as the CD47 binding site.

Also provided are antibodies that competitively block an anti-SIRPα antibody provided herein from binding to a SIRPα polypeptide.

Also provided are antibodies that compete for binding to a SIRPα polypeptide with an anti-SIRPα antibody provided herein.

In some embodiments, the anti-SIRPα antibodies block the binding of CD47 to a SIRPα polypeptide. In some embodiments, the anti-SIRPα antibodies compete for the binding of CD47 to a SIRPα polypeptide.

In certain embodiments, binding of CD47 to SIRPα is inhibited by the antibodies provided herein. In other embodiments, binding of CD47 to SIRPα is blocked by the antibodies provided herein.

The anti-SIRPα antibodies provided herein can also be conjugated or recombinantly fused, e.g., to a detectable agent. Further provided are compositions comprising an anti-SIRPα antibody.

Also provided herein are isolated nucleic acid molecules encoding an immunoglobulin heavy chain, light chain, VH region, VL region, VH CDR1, VH CDR2, VH CDR3, VL CDR1, VL CDR2, and/or VL CDR3 of anti-SIRPα antibodies that bind to a SIRPα polypeptide, a SIRPα polypeptide fragment, a SIRPα peptide, or a SIRPα epitope.

Further provided are vectors and host cells comprising nucleic acid molecules encoding anti-SIRPα antibodies that bind to a SIRPα polypeptide, a SIRPα polypeptide fragment, a SIRPα peptide, or a SIRPα epitope. Also provided are methods of making antibodies that bind to a SIRPα polypeptide, a SIRPα polypeptide fragment, a SIRPα peptide, or a SIRPα epitope.

4.3.1 Anti-SIRPα Antibodies

In one embodiment, the present disclosure provides anti-SIRPα antibodies that may find use herein as therapeutic agents. Exemplary antibodies include polyclonal, monoclonal, humanized, human, bispecific, and heteroconjugate antibodies, as well as variants thereof having improved affinity or other properties.

In some embodiments, provided herein are antibodies that bind to SIRPα, including a SIRPα polypeptide, a SIRPα polypeptide fragment, a SIRPα peptide, or a SIRPα epitope. In certain embodiments, the antibodies provided herein bind to human and/or cyno SIRPα. In other embodiments, the antibodies provided herein do not bind to rodent SIRPα (e.g., a mouse SIRPα). In one embodiment, an antibody provided herein binds to human SIRPα. In another embodiment, an antibody provided herein binds to cyno SIRPα. In another embodiment, an antibody provided herein binds to human SIRPα and cyno SIRPα. In some embodiments, an antibody provided herein binds to human SIRPα and does not bind to a rodent SIRPα (e.g., a mouse SIRPα). In some embodiments, an antibody provided herein binds to cyno SIRPα and does not bind to a rodent SIRPα (e.g., a mouse SIRPα). In some embodiments, an antibody provided herein binds to human SIRPα, binds to a cyno SIRPα, and does not bind to a rodent SIRPα (e.g., a mouse SIRPα). In some embodiments, the anti-SIRPα antibodies block or inhibit the binding of CD47 to a SIRPα polypeptide. In some embodiments, the anti-SIRPα antibodies compete with CD47 for the binding to a SIRPα polypeptide. In other embodiments, the anti-SIRPα antibodies are human or humanized antibodies (e.g., comprising human constant regions) that bind SIRPα, including a SIRPα polypeptide, a SIRPα polypeptide fragment, a SIRPα peptide, or a SIRPα epitope.

In certain embodiments, the anti-SIRPα antibody comprises a VH region, VL region, VH CDR1, VH CDR2, VH CDR3, VL CDR1, VL CDR2, and/or VL CDR3 of any one of the monoclonal antibodies described herein, such as an amino acid sequence depicted in Tables 1-4 and 9-10. Accordingly, in some embodiments, the isolated antibody or functional fragment thereof provided herein comprises one, two, and/or three heavy chain CDRs and/or one, two, and/or three light chain CDRs from: (a) the antibody SIRPAB-1, (b) the antibody SIRPAB-2, (c) the antibody SIRPAB-3, (d) the antibody SIRPAB-4, (e) the antibody SIRPAB-5, (f) the antibody SIRPAB-6, (g) the antibody SIRPAB-7, (h) the antibody SIRPAB-8, (i) the antibody SIRPAB-9, (j) the antibody SIRPAB-10, (k) the antibody SIRPAB-11, (l) the antibody SIRPAB-12, (m) the antibody SIRPAB-13, (n) the antibody SIRPAB-17, (o) the antibody SIRPAB-18, (p) the antibody SIRPAB-19, (q) the antibody SIRPAB-20, or (r) the antibody SIRPAB-21, as shown in Tables 1-2.

TABLE 1

VL CDR Amino Acid Sequences

| Antibody | VL CDR1 (SEQ ID NO:) | VL CDR2 (SEQ ID NO:) | VL CDR3 (SEQ ID NO:) |
|---|---|---|---|
| SIRPAB-1 | QASQDISNYLN (SEQ ID NO: 11) | DASNLAT (SEQ ID NO: 13) | QQFAYLPWT (SEQ ID NO: 15) |
| SIRPAB-2 | QASQDISNYLN (SEQ ID NO: 11) | DASNLAT (SEQ ID NO: 13) | QQFAYLPWT (SEQ ID NO: 15) |
| SIRPAB-3 | QASQDISNYLN (SEQ ID NO: 11) | DASNLAT (SEQ ID NO: 13) | QQFAYLPWT (SEQ ID NO: 15) |
| SIRPAB-4 | QASQDISNYLN (SEQ ID NO: 11) | DASNLAT (SEQ ID NO: 13) | QQFAYLPWT (SEQ ID NO: 15) |
| SIRPAB-5 | QASQDISNYLN (SEQ ID NO: 11) | DASNLAT (SEQ ID NO: 13) | QQFAYLPWT (SEQ ID NO: 15) |
| SIRPAB-6 | QASQDISNYLN (SEQ ID NO: 11) | DASNLET (SEQ ID NO: 43) | QQFAYLPYT (SEQ ID NO: 44) |
| SIRPAB-7 | QASQDISNYLN (SEQ ID NO: 11) | DASNLET (SEQ ID NO: 43) | QQFAYLPYT (SEQ ID NO: 44) |
| SIRPAB-8 | RASQGISSWLA (SEQ ID NO: 62) | AASNLQS (SEQ ID NO: 63) | QQGASFPIT (SEQ ID NO: 65) |
| SIRPAB-9 | RASQGISSWLA (SEQ ID NO: 62) | AASNLQS (SEQ ID NO: 63) | QQGASFPIT (SEQ ID NO: 65) |

TABLE 1-continued

VL CDR Amino Acid Sequences

| Antibody | VL CDR1 (SEQ ID NO:) | VL CDR2 (SEQ ID NO:) | VL CDR3 (SEQ ID NO:) |
|---|---|---|---|
| SIRPAB-10 | RASQGISSWLA (SEQ ID NO: 62) | AASNLQS (SEQ ID NO: 63) | QQGASFPIT (SEQ ID NO: 65) |
| SIRPAB-11 | RASQGISSWLA (SEQ ID NO: 62) | AASNLQS (SEQ ID NO: 63) | QQGASFPIT (SEQ ID NO: 65) |
| SIRPAB-12 | RASQGISSWLA (SEQ ID NO: 62) | AASNLQS (SEQ ID NO: 63) | QQGASFPIT (SEQ ID NO: 65) |
| SIRPAB-13 | RASQGISSWLA (SEQ ID NO: 62) | AASNLQS (SEQ ID NO: 63) | QQGASFPIT (SEQ ID NO: 65) |
| SIRPAB-17 | QASQDISNYLN (SEQ ID NO: 11) | DASNLAT (SEQ ID NO: 13) | QQFAYLPWT (SEQ ID NO: 15) |
| SIRPAB-18 | QASQDISNYLN (SEQ ID NO: 11) | DASNLAT (SEQ ID NO: 13) | QQFAYLPWT (SEQ ID NO: 15) |
| SIRPAB-19 | QASDDISDYLN (SEQ ID NO: 130) | DASNIED (SEQ ID NO: 131) | QQFAYLPWT (SEQ ID NO: 15) |
| SIRPAB-20 | QASQDISDYLN (SEQ ID NO: 135) | DADNLET (SEQ ID NO: 136) | QQFAYLPWT (SEQ ID NO: 15) |
| SIRPAB-21 | QASDDISDYLN (SEQ ID NO: 130) | DASNLET (SEQ ID NO: 43) | QQFAYLPWT (SEQ ID NO: 15) |

TABLE 2

VH CDR Amino Acid Sequences

| Antibody | VH CDR1 (SEQ ID NO:) | VH CDR2 (SEQ ID NO:) | VH CDR3 (SEQ ID NO:) |
|---|---|---|---|
| SIRPAB-1 | GSISSGGYYWS (SEQ ID NO: 2) | SIYYSGSTYYNPSLKS (SEQ ID NO: 4) | AREGYHSGMDV (SEQ ID NO: 6) |
| SIRPAB-2 | GSISSGGDYWA (SEQ ID NO: 19) | YIYPSGFTYYNPSLKS (SEQ ID NO: 20) | AREGYHSGMDV (SEQ ID NO: 6) |
| SIRPAB-3 | GSISSGGWYWQ (SEQ ID NO: 24) | TIYYSGSTFYNPSLKS (SEQ ID NO: 25) | AREGYHSGMDV (SEQ ID NO: 6) |
| SIRPAB-4 | GSISSGSPYWS (SEQ ID NO: 29) | YIYASGFTYYNPSLKS (SEQ ID NO: 30) | AREGYHSGMDV (SEQ ID NO: 6) |
| SIRPAB-5 | GSISSGPAYWS (SEQ ID NO: 34) | TIYYSGSTFYNPSLKS (SEQ ID NO: 25) | AREGYHSGMDV (SEQ ID NO: 6) |
| SIRPAB-6 | GSISSGGYYWS (SEQ ID NO: 2) | YIYYSGSTYYNPSLKS (SEQ ID NO: 38) | AREGLDGSYGSSA (SEQ ID NO: 39) |
| SIRPAB-7 | GSISSGEYYWE (SEQ ID NO: 47) | YIYSSGFTYYNPSLKS (SEQ ID NO: 48) | AREGLDGSYGSSA (SEQ ID NO: 39) |
| SIRPAB-8 | YTFTSYGIS (SEQ ID NO: 53) | WISPYNGNTNYAQKLQG (SEQ ID NO: 55) | AREAGSSWYDFDL (SEQ ID NO: 57) |
| SIRPAB-9 | YTFGGYGIS (SEQ ID NO: 68) | WISAYGGETNYAQKLQG (SEQ ID NO: 69) | AREAGSSWYDFDL (SEQ ID NO: 57) |
| SIRPAB-10 | YTFTGYPIS (SEQ ID NO: 73) | WIYAYGGNTNYAQKLQG (SEQ ID NO: 74) | AREAGSSWYDFDL (SEQ ID NO: 57) |
| SIRPAB-11 | YTFRGYGIS (SEQ ID NO: 78) | WISAYGGETNYAQKLQG (SEQ ID NO: 69) | AREAGSSWYDFDL (SEQ ID NO: 57) |
| SIRPAB-12 | YTFTGYGIV (SEQ ID NO: 82) | WISAYAGETNYAQKLQG (SEQ ID NO: 83) | AREAGSSWYDFDL (SEQ ID NO: 57) |
| SIRPAB-13 | YTFHGYGIS (SEQ ID NO: 87) | WISAYSGETNYAQKLQG (SEQ ID NO: 88) | AREAGSSWYDFDL (SEQ ID NO: 57) |

TABLE 2-continued

VH CDR Amino Acid Sequences

| Antibody | VH CDR1 (SEQ ID NO:) | VH CDR2 (SEQ ID NO:) | VH CDR3 (SEQ ID NO:) |
|---|---|---|---|
| SIRPAB-17 | GSISSGGYYWS (SEQ ID NO: 2) | AIYYSGPIYYNPSLKS (SEQ ID NO: 121) | AREGYHSGMDV (SEQ ID NO: 6) |
| SIRPAB-18 | GSISSGGYYWS (SEQ ID NO: 2) | AIYYSGPIYYNPSLKS (SEQ ID NO: 121) | SKEGYHSGMDV (SEQ ID NO: 125) |
| SIRPAB-19 | GSISSGGYYWS (SEQ ID NO: 2) | AIYYSGPIYYNPSLKS (SEQ ID NO: 121) | SKEGYHSGMDV (SEQ ID NO: 125) |
| SIRPAB-20 | GSISSGGYYWS (SEQ ID NO: 2) | AIYYSGPIYYNPSLKS (SEQ ID NO: 121) | SKEGYHSGMDV (SEQ ID NO: 125) |
| SIRPAB-21 | GSISSGGYYWS (SEQ ID NO: 2) | AIYYSGPIYYNPSLKS (SEQ ID NO: 121) | SKEGYHSGMDV (SEQ ID NO: 125) |

In some embodiments, an antibody provided herein comprises or consists of six CDRs, for example, VH CDR1, VH CDR2, VH CDR3, VL CDR1, VL CDR2, and/or VL CDR3 identified in Tables 1-2. In some embodiments, an antibody provided herein can comprise fewer than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3 identified in Tables 1-2. In some embodiments, the antibody comprises or consists of one, two, three, four, or five CDRs selected from the group consisting of VH CDR1, VH CDR2, VH CDR3, VL CDR1, VL CDR2, and/or VL CDR3 of the monoclonal antibody selected from the group consisting of: (a) the antibody SIRPAB-1, (b) the antibody SIRPAB-2, (c) the antibody SIRPAB-3, (d) the antibody SIRPAB-4, (e) the antibody SIRPAB-5, (f) the antibody SIRPAB-6, (g) the antibody SIRPAB-7, (h) the antibody SIRPAB-8, (i) the antibody SIRPAB-9, (j) the antibody SIRPAB-10, (k) the antibody SIRPAB-11, (l) the antibody SIRPAB-12, (m) the antibody SIRPAB-13, (n) the antibody SIRPAB-17, (o) the antibody SIRPAB-18, (p) the antibody SIRPAB-19, (q) the antibody SIRPAB-20, and (r) the antibody SIRPAB-21, described herein. Accordingly, in some embodiments, the antibody comprises or consists of one, two, three, four, or five CDRs of anyone of the VH CDR1, VH CDR2, VH CDR3, VL CDR1, VL CDR2, and/or VL CDR3 identified in Tables 1-2.

In some embodiments, the antibodies provided herein comprise one or more (e.g., one, two, or three) VH CDRs listed in Table 2. In other embodiments, the antibodies provided herein comprise one or more (e.g., one, two, or three) VL CDRs listed in Table 1. In yet other embodiments, the antibodies provided herein comprise one or more (e.g., one, two, or three) VH CDRs listed in Table 2 and one or more VL CDRs listed in Table 1. Accordingly, in some embodiments, the antibodies comprise a VH CDR1 having an amino acid sequence of any one of SEQ ID NOS:78 and 82. In some embodiments, the antibodies comprise a VH CDR2 having an amino acid sequence of any one of SEQ ID NOS:69 and 83. In some embodiments, the antibodies comprise a VH CDR3 having an amino acid sequence of SEQ ID NO:57. In some embodiments, the antibodies comprise a VH CDR1 and/or a VH CDR2 and/or a VH CDR3 independently selected from any one of the VH CDR1, VH CDR2, and VH CDR3 amino acid sequence(s) as depicted in Table 2. In some embodiments, the antibodies comprise a VL CDR1 having an amino acid sequence of SEQ ID NO:62. In another embodiment, the antibodies comprise a VL CDR2 having an amino acid sequence of SEQ ID NO:63. In some embodiments, the antibodies comprise a VL CDR3 having an amino acid sequence of SEQ ID NO:65. In some embodiments, the antibodies comprise a VL CDR1 and/or a VL CDR2 and/or a VL CDR3 independently selected from any one of the VL CDR1, VL CDR2, and VL CDR3 amino acid sequences as depicted in Table 1.

In certain embodiments, the antibodies provided herein comprise a VH region comprising: (1) a VH CDR1 having an amino acid sequence of SEQ ID NO:78; (2) a VH CDR2 having an amino acid sequence of SEQ ID NO:69; and (3) a VH CDR3 having an amino acid sequence of SEQ ID NO:57; and a VL region comprising: (1) a VL CDR1 having an amino acid sequence of SEQ ID NO:62; (2) a VL CDR2 having an amino acid sequence of SEQ ID NO:63; and (3) a VL CDR3 having an amino acid sequence of SEQ ID NO:65.

In certain embodiments, the antibodies provided herein comprise a VH region comprising: (1) a VH CDR1 having an amino acid sequence of SEQ ID NO:82; (2) a VH CDR2 having an amino acid sequence of SEQ ID NO:83; and (3) a VH CDR3 having an amino acid sequence of SEQ ID NO:57; and a VL region comprising: (1) a VL CDR1 having an amino acid sequence of SEQ ID NO:62; (2) a VL CDR2 having an amino acid sequence of SEQ ID NO:63; and (3) a VL CDR3 having an amino acid sequence of SEQ ID NO:65.

In some embodiments, the antibodies provided herein comprise a VH region comprising: (1) a VH CDR1 having an amino acid sequence of SEQ ID NO:78; (2) a VH CDR2 having an amino acid sequence of SEQ ID NO:69; and (3) a VH CDR3 having an amino acid sequence of SEQ ID NO:57.

In other embodiments, the antibodies provided herein comprise a VL region comprising: (1) a VL CDR1 having an amino acid sequence of SEQ ID NO:62; (2) a VL CDR2 having an amino acid sequence of SEQ ID NO:63; and (3) a VL CDR3 having an amino acid sequence of SEQ ID NO:65.

In some embodiments, the antibodies provided herein comprise a VH region comprising: (1) a VH CDR1 having an amino acid sequence of SEQ ID NOS:82; (2) a VH CDR2 having an amino acid sequence of SEQ ID NO:83; and (3) a VH CDR3 having an amino acid sequence of SEQ ID NO:57.

Also provided herein are antibodies comprising one or more (e.g., one, two, or three) VH CDRs and one or more (e.g., one, two, or three) VL CDRs listed in Tables 1-2. In particular, provided herein is an antibody comprising a VH CDR1 (SEQ ID NOS:78 or 82) and a VL CDR1 (SEQ ID NO:62). In one embodiment, the antibody comprises a VH CDR1 (SEQ ID NOS:78 or 82) and a VL CDR2 (SEQ ID NO:63). In other embodiments, the antibody comprises a VH CDR1 (SEQ ID NOS:78 or 82) and a VL CDR3 (SEQ ID NO:65). In another embodiment, the antibody comprises a VH CDR2 (SEQ ID NOS:69 or 83) and a VL CDR1 (SEQ ID NO:62). In some embodiments, the antibody comprises a VH CDR2 (SEQ ID NOS:69 or 83) and a VL CDR2 (SEQ ID NO:63). In one embodiment, the antibody comprises a VH CDR2 (SEQ ID NOS:69 or 83) and a VL CDR3 (SEQ ID NO:65). In another embodiment, the antibody comprises a VH CDR3 (SEQ ID NO:57) and a VL CDR1 (SEQ ID NO:62). In other embodiments, the antibody comprises a VH CDR3 (SEQ ID NO:57) and a VL CDR2 (SEQ ID NO:63). In some embodiments, the antibody comprises a VH CDR3 (SEQ ID NO:57) and a VL CDR3 (SEQ ID NO:65). In another embodiment, the antibody comprises a VH CDR1 (SEQ ID NOS:78 or 82), a VH CDR2 (SEQ ID NOS:69 or 83), and a VL CDR1 (SEQ ID NO:62). In one embodiment, the antibody comprises a VH CDR1 (SEQ ID NOS:78 or 82), a VH CDR2 (SEQ ID NOS:69 or 83), and a VL CDR2 (SEQ ID NO:63). In other embodiments, the antibody comprises a VH CDR1 (SEQ ID NOS:78 or 82), a VH CDR2 (SEQ ID NOS:69 or 83), and a VL CDR3 (SEQ ID NO:65). In another embodiment, the antibody comprises a VH CDR2 (SEQ ID NOS:69 or 83), a VH CDR3 (SEQ ID NO:57), and a VL CDR1 (SEQ ID NO:62). In some embodiments, the antibody comprises a VH CDR2 (SEQ ID NOS:69 or 83), a VH CDR3 (SEQ ID NO:57), and a VL CDR2 (SEQ ID NO:63). In one embodiment, the antibody comprises a VH CDR2 (SEQ ID NOS:69 or 83), a VH CDR3 (SEQ ID NO:57), and a VL CDR3 (SEQ ID NO:65). In another embodiment, the antibody comprises a VH CDR1 (SEQ ID NOS:78 or 82), a VH CDR3 (SEQ ID NO:57), and a VL CDR1 (SEQ ID NO:62). In other embodiments, the antibody comprises a VH CDR1 (SEQ ID NOS:78 or 82), a VH CDR3 (SEQ ID NO:57), and a VL CDR2 (SEQ ID NO:63). In some embodiments, the antibody comprises a VH CDR1 (SEQ ID NOS:78 or 82), a VH CDR3 (SEQ ID NO:57), and a VL CDR3 (SEQ ID NO:65). In another embodiment, the antibody comprises a VH CDR1 (SEQ ID NOS:78 or 82), a VL CDR1 (SEQ ID NO:62), and a VL CDR2 (SEQ ID NO:63). In one embodiment, the antibody comprises a VH CDR1 (SEQ ID NOS:78 or 82), a VL CDR1 (SEQ ID NO:62), and a VL CDR3 (SEQ ID NO:65). In other embodiments, the antibody comprises a VH CDR1 (SEQ ID NOS:78 or 82), a VL CDR2 (SEQ ID NO:63), and a VL CDR3 (SEQ ID NO:65). In another embodiment, the antibody comprises a VH CDR2 (SEQ ID NOS:69 or 83), a VL CDR1 (SEQ ID NO:62), and a VL CDR2 (SEQ ID NO:63). In some embodiments, the antibody comprises a VH CDR2 (SEQ ID NOS:69 or 83), a VL CDR1 (SEQ ID NO:62), and a VL CDR3 (SEQ ID NO:65). In one embodiment, the antibody comprises a VH CDR2 (SEQ ID NOS:69 or 83), a VL CDR2 (SEQ ID NO:63), and a VL CDR3 (SEQ ID NO:65). In another embodiment, the antibody comprises a VH CDR3 (SEQ ID NO:57), a VL CDR1 (SEQ ID NO:62), and a VL CDR2 (SEQ ID NO:63). In other embodiments, the antibody comprises a VH CDR3 (SEQ ID NO:57), a VL CDR1 (SEQ ID NO:62), and a VL CDR3 (SEQ ID NO:65). In some embodiments, the antibody comprises a VH CDR3 (SEQ ID NO:57), a VL CDR2 (SEQ ID NO:63), and a VL CDR3 (SEQ ID NO:65). In another embodiment, the antibody comprises a VH CDR1 (SEQ ID NOS:78 or 82), a VH CDR2 (SEQ ID NOS:69 or 83), a VH CDR3 (SEQ ID NO:57), and a VL CDR1 (SEQ ID NO:62). In one embodiment, the antibody comprises a VH CDR1 (SEQ ID NOS:78 or 82), a VH CDR2 (SEQ ID NOS:69 or 83), a VH CDR3 (SEQ ID NO:57), and a VL CDR2 (SEQ ID NO:63). In other embodiments, the antibody comprises a VH CDR1 (SEQ ID NOS:78 or 82), a VH CDR2 (SEQ ID NOS:69 or 83), a VH CDR3 (SEQ ID NO:57), and a VL CDR3 (SEQ ID NO:65). In another embodiment, the antibody comprises a VH CDR1 (SEQ ID NOS:78 or 82), a VH CDR2 (SEQ ID NOS:69 or 83), a VL CDR1 (SEQ ID NO:62), and a VL CDR2 (SEQ ID NO:63), In some embodiments, the antibody comprises a VH CDR1 (SEQ ID NOS:78 or 82), a VH CDR2 (SEQ ID NOS:69 or 83), a VL CDR1 (SEQ ID NO:62), and a VL CDR3 (SEQ ID NO:65). In one embodiment, the antibody comprises a VH CDR1 (SEQ ID NOS:78 or 82), a VH CDR2 (SEQ ID NOS:69 or 83), a VL CDR2 (SEQ ID NO:63), and a VL CDR3 (SEQ ID NO:65). In another embodiment, the antibody comprises a VH CDR1 (SEQ ID NOS:78 or 82), a VH CDR3 (SEQ ID NO:57), a VL CDR1 (SEQ ID NO:62), and a VL CDR2 (SEQ ID NO:63). In other embodiments, the antibody comprises a VH CDR1 (SEQ ID NOS:78 or 82), a VH CDR3 (SEQ ID NO:57), a VL CDR1 (SEQ ID NO:62), and a VL CDR3 (SEQ ID NO:65). In some embodiments, the antibody comprises a VH CDR1 (SEQ ID NOS:78 or 82), a VH CDR3 (SEQ ID NO:57), a VL CDR2 (SEQ ID NO:63), and a VL CDR3 (SEQ ID NO:65). In another embodiment, the antibody comprises a VH CDR2 (SEQ ID NOS:69 or 83), a VH CDR3 (SEQ ID NO:57), a VL CDR1 (SEQ ID NO:62), and a VL CDR2 (SEQ ID NO:63). In one embodiment, the antibody comprises a VH CDR2 (SEQ ID NOS:69 or 83), a VH CDR3 (SEQ ID NO:57), a VL CDR1 (SEQ ID NO:62), and a VL CDR3 (SEQ ID NO:65). In other embodiments, the antibody comprises a VH CDR2 (SEQ ID NOS:69 or 83), a VH CDR3 (SEQ ID NO:57), a VL CDR2 (SEQ ID NO:63), and a VL CDR3 (SEQ ID NO:65). In another embodiment, the antibody comprises a VH CDR1 (SEQ ID NOS:78 or 82), a VH CDR2 (SEQ ID NOS:69 or 83), a VH CDR3 (SEQ ID NO:57), a VL CDR1 (SEQ ID NO:62), and a VL CDR2 (SEQ ID NO:63), In some embodiments, the antibody comprises a VH CDR1 (SEQ ID NOS:78 or 82), a VH CDR2 (SEQ ID NOS:69 or 83), a VH CDR3 (SEQ ID NO:57), a VL CDR1 (SEQ ID NO:62), and a VL CDR3 (SEQ ID NO:65). In one embodiment, the antibody comprises a VH CDR1 (SEQ ID NOS:78 or 82), a VH CDR2 (SEQ ID NOS:69 or 83), a VH CDR3 (SEQ ID NO:57), a VL CDR2 (SEQ ID NO:63), and a VL CDR3 (SEQ ID NO:65). In another embodiment, the antibody comprises a VH CDR1 (SEQ ID NOS:78 or 82), a VH CDR3 (SEQ ID NO:57), a VL CDR1 (SEQ ID NO:62), a VL CDR2 (SEQ ID NO:63), and a VL CDR3 (SEQ ID NO:65). In other embodiments, the antibody comprises a VH CDR1 (SEQ ID NOS:78 or 82), a VH CDR3 (SEQ ID NO:57), a VL CDR1 (SEQ ID NO:62), a VL CDR2 (SEQ ID NO:63), and a VL CDR3 (SEQ ID NO:65). In some embodiments, the antibody comprises a VH CDR2 (SEQ ID NOS:69 or 83), a VH CDR3 (SEQ ID NO:57), a VL CDR1 (SEQ ID NO:62), a VL CDR2 (SEQ ID NO:63), and a VL CDR3 (SEQ ID NO:65). In another embodiment, the antibody comprises a VH CDR1 (SEQ ID NOS:78 or 82), a VL CDR1 (SEQ ID NO:62), a VL CDR2 (SEQ ID NO:63), and a VL CDR3 (SEQ ID NO:65). In one embodiment, the antibody comprises a VH CDR2 (SEQ ID NOS:69 or 83), a VL CDR1 (SEQ ID NO:62), a VL CDR2 (SEQ ID NO:63), and a VL CDR3 (SEQ ID NO:65). In other embodiments, the antibody comprises a VH CDR3 (SEQ ID NO:57), a VL CDR1 (SEQ ID NO:62), a VL CDR2 (SEQ ID NO:63), and a VL CDR3 (SEQ ID NO:65). In another embodiment, the antibody comprises any combination thereof of the VH CDRs and VL CDRs listed in Tables 1-2.

In yet another aspect, the CDRs disclosed herein include consensus sequences derived from groups of related antibodies (see, Tables 1-2). As described herein, a "consensus sequence" refers to amino acid sequences having conserved amino acids common among a number of sequences and variable amino acids that vary within a given amino acid sequences.

In some embodiments, the isolated antibody or functional fragment thereof provided herein further comprises one, two, three, and/or four heavy chain FRs and/or one, two, three, and/or four light chain FRs from: (a) the antibody SIRPAB-1, (b) the antibody SIRPAB-2, (c) the antibody SIRPAB-3, (d) the antibody SIRPAB-4, (e) the antibody SIRPAB-5, (f) the antibody SIRPAB-6, (g) the antibody SIRPAB-7, (h) the antibody SIRPAB-8, (i) the antibody SIRPAB-9, (j) the antibody SIRPAB-10, (k) the antibody SIRPAB-11, (l) the antibody SIRPAB-12, (m) the antibody SIRPAB-13, (n) the antibody SIRPAB-17, (o) the antibody SIRPAB-18, (p) the antibody SIRPAB-19, (q) the antibody SIRPAB-20, and (r) the antibody SIRPAB-21, as shown in Tables 3-4.

TABLE 3

VL FR Amino Acid Sequences

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| SIRPAB-1 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-2 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-3 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-4 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-5 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-6 | DIQLTQSPSSLSASVGDRVTITC (SEQ ID NO: 197) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-7 | DIQLTQSPSSLSASVGDRVTITC (SEQ ID NO: 197) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-8 | DIQMTQSPSSVSASVGDRVTITC (SEQ ID NO: 61) | WYQQKPGKAPKLLIY (SEQ ID NO: 12) | GVPSRFSGSGSGTDFTLTISSLQPEDFATYYC (SEQ ID NO: 64) | FGGGTKVEIK (SEQ ID NO: 16) |
| SIRPAB-9 | DIQMTQSPSSVSASVGDRVTITC (SEQ ID NO: 61) | WYQQKPGKAPKLLIY (SEQ ID NO: 12) | GVPSRFSGSGSGTDFTLTISSLQPEDFATYYC (SEQ ID NO: 64) | FGGGTKVEIK (SEQ ID NO: 16) |
| SIRPAB-10 | DIQMTQSPSSVSASVGDRVTITC (SEQ ID NO: 61) | WYQQKPGKAPKLLIY (SEQ ID NO: 12) | GVPSRFSGSGSGTDFTLTISSLQPEDFATYYC (SEQ ID NO: 64) | FGGGTKVEIK (SEQ ID NO: 16) |
| SIRPAB-11 | DIQMTQSPSSVSASVGDRVTITC (SEQ ID NO: 61) | WYQQKPGKAPKLLIY (SEQ ID NO: 12) | GVPSRFSGSGSGTDFTLTISSLQPEDFATYYC (SEQ ID NO: 64) | FGGGTKVEIK (SEQ ID NO: 16) |
| SIRPAB-12 | DIQMTQSPSSVSASVGDRVTITC (SEQ ID NO: 61) | WYQQKPGKAPKLLIY (SEQ ID NO: 12) | GVPSRFSGSGSGTDFTLTISSLQPEDFATYYC (SEQ ID NO: 64) | FGGGTKVEIK (SEQ ID NO: 16) |
| SIRPAB-13 | DIQMTQSPSSVSASVGDRVTITC (SEQ ID NO: 61) | WYQQKPGKAPKLLIY (SEQ ID NO: 12) | GVPSRFSGSGSGTDFTLTISSLQPEDFATYYC (SEQ ID NO: 64) | FGGGTKVEIK (SEQ ID NO: 16) |
| SIRPAB-17 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |

TABLE 3-continued

VL FR Amino Acid Sequences

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| SIRPAB-18 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-19 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-20 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |
| SIRPAB-21 | DIQMTQSPSSLSASVGDRVTITC (SEQ ID NO: 10) | WYQQKPGKAPKLLIY (SEQ ID NO: 12) | GVPSRFSGSGSGTDFTFTISSLQPEDIATYYC (SEQ ID NO: 14) | FGGGTKVEIK (SEQ ID NO: 16) |

TABLE 4

VH FR Amino Acid Sequences

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| SIRPAB-1 | QVQLQESGPGLVKPSQTLSLTCTVSG (SEQ ID NO: 1) | WIRQHPGKGLEWIG (SEQ ID NO: 3) | RVTISVDTSKNQFSLKLSSVTAADTAVYYC (SEQ ID NO: 5) | WGQGTTVTVSS (SEQ ID NO: 7) |
| SIRPAB-2 | QVQLQESGPGLVKPSQTLSLTCTVSG (SEQ ID NO: 1) | WIRQHPGKGLEWIG (SEQ ID NO: 3) | RVTISVDTSKNQFSLKLSSVTAADTAVYYC (SEQ ID NO: 5) | WGQGTTVTVSS (SEQ ID NO: 7) |
| SIRPAB-3 | QVQLQESGPGLVKPSQTLSLTCTVSG (SEQ ID NO: 1) | WIRQHPGKGLEWIG (SEQ ID NO: 3) | RVTISVDTSKNQFSLKLSSVTAADTAVYYC (SEQ ID NO: 5) | WGQGTTVTVSS (SEQ ID NO: 7) |
| SIRPAB-4 | QVQLQESGPGLVKPSQTLSLTCTVSG (SEQ ID NO: 1) | WIRQHPGKGLEWIG (SEQ ID NO: 3) | RVTISVDTSKNQFSLKLSSVTAADTAVYYC (SEQ ID NO: 5) | WGQGTTVTVSS (SEQ ID NO: 7) |
| SIRPAB-5 | QVQLQESGPGLVKPSQTLSLTCTVSG (SEQ ID NO: 1) | WIRQHPGKGLEWIG (SEQ ID NO: 3) | RVTISVDTSKNQFSLKLSSVTAADTAVYYC (SEQ ID NO: 5) | WGQGTTVTVSS (SEQ ID NO: 7) |
| SIRPAB-6 | QVQLQESGPGLVKPSQTLSLTCTVSG (SEQ ID NO: 1) | WIRQHPGKGLEWIG (SEQ ID NO: 3) | RVTISVDTSKNQFSLKLSSVTAADTAVYYC (SEQ ID NO: 5) | WGQGTLVTVSS (SEQ ID NO: 40) |
| SIRPAB-7 | QVQLQESGPGLVKPSQTLSLTCTVSG (SEQ ID NO: 1) | WIRQHPGKGLEWIG (SEQ ID NO: 3) | RVTISVDTSKNQFSLKLSSVTAADTAVYYC (SEQ ID NO: 5) | WGQGTLVTVSS (SEQ ID NO: 40) |
| SIRPAB-8 | QVQLVQSGAEVKKPGASVKVSCKASG (SEQ ID NO: 52) | WVRQAPGQGLEWMG (SEQ ID NO: 54) | RVTMTTDTSTSTAYMELRSLRSDDTAVYYC (SEQ ID NO: 56) | WGRGTLVTVSS (SEQ ID NO: 58) |
| SIRPAB-9 | QVQLVQSGAEVKKPGASVKVSCKASG (SEQ ID NO: 52) | WVRQAPGQGLEWMG (SEQ ID NO: 54) | RVTMTTDTSTSTAYMELRSLRSDDTAVYYC (SEQ ID NO: 56) | WGRGTLVTVSS (SEQ ID NO: 58) |
| SIRPAB-10 | QVQLVQSGAEVKKPGASVKVSCKASG (SEQ ID NO: 52) | WVRQAPGQGLEWMG (SEQ ID NO: 54) | RVTMTTDTSTSTAYMELRSLRSDDTAVYYC (SEQ ID NO: 56) | WGRGTLVTVSS (SEQ ID NO: 58) |
| SIRPAB-11 | QVQLVQSGAEVKKPGASVKVSCKASG (SEQ ID NO: 52) | WVRQAPGQGLEWMG (SEQ ID NO: 54) | RVTMTTDTSTSTAYMELRSLRSDDTAVYYC (SEQ ID NO: 56) | WGRGTLVTVSS (SEQ ID NO: 58) |
| SIRPAB-12 | QVQLVQSGAEVKKPGASVKVSCKASG (SEQ ID NO: 52) | WVRQAPGQGLEWMG (SEQ ID NO: 54) | RVTMTTDTSTSTAYMELRSLRSDDTAVYYC (SEQ ID NO: 56) | WGRGTLVTVSS (SEQ ID NO: 58) |

TABLE 4-continued

VH FR Amino Acid Sequences

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| SIRPAB-13 | QVQLVQSGAEVKKP GASVKVSCKASG (SEQ ID NO: 52) | WVRQAPGQGLEWMG (SEQ ID NO: 54) | RVTMTTDTSTSTAYME LRSLRSDDTAVYYC (SEQ ID NO: 56) | WGRGTLVTVSS (SEQ ID NO: 58) |
| SIRPAB-17 | QVQLQESGPGLVKP SQTLSLTCTVSG (SEQ ID NO: 1) | WIRQHPGKGLEWIG (SEQ ID NO: 3) | RVTISVDTSKNQFSLK LSSVTAADTAVYYC (SEQ ID NO: 5) | WGQGTTVTVSS (SEQ ID NO: 7) |
| SIRPAB-18 | QVQLQESGPGLVKP SQTLSLTCTVSG (SEQ ID NO: 1) | WIRQHPGKGLEWIG (SEQ ID NO: 3) | RVTISVDTSKNQFSLK LSSVTAADTAVYYC (SEQ ID NO: 5) | WGQGTTVTVSS (SEQ ID NO: 7) |
| SIRPAB-19 | QVQLQESGPGLVKP SQTLSLTCTVSG (SEQ ID NO: 1) | WIRQHPGKGLEWIG (SEQ ID NO: 3) | RVTISVDTSKNQFSLK LSSVTAADTAVYYC (SEQ ID NO: 5) | WGQGTTVTVSS (SEQ ID NO: 7) |
| SIRPAB-20 | QVQLQESGPGLVKP SQTLSLTCTVSG (SEQ ID NO: 1) | WIRQHPGKGLEWIG (SEQ ID NO: 3) | RVTISVDTSKNQFSLK LSSVTAADTAVYYC (SEQ ID NO: 5) | WGQGTTVTVSS (SEQ ID NO: 7) |
| SIRPAB-21 | QVQLQESGPGLVKP SQTLSLTCTVSG (SEQ ID NO: 1) | WIRQHPGKGLEWIG (SEQ ID NO: 3) | RVTISVDTSKNQFSLK LSSVTAADTAVYYC (SEQ ID NO: 5) | WGQGTTVTVSS (SEQ ID NO: 7) |

In certain embodiments, the isolated antibody or functional fragment thereof provided herein further comprises one, two, three, and/or four heavy chain FRs from: (a) the antibody SIRPAB-1, (b) the antibody SIRPAB-2, (c) the antibody SIRPAB-3, (d) the antibody SIRPAB-4, (e) the antibody SIRPAB-5, (f) the antibody SIRPAB-6, (g) the antibody SIRPAB-7, (h) the antibody SIRPAB-8, (i) the antibody SIRPAB-9, (j) the antibody SIRPAB-10, (k) the antibody SIRPAB-11, (l) the antibody SIRPAB-12, (m) the antibody SIRPAB-13, (n) the antibody SIRPAB-17, (o) the antibody SIRPAB-18, (p) the antibody SIRPAB-19, (q) the antibody SIRPAB-20, and (r) the antibody SIRPAB-21, as shown in Table 4. In some embodiments, the antibody heavy chain FR(s) is from the antibody SIRPAB-1. In some embodiments, the antibody heavy chain FR(s) is from the antibody SIRPAB-2. In other embodiments, the antibody heavy chain FR(s) is from the antibody SIRPAB-3. In certain embodiments, the antibody heavy chain FR(s) is from the antibody SIRPAB-4. In other embodiments, the antibody heavy chain FR(s) is from the antibody SIRPAB-5. In some embodiments, the antibody heavy chain FR(s) is from the antibody SIRPAB-6. In some embodiments, the antibody heavy chain FR(s) is from the antibody SIRPAB-7. In some embodiments, the antibody heavy chain FR(s) is from the antibody SIRPAB-8. In certain embodiments, the antibody heavy chain FR(s) is from the antibody SIRPAB-9. In some embodiments, the antibody heavy chain FR(s) is from the antibody SIRPAB-10. In some embodiments, the antibody heavy chain FR(s) is from the antibody SIRPAB-11. In certain embodiments, the antibody heavy chain FR(s) is from the antibody SIRPAB-12. In some embodiments, the antibody heavy chain FR(s) is from the antibody SIRPAB-13. In some embodiments, the antibody heavy chain FR(s) is from the antibody SIRPAB-17. In certain embodiments, the antibody heavy chain FR(s) is from the antibody SIRPAB-18. In some embodiments, the antibody heavy chain FR(s) is from the antibody SIRPAB-19. In certain embodiments, the antibody heavy chain FR(s) is from the antibody SIRPAB-20. In another embodiment, the antibody heavy chain FR(s) is from the antibody SIRPAB-21.

In some embodiments, the isolated antibody or functional fragment thereof provided herein further comprises one, two, three, and/or four light chain FRs from: (a) the antibody SIRPAB-1, (b) the antibody SIRPAB-2, (c) the antibody SIRPAB-3, (d) the antibody SIRPAB-4, (e) the antibody SIRPAB-5, (f) the antibody SIRPAB-6, (g) the antibody SIRPAB-7, (h) the antibody SIRPAB-8, (i) the antibody SIRPAB-9, (j) the antibody SIRPAB-10, (k) the antibody SIRPAB-11, (l) the antibody SIRPAB-12, (m) the antibody SIRPAB-13, (n) the antibody SIRPAB-17, (o) the antibody SIRPAB-18, (p) the antibody SIRPAB-19, (q) the antibody SIRPAB-20, and (r) the antibody SIRPAB-21, as shown in Table 3. In some embodiments, the antibody light chain FR(s) is from the antibody SIRPAB-1. In some embodiments, the antibody light chain FR(s) is from the antibody SIRPAB-2. In other embodiments, the antibody light chain FR(s) is from the antibody SIRPAB-3. In certain embodiments, the antibody light chain FR(s) is from the antibody SIRPAB-4. In other embodiments, the antibody light chain FR(s) is from the antibody SIRPAB-5. In some embodiments, the antibody light chain FR(s) is from the antibody SIRPAB-6. In some embodiments, the antibody light chain FR(s) is from the antibody SIRPAB-7. In some embodiments, the antibody light chain FR(s) is from the antibody SIRPAB-8. In contain embodiment, the antibody light chain FR(s) is from the antibody SIRPAB-9. In some embodiments, the antibody light chain FR(s) is from the antibody SIRPAB-10. In some embodiments, the antibody light chain FR(s) is from the antibody SIRPAB-11. In certain embodiments, the antibody light chain FR(s) is from the antibody SIRPAB-12. In some embodiments, the antibody light chain FR(s) is from the antibody SIRPAB-13. In some embodiments, the antibody light chain FR(s) is from the antibody SIRPAB-17. In certain embodiments, the antibody light chain FR(s) is from the antibody SIRPAB-18. In some embodiments, the antibody light chain FR(s) is from the antibody SIRPAB-19. In certain embodiments, the antibody light chain FR(s) is from the antibody SIRPAB-20. In another embodiment, the antibody light chain FR(s) is from the antibody SIRPAB-21.

In certain embodiments, an antibody of fragment thereof described herein comprises a VH region that comprises: (1) a VH FR1 having an amino acid sequence of SEQ ID NO:52; (2) a FR2 having an amino acid sequence of SEQ ID NO:54; (3) a VH FR3 having an amino acid sequence of SEQ ID NO:56; and/or (4) a VH FR4 having an amino acid sequence of SEQ ID NO:58. In specific embodiments, the antibody comprises a VH region comprising all four of the above-referenced. VH FR1, VH FR2, VH FR3, and VH FR4.

Accordingly, in some embodiments, the humanized antibody comprises a VH region that includes a VH FR1 having an amino acid sequence of SEQ ID NO:52. In some embodiments, the humanized antibody comprises a VH region that includes a VH FR2 having an amino acid sequence of SEQ ID NO:54. In some embodiments, the humanized antibody comprises a VH region that includes a VH FR3 having an amino acid sequence of SEQ ID NO:56, In other embodiments, the humanized antibody comprises a VH region that includes a VH FR4 having an amino acid sequence of SEQ ID NO:58.

In certain embodiments, an antibody or antigen binding fragment thereof described herein comprises a VL region that comprises: (1) a VL FR1 having an amino acid sequence of SEQ ID NO:61; (2) a VL FR2 having an amino acid sequence of SEQ ID NO:12; (3) a VL FR3 having an amino acid sequence of SEQ ID NO:64; and/or (4) a VL FR4 having an amino acid sequence of SEQ ID NO:16.

Accordingly, in some embodiments, the humanized antibody comprises a VL region that includes a VL FR1 having an amino acid sequence of SEQ ID NO:61. In certain embodiments, the humanized antibody comprises a VL region that includes a VL FR2 having an amino acid sequence of SEQ ID NO:12. In other embodiments, the humanized antibody comprises a VL region that includes a VL FR3 having an amino acid sequence of SEQ ID NO:64. In yet other embodiments, the humanized antibody comprises a VL region that includes a VL FR4 having an amino acid sequence of SEQ ID NO:16.

In certain embodiments, an antibody or antigen binding fragment thereof described herein comprises a VH region and a VL region, wherein the VH region comprises: (1) a VH FR1 having an amino acid sequence of SEQ ID NO:52; (2) a VH FR2 having an amino acid sequence of SEQ ID NO:54; (3) a VH FR3 having an amino acid sequence of SEQ ID NO:56; and/or (4) a VH FR4 having an amino acid sequence of SEQ ID NO:58; and wherein the VL region comprises: (1) a VL FR1 having an amino acid sequence of SEQ ID NO:61; (2) a VL FR2 having an amino acid sequence of SEQ ID NO:12; (3) a VL FR3 having an amino acid sequence of SEQ ID NO:64; and/or (4) a VL FR4 having an amino acid sequence of SEQ ID NO:16. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

Also provided herein are antibodies comprising one or more (e.g., one, two, three, or four) VH FRs and one or more (e.g., one, two, three, or four) VL FRs listed in Tables 3-4. In particular, provided herein is an antibody comprising a VH FR1 (SEQ ID NO:52) and a VL FR1 (SEQ ID NO:61).

In one embodiment, the antibody comprises a VH FR1 (SEQ ID NO:52) and a VL FR2 (SEQ ID NO:12). In some embodiments, the antibody comprises a VH FR1 (SEQ ID NO:52) and a VL FR3 (SEQ ID NO:64). In another embodiment, the antibody comprises a VH FR1 (SEQ 1D NO:52) and a VL FR4 (SEQ ID NO:16). In other embodiments, the antibody comprises a VH FR2 (SEQ ID NO:54) and a VL FR1 (SEQ ID NO:61). In one embodiment, the antibody comprises a VH FR2 (SEQ ID NO:54) and a VL FR2 (SEQ ID NO:12). In some embodiments, the antibody comprises a VH FR2 (SEQ ID NO:54) and a VL FR3 (SEQ ID NO:64). In another embodiment, the antibody comprises a VH FR2 (SEQ ID NO:54) and a VL FR4 (SEQ ID NO:16). In one embodiment, the antibody comprises a VH FR3 (SEQ ID NO:56) and a VL FR1 (SEQ ID NO:61). In other embodiments, the antibody comprises a VH FR3 (SEQ ID NO:56) and a VL FR2 (SEQ ID NO:12). In another embodiment, the antibody comprises a VH FR3 (SEQ ID NO:56) and a VL FR3 (SEQ ID NO:64). In some embodiments, the antibody comprises a VH FR3 (SEQ ID NO:56) and a VL FR4 (SEQ ID NO:16). In one embodiment, the antibody comprises a VH FR4 (SEQ ID NO:58) and a VL FR1 (SEQ ID NO:61). In another embodiment, the antibody comprises a VH FR4 (SEQ ID NO:58) and a VL FR2 (SEQ ID NO:12). In one embodiment, the antibody comprises a VH FR4 (SEQ ID NO:58) and a VL FR3 (SEQ ID NO:64). In some embodiments, the antibody comprises a VH FR4 (SEQ ID NO:58) and a VL FR4 (SEQ ID NO:16). In another embodiment, the antibody comprises a VH FR1 (SEQ ID NO:52), a VH FR2 (SEQ ID NO:54), and a VL FR1 (SEQ ID NO:61). In other embodiments, the antibody comprises a VH FRI (SEQ ID NO:52), a VH FR2 (SEQ ID NO:54), and a VL FR2 (SEQ ID NO:12). In one embodiment, the antibody comprises a VH FR1 (SEQ ID NO:52), a VH FR2 (SEQ ID NO:54), and a VL FR3 (SEQ ID NO:64). In another embodiment, the antibody comprises a VH FR1 (SEQ ID NO:52), a VH FR2 (SEQ ID NO:54), and a VL FR4 (SEQ ID NO:16). In some embodiments, the antibody comprises a VH FR2 (SEQ ID NO:54), a VH FR3 (SEQ ID NO:56), and a VL FR1 (SEQ ID NO:61). In one embodiment, the antibody comprises a VH FR2 (SEQ ID NO:54), a VH FR3 (SEQ ID NO:56), and a VL FR2 (SEQ ID NO:12). In another embodiment, the antibody comprises a VH FR2 (SEQ ID NO:54), a VH FR3 (SEQ ID NO:56), and a VL FR3 (SEQ ID NO:64). In other embodiments, the antibody comprises a VH FR2 (SEQ ID NO:54), a VH FR3 (SEQ ID NO:56), and a VL FR4 (SEQ ID NO:16). In some embodiments, the antibody comprises a VH FR1 (SEQ ID NO:52), a VL FR1 (SEQ ID NO:61), and a VL FR2 (SEQ ID NO:12). In another embodiment, the antibody comprises a VH FR1 (SEQ ID NO:52), a VL FR1 (SEQ ID NO:61), and a VL FR3 (SEQ ID NO:64). In one embodiment, the antibody comprises a VH FR1 (SEQ ID NO:52), a VL FR1 (SEQ ID NO:61), and a VL FR4 (SEQ ID NO:16). In one embodiment, the antibody comprises a VH FR1 (SEQ ID NO:52), a VL FR2 (SEQ ID NO:12) and a VL FR3 (SEQ ID NO:64). In another embodiment, the antibody comprises a VH FR1 (SEQ ID NO:52), a VL FR2 (SEQ ID NO:12) and a VL FR4 (SEQ ID NO:16). In some embodiments, the antibody comprises a VH FR1 (SEQ ID NO:52), a VL FR3 (SEQ ID NO:64), and a VL FR4 (SEQ ID NO:16). In other embodiments, the antibody comprises a VH FR2 (SEQ ID NO:54), a VL FR1 (SEQ ID NO:61), and a VL FR2 (SEQ ID NO:12). In another embodiment, the antibody comprises a VH FR2 (SEQ ID NO:54), a VL FR1 (SEQ ID NO:61), and a VL FR3 (SEQ ID NO:64). In one embodiment, the antibody comprises a VH FR2 (SEQ ID NO:54), a VL FR1 (SEQ ID NO:61), and a VL FR4 (SEQ ID NO:16). In some embodiments, the antibody comprises a VH FR2 (SEQ ID NO:54), a VL FR2 (SEQ ID NO:12) and a VL FR3 (SEQ ID NO:64). In another embodiment, the antibody comprises a VH FR2 (SEQ ID NO:54), a VL FR2 (SEQ ID NO:12) and a VL FR4 (SEQ ID NO:16). In one embodiment, the antibody comprises a VH FR2 (SEQ ID NO:54), a VL FR3 (SEQ ID NO:64), and a VL FR4 (SEQ ID NO:16). In another embodiment, the antibody comprises a VH FR3 (SEQ ID NO:56), a. VL FR1 (SEQ ID NO:61), and a VL FR2 (SEQ ID NO:12). In other embodiments, the antibody comprises a VH FR3 (SEQ ID NO:56), a VL FR1 (SEQ ID NO:61), and a VL FR3 (SEQ ID NO:64). In some embodiments, the antibody comprises a VH FR3 (SEQ ID NO:56), a VL FR1 (SEQ ID NO:61), and a VL FR4 (SEQ ID NO:16). In another embodiment, the antibody comprises a VH FR3 (SEQ ID NO:56), a VL FR2 (SEQ ID NO:12) and a VL FR3 (SEQ ID NO:64). In one embodiment, the antibody comprises a VH FR3 (SEQ ID NO:56), a VL FR2 (SEQ ID NO:12) and a VL FR4 (SEQ ID NO:16). In one embodiment, the antibody comprises a VH FR3 (SEQ ID NO:56), a VL FR3 (SEQ ID NO:64), and a VL FR4 (SEQ ID NO:16). In another embodiment, the antibody comprises a VH FR4 (SEQ ID NO:58), a VL FR1 (SEQ ID NO:61), and a VL FR2 (SEQ ID NO:12). In some embodiments, the antibody comprises a VH FR4 (SEQ ID NO:58), a VL FR1 (SEQ ID NO:61), and a VL FR3 (SEQ ID NO:64). In other embodiments, the antibody comprises a VH FR4 (SEQ ID NO:58), a VL FR1 (SEQ ID NO:61), and a VL FR4 (SEQ ID NO:16). In another embodiment, the antibody comprises a VH FR4 (SEQ ID NO:58), a VL FR2 (SEQ ID NO:12) and a VL FR3 (SEQ ID NO:64). In one embodiment, the antibody comprises a VH FR4 (SEQ ID NO:58), a VL FR2 (SEQ ID NO:12) and a VL FR4 (SEQ ID NO:16). In some embodiments, the antibody comprises a VH FR4 (SEQ ID NO:58), a VL FR3 (SEQ ID NO:64), and a VL FR4 (SEQ ID NO:16). In another embodiment, the antibody comprises a VH FR1 (SEQ ID NO:52), a VH FR2 (SEQ ID NO:54), a VH FR3 (SEQ ID NO:56), and a VL FR1 (SEQ ID NO:61). In one embodiment, the antibody comprises a VH FR1 (SEQ ID NO:52), a VH FR2 (SEQ ID NO:54), a VH FR3 (SEQ ID NO:56), and a VL FR2 (SEQ ID NO:12). In other embodiments, the antibody comprises a VH FR1 (SEQ ID NO:52), a VH FR2 (SEQ ID NO:54), a VH FR3 (SEQ ID NO:56), and a VL FR3 (SEQ ID NO:64). In another embodiment, the antibody comprises a VH FR1 (SEQ ID NO:52), a VH FR2 (SEQ ID NO:54), a VH FR3 (SEQ ID NO:56), and a VL FR4 (SEQ ID NO:16). In some embodiments, the antibody comprises a VH FR1 (SEQ ID NO:52), a VH FR2 (SEQ ID NO:54), a VH FR4 (SEQ ID NO:58), and a VL FR1 (SEQ ID NO:61). In one embodiment, the antibody comprises a VH F1I (SEQ ID NO:52), a VH FR2 (SEQ ID NO:54), a VH FR4 (SEQ ID NO:58), and a VL FR2 (SEQ ID NO:12). In another embodiment, the antibody comprises a VH FR1 (SEQ ID NO:52), a VH FR2 (SEQ ID NO:54), a VH FR4 (SEQ ID NO:58), and a VL FR3 (SEQ ID NO:64). In one embodiment, the antibody comprises a VH FR1 (SEQ ID NO:52), a VH FR2 (SEQ ID NO:54), a VH FR4 (SEQ ID NO:58), and a VL FR4 (SEQ ID NO:16). In some embodiments, the antibody comprises a VH FR1 (SEQ ID NO:52), a VH FR3 (SEQ ID NO:56), a VH FR4 (SEQ ID NO:58), and a VL FR1 (SEQ ID NO:61). In another embodiment, the antibody comprises a VH FR1 (SEQ ID NO:52), a VH FR3 (SEQ ID NO:56), a VH FR4 (SEQ ID NO:58), and a VL FR2 (SEQ ID NO:12). In other embodiments, the antibody comprises a VH FR1 (SEQ ID NO:52), VH FR3 (SEQ ID NO:56), a VH FR4 (SEQ ID NO:58), and a VL FR3 (SEQ ID NO:64). In one embodiment, the antibody comprises a VH FR1 (SEQ ID NO:52), a VH FR3 (SEQ ID NO:56), a VH FR4 (SEQ ID NO:58), and a VL FR4 (SEQ ID NO:16). In another embodiment, the antibody comprises a VH FR2 (SEQ NO:54), a VH FR3 (SEQ ID NO:56), a VH FR4 (SEQ ID NO:58), and a VL FR1 (SEQ ID NO:61). In some embodiments, the antibody comprises a VH FR2 (SEQ ID NO:54), a VH FR3 (SEQ ID NO:56), a VH FR4 (SEQ ID NO:58), and a VL FR2 (SEQ ID NO:12). In one embodiment, the antibody comprises a VH FR2 (SEQ ID NO:54), VH FR3 (SEQ ID NO:56), a VH FR4 (SEQ ID NO:58), and a VL FR3 (SEQ ID NO:64). In another embodiment, the antibody comprises a VH FR2 (SEQ ID NO:54), a VH FR3 (SEQ ID NO:56), a VH FR4 (SEQ ID NO:58), and a VL FR4 (SEQ ID NO:16). In other embodiments, the antibody comprises a VH FR1 (SEQ ID NO:52), a VH FR2 (SEQ ID NO:54), a VL FR1 (SEQ ID NO:61), and a VL FR2 (SEQ ID NO:12). In some embodiments, the antibody comprises a VG FR4 (SEQ ID NO:52), a VH FR2 (SEQ ID NO:54), a VL FR1 (SEQ ID NO:61), and a VL FR3 (SEQ ID NO:64). In another embodiment, the antibody comprises a VH FR1 (SEQ ID NO:52), a VH FR2 (SEQ ID NO:54), a VL FR1 (SEQ ID NO:61), and a VL FR4 (SEQ ID NO:16). In one embodiment, the antibody comprises a VH FR1 (SEQ ID NO:52), a VH FR2 (SEQ ID NO:54), a VL FR2 (SEQ ID NO:12), and a VL FR3 (SEQ ID NO:64). In one embodiment, the antibody comprises a VH FR1 (SEQ ID NO:52), a VH FR2 (SEQ ID NO:54), a VL FR2 (SEQ ID NO:12), and a VL FR4 (SEQ ID NO:16). In another embodiment, the antibody comprises a VH FR1 (SEQ ID NO:52), a VH FR2 (SEQ ID NO:54), a VL FR3 (SEQ ID NO:64), and a VL FR4 (SEQ ID NO:16). In some embodiments, the antibody comprises a VH FR1 (SEQ ID NO:52), a VH FR3 (SEQ ID NO:56), a VL FR1 (SEQ ID NO:61), and a VL FR2 (SEQ ID NO:12). In other embodiments, the antibody comprises a VH FR1 (SEQ ID NO:52), a VH FR3 (SEQ ID NO:56), a VL FR1 (SEQ ID NO:61), and a VL FR3 (SEQ ID NO:64). In another embodiment, the antibody comprises a VH FR1 (SEQ ID NO:52), a VH FR3 (SEQ ID NO:56), a VL FR1 (SEQ ID NO:61), and a VL FR4 (SEQ ID NO:16). In one embodiment, the antibody comprises a VH FR1 (SEQ ID NO:52), a VH FR3 (SEQ ID NO:56), a VL FR2 (SEQ ID NO:12), and a VL FR3 (SEQ ID NO:64). In some embodiments, the antibody comprises a VH FR1 (SEQ ID NO:52), a VH FR3 (SEQ ID NO:56), a VL FR2 (SEQ ID NO:12), and a VL FR4 (SEQ ID NO:16). In another embodiment, the antibody comprises a VH FR1 (SEQ ID NO:52), a VH FR3 (SEQ ID NO:56), a VL FR3 (SEQ ID NO:64), and a VL FR4 (SEQ ID NO:16). In one embodiment, the antibody comprises a VH FR1 (SEQ ID NO:52), a VH FR4 (SEQ ID NO:58), a VL FR1 (SEQ ID NO:61), and a VL FR2 (SEQ ID NO:12). In other embodiments, the antibody comprises a VH FR1 (SEQ ID NO:52), a VH FR4 (SEQ ID NO:58), a VL FR1 (SEQ ID NO:61), and a VL FR3 (SEQ ID NO:64). In another embodiment, the antibody comprises a VH FR1 (SEQ ID NO:52), a VH FR4 (SEQ ID NO:58), a VL FR1 (SEQ ID NO:61), and a VL FR4 (SEQ ID NO:16). In some embodiments, the antibody comprises a VH FR1 (SEQ ID NO:52), a VH FR4 (SEQ ID NO:58), a VL FR2 (SEQ ID NO:12), and a VL FR3 (SEQ ID NO:64). In one embodiment, the antibody comprises a VH FR1 (SEQ ID NO:52), a VH FR4 (SEQ ID NO:58), a VL FR2 (SEQ ID NO:12), and a VL FR4 (SEQ ID NO:16). In another embodiment, the antibody comprises a VH FR1 (SEQ ID NO:52), a VH FR4 (SEQ ID NO:58), a VL (SEQ ID NO:64), and a VL FR4 (SEQ ID NO:16). In one embodiment, the antibody comprises a VH FR2 (SEQ ID NO:54), a VH FR3 (SEQ ID NO:56), a VL FR1 (SEQ ID NO:61), and a VL (SEQ ID NO:12). In some embodiments, the antibody comprises a VH FR2 (SEQ ID NO:54), a VH FR3 (SEQ ID NO:56), a VL FR1 (SEQ ID NO:61), and a VL FR3 (SEQ ID NO:64). In another embodiment, the antibody comprises a VH FR2 (SEQ ID NO:54), a VH FR3 (SEQ ID NO:56), a VL FR1 (SEQ ID NO:61), and a VL FR4 (SEQ ID NO:16). In other embodiments, the antibody comprises a VH FR2 (SEQ ID NO:54), a VH FR3 (SEQ ID NO:56), a VL FR2 (SEQ ID NO:12), and a VL FR3 (SEQ ID NO:64). In one embodiment, the antibody comprises a VH FR2 (SEQ ID NO:54), a VH FR3 (SEQ ID NO:56), a VL FR2 (SEQ ID NO:12), and a VL FR4 (SEQ ID NO:16). In another embodiment, the antibody comprises a VH FR2 (SEQ ID NO:54), a VH FR3 (SEQ ID NO:56), a VL FR3 (SEQ ID NO:64), and a VL FR4 (SEQ ID NO:16). In some embodiments, the antibody comprises a VH FR2 (SEQ ID NO:54), a VH FR4 (SEQ ID NO:58), a VL FR1 (SEQ ID NO:61), and a VL FR2 (SEQ ID NO:12). In one embodiment, the antibody comprises a VH FR2 (SEQ ID NO:54), a VH FR4 (SEQ ID NO:58), a VL FR1 (SEQ ID NO:61), and a VL FR3 (SEQ ID NO:64). In another embodiment, the antibody comprises a VH FR2 (SEQ ID NO:54), a VH FR4 (SEQ ID NO:58), a VL FR1 (SEQ ID NO:61), and a VL FR4 (SEQ ID NO:16). In other embodiments, the antibody comprises a VH FR2 (SEQ ID NO:54), a VH FR4 (SEQ ID NO:58), a VL FR2 (SEQ ID NO:12), and a VL FR3 (SEQ ID NO:64). In some embodiments, the antibody comprises a VH FR2 (SEQ ID NO:54), a VH FR4 (SEQ ID NO:58), a VL FR2 (SEQ ID NO:12), and a VL FR4 (SEQ ID NO:16). In another embodiment, the antibody comprises a VH FR2 (SEQ ID NO:54), a VH FR4 (SEQ ID NO:58), a VL FR3 (SEQ ID NO:64), and a VL FR4 (SEQ ID NO:16). In one embodiment, the antibody comprises a VH FR3 (SEQ ID NO:56), a VH FR4 (SEQ ID NO:58), a VL FR1 (SEQ ID NO:61), and a VL FR2 (SEQ ID NO:12). In one embodiment, the antibody comprises a VH FR3 (SEQ ID NO:56), a VH FR4 (SEQ ID NO:58), a VL FR1 (SEQ ID NO:61), and a VL FR3 (SEQ ID NO:64). In another embodiment, the antibody comprises a VH FR3 (SEQ ID NO:56), a VH FR4 (SEQ ID NO:58), a VL FR1 (SEQ ID NO:61), and a VL FR4 (SEQ ID NO:16). In some embodiments, the antibody comprises a VH FR3 (SEQ ID NO:56), a VH FR4 (SEQ ID NO:58), a VL FR2 (SEQ ID NO:12), and a VL FR3 (SEQ ID NO:64). In other embodiments, the antibody comprises a VH FR3 (SEQ ID NO:56), a VH FR4 (SEQ ID NO:58), a VL FR2 (SEQ ID NO:12), and a VL FR4 (SEQ ID NO:16). In another embodiment, the antibody comprises a VH FR3 (SEQ ID NO:56), a VH FR4 (SEQ ID NO:58), a VL FR3 (SEQ ID NO:64), and a VL FR4 (SEQ ID NO:16). In one embodiment, the antibody comprises a VH FR1 (SEQ ID NO:52), a VL FR1 (SEQ ID NO:61), a VL FR2 (SEQ ID NO:12), and a VL FR3 (SEQ ID NO:64). In some embodiments, the antibody comprises a VH FR1 (SEQ ID NO:52), a VL FR1 (SEQ ID NO:61), a VL FR2 (SEQ ID NO:12), and a V. FR4 (SEQ ID NO:16). In another embodiment, the antibody comprises a VH FR1 (SEQ ID NO:52), a VL FR1 (SEQ ID NO:61), a VL FR3 (SEQ ID NO:64), and a VL FR4 (SEQ ID NO:16). In one embodiment, the antibody comprises a VH FR1 (SEQ ID NO:52), a VL FR2 (SEQ ID NO:12), a VL FR3 (SEQ ID NO:64), and a VL FR4 (SEQ ID NO:16). In other embodiments, the antibody comprises a VH FR2 (SEQ ID NO:54), a VL FR1 (SEQ ID NO:61), a VL FR2 (SEQ ID NO:12), and a VL FR3 (SEQ ID NO:64). In another embodiment, the antibody comprises a VH FR2 (SEQ ID NO:54), a VL FR1 (SEQ ID NO:61), a VL FR2 (SEQ ID NO:12), and a VL FR4 (SEQ ID NO:16). In some embodiments, the antibody comprises a VH FR2 (SEQ ID NO:54), a VL FR1 (SEQ ID NO:61), a VL FR3 (SEQ ID NO:64), and a VL FR4 (SEQ ID NO:16). In one embodiment, the antibody comprises a VH FR2 (SEQ ID NO:54), a VL FR2 (SEQ ID NO:12), a VL FR3 (SEQ ID NO:64), and a VL FR4 (SEQ ID NO:16). In another embodiment, the antibody comprises a VH FR3 (SEQ ID NO:56), a VL FR1 (SEQ ID NO:61), a VL FR2 (SEQ ID NO:12), and a VL FR3 (SEQ ID NO:64). In one embodiment, the antibody comprises a VH FR3 (SEQ ID NO:56), a VL FR1 (SEQ ID NO:61), a VL FR2 (SEQ ID NO:12), and a VL FR4 (SEQ ID NO:16). In some embodiments, the antibody comprises a VH FR3 (SEQ ID NO:56), a VL FR1 (SEQ ID NO:61), a VL FR3 (SEQ ID NO:64), and a VL FR4 (SEQ ID NO:16). In another embodiment, the antibody comprises a VH FR3 (SEQ ID NO:56), a VL FR2 (SEQ ID NO:12), a VL FR3 (SEQ ID NO:64), and a VL FR4 (SEQ ID NO:16). In other embodiments, the antibody comprises a VH FR4 (SEQ ID NO:58), a VL FR1 (SEQ ID NO:61), a VL FR2 (SEQ ID NO:12), and a VL FR3 (SEQ ID NO:64). In one embodiment, the antibody comprises a VH FR4 (SEQ ID NO:58), a VL FR1 (SEQ ID NO:61), a VL FR2 (SEQ ID NO:12), and a VL FR4 (SEQ ID NO:16). In another embodiment, the antibody comprises a VH FR4 (SEQ ID NO:58), a VL FR1 (SEQ ID NO:61), a VL FR3 (SEQ ID NO:64), and a VL FR4 (SEQ ID NO:16). In some embodiments, the antibody comprises a VH FR4 (SEQ ID NO:58), a VL FR2 (SEQ ID NO:12), a VL FR3 (SEQ ID NO:64), and a VL FR4 (SEQ ID NO:16). In one embodiment, the antibody comprises a VH FR1 (SEQ ID NO:52), a VH FR2 (SEQ ID NO:54), a VH FR3 (SEQ ID NO:56), a VH FR4 (SEQ ID NO:58), and a VL FR1 (SEQ ID NO:61). In another embodiment, the antibody comprises a VH FR1 (SEQ ID NO:52), a VH FR2 (SEQ ID NO:54), a VH FR3 (SEQ ID NO:56), a VH FR4 (SEQ ID NO:58), and a VL FR2 (SEQ ID NO:12). In other embodiments, the antibody comprises a VH FR1 (SEQ ID NO:52), a VH FR2 (SEQ ID NO:54), a VH FR3 (SEQ ID NO:56), a VH FR4 (SEQ ID NO:58), and a VL FR3 (SEQ ID NO:64). In some embodiments, the antibody comprises a VH FR1 (SEQ ID NO:52), a VH FR2 (SEQ ID NO:54), a VH FR3 (SEQ ID NO:56), a VH FR4 (SEQ ID NO:58), and a VL FR4 (SEQ ID NO:16). In another embodiment, the antibody comprises a VH FR1 (SEQ ID NO:52), a VH FR2 (SEQ ID NO:54), a VH FR3 (SEQ ID NO:56), a VL FR1 (SEQ ID NO:61), and a VL FR2 (SEQ ID NO:12). In one embodiment, the antibody comprises a VH FR1 (SEQ ID NO:52), a VH FR2 (SEQ ID NO:54), a VH FR3 (SEQ ID NO:56), a VL FR1 (SEQ ID NO:61), and a VL FR3 (SEQ ID NO:64). In one embodiment, the antibody comprises a VH FR1 (SEQ ID NO:52), a VH FR2 (SEQ ID NO:54), a VH FR3 (SEQ ID NO:56), a VL FR1 (SEQ ID NO:61), and a VL FR4 (SEQ ID NO:16). In another embodiment, the antibody comprises a VH FR1 (SEQ ID NO:52), a VH FR2 (SEQ ID NO:54), a VH FR3 (SEQ ID NO:56), a VL FR2 (SEQ ID NO:12), and a VL FR3 (SEQ ID NO:64). In some embodiments, the antibody comprises a VH FR1 (SEQ ID NO:52), a VH FR2 (SEQ ID NO:54), a VH FR3 (SEQ ID NO:56), a VL FR2 (SEQ ID NO:12), and a VL FR4 (SEQ ID NO:16). In other embodiments, the antibody comprises a VH FR1 (SEQ ID NO:52), a VH FR2 (SEQ ID NO:54), a VH FR3 (SEQ ID NO:56), a VL FR3 (SEQ ID NO:64), and a VL FR4 (SEQ ID NO:16). In another embodiment, the antibody comprises a VH FR1 (SEQ ID NO:52), a VH FR2 (SEQ ID NO:54), a VH FR4 (SEQ ID NO:58), a VL FR1 (SEQ ID NO:61), and a VL FR2 (SEQ ID NO:12). In one embodiment, the antibody comprises a VH FR1 (SEQ ID NO:52), a VH FR2 (SEQ ID NO:54), a VH FR4 (SEQ ID NO:58), a VL FR1 (SEQ ID NO:61), and a VL FR3 (SEQ ID NO:64). In some embodiments, the antibody comprises a VH FR1 (SEQ ID NO:52), a VH FR2 (SEQ ID NO:54), a VH FR4 (SEQ ID NO:58), a VL FR1 (SEQ ID NO:61), and a VL FR4 (SEQ ID NO:16). In another embodiment, the antibody comprises a VH FR1 (SEQ ID NO:52), a VH FR2 (SEQ ID NO:54), a VH FR4 (SEQ ID NO:58), a VL FR2 (SEQ ID NO:12), and a VL FR3 (SEQ ID NO:64). In one embodiment, the antibody comprises a VH FR1 (SEQ ID NO:52), a VH FR2 (SEQ ID NO:54), a VH FR4 (SEQ ID NO:58), a VL FR2 (SEQ ID NO:12), and a VL FR4 (SEQ ID NO:16). In other embodiments, the antibody comprises a VH FR1 (SEQ ID NO:52), a VH FR2 (SEQ ID NO:54), a VH FR4 (SEQ ID NO:58), a VL FR3 (SEQ ID NO:64), and a VL FR4 (SEQ ID NO:16). In another embodiment, the antibody comprises a VH FR1 (SEQ ID NO:52), a VH FR3 (SEQ ID NO:56), a VH FR4 (SEQ ID NO:58), a VL FR1 (SEQ ID NO:61), and a VL FR2 (SEQ ID NO:12). In some embodiments, the antibody comprises a VH FR1 (SEQ ID NO:52), a VH FR3 (SEQ ID NO:56), a VH FR4 (SEQ ID NO:58), a VL FR1 (SEQ ID NO:61), and a VL FR3 (SEQ ID NO:64). In one embodiment, the antibody comprises a VH FR1 (SEQ ID NO:52), a VH FR3 (SEQ ID NO:56), a VH FR4 (SEQ ID NO:58), a VL FR1 (SEQ ID NO:61), and a VL FR4 (SEQ ID NO:16). In another embodiment, the antibody comprises a VH FR1 (SEQ ID NO:52), a VH FR3 (SEQ ID NO:56), a VH FR4 (SEQ ID NO:58), a VL FR2 (SEQ ID NO:12), and a VL FR3 (SEQ ID NO:64). In one embodiment, the antibody comprises a VH FR1 (SEQ ID NO:52), a VH FR3 (SEQ ID NO:56), a VH FR4 (SEQ ID NO:58), a VL FR2 (SEQ ID NO:12), and a VL FR4 (SEQ ID NO:16). In some embodiments, the antibody comprises a VH FR1 (SEQ ID NO:52), a VH FR3 (SEQ ID NO:56), a VH FR4 (SEQ ID NO:58), a VL FR3 (SEQ ID NO:64), and a VL FR4 (SEQ ID NO:16). In another embodiment, the antibody comprises a VH FR2 (SEQ ID NO:54), a VH FR3 (SEQ ID NO:56), a VH FR4 (SEQ ID NO:58), a VL FR1 (SEQ ID NO:61), and a VL FR2 (SEQ ID NO:12). In other embodiments, the antibody comprises a VH FR2 (SEQ ID NO:54), a VH FR3 (SEQ ID NO:56), a VH FR4 (SEQ ID NO:58), a VL FR1 (SEQ ID NO:61), and a VL FR3 (SEQ ID NO:64). In one embodiment, the antibody comprises a VH FR2 (SEQ ID NO:54), a VH FR3 (SEQ ID NO:56), a VH FR4 (SEQ ID NO:58), a VL FR1 (SEQ ID NO:61), and a VL FR4 (SEQ ID NO:16). In another embodiment, the antibody comprises a VH FR2 (SEQ ID NO:54), a VH FR3 (SEQ ID NO:56), a VH FR4 (SEQ ID NO:58), a VL FR2 (SEQ ID NO:12), and a VL FR3 (SEQ ID NO:64). In some embodiments, the antibody comprises a VH FR2 (SEQ ID NO:54), a VH FR3 (SEQ ID NO:56), a VH FR4 (SEQ ID NO:58), a VL FR2 (SEQ ID NO:12), and a VL FR4 (SEQ ID NO:16). In one embodiment, the antibody comprises a VH FR2 (SEQ ID NO:54), a VH FR3 (SEQ ID NO:56), a VH FR4 (SEQ ID NO:58), a VL FR3 (SEQ ID NO:64), and a VL FR4 (SEQ ID NO:16). In another embodiment, the antibody comprises a VH FR1 (SEQ ID NO:52), a VH FR2 (SEQ ID NO:54), a VL FR1 (SEQ ID NO:61), a VL FR2 (SEQ ID NO:12), and a VL FR3 (SEQ ID NO:64). In other embodiments, the antibody comprises a VH FR1 (SEQ ID NO:52), a VH FR2 (SEQ ID NO:54), a VL FR1 (SEQ ID NO:61), a VL FR2 (SEQ ID NO:12), and a VL FR4 (SEQ ID NO:16). In some embodiments, the antibody comprises a VH FR1 (SEQ ID NO:52), a VH FR2 (SEQ ID NO:54), a VL FR1 (SEQ ID NO:61), a VL FR3 (SEQ ID NO:64), and a VL FR4 (SEQ ID NO:16). In another embodiment, the antibody comprises a VH FR1 (SEQ ID NO:52), a VH FR2 (SEQ ID NO:54), a VL FR2 (SEQ ID NO:12), a VL FR3 (SEQ ID NO:64), and a VL FR4 (SEQ ID NO:16). In one embodiment, the antibody comprises a VH FR1 (SEQ ID NO:52), a VH FR3 (SEQ ID NO:56), a VL FR1 (SEQ ID NO:61), a VL FR2 (SEQ ID NO:12), and a VL FR3 (SEQ ID NO:64). In one embodiment, the antibody comprises a VH FR1 (SEQ ID NO:52), a VH FR3 (SEQ ID NO:56), a VL FR1 (SEQ ID NO:61), a VL FR2 (SEQ ID NO:12), and a VL FR4 (SEQ ID NO:16). In another embodiment, the antibody comprises a VH FR1 (SEQ ID NO:52), a VH FR3 (SEQ ID NO:56), a VL FR1 (SEQ ID NO:61), a VL FR3 (SEQ ID NO:64), and a VL FR4 (SEQ ID NO:16). In some embodiments, the antibody comprises a VH FR1 (SEQ ID NO:52), a VH FR3 (SEQ ID NO:56), a VL FR2 (SEQ ID NO:12), a VL FR3 (SEQ ID NO:64), and a VL FR4 (SEQ ID NO:16). In other embodiments, the antibody comprises a VH FR1 (SEQ ID NO:52), a VH FR4 (SEQ ID NO:58), a VL FR1 (SEQ ID NO:61), a VL FR2 (SEQ ID NO:12), and a VL FR3 (SEQ ID NO:64). In another embodiment, the antibody comprises a VH FR1 (SEQ ID NO:52), a VH (SEQ ID NO:58), a VL FR1 (SEQ ID NO:61), a VL FR2 (SEQ ID NO:12), and a VL FR4 (SEQ ID NO:16). In one embodiment, the antibody comprises a VH FR1 (SEQ ID NO:52), a VH FR4 (SEQ ID NO:58), a VL FR1 (SEQ ID NO:61), a VL FR3 (SEQ ID NO:64), and a VL FR4 (SEQ ID NO:16). In some embodiments, the antibody comprises a VH FR1 (SEQ ID NO:52), a VH FR4 (SEQ ID NO:58), a VL FR2 (SEQ ID NO:12), a VL FR3 (SEQ ID NO:64), and a VL FR4 (SEQ ID NO:16). In another embodiment, the antibody comprises a VH FR2 (SEQ ID NO:54), a VH FR3 (SEQ ID NO:56), a VL FR1 (SEQ ID NO:61), a VL FR2 (SEQ ID NO:12), and a VL FR3 (SEQ ID NO:64). In one embodiment, the antibody comprises a VH FR2 (SEQ ID NO:54), a VH FR3 (SEQ ID NO:56), a VL FR1 (SEQ ID NO:61), a VL FR2 (SEQ ID NO:12), and a VL FR4 (SEQ ID NO:16). In other embodiments, the antibody comprises a VH FR2 (SEQ ID NO:54), a VH FR3 (SEQ ID NO:56), a VL FR1 (SEQ ID NO:61), a VL FR3 (SEQ ID NO:64), and a VL FR4 (SEQ ID NO:16). In another embodiment, the antibody comprises a VH FR2 (SEQ ID NO:54), a VH FR3 (SEQ ID NO:56), a VL FR2 (SEQ ID NO:12), a VL FR3 (SEQ ID NO:64), and a VL FR4 (SEQ ID NO:16). In some embodiments, the antibody comprises a VH FR2 (SEQ ID NO:54), a VH FR4 (SEQ ID NO:58), a VL FR1 (SEQ ID NO:61), a VL FR2 (SEQ ID NO:12), and a VL FR3 (SEQ ID NO:64). In one embodiment, the antibody comprises a VH FR2 (SEQ ID NO:54), a VH FR4 (SEQ ID NO:58), a VL FR1 (SEQ ID NO:61), a VL FR2 (SEQ ID NO:12), and a VL FR4 (SEQ ID NO:16). In another embodiment, the antibody comprises a VH FR2 (SEQ ID NO:54), a VH FR4 (SEQ ID NO:58), a VL FR1 (SEQ ID NO:61), a VL FR3 (SEQ ID NO:64), and a VL FR4 (SEQ ID NO:16). In one embodiment, the antibody comprises a VH FR2 (SEQ ID NO:54), a VH FR4 (SEQ ID NO:58), a VL FR2 (SEQ ID NO:12), a VL FR3 (SEQ ID NO:64), and a VL FR4 (SEQ ID NO:16). In some embodiments, the antibody comprises a VH FR3 (SEQ ID NO:56), a VH FR4 (SEQ ID NO:58), a VL FR1 (SEQ ID NO:61), a VL FR2 (SEQ ID NO:12), and a VL FR3 (SEQ ID NO:64). In another embodiment, the antibody comprises a VH FR3 (SEQ ID NO:56), a VH FR4 (SEQ ID NO:58), a VL FR1 (SEQ ID NO:61), a VL FR2 (SEQ ID NO:12), and a VL FR4 (SEQ ID NO:16). In other embodiments, the antibody comprises a VH FR3 (SEQ ID NO:56), a VH FR4 (SEQ ID NO:58), a VL FR1 (SEQ ID NO:61), a VL FR3 (SEQ ID NO:64), and a VL FR4 (SEQ ID NO:16). In one embodiment, the antibody comprises a VH FR3 (SEQ ID NO:56), a VH FR4 (SEQ ID NO:58), a VL FR2 (SEQ ID NO:12), a VL FR3 (SEQ ID NO:64), and a VL FR4 (SEQ ID NO:16). In another embodiment, the antibody comprises a VH FR1

(SEQ ID NO:52), a VL FR1 (SEQ ID NO:61), a VL FR2 (SEQ ID NO:12), a VL FR3 (SEQ ID NO:64), and a VL FR4 (SEQ ID NO:16). In some embodiments, the antibody comprises a VH FR2 (SEQ ID NO:54), a VL FR1 (SEQ ID NO:61), a VL FR2 (SEQ ID NO:12), a VL FR3 (SEQ ID NO:64), and a VL FR4 (SEQ ID NO:16). In one embodiment, the antibody comprises a VH FR3 (SEQ ID NO:56), a VL FR1 (SEQ ID NO:61), a VL FR2 (SEQ ID NO:12), a VL FR3 (SEQ ID NO:64), and a VL FR4 (SEQ ID NO:16). In another embodiment, the antibody comprises a VH FR4 (SEQ ID NO:58), a VL FR1 (SEQ ID NO:61), a VL FR2 (SEQ ID NO:12), a VL FR3 (SEQ ID NO:64), and a VL FR4 (SEQ ID NO:16). In other embodiments, the antibody comprises a VH FR1 (SEQ ID NO:52), a VH FR2 (SEQ ID NO:54), a VH FR3 (SEQ ID NO:56), a VH FR4 (SEQ ID NO:58), a VL FR1 (SEQ ID NO:61), and a VL FR2 (SEQ ID NO:12). In some embodiments, the antibody comprises a VH FR1 (SEQ ID NO:52), a VH FR2 (SEQ ID NO:54), a VH FR3 (SEQ ID NO:56), a VH FR4 (SEQ ID NO:58), a VL FR1 (SEQ ID NO:61), and a VL FR3 (SEQ ID NO:64). In another embodiment, the antibody comprises a VH FR1 (SEQ ID NO:52), a VH FR1 (SEQ ID NO:54), a VH FR3 (SEQ ID NO:56), a VH FR4 (SEQ ID NO:58), a VL FR1 (SEQ ID NO:61), and a VL FR4 (SEQ ID NO:16). In one embodiment, the antibody comprises a VH FR1 (SEQ NO:52), a VH FR2 (SEQ ID NO:54), a VH FR3 (SEQ ID NO:56), a VH FR4 (SEQ ID NO:58), a VL FR2 (SEQ ID NO:12), and a VL FR2 (SEQ ID NO:64). In one embodiment, the antibody comprises a VH FR1 (SEQ ID NO:52), a VH FR2 (SEQ ID NO:54), a VH FR3 (SEQ ID NO:56), a VH FR4 (SEQ ID NO:58), a VL FR2 (SEQ ID NO:12), and a VL FR4 (SEQ ID NO:16). In another embodiment, the antibody comprises a VH FR1 (SEQ ID NO:52), a VH FR2 (SEQ ID NO:54), a VH FR3 (SEQ ID NO:56), a VH FR4 (SEQ ID NO:58), a VL FR3 (SEQ ID NO:64), and a VL FR4 (SEQ ID NO:16). In some embodiments, the antibody comprises a VH FR1 (SEQ ID NO:52), a VH FR2 (SEQ ID NO:54), a VH FR3 (SEQ ID NO:56), a VL FR1 (SEQ ID NO:61), a VL FR2 (SEQ ID NO:12), and a VL FR3 (SEQ ID NO:64). In other embodiments, the antibody comprises a VH FR1 (SEQ ID NO:52), a VH FR2 (SEQ ID NO:54), a VH FR3 (SEQ ID NO:56), a VL FR1 (SEQ ID NO:61), a VL FR2 (SEQ ID NO:12), and a VL FR4 (SEQ ID NO:16). In another embodiment, the antibody comprises a VH FR1 (SEQ ID NO:52), a VH FR2 (SEQ ID NO:54), a VH FR3 (SEQ ID NO:56), a VL FR1 (SEQ ID NO:61), a VL FR3 (SEQ ID NO:64), and a VL FR4 (SEQ ID NO:16). In one embodiment, the antibody comprises a VH FR1 (SEQ ID NO:52), a VH FR2 (SEQ ID NO:54), a VH FR3 (SEQ ID NO:56), a VL FR2 (SEQ ID NO:12), a VL FR3 (SEQ ID NO:64), and a VL FR4 (SEQ ID NO:16). In some embodiments, the antibody comprises a VH FR1 (SEQ ID NO:52), a VH FR2 (SEQ ID NO:54), a VH FR4 (SEQ ID NO:58), a VL FR1 (SEQ ID NO:61), a VL FR2 (SEQ ID NO:12), and a VL FR3 (SEQ ID NO:64). In another embodiment, the antibody comprises a VH FR1 (SEQ ID NO:52), a VH FR2 (SEQ ID NO:54), a VH FR4 (SEQ ID NO:58), a VL FR1 (SEQ ID NO:61), a VL FR2 (SEQ ID NO:12), and a VL FR4 (SEQ ID NO:16). In one embodiment, the antibody comprises a VH FR1 (SEQ ID NO:52), a VH FR2 (SEQ ID NO:54), a VH FR4 (SEQ ID NO:58), a VL FR1 (SEQ ID NO:61), a VL FR3 (SEQ ID NO:64), and a VL FR4 (SEQ ID NO:16). In other embodiments, the antibody comprises a VH FR1 (SEQ ID NO:52), a VH FR2 (SEQ ID NO:54), a VH FR4 (SEQ ID NO:58), a VL FR2 (SEQ ID NO:12), a VL FR3 (SEQ ID NO:64), and a VL FR4 (SEQ ID NO:16). In another embodiment, the antibody comprises a VH FR1

(SEQ ID NO:52), a VH FR3 (SEQ ID NO:56), a VH FR4 (SEQ ID NO:58), a VL FR1 (SEQ ID NO:61), a VL FR2 (SEQ ID NO:12), and a VL FR3 (SEQ ID NO:64). In some embodiments, the antibody comprises a VH FR1 (SEQ ID NO:52), a VH FR3 (SEQ ID NO:56), a VH FR4 (SEQ ID NO:58), a VL FR1 (SEQ ID NO:61), a VL FR2 (SEQ ID NO:12), and a VL FR4 (SEQ ID NO:16). In one embodiment, the antibody comprises a VH FR1 (SEQ ID NO:52), a VH FR3 (SEQ ID NO:56), a VH FR4 (SEQ ID NO:58), a VL FR1 (SEQ ID NO:61), a VL FR3 (SEQ ID NO:64), and a VL FR4 (SEQ ID NO:16). In another embodiment, the antibody comprises a VH FR1 (SEQ ID NO:52), a VH FR3 (SEQ ID NO:56), a VH FR4 (SEQ ID NO:58), a VL FR2 (SEQ ID NO:12), a VL FR3 (SEQ ID NO:64), and a VL FR4 (SEQ ID NO:16). In one embodiment, the antibody comprises a VH FR2 (SEQ ID NO:54), a VH FR3 (SEQ ID NO:56), a VH FR4 (SEQ ID NO:58), a VL FR1 (SEQ ID NO:61), a VL FR2 (SEQ ID NO:12), and a VL FR3 (SEQ ID NO:64). In some embodiments, the antibody comprises a VH FR2 (SEQ ID NO:54), a VH FR3 (SEQ ID NO:56), a VH FR4 (SEQ ID NO:58), a VL FR1 (SEQ ID NO:61), a VL FR2 (SEQ ID NO:12), and a VL FR4 (SEQ ID NO:16). In another embodiment, the antibody comprises a VH FR2 (SEQ ID NO:54), a VH FR3 (SEQ ID NO:56), a VH FR4 (SEQ ID NO:58), a VL FR1 (SEQ ID NO:61), a VL FR3 (SEQ ID NO:64), and a VL FR4 (SEQ ID NO:16). In other embodiments, the antibody comprises a VH FR2 (SEQ ID NO:54), a VH FR3 (SEQ ID NO:56), a VH FR4 (SEQ ID NO:58), a VL FR2 (SEQ ID NO:12), a VL FR3 (SEQ ID NO:64), and a VL FR4 (SEQ ID NO:16). In one embodiment, the antibody comprises a VH FR1 (SEQ ID NO:52), a VH FR2 (SEQ ID NO:54), a VL FR1 (SEQ ID NO:61), a VL FR2 (SEQ ID NO:12), a VL FR3 (SEQ ID NO:64), and a VL FR4 (SEQ ID NO:16). In another embodiment, the antibody comprises a VH FR1 (SEQ ID NO:52), a VH FR3 (SEQ ID NO:56), a VL FR1 (SEQ ID NO:61), a VL FR2 (SEQ ID NO:12), a VL FR3 (SEQ ID NO:64), and a VL FR4 (SEQ ID NO:16). In some embodiments, the antibody comprises a VH FR1 (SEQ ID NO:52), a VH FR4 (SEQ ID NO:58), a VL FR1 (SEQ ID NO:61), a VL FR2 (SEQ ID NO:12), a VL FR3 (SEQ ID NO:64), and a VL FR4 (SEQ ID NO:16). In one embodiment, the antibody comprises a VH FR2 (SEQ ID NO:54), a VH FR3 (SEQ ID NO:56), a VL FR1 (SEQ ID NO:61), a VL FR2 (SEQ ID NO:12), a VL FR3 (SEQ ID NO:64), and a VL FR4 (SEQ ID NO:16). In another embodiment, the antibody comprises a VH FR2 (SEQ ID NO:54), a VH FR4 (SEQ ID NO:58), a VL FR1 (SEQ ID NO:61), a VL FR2 (SEQ ID NO:12), a VL FR3 (SEQ ID NO:64), and a VL FR4 (SEQ ID NO:16). In other embodiments, the antibody comprises a VH FR3 (SEQ ID NO:56), a VH FR4 (SEQ ID NO:58), a VL FR1 (SEQ ID NO:61), a VL FR2 (SEQ ID NO:12), a VL FR3 (SEQ ID NO:64), and a VL FR4 (SEQ ID NO:16). In some embodiments, the antibody comprises a VH FR1 (SEQ ID NO:52), a VH FR2 (SEQ ID NO:54), a VH FR3 (SEQ ID NO:56), a VH FR4 (SEQ ID NO:58), a VL FR1 (SEQ ID NO:61), a VL FR2 (SEQ ID NO:12), and a VL FR3 (SEQ ID NO:64). In another embodiment, the antibody comprises a VH FR1 (SEQ ID NO:52), a VH FR2 (SEQ ID NO:54), a VH FR3 (SEQ ID NO:56), a VH FR4 (SEQ ID NO:58), a VL FR1 (SEQ ID NO:61), a VL FR2 (SEQ ID NO:12), and a VL FR4 (SEQ ID NO:16). In one embodiment, the antibody comprises a VH FR1 (SEQ ID NO:52), a VH FR2 (SEQ ID NO:54), a VH FR3 (SEQ ID NO:56), a VH FR4 (SEQ ID NO:58), a VL FR1 (SEQ ID NO:61), a VL FR3 (SEQ ID NO:64), and a VL FR4 (SEQ ID NO:16). In one embodiment, the antibody comprises a VH FR1 (SEQ ID NO:52), a VH FR2 (SEQ ID NO:54), a VH FR3 (SEQ ID NO:56), a VH FR4 (SEQ ID NO:58), a VL FR2 (SEQ ID NO:12), a VL FR3 (SEQ ID NO:64), and a VL FR4 (SEQ ID NO:16). In another embodiment, the antibody comprises a VH FR1 (SEQ ID NO:52), a VH FR2 (SEQ ID NO:54), a VH FR3 (SEQ ID NO:56), a VL FR1 (SEQ ID NO:61), a VL FR2 (SEQ ID NO:12), a VL FR3 (SEQ ID NO:64), and a VL FR4 (SEQ ID NO:16). In some embodiments, the antibody comprises a VH FR1 (SEQ ID NO:52), a VH FR2 (SEQ ID NO:54), a VH FR4 (SEQ ID NO:58), a VL FR1 (SEQ ID NO:61), a VL FR2 (SEQ ID NO:12), a VL FR3 (SEQ ID NO:64), and a VL FR4 (SEQ ID NO:16). In other embodiments, the antibody comprises a VH FR1 (SEQ ID NO:52), a VH FR3 (SEQ ID NO:56), a VH FR4 (SEQ ID NO:58), a VL FR1 (SEQ ID NO:61), a VL FR2 (SEQ ID NO:12), a VL FR3 (SEQ ID NO:64), and a VL FR4 (SEQ ID NO:16). In one embodiment, the antibody comprises a VH FR2 (SEQ ID NO:54), a VH FR3 (SEQ ID NO:56), a VH FR4 (SEQ ID NO:58), a VL FR1 (SEQ ID NO:61), a VL FR2 (SEQ ID NO:12), a VL FR3 (SEQ ID NO:64), and a VL FR4 (SEQ ID NO:16). In some embodiments, the antibody comprises any combination thereof of the VH FRs (SEQ ID NOS:52, 54, 56, 58) and the VL FRs (SEQ ID NOS:61, 12, 64, 16) listed in Tables 3-4.

In some embodiments, the antibodies provided herein comprise a VH region or VH domain. In other embodiments, the antibodies provided herein comprise a VL region or VL domain. In certain embodiments, the antibodies provided herein have a combination of (i) a VH domain or VH region; and/or (ii) a VL domain or VL region. In yet other embodiments, the antibodies provided herein have a combination of (i) a VH domain or VH region; and/or (ii) a VL domain or VL region selected from the group consisting of SEQ ID NOS: 18, 46, 67, 133, 138, 141, 9, 22, 27, 32, 36, 42, 50, 60, 71, 76, 80, 85, 90, 123, and 127, as set forth in Tables 9-10. In still other embodiments, the antibodies provided herein have a combination of (i) a VH domain or VH region; and/or (ii) a VL domain or VL region of any one of antibodies SIRPAB-1, SIRPAB-2, SIRPAB-3, SIRPAB-4, SIRPAB-5, SIRPAB-6, SIRPAB-7, SIRPAB-8, SIRPAB-9, SIRPAB-10, SIRPAB-11, SIRPAB-12, SIRPAB-13, SIRPAB-17, SIRPAB-18, SIRPAB-19, SIRPAB-20, or SIRPAB-21, as set forth in Tables 9-10.

In certain embodiments, the antibodies provided herein comprise a VH region comprising: (1) a VH CDR1 having an amino acid sequence selected from the group consisting of SEQ ID NOS:78 and 82; (2) a VH CDR2 having an amino acid sequence selected from the group consisting of SEQ ID NOS:69 and 83; and (3) a VH CDR3 having an amino acid sequence of SEQ ID NO:57; and a VL region selected from the group consisting of SEQ ID NOS: 18, 46, 67, 133, 138, and 141, as set forth in Table 9. In some embodiments, the VL region has an amino acid sequence of SEQ ID NO:18. In other embodiments, the VL region has an amino acid sequence of SEQ ID NO:46. In some embodiments, the VL region has an amino acid sequence of SEQ ID NO:67.

In other embodiments, the antibodies provided herein comprise a VH region selected from the group consisting of SEQ ID NOS: 9, 22, 27, 32, 36, 42, 50, 60, 71, 76, 80, 85, 90, 123, and 127 as set forth in Table 10; and a VL region comprising: (1) a VL CDR1 having an amino acid sequence of SEQ ID NO:62; (2) a VL CDR2 having an amino acid sequence of SEQ ID NO:63; and (3) a VL CDR3 having an amino acid sequence of SEQ ID NO:65. In some embodiments, the VH region has an amino acid sequence of SEQ ID NO:9. In some embodiments, the VH region has an amino acid sequence of SEQ ID NO:22. In some embodiments, the VH region has an amino acid sequence of SEQ ID NO:27. In some embodiments, the VH region has an amino acid sequence of SEQ ID NO:32. In some embodiments, the VH region has an amino acid sequence of SEQ ID NO:36. In some embodiments, the VH region has an amino acid sequence of SEQ ID NO:42. In some embodiments, the VH region has an amino acid sequence of SEQ ID NO:50. In some embodiments, the VH region has an amino acid sequence of SEQ ID NO:60. In some embodiments, the VH region has an amino acid sequence of SEQ ID NO:71. In some embodiments, the VH region has an amino acid sequence of SEQ ID NO:76. In some embodiments, the VH region has an amino acid sequence of SEQ ID NO:80. In some embodiments, the VH region has an amino acid sequence of SEQ ID NO:85. In some embodiments, the VH region has an amino acid sequence of SEQ ID NO:90. In some embodiments, the VH region has an amino acid sequence of SEQ ID NO:123. In some embodiments, the VH region has an amino acid sequence of SEQ ID NO:127.

TABLE 9

VL Domain Amino Acid Sequences

| Antibody | VL (SEQ ID NO:) |
|---|---|
| SIRPAB-1 | DIQMTQSPSSLSASVGDRVTITCQASQDISNYLNWYQQKPGKAPKLLIYDASNLATGVPSRFSGSGSG TDFTFTISSLQPEDIATYYCQQFAYLPWTFGGGTKVEIK (SEQ ID NO: 18) |
| SIRPAB-2 | DIQMTQSPSSLSASVGDRVTITCQASQDISNYLNWYQQKPGKAPKLLIYDASNLATGVPSRFSGSGSG TDFTFTISSLQPEDIATYYCQQFAYLPWTFGGGTKVEIK (SEQ ID NO: 18) |
| SIRPAB-3 | DIQMTQSPSSLSASVGDRVTITCQASQDISNYLNWYQQKPGKAPKLLIYDASNLATGVPSRFSGSGSG TDFTFTISSLQPEDIATYYCQQFAYLPWTFGGGTKVEIK (SEQ ID NO: 18) |
| SIRPAB-4 | DIQMTQSPSSLSASVGDRVTITCQASQDISNYLNWYQQKPGKAPKLLIYDASNLATGVPSRFSGSGSG TDFTFTISSLQPEDIATYYCQQFAYLPWTFGGGTKVEIK (SEQ ID NO: 18) |
| SIRPAB-5 | DIQMTQSPSSLSASVGDRVTITCQASQDISNYLNWYQQKPGKAPKLLIYDASNLATGVPSRFSGSGSG TDFTFTISSLQPEDIATYYCQQFAYLPWTFGGGTKVEIK (SEQ ID NO: 18) |
| SIRPAB-6 | DIQLTQSPSSLSASVGDRVTITCQASQDISNYLNWYQQKPGKAPKLLIYDASNLETGVPSRFSGSGSG TDFTFTISSLQPEDIATYYCQQFAYLPYTFGGGTKVEIK (SEQ ID NO: 46) |
| SIRPAB-7 | DIQLTQSPSSLSASVGDRVTITCQASQDISNYLNWYQQKPGKAPKLLIYDASNLETGVPSRFSGSGSG TDFTFTISSLQPEDIATYYCQQFAYLPYTFGGGTKVEIK (SEQ ID NO: 46) |

TABLE 9-continued

VL Domain Amino Acid Sequences

| Antibody | VL (SEQ ID NO:) |
|---|---|
| SIRPAB-8 | DIQMTQSPSSVSASVGDRVTITCRASQGISSWLAWYQQKPGKAPKLLIYAASNLQSGVPSRFSGSGSG<br>TDFTLTISSLQPEDFATYYCQQGASFPITFGGGTKVEIK (SEQ ID NO: 67) |
| SIRPAB-9 | DIQMTQSPSSVSASVGDRVTITCRASQGISSWLAWYQQKPGKAPKLLIYAASNLQSGVPSRFSGSGSG<br>TDFTLTISSLQPEDFATYYCQQGASFPITFGGGTKVEIK (SEQ ID NO: 67) |
| SIRPAB-10 | DIQMTQSPSSVSASVGDRVTITCRASQGISSWLAWYQQKPGKAPKLLIYAASNLQSGVPSRFSGSGSG<br>TDFTLTISSLQPEDFATYYCQQGASFPITFGGGTKVEIK (SEQ ID NO: 67) |
| SIRPAB-11 | DIQMTQSPSSVSASVGDRVTITCRASQGISSWLAWYQQKPGKAPKLLIYAASNLQSGVPSRFSGSGSG<br>TDFTLTISSLQPEDFATYYCQQGASFPITFGGGTKVEIK (SEQ ID NO: 67) |
| SIRPAB-12 | DIQMTQSPSSVSASVGDRVTITCRASQGISSWLAWYQQKPGKAPKLLIYAASNLQSGVPSRFSGSGSG<br>TDFTLTISSLQPEDFATYYCQQGASFPITFGGGTKVEIK (SEQ ID NO: 67) |
| SIRPAB-13 | DIQMTQSPSSVSASVGDRVTITCRASQGISSWLAWYQQKPGKAPKLLIYAASNLQSGVPSRFSGSGSG<br>TDFTLTISSLQPEDFATYYCQQGASFPITFGGGTKVEIK (SEQ ID NO: 67) |
| SIRPAB-17 | DIQMTQSPSSLSASVGDRVTITCQASQDISNYLNWYQQKPGKAPKLLIYDASNLATGVPSRFSGSGSG<br>TDFTFTISSLQPEDIATYYCQQFAYLPWTFGGGTKVEIK (SEQ ID NO: 18) |
| SIRPAB-18 | DIQMTQSPSSLSASVGDRVTITCQASQDISNYLNWYQQKPGKAPKLLIYDASNLATGVPSRFSGSGSG<br>TDFTFTISSLQPEDIATYYCQQFAYLPWTFGGGTKVEIK (SEQ ID NO: 18) |
| SIRPAB-19 | DIQMTQSPSSLSASVGDRVTITCQASDDISDYLNWYQQKPGKAPKLLIYDASNIEDGVPSRFSGSGSG<br>TDFTFTISSLQPEDIATYYCQQFAYLPWTFGGGTKVEIK (SEQ ID NO: 133) |
| SIRPAB-20 | DIQMTQSPSSLSASVGDRVTITCQASQDISDYLNWYQQKPGKAPKLLIYDADNLETGVPSRFSGSGSG<br>TDFTFTISSLQPEDIATYYCQQFAYLPWTFGGGTKVEIK (SEQ ID NO: 138) |
| SIRPAB-21 | DIQMTQSPSSLSASVGDRVTITCQASDDISDYLNWYQQKPGKAPKLLIYDASNLETGVPSRFSGSGSG<br>TDFTFTISSLQPEDIATYYCQQFAYLPWTFGGGTKVEIK (SEQ ID NO: 141) |

TABLE 10

VH Domain Amino Acid Sequences

| Antibody | VH (SEQ ID NO:) |
|---|---|
| SIRPAB-1 | QVQLQESGPGLVKPSQTLSLTCTVSGGSISSGGYYWSWIRQHPGKGLEWIGSIYYSGSTYYNPSLKS<br>RVTISVDTSKNQFSLKLSSVTAADTAVYYCAREGYHSGMDVWGQGTTVTVSS (SEQ ID NO: 9) |
| SIRPAB-2 | QVQLQESGPGLVKPSQTLSLTCTVSGGSISSGGDYWAWIRQHPGKGLEWIGYIYPSGFTYYNPSLKS<br>RVTISVDTSKNQFSLKLSSVTAADTAVYYCAREGYHSGMDVWGQGTTVTVSS (SEQ ID NO: 22) |
| SIRPAB-3 | QVQLQESGPGLVKPSQTLSLTCTVSGGSISSGGWYWQWIRQHPGKGLEWIGTIYYSGSTFYNPSLKS<br>RVTISVDTSKNQFSLKLSSVTAADTAVYYCAREGYHSGMDVWGQGTTVTVSS (SEQ ID NO: 27) |
| SIRPAB-4 | QVQLQESGPGLVKPSQTLSLTCTVSGGSISSGSPYWSWIRQHPGKGLEWIGYIYASGFTYYNPSLKS<br>RVTISVDTSKNQFSLKLSSVTAADTAVYYCAREGYHSGMDVWGQGTTVTVSS (SEQ ID NO: 32) |
| SIRPAB-5 | QVQLQESGPGLVKPSQTLSLTCTVSGGSISSGPAYWSWIRQHPGKGLEWIGTIYYSGSTFYNPSLKS<br>RVTISVDTSKNQFSLKLSSVTAADTAVYYCAREGYHSGMDVWGQGTTVTVSS (SEQ ID NO: 36) |
| SIRPAB-6 | QVQLQESGPGLVKPSQTLSLTCTVSGGSISSGGYYWSWIRQHPGKGLEWIGYIYYSGSTYYNPSLKS<br>RVTISVDTSKNQFSLKLSSVTAADTAVYYCAREGLDGSYGSSAWGQGTLVTVSS (SEQ ID<br>NO: 42) |
| SIRPAB-7 | QVQLQESGPGLVKPSQTLSLTCTVSGGSISSGEYYWEWIRQHPGKGLEWIGYIYSSGFTYYNPSLKS<br>RVTISVDTSKNQFSLKLSSVTAADTAVYYCAREGLDGSYGSSAWGQGTLVTVSS (SEQ ID<br>NO: 50) |
| SIRPAB-8 | QVQLVQSGAEVKKPGASVKVSCKASGYTFTSYGISWVRQAPGQGLEWMGWISPYNGNTNYAQKLQGR<br>VTMTTDTSTSTAYMELRSLRSDDTAVYYCAREAGSSWYDFDLWGRGTLVTVSS (SEQ ID<br>NO: 60) |
| SIRPAB-9 | QVQLVQSGAEVKKPGASVKVSCKASGYTFGGYGISWVRQAPGQGLEWMGWISAYGGETNYAQKLQGR<br>VTMTTDTSTSTAYMELRSLRSDDTAVYYCAREAGSSWYDFDLWGRGTLVTVSS (SEQ ID<br>NO: 71) |
| SIRPAB-10 | QVQLVQSGAEVKKPGASVKVSCKASGYTFTGYPISWVRQAPGQGLEWMGWIYAYGGNTNYAQKLQGR<br>VTMTTDTSTSTAYMELRSLRSDDTAVYYCAREAGSSWYDFDLWGRGTLVTVSS (SEQ ID<br>NO: 76) |

TABLE 10-continued

VH Domain Amino Acid Sequences

| Antibody | VH (SEQ ID NO:) |
|---|---|
| SIRPAB-11 | QVQLVQSGAEVKKPGASVKVSCKASGYTFRGYGISWVRQAPGQGLEWMGWISAYGGETNYAQKLQGR VTMTTDTSTSTAYMELRSLRSDDTAVYYCAREAGSSWYDFDLWGRGTLVTVSS (SEQ ID NO: 80) |
| SIRPAB-12 | QVQLVQSGAEVKKPGASVKVSCKASGYTFTGYGIVWVRQAPGQGLEWMGWISAYAGETNYAQKLQGR VTMTTDTSTSTAYMELRSLRSDDTAVYYCAREAGSSWYDFDLWGRGTLVTVSS (SEQ ID NO: 85) |
| SIRPAB-13 | QVQLVQSGAEVKKPGASVKVSCKASGYTFHGYGISWVRQAPGQGLEWMGWISAYSGETNYAQKLQGR VTMTTDTSTSTAYMELRSLRSDDTAVYYCAREAGSSWYDFDLWGRGTLVTVSS (SEQ ID NO: 90) |
| SIRPAB-17 | QVQLQESGPGLVKPSQTLSLTCTVSGGSISSGGYYWSWIRQHPGKGLEWIGAIYYSGPIYYNPSLKS RVTISVDTSKNQFSLKLSSVTAADTAVYYCAREGYHSGMDVWGQGTTVTVSS (SEQ ID NO: 123) |
| SIRPAB-18 | QVQLQESGPGLVKPSQTLSLTCTVSGGSISSGGYYWSWIRQHPGKGLEWIGAIYYSGPIYYNPSLKS RVTISVDTSKNQFSLKLSSVTAADTAVYYCSKEGYHSGMDVWGQGTTVTVSS (SEQ ID NO: 127) |
| SIRPAB-19 | QVQLQESGPGLVKPSQTLSLTCTVSGGSISSGGYYWSWIRQHPGKGLEWIGAIYYSGPIYYNPSLKS RVTISVDTSKNQFSLKLSSVTAADTAVYYCSKEGYHSGMDVWGQGTTVTVSS (SEQ ID NO: 127) |
| SIRPAB-20 | QVQLQESGPGLVKPSQTLSLTCTVSGGSISSGGYYWSWIRQHPGKGLEWIGAIYYSGPIYYNPSLKS RVTISVDTSKNQFSLKLSSVTAADTAVYYCSKEGYHSGMDVWGQGTTVTVSS (SEQ ID NO: 127) |
| SIRPAB-21 | QVQLQESGPGLVKPSQTLSLTCTVSGGSISSGGYYWSWIRQHPGKGLEWIGAIYYSGPIYYNPSLKS RVTISVDTSKNQFSLKLSSVTAADTAVYYCSKEGYHSGMDVWGQGTTVTVSS (SEQ ID NO: 127) |

Also provided herein are isolated nucleic acid molecules encoding an immunoglobulin heavy chain, light chain, VH region, VL region, VH CDR1, VH CDR2, VH CDR3, VL CDR1, VL CDR2, and/or VL CDR3 of anti-SIRPα antibodies that bind to a SIRPα polypeptide, a SIRPα polypeptide fragment, a SIRPα peptide, or a SIRPα epitope. The exemplary nucleic acid sequences for the VL region and the VH region of any one of antibodies SIRPAB-1, SIRPAB-2, SIRPAB-3, SIRPAB-4, SIRPAB-5, SIRPAB-6, SIRPAB-7, SIRPAB-5, SIRPAB-9, SIRPAB-10, SIRPAB-11, SIRPAB-12, SIRPAB-13, SIRPAB-18, SIRPAB-19, SIRPAB-20, or SIRPAB-21, are shown in Tables 11-12.

TABLE 11

VL Nucleic Acid Sequences

| Antibody | Nucleotide sequences |
|---|---|
| SIRPAB-1 | GACATCCAGATGACCCAGTCTCCATCCTCCCTGTCTGCATCTGTAGGAGACAGAGTCACCATCAC TTGCCAGGCGAGTCAGGACATTAGCAACTATTTAAATTGGTATCAGCAGAAACCAGGGAAAGCCC CTAAGCTCCTGATCTACGATGCATCCAATTTGGCAACAGGGGTCCCATCAAGGTTCAGTGGAAGT GGATCTGGGACAGATTTTACTTTCACCATCAGCAGCCTGCAGCCTGAAGATATTGCAACATATTA CTGTCAGCAGTTCGCCTACCTCCCTTGGACTTTTGGCGGAGGGACCAAGGTTGAGATCAAA (SEQ ID NO: 17) |
| SIRPAB-2 | GACATCCAGATGACCCAGTCTCCATCCTCCCTGTCTGCATCTGTAGGAGACAGAGTCACCATCAC TTGCCAGGCGAGTCAGGACATTAGCAACTATTTAAATTGGTATCAGCAGAAACCAGGGAAAGCCC CTAAGCTCCTGATCTACGATGCATCCAATTTGGCAACAGGGGTCCCATCAAGGTTCAGTGGAAGT GGATCTGGGACAGATTTTACTTTCACCATCAGCAGCCTGCAGCCTGAAGATATTGCAACATATTA CTGTCAGCAGTTCGCCTACCTCCCTTGGACTTTTGGCGGAGGGACCAAGGTTGAGATCAAA (SEQ ID NO: 23) |
| SIRPAB-3 | GACATCCAGATGACCCAGTCTCCATCCTCCCTGTCTGCATCTGTAGGAGACAGAGTCACCATCAC TTGCCAGGCGAGTCAGGACATTAGCAACTATTTAAATTGGTATCAGCAGAAACCAGGGAAAGCCC CTAAGCTCCTGATCTACGATGCATCCAATTTGGCAACAGGGGTCCCATCAAGGTTCAGTGGAAGT GGATCTGGGACAGATTTTACTTTCACCATCAGCAGCCTGCAGCCTGAAGATATTGCAACATATTA CTGTCAGCAGTTCGCCTACCTCCCTTGGACTTTTGGCGGAGGGACCAAGGTTGAGATCAAA (SEQ ID NO: 28) |

TABLE 11-continued

VL Nucleic Acid Sequences

| Antibody | Nucleotide sequences |
|---|---|
| SIRPAB-4 | GACATCCAGATGACCCAGTCTCCATCCTCCCTGTCTGCATCTGTAGGAGACAGAGTCACCATCAC<br>TTGCCAGGCGAGTCAGGACATTAGCAACTATTTAAATTGGTATCAGCAGAAACCAGGGAAAGCCC<br>CTAAGCTCCTGATCTACGATGCATCCAATTTGGCAACAGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTGGACTTTTGGCGGAGGGACCAAGGTTGAGATCAAA<br>(SEQ ID NO: 33) |
| SIRPAB-5 | GACATCCAGATGACCCAGTCTCCATCCTCCCTGTCTGCATCTGTAGGAGACAGAGTCACCATCAC<br>TTGCCAGGCGAGTCAGGACATTAGCAACTATTTAAATTGGTATCAGCAGAAACCAGGGAAAGCCC<br>CTAAGCTCCTGATCTACGATGCATCCAATTTGGCAACAGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTGGACTTTTGGCGGAGGGACCAAGGTTGAGATCAAA<br>(SEQ ID NO: 37) |
| SIRPAB-6 | GACATCCAGTTGACCCAGTCTCCATCCTCCCTGTCTGCATCTGTAGGAGACAGAGTCACCATCAC<br>TTGCCAGGCGAGTCAGGACATTAGCAACTATTTAAATTGGTATCAGCAGAAACCAGGGAAAGCCC<br>CTAAGCTCCTGATCTACGATGCATCCAATTTGGAAACAGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTACACTTTTGGCGGAGGGACCAAGGTTGAGATCAAA<br>(SEQ ID NO: 45) |
| SIRPAB-7 | GACATCCAGTTGACCCAGTCTCCATCCTCCCTGTCTGCATCTGTAGGAGACAGAGTCACCATCAC<br>TTGCCAGGCGAGTCAGGACATTAGCAACTATTTAAATTGGTATCAGCAGAAACCAGGGAAAGCCC<br>CTAAGCTCCTGATCTACGATGCATCCAATTTGGAAACAGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTACACTTTTGGCGGAGGGACCAAGGTTGAGATCAAA<br>(SEQ ID NO: 51) |
| SIRPAB-8 | GACATCCAGATGACCCAGTCTCCATCTTCCGTGTCTGCATCTGTAGGAGACAGAGTCACCATCAC<br>TTGTCGGGCGAGTCAGGGTATTAGCAGCTGGTTAGCCTGGTATCAGCAGAAACCAGGGAAAGCCC<br>CTAAGCTCCTGATCTATGCTGCATCCAATTTGCAAAGTGGGGTCCCATCAAGGTTCAGCGGCAGT<br>GGATCTGGGACAGATTTCACTCTCACCATCAGCAGCCTGCAGCCTGAAGATTTTGCAACTTATTA<br>CTGTCAGCAGGGAGCCAGTTTCCCTATCACTTTTGGCGGAGGGACCAAGGTTGAGATCAAA<br>(SEQ ID NO: 66) |
| SIRPAB-9 | GACATCCAGATGACCCAGTCTCCATCTTCCGTGTCTGCATCTGTAGGAGACAGAGTCACCATCAC<br>TTGTCGGGCGAGTCAGGGTATTAGCAGCTGGTTAGCCTGGTATCAGCAGAAACCAGGGAAAGCCC<br>CTAAGCTCCTGATCTATGCTGCATCCAATTTGCAAAGTGGGGTCCCATCAAGGTTCAGCGGCAGT<br>GGATCTGGGACAGATTTCACTCTCACCATCAGCAGCCTGCAGCCTGAAGATTTTGCAACTTATTA<br>CTGTCAGCAGGGAGCCAGTTTCCCTATCACTTTTGGCGGAGGGACCAAGGTTGAGATCAAA<br>(SEQ ID NO: 72) |
| SIRPAB-10 | GACATCCAGATGACCCAGTCTCCATCTTCCGTGTCTGCATCTGTAGGAGACAGAGTCACCATCAC<br>TTGTCGGGCGAGTCAGGGTATTAGCAGCTGGTTAGCCTGGTATCAGCAGAAACCAGGGAAAGCCC<br>CTAAGCTCCTGATCTATGCTGCATCCAATTTGCAAAGTGGGGTCCCATCAAGGTTCAGCGGCAGT<br>GGATCTGGGACAGATTTCACTCTCACCATCAGCAGCCTGCAGCCTGAAGATTTTGCAACTTATTA<br>CTGTCAGCAGGGAGCCAGTTTCCCTATCACTTTTGGCGGAGGGACCAAGGTTGAGATCAAA<br>(SEQ ID NO: 77) |
| SIRPAB-11 | GACATCCAGATGACCCAGTCTCCATCTTCCGTGTCTGCATCTGTAGGAGACAGAGTCACCATCAC<br>TTGTCGGGCGAGTCAGGGTATTAGCAGCTGGTTAGCCTGGTATCAGCAGAAACCAGGGAAAGCCC<br>CTAAGCTCCTGATCTATGCTGCATCCAATTTGCAAAGTGGGGTCCCATCAAGGTTCAGCGGCAGT<br>GGATCTGGGACAGATTTCACTCTCACCATCAGCAGCCTGCAGCCTGAAGATTTTGCAACTTATTA<br>CTGTCAGCAGGGAGCCAGTTTCCCTATCACTTTTGGCGGAGGGACCAAGGTTGAGATCAAA<br>(SEQ ID NO: 81) |
| SIRPAB-12 | GACATCCAGATGACCCAGTCTCCATCTTCCGTGTCTGCATCTGTAGGAGACAGAGTCACCATCAC<br>TTGTCGGGCGAGTCAGGGTATTAGCAGCTGGTTAGCCTGGTATCAGCAGAAACCAGGGAAAGCCC<br>CTAAGCTCCTGATCTATGCTGCATCCAATTTGCAAAGTGGGGTCCCATCAAGGTTCAGCGGCAGT<br>GGATCTGGGACAGATTTCACTCTCACCATCAGCAGCCTGCAGCCTGAAGATTTTGCAACTTATTA<br>CTGTCAGCAGGGAGCCAGTTTCCCTATCACTTTTGGCGGAGGGACCAAGGTTGAGATCAAA<br>(SEQ ID NO: 86) |
| SIRPAB-13 | GACATCCAGATGACCCAGTCTCCATCTTCCGTGTCTGCATCTGTAGGAGACAGAGTCACCATCAC<br>TTGTCGGGCGAGTCAGGGTATTAGCAGCTGGTTAGCCTGGTATCAGCAGAAACCAGGGAAAGCCC<br>CTAAGCTCCTGATCTATGCTGCATCCAATTTGCAAAGTGGGGTCCCATCAAGGTTCAGCGGCAGT<br>GGATCTGGGACAGATTTCACTCTCACCATCAGCAGCCTGCAGCCTGAAGATTTTGCAACTTATTA<br>CTGTCAGCAGGGAGCCAGTTTCCCTATCACTTTTGGCGGAGGGACCAAGGTTGAGATCAAA<br>(SEQ ID NO: 91) |

TABLE 11-continued

VL Nucleic Acid Sequences

| Antibody | Nucleotide sequences |
|---|---|
| SIRPAB-17 | GACATCCAGATGACCCAGTCTCCATCCTCCCTGTCTGCATCTGTAGGAGACAGAGTCACCATCAC<br>TTGCCAGGCGAGTCAGGACATTAGCAACTATTTAAATTGGTATCAGCAGAAACCAGGGAAAGCCC<br>CTAAGCTCCTGATCTACGATGCATCCAATTTGGCAACAGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTGGACTTTTGGCGGAGGGACCAAGGTTGAGATCAAA<br>(SEQ ID NO: 124) |
| SIRPAB-18 | GACATCCAGATGACCCAGTCTCCATCCTCCCTGTCTGCATCTGTAGGAGACAGAGTCACCATCAC<br>TTGCCAGGCGAGTCAGGACATTAGCAACTATTTAAATTGGTATCAGCAGAAACCAGGGAAAGCCC<br>CTAAGCTCCTGATCTACGATGCATCCAATTTGGCAACAGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTGGACTTTTGGCGGAGGGACCAAGGTTGAGATCAAA<br>(SEQ ID NO: 128) |
| SIRPAB-19 | GACATCCAGATGACCCAGTCTCCATCCTCCCTGTCTGCATCTGTAGGAGACAGAGTCACCATCAC<br>TTGCCAGGCGAGTGACGACATTAGCGACTATTTAAATTGGTATCAGCAGAAACCAGGGAAAGCCC<br>CTAAGCTCCTGATCTACGATGCATCCAATATCGAAGACGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTGGACTTTTGGCGGAGGGACCAAGGTTGAGATCAAA<br>(SEQ ID NO: 132) |
| SIRPAB-20 | GACATCCAGATGACCCAGTCTCCATCCTCCCTGTCTGCATCTGTAGGAGACAGAGTCACCATCAC<br>TTGCCAGGCGAGTCAGGACATTTCCGACTATTTAAATTGGTATCAGCAGAAACCAGGGAAAGCCC<br>CTAAGCTCCTGATCTACGACGCAGACAATTTGGAAACAGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTGGACTTTTGGCGGAGGGACCAAGGTTGAGATCAAA<br>(SEQ ID NO: 137) |
| SIRPAB-21 | GACATCCAGATGACCCAGTCTCCATCCTCCCTGTCTGCATCTGTAGGAGACAGAGTCACCATCAC<br>TTGCCAGGCGAGTGACGACATTAGCGACTATTTAAATTGGTATCAGCAGAAACCAGGGAAAGCCC<br>CTAAGCTCCTGATCTACGACGCATCCAATTTGGAAACAGGGGTCCCATCAAGGTTCAGTGGAAGT<br>GGATCTGGGACAGATTTTACTTTCACCATCAGCAGCCTGCAGCCTGAAGATATTGCAACATATTA<br>CTGTCAGCAGTTCGCCTACCTCCCTTGGACTTTTGGCGGAGGGACCAAGGTTGAGATCAAA<br>(SEQ ID NO: 140) |

TABLE 12

VH Nucleic Acid Sequences

| Antibody | Nucleotide sequences |
|---|---|
| SIRPAB-1 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTTACTACTGGAGCTGGATCCGCCAGCACCCAG<br>GGAAGGGCCTGGAGTGGATTGGGTCAATCTATTACAGTGGGAGCACCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCGCCAGAGAGGGATACCACTCAGGAATGGACGTAT<br>GGGGCCAGGGAACAACTGTCACCGTCTCCTCA ((SEQ ID NO: 8) |
| SIRPAB-2 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTGATTACTGGGCTTGGATCCGCCAGCACCCAG<br>GGAAGGGCCTGGAGTGGATTGGGTACATCTATCCTAGTGGGTTTACCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCGCCAGAGAGGGATACCACTCAGGAATGGACGTAT<br>GGGGCCAGGGAACAACTGTCACCGTCTCCTCA (SEQ ID NO: 21) |
| SIRPAB-3 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTTGGTACTGGCAGTGGATCCGCCAGCACCCAG<br>GGAAGGGCCTGGAGTGGATTGGGACGATCTATTACAGTGGGAGCACCTTTTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCGCCAGAGAGGGATACCACTCAGGAATGGACGTAT<br>GGGGCCAGGGAACAACTGTCACCGTCTCCTCA (SEQ ID NO: 26) |
| SIRPAB-4 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTAGTCCGTACTGGAGCTGGATCCGCCAGCACCCAG<br>GGAAGGGCCTGGAGTGGATTGGGTACATCTATGCTAGTGGGTTTACCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCGCCAGAGAGGGATACCACTCAGGAATGGACGTAT<br>GGGGCCAGGGAACAACTGTCACCGTCTCCTCA (SEQ ID NO: 31) |
| SIRPAB-5 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTCCGGCTTACTGGAGCTGGATCCGCCAGCACCCAG<br>GGAAGGGCCTGGAGTGGATTGGGACTATCTATTACAGTGGGAGCACCTTTTACAACCCGTCCCTC |

TABLE 12-continued

VH Nucleic Acid Sequences

| Antibody | Nucleotide sequences |
|---|---|
| | AAGAGTCGAGTTACCATATCAGTAGACACGTCTAAGAACCAGTTCTCCCTGAAGCTGAGTTCTGT<br>GACCGCCGCAGACACGGCGGTGTACTACTGCGCCAGAGAGGGATACCACTCAGGAATGGACGTAT<br>GGGGCCAGGGAACAACTGTCACCGTCTCCTCA (SEQ ID NO: 35) |
| SIRPAB-6 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTTACTACTGGAGCTGGATCCGCCAGCACCCAG<br>GGAAGGGCCTGGAGTGGATTGGGTACATCTATTACAGTGGGAGCACCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCGCCAGAGAGGGCTTGGACGGATCCTACGGTTCAA<br>GCGCATGGGGACAGGGTACATTGGTCACCGTCTCCTCA (SEQ ID NO: 41) |
| SIRPAB-7 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGAGTACTACTGGAGTGGATCCGCCAGCACCCAG<br>GGAAGGGCCTGGAGTGGATTGGGTACATCTATTCTAGTGGGTTTACCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCGCCAGAGAGGGCTTGGACGGATCCTACGGTTCAA<br>GCGCATGGGGACAGGGTACATTGGTCACCGTCTCCTCA (SEQ ID NO: 49) |
| SIRPAB-8 | CAGGTTCAGCTGGTGCAGTCTGGAGCTGAGGTGAAGAAGCCTGGGGCCTCAGTGAAGGTCTCCTG<br>CAAGGCTTCTGGTTACACCTTTACCAGCTATGGTATCAGCTGGGTGCGACAGGCCCCTGGACAAG<br>GGCTTGAGTGGATGGGATGGATCAGCCCTTACAATGGTAACACAAACTATGCACAGAAGCTCCAG<br>GGCAGAGTCACCATGACCACAGACACATCCACGAGCACAGCCTACATGGAGCTGAGGAGCCTGAG<br>ATCTGACGACACGGCGGTGTACTACTGCGCCAGAGAAGCCGGAAGCAGCTGGTACGACTTCGACC<br>TATGGGGGAGAGGTACATTGGTCACCGTCTCCTCA (SEQ ID NO: 59) |
| SIRPAB-9 | CAGGTTCAGCTGGTGCAGTCTGGAGCTGAGGTGAAGAAGCCTGGGGCCTCAGTGAAGGTCTCCTG<br>CAAGGCTTCTGGTTACACCTTTGGGGGTTATGGTATCAGCTGGGTGCGACAGGCCCCTGGACAAG<br>GGCTTGAGTGGATGGGATGGATCAGCGCTTACGGGGGTGAGACAAACTATGCACAGAAGCTCCAG<br>GGCAGAGTCACCATGACCACAGACACATCCACGAGCACAGCCTACATGGAGCTGAGGAGCCTGAG<br>ATCTGACGACACGGCGGTGTACTACTGCGCCAGAGAAGCCGGAAGCAGCTGGTACGACTTCGACC<br>TATGGGGGAGAGGTACATTGGTCACCGTCTCCTCA (SEQ ID NO: 70) |
| SIRPAB-10 | CAGGTTCAGCTGGTGCAGTCTGGAGCTGAGGTGAAGAAGCCTGGGGCCTCAGTGAAGGTCTCCTG<br>CAAGGCTTCTGGTTACACCTTTACCGGTTATCCTATCAGCTGGGTGCGACAGGCCCCTGGACAAG<br>GGCTTGAGTGGATGGGATGGATCTATGCTTACGGGGGTAACACAAACTATGCACAGAAGCTCCAG<br>GGCAGAGTCACCATGACCACAGACACATCCACGAGCACAGCCTACATGGAGCTGAGGAGCCTGAG<br>ATCTGACGACACGGCGGTGTACTACTGCGCCAGAGAAGCCGGAAGCAGCTGGTACGACTTCGACC<br>TATGGGGGAGAGGTACATTGGTCACCGTCTCCTCA (SEQ ID NO: 75) |
| SIRPAB-11 | CAGGTTCAGCTGGTGCAGTCTGGAGCTGAGGTGAAGAAGCCTGGGGCCTCAGTGAAGGTCTCCTG<br>CAAGGCTTCTGGTTACACCTTTAGGGGGTATGGTATCAGCTGGGTGCGACAGGCCCCTGGACAAG<br>GGCTTGAGTGGATGGGATGGATCAGCGCTTACGGGGGTGAGACAAACTATGCACAGAAGCTCCAG<br>GGCAGAGTCACCATGACCACAGACACATCCACGAGCACAGCCTACATGGAGCTGAGGAGCCTGAG<br>ATCTGACGACACGGCGGTGTACTACTGCGCCAGAGAAGCCGGAAGCAGCTGGTACGACTTCGACC<br>TATGGGGGAGAGGTACATTGGTCACCGTCTCCTCA (SEQ ID NO: 79) |
| SIRPAB-12 | CAGGTTCAGCTGGTGCAGTCTGGAGCTGAGGTGAAGAAGCCTGGGGCCTCAGTGAAGGTCTCCTG<br>CAAGGCTTCTGGTTACACCTTTACCGGGTATGGTATCGTTTGGGTGCGACAGGCCCCTGGACAAG<br>GGCTTGAGTGGATGGGATGGATCAGCGCTTACGCTGGTGAGACAAACTATGCACAGAAGCTCCAG<br>GGCAGAGTCACCATGACCACAGACACATCCACGAGCACAGCCTACATGGAGCTGAGGAGCCTGAG<br>ATCTGACGACACGGCGGTGTACTACTGCGCCAGAGAAGCCGGAAGCAGCTGGTACGACTTCGACC<br>TATGGGGGAGAGGTACATTGGTCACCGTCTCCTCA (SEQ ID NO: 84) |
| SIRPAB-13 | CAGGTTCAGCTGGTGCAGTCTGGAGCTGAGGTGAAGAAGCCTGGGGCCTCAGTGAAGGTCTCCTG<br>CAAGGCTTCTGGTTACACCTTTCATGGGTATGGTATCAGCTGGGTGCGACAGGCCCCTGGACAAG<br>GGCTTGAGTGGATGGGATGGATCAGCGCTTACTCGGGTGAGACAAACTATGCACAGAAGCTCCAG<br>GGCAGAGTCACCATGACCACAGACACATCCACGAGCACAGCCTACATGGAGCTGAGGAGCCTGAG<br>ATCTGACGACACGGCGGTGTACTACTGCGCCAGAGAAGCCGGAAGCAGCTGGTACGACTTCGACC<br>TATGGGGGAGAGGTACATTGGTCACCGTCTCCTCA (SEQ ID NO: 89) |
| SIRPAB-17 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTTACTACTGGAGCTGGATCCGCCAGCACCCAG<br>GGAAGGGCCTGGAGTGGATTGGGGCTATCTATTACAGTGGGCCGATCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCGCCAGAGAGGGATACCACTCAGGAATGGACGTAT<br>GGGGCCAGGGAACAACTGTCACCGTCTCCTCA (SEQ ID NO: 122) |
| SIRPAB-18 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTTACTACTGGAGCTGGATCCGCCAGCACCCAG<br>GGAAGGGCCTGGAGTGGATTGGGGCTATCTATTACAGTGGGCCGATCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCAGTAAGGAGGGATACCACTCAGGAATGGACGTAT<br>GGGGGCAAGGGACCACGGTCACCGTCTCCTCA (SEQ ID NO: 126) |

TABLE 12-continued

VH Nucleic Acid Sequences

| Antibody | Nucleotide sequences |
|---|---|
| SIRPAB-19 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTTACTACTGGAGCTGGATCCGCCAGCACCCAG<br>GGAAGGGCCTGGAGTGGATTGGGGCTATCTATTACAGTGGGCCGATCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCAGTAAGGAGGGATACCACTCAGGAATGGACGTAT<br>GGGGGCAAGGGACCACGGTCACCGTCTCCTCA (SEQ ID NO: 129) |
| SIRPAB-20 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTTACTACTGGAGCTGGATCCGCCAGCACCCAG<br>GGAAGGGCCTGGAGTGGATTGGGGCTATCTATTACAGTGGGCCGATCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCAGTAAGGAGGGATACCACTCAGGAATGGACGTAT<br>GGGGGCAAGGGACCACGGTCACCGTCTCCTCA (SEQ ID NO: 134) |
| SIRPAB-21 | CAGGTGCAGCTGCAGGAGTCGGGCCCAGGACTGGTGAAGCCTTCACAGACCCTGTCCCTCACCTG<br>TACTGTCTCTGGTGGCTCCATCAGCAGTGGTGGTTACTACTGGAGCTGGATCCGCCAGCACCCAG<br>GGAAGGGCCTGGAGTGGATTGGGGCTATCTATTACAGTGGGCCGATCTACTACAACCCGTCCCTC<br>AAGAGTCGAGTTACCATATCAGTAGACACGTCTAAGAACCAGTTCTCCCTGAAGCTGAGTTCTGT<br>GACCGCCGCAGACACGGCGGTGTACTACTGCAGTAAGGAGGGATACCACTCAGGAATGGACGTAT<br>GGGGGCAAGGGACCACGGTCACCGTCTCCTCA (SEQ ID NO: 139) |

In some embodiments, an antibody provided herein has a VH and a VL amino acid sequence of SIRPAB-1. In some embodiments, an antibody comprises a VH amino acid sequence of SEQ ID NO:9, and a VL amino acid sequence of SEQ ID NO:18.

In other embodiments, an antibody provided herein has a VH and a VL amino acid sequence of SIRPAB-2. In some embodiments, an antibody comprises a VH amino acid sequence of SEQ ID NO:22, and a VL amino acid sequence of SEQ ID NO:18.

In some embodiments, an antibody provided herein has a VH and a VL amino acid sequence of SIRPAB-3. In some embodiments, an antibody comprises a VH amino acid sequence of SEQ ID NO:27, and a VL amino acid sequence of SEQ ID NO:18.

In other embodiments, an antibody provided herein has a VH and a VL amino acid sequence of SIRPAB-4. In some embodiments, an antibody comprises a VH amino acid sequence of SEQ ID NO:32, and a VL amino acid sequence of SEQ ID NO:18.

In some embodiments, an antibody provided herein has a VH and a VL amino acid sequence of SIRPAB-5. In some embodiments, an antibody comprises a VH amino acid sequence of SEQ ID NO:36, and a VL amino acid sequence of SEQ ID NO:18.

Additionally, in some embodiments, an antibody comprises a VH amino acid sequence of SEQ ID NO:42, and a VL amino acid sequence of SEQ ID NO:18. In some embodiments, an antibody comprises a VH amino acid sequence of SEQ ID NO:50, and a VL amino acid sequence of SEQ ID NO:18. In some embodiments, an antibody comprises a VH amino acid sequence of SEQ ID NO:60, and a VL amino acid sequence of SEQ ID NO:18. In some embodiments, an antibody comprises a VH amino acid sequence of SEQ ID NO:71, and a VL amino acid sequence of SEQ ID NO:18. In some embodiments, an antibody comprises a VH amino acid sequence of SEQ ID NO:76, and a VL amino acid sequence of SEQ ID NO:18. In some embodiments, an antibody comprises a VH amino acid sequence of SEQ ID NO:80, and a VL amino acid sequence of SEQ ID NO:18. In some embodiments, an antibody comprises a VH amino acid sequence of SEQ ID NO:85, and a VL amino acid sequence of SEQ ID NO:18. In some embodiments, an antibody comprises a VH amino acid sequence of SEQ ID NO:90, and a VL amino acid sequence of SEQ ID NO:18. In some embodiments, an antibody comprises a VH amino acid sequence of SEQ ID NO:123, and a VL amino acid sequence of SEQ ID NO:18. In some embodiments, an antibody comprises a VH amino acid sequence of SEQ ID NO:127, and a VL amino acid sequence of SEQ ID NO:18.

In other embodiments, an antibody provided herein has a VH and a VL amino acid sequence of SIRPAB-6. In some embodiments, an antibody comprises a VH amino acid sequence of SEQ ID NO:42, and a VL amino acid sequence of SEQ ID NO:46.

In some embodiments, an antibody provided herein has a VH and a VL amino acid sequence of SIRPAB-7. In some embodiments, an antibody comprises a VH amino acid sequence of SEQ ID NO:50, and a VL amino acid sequence of SEQ ID NO:46.

Additionally, in some embodiments, an antibody comprises a VH amino acid sequence of SEQ ID NO:9, and a VL amino acid sequence of SEQ ID NO:46. In some embodiments, an antibody comprises a VH amino acid sequence of SEQ ID NO:22, and a VL amino acid sequence of SEQ ID NO:46. In some embodiments, an antibody comprises a VH amino acid sequence of SEQ ID NO:27, and a VL amino acid sequence of SEQ ID NO:46. In some embodiments, an antibody comprises a VH amino acid sequence of SEQ ID NO:32, and a VL amino acid sequence of SEQ ID NO:46. In some embodiments, an antibody comprises a VH amino acid sequence of SEQ ID NO:36, and a VL amino acid sequence of SEQ ID NO:46. In some embodiments, an antibody comprises a VH amino acid sequence of SEQ ID NO:60, and a VL amino acid sequence of SEQ ID NO:46. In some embodiments, an antibody comprises a VH amino acid sequence of SEQ ID NO:71, and a VL amino acid sequence of SEQ ID NO:46. In some embodiments, an antibody comprises a VH amino acid sequence of SEQ ID NO:76, and a VL amino acid sequence of SEQ ID NO:46. In some embodiments, an antibody comprises a VH amino acid sequence of SEQ ID NO:80, and a VL amino acid sequence of SEQ ID NO:46. In some embodiments, an antibody comprises a VH amino acid sequence of SEQ ID NO:85, and a VL amino acid sequence of SEQ ID NO:46. In some embodiments, an antibody comprises a VH amino acid sequence of SEQ ID NO:90, and a VL amino acid sequence of SEQ ID NO:46. In some embodiments, an antibody comprises a VH amino acid sequence of SEQ ID NO:123, and a VL amino acid sequence of SEQ ID NO:46. In some embodiments, an antibody comprises a VH amino acid sequence of SEQ ID NO:127, and a VL amino acid sequence of SEQ ID NO:46.

In other embodiments, an antibody provided herein has a VH and a VL amino acid sequence of SIRPAB-8. In some embodiments, an antibody comprises a VH amino acid sequence of SEQ ID NO:60, and a VL amino acid sequence of SEQ ID NO:67.

In some embodiments, an antibody provided herein has a VH and a VL amino acid sequence of SIRPAB-9. In some embodiments, an antibody comprises a VH amino acid sequence of SEQ ID NO:71, and a VL amino acid sequence of SEQ ID NO:67.

In other embodiments, an antibody provided herein has a VH and a VL amino acid sequence of SIRPAB-10. In some embodiments, an antibody comprises a VH amino acid sequence of SEQ ID NO:76, and a VL amino acid sequence of SEQ ID NO:67.

In some embodiments, an antibody provided herein has a VH and a VL amino acid sequence of SIRPAB-11. In some embodiments, an antibody comprises a VH amino acid sequence of SEQ ID NO:80, and a VL amino acid sequence of SEQ ID NO:67.

In other embodiments, an antibody provided herein has a VH and a VL amino acid sequence of SIRPAB-12. In some embodiments, an antibody comprises a VH amino acid sequence of SEQ ID NO:85, and a VL amino acid sequence of SEQ ID NO:67.

In some embodiments, an antibody provided herein has a VH and a VL amino acid sequence of SIRPAB-13. In some embodiments, an antibody comprises a VH amino acid sequence of SEQ ID NO:90, and a VL amino acid sequence of SEQ ID NO:67.

Additionally, in some embodiments, an antibody comprises a VH amino acid sequence of SEQ ID NO:9, and a VL amino acid sequence of SEQ ID NO:67. In some embodiments, an antibody comprises a VH amino acid sequence of SEQ ID NO:22, and a VL amino acid sequence of SEQ ID NO:67. In some embodiments, an antibody comprises a VH amino acid sequence of SEQ ID NO:27, and a VL amino acid sequence of SEQ ID NO:67. In some embodiments, an antibody comprises a VH amino acid sequence of SEQ ID NO:32, and a VL amino acid sequence of SEQ ID NO:67. In some embodiments, an antibody comprises a VH amino acid sequence of SEQ ID NO:36, and a VL amino acid sequence of SEQ ID NO:67. In some embodiments, an antibody comprises a VH amino acid sequence of SEQ ID NO:42, and a VL amino acid sequence of SEQ ID NO:67. In some embodiments, an antibody comprises a VH amino acid sequence of SEQ ID NO:50, and a VL amino acid sequence of SEQ ID NO:67. In some embodiments, an antibody comprises a VH amino acid sequence of SEQ ID NO:123, and a VL amino acid sequence of SEQ ID NO:67. In some embodiments, an antibody comprises a VH amino acid sequence of SEQ ID NO:127, and a VL amino acid sequence of SEQ ID NO:67.

In some embodiments, an antibody provided herein has a VH and a VL amino acid sequence of SIRPAB-17. In some embodiments, an antibody comprises a VH amino acid sequence of SEQ ID NO:123, and a VL amino acid sequence of SEQ ID NO:18.

In other embodiments, an antibody provided herein has a VH and a VL amino acid sequence of SIRPAB-18. In some embodiments, an antibody comprises a VH amino acid sequence of SEQ ID NO:127, and a VL amino acid sequence of SEQ ID NO:18.

In some embodiments, an antibody provided herein has a VH and a VL amino acid sequence of SIRPAB-19. In some embodiments, an antibody comprises a VH amino acid sequence of SEQ ID NO:127, and a VL amino acid sequence of SEQ ID NO:133.

Additionally, in some embodiments, an antibody comprises a VH amino acid sequence of SEQ ID NO:9, and a VL amino acid sequence of SEQ ID NO:133. In some embodiments, an antibody comprises a VH amino acid sequence of SEQ ID O:22, and a VL amino acid sequence of SEQ ID NO:133. In some embodiments, an antibody comprises a VH amino acid sequence of SEQ ID NO:27, and a VL amino acid sequence of SEQ ID NO:133. In some embodiments, an antibody comprises a VH amino acid sequence of SEQ ID NO:32, and a VL amino acid sequence of SEQ ID NO:133. In some embodiments, an antibody comprises a VH amino acid sequence of SEQ ID NO:36, and a VL amino acid sequence of SEQ ID NO:133. In some embodiments, an antibody comprises a VH amino acid sequence of SEQ ID NO:42, and a VL amino acid sequence of SEQ ID NO:133. In some embodiments, an antibody comprises a VH amino acid sequence of SEQ ID NO:50, and a VL amino acid sequence of SEQ ID NO:133. In some embodiments, an antibody comprises a VH amino acid sequence of SEQ ID NO:60, and a VL amino acid sequence of SEQ ID NO:133. In some embodiments, an antibody comprises a VH amino acid sequence of SEQ ID NO:71, and a VL amino acid sequence of SEQ ID NO:133. In some embodiments, an antibody comprises a VH amino acid sequence of SEQ ID NO:76, and a VL amino acid sequence of SEQ ID NO:133. In some embodiments, an antibody comprises a VH amino acid sequence of SEQ ID NO:80, and a VL amino acid sequence of SEQ ID NO:133. In some embodiments, an antibody comprises a VH amino acid sequence of SEQ ID NO:85, and a VL amino acid sequence of SEQ ID NO:133. In some embodiments, an antibody comprises a VH amino acid sequence of SEQ ID NO:90, and a VL amino acid sequence of SEQ ID NO:133. In some embodiments, an antibody comprises a VH amino acid sequence of SEQ ID NO:123, and a VL amino acid sequence of SEQ ID NO:133.

In other embodiments, an antibody provided herein has a VH and a VL amino acid sequence of SIRPAB-20. In some embodiments, an antibody comprises a VH amino acid sequence of SEQ ID NO:127, and a VL amino acid sequence of SEQ ID NO:138.

Additionally, in some embodiments, an antibody comprises a VH amino acid sequence of SEQ ID NO:9, and a VL amino acid sequence of SEQ ID NO:138. In some embodiments, an antibody comprises a VH amino acid sequence of SEQ ID NO:22, and a VL amino acid sequence of SEQ ID NO:138. In some embodiments, an antibody comprises a VU amino acid sequence of SEQ ID NO:27, and a VL amino acid sequence of SEQ ID NO:138. In some embodiments, an antibody comprises a VH amino acid sequence of SEQ ID NO:32, and a VL amino acid sequence of SEQ ID NO:138. In some embodiments, an antibody comprises a VH amino acid sequence of SEQ ID NO:36, and a VL amino acid sequence of SEQ ID NO:138. In some embodiments, an antibody comprises a VH amino acid sequence of SEQ ID NO:42, and a VL amino acid sequence of SEQ ID NO:138. In some embodiments, an antibody comprises a VH amino acid sequence of SEQ ID NO:50, and a VL amino acid sequence of SEQ ID NO:138. In some embodiments, an antibody comprises a VH amino acid sequence of SEQ ID NO:60, and a VL amino acid sequence of SEQ ID NO:138. In some embodiments, an antibody comprises a VH amino acid sequence of SEQ ID NO:71, and a VL amino acid sequence of SEQ ID NO:138. In some embodiments, an antibody comprises a VH amino acid sequence of SEQ ID NO:76, and a VL amino acid sequence of SEQ ID NO:138. In some embodiments, an antibody comprises a VH amino acid sequence of SEQ ID NO:80, and a VL amino acid sequence of SEQ ID NO:138. In some embodiments, an antibody comprises a VH amino acid sequence of SEQ ID NO:85, and a VL amino acid sequence of SEQ ID NO:138. In some embodiments, an antibody comprises a VH amino acid sequence of SEQ ID NO:90, and a VL amino acid sequence of SEQ ID NO:138. In some embodiments, an antibody comprises a VH amino acid sequence of SEQ ID NO:123, and a VL amino acid sequence of SEQ ID NO:138.

In some embodiments, an antibody provided herein has a VH and a VL amino acid sequence of SIRPAB-21. In some embodiments, an antibody comprises a VH amino acid sequence of SEQ ID NO:127, and a VL amino acid sequence of SEQ ID NO:141.

Additionally, in some embodiments, an antibody comprises a VH amino acid sequence of SEQ ID NO:9, and a VL amino acid sequence of SEQ ID NO:141. In some embodiments, an antibody comprises a VH amino acid sequence of SEQ ID NO:22, and a VL amino acid sequence of SEQ ID NO:141. In some embodiments, an antibody comprises a VH amino acid sequence of SEQ ID NO:27, and a VL amino acid sequence of SEQ ID NO:141. In some embodiments, an antibody comprises a VH amino acid sequence of SEQ ID NO:32, and a VL amino acid sequence of SEQ ID NO:141. In some embodiments, an antibody comprises a VH amino acid sequence of SEQ ID NO:36, and a VL amino acid sequence of SEQ ID NO:141. In some embodiments, an antibody comprises a VH amino acid sequence of SEQ ID NO:42, and a VL amino acid sequence of SEQ ID NO:141. In some embodiments, an antibody comprises a VH amino acid sequence of SEQ ID NO:50, and a VL amino acid sequence of SEQ ID NO:141. In some embodiments, an antibody comprises a VH amino acid sequence of SEQ ID NO:60, and a VL amino acid sequence of SEQ ID NO:141. In some embodiments, an antibody comprises a VH amino acid sequence of SEQ ID NO:71, and a VL amino acid sequence of SEQ ID NO:141. In some embodiments, an antibody comprises a VH amino acid sequence of SEQ ID NO:76, and a VL amino acid sequence of SEQ ID NO:141. In some embodiments, an antibody comprises a VH amino acid sequence of SEQ ID NO:80, and a VL amino acid sequence of SEQ ID NO:141. In some embodiments, an antibody comprises a VH amino acid sequence of SEQ ID NO:85, and a VL amino acid sequence of SEQ ID NO:141. In some embodiments, an antibody comprises a VH amino acid sequence of SEQ ID NO:90, and a VL amino acid sequence of SEQ ID NO:141. In some embodiments, an antibody comprises a VH amino acid sequence of SEQ ID NO:123, and a VL amino acid sequence of SEQ ID NO:141.

In certain embodiments, an antibody or antigen-binding fragment thereof described herein, which specifically binds to a SIRPα polypeptide (e.g., an ECD of SIRPα, for example human SIRPα), comprises a light chain and a heavy chain, wherein the light chain comprises a constant region having an amino acid sequence of:

(SEQ ID NO: 211)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

In other embodiments, an antibody or antigen-binding fragment thereof described herein, which specifically binds to a SIRPα polypeptide (e.g., an ECD of SIRPα, for example human SIRPα), comprises a light chain and a heavy chain, wherein the heavy chain comprises a human IgG1 Fc region having an amino acid sequence of:

(SEQ ID NO: 155, K322 emphasized)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In some embodiments, an antibody or antigen-binding fragment thereof described herein, which specifically binds to a SIRPα polypeptide (e.g., an ECD of SIRPα, for example human SIRPα), comprises a light chain and a heavy chain, wherein the heavy chain does not comprise a human IgG1 Fc region having an amino acid sequence of SEQ ID NO:155.

In certain embodiments, an antibody or antigen-binding fragment thereof described herein, which specifically binds to a SIRPα polypeptide (e.g., an ECD of SIRPα, for example human SIRPα), comprises a light chain and a heavy chain, wherein the heavy chain comprises a human IgG1-K322A Fc region having an amino acid sequence of:

(SEQ ID NO: 157, K322A substitution emphasized)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCAVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In some embodiments, an antibody or antigen-binding fragment thereof described herein, which specifically binds to a SIRPα polypeptide (e.g., an ECD of SIRPα, for example human SIRPα), comprises a light chain and a heavy chain, wherein the heavy chain comprises a human IgG4 Fc region having an amino acid sequence of:

(SEQ ID NO: 156, S228 and L235 emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

-continued

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK.

In another embodiment, an antibody or antigen-binding fragment thereof described herein, which specifically binds to a SIRPα polypeptide (e.g., an ECD of SIRPα, for example human SIRPα), comprises a light chain and a heavy chain, wherein the heavy chain comprises a human IgG4P Fc region haying an amino acid sequence of:

(SEQ ID NO: 158, S228P substitution emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK.

In yet another embodiment, an antibody or antigen-binding fragment thereof described herein, which specifically binds to a SIRPα of polypeptide (e.g., an ECD of SIRPα, for example human SIRPα), comprises a light chain and a heavy chain, wherein the heavy chain comprises a human IgG4PE Fc region having an amino acid sequence of:

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK. (SEQ ID NO: 159,

S228P and L235E substitutions emphasized)

In some embodiments, an antibody or antigen-binding fragment thereof described herein, which specifically binds to a SIRPα polypeptide (e.g., an ECD of SIRPα, for example human SIRPα), comprises a light chain and a heavy chain, wherein the heavy chain does not comprise a human IgG4PE Fc region having an amino add sequence of SEQ ID NO:159.

In still another embodiment, an antibody or antigen-binding fragment thereof described herein, which specifically binds to a SIRPα polypeptide (e.g., an ECD of SIRPα, for example human SIRPα), comprises a light chain and a heavy chain, wherein the light chain comprises a constant region having an amino acid sequence of SEQ ID NO:211; and the heavy chain comprises an Fc region having an amino acid sequence selected from the group consisting of SEQ ID NOS:144, and 155-159.

In certain embodiments, an antibody described herein, which specifically binds to a SIRPα polypeptide (e.g., an ECD of SIRPα, for example human SIRPα), comprises a light chain and a heavy chain, wherein the light chain comprises an amino acid sequence as follows:

(SEQ ID NO: 143, LC_SIRPAB-11)
DIQMTQSPSSVSASVGDRVTITCRASQGISSWLAWYQQKPGKAPKLLIYA

ASNLQSGVPSRFSGSGSGTDFTLTISSLQPEDFATYYCQQGASFPITFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some embodiments, an antibody described herein, which specifically binds to a SIRPα polypeptide (e.g., an ECD of SIRPα, for example human SIRPα), comprises a light chain and a heavy chain, wherein the heavy chain comprises an amino acid sequence as follows:

(SEQ ID NO: 142, HC_SIRPAB-11, K322 emphasized)
QVQLVQSGAEVKKPGASVKVSCKASGYTFRGYGISWVRQAPGQGLEWMGW

ISAYGGETNYAQKLQGRVTMTTDTSTSTAYMELRSLRSDDTAVYYCAREA

GSSWYDFDLWGRGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLS

PGK.

In other embodiments, an antibody described herein, which specifically binds to a SIRPα polypeptide (e.g., an ECD of SIRPα, for example human SIRPα), comprises a light chain and a heavy chain, wherein the heavy chain comprises an amino acid sequence as follows:

QVQLVQSGAEVKKPGASVKVSCKASGYTFRGYGISWVRQAPGQGLEWMGW

ISAYGGETNYAQKLQGRVTMTTDTSTSTAYMELRSLRSDDTAVYYCAREA

GSSWYDFDLWGRGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCAVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLS

PGK. (SEQ ID NO: 119, HC_SIRPAB-11-IgG1-K322A,

K322A substitution emphasized)

In another embodiment, an antibody described herein, which specifically binds to a SIRPα polypeptide (e.g., an ECD of SIRPα, for example human SIRPα), comprises a light chain and a heavy chain, wherein the heavy chain comprises an amino acid sequence as follows:

QVQLVQSGAEVKKPGASVKVSCKASGYTFRGYGISWVRQAPGQGLEWMGW

ISAYGGETNYAQKLQGRVTMTTDTSTSTAYMELRSLRSDDTAVYYCAREA

GSSWYDFDLWGRGTLVTVSS*ASTKGPSVFPLAPCSRSTSESTAALGCLVK*

*DYFPEPVTVSWNSGALTSGVHTFPAVLQSSGLYSLSSVVTVPSSSLGTKT*

*YTCNVDHKPSNTKVDKRVESKYGPPCPPCPAPEFLGGPSVFLFPPKPKDT*

*LMISRTPEVTCVVVDVSQEDPEVQFNWYVDGVEVHNAKTKPREEQFNSTY*

*RVVSVLTVLHQDWLNGKEYKCKVSNKGLPSSIEKTISKAKGQPREPQVYT*

*LPPSQEEMTKNQVSLTCLVKGFYPSDIAVEWESNGQPENNYKTTPPVLDS*

*DGSFFLYSRLTVDKSRWQEGNVFSCSVMHEALHNHYTQKSLSLSLGK*.

(SEQ ID NO: 112, HC_SIRPAB-11-IgG4P,

IgG4P Fc backbone italicized and underlined)

In yet another embodiment, an antibody described herein, which specifically binds to a SIRPα polypeptide (e.g., an ECD of SIRPα, for example human SIRPα), comprises a light chain and a heavy chain, wherein the heavy chain comprises an amino acid sequence as follows:

QVQLVQSGAEVKKPGASVKVSCKASGYTFRGYGISWVRQAPGQGLEWMGW

ISAYGGETNYAQKLQGRVTMTTDTSTSTAYMELRSLRSDDTAVYYCAREA

GSSWYDFDLWGRGTLVTVSS*ASTKGPSVFPLAPCSRSTSESTAALGCLVK*

*DYFPEPVTVSWNSGALTSGVHTFPAVLQSSGLYSLSSVVTVPSSSLGTKT*

*YTCNVDHKPSNTKVDKRVESKYGPPCPPCPAPEFEGGPSVFLFPPKPKDT*

*LMISRTPEVTCVVVDVSQEDPEVQFNWYVDGVEVHNAKTKPREEQFNSTY*

*RVVSVLTVLHQDWLNGKEYKCKVSNKGLPSSIEKTISKAKGQPREPQVYT*

*LPPSQEEMTKNQVSLTCLVKGFYPSDIAVEWESNGQPENNYKTTPPVLDS*

*DGSFFLYSRLTVDKSRWQEGNVFSCSVMHEALHNHYTQKSLSLSLGK*.

(SEQ ID NO: 120, HC_SIRPAB-11-IgG4PE,

IgG4PE Fc backbone italicized and underlined)

In yet another embodiment, an antibody described herein, which specifically binds to a SIRPα polypeptide (e.g., an ECD of SIRPα, for example human SIRPα, comprises a light chain and a heavy chain, wherein the heavy chain comprises an amino acid sequence as follows:

QVQLVQSGAEVKKPGASVKVSCKASGYTFRGYGISWVRQAPGQGLEWMGW

ISAYGGETNYAQKLQGRVTMTTDTSTSTAYMELRSLRSDDTAVYYCAREA

GSSWYDFDLWGRGTLVTVSS*ASTKGPSVFPLAPSSKSTSGGTAALGCLVK*

*DYFPEPVTVSWNSGALTSGVHTFPAVLQSSGLYSLSSVVTVPSSSLGTQT*

*YICNVNHKPSNTKVDKKVEPKSCDKTHTCPPCPAPEAAGGPSVFLFPPKP*

*KDTLMISRTPEVTCVVVSVSHEDPEVKFNWYVDGVEVHNAKTKPREEQYN*

*STYRVVSVLTVLHQDWLNGKEYKCKVSNKALPAPIEKTISKAKGQPREPQ*

*VYTLPPSREEMTKNQVSLTCLVKGFYPSDIAVEWESNGQPENNYKTTPPV*

*LDSDGSFFLYSKLTVDKSRWQQGNVFSCSVMHEALHNHYTQKSLSLS*

*PGK*. (SEQ ID NO: 98, HC_SIRPAB-11-IgG1-AAS, IgG1-

AAS Fc backbone italicized and underlined)

In one particular embodiment, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:142.

In another particular embodiment, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:119.

In some embodiments, an antibody described herein, which specifically binds to a SIRPα polypeptide (e.g., an ECD of SIRPα, for example human SIRPα), comprises a light chain and a heavy chain; wherein (i) the light chain comprises an amino acid sequence of SEQ ID NO:143; and (ii) the heavy chain comprises an amino acid sequence of SEQ ID NO:98.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:120.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:112.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:204.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:205.

In yet another particular embodiment, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:200; and (ii) the heavy chain comprises an amino acid sequence of SEQ ID NO:212.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:200; and (ii) the heavy chain comprises an amino acid sequence of SEQ ID NO:213.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:200; and (ii) the heavy chain comprises an amino acid sequence of SEQ ID NO:214.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:200; and (ii) the heavy chain comprises an amino acid sequence of SEQ ID NO:215.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:200; and (ii) the heavy chain comprises an amino acid sequence of SEQ ID NO:216.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:202; and (ii) the heavy chain comprises an amino acid sequence of SEQ ID NO:217.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:202; and (ii) the heavy chain comprises an amino acid sequence of SEQ ID NO:218.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:219.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:220.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:221.

In some embodiments, an antibody described herein, which specifically hinds to a SIRPα polypeptide (e.g., and ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:222.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:200; and (ii) the heavy chain comprises an amino acid sequence of SEQ ID NO:223.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:200; and (ii) the heavy chain comprises an amino acid sequence of SEQ ID NO:207.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:208; and (ii) the heavy chain comprises an amino acid sequence of SEQ ID NO:117.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:209; and (ii) the heavy chain comprises an amino acid sequence of SEQ ID NO:110.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:210; and (ii) the heavy chain comprises an amino acid sequence of SEQ ID NO:148.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:106.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143; and (ii) the heavy chain comprises an amino acid sequence of SEQ ID NO:118.

In some embodiments, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:143 and (ii) the heavy chain comprises an amino acid sequence of SEQ ID NO:111.

The exemplary light chain and heavy chain sequences are summarized in the following Table 13:

TABLE 13 light chain and heavy chain sequences

| Chain Type | Amino Acid Sequences |
| --- | --- |
| Light chain (SIRPAB-1, SIRPAB-2, SIRPAB-3, SIRPAB-4, SIRPAB-5, SIRPAB-17, SIRPAB-18) | DIQMTQSPSSLSASVGDRVTITCQASQDISNYLNWYQQKPGKAPKLLIYDASNL ATGVPSRFSGSGSGTDFTFTISSLQPEDIATYYCQQFAYLPWTFGGGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 200) |
| Light chain (SIRPAB-6, SIRPAB-7) | DIQLTQSPSSLSASVGDRVTITCQASQDISNYLNWYQQKPGKAPKLLIYDASNL ETGVPSRFSGSGSGTDFTFTISSLQPEDIATYYCQQFAYLPYTFGGGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 202) |
| Light chain (SIRPAB-8, SIRPAB-9, SIRPAB-10, SIRPAB-11, SIRPAB-12, SIRPAB-13) | DIQMTQSPSSVSASVGDRVTITCRASQGISSWLAWYQQKPGKAPKLLIYAASNL QSGVPSRFSGSGSGTDFTLTISSLQPEDFATYYCQQGASFPITFGGGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 143) |
| Light chain (SIRPAB-19) | DIQMTQSPSSLSASVGDRVTITCQASDDISDYLNWYQQKPGKAPKLLIYDASNI EDGVPSRFSGSGSGTDFTFTISSLQPEDIATYYCQQFAYLPWTFGGGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 208) |
| Light chain (SIRPAB-20) | DIQMTQSPSSLSASVGDRVTITCQASQDISDYLNWYQQKPGKAPKLLIYDADNL ETGVPSRFSGSGSGTDFTFTISSLQPEDIATYYCQQFAYLPWTFGGGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 209) |
| Light chain (SIRPAB-21) | DIQMTQSPSSLSASVGDRVTITCQASDDISDYLNWYQQKPGKAPKLLIYDASNL ETGVPSRFSGSGSGTDFTFTISSLQPEDIATYYCQQFAYLPWTFGGGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 210) |
| Heavy chain (SIRPAB-11) | QVQLVQSGAEVKKPGASVKVSCKASGYTFRGYGISWVRQAPGQGLEWMGWISAY GGETNYAQKLQGRVTMTTDTSTSTAYMELRSLRSDDTAVYYCAREAGSSWYDFD LWGRGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYPS DIAVEWESNGQPENNYKTTPPVLDSDGSFFLYSKLTVDKSRWQQGNVFSCSVMH EALHNHYTQKSLSLSPGK (SEQ ID NO: 142) |
| Heavy chain (SIRPAB-11-K322A) | QVQLVQSGAEVKKPGASVKVSCKASGYTFRGYGISWVRQAPGQGLEWMGWISAY GGETNYAQKLQGRVTMTTDTSTSTAYMELRSLRSDDTAVYYCAREAGSSWYDFD LWGRGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKC AVSNKALPAPIEKTISKAKGQPREPQVYTLPPSREEMTKNQVSLTCLVKGFYPS DIAVEWESNGQPENNYKTTPPVLDSDGSFFLYSKLTVDKSRWQQGNVFSCSVMH EALHNHYTQKSLSLSPGK (SEQ ID NO: 119) |
| Heavy chain (SIRPAB-12) | QVQLVQSGAEVKKPGASVKVSCKASGYTFTGYGIVWVRQAPGQGLEWMGWISAY AGETNYAQKLQGRVTMTTDTSTSTAYMELRSLRSDDTAVYYCAREAGSSWYDFD LWGRGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDK |

TABLE 13-continued light chain and heavy chain sequences

| Chain Type | Amino Acid Sequences |
|---|---|
| | KVEPKSCDKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWLNGKEYKC<br>KVSNKALPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVFSCSVMH<br>EALHNHYTQKSLSLSPGK (SEQ ID NO: 204) |
| Heavy chain<br>(SIRPAB-12-<br>K322A) | QVQLVQSGAEVKKPGASVKVSCKASGYTFTGYGIVWVRQAPGQGLEWMGWISAY<br>AGETNYAQKLQGRVTMTTDTSTSTAYMELRSLRSDDTAVYYCAREAGSSWYDFD<br>LWGRGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWLNGKEYKC<br>AVSNKALPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVFSCSVMH<br>EALHNHYTQKSLSLSPGK (SEQ ID NO: 205) |
| Heavy chain<br>(SIRPAB-11-<br>AAS) | QVQLVQSGAEVKKPGASVKVSCKASGYTFRGYGISWVRQAPGQGLEWMGWISAY<br>GGETNYAQKLQGRVTMTTDTSTSTAYMELRSLRSDDTAVYYCAREAGSSWYDFD<br>LWGRGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDK<br>KVEPKSCDKTHTCPPCPAPEAAGGPSVFLFPPKPKDTLMISRTPEVTCVVVSVS<br>HEDPEVKFNWYVDGVEVHNAKTKPREEQYNSTYRVVSVLTVLHQDWLNGKEYKC<br>KVSNKALPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVFSCSVMH<br>EALHNHYTQKSLSLSPGK (SEQ ID NO: 98) |
| Heavy chain<br>(SIRPAB-11-<br>4PE) | QVQLVQSGAEVKKPGASVKVSCKASGYTFRGYGISWVRQAPGQGLEWMGWISAY<br>GGETNYAQKLQGRVTMTTDTSTSTAYMELRSLRSDDTAVYYCAREAGSSWYDFD<br>LWGRGTLVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFEGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK (SEQ ID NO: 120) |
| Heavy chain<br>(SIRPAB-11-<br>4P) | QVQLVQSGAEVKKPGASVKVSCKASGYTFRGYGISWVRQAPGQGLEWMGWISAY<br>GGETNYAQKLQGRVTMTTDTSTSTAYMELRSLRSDDTAVYYCAREAGSSWYDFD<br>LWGRGTLVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK (SEQ ID NO: 112) |
| Heavy chain<br>(SIRPAB-1) | QVQLQESGPGLVKPSQTLSLTCTVSGGSISSGGYYWSWIRQHPGKGLEWIGSIY<br>YSGSTYYNPSLKSRVTISVDTSKNQFSLKLSSVTAADTAVYYCAREGYHSGMDV<br>WGQGTTVTVSSASTKGPSVFPLAPSSKSTSGGTAALGCLVKDYFPEPVTVSWNS<br>GALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHE<br>ALHNHYTQKSLSLSPGK (SEQ ID NO: 212) |
| Heavy chain<br>(SIRPAB-2) | QVQLQESGPGLVKPSQTLSLTCTVSGGSISSGGDYWAWIRQHPGKGLEWIGYIY<br>PSGFTYYNPSLKSRVTISVDTSKNQFSLKLSSVTAADTAVYYCAREGYHSGMDV<br>WGQGTTVTVSSASTKGPSVFPLAPSSKSTSGGTAALGCLVKDYFPEPVTVSWNS<br>GALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHE<br>ALHNHYTQKSLSLSPGK (SEQ ID NO: 213) |
| Heavy chain<br>(SIRPAB-3) | QVQLQESGPGLVKPSQTLSLTCTVSGGSISSGGWYWQWIRQHPGKGLEWIGTIY<br>YSGSTFYNPSLKSRVTISVDTSKNQFSLKLSSVTAADTAVYYCAREGYHSGMDV<br>WGQGTTVTVSSASTKGPSVFPLAPSSKSTSGGTAALGCLVKDYFPEPVTVSWNS<br>GALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHE<br>ALHNHYTQKSLSLSPGK (SEQ ID NO: 214) |

TABLE 13-continued light chain and heavy chain sequences

Chain Type   Amino Acid Sequences

Heavy chain  QVQLQESGPGLVKPSQTLSLTCTVSGGSISSGSPYWSWIRQHPGKGLEWIGYIY
(SIRPAB-4)   ASGFTYYNPSLKSRVTISVDTSKNQFSLKLSSVTAADTAVYYCAREGYHSGMDV
             WGQGTTVTVSSASTKGPSVFPLAPSSKSTSGGTAALGCLVKDYFPEPVTVSWNS
             GALTSGVHTFPAVLQSSGLYSLSSVVTVPSSSLGTQTYICNVNHKPSNTKVDKK
             VEPKSCDKTHTCPPCPAPELLGGPSVFLFPPKPKDTLMISRTPEVTCVVVDVSH
             EDPEVKFNWYVDGVEVHNAKTKPREEQYNSTYRVVSVLTVLHQDWLNGKEYKCK
             VSNKALPAPIEKTISKAKGQPREPQVYTLPPSREEMTKNQVSLTCLVKGFYPSD
             IAVEWESNGQPENNYKTTPPVLDSDGSFFLYSKLTVDKSRWQQGNVFSCSVMHE
             ALHNHYTQKSLSLSPGK (SEQ ID NO: 215)

Heavy chain  QVQLQESGPGLVKPSQTLSLTCTVSGGSISSGPAYWSWIRQHPGKGLEWIGTIY
(SIRPAB-5)   YSGSTFYNPSLKSRVTISVDTSKNQFSLKLSSVTAADTAVYYCAREGYHSGMDV
             WGQGTTVTVSSASTKGPSVFPLAPSSKSTSGGTAALGCLVKDYFPEPVTVSWNS
             GALTSGVHTFPAVLQSSGLYSLSSVVTVPSSSLGTQTYICNVNHKPSNTKVDKK
             VEPKSCDKTHTCPPCPAPELLGGPSVFLFPPKPKDTLMISRTPEVTCVVVDVSH
             EDPEVKFNWYVDGVEVHNAKTKPREEQYNSTYRVVSVLTVLHQDWLNGKEYKCK
             VSNKALPAPIEKTISKAKGQPREPQVYTLPPSREEMTKNQVSLTCLVKGFYPSD
             IAVEWESNGQPENNYKTTPPVLDSDGSFFLYSKLTVDKSRWQQGNVFSCSVMHE
             ALHNHYTQKSLSLSPGK (SEQ ID NO: 216)

Heavy chain  QVQLQESGPGLVKPSQTLSLTCTVSGGSISSGGYYWSWIRQHPGKGLEWIGYIY
(SIRPAB-6)   YSGSTYYNPSLKSRVTISVDTSKNQFSLKLSSVTAADTAVYYCAREGLDGSYGS
             SAWGQGTLVTVSSASTKGPSVFPLAPSSKSTSGGTAALGCLVKDYFPEPVTVSW
             NSGALTSGVHTFPAVLQSSGLYSLSSVVTVPSSSLGTQTYICNVNHKPSNTKVD
             KKVEPKSCDKTHTCPPCPAPELLGGPSVFLFPPKPKDTLMISRTPEVTCVVVDV
             SHEDPEVKFNWYVDGVEVHNAKTKPREEQYNSTYRVVSVLTVLHQDWLNGKEYK
             CKVSNKALPAPIEKTISKAKGQPREPQVYTLPPSREEMTKNQVSLTCLVKGFYP
             SDIAVEWESNGQPENNYKTTPPVLDSDGSFFLYSKLTVDKSRWQQGNVFSCSVM
             HEALHNHYTQKSLSLSPGK (SEQ ID NO: 217)

Heavy chain  QVQLQESGPGLVKPSQTLSLTCTVSGGSISSGEYYWEWIRQHPGKGLEWIGYIY
(SIRPAB-7)   SSGFTYYNPSLKSRVTISVDTSKNQFSLKLSSVTAADTAVYYCAREGLDGSYGS
             SAWGQGTLVTVSSASTKGPSVFPLAPSSKSTSGGTAALGCLVKDYFPEPVTVSW
             NSGALTSGVHTFPAVLQSSGLYSLSSVVTVPSSSLGTQTYICNVNHKPSNTKVD
             KKVEPKSCDKTHTCPPCPAPELLGGPSVFLFPPKPKDTLMISRTPEVTCVVVDV
             SHEDPEVKFNWYVDGVEVHNAKTKPREEQYNSTYRVVSVLTVLHQDWLNGKEYK
             CKVSNKALPAPIEKTISKAKGQPREPQVYTLPPSREEMTKNQVSLTCLVKGFYP
             SDIAVEWESNGQPENNYKTTPPVLDSDGSFFLYSKLTVDKSRWQQGNVFSCSVM
             HEALHNHYTQKSLSLSPGK (SEQ ID NO: 218)

Heavy chain  QVQLVQSGAEVKKPGASVKVSCKASGYTFTSYGISWVRQAPGQGLEWMGWISPY
(SIRPAB-8)   NGNTNYAQKLQGRVTMTTDTSTSTAYMELRSLRSDDTAVYYCAREAGSSWYDFD
             LWGRGTLVTVSSASTKGPSVFPLAPSSKSTSGGTAALGCLVKDYFPEPVTVSWN
             SGALTSGVHTFPAVLQSSGLYSLSSVVTVPSSSLGTQTYICNVNHKPSNTKVDK
             KVEPKSCDKTHTCPPCPAPELLGGPSVFLFPPKPKDTLMISRTPEVTCVVVDVS
             HEDPEVKFNWYVDGVEVHNAKTKPREEQYNSTYRVVSVLTVLHQDWLNGKEYKC
             KVSNKALPAPIEKTISKAKGQPREPQVYTLPPSREEMTKNQVSLTCLVKGFYPS
             DIAVEWESNGQPENNYKTTPPVLDSDGSFFLYSKLTVDKSRWQQGNVFSCSVMH
             EALHNHYTQKSLSLSPGK (SEQ ID NO: 219)

Heavy chain  QVQLVQSGAEVKKPGASVKVSCKASGYTFGGYGISWVRQAPGQGLEWMGWISAY
(SIRPAB-9)   GGETNYAQKLQGRVTMTTDTSTSTAYMELRSLRSDDTAVYYCAREAGSSWYDFD
             LWGRGTLVTVSSASTKGPSVFPLAPSSKSTSGGTAALGCLVKDYFPEPVTVSWN
             SGALTSGVHTFPAVLQSSGLYSLSSVVTVPSSSLGTQTYICNVNHKPSNTKVDK
             KVEPKSCDKTHTCPPCPAPELLGGPSVFLFPPKPKDTLMISRTPEVTCVVVDVS
             HEDPEVKFNWYVDGVEVHNAKTKPREEQYNSTYRVVSVLTVLHQDWLNGKEYKC
             KVSNKALPAPIEKTISKAKGQPREPQVYTLPPSREEMTKNQVSLTCLVKGFYPS
             DIAVEWESNGQPENNYKTTPPVLDSDGSFFLYSKLTVDKSRWQQGNVFSCSVMH
             EALHNHYTQKSLSLSPGK (SEQ ID NO: 220)

Heavy chain  QVQLVQSGAEVKKPGASVKVSCKASGYTFTGYPISWVRQAPGQGLEWMGWIYAY
(SIRPAB-10)  GGNTNYAQKLQGRVTMTTDTSTSTAYMELRSLRSDDTAVYYCAREAGSSWYDFD
             LWGRGTLVTVSSASTKGPSVFPLAPSSKSTSGGTAALGCLVKDYFPEPVTVSWN
             SGALTSGVHTFPAVLQSSGLYSLSSVVTVPSSSLGTQTYICNVNHKPSNTKVDK
             KVEPKSCDKTHTCPPCPAPELLGGPSVFLFPPKPKDTLMISRTPEVTCVVVDVS
             HEDPEVKFNWYVDGVEVHNAKTKPREEQYNSTYRVVSVLTVLHQDWLNGKEYKC
             KVSNKALPAPIEKTISKAKGQPREPQVYTLPPSREEMTKNQVSLTCLVKGFYPS
             DIAVEWESNGQPENNYKTTPPVLDSDGSFFLYSKLTVDKSRWQQGNVFSCSVMH
             EALHNHYTQKSLSLSPGK (SEQ ID NO: 221)

Heavy chain  QVQLVQSGAEVKKPGASVKVSCKASGYTFHGYGISWVRQAPGQGLEWMGWISAY
(SIRPAB-13)  SGETNYAQKLQGRVTMTTDTSTSTAYMELRSLRSDDTAVYYCAREAGSSWYDFD
             LWGRGTLVTVSSASTKGPSVFPLAPSSKSTSGGTAALGCLVKDYFPEPVTVSWN
             SGALTSGVHTFPAVLQSSGLYSLSSVVTVPSSSLGTQTYICNVNHKPSNTKVDK
             KVEPKSCDKTHTCPPCPAPELLGGPSVFLFPPKPKDTLMISRTPEVTCVVVDVS
             HEDPEVKFNWYVDGVEVHNAKTKPREEQYNSTYRVVSVLTVLHQDWLNGKEYKC TABLE 13-continued light chain and heavy chain sequences Chain Type  Amino Acid Sequences KVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 222)

Heavy chain QVQLQESGPGLVKPSQTLSLTCTVSGGSISSGGYYWSWIRQHPGKGLEWIGAIY
(SIRPAB-17) YSGPIYYNPSLKSRVTISVDTSKNQFSLKLSSVTAADTAVYYCAREGYHSGMDV
WGQGTTVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHE
ALHNHYTQKSLSLSPGK (SEQ ID NO: 223)

Heavy chain QVQLQESGPGLVKPSQTLSLTCTVSGGSISSGGYYWSWIRQHPGKGLEWIGAIY
(SIRPAB-18) YSGPIYYNPSLKSRVTISVDTSKNQFSLKLSSVTAADTAVYYCSKEGYHSGMDV
WGQGTTVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHE
ALHNHYTQKSLSLSPGK (SEQ ID NO: 207)

Heavy chain QVQLQESGPGLVKPSQTLSLTCTVSGGSISSGGYYWSWIRQHPGKGLEWIGAIY
(SIRPAB-19) YSGPIYYNPSLKSRVTISVDTSKNQFSLKLSSVTAADTAVYYCSKEGYHSGMDV
WGQGTTVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHE
ALHNHYTQKSLSLSPGK (SEQ ID NO: 117)

Heavy chain QVQLQESGPGLVKPSQTLSLTCTVSGGSISSGGYYWSWIRQHPGKGLEWIGAIY
(SIRPAB-20) YSGPIYYNPSLKSRVTISVDTSKNQFSLKLSSVTAADTAVYYCSKEGYHSGMDV
WGQGTTVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHE
ALHNHYTQKSLSLSPGK (SEQ ID NO: 110)

Heavy chain QVQLQESGPGLVKPSQTLSLTCTVSGGSISSGGYYWSWIRQHPGKGLEWIGAIY
(SIRPAB-21) YSGPIYYNPSLKSRVTISVDTSKNQFSLKLSSVTAADTAVYYCSKEGYHSGMDV
WGQGTTVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHE
ALHNHYTQKSLSLSPGK (SEQ ID NO: 148)

Heavy chain QVQLVQSGAEVKKPGASVKVSCKASGYTFTGYGIVWVRQAPGQGLEWMGWISAY
(SIRPAB-12- AGETNYAQKLQGRVTMTTDTSTSTAYMELRSLRSDDTAVYYCAREAGSSWYDFD
AAS)        LWGRGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDK
KVEPKSCDKTHTCPPCPAPEAAGGPSVFLFPPKPKDTLMISRTPEVTCVVVSVS
HEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 106)

Heavy chain QVQLVQSGAEVKKPGASVKVSCKASGYTFTGYGIVWVRQAPGQGLEWMGWISAY
(SIRPAB-12- AGETNYAQKLQGRVTMTTDTSTSTAYMELRSLRSDDTAVYYCAREAGSSWYDFD
4PE)        LWGRGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDK
RVESKYGPPCPPCPAPEFEGGPSVFLFPPKPKDTLMISRTPEVTCVVVDVSQED
PEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEAL
HNHYTQKSLSLSLGK (SEQ ID NO: 118)

TABLE 13-continued light chain and heavy chain sequences

Chain Type  Amino Acid Sequences

Heavy chain  QVQLVQSGAEVKKPGASVKVSCKASGYTFTGYGIVWVRQAPGQGLEWMGWISAY
(SIRPAB-12-  AGETNYAQKLQGRVTMTTDTSTSTAYMELRSLRSDDTAVYYCAREAGSSWYDFD
4P)          LWGRGTLVTVSSASTKGPSVFPLAPCSRSTSESTAALGCLVKDYFPEPVTVSWN
             SGALTSGVHTFPAVLQSSGLYSLSSVVTVPSSSLGTKTYTCNVDHKPSNTKVDK
             RVESKYGPPCPPCPAPEFLGGPSVFLFPPKPKDTLMISRTPEVTCVVVDVSQED
             PEVQFNWYVDGVEVHNAKTKPREEQFNSTYRVVSVLTVLHQDWLNGKEYKCKVS
             NKGLPSSIEKTISKAKGQPREPQVYTLPPSQEEMTKNQVSLTCLVKGFYPSDIA
             VEWESNGQPENNYKTTPPVLDSDGSFFLYSRLTVDKSRWQEGNVFSCSVMHEAL
             HNHYTQKSLSLSLGK (SEQ ID NO: 111)

In some embodiments, the antibody provided herein comprises any one of the light chains provided herein and any one of the heavy chains provided herein, in any combination or permutation. In certain embodiments, the antibody provided herein includes light chain and heavy chain pairs as listed in the following Table 14:

TABLE 14 exemplary light chain and heavy chain pairs for the anti-SIRPα antibodies

| Antibody | Light Chain | Heavy Chain |
|---|---|---|
| SIRPAB-1 | SEQ ID NO: 200 | SEQ ID NO: 212 |
| SIRPAB-2 | SEQ ID NO: 200 | SEQ ID NO: 213 |
| SIRPAB-3 | SEQ ID NO: 200 | SEQ ID NO: 214 |
| SIRPAB-4 | SEQ ID NO: 200 | SEQ ID NO: 215 |
| SIRPAB-5 | SEQ ID NO: 200 | SEQ ID NO: 216 |
| SIRPAB-6 | SEQ ID NO: 202 | SEQ ID NO: 217 |
| SIRPAB-7 | SEQ ID NO: 202 | SEQ ID NO: 218 |
| SIRPAB-8 | SEQ ID NO: 143 | SEQ ID NO: 219 |
| SIRPAB-9 | SEQ ID NO: 143 | SEQ ID NO: 220 |
| SIRPAB-10 | SEQ ID NO: 143 | SEQ ID NO: 221 |
| SIRPAB-11 | SEQ ID NO: 143 | SEQ ID NO: 142 |
| SIRPAB-12 | SEQ ID NO: 143 | SEQ ID NO: 204 |
| SIRPAB-13 | SEQ ID NO: 143 | SEQ ID NO: 222 |
| SIRPAB-17 | SEQ ID NO: 200 | SEQ ID NO: 223 |
| SIRPAB-18 | SEQ ID NO: 200 | SEQ ID NO: 207 |
| SIRPAB-19 | SEQ ID NO: 208 | SEQ ID NO: 117 |
| SIRPAB-20 | SEQ ID NO: 209 | SEQ ID NO: 110 |
| SIRPAB-21 | SEQ ID NO: 210 | SEQ ID NO: 148 |
| SIRPAB-11-K322A | SEQ ID NO: 143 | SEQ ID NO: 119 |
| SIRPAB-11-AAS | SEQ ID NO: 143 | SEQ ID NO: 98 |
| SIRPAB-11-4PE | SEQ ID NO: 143 | SEQ ID NO: 120 |
| SIRPAB-11-4P | SEQ ID NO: 143 | SEQ ID NO: 112 |
| SIRPAB-12-K322A | SEQ ID NO: 143 | SEQ ID NO: 205 |
| SIRPAB-12-AAS | SEQ ID NO: 143 | SEQ ID NO: 106 |
| SIRPAB-12-4PE | SEQ ID NO: 143 | SEQ ID NO: 118 |
| SIRPAB-12-4P | SEQ ID NO: 143 | SEQ ID NO: 111 |

In still another particular embodiment, an antibody described herein, which specifically binds to a SIRPα polypeptide (e.g., an ECD of SIRPα, for example human SIRPα), comprises a light chain and a heavy chain, wherein (i) the light chain comprises an amino acid sequence of SEQ ID NO:200; and (ii) the heavy chain comprises an amino acid sequence of SEQ ID NO:213.

In yet another aspect, antibodies are provided that compete with one of the exemplified antibodies or functional fragments for binding to SIRPα. Such antibodies may also bind to the same epitope as one of the herein exemplified antibodies, or an overlapping epitope. Antibodies and fragments that compete with or bind to the same epitope as the exemplified antibodies are expected to show similar functional properties. The exemplified antigen-binding proteins and fragments include those with the VH and VL regions, and CDRs provided herein, including those in Tables 1-4 and 9-10. Thus, as a specific example, the antibodies that are provided include those that compete with an antibody comprising: (a) 1, 2, 3, 4, 5, or all 6 of the CDRs listed for an antibody listed in Tables 1-2; (b) a VH and a VL selected from the VH and the VL regions listed for an antibody listed in Tables 9-10; or (c) two light chains and two heavy chains comprising a VH and a VL as specified for an antibody listed in Tables 9-10. In some embodiments, the antibody is SIRPAB-1. In some embodiments, the antibody is SIRPAB-2. In some embodiments, the antibody is SIRPAB-3. In some embodiments, the antibody is SIRPAB-4. In some embodiments, the antibody is SIRPAB-5. In some embodiments, the antibody is SIRPAB-6. In some embodiments, the antibody is SIRPAB-7. In some embodiments, the antibody is SIRPAB-8. In some embodiments, the antibody is SIRPAB-9. In some embodiments, the antibody is SIRPAB-10. In some embodiments, the antibody is SIRPAB-11. In some embodiments, the antibody is SIRPAB-12. In some embodiments, the antibody is SIRPAB-13. In some embodiments, the antibody is SIRPAB-17. In some embodiments, the antibody is SIRPAB-18. In some embodiments, the antibody is SIRPAB-19. In some embodiments, the antibody is SIRPAB-20. In some embodiments, the antibody is SIRPAB-21.

In another aspect, antibodies or antigen-binding fragments thereof provided herein bind to a region, including an epitope, of human SIRPα or cyno SIRPα. For example, in some embodiments, an antibody provided herein binds to a region of human SIRPα (SEQ ID NO:146) comprising amino acid residues 30 to 98 of human SIRPα. In still another aspect, antibodies provided herein bind to a specific epitope of human SIRPα.

In certain embodiments, the antibody or antigen-binding fragment thereof, when bound to SIRPα, binds to at least one of residues 30-36 (SEQ ID NO:147) within an amino acid sequence of SEQ ID NO:146. In some embodiments, the antibody or antigen-binding fragment thereof, when bound to SIRPα, binds to at least one of residues 30-52 (SEQ ID NO:160) within an amino acid sequence of SEQ ID NO:146. In some embodiments, the antibody or antigen-binding fragment thereof, when bound to SIRPα, binds to at least one of residues 30-67 (SEQ ID NO:161) within an amino acid sequence of SEQ ID NO:146. In some embodiments, the antibody or antigen-binding fragment thereof, when bound to SIRPα, binds to at least one of residues 30-69 (SEQ ID NO:162) within an amino acid sequence of SEQ ID NO:146. In some embodiments, the antibody or antigen-binding fragment thereof, when bound to SIRPα, binds to at least one of residues 30-74 (SEQ ID NO:163) within an amino acid sequence of SEQ ID NO:146. In some embodiments, the antibody or antigen-binding fragment thereof, when bound to SIRPα, binds to at least one of residues 30-93 (SEQ ID NO:164) within an amino acid sequence of SEQ ID NO:146. In some embodiments, the antibody or antigen-binding fragment thereof, when bound to SIRPα, binds to at least one of residues 30-95 (SEQ ID NO:165) within an amino acid sequence of SEQ ID NO:146. In some embodiments, the antibody or antigen-binding fragment thereof, when bound to SIRPα, binds to at least one of residues 30-96 (SEQ ID NO:166) within an amino acid sequence of SEQ ID NO:146. In some embodiments, the antibody or antigen-binding fragment thereof, when bound to SIRPα, binds to at least one of residues 30-98 (SEQ ID NO:167) within an amino acid sequence of SEQ ID NO:146.

In certain embodiments, the antibody or antigen-binding fragment thereof, when bound to SIRPα, binds to at least one of residues 36-52 (SEQ ID NO:168) within an amino acid sequence of SEQ ID NO:146. In some embodiments, the antibody or antigen-binding fragment thereof, when bound to SIRPα, binds to at least one of residues 36-67 (SEQ ID NO:169) within an amino acid sequence of SEQ ID NO:146. In some embodiments, the antibody or antigen-binding fragment thereof, when bound to SIRPα, binds to at least one of residues 36-69 (SEQ ID NO:170) within an amino acid sequence of SEQ ID NO:146. In some embodiments, the antibody or antigen-binding fragment thereof, when bound to SIRPα, binds to at least one of residues 36-74 (SEQ ID NO:171) within an amino acid sequence of SEQ ID NO:146. In some embodiments, the antibody or antigen-binding fragment thereof, when bound to SIRPα, binds to at least one of residues 36-93 (SEQ ID NO:172) within an amino acid sequence of SEQ ID NO:146. In some embodiments, the antibody or antigen-binding fragment thereof, when bound to SIRPα, binds to at least one of residues 36-95 (SEQ ID NO:173) within an amino acid sequence of SEQ ID NO:146. In some embodiments, the antibody or antigen-binding fragment thereof, when bound to SIRPα, binds to at least one of residues 36-96 (SEQ ID NO:174) within an amino acid sequence of SEQ ID NO:146. In some embodiments, the antibody or antigen-binding fragment thereof, when bound to SIRPα, binds to at least one of residues 36-98 (SEQ ID NO:175) within an amino acid sequence of SEQ ID NO:146.

In certain embodiments, the antibody or antigen-binding fragment thereof, when bound to SIRPα, binds to at least one of residues 52-67 (SEQ ID NO:176) within an amino acid sequence of SEQ ID NO:146. In some embodiments, the antibody or antigen-binding fragment thereof, when bound to SIRPα, binds to at least one of residues 52-69 (SEQ ID NO:177) within an amino acid sequence of SEQ ID NO:146. In some embodiments, the antibody or antigen-binding fragment thereof, when bound to SIRPα, binds to at least one of residues 52-74 (SEQ ID NO:178) within an amino acid sequence of SEQ ID NO:146. In some embodiments, the antibody or antigen-binding fragment thereof, when bound to SIRPα, binds to at least one of residues 52-93 (SEQ ID NO:179) within an amino acid sequence of SEQ ID NO:146. In some embodiments, the antibody or antigen-binding fragment thereof, when bound to SIRPα, binds to at least one of residues 52-95 (SEQ ID NO:180) within an amino acid sequence of SEQ ID NO:146. In some embodiments, the antibody or antigen-binding fragment thereof, when bound to SIRPα, binds to at least one of residues 52-96 (SEQ ID NO:181) within an amino acid sequence of SEQ ID NO:146. In some embodiments, the antibody or antigen-binding fragment thereof, when bound to SIRPα, binds to at least one of residues 52-98 (SEQ ID NO:182) within an amino acid sequence of SEQ ID NO:146.

In certain embodiments, the antibody or antigen-binding fragment thereof, when bound to SIRPα, binds to at least one of residues 67-69 (having the amino acid sequence of TKR) within an amino acid sequence of SEQ ID NO:146. In some embodiments, the antibody or antigen-binding fragment thereof, when bound to SIRPα, binds to at least one of residues 67-74 (SEQ ID NO:183) within an amino acid sequence of SEQ ID NO:146. In some embodiments, the antibody or antigen-binding fragment thereof, when bound to SIRPα, binds to at least one of residues 67-93 (SEQ ID NO:184) within an amino acid sequence of SEQ ID NO:146. In some embodiments, the antibody or antigen-binding fragment thereof, when bound to SIRPα, binds to at least one of residues 67-95 (SEQ ID NO:185) within an amino acid sequence of SEQ ID NO:146. In some embodiments, the antibody or antigen-binding fragment thereof, when bound to SIRPα, binds to at least one of residues 67-96 (SEQ ID NO:186) within an amino acid sequence of SEQ ID NO:146. In some embodiments, the antibody or antigen-binding fragment thereof, when bound to SIRPα, binds to at least one of residues 67-98 (SEQ ID NO:187) within an amino acid sequence of SEQ ID NO:146.

In certain embodiments, the antibody or antigen-binding fragment thereof, when bound to SIRPα, binds to at least one of residues 69-74 (SEQ ID NO:188) within an amino acid sequence of SEQ ID NO:146. In some embodiments, the antibody or antigen-binding fragment thereof, when bound to SIRPα, binds to at least one of residues 69-93 (SEQ ID NO:189) within an amino acid sequence of SEQ ID NO:146. In some embodiments, the antibody or antigen-binding fragment thereof, when bound to SIRPα, binds to at least one of residues 69-95 (SEQ ID NO:190) within an amino acid sequence of SEQ ID NO:146. In some embodiments, the antibody or antigen-binding fragment thereof, when bound to SIRPα, binds to at least one of residues 69-96 (SEQ ID NO:191) within an amino acid sequence of SEQ ID NO:146. In some embodiments, the antibody or antigen-binding fragment thereof, when bound to SIRPα, binds to at least one of residues 69-98 (SEQ ID NO:192) within an amino acid sequence of SEQ ID NO:146.

In certain embodiments, the antibody or antigen-binding fragment thereof, when bound to SIRPα, binds to at least one of residues 74-93 (SEQ ID NO:193) within an amino acid sequence of SEQ ID NO:146. In some embodiments, the antibody or antigen-binding fragment thereof, when bound to SIRPα, binds to at least one of residues 74-95 (SEQ ID NO:194) within an amino acid sequence of SEQ ID NO:146. In some embodiments, the antibody or antigen-binding fragment thereof, when bound to SIRPα, binds to at least one of residues 74-96 (SEQ ID NO:195) within an amino acid sequence of SEQ ID NO:146. In some embodiments, the antibody or antigen-binding fragment thereof, when bound to SIRPα, binds to at least one of residues 74-98 (SEQ ID NO:196) within an amino acid sequence of SEQ ID NO:146.

In certain embodiments, the antibody or antigen-binding fragment thereof, when bound to SIRPα, binds to at least one of residues 93-95 (having the amino acid sequence of KFR) within an amino acid sequence of SEQ ID NO:146. In some embodiments, the antibody or antigen-binding fragment thereof, when bound to SIRPα, binds to at least one of residues 93-96 (SEQ ID NO:198) within an amino acid sequence of SEQ ID NO:146. In some embodiments, the antibody or antigen-binding fragment thereof, when bound to SIRPα, binds to at least one of residues 93-98 (SEQ ID NO:199) within an amino acid sequence of SEQ ID NO:146. In some embodiments, the antibody or antigen-binding fragment thereof, when bound to SIRPα, binds to at least one of residues 95-96 (having the amino acid sequence of RK) within an amino acid sequence of SEQ ID NO:146. In some embodiments, the antibody or antigen-binding fragment thereof, when bound to SIRPα, binds to at least one of residues 95-98 (SEQ ID NO:201) within an amino acid sequence of SEQ ID NO:146. In some embodiments, the antibody or antigen-binding fragment thereof, when bound to SIRPα, binds to at least one of residues 96-98 (having the amino acid sequence of KGS) within an amino acid sequence of SEQ ID NO:146.

In particular embodiments, the antibody or antigen-binding fragment thereof, when bound to SIRPα, binds to at least one residue selected from the group consisting of L30, I36, Q52, T67, R69, F74, K93, R95, K96, and S98 within an amino acid sequence of SEQ ID NO:146. In some embodiments, the antibody or antigen-binding fragment thereof, when bound to SIRPα, binds to at least one residue selected from the group consisting of T67, R69, R95, K96, and S98 within an amino acid sequence of SEQ ID NO:146.

In some embodiments, the antibody or antigen-binding fragment thereof, when bound to SIRPα, binds to two or more residues selected from the group consisting of L30, I36, Q52, T67, R69, F74, K93, R95, K96, and S98 within an amino acid sequence of SEQ ID NO:146. In some embodiments, the antibody or antigen-binding fragment thereof, when bound to SIRPα, binds to two or more residues selected from the group consisting of T67, R69, R95, K96, and S98 within an amino acid sequence of SEQ ID NO:146.

In other embodiments, the antibody or antigen-binding fragment thereof, when bound to SIRPα, binds to three or more residues selected from the group consisting of L30, I36, Q52, T67, R69, F74, K93, R95, K96, and S98 within an amino acid sequence of SEQ ID NO:146. In some embodiments, the antibody or antigen-binding fragment thereof, when bound to SIRPα, binds to three or more residues selected from the group consisting of T67, R69, R95, K96, and S98 within an amino acid sequence of SEQ ID NO:146.

In certain embodiments, the antibody or antigen-binding fragment thereof, when bound to SIRPα, binds to four or more residues selected from the group consisting of L30, I36, Q52, T67, R69, F74, K93, R95, K96, and S98 within an amino acid sequence of SEQ ID NO:146. In some embodiments, the antibody or antigen-binding fragment thereof, when bound to SIRPα, binds to four or more residues selected from the group consisting of T67, R69, R95, K96, and S98 within an amino acid sequence of SEQ ID NO:146.

In one embodiment, the antibody or antigen-binding fragment thereof, when bound to SIRPα, binds to five or more residues selected from the group consisting of L30, I36, Q52, T67, R69, F74, K93, R95, K96, and S98 within an amino acid sequence of SEQ ID NO:146. In other embodiments, the antibody or antigen-binding fragment thereof, when bound to SIRPα, binds to five residues consisting of T67, R69, R95, K96, and S98 within an amino acid sequence of SEQ ID NO:146.

In another embodiment, the antibody or antigen-binding fragment thereof, when bound to SIRPα, binds to six or more residues selected from the group consisting of L30, I36, Q52, T67, R69, F74, K93, R95, K96, and S98 within an amino acid sequence of SEQ ID NO:146.

In yet another embodiment, the antibody or antigen-binding fragment thereof, when bound to SIRPα, binds to seven or more residues selected from the group consisting of L30, I36, Q52 T67, R69, F74, K93, R95, K96, and S98 within an amino acid sequence of SEQ ID NO:146.

In still another embodiment, the antibody or antigen-binding fragment thereof, when bound to SIRPα, binds to eight or more residues selected from the group consisting of L30, I36, Q52, T67, R69, F74, K93, R95, K96, and S98 within an amino acid sequence of SEQ ID NO:146.

In certain embodiments, the antibody or antigen-binding fragment thereof, when bound to SIRPα, binds to nine or more residues selected from the group consisting of L30, I36, Q52, T67, R69, F74, K93, R95, K96, and S98 within an amino acid sequence of SEQ ID NO:146.

In other embodiments, the antibody or antigen-binding fragment thereof, when bound to SIRPα, binds to all ten residues from the group consisting of L30, I36, Q52, T67, R69, F74, K93, R95, K96, and S98 within an amino acid sequence of SEQ ID NO:146.

In another embodiment, the antibody or antigen-binding fragment thereof, when bound to SIRPα, binds to L30 within an amino acid sequence of SEQ ID NO:146. In another embodiment, the antibody or antigen-binding fragment thereof, when bound to SIRPα, binds to I36 within an amino acid sequence of SEQ ID NO:146. In a particular embodiment, the antibody or antigen-binding fragment thereof, when bound to SIRPα, binds to Q52 within an amino acid sequence of SEQ ID NO:146. In one specific embodiment, the antibody or antigen-binding fragment thereof when bound to SIRPα, binds to T67 within an amino acid sequence of SEQ ID NO:146. In some embodiments, the antibody or antigen-binding fragment thereof when bound to SIRPα, binds to R69 within an amino acid sequence of SEQ ID NO:146. In other embodiments, the antibody or antigen-binding fragment thereof when bound to SIRPα, binds to F74 within an amino acid sequence of SEQ ID NO:146. In another embodiment, the antibody or antigen-binding fragment thereof, when bound to SIRPα, binds to K93 within an amino acid sequence of SEQ ID NO:146. In yet another embodiment, the antibody or antigen-binding fragment thereof, when bound to SIRPα, binds to R95 within an amino acid sequence of SEQ ID NO:146. In still another embodiment, the antibody or antigen-binding fragment thereof, when bound to SIRPα, binds to K96 within an amino acid sequence of SEQ ID NO:146. In some embodiments, the antibody or antigen-binding fragment thereof, when bound to SIRPα, binds to S98 within an amino acid sequence of SEQ ID NO:146. Any combination of two, three, four, five, six, seven, eight, nine, or ten of the above-referenced amino acid SIRPα binding sites is also contemplated.

In one aspect, provided herein are antibodies that specifically bind to SIRPα and can reduce binding between SIRPα and CD47. As is known to a person skilled in the art, there are many naturally occurring SIRPα polymorphism. The anti-SIRPα antibodies or fragments thereof provided herein can bind to one, two, three, four, five, six, seven, eight, nine, ten or more or all of the SIRPα polymorphism known to a person skilled in the art, for example one, two, three, four, five, six, seven, eight, nine, ten or more, or all of the SIRPα polymorphism described in Takenaka K, et al., Nat Immunol. 2007 December;8(12):1313-23. In some specific embodiments, the anti-SIRPα antibodies or fragments thereof provided herein can bind to one or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce binding between CD47 and one or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein can bind to two or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce binding between CD47 and two or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In certain embodiments, the anti-SIRPα antibodies or fragments thereof provided herein can bind to three or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce binding between CD47 and three or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ NO:154 in the IgV-domain.

In some embodiments, the anti-SIRPα antibodies or fragments thereof provided herein can bind to four or more SIRPα polymorphisms selected from the group consisting of SIRPα v1 comprising SEQ ID NO:149 in the IgV-domain, SIRPα v2 comprising SEQ ID NO: in the IgV-domain, SIRPα v3 comprising SEQ ID NO: in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce binding between CD47 and four or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ NO:154 in the IgV-domain.

In certain embodiments, the anti-SIRPα antibodies or fragments thereof provided herein can bind to five or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce binding between CD47 and five or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein can bind to all six SIRPα polymorphisms consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce binding between CD47 and all six SIRPα polymorphisms consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein can bind to SIRPα v1 comprising SEQ ID NO:149 in the IgV-domain, and/or reduce binding between CD47 and SIRPα v1 comprising SEQ ID NO:149 in the IgV-domain. In some embodiments, the anti-SIRPα antibodies or fragments thereof provided herein can bind to SIRPα v2 comprising SEQ ID NO:150 in the IgV-domain, and/or reduce binding between CD47 and SIRPα v2 comprising SEQ ID NO:150 in the IgV-domain. In some embodiments, the anti-SIRPα antibodies or fragments thereof provided herein can bind to SIRPα v3 comprising SEQ ID NO:151 in the IgV-domain, and/or reduce binding between CD47 and SIRPα v3 comprising SEQ ID NO:151 in the IgV-domain. In some embodiments, the anti-SIRPα antibodies or fragments thereof provided herein can bind to SIRPα v4 comprising SEQ ID NO:152 in the IgV-domain, and/or reduce binding between CD47 and SIRPα v4 comprising SEQ ID NO:152 in the IgV-domain. In some embodiments, the anti-SIRPα antibodies or fragments thereof provided herein can bind to SIRPα v5 comprising SEQ ID NO:153 in the IgV-domain, and/or reduce binding between CD47 and SIRPα v5 comprising SEQ ID NO:153 in the IgV-domain. In some embodiments, the anti-SIRPα antibodies or fragments thereof provided herein can bind to SIRPα v6 comprising SEQ ID NO:154 in the IgV-domain, and/or reduce binding between CD47 and SIRPα v6 comprising SEQ ID NO:154 in the IgV-domain.

In some embodiments, the anti-SIRPα antibodies or fragments thereof provided herein can bind to SIRPα v1 comprising SEQ ID NO:149 in the IgV-domain and SIRPα v2 comprising SEQ ID NO:150 in the IgV-domain, and/or reduce binding between CD47 and said SIRPα v1 and binding between CD47 said SIRPα v2. In some embodiments, the anti-SIRPα antibodies or fragments thereof provided herein can bind to SIRPα v1 comprising SEQ ID NO:149 in the IgV-domain and SIRPα v3 comprising SEQ ID NO:151 in the IgV-domain, and/or reduce binding between CD47 and said SIRPα v1 and binding between CD47 said SIRPα v3. In some embodiments, the anti-SIRPα antibodies or fragments thereof provided herein can bind to SIRPα v1 comprising SEQ ID NO:149 in the IgV-domain and SIRPα v4 comprising SEQ ID NO:152 in the IgV-domain, and/or reduce binding between CD47 and said SIRPα v1 and binding between CD47 said SIRPα v4. In some embodiments, the anti-SIRPα antibodies or fragments thereof provided herein can bind to SIRPα v1 comprising SEQ ID NO:149 in the IgV-domain and SIRPα v5 comprising SEQ ID NO:153 in the IgV-domain, and/or reduce binding between CD47 and said SIRPα v1 and binding between CD47 said SIRPα v5. In some embodiments, the anti-SIRPα antibodies or fragments thereof provided herein can bind to SIRPα v1 comprising SEQ ID NO:149 in the IgV-domain and SIRPα v6 comprising SEQ ID NO:154 in the IgV-domain, and/or reduce binding between CD47 and said SIRPα v1 and binding between CD47 said SIRPα v6.

In some embodiments, the anti-SIRPα antibodies or fragments thereof provided herein can bind to SIRPα v2 comprising SEQ ID NO:150 in the IgV-domain and SIRPα v3 comprising SEQ ID NO:151 in the IgV-domain, and/or reduce binding between CD47 and said SIRPα v2 and binding between CD47 said SIRPα v3. In some embodiments, the anti-SIRPα antibodies or fragments thereof provided herein can bind to SIRPα v2 comprising SEQ ID NO:150 in the IgV-domain and SIRPα v4 comprising SEQ ID NO:152 in the IgV-domain, and/or reduce binding between CD47 and said SIRPα v2 and binding between CD47 said SIRPα v4. In some embodiments, the anti-SIRPα antibodies or fragments thereof provided herein can bind to SIRPα v2 comprising SEQ ID NO:150 in the IgV-domain and SIRPα v5 comprising SEQ ID NO:153 in the IgV-domain, and/or reduce binding between CD47 and said SIRPα v2 and binding between CD47 said SIRPα v5. In some embodiments, the anti-SIRPα antibodies or fragments thereof provided herein can bind to SIRPα v2 comprising SEQ ID NO:150 in the IgV-domain and SIRPα v6 comprising SEQ ID NO:154 in the IgV-domain, and/or reduce binding between CD47 and said SIRPα v2 and binding between CD47 said SIRPα v6.

In some embodiments, the anti-SIRPα antibodies or fragments thereof provided herein can bind to SIRPα v3 comprising SEQ ID NO:151 in the IgV-domain and SIRPα v4 comprising SEQ ID NO:152 in the IgV-domain, and/or reduce binding between CD47 and said SIRPα v3 and binding between CD47 said SIRPα v4. In some embodiments, the anti-SIRPα antibodies or fragments thereof provided herein can bind to SIRPα v3 comprising SEQ ID NO:151 in the IgV-domain and SIRPα v5 comprising SEQ ID NO:153 in the IgV-domain, and/or reduce binding between CD47 and said SIRPα v3 and binding between CD47 said SIRPα v5. In some embodiments, the anti-SIRPα antibodies or fragments thereof provided herein can bind to SIRPα v3 comprising SEQ ID NO:151 in the IgV-domain and SIRPα v6 comprising SEQ ID NO:154 in the IgV-domain, and/or reduce binding between CD47 and said SIRPα v3 and binding between CD47 said SIRPα v6.

In some embodiments, the anti-SIRPα antibodies or fragments thereof provided herein can bind to SIRPα v4 comprising SEQ ID NO:152 in the IgV-domain and SIRPα v5 comprising SEQ ID NO:153 in the IgV-domain, and/or reduce binding between CD47 and said SIRPα v4 and binding between CD47 said SIRPα v5. In some embodiments, the anti-SIRPα antibodies or fragments thereof provided herein can bind to SIRPα v4 comprising SEQ ID NO:152 in the IgV-domain and SIRPα v6 comprising SEQ ID NO:154 in the IgV-domain, and/or reduce binding between CD47 and said SIRPα v4 and binding between CD47 said SIRPα v6. In some embodiments, the anti-SIRPα antibodies or fragments thereof provided herein can bind to SIRPα v5 comprising SEQ ID NO:153 in the IgV-domain and SIRPα v6 comprising SEQ ID NO:154 in the IgV-domain, and/or reduce binding between CD47 and said SIRPα v5 and binding between CD47 said SIRPα v6.

In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, and SIRPα v3 comprising SEQ ID NO:151 in the IgV-domain, and/or reduce CD47 binding to each and all of said SIRPα v1, SIRPα v2, and SIRPα v3. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, and SIRPα v4 comprising SEQ ID NO:152 in the IgV-domain, and/or reduce CD47 binding to each and all of said SIRPα v1, SIRPα v2, and SIRPα v4. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, and SIRPα v5 comprising SEQ ID NO:153 in the IgV-domain, and/or reduce CD47 binding to each and all of said SIRPα v1, SIRPα v2, and SIRPα v5. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, and SIRPα v6 comprising SEQ ID NO:154 in the IgV-domain, and/or reduce CD47 binding to each and all of said SIRPα v1, SIRPα v2, and SIRPα v6.

In some embodiments, the anti-SIRPα antibodies or fragments thereof provided herein can bind to SIRPα v1 comprising SEQ ID NO:149 in the IgV-domain, SIRPα v3 comprising SEQ ID NO:151 in the IgV-domain, and SIRPα v4 comprising SEQ ID NO:152 in the IgV-domain, and/or reduce CD47 binding to each and all of said SIRPα v1, SIRPα v3, and SIRPα v4. In some embodiments, the anti-SIRPα antibodies or fragments thereof provided herein can bind to SIRPα v1 comprising SEQ ID NO:149 in the IgV-domain, SIRPα v3 comprising SEQ ID NO:151 in the IgV-domain, and SIRPα v5 comprising SEQ ID NO:153 in the IgV-domain, and/or reduce CD47 binding to each and all of said SIRPα v1, SIRPα v3, and SIRPα v5. In some embodiments, the anti-SIRPα antibodies or fragments thereof provided herein can bind to SIRPα v1 comprising SEQ ID NO:149 in the IgV-domain, SIRPα v3 comprising SEQ ID NO:151 in the IgV-domain, and SIRPα v6 comprising SEQ ID NO:154 in the IgV-domain, and/or reduce CD47 binding to each and all of said SIRPα v1, SIRPα v3, and SIRPα v6.

In some embodiments, the anti-SIRPα antibodies or fragments thereof provided herein can bind to SIRPα v1 comprising SEQ ID NO:149 in the IgV-domain, SIRPα v4 comprising SEQ ID NO:152 in the IgV-domain, and SIRPα v5 comprising SEQ ID NO:153 in the IgV-domain, and/or reduce CD47 binding to each and all of said SIRPα v1, SIRPα v4, and SIRPα v5. In some embodiments, the anti-SIRPα antibodies or fragments thereof provided herein can bind to SIRPα v1 comprising SEQ ID NO:149 in the IgV-domain, SIRPα v4 comprising SEQ ID NO:152 in the IgV-domain, and SIRPα v6 comprising SEQ ID NO:154 in the IgV-domain, and/or reduce CD47 binding to each and all of said SIRPα v1, SIRPα v4, and SIRPα v6.

In some embodiments, the anti-SIRPα antibodies or fragments thereof provided herein can bind to SIRPα v1 comprising SEQ ID NO:149 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v1, SIRPα v5, and SIRPα v6.

In some embodiments, the anti-SIRPα antibodies or fragments thereof provided herein can bind to SIRPα v2 comprising SEQ ID NO:150 in the IgV-domain, SIRPα v3 comprising SEQ ID NO:151 in the IgV-domain, and SIRPα v4 comprising SEQ ID NO:152 in the IgV-domain, and/or reduce CD47 binding to each and all of said SIRPα v2, SIRPα v3, and SIRPα v4. In some embodiments, the anti-SIRPα antibodies or fragments thereof provided herein can bind to SIRPα v2 comprising SEQ ID NO:150 in the IgV-domain, SIRPα v3 comprising SEQ ID NO:151 in the IgV-domain, and SIRPα v5 comprising SEQ ID NO:153 in the IgV-domain, and/or reduce CD47 binding to each and all of said SIRPα v2, SIRPα v3, and SIRPα v5. In some embodiments, the anti-SIRPα antibodies or fragments thereof provided herein can bind to SIRPα v2 comprising SEQ ID NO:150 in the IgV-domain, SIRPα v3 comprising SEQ ID NO:151 in the IgV-domain, and SIRPα v6 comprising SEQ ID NO:154 in the IgV-domain, and/or reduce CD47 binding to each and all of said SIRPα v2, SIRPα v3, and SIRPα v6.

In some embodiments, the anti-SIRPα antibodies or fragments thereof provided herein can bind to SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain, and/or reduce CD47 binding to each and all of said SIRPα v3, SIRPα v4, and SIRPα v5. In some embodiments, the anti-SIRPα antibodies or fragments thereof provided herein can bind to SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain, and/or reduce CD47 binding to each and all of said SIRPα v3, SIRPα v4, and SIRPα v6. In some embodiments, the anti-SIRPα antibodies or fragments thereof provided herein can bind to SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v4, SIRPα v5, and SIRPα v6.

In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v4 comprising SEQ ID NO:152 in the IgV-domain, and/or reduce CD47 binding to each and all of said SIRPα v1, SIRPα v2, SIRPα v3, and SIRPα v4. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v5 comprising SEQ ID NO:153 in the IgV-domain, and/or reduce CD47 binding to each and all of said SIRPα v1, SIRPα v2, SIRPα v3, and SIRPα v5. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v6 comprising SEQ ID NO:154 in the IgV-domain, and/or reduce CD47 binding to each and all of said SIRPα v1, SIRPα v2, SIRPα v3, and SIRPα v6.

In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, and SIRPα v5 comprising SEQ ID NO:153 in the IgV-domain, and/or reduce CD47 binding to each and all of said SIRPα v1, SIRPα v2, SIRPα v4, and SIRPα v5. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the SIRPα v4 comprising SEQ ID NO:152 in the IgV-domain, and SIRPα v6 comprising SEQ ID NO:154 in the IgV-domain, and/or reduce CD47 binding to each and all of said SIRPα v1, SIRPα v2, SIRPα v4, and SIRPα v6. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v1, SIRPα v2, SIRPα v5, and SIRPα v6.

In some embodiments, the anti-SIRPα antibodies or fragments thereof provided herein can bind to SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain, and/or reduce CD47 binding to each and all of said SIRPα v1, SIRPα v3, SIRPα v4, and SIRPα v5. In some embodiments, the anti-SIRPα antibodies or fragments thereof provided herein can bind to SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain, and/or reduce CD47 binding to each and all of said SIRPα v1, SIRPα v3, SIRPα v4, and SIRPα v6. In some embodiments, the anti-SIRPα antibodies or fragments thereof provided herein can bind to SIRPα v1 comprising SEQ ID NO:149 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v1, SIRPα v3, SIRPα v5, and SIRPα v6.

In some embodiments, the anti-SIRPα antibodies or fragments thereof provided herein can bind to SIRPα v1 comprising SEQ ID NO:149 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v1, SIRPα v4, SIRPα v5, and SIRPα v6.

In some embodiments, the anti-SIRPα antibodies or fragments thereof provided herein can bind to SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain, and/or reduce CD47 binding to each and all of said SIRPα v2, SIRPα v3, SIRPα v4, and SIRPα v5. In some embodiments, the anti-SIRPα antibodies or fragments thereof provided herein can bind to SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain, and/or reduce CD47 binding to each and all of said SIRPα v2, SIRPα v3, SIRPα v4, and SIRPα v6. In some embodiments, the anti-SIRPα antibodies or fragments thereof provided herein can bind to SIRPα v2 comprising SEQ ID NO:150 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v2, SIRPα v3, SIRPα v5, and SIRPα v6.

In some embodiments, the anti-SIRPα antibodies or fragments thereof provided herein can bind to SIRPα v2 comprising SEQ ID NO:150 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v2, SIRPα v4, SIRPα v5, and SIRPα v6. In some embodiments, the anti-SIRPα antibodies or fragments thereof provided herein can bind to SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v3, SIRPα v4, SIRPα v5, and SIRPα v6.

In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v3 comprising SEQ ID NO:151 in the SIRPα v4 comprising SEQ ID NO:152 in the IgV-domain, and SIRPα v5 comprising SEQ ID NO:153 in the IgV-domain, and/or reduce CD47 binding to each and all of said SIRPα v1, SIRPα v2, SIRPα v3, SIRPα v4, and SIRPα v5. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain, and/or reduce CD47 binding to each and all of said SIRPα v1, SIRPα v2, SIRPα v3, SIRPα v4, and SIRPα v6. In some embodiments, the anti-SIRPα antibodies or fragments thereof provided herein can bind to SIRPα v1 comprising SEQ ID NO:149 in the IgV-domain, SIRPα v2 comprising SEQ ID N0:150 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v1, SIRPα v2, SIRPα v3, SIRPα v5, and SIRPα v6. In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v1, SIRPα v2, SIRPα v4, SIRPα v5, and SIRPα v6. In some embodiments, the anti-SIRPα antibodies or fragments thereof provided herein can bind to SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v1, SIRPα v3, SIRPα v4, SIRPα v5, and SIRPα v6. In some embodiments, the anti-SIRPα antibodies or fragments thereof provided herein can bind to SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v2, SIRPα v3, SIRPα v4, SIRPα v5, and SIRPα v6.

In some embodiments, the anti-SIRPα antibodies or fragments thereof provided herein can bind to SIRPα v1 comprising SEQ ID NO:149 in the IgV-domain, SIRPα v2 comprising SEQ ID NO:150 in the IgV-domain, SIRPα v3 comprising SEQ NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain, and/or reduce CD47 binding to each and all of said SIRPα v1, SIRPα v2, SIRPα v3, SIRPα v4, SIRPα v5, and SIRPα v6.

in specific embodiments, an anti-SIRPα antibody or fragment thereof provided herein inserts into a large SIRPα pocket formed predominantly by residues Phe74, Ile36, Leu30, Lys93, and Asn52 of SIRPα having SEQ ID NO:146, which is the same pocket recognized and interacted with by the CD47 F-G loop. As such, in some embodiments, an anti-SIRPα antibody or fragment thereof provided herein binds to about 50% or at least 50% of the SIRPα polymorphisms in the CD47-binding interface in the Ig-V domain of SIRPα. In certain embodiments, an anti-SIRPα antibody or fragment thereof provided herein binds to about 55% or at least 55% of the SIRPα polymorphisms in the CD47-binding interface in the Ig-V domain of SIRPα. In some embodiments, an anti-SIRPα antibody or fragment thereof provided herein binds to about 60% or at least 60% of the SIRPα polymorphisms in the CD47-binding interface in the Ig-V domain of SIRPα. In certain embodiments, an anti-SIRPα antibody or fragment thereof provided herein binds to about 65% or at least 65% of the SIRPα polymorphisms in the CD47-binding interface in the Ig-V domain of SIRPα. In some embodiments, an anti-SIRPα antibody or fragment thereof provided herein binds to about 70% or at least 70% of the SIRPα polymorphisms in the CD47-binding interface in the Ig-V domain of SIRPα. In certain embodiments, an anti-SIRPα antibody or fragment thereof provided herein binds to about 75% or at least 75% of the SIRPα polymorphisms in the CD47-binding interface in the Ig-V domain of SIRPα. In some embodiments, an anti-SIRPα antibody or fragment thereof provided herein binds to about 80% or at least 80% of the SIRPα polymorphisms in the CD47-binding interface in the Ig-V domain of SIRPα. In certain embodiments, an anti-SIRPα antibody or fragment thereof provided herein binds to about 85% or at least 85% of the SIRPα polymorphisms in the CD47-binding interface in the Ig-V domain of SIRPα. In some embodiments, an anti-SIRPα antibody or fragment thereof provided herein binds to about 90% or at least 90% of the SIRPα polymorphisms in the CD47-binding interface in the Ig-V domain of SIRPα. In certain embodiments, an anti-SIRPα antibody or fragment thereof provided herein binds to about 95% or at least 95% of the SIRPα polymorphisms in the CD47-binding interface in the Ig-V domain of SIRPα. In other embodiments, an anti-SIRPα antibody or fragment thereof provided herein binds to about 99% or at least 99% of the SIRPα polymorphisms in the CD47-binding interface in the Ig-V domain of SIRPα.

As described in the foregoing paragraphs, the anti-SIRPα antibodies or fragments thereof provided herein can bind to SIRPα and/or reduce CD47 binding to SIRPα (for example, any one or any combination of two, three, four, five, or six of SIRPα selected from the group consisting of SIRPα v1, v3, v4, v5 and v6 haplotypes), the reduction in the CD47-SIRPα binding can be about 10%, about 20%, about 30%, about 40%, about 50%, about 60%, about 70%, about 80%, about 90%, about 95%, about 99%, or about 99.99%. Similarly, the reduction in CD47-SIRPα binding (e.g. CD47 binding to any one or any combination of two, three, four, five, or six of SIRPα selected from the group consisting of SIRPα v1, 42, v3, v4, v5 and v6 haplotypes) by the anti-SIRPα antibodies or fragments thereof provided herein can be at least 10%, at least 20%, at least 30%, at least 40%, at least 50%, at least 60%, at least 70%, at least 80%, at least 90%, at least 95%, at least 99%, or at least 99.99%. Additionally, the reduction in CD47-SIRPα binding (e.g. CD47 binding to any one or any combination of two, three, four, five, or six of SIRPα selected from the group consisting of SIRPα v1, v2, v3, v4, v5 and v6 haplotypes) by the anti-SIRPα antibodies or fragments thereof can range from about 50% to about 90%, about 60% to about 90%, about 70% to about 90%, about 80% to about 90%, about 50% to about 99%, about 60% to about 99%, about 70% to about 99%, about 80% to about 99%, or about 90% to about 99%.

In another aspect, an anti-SIRPα antibody or fragment thereof provided herein that specifically binds to SIRPα can modulate SIRPα activity (e.g., inhibit SIRPα signaling). In certain embodiments, an anti-SIRPα antibody or functional fragment thereof provided herein is an antibody described herein that specifically binds to an ECD of human SIRPα, and activates (e.g., partially activates) at least one SIRPα activity (e.g., increase production and/or secretion of certain cytokines).

In some specific embodiments, the anti-SIRPα antibodies or functional fragments thereof provided herein bind to SIRPα (for example, any one or any combination of two, three, four, five, or six of SIRPα selected from the group consisting of SIRPα v1, v2, v3, v4, v5 and v6 haplotypes) with a $K_D$ value from about 1 pM to about 10 pM, from about 10 pM to about 100 pM, from about 100 pM to about 1 nM, from about 1 nM to about 10 nM, from about 10 nM to about 100 nM, from about 1 pM to about 100 pM, from about 10 pM to about 1 nM, from about 100 pM to about 10 nM, from about 1 nM to about 100 nM, or from about 10 nM to about 1000 nM, and/or reduce CD47 binding to SIRPα (for example, any one or any combination of two, three, four, five, or six of SIRPα selected from the group consisting of SIRPα v1, v2, v3, v4, v5 and v6 haplotypes) with $EC_{50}$ from about 1 pM to about 10 pM, from about 10 pM to about 100 pM, from about 100 pM to about 1 nM, from about 1 nM to about 10 nM, from about 10 nM to about 100 nM, from about 1 pM to about 100 pM, from about 10 pM to about 1 nM, from about 100 pM to about 10 nM, from about 1 nM to about 100 nM, or from about 10 nM to about 1000 nM.

In some embodiments, an anti-SIRPα antibody provided herein binds to SIRPα with a $K_D$ value of about 0.01 nM, about 0.02 nM, about 0.03 nM, about 0.04 nM, about 0.05 nM, about 0.06 nM, about 0.07 nM, about 0.08 nM, about 0.09 nM, about 0.1 nM, about 0.11 nM, about 0.12 nM, about 0.13 nM, about 0.14 nM, about 0.15 nM, about 0.16 nM, about 0.17 nM, about 0.18 nM, about 0.19 nM, about 0.2 nM, about 0.3 nM, about 0.4 nM, about 0.5 nM, about 0.6 nM, about 0.7 nM, about 0.8 nM, about 0.9 nM, about 1.0 nM, about 1.2 nM, about 1.3 nM, about 1.4 nM, about 1.5 nM, about 1.6 nM, about 1.7 nM, about 1.8 nM, about 1.9 nM, 2 nM, about 2.1 nM, about 2.2 nM, about 2.3 nM, about 2.4 nM, about 2.5 nM, about 2.6 nM, about 2.7 nM, about 2.8 nM, about 2.9 nM, about 3 nM, about 3.1 nM, about 3.2 nM, about 3.3 nM, about 3.4 nM, about 3.5 nM, about 3.6 nM, about 3.7 nM, about 3.8 nM, about 3.9 nM, about 4.0 nM, about 4.1 nM, about 4.2 nM, about 4.3 nM, about 4.4 nM, about 4.5 nM, about 4.6 nM, about 4.7 nM, about 4.8 nM, about 4.9 nM, about 5.0 nM, about 5.1 nM, about 5.2 nM, about 5.3 nM, about 5.4 nM, about 5.5 nM, about 5.6 nM, about 5.7 nM, about 5.8 nM, about 5.9 nM, about 6.0 nM, about 6.1 nM, about 6.2 nM, about 6.3 nM, about 6.4 nM, about 6.5 nM, about 6.6 nM, about 6.7 nM, about 6.8 nM, about 6.9 nM, about 7.0 nM, about 7.1 nM, about 7.2 nM, about 7.3 nM, about 7.4 nM, about 7.5 nM, about 7.6 nM, about 7.7 nM, about 7.8 nM, about 7.9 nM, about 8.0 nM, about 8.1 nM, about 8.2 nM, about 8.3 nM, about 8.4 nM, about 8.5 nM, about 8.6 nM, about 8.7 nM, about 8.8 nM, about 8.9 nM, about 9.0 nM, about 9.1 nM, about 9.2 nM, about 9.3 nM, about 9.4 nM, about 9.5 nM, about 9.6 nM, about 9.7 nM, about 9.8 nM, about 9.9 nM, or about 10.0 nM. In some embodiments, an anti-SIRPα antibody provided herein binds to SIRPα with a $K_D$ value of no more than 0.01 nM, no more than 0.02 nM, no more than 0.03 nM, no more than 0.04 nM, no more than 0.05 nM, no more than 0.06 nM, no more than 0.07 nM, no more than 0.08 nM, no more than 0.09 nM, no more than 0.1 nM, no more than 0.11 nM, no more than 0.12 nM, no more than 0.13 nM, no more than 0.14 nM, no more than 0.15 nM, no more than 0.16 nM, no more than 0.17 nM, no more than 0.18 nM, no more than 0.19 nM, no more than 0.2 nM, no more than 0.3 nM, no more than 0.4 nM, no more than 0.5 nM, no more than 0.6 nM, no more than 0.7 nM, no more than 0.8 nM, no more than 0.9 nM, no more than 1.0 nM, no more than 1.2 nM, no more than 1.3 nM, no more than 1.4 nM, no more than 1.5 nM, no more than 1.6 nM, no more than 1.7 nM, no more than 1.8 nM, no more than 1.9 nM, 2 nM, no more than 2.1 nM, no more than 2.2 nM, no more than 2.3 nM, no more than 2.4 nM, no more than 2.5 nM, no more than 2.6 nM, no more than 2.7 nM, no more than 2.8 nM, no more than 2.9 nM, no more than 3 nM, no more than 3.1 nM, no more than 3.2 nM, no more than 3.3 nM, no more than 3.4 nM, no more than 3.5 nM, no more than 3.6 nM, no more than 3.7 nM, no more than 3.8 nM, no more than 3.9 nM, no more than 4.0 nM, no more than 4.1 nM, no more than 4.2 nM, no more than 4.3 nM, no more than 4.4 nM, no more than 4.5 nM, no more than 4.6 nM, no more than 4.7 nM, no more than 4.8 nM, no more than 4.9 nM, no more than 5.0 nM, no more than 5.1 nM, no more than 5.2 nM, no more than 5.3 nM, no more than 5.4 nM, no more than 5.5 nM, no more than 5.6 nM, no more than 5.7 nM, no more than 5.8 nM, no more than 5.9 nM, no more than 6.0 nM, no more than 6.1 nM, no more than 6.2 nM, no more than 6.3 nM, no more than 6.4 nM, no more than 6.5 nM, no more than 6.6 nM, no more than 6.7 nM, no more than 6.8 nM, no more than 6.9 nM, no more than 7.0 nM, no more than 7.1 nM, no more than 7.2 nM, no more than 7.3 nM, no more than 7.4 nM, no more than 7.5 nM, no more than 7.6 nM, no more than 7.7 nM, no more than 7.8 nM, no more than 7.9 nM, no more than 8.0 nM, no more than 8.1 nM, no more than 8.2 nM, no more than 8.3 nM, no more than 8.4 nM, no more than 8.5 nM, no more than 8.6 nM, no more than 8.7 nM, no more than 8.8 nM, no more than 8.9 nM, no more than 9.0 nM, no more than 9.1 nM, no more than 9.2 nM, no more than 9.3 nM, no more than 9.4 nM, no more than 9.5 nM, no more than 9.6 nM, no more than 9.7 nM, no more than 9.8 nM, no more than 9.9 nM, or no more than 10.0 nM. In some embodiments, the anti-SIRPα antibody or functional fragment thereof is an anti-SIRPα antibody. In some embodiments, the anti-SIRPα antibody or functional fragment thereof is a functional fragment of an anti-SIRPα antibody. In some embodiments, the SIRPα is selected from SIRPα v1, v2, v3, v4, v5 and v6 haplotypes. In some embodiments, the SIRPα is a SIRPα v1 comprising SEQ ID NO:149 in the IgV-domain. In some embodiments, the SIRPα is a SIRPα v2 comprising SEQ ID NO:150 in the IgV-domain. In some embodiments, the SIRPα is a SIRPα v3 comprising SEQ ID NO:151 in the IgV-domain. In some embodiments, the SIRPα is a SIRPα v4 comprising SEQ ID NO:152 in the IgV-domain. In some embodiments, the SIRPα is a SIRPα v5 comprising SEQ ID NO:153 in the IgV-domain. In some embodiments, the SIRPα is a SIRPα v6 comprising SEQ ID NO:154 in the IgV-domain. In some embodiments, the SIRPα is a cynomolgus SIRPα.

In some embodiments, an anti-SIRPα antibody provided herein reduces CD47 binding to SIRPα with an $EC_{50}$ of about 0.01 nM, about 0.02 nM, about 0.03 nM, about 0.04 nM, about 0.05 nM, about 0.06 nM, about 0.07 nM, about 0.08 nM, about 0.09 nM, about 0.1 nM, about 0.11 nM, about 0.12 nM, about 0.13 nM, about 0.14 nM, about 0.15 nM, about 0.16 nM, about 0.17 nM, about 0.18 nM, about 0.19 nM, about 0.2 nM, about 0.3 nM, about 0.4 nM, about 0.5 nM, about 0.6 nM, about 0.7 nM, about 0.8 nM, about 0.9 nM, about 1.0 nM, about 1.2 nM, about 1.3 nM, about 1.4 nM, about 1.5 nM, about 1.6 nM, about 1.7 nM, about 1.8 nM, about 1.9 nM, 2 nM, about 2.1 nM, about 2.2 nM, about 2.3 nM, about 2.4 nM, about 2.5 nM, about 2.6 nM, about 2.7 nM, about 2.8 nM, about 2.9 nM, about 3 nM, about 3.1 nM, about 3.2 nM, about 3.3 nM, about 3.4 nM, about 3.5 nM, about 3.6 nM, about 3.7 nM, about 3.8 nM, about 3.9 nM, about 4.0 nM, about 4.1 nM, about 4.2 nM, about 4.3 nM, about 4.4 nM, about 4.5 nM, about 4.6 nM, about 4.7 nM, about 4.8 nM, about 4.9 nM, about 5.0 nM, about 5.1 nM, about 5.2 nM, about 5.3 nM, about 5.4 nM, about 5.5 nM, about 5.6 nM, about 5.7 nM, about 5.8 nM, about 5.9 nM, about 6.0 nM, about 6.1 nM, about 6.2 nM, about 6.3 nM, about 6.4 nM, about 6.5 nM, about 6.6 nM, about 6.7 nM, about 6.8 nM, about 6.9 nM, about 7.0 nM, about 7.1 nM, about 7.2 nM, about 7.3 nM, about 7.4 nM, about 7.5 nM, about 7.6 nM, about 7.7 nM, about 7.8 nM, about 7.9 nM, about 8.0 nM, about 8.1 nM, about 8.2 nM, about 8.3 nM, about 8.4 nM, about 8.5 nM, about 8.6 nM, about 8.7 nM, about 8.8 nM, about 8.9 nM, about 9.0 nM, about 9.1 nM, about 9.2 nM, about 9.3 nM, about 9.4 nM, about 9.5 nM, about 9.6 nM, about 9.7 nM, about 9.8 nM, about 9.9 nM, or about 10.0 nM. In some embodiments, an anti-SIRPα antibody provided herein reduces CD47 binding to SIRPα with an $EC_{50}$ of no more than 0.01 nM, no more than 0.02 nM, no more than 0.03 nM, no more than 0.04 nM, no more than 0.05 nM, no more than 0.06 nM, no more than 0.07 nM, no more than 0.08 nM, no more than 0.09 nM, no more than 0.1 nM, no more than 0.11 nM, no more than 0.12 nM, no more than 0.13 nM, no more than 0.14 nM, no more than 0.15 nM, no more than 0.16 nM, no more than 0.17 nM, no more than 0.18 nM, no more than 0.19 nM, no more than 0.2 nM, no more than 0.3 nM, no more than 0.4 nM, no more than 0.5 nM, no more than 0.6 nM, no more than 0.7 nM, no more than 0.8 nM, no more than 0.9 nM, no more than 1.0 nM, no more than 1.2 nM, no more than 1.3 nM, no more than 1.4 nM, no more than 1.5 nM, no more than 1.6 nM, no more than 1.7 nM, no more than 1.8 nM, no more than 1.9 nM, 2 nM, no more than 2.1 nM, no more than 2.2 nM, no more than 2.3 nM, no more than 2.4 nM, no more than 2.5 nM, no more than 2.6 nM, no more than 2.7 nM, no more than 2.8 nM, no more than 2.9 nM, no more than 3 nM, no more than 3.1 nM, no more than 3.2 nM, no more than 3.3 nM, no more than 3.4 nM, no more than 3.5 nM, no more than 3.6 nM, no more than 3.7 nM, no more than 3.8 nM, no more than 3.9 nM, no more than 4.0 nM, no more than 4.1 nM, no more than 4.2 nM, no more than 4.3 nM, no more than 4.4 nM, no more than 4.5 nM, no more than 4.6 nM, no more than 4.7 nM, no more than 4.8 nM, no more than 4.9 nM, no more than 5.0 nM, no more than 5.1 nM, no more than 5.2 nM, no more than 5.3 nM, no more than 5.4 nM, no more than 5.5 nM, no more than 5.6 nM, no more than 5.7 nM, no more than 5.8 nM, no more than 5.9 nM, no more than 6.0 nM, no more than 6.1 nM, no more than 6.2 nM, no more than 6.3 nM, no more than 6.4 nM, no more than 6.5 nM, no more than 6.6 nM, no more than 6.7 nM, no more than 6.8 nM, no more than 6.9 nM, no more than 7.0 nM, no more than 7.1 nM, no more than 7.2 nM, no more than 7.3 nM, no more than 7.4 nM, no more than 7.5 nM, no more than 7.6 nM, no more than 7.7 nM, no more than 7.8 nM, no more than 7.9 nM, no more than 8.0 nM, no more than 8.1 nM, no more than 8.2 nM, no more than 8.3 nM, no more than 8.4 nM, no more than 8.5 nM, no more than 8.6 nM, no more than 8.7 nM, no more than 8.8 nM, no more than 8.9 nM, no more than 9.0 nM, no more than 9.1 nM, no more than 9.2 nM, no more than 9.3 nM, no more than 9.4 nM, no more than 9.5 nM, no more than 9.6 nM, no more than 9.7 nM, no more than 9.8 nM, no more than 9.9 nM, or no more than 10.0 nM. In some embodiments, the anti-SIRPα antibody or functional fragment thereof is an anti-SIRPα antibody. In some embodiments, the anti-SIRPα antibody or functional fragment thereof is a functional fragment of an anti-SIRPα antibody. In some embodiments, the SIRPα is selected from SIRPα v1, v2, v3, v4, v5 and v6 haplotypes. In some embodiments, the SIRPα is a SIRPα v1 comprising SEQ ID NO:149 in the IgV-domain. In some embodiments, the SIRPα is a SIRPα v2 comprising SEQ ID NO:150 in the IgV-domain. In some embodiments, the SIRPα is a SIRPα v3 comprising SEQ ID NO:151 in the IgV-domain. In some embodiments, the SIRPα is a SIRPα v4 comprising SEQ ID NO:152 in the IgV-domain. In some embodiments, the SIRPα is a SIRPα v5 comprising SEQ ID NO:153 in the IgV-domain. In some embodiments, the SIRPα is a SIRPα v6 comprising SEQ ID NO:154 in the IgV-domain.

In some embodiments, the SIRPα is a cynomolgus SIRPα. In other embodiments, an anti-SIRPα antibody provided herein both binds to SIRPα and reduces CD47 binding to SIRPα.

In one aspect, the anti-SIRPα antibodies or fragments thereof provided herein have reduced immunogenicity when compared to a reference antibody. In one embodiment, the anti-SIRPα antibodies or fragments thereof provided herein have reduced immunogenicity when compared to a reference antibody, wherein the reference antibody is an IgG1, IgG2, IgG3, or IgG4 isotype control. In some embodiments, the anti-SIRPα antibodies or fragments thereof provided herein have reduced immunogenicity when compared to a reference antibody, wherein the reference antibody is a reference anti-SIRPα antibody. In certain embodiments, the anti-SIRPα antibodies or fragments thereof provided herein have reduced immunogenicity when compared to a reference anti-SIRPα antibody, wherein the reference anti-SIRPα antibody comprises a light chain comprising or consisting of an amino acid sequence of QIVLTQSPAIM- SASPGEKVTLTCSASSSVSSSY-
LYWYQQKPGSSPKLWIYSTSNLASGVPARFS
GSGSGTSYSLTISSMEAEDAASYFCHQWSSY-
FRTFGAGTKLELKRTVAASVFIFPPSDEQLKS
GTASVVCLLNNFYPREAKVQWKVD-
NALQSGNSQESVTEQDSKDSTYSLSSTLTL-
SKADYEKHKV YACEVTHQGLSSPVTKSFNRGEC (SEQ ID NO:224) and a heavy chain comprising or consisting of an amino acid sequence of EVQLQQSGAEL-
VKPGASVKLSCTASGFNIKDYYIHWVQQRTEQ-
GLEWIGRIDPEDGETKYAPKF
QDKATITADTSSNTAYLHLSSLTSEDTAVYYCARW-
GAYWGQGTLVTVSAASTKGPSVFPLAPSS KST-
SGGTAALGCLVKDYFPEFVTVSWNSGALT-
SGVHTFPAVLQSSGLYSLSSVVTVPSSSLGTQ
TYICNVNHKPSNTKVDKKVEPKSCDKTHTCPPCPA-
PELLGGPSVFLFPPKPKDTLMISRTPEVT
CVVVDVSHEDPEVKFNWYVDGVEVHNAKTKPRE-
EQYNSYRVVSVLTVLHQDWLNGKEYKCAVS NKAL-
PAPIEKTISKAKGQPREPQVYTLPPSREEMT-
KNQVSLTCLVKGFYSDIAVEWESNGQPE
NNYKTTPPVLDSDGSFFLYSK-
LTVDKSRWQQGNVFSCSVMHLALHNHYTQKSLSL-
SPGR (SEQ ID NO:225).

In some embodiments, the anti-SIRPα antibodies or fragments thereof provided herein have reduced immunogenicity when compared to a reference antibody, such as an IgG1 isotype control or a reference anti-SIRPα antibody, wherein the reduction in immunogenicity can be about 10%, about 20%, about 30%, about 40%, about 50%, about 60%, about 70%, about 80%, about 90%, about 95%, about 99%, or about 99.99%. In some embodiments, the anti-SIRPα antibodies or fragments thereof provided herein have reduced immunogenicity when compared to a reference antibody, such as an IgG1 isotype control or a reference anti-SIRPα antibody, wherein the reduction in immunogenicity can be at least 10%, at least 20%, at least 30%, at least 40%, at least 50%, at least 60%, at least 70%, at least 80%, at least 90%, at least 95%, at least 99%, or at least 99.99%. Additionally, the reduction in immunogenicity can range from about 50% to about 90%, about 60% to about 90%, about 70% to about 90%, about 80% to about 90%, about 50% to about 99%, about 60% to about 99%, about 70% to about 99%, about 80% to about 99%, or about 90% to about 99%.

In some embodiments, the anti-SIRPα antibodies or fragments thereof provided herein have reduced immunogenicity when compared to a reference antibody, such as an IgG1 isotype control or a reference anti-SIRPα antibody, wherein the immunogenicity of the anti-SIRPα antibodies or fragments thereof is no more than 20%, no more than 19%, no more than 18%, no more than 17%, no more than 16%, no more than 15%, no more than 14%, no more than 13%, no more than 12%, no more than 11%, no more than 10%, no more than 9.5%, no more than 9%, no more than 8.5%, no more than 8%, no more than 7.5%, no more than 7%, no more than 6.5%, no more than 6%, no more than 5.5%, no more than 5%, no more than 4.5%, no more than 4%, no more than 3.5%, no more than 3%, no more than 2.5%, no more than 2%, no more than 1.5%, no more than 1%, no more than 0.9%, no more than 0.8%, no more than 0.7%, no more than 0.6%, no more than 0.5%, no more than 0.4%, no more than 0.3%, no more than 0.2%, no more than 0.1%, or lower, as determined in EpiMatrix Antibody Immunogenicity Scale as further described in Example 7. In some embodiments, the anti-SIRPα antibodies or fragments thereof provided herein has the upper limit of the immunogenicity described in the previous sentence and a lower limit of 0.01 or 0.001%, as determined in EpiMatrix Antibody Immunogenicity Scale as described in Example 7.

In some embodiments, the anti-SIRPα antibodies or fragments thereof provided herein have reduced immunogenicity when compared to a reference antibody, such as an IgG1 isotype control or a reference anti-SIRPα antibody, wherein the immunogenicity of the anti-SIRPα antibodies or fragments thereof is about 1%, about 0.9%, about 0.8%, about 0,.%, about 0.6%, about 0.5%, about 0.4%, about 0.3%, about 0.2%, about 0.15%, about 0.1%, or lower, as determined in EpiMatrix Antibody Immunogenicity Scale as described in Example 7.

In some embodiments, the $K_D$ and $EC_{50}$ values are assessed by methods described herein. In other embodiments, the $K_D$ and $EC_{50}$ values are assessed by other methods known to one of skill in the art (e.g., Surface Plasmon Resonance implemented in BiaCore®, fluorescence activated cell sorting (FACS) based binding assay, and/or ELISA assays). In a specific embodiment, the $K_D$ and $EC_{50}$ values are assessed by Surface Plasmon Resonance implemented in BiaCore® assays, fluorescence activated cell sorting (FACS) based binding assays, and/or ELISA assays.

In one aspect, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages as compared to a control of no treatment or an isotype control antibody, wherein the cancer cells and/or the macrophages include one, two, three, four, five, six, seven, eight, nine, ten or more or all of the SIRPα polymorphism known to a person skilled in the art, for example one, two, three, four, five, six, seven, eight, nine, ten or more, or all of the SIRPα polymorphism described in Takenaka K, et al., Nat Immunol. 2007 December;8(12): 1313-23, which is hereby incorporated in its entirety by reference.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages as compared to a control of no treatment or an isotype control antibody, wherein the cancer cells and/or the macrophages include any one or any combination of two, three, four, five, or six of SIRPα selected from the group consisting of SIRPα v1, v2, v3, v4, v5 and v6 haplotypes (SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain).

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages as compared to a control of no treatment or an isotype control antibody, wherein the cancer cells and/or the macrophages include any one SIRPα polymorphism selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages as compared to a control of no treatment or an isotype control antibody, wherein the cancer cells and/or the macrophages include two or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages as compared to a control of no treatment or an isotype control antibody, wherein the cancer cells and/or the macrophages include three or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages as compared to a control of no treatment or an isotype control antibody, wherein the cancer cells and/or the macrophages include four or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages as compared to a control of no treatment or an isotype control antibody, wherein the cancer cells and/or the macrophages include five or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages as compared to a control of no treatment or an isotype control antibody, wherein the cancer cells and/or the macrophages include six or more SIRPα polymorphisms including SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v3 comprising SEQ ID NO:151 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v4 comprising SEQ ID NO:152 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v5 comprising SEQ ID NO:153 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain and SIRPα v2 comprising SEQ ID NO:150 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain and SIRPα v3 comprising SEQ ID NO:151 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain and SIRPα v4 comprising SEQ ID NO:152 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain and SIRPα v5 comprising SEQ ID NO:153 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain and SIRPα v3 comprising SEQ ID NO:151 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain and SIRPα v4 comprising SEQ ID NO:152 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain and SIRPα v5 comprising SEQ ID NO:153 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v3 comprising SEQ ID NO:151 in the IgV-domain and SIRPα v4 comprising SEQ ID NO:152 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v3 comprising SEQ ID NO:151 in the IgV-domain and SIRPα v5 comprising SEQ ID NO:153 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v3 comprising SEQ ID NO:151 in the IgV-domain and SIRPα v6 comprising SEQ ID NO:154 in the IgV-domain.

In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v4 comprising SEQ ID NO:152 in the IgV-domain and SIRPα v5 comprising SEQ ID NO:153 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v4 comprising SEQ ID NO:152 in the IgV-domain and SIRPα v6 comprising SEQ ID NO:154 in the IgV-domain. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v5 comprising SEQ ID NO:153 in the IgV-domain and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, and SIRPα v3 comprising SEQ ID NO:151 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, and SIRPα v4 comprising SEQ ID NO:152 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v3 comprising SEQ ID NO:151 in the IgV-domain, and SIRPα v4 comprising SEQ ID NO:152 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v3 comprising SEQ ID NO:151 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v3 comprising SEQ ID NO:151 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v4 comprising SEQ ID NO:152 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v4 comprising SEQ ID NO:152 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4,v5 and v6 haplotypes) and increases phagocytosis of cancer cells by co-cultured macrophages, wherein the cancer cells and/or the macrophages include SIRPα v2 comprising SEQ ID NO:150 in the IgV-domain, SIRPα v3 comprising SEQ ID NO:151 in the IgV-domain, and SIRPα v4 comprising SEQ ID NO:152 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain, SIRPα v3 comprising SEQ ID NO:151 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain, SIRPα v3 comprising SEQ ID NO:151 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v4 comprising SEQ ID NO:152 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, and SIRPα v6 comprising SEQ ID NO:154 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain. In some embodiments, the anti-SIRPα antibodies or fragments thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of cancer cells by co-cultured macrophages, wherein the cancer cells and/or the macrophages include SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

As is known to a person skilled in the art, one clinical evaluation of biologic agents targeting cellular antigens is receptor occupancy (RO), to demonstrate that the drug is binding the appropriate target. RO can be assessed by methods known to a person skilled in the art, for example, as described in Liang M. et al., Cytometry B Clin Cytons. 2016 March; 90(2): 117-127, which is hereby incorporated in its entirety by reference. The disclosure further provides a competitive receptor binding assay. The assay utilizes a non-competing anti-SIRPα antibody that can be used to identify SIRPα molecules both bound and unbound by SIRPAB-11-K322A on SIRPα expressing cells. Briefly, whole blood was incubated with fluorescently labeled antibodies to identify key leukocyte subsets, as well as two antibodies specific for SIRPα, one which binds in the presence of SIRPAB-11-K322A (non-competitive) labeled with alexa fluor 488, and one that only binds in the absence of SIRPAB-11-K322A (competitive) labeled with alexa fluor 647. The levels of staining of the two SIRPα antibodies is calculated for leukocyte subgroups, and from this, the levels of receptor occupancy by SIRPAB-11-K322A can be calculated using this equation: % SIRPα RO=100%*((1−(competitive AF647 actual/competitive AF647 pre-dose)÷(non-competitive AF488 actual/non-competitive AF488 pre-dose)).

In some embodiments, an anti-SIRPα antibody or antigen-binding fragment thereof provided herein achieves about 100% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 95% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 90% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 85% SIRPα receptor occupancy in about 6, 12, 24, 36, 48, 60, or 72. hours after administration into a patient. In some embodiments, an anti-SIRPα antibody or antigen-binding fragment thereof provided herein achieves about or at least 80% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 75% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 70% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 65% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 60% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 55% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 50% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 45% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 40% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 35% SIRPα receptor occupancy in about 6, 12, 24, 36, 48, 60, or 72 hours after administration into a patient. In some embodiments, an anti-SIRPα antibody or antigen-binding fragment thereof provided herein achieves about or at least 30% SIRPα receptor occupancy in about 6, 12, 24, 36, 48, 60, or 72 hours after administration into a patient.

In some embodiments, an anti-SIRPα antibody or antigen-binding fragment thereof provided herein achieves about 100% SIRPα receptor occupancy in about 6, 12, 24, 36, 48, 60, or 72 hours after administration into a patient and maintains about 100% occupancy for further 6, 12, 24. 36, 48, 60, 72, 84, or 96 hours. In some embodiments, an anti-SIRPα antibody or antigen-binding fragment thereof provided herein achieves about or at least 95% SIRPα receptor occupancy in about 6, 12, 24, 36, 48, 60, or 72 hours after administration into a patient and maintains about or at least 95% occupancy for another 6, 12, 24, 36, 48, 60, 72, 84, or 96 hours. In some embodiments, an anti-SIRPα antibody or antigen-binding fragment thereof provided herein achieves about or at least 90% SIRPα receptor occupancy in about 6, 12, 24, 36, 48, 60, or 72 hours after administration into a patient and maintains about or at least 90% occupancy for another 6, 12, 24, 36. 48, 60, 72, 84, or 96 hours. In some embodiments, an anti-SIRPα antibody or antigen-binding fragment thereof provided herein achieves about or at least 85% SIRPα receptor occupancy in about 6, 12, 24, 36, 48, 60, or 72 hours after administration into a patient and maintains about or at least 85% occupancy for another 6, 12, 24, 36, 48, 60, 72, 84, or 96 hours. In some embodiments, an anti-SIRPα antibody or antigen-binding fragment thereof provided herein achieves about or at least 80% SIRPα receptor occupancy in about 6, 12, 24, 36, 48, 60, or 72 hours after administration into a patient and maintains about or at least 80% occupancy for another 6, 12, 24, 36, 48, 60, 72, 84, or 96 hours. In some embodiments, an anti-SIRPα antibody or antigen-binding fragment thereof provided herein achieves about or at least 75% SIRPα receptor occupancy in about 6, 12, 24, 36, 48, 60, or 72 hours after administration into a patient and maintains about or at least 75% occupancy for another 6, 12, 24, 36, 48, 60, 72, 84, or 96 hours. In some embodiments, an anti-SIRPα antibody or antigen-binding fragment thereof provided herein achieves about or at least 70% SIRPα receptor occupancy in about 6, 12, 24, 36, 48, 60, or 72 hours after administration into a patient and maintains about or at least 70% occupancy for another 6, 12, 24, 36, 48, 60, 72, 84, or 96 hours. In some embodiments, an anti-SIRPα antibody or antigen-binding fragment thereof provided herein achieves about or at least 65% SIRPα receptor occupancy in about 6, 12, 24, 36, 48, 60, or 72 hours after administration into a patient and maintains about or at least 65% occupancy for another 6, 12, 24, 36, 48, 60, 72, 84, or 96 hours. In some embodiments, an anti-SIRPα antibody or antigen-binding fragment thereof provided herein achieves about or at least 60% SIRPα receptor occupancy in about 6, 12, 24, 36, 48, 60, or 72 hours after administration into a patient and maintains about or at least 60% occupancy for another 6, 12, 24, 36, 48, 60, 72, 84, or 96 hours. In some embodiments, an anti-SIRPα antibody or antigen-binding fragment thereof provided herein achieves about or at least 55% SIRPα receptor occupancy in about 6, 12, 24, 36, 48, 60, or 72 hours after administration into a patient and maintains about or at least 55% occupancy for another 6, 12, 24, 36, 48, 60, 72, 84, or 96 hours. In some embodiments, an anti-SIRPα antibody or antigen-binding fragment thereof provided herein achieves about or at least 50% SIRPα receptor occupancy in about 6, 12, 24, 36, 48, 60, or 72 hours after administration into a patient and maintains about or at least 50% occupancy for another 6, 12, 24, 36, 48, 60, 72, 84, or 96 hours. In some embodiments, an anti-SIRPα antibody or antigen-binding fragment thereof provided herein achieves about or at least 45% SIRPα receptor occupancy in about 6, 12, 24, 36, 48, 60, or 72 hours after administration into a patient and maintains about or at least 45% occupancy for another 6, 12, 24, 36, 48, 60, 72, 84, or 96 hours. In some embodiments, an anti-SIRPα antibody or antigen-binding fragment thereof provided herein achieves about or at least 40% SIRPα receptor occupancy in about 6, 12, 24, 36, 48, 60, or 72 hours after administration into a patient and maintains about or at least 40% occupancy for another 6, 12, 24, 36, 48, 60, 72, 84, or 96 hours. In some embodiments, an anti-SIRPα antibody or antigen-binding fragment thereof provided herein achieves about or at least 35% SIRPα receptor occupancy in about 6, 12, 24, 36, 48, 60, or 72 hours after administration into a patient and maintains about or at least 35% occupancy for another 6, 12, 24, 36, 48, 60, 72, 84, or 96 hours. In some embodiments, an anti-SIRPα antibody or antigen-binding fragment thereof provided herein achieves about or at least 30% SIRPα receptor occupancy in about 6, 12, 24, 36, 48, 60, or 72 hours after administration into a patient and maintains about or at least 30% occupancy for another 6, 12, 24, 36, 48, 60, 72, 84, or 96 hours.

In some embodiments, an anti-SIRPα antibody or antigen-binding fragment thereof provided herein achieves about 100% SIRPα receptor occupancy in about 6, 12, 24, 36, 48, 60, or 72 hours after administration into a patient and maintains about or at least 90% occupancy for further 6, 12, 24, 36, 48, 60, 72, 84, or 96 hours. In some embodiments, an anti-SIRPα antibody or antigen-binding fragment thereof provided herein achieves about or at least 95% SIRPα receptor occupancy in about 6, 12, 24, 36, 48, 60, or 72 hours after administration into a patient and maintains about or at least 85% occupancy for another 6, 12, 24, 36, 48, 60, 72, 84, or 96 hours. In some embodiments, an anti-SIRPα antibody or antigen-binding fragment thereof provided herein achieves about or at least 90% SIRPα receptor occupancy in about 6, 12, 24, 36, 48, 60, or 72 hours after administration into a patient and maintains about or at least 80% occupancy for another 6, 12, 24, 36, 48, 60, 72, 84, or 96 hours. In some embodiments, an anti-SIRPα antibody or antigen-binding fragment thereof provided herein achieves about or at least 85% SIRPα receptor occupancy in about 6, 12, 24, 36, 48, 60, or 72 hours after administration into a patient and maintains about or at least 75% occupancy for another 6, 12, 24, 36, 48, 60, 72, 84, or 96 hours. In some embodiments, an anti-SIRPα antibody or antigen-binding fragment thereof provided herein achieves about or at least 80% SIRPα receptor occupancy in about 6, 12, 24, 36, 48, 60, or 72 hours after administration into a patient and maintains about or at least 70% occupancy for another 6, 12, 24, 36, 48, 60, 72, 84, or 96 hours. In some embodiments, an anti-SIRPα antibody or antigen-binding fragment thereof provided herein achieves about or at least 75% SIRPα receptor occupancy in about 6, 12, 24, 36, 48, 60, or 72 hours after administration into a patient and maintains about or at least 65% occupancy for another 6, 12, 24, 36, 48, 60, 72, 84, or 96 hours. In some embodiments, an anti-SIRPα antibody or antigen-binding fragment thereof provided herein achieves about or at least 70% SIRPα receptor occupancy in about 6, 12, 24, 36, 48, 60, or 72 hours after administration into a patient and maintains about or at least 60% occupancy for another 6, 12, 24, 36, 48, 60, 72, 84, or 96 hours. In some embodiments, an anti-SIRPα antibody or antigen-binding fragment thereof provided herein achieves about or at least 65% SIRPα receptor occupancy in about 6, 12, 24, 36, 48, 60, or 72 hours after administration into a patient and maintains about or at least 55% occupancy for another 6, 12, 24, 36, 48, 60, 72, 84, or 96 hours. In some embodiments, an anti-SIRPα antibody or antigen-binding fragment thereof provided herein achieves about or at least 60% SIRPα receptor occupancy in about 6, 12, 24, 36, 48, 60, or 72 hours after administration into a patient and maintains about or at least 50% occupancy for another 6, 12, 24, 36, 48, 60, 72, 84, or 96 hours. In some embodiments, an anti-SIRPα antibody or antigen-binding fragment thereof provided herein achieves about or at least 55% SIRPα receptor occupancy in about 6, 12, 24, 36, 48, 60, or 72 hours after administration into a patient and maintains about or at least 45% occupancy for another 6, 12, 24, 36, 48, 60, 72, 84, or 96 hours. In some embodiments, an anti-SIRPα antibody or antigen-binding fragment thereof provided herein achieves about or at least 50% SIRPα receptor occupancy in about 6, 12, 24, 36, 48, 60, or 72 hours after administration into a patient and maintains about or at least 40% occupancy for another 6, 12, 24, 36, 48, 60, 72, 84, or 96 hours. In some embodiments, an anti-SIRPα antibody or antigen-binding fragment thereof provided herein achieves about or at least 45% SIRPα receptor occupancy in about 6, 12, 24, 36, 48, 60, or 72 hours after administration into a patient and maintains about or at least 35% occupancy for another 6, 12, 24, 36, 48, 60, 72, 84, or 96 hours. In some embodiments, an anti-SIRPα antibody or antigen-binding fragment thereof provided herein achieves about or at least 40% SIRPα receptor occupancy in about 6, 12, 24, 36, 48, 60, or 72 hours after administration into a patient and maintains about or at least 30% occupancy for another 6, 12, 24, 36, 48, 60, 72, 84, or 96 hours. In some embodiments, an anti-SIRPα antibody or antigen-binding fragment thereof provided herein achieves about or at least 35% SIRPα receptor occupancy in about 6, 12, 24, 36, 48, 60, or 72 hours after administration into a patient and maintains about or at least 25% occupancy for another 6, 12, 24, 36, 48, 60, 72, 84, or 96 hours. In some embodiments, an anti-SIRPα antibody or antigen-binding fragment thereof provided herein achieves about or at least 30% SIRPα receptor occupancy in about 6, 12, 24, 36, 48, 60, or 72 hours after administration into a patient and maintains about or at least 20% occupancy for another 6, 12, 24, 36, 48, 60, 72, 84, or 96 hours.

In some embodiments, an anti-SIRPα antibody or antigen-binding fragment thereof provided herein achieves about 100% SIRPα receptor occupancy in about 6, 12, 24, 36, 48, 60, or 72 hours after administration into a patient and maintains about or at least 80% occupancy for further 6, 12, 24, 36, 48, 60, 72, 84, or 96 hours. In some embodiments, an anti-SIRPα antibody or antigen-binding fragment thereof provided herein achieves about or at least 95% SIRPα receptor occupancy in about 6, 12, 24, 36, 48, 60, or 72 hours after administration into a patient and maintains about or at least 75% occupancy for another 6, 12, 24, 36, 48, 60, 72, 84, or 96 hours. In some embodiments, an anti-SIRPα antibody or antigen-binding fragment thereof provided herein achieves about or at least 90% SIRPα receptor occupancy in about 6, 12, 24, 36, 48, 60, or 72 hours after administration into a patient and maintains about or at least 70% occupancy for another 6, 12, 24, 36, 48, 60, 72, 84, or 96 hours. In some embodiments, an anti-SIRPα antibody or antigen-binding fragment thereof provided herein achieves about or at least 85% SIRPα receptor occupancy in about 6, 12, 24, 36, 48, 60, or 72 hours after administration into a patient and maintains about or at least 65% occupancy for another 6, 12, 24, 36, 48, 60, 72, 84, or 96 hours. In some embodiments, an anti-SIRPα antibody or antigen-binding fragment thereof provided herein achieves about or at least 80% SIRPα receptor occupancy in about 6, 12, 24, 36, 48, 60, or 72 hours after administration into a patient and maintains about or at least 60% occupancy for another 6, 12, 24, 36, 48, 60, 72, 84, or 96 hours. In some embodiments, an anti-SIRPα antibody or antigen-binding fragment thereof provided herein achieves about or at least 75% SIRPα receptor occupancy in about 6, 12, 24, 36, 48, 60, or 72 hours after administration into a patient and maintains about or at least 55% occupancy for another 6, 12, 24, 36, 48, 60, 72, 84, or 96 hours. In some embodiments, an anti-SIRPα antibody or antigen-binding fragment thereof provided herein achieves about or at least 70% SIRPα receptor occupancy in about 6, 12, 24, 36, 48, 60, or 72 hours after administration into a patient and maintains about or at least 50% occupancy for another 6, 12, 24, 36, 48, 60, 72, 84, or 96 hours. In some embodiments, an anti-SIRPα antibody or antigen-binding fragment thereof provided herein achieves about or at least 65% SIRPα receptor occupancy in about 6, 12, 24, 36, 48, 60, or 72 hours after administration into a patient and maintains about or at least 45% occupancy for another 6, 12, 24, 36, 48, 60, 72, 84, or 96 hours. In some embodiments, an anti-SIRPα antibody or antigen-binding fragment thereof provided herein achieves about or at least 60% SIRPα receptor occupancy in about 6, 12, 24, 36, 48, 60, or 72 hours after administration into a patient and maintains about or at least 40% occupancy for another 6, 12, 24, 36, 48, 60, 72, 84, or 96 hours. In some embodiments, an anti-SIRPα antibody or antigen-binding fragment thereof provided herein achieves about or at least 55% SIRPα receptor occupancy in about 6, 12, 24, 36, 48, 60, or 72 hours after administration into a patient and maintains about or at least 35% occupancy for another 6, 12, 24, 36, 48, 60, 72, 84, or 96 hours. In some embodiments, an anti-SIRPα antibody or antigen-binding fragment thereof provided herein achieves about or at least 50% SIRPα receptor occupancy in about 6, 12, 24, 36, 48, 60, or 72 hours after administration into a patient and maintains about or at least 30% occupancy for another 6, 12, 24, 36, 48, 60, 72, 84, or 96 hours. In some embodiments, an anti-SIRPα antibody or antigen-binding fragment thereof provided herein achieves about or at least 45% SIRPα receptor occupancy in about 6, 12, 24, 36, 48, 60, or 72 hours after administration into a patient and maintains about or at least 25% occupancy for another 6, 12, 24, 36, 48, 60, 72, 84, or 96 hours. In some embodiments, an anti-SIRPα antibody or antigen-binding fragment thereof provided herein achieves about or at least 40% SIRPα receptor occupancy in about 6, 12, 24, 36, 48, 60, or 72 hours after administration into a patient and maintains about or at least 20% occupancy for another 6, 12, 24, 36, 48, 60, 72, 84, or 96 hours. In some embodiments, an anti-SIRPα antibody or antigen-binding fragment thereof provided herein achieves about or at least 35% SIRPα receptor occupancy in about 6, 12, 24, 36, 48, 60, or 72 hours after administration into a patient and maintains about or at least 15% occupancy for another 6, 12, 24, 36, 48, 60, 72, 84, or 96 hours. in some embodiments, an anti-SIRPα antibody or antigen-binding fragment thereof provided herein achieves about or at least 30% SIRPα receptor occupancy in about 6, 12, 24, 36, 48, 60, or 72 hours after administration into a patient and maintains about or at least 10% occupancy for another 6, 12, 24, 36, 48, 60, 72, 84, or 96 hours.

In some embodiments, the receptor occupancy provided in the preceding 4 paragraphs can be achieved and/or maintained with a single dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, or 3.0 mg/kg of an anti-SIRPα antibody or antigen-binding fragment thereof provided herein. In some embodiments, the receptor occupancy provided in the preceding 4 paragraphs can be achieved and/or maintained as provided in this paragraph with a single dose of 25 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, or 4000 mg of an anti-SIRPα antibody or antigen-binding fragment thereof provided herein.

As is known to a person skilled in the art, phagocytosis of cancer cells by co-cultured macrophages can be determined as percentage of phagocytotic macrophages, and increases in phagocytosis of cancer cells by co-cultured macrophages can be determined as percent or fold increase, or as changes in the percentage of phagocytotic macrophages. As such, in some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases the percentage of phagocytotic macrophages in a population of macrophages (e.g. a population of macrophages co-cultured with cancer cells) to about 10%, about 15%, about 20%, about 25%, about 30%, about 35%, about 40%, about 45%, about 50%, about 55%, about 60%, about 65%, about 70%, about 75%, about 80%, about 85%, about 90%, about 95%. or about 99%.

In other embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases the percentage of phagocytotic macrophages in a population of macrophages (e.g. a population of macrophages co-cultured with cancer cells) to at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In certain embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of the macrophage (e.g. macrophages co-cultured with cancer cells) by about 10%, about 20%, about 30%, about 40%, about 45%, about 50%, about 55%, about 60%, about 65%, about 70%, about 75%, about 80%, about 85%, about 90%, about 95%, about 100%, about 125%, about 150%, about 175%, about 200%, about 250%, about 300%, about 400%, about 500%, about 600%, about 700%, about 800%, about 900% or about 1000%, as compared to a control of no treatment or an isotype control antibody. In other embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and increases phagocytosis of the macrophage (e.g. macrophages co-cultured with cancer cells) by at least 10%, at least 20%, at least 30%, at least 40%, at least 45%, at least 50%, at least 55%, at least 60%, at least 65%, at least 70%, at least 75%, at least 80%, at least 85%, at least 90%, at least 95%, at least 100%, at least 125%, at least 150%, at least 175%, at least 200%, at least 250%, at least 300%, at least 400%, at least 500%, at least 600%, at least 700%, at least 800%, at least 900% or at least 1000%, as compared to a control of no treatment or an isotype control antibody.

In some embodiments, the increase in phagocytosis of certain cancer cells by co-cultured macrophages described above results from reduction of the binding between CD47 on certain cancer cells and SIRPα on macrophages, reduction of the binding between SIRPα on certain cancer cells and CD47 on macrophages, and/or reduction of both the binding between CD47 on certain cancer cells and SIRPα on macrophages and the binding between SIRPα on certain cancer cells and CD47 on macrophages. The disclosure further provides that the cancer cells can be from colorectal cancer, head and neck squamous cell carcinoma, acute myeloid leukemia, or DLBCL that have a cell expressing CD47, SIRPα, or both CD47 and SIRPα. The disclosure further provides that the cancer cells can be from NHL such as DLBCL, follicular lymphoma, marginal zone lymphoma, and mantle cell lymphoma that have a cell expressing CD47, SIRPα, or both CD47 and SIRPα. The disclosure additionally provides that the cancer cells can be from Grade 1 follicular lymphoma, Grade 2 follicular lymphoma, Grade 3a follicular lymphoma, Grade 3b follicular lymphoma, relapsed follicular lymphoma (including e.g. Grade 1, 2, 3a and 3b), refractory follicular lymphoma (including e.g. Grade 1, 2, 3a and 3b), relapsed DLBCL, or refractory DLBCL, wherein the cancer have a cell expressing CD47, SIRPα, or both CD47 and SIRPα.

In some embodiments, an anti-SIRPα antibody or antigen-binding fragment thereof provided herein increases the phagocytotic activity of the macrophages (e.g. macrophages co-cultured with cancer cells) as a monotherapy, for example, as the single and only therapeutic agent for the elimination of the cancer cells co-cultured with the macrophages. In some embodiments, an anti-SIRPα antibody or antigen-binding fragment thereof provided herein increases the phagocytotic activity of the macrophages (e.g. macrophages co-cultured with cancer cells) when an anti-SIRPα antibody or antigen-binding fragment thereof is used in combination with a second therapeutic agent for the elimination of the cancer cells, for example, a second therapeutic agent selected from the group consisting of cetuximab and rituximab. In one embodiment, the second therapeutic agent is cetuximab. In another embodiment, the second therapeutic agent is rituximab.

The disclosure further provides that, in some embodiments, an anti-SIRPα antibody or antigen-binding fragment thereof provided herein synergizes with a second therapeutic agent in increasing the phagocytotic activity of the macrophages (e.g. macrophages co-cultured with cancer cells). Such synergy in increasing phagocytotic activity refers to that an anti-SIRPα antibody (or antigen-binding fragment) thereof provided herein and a second therapeutic agent, when used in combination, produce an increase in the phagocytotic activity of the macrophages greater than the sum of the increases induced by the anti-SIRPα antibody (or antigen-binding fragment thereof) and the second therapeutic agent separately. In some embodiments, an anti-SIRPα antibody or antigen-binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and synergizes with a second therapeutic agent in increasing the phagocytotic activity of the macrophages (e.g. macrophages co-cultured with cancer cells), wherein the difference between the percentage of the phagocytotic macrophages synergistically induced and the sum of the phagocytotic percentage induced by the anti-SIRPα antibody (or antigen-binding fragment thereof) and the second therapeutic agent separately (e.g. mathematically: Phagocytotic-Pereentage$_{synergy}$–(Phagocytotic-Percentage$_{anti-SIRP\alpha}$+Phagocytotic-Percentage$_{second-agent}$)) is at least 10%, at least 15%, at least 20%, at least 25%, at least 30%, at least 35%, at least 40%, at least 45%, at least 50%, at least 55%, at least 60%, at least 65%, at least 70%, at least 75%, or at least 80%. In other embodiments, an anti-SIRPα antibody or antigen binding fragment thereof provided herein specifically binds to human SIRPα (for example, any one or any combination of two, three, four, five, or six of SIRPα selected from the group consisting of SIRPα v1, v2, v3, v4, v5 and v6 haplotypes) and synergizes with a second therapeutic agent in increasing the phagocytotic activity of the macrophages e.g. macrophages co-cultured with cancer cells), wherein the difference between the percentage of the phagocytotic macrophages synergistically induced and the sum of the phagocytic percentage induced by the anti-SIRPα (antibody (or antigen-binding fragment thereof) and the second therapeutic agent separately is about 10%, about 15%, about 20%, about 25%, about 30%, about 35%, about 40%, about 45%, about 50%, about 55%, about 60%, about 65%, about 70%, about 75%, or about 80%.

Assays for phagocytosis, including phagocytosis of macrophages (e.g. human macrophages) are known to a person skilled in the art. In an exemplary phagocytosis assay, assessment of an anti-SIRPα antibody or antigen-binding fragment thereof provided herein in blocking CD47 binding and increasing cancer cell phagocytosis is determined in vitro by automated counting of "eaten" cancer cells labeled with a first dye inside of macrophages labeled with a second dye. Briefly, titrated anti-SIRPα antibodies or antigen-binding fragments thereof provided herein are added to pre-differentiated macrophages, followed by coculturing with carboxyfluorescein succinimidyl ester (CSFE, the first dye)-labeled cancer cells opsonized with specific anti-SIRPα antibodies or antigen-binding fragments thereof provided herein (single-agent or monotherapy), or a second cancer targeting antibody and anti-SIRPα antibodies or antigen-binding fragments thereof provided herein (for combination). Phagocytosis activity is quantitatively determined by the number of labeled cancer cells within the macrophages labeled with allophycocyanin (APC, the second dye) (for example, CD14 APC-labeled macrophage). Green intensity (CFSE) is measured in each of the APC-labeled macrophage, and a threshold gate is used to identify CFSE positive macrophages. In some embodiments, a threshold of approximately 1000 MFI, with variance of no more than a few hundred MFI are observed across experiments. For each sample, the calculated percentage of phagocytosis is determined as: [(Number of CFSE positive macrophages)/(number of total macrophage)]×100. Other phagocytosis assays are also known to a person skilled in the art and provided herein, for example, as described in Hamczyk M R et al., Methods Mol Biol. 2015;1339:235-46, and Yan, Q et al., Bio Protoc. 2015 February 20; 5(4):e1406, which are incorporated in their entirety by reference. Commercial assay formats/kits for phagocytosis are also available and provided herein, including, for example, IncuCyte® Phagocytosis Assay by Essen BioScience (Ann Arbor, Mich.) and CytoSelect™ Phagocytosis Assays by Cell Biolabs, Inc. (San Diego, Calif.).

As is clear from the descriptions throughout the disclosure, in some embodiments, an anti-SIRPα antibody or antigen-binding fragment thereof provided herein increases phagocytotic activity of macrophages or other immune cells having phagocytotic activity, wherein SIRPα (e.g. any one or any combination of two SIRPα (haplotypes selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain) is expressed on the macrophage and/or other immune cells having phagocytotic activity. In some embodiments, an anti-SIRPα antibody or antigen-binding fragment thereof provided herein increases phagocytotic activity of macrophages or other immune cells having phagocytotic activity, wherein SIRPα (e.g. any one or any combination of two SIRPα haplotypes selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain) is expressed on the cancer cells. In other embodiments, an anti-SIRPα antibody or antigen-binding fragment thereof provided herein increases phagocytotic activity of macrophages or other immune cells having phagocytotic activity, wherein SIRPα (e.g. any one or any combination of two SIRPα haplotypes selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain) is expressed on both the cancer cells and immune cells having phagocytotic activity, including macrophages.

Antibodies that induce target crosslinking of human T, NK, or monocytic lineages have the potential of initiating a cascade of systemic release of certain proinflammatory cytokines, resulting in potential adverse systemic immune reaction. In some embodiments, an anti-SIRPα antibody or antigen-binding fragment thereof provided herein binds to human SIRPα (for example, any one or any combination of two, three, four, five, or six of SIRPα selected from the group consisting of SIRPα v1, v2, v3, v4, v5 and v6 haplotypes), increases phagocytosis of the macrophage (e.g. macrophages co-cultured with cancer cells), but does not result in an increase of the release of proinflammatory cytokines including, for example, IL-1β, IL-2, IL-6, IL-8, IL-10, IL-12p70, TNFα, interferon gamma, and granulocyte macrophage colony-stimulating factor, in an animal (e.g. an human or a monkey) or cultured cells (e.g. cultured immune cells or peripheral blood mononuclear cells). In certain embodiments, the absence of an increase of the proinflammatory cytokine release in an animal (e.g. an human or a monkey) or in cultured cells (e.g. cultured immune cells or peripheral blood mononuclear cells) is assessed by comparing the release of the proinflammatory cytokines after treatment of an anti-SIRPα antibody or antigen-binding fragment thereof provided herein and that after treatment of a control antibody (e.g. clinically proven safe antibodies such as cetuximab), and absence of an increase of the proinflammatory cytokine release is determined when levels of proinflammatory cytokine release induced by binding of an anti-SIRPα antibody or antigen-binding fragment thereof provided herein is not significantly different from that induced by the control antibody. In certain embodiments, the control antibody is an antibody isotype control antibody. In other embodiments, the control antibody is a clinically approved safe therapeutic antibody. In some embodiments, the clinically approved antibody is cetuximab.

In other embodiments, an anti-SIRPα antibody or antigen-binding fragment thereof provided herein binds to human SIRPα (for example, any one or any combination of two, three, four, five, or six of SIRPα selected from the group consisting of SIRPα v1, v2, v3, v4, v5 and v6 haplotypes), increases phagocytosis of the macrophage (e.g. macrophages co-cultured with cancer cells), but does not increase of the release of any one or any combination of two, three, four, five, six, seven, eight or nine proinflammatory cytokines selected from the group consisting of IL-1β, IL-2, IL-6, IL-8, IL-10, IL-12p70, INFα, interferon gamma, and granulocyte macrophage colony-stimulating factor, in an animal (e.g. an human or a monkey) or cultured cells (e.g. cultured immune cells or peripheral blood mononuclear cells).

As discussed above, in certain situations, ADCC, ADCP, and/or CDC can be undesirable cytotoxicity adverse to the cells or the animals. In some embodiments, provided herein are anti-SIRPα antibodies or antigen-binding fragments thereof with attenuated ADCC, ADCP, and/or CDC activity as compared to an isotype control antibody. In certain embodiments, an anti-SIRPα antibody or antigen-binding fragment thereof provided herein has attenuated ADCC activity as compared to an isotype control antibody. In other embodiments, an anti-SIRPα antibody or antigen-binding fragment thereof provided herein has attenuated CDC activity as compared to an isotype control antibody. In some embodiments, an anti-SIRPα antibody or antigen-binding fragment thereof provided herein has attenuated ADCP activity as compared to an isotype control antibody. In some embodiments, an anti-SIRPα antibody or antigen-binding fragment thereof provided herein has both attenuated ADCC activity and attenuated CDC activity as compared to an isotype control antibody. In some embodiments, an anti-SIRPα antibody or antigen-binding fragment thereof provided herein has both attenuated ADCC activity and attenuated ADCP activity as compared to an isotype control antibody. In some embodiments, an anti-SIRPα antibody or antigen-binding fragment thereof provided herein has both attenuated CDC activity and attenuated CDC activity as compared to an isotype control antibody. In other embodiments, an anti-SIRPα antibody or antigen-binding fragment thereof provided herein has attenuated ADCC activity, attenuated ADCP activity, and attenuated CDC activity as compared to an isotype control antibody.

As is known to a person skilled in the art and as described above, in one embodiment, the ADCC activity of an antibody can be quantitated as percentage of target cells killed by effector cells (such as NK cells) treated with the antibody, (mathematically as 100×(target cells killed)/(total target cells)), for example, as performed in Tang, Y et al., J Immunol, 2007, 179 (5) 2815-2823, which is hereby incorporated in its entirety by reference. In some embodiments, an anti-SIRPα antibody or antigen-binding fragment thereof provided herein has attenuated ADCC activity such that the maximal ADCC activity is about 5%, about 10%, about 15%, about 20%, about 25%, about 30%, about 35%, about 40%, about 45%, or about 50% cytotoxicity as measured by the percentage of target cells killed. In other embodiments, an anti-SIRPα antibody or antigen-binding fragment thereof provided herein has attenuated ADCC activity such that the maximal ADCC activity is no more than 5%, no more than 10%, no more than 15%, no more than 20%, no more than 25%, no more than 30%, no more than 35%, no more than 40%, no more than 45%, or no more than 50% cytotoxicity as measured by the percentage of target cells killed.

As is also known to a person skilled in the art and as described above, in one embodiment, the ADCP activity of an antibody can be quantitated as percentage of phagocytotic effector cells (such as macrophages) when the effector cells are co-cultured with target cells treated with the antibody, (mathematically as 100×(effector cells that have devoured one or more target cells)/(total effector cells)). In some specific embodiments, the ADCP activity of an antibody can be quantitated as percentage of phagocytotic macrophages co-cultured with autologous CD3+ immune cells (self target) opsonized with the antibody. In some embodiments, an anti-SIRPα antibody or antigen-binding fragment thereof provided herein has attenuated ADCP activity such that the maximal ADCP activity is about 1%, about 2%, about 3%, about 4%, about 5%, about 6%, about 7%, about 8%, about 9%, about 10%, about 10%, about 11%, about 12%, about 13%, about 14%, about 15%, about 16%, about 17%, about 18%, about 19%, about 20%, about 25%, about 30%, about 35%, about 40%, about 45%, or about 50% of phagocytotic macrophages targeting autologous T cells and/or monocytes. In some embodiments, an anti-SIRPα antibody or antigen-binding fragment thereof provided herein has attenuated ADCP activity such that the maximal ADCP activity is no more than 1%, no more than 2%, no more than 3%, no more than 4%, no more than 5%, no more than 6%, no more than 7%, no more than 8%, no more than 9%, no more than 10%, no more than 10%, no more than 11%, no more than 12%, no more than 13%, no more than 14%, no more than no more than 15%, no more than 16%, no more than 17%, no more than 18%, no more than 19%, no more than 20%, no more than 25%, no more than 30%, no more than 35%, no more than 40%, no more than 45%, or no more than 50% of phagocytotic macrophages targeting autologous T cells and/or monocytes.

Similarly, as known to a person skilled in the art, the CDC activity of an antibody can be assessed according to the $EC_{50}$ of the antibody that induces CDC. In such assessment, an antibody with a higher $EC_{50}$ value for CDC would indicate that antibody has attenuated CDC activity comparing to another antibody having a lower $EC_{50}$ value. In some specific embodiments, an anti-SIRPα antibody or antigen-binding, fragment thereof provided herein has attenuated CDC activity such that its $EC_{50}$ value for CDC is about 50 nM, about 100 nM, about 200 nM, about 300 nM, about 400 nM, about 500 nM, about 600 nM, about 700 nM, about 800 nM, about 900 nM, about 1000 nM, about 2000 nM, about 3000 nM, about 4000 nM, about 5000 nM, about 6000 nM, about 7000 nM, about 8000 nM, about 9000 nM, about $10^4$ nM, about $10^5$ nM, about $10^6$ nM, about $10^7$ nM, about $10^8$ nM, about $10^9$ nM, about $10^{10}$ nM, about $10^{11}$ nM, about $10^{12}$ nM, about $10^{13}$ nM, about $10^{14}$ nM, about $10^{15}$ nM, about $10^{16}$ nM, or about $10^{17}$ nM. In other specific embodiments, an anti-SIRPα antibody or antigen-binding fragment thereof provided herein has attenuated CDC activity such that its $EC_{50}$ value for CDC is at least 50 nM, at least 100 nM, at least 200 nM, at least 300 nM, at least 400 nM, at least 500 nM, at least 600 nM, at least 700 nM, at least 800 nM, at least 900 nM, at least 1000 nM, at least 2000 nM, at least 3000 nM, at least 4000 nM, at least 5000 nM, at least 6000 nM, at least 7000 nM, at least 8000 nM, at least 9000 nM, at least $10^4$ nM, at least $10^5$ nM, at least $10^6$ nM, at least $10^7$ nM, at least $10^8$ nM, at least $10^9$ nM, at least $10^{10}$ nM, at least $10^{11}$ nM, at least $10^{12}$ nM, at least $10^{13}$ nM, at least $10^{14}$ nM, at least $10^{15}$ nM, at least $10^{16}$ nM, or at least $10^{17}$ nM.

4.3.1.1 Polyclonal Antibodies

The antibodies of the present disclosure may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a SIRPα polypeptide or a fusion protein thereof. It may be useful to conjugate the immunizing agent to a protein known to be immunogenic in the mammal being immunized or to immunize the mammal with the protein and one or more adjuvants. Examples of such immunogenic proteins include, but are not limited to, keyhole limpet hemocyanin, serum albumin, bovine thyroglobulin, and soybean trypsin inhibitor. Examples of adjuvants which may be employed include Ribi, CpG, Poly 1C, Freund's complete adjuvant, and MPL-TDM adjuvant (monophosphoryl Lipid A, synthetic trehalose dicorynomycolate). The immunization protocol may be selected by one skilled in the art without undue experimentation. The mammal can then be bled, and the serum assayed for anti-SIRPα antibody titer. If desired, the mammal can be boosted until the antibody titer increases or plateaus. Additionally or alternatively, lymphocytes may be obtained from the immunized animal for fusion and preparation of monoclonal antibodies from hybridoma as described below.

4.3.1.2 Monoclonal Antibodies

The antibodies of the present disclosure may alternatively be monoclonal antibodies. Monoclonal antibodies may be made using the hybridoma method first described by Kohler et al., 1975, Nature 256:495-97, or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice* 59-103 (1986)).

The hybridoma cells thus prepared are seeded and grown in a suitable culture medium which, in certain embodiments, contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which prevent the growth of HGPRT-deficient cells.

Exemplary fusion partner myeloma cells are those that fuse efficiently, support stable high-level production of antibody by the selected antibody-producing cells, and are sensitive to a selective medium that selects against the unfused parental cells. Exemplary myeloma cell lines are murine myeloma lines, such as SP-2 and derivatives, for example, X63-Ag8-653 cells available from the American Type Culture Collection (Manassas, Va.), and those derived from MOPC-21 and MPC-11 mouse tumors available from the Salk Institute Cell Distribution Center (San Diego, Calif.). Human myeloma and mouse-human heteromyeloma cell lines also have been described for the production of human monoclonal antibodies (Kozbor, 1984, Immunol. 133:3001-05; and Brodeur et al., *Monoclonal Antibody Production Techniques and Applications* 51-63 (1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as RIA or ELISA. The binding affinity of the monoclonal antibody can, for example, be determined by the Scatchard analysis described in Munson et al., 1980, Anal. Biochem, 107:220-39.

Once hybridoma cells that produce antibodies of the desired specificity, affinity, and/or activity are identified, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA may be placed into expression vectors, which are then transfected into host cells, such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., 1993, Curr. Opinion in Immunol, 5:256-62 and Plückthun, 1992, Immunol, Revs. 130:151-88.

In some embodiments, an antibody that binds a SIRPα epitope comprises an amino acid sequence of a VH domain and/or an amino acid sequence of a VL domain encoded by a nucleotide sequence that hybridizes to (1) the complement of a nucleotide sequence encoding any one of the VH and/or VL domain described herein under stringent conditions (e.g., hybridization to filter-bound DNA in 6× sodium chloride/sodium citrate (SSC) at about 45° C. followed by one or more washes in 0.2× SSC/0.1% SDS at about 50-65° C.), under highly stringent conditions (e.g., hybridization to filter-bound nucleic acid in 6× SSC at about 45° C. followed by one or more washes in 0.1× SSC/0.2% SDS at about 68° C.), or under other stringent hybridization conditions which are known to those of skill in the art. See, e.g., *Current Protocols in Molecular Biology* Vol. I, 6.3.1-6.3.6 and 2.10.3 (Ausubel et al eds., 1989).

In some embodiments, an antibody that binds a SIRPα epitope comprises an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Tables 1-2 under stringent conditions (e.g., hybridization to filter-bound DNA in 6× SSC at about 45° C. followed by one or more washes in 0.2× SSC/0.1% SDS at about 50-65° C.), under highly stringent conditions (e.g., hybridization to filter-bound nucleic acid in 6× SSC at about 45° C. followed by one or more washes in 0.1× SSC/0.2% SDS at about 68° C.), or under other stringent hybridization conditions which are known to those of skill in the art (see, e.g.. Ausubel et al., supra).

In a further embodiment, monoclonal antibodies or antibody fragments can be isolated from antibody phage libraries generated using the techniques described in, for example, *Antibody Phage Display: Methods and Protocols* (O'Brien and Aitken eds., 2002). In principle, synthetic antibody clones are selected by screening phage libraries containing phages that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., 1994, Ann. Rev. Immunol. 12:433-55.

Repertoires of VH and VL genes can be separately cloned by PCR and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., 1993, EMBO J 12:725-34. Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, 1992, J. Mol. Biol. 227:381-88.

Screening of the libraries can be accomplished by various techniques known in the art. For example, SIRPα (e.g., a SIRPα polypeptide, fragment, or epitope) can be used to coat the wells of adsorption plates, expressed on host cells affixed to adsorption plates or used in cell sorting, conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., 1990, Proteins 8:309-14 and WO 92/09690, and by use of a low coating density of antigen as described in Marks et al., 1992, Biotechnol. 10:779-83.

Anti-SIRPα antibodies can be obtained by designing a suitable antigen screening procedure to select for the phage clone of interest followed by construction of a full length anti-SIRPα antibody clone using VH and/or VL sequences (e.g., the Fv sequences), or various CDR sequences from VH and VL sequences, from the phage clone of interest and suitable constant region (e.g., Fc) sequences described in Kabat et al., supra.

In another embodiment, anti-SIRPα antibody is generated by using methods as described in Bowers et al., 2011. Proc Natl Acad Sci USA. 108:20455-60, e.g., the SHM-XHL™ platform (AnaptysBio, San Diego, Calif.). Briefly, in this approach, a fully human library of IgGs is constructed in a mammalian cell line (e.g., HEK293) as a starting library. Mammalian cells displaying immunoglobulin that binds to a target peptide or epitope are selected (e.g., by FACS sorting), then activation-induced cytidine deaminase (AID)-triggered somatic hypermutation is reproduced in vitro to expand diversity of the initially selected pool of antibodies. After several rounds of affinity maturation by coupling mammalian cell surface display with in vitro somatic hypermutation, high affinity, high specificity anti-SIRPα antibodies are generated. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

4.3.1.3 Antibody Fragments

The present disclosure provides antibodies and antibody fragments that bind to SIRPα. In certain circumstances there are advantages of using antibody fragments, rather than whole antibodies. The smaller size of the fragments allows for rapid clearance, and may lead to improved access to cells, tissues, or organs. For a review of certain antibody fragments, see Hudson et al., 2003, Nature Med. 9:129-34.

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et al., 1985, Science 229:81-83). However, these fragments can now be produced directly by recombinant host cells. Fab, Fv, and scFv antibody fragments can all be expressed in and secreted from E. coli or yeast cells, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., 1992, Bio/Technology 10:163-67). According to another approach, F(ab')$_2$ fragments can be isolated directly from recombinant host cell culture. Fab and F(ab')$_2$ fragment with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv (See, e.g., Borrebaeck ed., supra). The antibody fragment may also be a "linear antibody," for example, as described in the references cited above. Such linear antibodies may be monospecific or multi-specific, such as bispecific.

Smaller antibody-derived binding structures are the separate variable domains (V domains) also termed single variable domain antibodies (sdAbs). Certain types of organisms, the camelids and cartilaginous fish, possess high affinity single V-like domains mounted on an Fc equivalent domain structure as part of their immune system. (Woolven et al., 1999, Immunogenetics 50: 98-101; and Streltsov et al., 2004, Proc Natl Acad Sci USA. 101:12444-49). The V-like domains (called VhH in camelids and V-NAR in sharks) typically display long surface loops, which allow penetration of cavities of target antigens. They also stabilize isolated VH domains by masking hydrophobic surface patches.

These VhH and V-NAR domains have been used to engineer sdAbs. Human V domain variants have been designed using selection from phage libraries and other approaches that have resulted in stable, high binding VL- and VH-derived domains.

Antibodies provided herein include, but are not limited to, immunoglobulin molecules and immunologically active portions of immunoglobulin molecules, for example, molecules that contain an antigen binding site that bind to a SIRPα epitope. The immunoglobulin molecules provided herein can be of any class (e.g., IgG, IgE, IgM, IgD, and IgA) or any subclass (e.g., IgG1, IgG2, IgG3, IgG4, IgA1, and IgA2) of immunoglobulin molecule.

Variants and derivatives of antibodies include antibody functional fragments that retain the ability to bind to a SIRPα epitope. Exemplary functional fragments include Fab fragments (e.g., an antibody fragment that contains the antigen-binding domain and comprises a light chain and part of a heavy chain bridged by a disulfide bond); Fab' (e.g., an antibody fragment containing a single antigen-binding domain comprising an Fab and an additional portion of the heavy chain through the hinge region); F(ab')$_2$ (e.g., two Fab' molecules joined by interchain disulfide bonds in the hinge regions of the heavy chains; the Fab' molecules may be directed toward the same or different epitopes); a bispecific Fab (e.g., a Fab molecule having two antigen binding domains, each of which may be directed to a different epitope); a single chain comprising a variable region, also known as, scFv (e.g., the variable, antigen-binding determinative region of a single light and heavy chain of an antibody linked together by a chain of 10-25 amino acids); a disulfide-linked Fv, or dsFv (e.g., the variable, antigen-binding determinative region of a single light and heavy chain of an antibody linked together by a disulfide bond); a camelized VH (e.g., the variable, antigen-binding determinative region of a single heavy chain of an antibody in which some amino acids at the VH interface are those found in the heavy chain of naturally occurring camel antibodies); a bispecific scFv (e.g., an scFv or a dsFv molecule having two antigen-binding domains, each of which may be directed to a different epitope); a diabody (e.g., a dimerized scFv formed when the VH domain of a first scFv assembles with the VL domain of a second scFv and the VL domain of the first scFv assembles with the VH domain of the second scFv; the two antigen-binding regions of the diabody may be directed towards the same or different epitopes); and a triabody (e.g., a trimerized scFv, formed in a manner similar to a diabody, but in which three antigen-binding domains are created in a single complex; the three antigen-binding domains may be directed towards the same or different epitopes).

4.3.1.4 Humanized Antibodies

In some embodiments, antibodies provided herein can be humanized antibodies that bind SIRPα, including human and/or cyno SIRPα. For example, humanized antibodies of the present disclosure may comprise one or more CDRs as shown in Tables 1-2. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., 1986, Nature 321:522-25; Riechmann et al., 1988, Nature 332: 323-27; and Verhoeyen et al., 1988, Science 239:1534-36), by substituting hypervariable region sequences for the corresponding sequences of a human antibody.

In some cases, the humanized antibodies are constructed by CDR grafting, in which the amino acid sequences of the six CDRs of the parent non-human antibody (e.g., rodent) are grafted onto a human antibody framework. For example, Padlan et al. determined that only about one third of the residues in the CDRs actually contact the antigen, and termed these the "specificity determining residues," or SDRs (Padlan et al., 1995, FASEB J. 9:133-39). In the technique of SDR grafting, only the SDR residues are grafted onto the human antibody framework (see, e.g., Kashmiri et al., 2005, Methods 36:25-34).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence that is closest to that of the rodent may be selected as the human framework for the humanized antibody (Sims et al., 1993, J. Immunol. 151:2296-308; and Chothia et al., 1987, J. Mol. Biol. 196:901-17). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285-89; and Presta et al., 1993, J. Immunol. 151:2623-32). In some cases, the framework is derived from the consensus sequences of the most abundant human subclasses, $V^L6$ subgroup I ($V_L6I$) and $V_H$ subgroup III ($V_H III$). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., 2002, J. Immunol. 169:1119-25).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, 2000, Protein Eng. 13:819-24), Modeller (Sali and Blundell, 1993, J. Mol. Biol. 234:779-815), and Swiss PDB Viewer (Guex and Peitsch, 1997, Electrophoresis 18:2714-23). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., 2007, Mol. Immunol. 44:1986-98).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see, e.g., Hoogenboom, 2005, Nat. Biotechnol. 23:1105-16; Dufner et al., 2006, Trends Biotechnol. 24:523-29; Feldhaus et al., 2003, Nat. Biotechnol. 21:163-70; and Schlapschy et al., 2004, Protein Eng. Des. Sel. 17:847-60).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, 1992, J. Mol. Biol. 224:487-99), or from the more limited set of target residues identified by Baca et al. (1997, J. Biol. Chem. 272:10678-84).

In FR shuffling, whole FRs are combined with the non-human CDRs instead of creating combinatorial libraries of selected residue variants (see, e.g., Dall'Acqua et al., 2005, Methods 36:43-60). The libraries may be screened for binding in a two-step process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity, and thermal stability (see, e.g., Damschroder et al., 2007, Mol. Immunol. 44:3049-60).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple subclasses with distinct human V-segment CDRs. Humaneering allows for isolation of antibodies that are 91-96% homologous to human germline gene antibodies (see, e.g., Alfenito, Cambridge Healthtech Institute's Third Annual PEGS, The Protein Engineering Summit, 2007).

The "human engineering" method involves altering a non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., 1994, Protein Engineering 7:805-14; U.S. Pat. Nos. 5,766,886; 5,770,196; 5,821,123; and 5,869,619; and PCT Publication WO 93/11794.

4.3.1.5 Human Antibodies

Human anti-SIRPα antibodies can be constructed by combining Fv clone variable domain sequence(s) selected from human-derived phage display libraries with known human constant domain sequences(s). Alternatively, human monoclonal anti-SIRPα antibodies of the present disclosure can be made by the hybridoma method. Human myeloma and mouse-human heteromyeloma cell lines for the production of human monoclonal antibodies have been described, for example, by Kozbor, 1984, J. Immunol. 133:3001-05; Brodeur et al., *Monoclonal Antibody Production Techniques and Applications* 51-63 (1987); and Boerner et al., 1991, J. Immunol. 147:86-95.

It is also possible to produce transgenic animals (e.g., mice) that are capable, upon immunization, of producing a full repertoire of human antibodies in the absence of endogenous immunoglobulin production. Transgenic mice that express human antibody repertoires have been used to generate high-affinity human sequence monoclonal antibodies against a wide variety of potential drug targets (see, e.g., Jakobovits, A., 1995, Curr. Opin. Biotechnol. 6(5):561-66; Brüggemann and Taussing, 1997, Curr. Opin. Biotechnol. 8(4):455-58; U.S. Pat. Nos. 6,075,181 and 6,150,584; and Lonberg et al., 2005, Nature Biotechnol. 23:1117-25).

Alternatively, the human antibody may be prepared via immortalization of human B lymphocytes producing an antibody directed against a target antigen (e.g., such B lymphocytes may be recovered from an individual or may have been immunized in vitro) (see, e.g., Cole et al., *Monoclonal Antibodies and Cancer Therapy* (1985); Boerner et al., 1991 J. Immunol. 147(1):86-95; and U.S. Pat. No. 5,750,373).

Gene shuffling can also be used to derive human antibodies from non-human, for example, rodent, antibodies, where the human antibody has similar affinities and specificities to the starting non-human antibody. According to this method, which is also called "epitope imprinting" or "guided selection," either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone (e.g., the epitope guides (imprints) the choice of the human chain partner). When the process is repeated in order to replace the remaining non-human chain, a human antibody is obtained (see, e.g., PCT WO 93/06213; and Osbourn et al., 2005, Methods 36:61-68). Unlike traditional humanization of non-human antibodies by CDR grafting, this technique provides completely human antibodies, which have no FR or CDR residues of non-human origin. Examples of guided selection to humanize mouse antibodies towards cell surface antigens include the folate-binding protein present on ovarian cancer cells (see, e.g., Figini et al., 1998, Cancer Res. 58:991-96) and CD147, which is highly expressed on hepatocellular carcinoma (see, e.g., Bao et al., 2005, Cancer Biol. Ther. 4:1374-80).

A potential disadvantage of the guided selection approach is that shuffling of one antibody chain while keeping the other constant could result in epitope drift. In order to maintain the epitope recognized by the non-human antibody, CDR retention can be applied (see, e.g., Klimka et al., 2000, Br. J. Cancer. 83:252-60; and Beiboer et al., 2000, J. Mol. Biol. 296:833-49). In this method, the non-human VH CDR3 is commonly retained, as this CDR may be at the center of the antigen-binding site and may be the most important region of the antibody for antigen recognition. In some instances, however, VH CDR3 and VL CDR3, as well as VH CDR2, VL CDR2, and VL CDR1 of the non-human antibody may be retained.

4.3.1.6 Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for SIRPα and the other is for any other antigen. In some embodiments, one of the binding specificities is for SIRPα, and the other is for another surface antigen expressed on cells expressing SIRPα. In certain embodiments, bispecific antibodies may bind to two different epitopes of SIRPα. Bispecific antibodies can be prepared as full length antibodies or antibody fragments (e.g., F(ab')$_2$ bispecific antibodies).

Methods for making bispecific antibodies are known in the art, such as, by co-expression of two immunoglobulin heavy chain-light chain pairs, where the two heavy chains have different specificities (see, e.g., Milstein and Cuello, 1983, Nature 305:537-40). For further details of generating bispecific antibodies, see, for example, *Bispecific Antibodies* (Kontermann ed., 2011).

In some embodiments, the bispecific antibody comprises an anti-SIRPα antibody comprising a VL CDR1 VL CDR2, VL CDR3 of an antibody as set forth in Table 1, and a VH CDRI1 VH CDR2, and VH CDR3 of an antibody as set forth in Table 2. In some embodiments, the bispecific antibody comprises an anti-SIRPα antibody comprising a VL CDR1, VL CDR2, VL CDR3, VH CDR1, VH CDR2, and VH CDR3 of SIRPAB-1. In some embodiments, the bispecific antibody comprises an anti-SIRPα antibody comprising a VL CDR1, VL CDR2, VL CDR3, VH CDR1, VH CDR2, and VH CDR3 of SIRPAB-2. In some embodiments, the bispecific antibody comprises an anti-SIRPα antibody comprising a VL CDR1, VL CDR2, VL CDR3, VH CDR1, VH CDR2, and VH CDR3 of SIRPAB-3. In some embodiments, the bispecific antibody comprises an anti-SIRPα antibody comprising a VL CDR1, VL CDR2, VL CDR3, VH CDR1, VH CDR2, and VH CDR3 of SIRPAB-4. In some embodiments, the bispecific antibody comprises an anti-SIRPα antibody comprising a VL CDR1, VL CDR2, VL CDR3, VH CDR1, VH CDR2, and VH CDR3 of SIRPAB-5. In some embodiments, the bispecific antibody comprises an anti-SIRPα antibody comprising a VL CDR1, VL CDR2, VL CDR3, VH CDR1, VH CDR2, and VH CDR3 of SIRPAB-6. In some embodiments, the bispecific antibody comprises an anti-SIRPα antibody comprising a VL CDR1, VL CDR2, VL CDR3, VH CDR1, VH CDR2, and VH CDR3 of SIRPAB-7. In some embodiments, the bispecific antibody comprises an anti-SIRPα antibody comprising a VL CDR1, VL CDR2, VL CDR3, VH CDRI, VH CDR2, and VH CDR3 of SIRPAB-8. In some embodiments, the bispecific antibody comprises an anti-SIRPα antibody comprising a VL CDR1, VL CDR2, VL CDR3, VH CDR1, VH CDR2, and VH CDR3 of SIRPAB-9. In some embodiments, the bispecific antibody comprises an anti-SIRPα antibody comprising a VL CDR1, VL CDR2, VL CDR3, VH CDR1, VH CDR2, and VH CDR3 of SIRPAB-10. In some embodiments, the bispecific antibody comprises an anti-SIRPα antibody comprising a VL CDR1, VL CDR2, VL CDR3, VH CDR1, VH CDR2, and VH CDR3 of SIRPAB-11. In some embodiments, the bispecific antibody comprises an anti-SIRPα antibody comprising a VL CDR1, VL CDR2, VL CDR3, VH CDR1, VH CDR2, and VH CDR3 of SIRPAB-12. In some embodiments, the bispecific antibody comprises an anti-SIRPα antibody comprising a VL CDR1, VL CDR2, VL CDR3, VH CDR1, VH CDR2, and VH CDR3 of SIRPAB-13. In some embodiments, the bispecific antibody comprises an anti-SIRPα antibody comprising a VL domain of an antibody as set forth in Table 9, and a VH domain of an antibody as set forth in Table 10. In some embodiments, the bispecific antibody comprises an anti-SIRPα antibody comprising a VL domain and a VH domain of SIRPAB-1. In some embodiments, the bispecific antibody comprises an anti-SIRPα antibody comprising a VL domain and a VH domain of SIRPAB-2. In some embodiments, the bispecific antibody comprises an anti-SIRPα antibody comprising a VL domain and a VH domain of SIRPAB-3. In some embodiments, the bispecific antibody comprises an anti-SIRPα antibody comprising a VL domain and a VH domain of SIRPAB-4. In some embodiments, the bispecific antibody comprises an anti-SIRPα antibody comprising a VL domain and a VH domain of SIRPAB-5. In some embodiments, the bispecific antibody comprises an anti-SIRPα antibody comprising a VL domain and a VH domain of SIRPAB-6. In some embodiments, the bispecific antibody comprises an anti-SIRPα antibody comprising a VL domain and a VH domain of SIRPAB-7. In some embodiments, the bispecific antibody comprises an anti-SIRPα antibody comprising a VL domain and a VH domain of SIRPAB-8. In some embodiments, the bispecific antibody comprises an anti-SIRPα antibody comprising a VL domain and a VH domain of SIRPAB-9. In some embodiments, the bispecific antibody comprises an anti-SIRPα antibody comprising a VL domain and a VH domain of SIRPAB-10. In some embodiments, the bispecific antibody comprises an anti-SIRPα antibody comprising a VL domain and a VH domain of SIRPAB-11. In some embodiments, the bispecific antibody comprises an anti-SIRPα antibody comprising a VL domain and a VH domain of SIRPAB-12. In some embodiments, the bispecific antibody comprises an anti-SIRPα antibody comprising a VL domain and a VH domain of SIRPAB-13.

In certain embodiments, the bispecific antibody comprises (i) an anti-SIRPα antibody provided herein, and (ii) cetuximab. In another embodiment, the bispecific antibody comprises (i) an anti-SIRPα antibody provided herein, and (ii) rituximab.

In some embodiments, the bispecific antibody comprises (i) an anti-SIRPα antibody comprising a VL CDR 1, VL CDR2, and VL CDR3 of an antibody as set forth in Table 1, and a VH CDR1, VH CDR2, and VH CDR3 of an antibody as set forth in Table 2, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-1, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-2, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-3, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-4, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-5, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-6, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-7, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-8, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-9, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-10, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-11, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-12, and (ii) cetuximab. In some embodiments, the bispecific antibody comprises an anti-SIRPα antibody comprising a VL CDR1, VL CDR2, VL CDR3, VH CDR1, VH CDR2, and VH CDR3 of SIRPAB-13, and (ii) cetuximab. In some embodiments, the bispecific antibody comprises an anti-SIRPα antibody comprising a VL domain of an antibody as set forth in Table 9, and a VH domain of an antibody as set forth in Table 10, and (ii) cetuximab. In some embodiments, the bispecific antibody comprises an anti-SIRPα antibody comprising a VL domain and a VH domain of SIRPAB-1, and (ii) cetuximab. In some embodiments, the bispecific antibody comprises an anti-SIRPα antibody comprising a VL domain and a VH domain of SIRPAB-2, and (ii) cetuximab. In some embodiments, the bispecific antibody comprises an anti-SIRPα antibody comprising a VL domain and a VH domain of SIRPAB-3, and (ii) cetuximab. In some embodiments, the bispecific antibody comprises an anti-SIRPα antibody comprising a VL domain and a VH domain of SIRPAB-4, and (ii) cetuximab. In some embodiments, the bispecific antibody comprises an anti-SIRPα antibody comprising a VL domain and a VH domain of SIRPAB-5, and (ii) cetuximab. In some embodiments, the bispecific antibody comprises an anti-SIRPα antibody comprising a VL domain and a VH domain of SIRPAB-6, and (ii) cetuximab. In some embodiments, the bispecific antibody comprises an anti-SIRPα antibody comprising a VL domain and a VH domain of SIRPAB-7, and (ii) cetuximab. In some embodiments, the bispecific antibody comprises an anti-SIRPα antibody comprising a VL domain and a VH domain of SIRPAB-8, and (ii) cetuximab. In some embodiments, the bispecific antibody comprises an anti-SIRPα antibody comprising a VL domain and a VH domain of SIRPAB-9, and (ii) cetuximab. In some embodiments, the bispecific antibody comprises an anti-SIRPα antibody comprising a VL domain and a VH domain of SIRPAB-10, and (ii) cetuximab. In some embodiments, the bispecific antibody comprises an anti-SIRPα antibody comprising a VL domain and a VH domain of SIRPAB-11, and (ii) cetuximab. In some embodiments, the bispecific antibody comprises an anti-SIRPα antibody comprising a VL domain and a VH domain of SIRPAB-12, and (ii) cetuximab. In some embodiments, the bispecific antibody comprises an anti-SIRPα antibody comprising a VL domain and a VH domain of SIRPAB-13, and (ii) cetuximab.

In some embodiments, the bispecific antibody comprises (i) an anti-SIRPα antibody comprising a VL CDR1, VL CDR2, and VL CDR3 of an antibody as set forth in Table 1, and a VH CDR1, VH CDR2, and VH CDR3 of an antibody as set forth in Table 2, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-1, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-2, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-3, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-4, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-5, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-6, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-7, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-8, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-9, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-10, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-11, and (ii) rituximab. In some embodiments, the bispecific antibody comprises an anti-SIRPα antibody comprising a VL CDR1, VL CDR2, VL CDR3, VH CDR1, CDR2, and VH CDR3 of SIRPAB-12, and (ii) rituximab. In some embodiments, the bispecific antibody comprises an anti-SIRPα antibody comprising a VL CDR1, VL CDR2, VL CDR3, VH CDR1, VH CDR2, and VH CDR3 of SIRPAB-13, and (ii) rituximab, In some embodiments, the bispecific antibody comprises an anti-SIRPα antibody comprising a VL domain of an antibody as set forth in Table 9, and a VH domain of an antibody as set forth in Table 10, and (ii) rituximab. In some embodiments, the bispecific antibody comprises an anti-SIRPα antibody comprising a VL domain and a VH domain of SIRPAB-1, and (ii) rituximab. In some embodiments, the bispecific antibody comprises an anti-SIRPα antibody comprising a VL domain and a VH domain of SIRPAB-2, and (ii) rituximab. In some embodiments, the bispecific antibody comprises an anti-SIRPα antibody comprising a VL domain and a VH domain of SIRPAB-3, and (ii) rituximab. In some embodiments, the bispecific antibody comprises an anti-SIRPα antibody comprising a VL domain and a VH domain of SIRPAB-4, and (ii) rituximab. In some embodiments, the bispecific antibody comprises an anti-SIRPα antibody comprising a VL domain and a VH domain of SIRPAB-5, and (ii) rituximab. In some embodiments, the bispecific antibody comprises an anti-SIRPα antibody comprising a VL domain and a VH domain of SIRPAB-6, and (ii) rituximab. In some embodiments, the bispecific antibody comprises an anti-SIRPα antibody comprising a VL domain and a VH domain of SIRPAB-7, and (ii) rituximab. In some embodiments, the bispecific antibody comprises an anti-SIRPα antibody comprising a VL domain and a VH domain of SIRPAB-8, and (ii) rituximab. In some embodiments, the bispecific antibody comprises an anti-SIRPα antibody comprising a VL domain and a VH domain of SIRPAB-9, and (ii) rituximab. In some embodiments, the bispecific antibody comprises an anti-SIRPα antibody comprising a VL domain and a VH domain of SIRPAB-10, and (ii) rituximab. In some embodiments, the bispecific antibody comprises an anti-SIRPα antibody comprising a VL domain and a VH domain of SIRPAB-11, and (ii) rituximab. In some embodiments, the bispecific antibody comprises an anti-SIRPα antibody comprising a VL domain and a VH domain of SIRPAB-12, and (ii) rituximab. In some embodiments, the bispecific antibody comprises an anti-SIRPα antibody comprising a VL domain and a VH domain of SIRPAB-13, and (ii) rituximab.

4.3.1.7 Multivalent Antibodies

A multivalent antibody may be internalized (and/or catabolized) faster than a bivalent antibody by a cell expressing an antigen to which the antibodies bind. The antibodies of the present disclosure can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (e.g., two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (e.g., four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

4.3.1.8 Fc Engineering

It may be desirable to modify an anti-SIRPα antibody provided herein by Fc engineering. In certain embodiments, the modification to the Fc region of the antibody results in the decrease or elimination of an effector function of the antibody. In certain embodiments, the effector function is ADCC, ADCP, and/or CDC. In some embodiments, the effector function is ADCC. In other embodiments, the effector function is ADCP. In other embodiments, the effector function is CDC. In one embodiment, the effector function is ADCC and ADCP. In one embodiment, the effector function is ADCC and CDC. In one embodiment, the effector function is ADCP and CDC. In one embodiment, the effector function is ADCC, ADCP and CDC. This may be achieved by introducing one or more amino acid substitutions in an Fc region of the antibody. For example, substitutions into human IgG1 using IgG2 residues at positions 233-236 and IgG4 residues at positions 327, 330, and 331 were shown to greatly reduce ADCC and CDC (see, e.g., Armour et al., 1999, Eur. J. Immunol. 29(8):2613-24; and Shields et al., 2001, J. Biol. Chem. 276(9): 6591-604). Other Fc variants are provided elsewhere herein.

To increase the serum half-life of the antibody, one may incorporate a salvage receptor binding epitope into the antibody (especially an antibody fragment), for example, as described in U.S. Pat. No. 5,739,277. Term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

4.3.1.9 Alternative Binding Agents

The present disclosure encompasses non-immunoglobulin binding agents that specifically bind to the same epitope as an anti-SIRPα antibody disclosed herein. In some embodiments, a non-immunoglobulin binding agent is identified as an agent that displaces or is displaced by an anti-SIRPα antibody of the present disclosure in a competitive binding assay. These alternative binding agents may include, for example, any of the engineered protein scaffolds known in the art. Such scaffolds may comprise one or more CDRs as shown in Tables 1-2. Such scaffolds include, for example, anticalins, which are based upon the lipocalin scaffold, a protein structure characterized by a rigid beta-barrel that supports four hypervariable loops which form the ligand binding site. Novel binding specificities may be engineered by targeted random mutagenesis in the loop regions, in combination with functional display and guided selection (see, e.g., Skerra, 2008, FEBS J. 275:2677-83). Other suitable scaffolds may include, for example, adnectins, or monobodies, based on the tenth extracellular domain of human fibronectin III (see, e.g., Koide and Koide, 2007, Methods Mol. Biol. 352: 95-109); affibodies, based on the Z domain of staphylococcal protein A (see, e.g., Nygren et al., 2008, FEBS J. 275:2668-76); DARPins, based on ankyrin repeat proteins (see, e.g., Stumpp et al., 2008, Drug, Discov. Today 13:695-701); fynomers, based on the SH3 domain of the human Fyn protein kinase (see, e.g., Grabulovski et al., 2007, J. Biol. Chem. 282:3196-204); affitins, based on Sac7d from Sulfolobus acidolarius (see, e.g., Krehenbrink et al., 2008, J. Mol. Biol. 383:1058-68); affilins, based on human y-B-crystallin (see, e.g., Ebersbach et al., 2007, J. Mol. Biol. 372:172-85); avimers, based on the A domain of membrane receptor proteins (see, e.g., Silverman et al., 2005, Biotechnol. 23:1556-61); cysteine-rich knottin peptides (see, e.g., Kolmar, 2008, FEBS J. 275:2684-90); and engineered Kunitz-type inhibitors (see, e.g., Nixon and Wood, 2006, Curr. Opin. Drug. Discov. Dev. 9:261-68). For a review, see, for example, Gebauer and Skerra, 2009, Curr. Opin. Chem. Biol. 13:245-55.

4.3.2 Antibody Variants

In some embodiments, amino acid sequence modification(s) of the antibodies that bind to SIRPα or described herein are contemplated. For example, it may be desirable to improve the binding affinity and/or other biological properties of the antibody, including but not limited to specificity, thermostability, expression level, effector functions, glycosylation, reduced immunogenicity, or solubility. Thus, in addition to the anti-SIRPα antibodies described herein, it is contemplated that anti-SIRPα antibody variants can be prepared. For example, anti-SIRPα antibody variants can be prepared by introducing appropriate nucleotide changes into the encoding DNA, and/or by synthesis of the desired antibody or polypeptide. Those skilled in the art who appreciate that amino acid changes may alter post-translational processes of the anti-SIRPα antibody, such as changing the number or position of glycosylation sites or altering the membrane anchoring characteristics.

In some embodiments, antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

Variations may be a substitution, deletion, or insertion of one or more codons encoding the antibody or polypeptide that results in a change in the amino acid sequence as compared to the native sequence antibody or polypeptide. Amino acid substitutions can be the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the full-length or mature native sequence.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for antibody-directed enzyme prodrug therapy) or a polypeptide which increases the serum half-life of the antibody.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Alternatively, conservative (e.g., within an amino acid group with similar properties and/or side chains) substitutions may be made, so as to maintain or not significantly change the properties. Amino acids may be grouped according to similarities in the properties of their side chains (see, e.g., Lehninger, Biochemistry 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His (H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions entail exchanging a member of one of these classes for another class. Such substituted residues also may be introduced into the conservative substitution sites or, into the remaining (non-conserved) sites. Accordingly, in one embodiment, an antibody or fragment thereof that binds to a SIRPα epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a murine monoclonal antibody described herein. In one embodiment, an antibody or fragment thereof that binds to a SIRPα epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in Tables 1-4 and 9-10. In yet another embodiment, an antibody or fragment thereof that binds to a SIRPα epitope comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence depicted in Table 2 and/or a VL CDR amino acid sequence depicted in Table 1. The variations can be made using methods known in the art such as oligonucleotide-mediated (site-directed) mutagenesis, alanine scanning, and PCR mutagenesis. Site-directed mutagenesis (see, e.g., Carter, 1986, Biochem J. 237:1-7; and Zoller et al., 1982, Nucl. Acids Res. 10:6487-500), cassette mutagenesis (see, e.g., Wells et al., 1985, Gene 34:315-23), or other known techniques can be performed on the cloned DNA to produce the anti-SIRPα antibody variant DNA.

Any cysteine residue not involved in maintaining the proper conformation of the anti-SIRPα antibody also may be substituted, for example, with another amino acid, such as alanine or serine, to improve the oxidative stability of the molecule and to prevent aberrant crosslinking. Conversely, cysteine bond(s) may be added to the anti-SIRPα antibody to improve its stability (e.g., where the antibody is an antibody fragment such as an Fv fragment).

In some embodiments, an anti-SIRPα antibody molecule of the present disclosure is a "de-immunized" antibody. A "de-immunized" anti-SIRPα antibody is an antibody derived from a humanized or chimeric anti-SIRPα antibody, which has one or more alterations in its amino acid sequence resulting in a reduction of immunogenicity of the antibody, compared to the respective original non-de-immunized antibody. One of the procedures for generating such antibody mutants involves the identification and removal of T-cell epitopes of the antibody molecule. In a first step, the immunogenicity of the antibody molecule can be determined by several methods, for example, by in vitro determination of T-cell epitopes or in silico prediction of such epitopes, as known in the art. Once the critical residues for T-cell epitope function have been identified, mutations can be made to remove immunogenicity and retain antibody activity. For review, see, for example, Jones et al., 2009, Methods in Molecular Biology 525:405-23.

4.3.2.1 In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed as Fab, scFv, or V domain fragments either on the surface of an organism (e.g., phage, bacteria, yeast, or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and used to infect bacteria to produce phage for further rounds of selection. For review, see, for example, Hoogenboom, 2002, Methods. Mol. Biol. 178:1-37; and Bradbury and Marks, 2004, J. Immunol. Methods 290:29-49.

In a yeast display system (see, e.g., Boder et al., 1997, Nat. Biotech. 15:553-57; and Chao et al., 2006, Nat. Protocols 1:755-68), the antibody may be displayed as single-chain variable fusions (scFv) in which the heavy and light chains are connected by a flexible linker. The scFv is fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the scFv. Expression has been shown to correlate with the stability of the displayed protein, and thus antibodies can be selected for improved stability as well as affinity (see, e.g., Shusta et al., 1999, J. Mol. Biol. 292:949-56). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., 2004, Gene 342:211-18).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reverse transcribed back into cDNA, which can then undergo mutagenesis and be used in the next round of selection (see, e.g., Fukuda et al., 2006, Nucleic Acids Res. 34:e127). In mRNA display, a covalent bond between antibody and mRNA is established using puromycin as an adaptor molecule (Wilson et al., 2001, Proc. Natl. Acad. Sci. USA 98:3750-55).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by nonproofreading polymerases, as no library must be transformed after any diversification step.

In a mammalian cell display system (see, e.g., Bowers et al., 2011, Proc Natl Acad Sci USA. 108:20455-60), a fully human library of IgGs is constructed based on germline sequence V-gene segments joined to prerecombined D(J) regions. Full-length V regions for heavy chain and light chain are assembled with human heavy chain and light chain constant regions and transfected into a mammalian cell line (e.g., HEK293). The transfected library is expanded and subjected to several rounds of negative selection against streptavidin (SA)-coupled magnetic beads, followed by a round of positive selection against SA-coupled magnetic beads coated with biotinylated target protein, peptide fragment, or epitope. Positively selected cells are expanded, and then sorted by rounds of FACS to isolate single cell clones displaying antibodies that specifically bind to the target protein, peptide fragment, or epitope. Heavy and light chain pairs from these single cell clones are retransfected with AID for further maturation. Several rounds of mammalian cell display, coupled with AID-triggered somatic hypermutation, generate high specificity, high affinity antibodies.

Diversity may also be introduced into the CDRs or the whole V genes of the antibody libraries in a targeted manner or via random introduction. The former approach includes sequentially targeting all the CDRs of an antibody via a high or low level of mutagenesis or targeting isolated hot spots of somatic hypermutations (see, e.g., Ho et al., 2005, J. Biol. Chem. 280:607-17) or residues suspected of affecting affinity on experimental basis or structural reasons. In a specific embodiment, somatic hypermutation is performed by AID-triggered somatic hypermutation, e.g., using the SHM-XEL™ platform (AnaptysBio, San Diego, Calif.). Random mutations can be introduced throughout the whole V gene using E. coli mutator strains, error-prone replication with DNA polymerases (see, e.g., Hawkins et al., 1992, J. Mol. Biol. 226:889-96), or RNA replicases. Diversity may also be introduced by replacement of regions that are naturally diverse via DNA shuffling or similar techniques (see, e.g., Lu et al., 2003, J. Biol. Chem. 278:43496-507; U.S. Pat. Nos. 5,565,332 and 6,989,250). Alternative techniques target hypervariable loops extending into framework-region residues (see, e.g., Bond et al., 2005, J. Mol. Biol. 348:699-709) employ loop deletions and insertions in CDRs or use hybridization-based diversification (see, e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, SIRPα can be immobilized onto solid supports, columns, pins, or cellulose/poly(vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, 2005, Nature Biotechnology 23:1105-16; Quiroz and Sinclair, 2010, Revista Ingeneria. Biomedia 4:39-51; and references therein.

4.3.2.2 Modifications of Anti-SIRPα Antibodies

Covalent modifications of anti-SIRPα antibodies are included within the scope of the present disclosure. Covalent modifications include reacting targeted amino acid residues of an anti-SIRPα antibody with an organic derivatizing agent that is capable of reacting with selected side chains or the N- or C-terminal residues of the anti-SIRPα antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., Creighton, *Proteins: Structure and Molecular Properties* 79-86 (1983)), acetylation of the N-terminal amine, and amidation of any C-terminal carboxyl group.

Other types of covalent modification of the anti-SIRPα antibody included within the scope of this present disclosure include altering the native glycosylation pattern of the antibody or polypeptide (see, e.g., Beck et al., 2008, Curr. Pharm. Biotechnol. 9:482-501; and Walsh, 2010, Drug Discov. Today 15:773-80), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192; or 4,179,337.

An anti-SIRPα antibody of the present disclosure may also be modified to form chimeric molecules comprising an anti-SIRPα antibody fused to another, heterologous polypeptide or amino acid sequence, for example, an epitope tag (see, e.g., Terpe, 2003, Appl. Microbiol. Biotechnol. 60:523-33) or the Fc region of an IgG molecule (see, e.g., Aruffo, *Antibody Fusion Proteins* 221-42 (Chamow and Ashkenazi eds., 1999)).

Also provided herein are fusion proteins comprising an antibody provided herein that binds to a SIRPα antigen and a heterologous polypeptide. In some embodiments, the heterologous polypeptide to which the antibody is fused is useful for targeting the antibody to cells having cell surface-expressed SIRPα.

Also provided herein are panels of antibodies that bind to a SIRPα antigen. In specific embodiments, the panels of antibodies have different association rates, different dissociation rates, different affinities for a SIRPα antigen, and/or different specificities for a SIRPα antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96-well or 384-well plates, for assays such as ELISAs.

4.3.3 Preparation of Anti-SIRPα Antibodies

Anti-SIRPα antibodies may be produced by culturing cells transformed or transfected with a vector containing anti-SIRPα antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression, and purification are further described in Plückthun et al., Antibody Engineering: Producing antibodies in *Escherichia coli*: From PCR to fermentation 203-52 (McCafferty et al. eds., 1996); Kwong and Rader, *E. coil Expression and Purification of Fab Antibody Fragments*. in Current Protocols in Protein Science (2009); Tachibana and Takekoshi, *Production of Antibody Fab Fragments in Escherischia coil*, in Antibody Expression and Production (Al-Rubeai ed., 2011); and Therapeutic Monoclonal Antibodies: From Bench to Clinic (An ed., 2009).

It is, of course, contemplated that alternative methods, which are well known in the art, may be employed to prepare anti-SIRPα antibodies. For instance, the appropriate amino acid sequence, or portions thereof, may be produced by direct peptide synthesis using solid-phase techniques (see, e.g., Stewart et. al., *Solid-Phase Peptide Synthesis* (1969); and Merrifield, 1963, J. Am. Chem. Soc. 85:2149-54). In vitro protein synthesis may be performed using manual techniques or by automation. Various portions of the anti-SIRPα antibody may be chemically synthesized separately and combined using chemical or enzymatic methods to produce the desired anti-SIRPα antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

4.3.4 Immunoconjugates

The present disclosure also provides conjugates comprising any one of the anti-SIRPα antibodies of the present disclosure covalently bound by a synthetic linker to one or more non-antibody agents.

In some embodiments, antibodies provided herein are conjugated or recombinantly fused, e.g., to a detectable molecule.

Such detection can he accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, but not limited to, an acridinium based compound or a HALOTAG; radioactive materials, such as, but not limited to, iodine ($^{131}$I, $^{125}$I, $^{123}$I, and $^{121}$L), carbon ($^{14}$C), sulfur ($^{35}$S), tritium ($^{3}$H), indium ($^{125}$In, $^{113}$In, $^{112}$In, and $^{111}$In), technetium ($^{99}$Tc), thallium ($^{201}$Ti), gallium ($^{68}$Ga and $^{67}$Ga), palladium ($^{103}$Pd), molybdenum ($^{99}$Mo), xenon ($^{133}$Xe), fluorine ($^{18}$F), $^{151}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{185}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, or $^{117}$Sn; positron emitting metals using various positron emission tomographies; and non-radioactive paramagnetic metal ions.

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, or about 100 amino acids) to generate fusion proteins, as well as uses thereof. In particular, provided herein are fusion proteins comprising an antigen-binding fragment of an antibody provided herein (e.g., a Fab fragment, Fc fragment, Fv fragment, F(ab)$_2$ fragment, a VH domain, a VH CDR, a VL domain, or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses SIRPα. For example, an antibody that binds to a cell surface receptor expressed by a particular cell type may be fused or conjugated to a modified antibody provided herein.

Moreover, antibodies provided herein can be fused to marker or "tag" sequences, such as a peptide, to facilitate purification. In specific embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-24, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767-78), and the "FLAG" tag.

Methods for fusing or conjugating moieties (including polypeptides) to antibodies are known (see, e.g, Amon et al., *Monoclonal Antibodies for Immunotargeting of Drugs in Cancer Therapy*, in Monoclonal Antibodies and Cancer Therapy 243-56 (Reisfeld et al. eds., 1985); Hellstrom et al., *Antibodies for Drug Delivery*, in Controlled Drug Delivery 623-53 (Robinson et al. eds., 2d ed. 1987); Thorpe, *Antibody Carriers of Cytotoxic Agents in Cancer Therapy: A Review*, in Monoclonal Antibodies: Biological and Clinical Applications 475-506 (Pinchera et al. eds., 1985); *Analysis, Results, and Future Prospective of therapeutic Use of Radiolabeled Antibody in Cancer Therapy*, in Monoclonal Antibodies for Cancer Detection and Therapy 303-16 (Baldwin et al. eds., 1985); Thorpe et al., 1982, Immunol. Rev. 62:119-58); U.S. Pat. Nos. 5,336,603; 5,622,929; 5,359,046; 5,349,053; 5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., 1991, Proc. Natl. Acad. Sci. USA, 88: 10535-39; Traunecker el al., 1988, Nature, 331:84-86; Zheng et al., 1995, J. Immunol. 154:5590-600; and Vil et al., 1992, Proc. Natl. Acad. Sci. USA 89:11337-41).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of anti-SIRPα antibodies as provided herein, including, for example, antibodies with higher affinities and lower dissociation rates (see, e.g., U.S. Pat. Nos. 5,605,793; 5,811,238; 5,830,721; 5,834,252; and 5,837,458; Patten et al., 1997, Curr. Opinion Biotechnol. 8:724-33; Harayama, 1998, Trends Biotechnol. 16(2):76-82; Hansson et at., 1999. J. Mol. Biol. 287:265-76; and Lorenzo and Blasco, 1998, Biotechniques 24(2):308-13). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described, for example, in U.S. Pat. No. 4,676,980.

Antibodies that bind to SIRPα as provided herein may also be attached to solid supports, which are particularly useful for immunoassays or purification of the target antigen. Such solid supports include, but are not limited to, glass, cellulose, polyacrylamide, nylon, polystyrene, polyvinyl chloride, or polypropylene.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (see, e.g., Chari et al., 1992, Cancer Res. 52:127-31; and U.S. Pat. No. 5,208,020), thioether linkers, or hydrophilic linkers designed to evade multidrug transporter-mediated resistance (see, e.g., Kovtun et al., 2010, Cancer Res. 70:2528-37).

Conjugates of the antibody and agent may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfa-EMCS, sulfo-GMBS, sulfo-KMUS, sulfo-MBS, sulfo-SGIA, sulfo-SMCC, sulfo-SMPB, and SVSB (succinimidyl-(4-vinylsulfone)benzoate). The present disclosure further contemplates that conjugates of antibodies and agents may be prepared using any suitable methods as disclosed in the art (see, e.g., *Bioconjugate Techniques* (Hermanson ed., 2d ed. 2008)).

Conventional conjugation strategies for antibodies and agents have been based on random conjugation chemistries involving the ε-amino group of Lys residues or the thiol group of Cys residues, which results in heterogenous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (see, e.g., Junutula et al., 2008, J. Immunol. Meth. 332: 41-52; and Junutula et al., 2008, Nature Biotechnol. 26:925-32). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., 2008, Proc. Natl. Acad. Sci. USA 105: 12451-56; and Hofer et al., 2009, Biochemistry 48(50): 12047-57).

4.4 Methods of Using the Antibodies and Compositions

Provided herein are methods of increasing phagocytosis by a macrophage, including contacting the macrophage with an effective amount of an anti-SIRPα antibody or antigen binding fragment thereof provided herein, whereby the phagocytosis by a macrophage is increased as compared to that by an untreated macrophage or by a macrophage treated with an isotype control antibody.

Also provided herein are methods of increasing a percentage of phagocytotic macrophages in a population of macrophages, comprising contacting the macrophages with an effective amount of an antibody or antigen binding fragment thereof provided herein, whereby the percentage of phagocytotic macrophages in a population of macrophages is increased as compared to untreated macrophages or macrophages treated with an isotype control antibody.

Further provided herein are methods of increasing phagocytosis of cancer cells by a population of macrophages, comprising contacting the cancer cells, the macrophages, or both the cancer cells and the macrophages with an effective amount of an antibody or antigen binding fragment thereof provided herein, whereby the phagocytosis of cancer cells by a population of macrophages is increased as compared to that by untreated macrophages or by macrophages treated with an isotype control antibody.

As discussed further above, in certain embodiments of the various methods provided herein, the cancer cells and/or the macrophages can include one, two, three, four, five, six, seven, eight, nine, ten or more or all of the SIRPα haplotypes known to a person skilled in the art, for example one, two, three, four, five, six, seven, eight, nine, ten or more, or all of the SIRPα polymorphism described in Takenaka K, et al., Nat Immunol. 2007 December;8(12):1313-23.

In some embodiments of the various methods provided herein, the cancer cells and/or the macrophages include any one or any combination of two, three, four, five, or six of SIRPα selected from the group consisting of SIRPα v1, v2, v3, v4, v5 and v6 haplotypes (SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include one SIRPα polymorphism selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include two or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain. In some embodiments of the various methods provided herein, the cancer cells and/or the macrophages include SIRPα v2 comprising SEQ ID NO:150 in the IgV-domain. In some embodiments of the various methods provided herein, the cancer cells and/or the macrophages include SIRPα v3 comprising SEQ ID NO:151 in the IgV-domain. In some embodiments of the various methods provided herein, the cancer cells and/or the macrophages include SIRPα v4 comprising SEQ ID NO:152 in the IgV-domain. In some embodiments of the various methods provided herein, the cancer cells and/or the macrophages include SIRPα v5 comprising SEQ ID NO:153 in the IgV-domain. In some embodiments of the various methods provided herein, the cancer cells and/or the macrophages include SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain and SIRPα v2 comprising SEQ ID NO:150 in the IgV-domain. In some embodiments of the various methods provided herein, the cancer cells and/or the macrophages include SIRPα v1 comprising SEQ ID NO:149 in the IgV-domain and SIRPα v3 comprising SEQ ID NO:151 in the IgV-domain. In some embodiments of the various methods provided herein, the cancer cells and/or the macrophages include SIRPα v1 comprising SEQ ID NO:149 in the IgV-domain and SIRPα v4 comprising SEQ ID NO:152 in the IgV-domain. In some embodiments of the various methods provided herein, the cancer cells and/or the macrophages include SIRPα v1 comprising SEQ ID NO:149 in the IgV-domain and SIRPα v5 comprising SEQ ID NO:153 in the IgV-domain. In some embodiments of the various methods provided herein, the cancer cells and/or the macrophages include SIRPα v1 comprising SEQ ID NO:149 in the IgV-domain and SIRPα v6 comprising SEQ ID NO:154 in the IgV-domain.

In some embodiments of the various methods provided herein, the cancer cells and/or the macrophages include SIRPα v2 comprising SEQ ID NO:150 in the IgV-domain and SIRPα v3 comprising SEQ ID NO:151 in the IgV-domain. In some embodiments of the various methods provided herein, the cancer cells and/or the macrophages include SIRPα v2 comprising SEQ ID NO:150 in the IgV-domain and SIRPα v4 comprising SEQ ID NO:152 in the IgV-domain. In some embodiments of the various methods provided herein, the cancer cells and/or the macrophages include SIRPα v2 comprising SEQ ID NO:150 in the IgV-domain and SIRPα v5 comprising SEQ ID NO:153 in the IgV-domain. In some embodiments of the various methods provided herein, the cancer cells and/or the macrophages include SIRPα v2 comprising SEQ ID NO:150 in the IgV-domain and SIRPα v6 comprising SEQ ID NO:154 in the IgV-domain.

In some embodiments of the various methods provided herein, the cancer cells and/or the macrophages include SIRPα v3 comprising SEQ ID NO:151 in the IgV-domain and SIRPα v4 comprising SEQ ID NO:152 in the IgV-domain. In some embodiments of the various methods provided herein, the cancer cells and/or the macrophages include SIRPα v3 comprising SEQ ID NO:151 in the IgV-domain and SIRPα v5 comprising SEQ ID NO:153 in the IgV-domain. In some embodiments of the various methods provided herein, the cancer cells and/or the macrophages include SIRPα v3 comprising SEQ ID NO:151 in the IgV-domain and SIRPα v6 comprising SEQ ID NO:154 in the IgV-domain.

In some embodiments of the various methods provided herein, the cancer cells and/or the macrophages include SIRPα v4 comprising SEQ ID NO:152 in the IgV-domain and SIRPα v5 comprising SEQ ID NO:153 in the IgV-domain. In some embodiments of the various methods provided herein, the cancer cells and/or the macrophages include SIRPα v4 comprising SEQ ID NO:152 in the IgV-domain and SIRPα v6 comprising SEQ ID NO:154 in the IgV-domain. In some embodiments of the various methods provided herein, the cancer cells and/or the macrophages suitable for the methods provided herein include SIRPα v5 comprising SEQ ID NO:153 in the IgV-domain and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, and SIRPα v3 comprising SEQ ID NO:151 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, and SIRPα v4 comprising SEQ ID NO:152 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, and SIRPα v5 comprising SEQ ID NO:153 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, and SIRPα v6 comprising SEQ ID NO: in the IgV-domain.

In some embodiments of the various methods provided herein, the cancer cells and/or the macrophages include SIRPα v1 comprising SEQ ID NO:149 in the IgV-domain, SIRPα v3 comprising SEQ ID NO:151 in the IgV-domain, and SIRPα v4 comprising SEQ ID NO:152 in the IgV-domain. In some embodiments of the various methods provided herein, the cancer cells and/or the macrophages include SIRPα v1 comprising SEQ ID NO:149 in the IgV-domain, SIRPα v3 comprising SEQ ID NO:151 in the IgV-domain, and SIRPα v5 comprising SEQ ID NO:153 in the IgV-domain. In some embodiments of the various methods provided herein, the cancer cells and/or the macrophages include SIRPα v1 comprising SEQ ID NO:149 in the IgV-domain, SIRPα v3 comprising SEQ ID NO:151 in the IgV-domain, and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the cancer cells and/or the macrophages include SIRPα v1 comprising SEQ ID NO:149 in the IgV-domain, SIRPα v4 comprising SEQ ID NO:152 in the IgV-domain, and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include SIRPα v2 comprising SEQ ID NO:150 in the IgV-domain, SIRPα v3 comprising SEQ ID NO:151 in the IgV-domain, and SIRPα v4 comprising SEQ ID NO:152 in the IgV-domain. In some embodiments of the various methods provided herein, the cancer cells and/or the macrophages include SIRPα v2 comprising SEQ ID NO:150 in the IgV-domain, SIRPα v3 comprising SEQ ID NO:151 in the IgV-domain, and SIRPα v5 comprising SEQ ID NO:153 in the IgV-domain. In some embodiments of the various methods provided herein, the cancer cells and/or the macrophages include SIRPα v2 comprising SEQ ID NO:150 in the IgV-domain, SIRPα v3 comprising SEQ ID NO:151 in the IgV-domain, and SIRPα v6 comprising SEQ ID NO:154 in the IgV-domain.

In some embodiments of the various methods provided herein, the cancer cells and/or the macrophages include SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the cancer cells and/or the macrophages include SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the cancer cells and/or the macrophages include SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v4 comprising SEQ ID NO:152 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v5 comprising SEQ ID NO:153 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the cancer cells and/or the macrophages include SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the cancer cells and/or the macrophages include SIRPα v1 comprising SEQ ID NO:149 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the cancer cells and/or the macrophages include SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO: 154 in the IgV-domain. In some embodiments of the various methods provided herein, the cancer cells and/or the macrophages include SIRPα v2 comprising SEQ ID NO:150 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include SIRPα v2 comprising SEQ ID NO:150 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain. In some embodiments of the various methods provided herein, the cancer cells and/or the macrophages include SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the cancer cells and/or the macrophages include SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain, In some embodiments, the anti-SIRPα antibodies or fragments thereof provided herein specifically bind to human SIRPα (for example, any one or any combination of two, three, four, five, or six of SIRPα selected from the group consisting of SIRPα v1, v2, v3, v4, v5 and v6 haplotypes) and increase phagocytosis of cancer cells by co-cultured macrophages, wherein the cancer cells and/or the macrophages include SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain. In some embodiments of the various methods provided herein, the cancer cells and/or the macrophages include SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain. In some embodiments of the various methods provided herein, the cancer cells and/or the macrophages include SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

Additionally provided herein are methods of increasing phagocytosis of cancer cells in a subject, comprising administering an effective amount of an antibody or antigen binding fragment thereof provided herein, whereby the phagocytosis of cancer cells in a subject is increased as compared to that in an untreated subject or in a subject treated with an isotype control antibody.

Provided herein are methods of increasing elimination of cancer cells by phagocytosis in a subject, comprising administering an effective amount of an antibody or antigen binding fragment thereof provided herein.

Provided herein are methods of targeting cancer cells for immunodepletion in a subject, comprising administering an effective amount of an antibody or antigen binding fragment thereof provided herein.

Also provided herein are methods of treating cancer in a subject, comprising administering an effective amount of an antibody or antigen binding fragment thereof provided herein.

In certain embodiments of the various methods provided herein, a subject has one, two, three, four, five, six, seven, eight, nine, ten or more or all of the SIRPα haplotypes known to a person skilled in the art, for example one, two, three, four, five, six, seven, eight, nine, ten or more, or all of the SIRPα polymorphism described in Takenaka K, et al., Nat Immunol. 2007 December;8(12):1313-23.

In some embodiments of the various methods provided herein, a subject has any one or any combination of two, three, four, five, or six of SIRPα selected from the group consisting of SIRPα v1, v2, v3, v4, v5 and v6 haplotypes (SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain).

In certain embodiments of the various methods provided herein, a subject has one SIRPα polymorphism selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, a subject has two or more SIRPα polymorphisms selected from the group consisting of SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In certain embodiments of the various methods provided herein, a subject, has SIRPα v1 comprising SEQ ID NO:149 in the IgV-domain. In other embodiments, In certain embodiments of the various methods provided herein, a subject has SIRPα v2 comprising SEQ ID NO:150 in the IgV-domain. In some embodiments of the various methods provided herein, a subject has SIRPα v3 comprising SEQ ID NO:151 in the IgV-domain. In certain embodiments of the various methods provided herein, a subject has SIRPα v4 comprising SEQ ID NO:152 in the IgV-domain. In other embodiments of the various methods provided herein, a subject has SIRPα v5 comprising SEQ ID NO:153 in the IgV-domain. In some embodiments of the various methods provided herein, a subject has SIRPα v6 comprising SEQ ID NO:154 in the IgV-domain.

In some embodiments of the various methods provided herein, the subject has SIRPα v1 comprising SEQ ID NO:149 in the IgV-domain and SIRPα v2 comprising SEQ ID NO:150 in the IgV-domain. In some embodiments of the various methods provided herein, the subject has SIRPα v1 comprising SEQ ID NO:149 in the IgV-domain and SIRPα v3 comprising SEQ ID NO:151 in the IgV-domain. In some embodiments of the various methods provided herein, the subject has SIRPα v1 comprising SEQ ID NO:149 in the Ig4V-domain and SIRPα v4 comprising SEQ ID NO:152 in the IgV-domain. In some embodiments of the various methods provided herein, the subject has SIRPα v1 comprising SEQ ID NO:149 in the IgV-domain and SIRPα v5 comprising SEQ ID NO:153 in the IgV-domain. In some embodiments of the various methods provided herein, the subject has SIRPα v1 comprising SEQ ID NO: 149 in the IgV-domain and SIRPα v6 comprising SEQ ID NO:154 in the IgV-domain.

In some embodiments of the various methods provided herein, the subject has SIRPα v2 comprising SEQ ID NO:150 in the IgV-domain and SIRPα v3 comprising SEQ ID NO:151 in the IgV-domain. In some embodiments of the various methods provided herein, the subject has SIRPα v2 comprising SEQ ID NO:150 in the IgV-domain and SIRPα v4 comprising SEQ ID NO:152 in the IgV-domain. In some embodiments o1 the various methods provided herein, the subject has SIRPα v2 comprising SEQ ID NO:150 in the IgV-domain and SIRPα v5 comprising SEQ ID NO:153 in the IgV-domain. In some embodiments of the various methods provided herein, the subject has SIRPα v2 comprising SEQ ID NO:150 in the IgV-domain and SIRPα v6 comprising SEQ ID NO:154 in the IgV-domain.

In some embodiments of the various methods provided herein, the subject has SIRPα v3 comprising SEQ ID NO:151 in the IgV-domain and SIRPα v4 comprising SEQ ID NO:152 in the IgV-domain. In some embodiments of the various methods provided herein, the subject has SIRPα v3 comprising SEQ ID NO:151 in the IgV-domain and SIRPα v5 comprising SEQ ID NO:153 in the IgV-domain. In some embodiments o1 the various methods provided herein, the subject has SIRPα v3 comprising SEQ ID NO:151 in the IgV-domain and SIRPα v6 comprising SEQ ID NO:154 in the IgV-domain.

In some embodiments of the various methods provided herein, the subject has SIRPα v4 comprising SEQ ID NO:152 in the IgV-domain and SIRPα v5 comprising SEQ ID NO:153 in the IgV-domain. In some embodiments of the various methods provided herein, the subject has SIRPα v4 comprising SEQ ID NO:152 in the IgV-domain and SIRPα v6 comprising SEQ ID NO:154 in the IgV-domain. In some embodiments of the various methods provided herein, the subject has SIRPα v5 comprising SEQ ID NO:153 in the IgV-domain and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v2 comprising SEQ ID NO:150 in the IgV-domain, and SIRPα v3 comprising SEQ ID NO:151 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, and SIRPα v4 comprising SEQ ID NO:152 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, and SIRPα v5 comprising SEQ ID NO:153 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v3 comprising SEQ ID NO:151 in the IgV-domain, and SIRPα v4 comprising SEQ ID NO:152 in the IgV-domain. In some embodiments of the various methods provided herein, the subject has SIRPα v1 comprising SEQ ID NO:149 in the IgV-domain, SIRPα v3 comprising SEQ ID NO:151 in the IgV-domain, and SIRPα v5 comprising SEQ ID NO:153 in the IgV-domain. In some embodiments of the various methods provided herein, the subject has SIRPα v1 comprising SEQ ID NO:149 in the IgV-domain, SIRPα v3 comprising SEQ ID NO:151 in the IgV-domain, and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the subject has SIRPα v1 comprising SEQ ID NO:149 in the IgV-domain, SIRPα v4 comprising SEQ ID NO:152 in the IgV-domain, and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the subject has SIRPα v2 comprising SEQ ID NO: in the IgV-domain, SIRPα v3 comprising SEQ ID NO:151 in the IgV-domain, and SIRPα v4 comprising SEQ ID NO:152 in the IgV-domain. In some embodiments of the various methods provided herein, the subject has SIRPα v2 comprising SEQ ID NO:150 in the IgV-domain, SIRPα v3 comprising SEQ ID NO:151 in the IgV-domain, and SIRPα v5 comprising SEQ ID NO:153 in the IgV-domain. In some embodiments of the various methods provided herein, the subject has SIRPα v2 comprising SEQ ID NO:150 in the IgV-domain, SIRPα v3 comprising SEQ ID NO:151 in the IgV-domain, and SIRPα v6 comprising SEQ ID NO:154 in the IgV-domain.

In some embodiments of the various methods provided herein, the subject has SIRPα v3 comprising SEQ ID NO: in the IgV-domain, SIRPα v4 comprising SEQ ID NO:152 in the IgV-domain, and SIRPα v5 comprising SEQ ID NO:153 in the IgV-domain. In some embodiments of the various methods provided herein, the subject has SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the subject has SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v4 comprising SEQ ID NO:152 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, and SIRPα v5 comprising SEQ ID NO:153 in the IgV-domain. In some embodiments of the various methods provided herein, the subject has SIRPα v1 comprising SEQ ID NO:149 in the IgV-domain, SIRPα v2 comprising SEQ ID N0:150 in the IgV-domain, SIRPα v3 comprising SEQ ID NO:151 in the IgV-domain, and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the subject has SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the subject has SIRPα v1 comprising SEQ ID NO:149 in the IgV-domain, SIRPα v3 comprising SEQ ID NO:151 in the IgV-domain, SIRPα v5 comprising SEQ NO:153 in the IgV-domain, and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the subject has SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the subject has SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the subject has SIRPα v2 comprising SEQ ID NO:150 in the IgV-domain, SIRPα v4 comprising SEQ ID NO:152 in the IgT-domain, SIRPα v5 comprising SEQ ID NO:153 in the IgT-domain, and SIRPα v6 comprising SEQ ID NO:154 in the IgV-domain. In some embodiments of the various methods provided herein, the subject has SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

In some embodiments of the various methods provided herein, the subject has SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v5 comprising SEQ ID NO:153 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, and SIRPα v6 comprising SEQ ID NO:154 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v5 comprising SEQ ID NO:153 in the IgV-domain, and SIRPα v6 comprising SEQ ID NO:154 in the IgV-domain. In some embodiments of the various methods provided herein, the subject has SIRPα v1 comprising SEQ ID NO:149 in the IgV-domain, SIRPα v2 comprising SEQ ID NO:150 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain. In some embodiments of the various methods provided herein, the subject has SIRPα v1 comprising SEQ ID NO:149 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain. In some embodiments of the various methods provided herein, the subject has SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain.

As discussed above, phagocytosis of cancer cells by co-cultured macrophages or phagocytosis of cancer cells by macrophages in a subject can be determined as percentage of phagocytotic macrophages, and increases in phagocytosis of cancer cells by co-cultured macrophages or in phagocytosis of cancer cells by macrophages in a subject can be determined as percent or fold increase of phagocytosis, or as changes in the percentage of phagocytotic macrophages. As such, the percentage of phagocytotic macrophages can be used as a measurement for phagocytosis by macrophages and/or phagocytosis of cancer cells by macrophages in vitro or in a subject. The percentage of phagocytotic macrophages in a population of macrophages in certain embodiments of the various methods provided herein increases to about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%. In some embodiments, the population is a population of macrophages co-cultured with cancer cells or a population of macrophages in a subject.

In other embodiments of the various methods provided herein, the percentage of phagocytotic macrophages in a population of macrophages increases to at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the population is a population of macrophages co-cultured with cancer cells or a population of macrophages in a subject.

In certain embodiments of the various methods provided herein, phagocytosis by the macrophages or phagocytosis of the cancer cells by the macrophages increases by about 10%, about 20%, about 30%, about 40%, about 45%, about 50%, about 55%, about 60%, about 65%, about 70%, about 75%, about 80%, about 85%, about 90%, about 95%, about 100%, about 125%, about 150%, about 175%, about 200%, about 250%, about 300%, about 400%, about 500%, about 600%, about 700%, about 800%, about 900% or about 1000% as compared to that by untreated macrophages or by macrophages treated with an isotype control antibody. In other embodiments of the various methods provided herein, phagocytosis by the macrophages or phagocytosis of the cancer cells by the macrophages increases by at least 10%, at least 20%, at least 30%, at least 40%, at least 45%, at least 50%, at least 55%, at least 60%, at least 65%, at least 70%, at least 75%, at least 80%, at least 85%, at least 90%, at least 95%, at least 100%, at least 125%, at least 150%, at least 175%, at least 200%, at least 250%, at least 300%, at least 400%, at least 500%, at least 600%, at least 700%, at least 800%, at least 900% or at least 1000% as compared to that by untreated macrophages or by macrophages treated with an isotype control antibody. In some embodiments, the population is a population of macrophages co-cultured with cancer cells or a population of macrophages in a subject.

The disclosure thus further provides that the methods provided herein can be used to increase phagocytosis of cancer cells from colorectal cancer, head and neck squamous cell carcinoma, acute myeloid leukemia, or DLBCL, wherein the cancer cells expresses CD47, SIRPα, or both CD47 and SIRPα. The disclosure also provides that the methods provided herein can be used to increase phagocytosis of cancer cells from NHL such as DLBCL, follicular lymphoma, marginal zone lymphoma, and mantle cell lymphoma, wherein the cancer cells expresses CD47, SIRPα, or both CD47 and SIRPα. The disclosure additionally provides that the methods provided herein can be used to increase phagocytosis of cancer cells from Grade 1 follicular lymphoma, Grade 2 follicular lymphoma, Grade 3a follicular lymphoma, Grade 3b follicular lymphoma, relapsed follicular lymphoma (including e.g. Grade 1, 2, 3a and 3b), refractory follicular lymphoma (including e.g. Grade 1, 2, 3a and 3b), relapsed DLBCL, or refractory DLBCL, wherein the cancer cells expresses CD47, SIRPα, or both CD47 and SIRPα. In some embodiment, the methods provided herein can be used to increase phagocytosis of cancer cells from colorectal cancer. In some embodiment, the methods provided herein can be used to increase phagocytosis of cancer cells from colorectal cancer, wherein the cancer expresses CD47, SIRPα, or both CD47 and SIRPα. In some embodiment, the methods provided herein can be used to increase phagocytosis of cancer cells from head and neck squamous cell carcinoma. In some embodiment, the methods provided herein can be used to increase phagocytosis of cancer cells from head and neck squamous cell carcinoma, wherein the cancer cells expresses CD47, SIRPα, or both CD47 and SIRPα. In some embodiment, the methods provided herein can be used to increase phagocytosis of cancer cells from acute myeloid leukemia. In some embodiment, the methods provided herein can be used to increase phagocytosis of cancer cells from acute myeloid leukemia, wherein the cancer cells expresses CD47, SIRPα, or both CD47 and SIRPα. In some embodiment, the methods provided herein can be used to increase phagocytosis of cancer cells from DLBCL. In some embodiment, the methods provided herein can be used to increase phagocytosis of cancer cells from DLBCL, wherein the cancer cells expresses CD47, SIRPα, or both CD47 and SIRPα. In some embodiment, the methods provided herein can be used to increase phagocytosis of cancer cells from follicular lymphoma. In some embodiment, the methods provided herein can be used to increase phagocytosis of cancer cells from follicular lymphoma, wherein the cancer cells expresses CD47, SIRPα, or both CD47 and SIRPα. In some embodiment, the methods provided herein can be used to increase phagocytosis of cancer cells from marginal zone lymphoma. In some embodiment, the methods provided herein can be used to increase phagocytosis of cancer cells from marginal zone lymphoma, wherein the cancer cells expresses CD47, SIRPα, or both CD47 and SIRPα. In some embodiment, the methods provided herein can be used to increase phagocytosis of cancer cells from mantle cell lymphoma. In some embodiment, the methods provided herein can be used to increase phagocytosis of cancer cells from mantle cell lymphoma, wherein the cancer cells expresses CD47, SIRPα, or both CD47 and SIRPα. In some embodiment, the methods provided herein can be used to increase phagocytosis of cancer cells from NHL. In some embodiment, the methods provided herein can be used to increase phagocytosis of cancer cells from NHL, wherein the cancer cells expresses CD47, SIRPα, or both CD47 and SIRPα. In some embodiment, the methods provided herein can be used to increase phagocytosis of cancer cells from Grade 1 follicular lymphoma. In some embodiment, the methods provided herein can be used to increase phagocytosis of cancer cells from Grade 1 follicular lymphoma, wherein the cancer cells expresses CD47, SIRPα, or both CD47 and SIRPα. In some embodiment, the methods provided herein can be used to increase phagocytosis of cancer cells from Grade 2 follicular lymphoma. In some embodiment, the methods provided herein can be used to increase phagocytosis of cancer cells from Grade 2 follicular lymphoma, wherein the cancer cells expresses CD47, SIRPα, or both CD47 and SIRPα. In some embodiment, the methods provided herein can be used to increase phagocytosis of cancer cells from Grade 3a follicular lymphoma. In some embodiment, the methods provided herein can be used to increase phagocytosis of cancer cells from Grade 3a follicular lymphoma, wherein the cancer cells expresses CD47, SIRPα, or both CD47 and SIRPα. In some embodiment, the methods provided herein can be used to increase phagocytosis of cancer cells from Grade 3b follicular lymphoma. In some embodiment, the methods provided herein can be used to increase phagocytosis of cancer cells from Grade 3b follicular lymphoma, wherein the cancer cells expresses CD47, SIRPα, or both CD47 and SIRPα. In some embodiment, the methods provided herein can be used to increase phagocytosis of cancer cells from replased follicular lymphoma (including e.g. Grade 1, 2, 3a and 3b). In some embodiment, the methods provided herein can be used to increase phagocytosis of cancer cells from relapsed follicular lymphoma (including e.g. Grade 1, 2, 3a and 3b), wherein the cancer cells expresses CD47, SIRPα, or both CD47 and SIRPα. In some embodiment, the methods provided herein can be used to increase phagocytosis of cancer cells from refractory follicular lymphoma (including e.g. Grade 1, 2, 3a and 3b). In some embodiment, the methods provided herein can be used to increase phagocytosis of cancer cells from refractory follicular lymphoma (including e.g. Grade 1, 2, 3a and 3b), wherein the cancer cells expresses CD47, SIRPα, or both CD47 and SIRPα. In some embodiment, the methods provided herein can be used to increase phagocytosis of cancer cells from relapsed DLBCL. In some embodiment, the methods provided herein can be used to increase phagocytosis of cancer cells from relapsed DLBCL, wherein the cancer cells expresses CD47, SIRPα, or both CD47 and SIRPα. In some embodiment, the methods provided herein can be used to increase phagocytosis of cancer cells from refractory DLBCL. In some embodiment, the methods provided herein can be used to increase phagocytosis of cancer cells from refractory DLBCL, wherein the cancer cells expresses CD47, SIRPα, or both CD47 and SIRPα.

In certain embodiments, the follicular lymphoma can be classified according to the World Health Organisation (WHO) classification (Nathwani B N, et al., Follicular lymphoma World Health Organization Classification of Tumours. Pathology & Genetics of Tumours of Haematopoietic and Lymphoid Tissues Lyon: IARC Press; 162-167, Jaffe E S, Harris N L, Stein H, Vardiman J W (eds) (2001)). In some embodiments, the three-grade system (Grades 1-3) adopted by WHO is based on counting the absolute number of centroblasts in 10 neoplastic follicles, expressed per high-power microscopic field (h.p.f.) of 0.159 $mm^2$. Grade 1 follicular lymphoma has 0-5 centroblasts per h.p.f., Grade 2 follicular lymphoma has 6-15 centroblasts per h.p.f, and Grade 3 follicular lymphoma has >15 centroblasts per h.p.f. This method of histological grading can predict both overall survival (OS) and failure-free survival (FFS) (see e.g. Martin A R, et al., Blood. 85:3671-3678 (1995)). Furthermore, Grade 3 follicular lymphoma can be subdivided according to the number of centroblasts. In Grade 3a follicular lymphoma, there are >15 centroblasts per h.p.f., but centrocytes are still present, while Grade 3b follicular lymphoma has solid sheets of centroblasts with no centrocytes.

In some embodiments of the various methods provided herein, use an anti-SIRPα antibody or antigen-binding fragment thereof provided herein as a monotherapy, for example, as the single and only therapeutic agent in the methods. In other embodiments of the various methods provided herein, an anti-SIRPα antibody or antigen-binding fragment thereof is used in combination with a second therapeutic agent for the elimination of the cancer cells. In certain embodiments, the second therapeutic agent is cetuximab or rituximab. In one embodiment, the second therapeutic agent is cetuximab. In another embodiment, the second therapeutic agent is rituximab.

Provided herein are methods of increasing phagocytosis of cancer cells in a subject, comprising administering an effective amount of an anti-SIRPα antibody or antigen binding fragment thereof provided herein and an anti-EGFR antibody, whereby the phagocytosis of cancer cells in a subject is increased as compared to that in an untreated subject or in a subject treated with an isotype control antibody.

Additionally provided herein are methods of increasing elimination of cancer cells by phagocytosis in a subject, comprising administering an effective amount of an anti-SIRPα antibody or antigen binding fragment thereof provided herein and an anti-EGFR antibody.

Further provided herein are methods of targeting cancer cells for immunodepletion in a subject, comprising administering an effective amount of an anti-SIRPα antibody or antigen binding fragment thereof provided herein and an anti-EGFR antibody.

Also provided herein are methods of treating cancer in a subject, comprising administering an effective amount of an anti-SIRPα antibody or antigen binding fragment thereof provided herein and an anti-EGFR antibody.

Provided herein are methods of increasing phagocytosis by a macrophage, including contacting the macrophage with an effective amount of an anti-SIRPα antibody or antigen binding fragment thereof provided herein and an anti-EGFR antibody, whereby the phagocytosis by a macrophage is increased as compared to that by an untreated macrophage or by a macrophage treated with an isotype control antibody.

Also provided herein are methods of increasing a percentage of phagocytotic macrophages in a population of macrophages, comprising contacting the macrophages with an effective amount of an anti-SIRPα antibody or antigen binding fragment thereof provided herein and an anti-EGFR antibody, whereby the percentage of phagocytotic macrophages in a population of macrophages is increased as compared to untreated macrophages or macrophages treated with an isotype control antibody.

Further provided herein are methods of increasing phagocytosis of cancer cells by a population of macrophages, comprising contacting the cancer cells, the macrophages, or both the cancer cells and the macrophages with an effective amount of an anti-SIRPα antibody or antigen binding fragment thereof provided herein and an anti-EGFR antibody, whereby the phagocytosis of cancer cells by a population of macrophages is increased as compared to that by untreated macrophages or by macrophages treated with an isotype control antibody.

In some embodiments, the anti-EGFR antibodies include an anti-EGFR antibody that blocks dimerization of EGFR and an anti-EGFR antibody that competes for ligand-receptor binding by occluding the ligand-binding on the receptor from access to the ligand. In some embodiments, the anti-EGFR antibody is selected from the group consisting of cetuximab, panitumumab, nitnotuzumab, zalutumumab, necituniumab, and matuzumab, all of which are anti-EGFR. antibodies used or tested in cancer therapies well-known to a person of ordinary skill in the art. Other therapeutic anti-EGFR antibodies that can be used in the methods provided herein are described in Martinelli E et al., Clinical and Experimental Immunology, 158:1-9; Russell J S et al., Chemother Res Pract. 2012; 2012: 761518; Capdevila J et al., Cancer Treatment Reviews 2009; 35(4): 354-363, all of which are hereby incorporated in their entirety by reference.

In some specific embodiments, the anti-EGFR antibody is cetuximab. In some embodiments, the anti-EGFR antibody is panitumumab. In some embodiments, the anti-EGFR antibody is nimotuzumab. In some embodiments, the anti-EGFR antibody is zalutumumab. In some embodiments, the anti-EGFR antibody is necitumumab. In some embodiments, the anti-EGFR antibody is matuzumab.

Provided herein are methods of increasing phagocytosis of cancer cells in a subject, comprising administering an effective amount of an anti-SIRPα antibody or antigen binding fragment thereof provided herein and an anti-CD20 antibody, whereby the phagocytosis of cancer cells in a subject is increased as compared to that in an untreated subject or in a subject treated with an isotype control antibody.

Additionally provided herein are methods of increasing elimination of cancer cells by phagocytosis in a subject, comprising administering an effective amount of an anti-SIRPα antibody or antigen binding fragment thereof provided herein and an anti-CD20 antibody.

Further provided herein are methods of targeting cancer cells for immunodepletion in a subject, comprising administering an effective amount of an anti-SIRPα antibody or antigen binding fragment thereof provided herein and an anti-CD20 antibody.

Also provided herein are methods of treating cancer in a subject, comprising administering an effective amount of an anti-SIRPα antibody or antigen binding fragment thereof provided herein and an anti-CD20 antibody.

Provided herein are methods of increasing phagocytosis by a macrophage, including contacting the macrophage with an effective amount of an anti-SIRPα antibody or antigen binding fragment thereof provided herein and an anti-CD20 antibody, whereby the phagocytosis by a macrophage is increased as compared to that by an untreated macrophage or by a macrophage treated with an isotype control antibody.

Also provided herein are methods of increasing a percentage of phagocytic macrophages in a population of macrophages, comprising contacting the macrophages with an effective amount of an antibody or antigen binding fragment thereof provided herein and an anti-CD20 antibody, whereby the percentage of phagocytotic macrophages in a population of macrophages is increased as compared to untreated macrophages or macrophages treated with an isotype control antibody.

Further provided herein are methods of increasing phagocytosis of cancer cells by a population of macrophages, comprising contacting the cancer cells, the macrophages, or both the cancer cells and the macrophages with an effective amount of an anti-SIRPα antibody or antigen binding fragment thereof provided herein and an anti-CD20 antibody, whereby the phagocytosis of cancer cells by a population of macrophages is increased as compared to that by untreated macrophages or by macrophages treated with an isotype control antibody.

In some embodiments, the anti-CD20 antibody is selected from the group consisting of rituximab, ocrelizumab, obinutuzumab, ofatumumab, tositumomab, ocaratuzumab, veltuzumab, and ublituximab. Other therapeutic anti-CD20 antibodies that can be used in the methods provided herein are described in Alduaij W et al., Blood 117:2993-3001 (2011); Du, F H et al,, Auto Immun Highlights. 2017 December; 8(1): 12, both of which are hereby incorporated in their entirety by reference.

In some specific embodiments, the anti-CD20 antibody is rituximab. In some embodiments, the anti-CD20 antibody is ocrelizumab. In some embodiments, the anti-CD20 antibody is obinutuzumab. In some embodiments, the anti-CD20 antibody is ofatumumab. In some embodiments, the anti-CD20 antibody is tositumomab. In some embodiments, the anti-CD20 antibody is ocaratuzumab. In some embodiments, the anti-CD20 antibody is veltuzumab. In some embodiments, the anti-CD20 antibody is ublituximab.

In certain embodiments of the various methods provided herein, the subject is a mammal. In some embodiments, the subject is a mammal selected from the group consisting of *Caviinae* (guinea pig), *Sus* (pigs), *Macaca Fascicularis* (monkeys, e.g. cynomolgus monkey), *Hominoid* apes (gibbons, orangutans, gorillas, chimpanzees, and humans), *Canis* (dog), *Rattus* (rat), and *Mus musculus* (mouse). In a specific embodiment, the subject is a human.

In certain embodiments of the various methods provided herein, an effective amount of an anti-SIRPα antibody or antigen-binding fragment thereof (e.g., SIRPAB-11-K322A) is administered to the subject. A therapeutically or prophylactically effective amount of an anti-SIRPα antibody or antigen-binding fragment thereof is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day. In one embodiment, the recommended daily dose is given as a single once-a-day dose, or in divided doses throughout a day.

In certain embodiments, the effective amount of an anti-SIRPα antibody or antigen-binding fragment thereof (e.g., SIRPAB-11-K322A) is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, from about 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 mg/kg/day to about 0.3 mg/kg/day. In one embodiment, the effective amount of an anti-SIRPα antibody is 100 mg/kg/day. In one embodiment, the effective amount of an anti-SIRPα antibody is 95 mg/kg/day. In one embodiment, the effective amount of an anti-SIRPα antibody is 90 mg/kg/day. In one embodiment, the effective amount of an anti-SIRPα antibody is 85 mg/kg/day. In one embodiment, the effective amount of an anti-SIRPα antibody is 80 mg/kg/day. In one embodiment, the effective amount of an anti-SIRPα antibody is 75 mg/kg/day. In one embodiment, the effective amount of an anti-SIRPα antibody is 70 mg/kg/day. In one embodiment, the effective amount of an anti-SIRPα antibody is 65 mg/kg/day. In one embodiment, the effective amount of an anti-SIRPα antibody is 60 mg/kg/day, In one embodiment, the effective amount of an anti-SIRPα antibody is 55 mg/kg/day. In one embodiment, the effective amount of an anti-SIRPα antibody is 50 mg/kg/day. In one embodiment, the effective amount of an anti-SIRPα antibody is 45 mg/kg/day. In one embodiment, the effective amount of an anti-SIRPα antibody is 40 mg/kg/day. In one embodiment, the effective amount of an anti-SIRPα antibody is 35 mg/kg/day. In one embodiment, the effective amount of an anti-SIRPα antibody is 30 mg/kg/day. In one embodiment, the effective amount of an anti-SIRPα antibody is 25 mg/kg/day. In one embodiment, the effective amount of an anti-SIRPα antibody is 20 mg/kg/day. In one embodiment, the effective amount of an anti-SIRPα antibody is 15 mg/kg/day. In one embodiment, the effective amount of an anti-SIRPα antibody is 10 mg/kg/day. In one embodiment, the effective amount of an anti-SIRPα antibody is 5 mg/kg/day. In one embodiment, the effective amount of an anti-SIRPα antibody is 3 mg/kg/day. In one embodiment, the effective amount of an anti-SIRPα antibody is 1 mg/kg/day. In one embodiment, the effective amount of an anti-SIRPα antibody is 0.5 mg/kg/day. In one embodiment, the effective amount of an anti-SIRPα antibody is 0.3 mg/kg/day. In one embodiments, the effective amount of an anti-SIRPα antibody is 0.1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of the anti-SIRPα antibody or antigen-binding fragment thereof (e.g., SIRPAB-11-K322A) is administered is sufficient to provide a plasma concentration of the antibody at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the anti-SIRPα antibody or antigen-binding fragment thereof (e.g., SIRPAB-11-K322A) is administered is sufficient to provide a plasma concentration of the antibody at steady state, ranging from about 5 to about 100 nM, about 5 to about 50 nM, about 10 to about 100 nM, about 10 to about 50 nM, or from about 50 to about 100 nM.

As used herein, the term "plasma concentration at steady state" is the concentration reached after a period of administration of an anti-SIRPα antibody or antigen-binding fragment thereof provided herein. Once steady state is reached, there are minor peaks and troughs on the time dependent curve of the plasma concentration of the antibody.

In certain embodiments, the amount of the anti-SIRPα antibody or antigen-binding fragment thereof (e.g., SIRPAB-11-K322A) is administered is sufficient to provide a maximum plasma concentration (peak concentration) of the antibody, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the anti-SIRPα antibody or antigen-binding fragment thereof (e.g., SIRPAB-11-K322A) is administered is sufficient to provide a minimum plasma concentration (trough concentration) of the antibody, ranging from about 0.001 to about 500 μM, about 0.002 to about 200 μM, about 0..005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the anti-SIRPα antibody or antigen-binding fragment thereof (e.g., SIRPAB-11-K322A) is administered is sufficient to provide an area under the curve (AUC) of the antibody, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

The anti-SIRPα antibody or antigen-binding fragment thereof (e.g., SIRPAB-11-K322A) is provided herein can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that an anti-SIRPα antibody provided herein is administered once or more than once each day, for example, for a period of time. The term "continuous" is intended to mean that an anti-SIRPα antibody provided herein is administered daily for an uninterrupted period of at least 10 days to 52 weeks. The term "intermittent" or "intermittently" as used herein is intended to mean stopping and starting at either regular or irregular intervals. For example, intermittent administration of the anti-SIRPα antibody provided herein is administration for one to six days per week, administration in cycles (e.g., daily administration for two to eight consecutive weeks, then a rest period with no administration for up to one week), or administration on alternate days. The term "cycling" as used herein is intended to mean that an anti-SIRPα antibody provided herein is administered daily or continuously but with a rest period.

In some embodiments, the frequency of administration of an anti-SIRPα antibody provided herein (e.g., SIRPAB-11-K322A) is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, an anti-SIRPα antibody provided herein is administered once a day. In another embodiment, an anti-SIRPα antibody provided herein is administered twice a day. In yet another embodiment, an anti-SIRPα antibody provided herein is administered three times a day. In still another embodiment, an anti-SIRPα antibody provided herein is administered four times a day.

In certain embodiments, an anti-SIRPα antibody provided herein (e.g., SIRPAB-11-K322A) is administered once per day from one day to six months, from one week to three months, from one week to four weeks, from one week to three weeks, or from one week to two weeks. In certain embodiments, an anti-SIRPα antibody provided herein is administered once per day for one week, two weeks, three weeks, or four weeks. In one embodiment an anti-SIRPα antibody provided herein is administered once per day for one week. In another embodiment, an anti-SIRPα antibody provided herein is administered once per day for two weeks. In yet another embodiment, an anti-SIRPα antibody provided herein is administered once per day for three weeks. In still another embodiment, an anti-SIRPα antibody provided herein is administered once per day for four weeks. In certain embodiments, the dose is administered once per week.

In some embodiments, the effective amount of an anti-SIRPα antibody or antigen-binding fragment thereof (e.g., SIRPAB-11-K322A) is from about 0.001 to about 50 mg/kg, from about 0.01 to about 50 mg/kg, from about 0.01 to about 25 mg/kg, from about 0.01 to about 10 mg/kg, from about 0.01 to about 9 mg/kg, from about 0.01 to about 8 mg/kg, from about 0.01 to about 7 mg/kg, from about 0.01 to about 6 mg/kg, from about 0.01 to about 5 mg/kg, from about 0.01 to about 4 mg/kg, from about 0.01 to about 3 mg/kg, from about 0.01 to about 2 mg/kg, or from about 0.01 to about 1 mg/kg. In certain embodiments, the effective amount of an anti-SIRPα antibody or antigen-binding fragment thereof is about 0.001, about 0.003, about 0.005, about 0.01, about 0.03, about 0.05, about 0.1, about 0.3, about 0.5, about 1, about 3, about 5, about 10, about 30, or about 50 mg/kg. In one embodiment, the effective amount of an anti-SIRPα antibody or antigen-binding fragment thereof is 0.001 mg/kg. In one embodiment, the effective amount of an anti-SIRPα antibody or antigen-binding fragment thereof is 0.01 mg/kg. In one embodiment, the effective amount of an anti-SIRPα antibody or antigen-binding fragment thereof is 0.1 mg/kg. In another embodiment, the effective amount of an anti-SIRPα antibody or antigen-binding fragment thereof is 0.3 mg/kg. In another embodiment, the effective amount of an anti-SIRPα antibody or antigen-binding fragment thereof is 0.5 mg/kg. In yet another embodiment, the effective amount of an anti-SIRPα antibody or antigen-binding fragment thereof is 1 mg/kg. In still another embodiment, the effective amount of an anti-SIRPα antibody or antigen-binding fragment thereof is 3 mg/kg. In one embodiment, the effective amount of an anti-SIRPα antibody or antigen-binding fragment thereof is 5 mg/kg. In another embodiment, the effective amount of an anti-SIRPα antibody or antigen-binding fragment thereof is 10 mg/kg. In yet another embodiment, the effective amount of an anti-SIRPα antibody or antigen-binding fragment thereof is 30 mg/kg. In yet another embodiment, the effective amount of an anti-SIRPα antibody or antigen-binding fragment thereof is 50 mg/kg. In certain embodiments, the antibody is administered once per day. In certain embodiments, the antibody is administered once per week. In certain embodiments, the antibody is administered once per month.

In some embodiments, the effective amount of an anti-SIRPα antibody or antigen-binding fragment thereof provided herein is 25 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, or 4000 mg per dose. In some embodiments, the effective amount provided in this paragraph can be combined in any combination or permutation with any dosing frequency as provided herein, for example, once per day, once per week, once every two weeks, once every three weeks, or once every four weeks, or once per month. In some embodiments, the effective amount provided in this paragraph can be administered in any combination or permutation with any dosing frequency as provided herein, for example, once per day, once per week, once every two weeks, once every three weeks, or once every four weeks, or once per month, for any duration as provided herein, for example, for one week, two weeks, three weeks, four weeks, one month, two months, three months, four months, five months, six months, seven months, right months, nine months, ten months, eleven months, one year, one and half years, two years, two and half years, or three years.

In some embodiments, the frequency of administration of an anti-SIRPα antibody provided herein (e.g., SIRPAB-11-K322A) can be once every week, once every two weeks, once every three weeks, or once every four weeks. In one embodiment, an anti-SIRPα antibody provided herein is administered once every week. In another embodiment, an anti-SIRPα antibody provided herein is administered once every two weeks. In yet another embodiment, an anti-SIRPα antibody provided herein is administered once every three weeks. In still another embodiment, an anti-SIRPα antibody provided herein is administered once every four weeks.

In one embodiment, an anti-SIRPα antibody provided herein (e.g., SIRPAB-11-K322A) is administered once every week at a dosage of 0.1 mg/kg. In another embodiment, an anti-SIRPα antibody provided herein is administered once every week at a dosage of 0.3 mg/kg. In yet another embodiment, an anti-SIRPα antibody provided herein is administered once every week at a dosage of 0.5 mg/kg. In still another embodiment, an anti-SIRPα antibody provided herein is administered once every week at a dosage of 1 mg/kg. In one embodiment, an anti-SIRPα antibody provided herein is administered once every week at a dosage of 3 mg/kg. In another embodiment, an anti-SIRPα antibody provided herein is administered once every week at a dosage of 5 mg/kg. In yet another embodiment, an anti-SIRPα antibody provided herein is administered once every week at a dosage of 10 mg/kg. In still another embodiment, an anti-SIRPα antibody provided herein is administered once every week at a dosage of 30 mg/kg.

In one embodiment, an anti-SIRPα antibody provided herein (e.g., SIRPAB-11-K322A) is administered once every two weeks at a dosage of 0.1 mg/kg. In another embodiment, an anti-SIRPα antibody provided herein is administered once every two weeks at a dosage of 0.3 mg/kg. In yet another embodiment, an anti-SIRPα antibody provided herein is administered once every two weeks at a dosage of 0.5 mg/kg. In still another embodiment, an anti-SIRPα antibody provided herein is administered once every two weeks at a dosage of 1 mg/kg. In one embodiment, an anti-SIRPα antibody provided herein is administered once every two weeks at a dosage of 3 mg/kg. In another embodiment, an anti-SIRPα antibody provided herein is administered once every two weeks at a dosage of 5 mg/kg. In yet another embodiment, an anti-SIRPα antibody provided herein is administered once every two weeks at a dosage of 10 mg/kg. In still another embodiment, an anti-SIRPα antibody provided herein is administered once every two weeks at a dosage of 30 mg/kg.

In one embodiment, an anti-SIRPα antibody provided herein (e.g., SIRPAB-11-K322A) is administered once every three weeks at a dosage of 0.1 mg/kg. In another embodiment, an anti-SIRPα antibody provided herein is administered once every three weeks at a dosage of 0.3 mg/kg. In yet another embodiment, an anti-SIRPα antibody provided herein is administered once every three weeks at a dosage of 0.5 mg/kg. In still another embodiment, an anti-SIRPα antibody provided herein is administered once every three weeks at a dosage of 1 mg/kg. In one embodiment, an anti-SIRPα antibody provided herein is administered once every three weeks at a dosage of 3 mg/kg. In another embodiment, an anti-SIRPα antibody provided herein is administered once every three weeks at a dosage of 5 mg/kg. In yet another embodiment, an anti-SIRPα antibody provided herein is administered once every three weeks at a dosage of 10 mg/kg. In still another embodiment, an anti-SIRPα antibody provided herein is administered once every three weeks at a dosage of 30 mg/kg.

In one embodiment, an anti-SIRPα antibody provided herein (e.g., SIRPAB-11-K322A) is administered once every four weeks at a dosage of 0.1 mg/kg. In another embodiment, an anti-SIRPα antibody provided herein is administered once every four weeks at a dosage of 0.3 mg/kg. In yet another embodiment, an anti-SIRPα antibody provided herein is administered once every four weeks at a dosage of 0.5 mg/kg. In still another embodiment, an anti-SIRPα antibody provided herein is administered once every four weeks at a dosage of 1 mg/kg. In one embodiment, an anti-SIRPα antibody provided herein is administered once every four weeks at a dosage of 3 mg/kg. In another embodiment, an anti-SIRPα antibody provided herein is administered once every four weeks at a dosage of 5 mg/kg. In yet another embodiment, an anti-SIRPα antibody provided herein is administered once every four weeks at a dosage of 10 mg/kg. In still another embodiment, an anti-SIRPα antibody provided herein is administered once every four weeks at a dosage of 30 mg/kg.

Depending on the disease to be treated and the subject's condition, the anti-SIRPα antibody provided herein (e.g., SIRPAB-11-K322A) may be administered by parenteral (e.g., intramuscular, intrapetitoneal, intravenous, continuous intravenous, intracisternal injection or infusion, subcutaneous injection, or implant), inhalation, nasal, vaginal, rectal, sublingual, or topical (e.g., transdermal or local) routes of administration. In one embodiment, the administration route is subcutaneous. In another embodiment, the administration route is intravenous. In yet another embodiment, the administration route is intramuscular. In still another embodiment, the administration route is intraperitoneal. In one embodiment, the administration route is continuous intravenous. In another embodiment, the administration route is intracisternal injection or infusion. In yet another embodiment, the administration route is implant. In still another embodiment, the administration route is inhalation. In one embodiment, the administration route is nasal. In another embodiment, the administration route is rectal. In yet another embodiment, the administration route is sublingual. In still another embodiment, the administration route is transdermal. Any anti-SIRPα antibody provided herein may be formulated, alone or together, in suitable dosage unit with pharmaceutically acceptable excipients, carriers, adjuvants, and vehicles, appropriate for each route of administration.

In some embodiments of the various methods provided herein, the method further comprises administering a therapeutically effective amount of a second active agent or a support care therapy. Second active agents can be large molecules (e.g., proteins) or small molecules (e.g., synthetic inorganic, organometallic, or organic molecules). In some embodiments, the second active agents are small molecules that can alleviate adverse effects associated with the administration of an antibody provided herein. However, like some large molecules, many are believed to be capable of providing a synergistic effect when administered with (e.g., before, after or simultaneously) an antibody provided herein. Examples of small molecule second active agents include, but are not limited to, anti-cancer agents, anti-inflammatory agents, immunosuppressive agents, and steroids. In a one embodiment, the second active agent is an anti-EGFR antibody. In a certain embodiment, the second active agent is cetuximab. In a one embodiment, the second active agent is an anti-CD20 antibody. In another embodiment, the second active agent is rituximab.

4.5 Pharmaceutical Compositions

In one aspect, the present disclosure further provides pharmaceutical compositions comprising at least one anti-SIRPα antibody provided herein. In some embodiments, a pharmaceutical composition comprises 1) an anti-SIRPα antibody, and 2) a pharmaceutically acceptable carrier.

Pharmaceutical compositions comprising an antibody are prepared for storage by mixing the antibody having the desired degree of purity with optional physiologically acceptable carriers, excipients, or stabilizers (see, e.g., Remington, *Remington's Pharmaceutical Sciences* (18th ed, 1980)) in the form of aqueous solutions or lyophilized or other dried forms.

The antibodies of the present disclosure may be formulated in any suitable form for delivery to a target cell/tissue, e.g., as microcapsules or macroemulsions (Remington, supra; Park et al., 2005, Molecules 10:146-61; Malik et al., 2007, Curr. Drug. Deliv. 4:141-51), as sustained release formulations (Putney and Burke, 1998, Nature Biotechnol. 16:153-57), or in liposomes (Maclean et al., 1997, Int. J. Oncol. 11:325-32; Kontermann, 2006, Curr. Opin. Mol. Ther. 8:39-45).

An antibody provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles, and nano-capsules) or in macroemulsions. Such techniques are disclosed, for example, in Remington, supra.

Various compositions and delivery systems are known and can be used with an antibody that binds to SIRPα as described herein, including, but not limited to, encapsulation in liposomes, microparticles, microcapsules, recombinant cells capable of expressing the antibody, receptor-mediated endocytosis (see, e.g., Wu and Wu, 1987, J. Biol. Chem. 262:4429-32), construction of a nucleic acid as part of a retroviral or other vector, etc. In another embodiment, a composition can be provided as a controlled release or sustained release system. In one embodiment, a pump may be used to achieve controlled or sustained release (see, e.g., Langer, supra; Sefton, 1987, Crit. Ref. Biomed. Eng. 14:201-40; Buchwald et al., 1980, Surgery 88:507-16; and Saudek et al., 1989, N. Engl. J. Med. 321:569-74). In another embodiment, polymeric materials can be used to achieve controlled or sustained release of a prophylactic or therapeutic agent (e.g., an antibody that binds to SIRPα as described herein) or a composition of the invention (see, e.g., *Medical Applications of Controlled Release* (Langer and Wise eds., 1974); *Controlled Drug Bioavailability, Drug Product Design and Performance* (Smolen and Ball eds., 1984); Ranger and Peppas, 1983, J. Macromol. Sci. Rev. Macromol. Chem. 23:61-126; Levy et al., 1985, Science 228:190-92; During et al., 1989, Ann. Neurol. 25:351-56; Howard et al., 1989, J. Neurosurg. 71:105-12; U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of a particular target tissue, for example, the nasal passages or lungs, thus requiring only a fraction of the systemic dose (see, e.g., Goodson, *Medical Applications of Controlled Release* Vol. 2, 115-38 (1984)). Controlled release systems are discussed, for example, by Langer, 1990, Science 249:1527-33. Any technique known to one of skill in the art can be used to produce sustained release formulations comprising one or more antibodies that bind to SIRPα as described herein (see, e.g., U.S. Pat. No. 4,526,938, PCT publication Nos. WO 91/05548 and WO 96/20698, Ning et al., 1996, Radiotherapy & Oncology 39:179-89; Song et al., 1995, PDA J. of Pharma. Sci. & Tech. 50:372-97; Cleek et al., 1997, Pro. Int'l. Symp. Control, Rel. Bioact. Mater. 24:853-54; and Lam et al., 1997, Proc. Int'l. Symp. Control Rel. Bioact. Mater. 24:759-60).

4.6 Kits

Also provided herein are kits comprising an antibody (e.g., an anti-SIRPα antibody) provided herein, or a composition (e.g., a pharmaceutical composition) thereof, packaged into suitable packaging material. A kit optionally includes a label or packaging insert including a description of the components or instructions for use in vitro, in vivo, or ex vivo, of the components therein.

The term "packaging material" refers to a physical structure housing the components of the kit. The packaging material can maintain the components sterilely, and can be made of material commonly used for such purposes (e.g., paper, corrugated fiber, glass, plastic, foil, ampoules, vials, tubes, etc.).

Kits provided herein can include labels or inserts. Labels or inserts include "printed matter," e.g., paper or cardboard, separate or affixed to a component, a kit or packing material (e.g., a box), or attached to, for example, an ampoule, tube, or vial containing a kit component. Labels or inserts can additionally include a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media, or memory type cards. Labels or inserts can include information identifying manufacturer information, lot numbers, manufacturer location, and date.

Kits provided herein can additionally include other components. Each component of the kit can be enclosed within an individual container, and all of the various containers can be within a single package. Kits can also be designed for cold storage. A kit can further be designed to contain antibodies provided herein, or cells that contain nucleic acids encoding the antibodies provided herein. The cells in the kit can be maintained under appropriate storage conditions until ready to use.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to "a peptide sequence" includes a plurality of such sequences and so forth.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth, Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%. 92.5%, etc., and so forth.

In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1,000, 1,000-2,500, 2,500-5,000, 5,000-25,000, 25,000-50,000 includes any numerical value or range within or encompassing such values, e.g., 25, 26, 27, 28, 29 . . . 250, 251, 252, 253, 254 . . . 500, 501, 502, 503, 504 . . . , etc.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

Aspects of the disclosure and the numerous embodiments are generally described herein using affirmative language. Aspects of the disclosure also specifically include embodiments in which particular subject matter is excluded, in full or in part, such as substances or materials, method steps and conditions, protocols, procedures, assays or analysis. Thus, even though the disclosure is generally not expressed herein in terms of what the disclosure does not include, aspects that are not expressly included in the various embodiments or descriptions of the disclosure are nevertheless disclosed herein.

A number of embodiments have been described. Nevertheless, it will be understood that various modifications may be made without departing from the spirit and scope of the disclosure. Accordingly, the following examples are intended to illustrate but not limit the scope as described in the claims.

5. EXAMPLES

The examples in this section (i.e., Section 5) are offered by way of illustration, and not by way of limitation.

5.1 Example 1: Generation of Anti-SIRPα Antibodies

5.1.1 Generation of Anti-SIRPα Antibodies

Screening and discovery of fully human immunoglobulin G (IgG) antibodies against SIRPα was performed by utilizing yeast display platform (FIG. 1). Recombinant human SIRPα extracellular domain (ECD) was used as bait to isolate binders from eight libraries totaling ~1010 fully human IgG antibodies expressed on yeast cells. Heavy chains (HCs) from selection outputs were further shuffled against nine light chain (LC) libraries for additional diversity. Successive rounds of selective sorting yielded more than 1300 naïve isolates for sequencing and were further triaged down to 564 for production, binding, and CD47-blocking analysis. Testing identified seven naïve IgG binders for affinity maturation; focused complementarity-determining region heavy chain (CDRH)1 and CDRH2 libraries for each lineage (each >$10^8$) were paired with corresponding light chains and screened for high-affinity human and cyno SIRPα binders. Greater than 350 "offsprings" from 6 parental lineages were sequenced and produced for characterization towards SIRPα binding, polymorphic coverage, and cross-reactivity profiles. The top 24 clones, across six lineages, were delivered for internal characterization, including cell binding, affinity determination by surface plasmon resonance (SPR), ligand blocking, and in vitro functional assays. (See FIG. 1 for an outline of the process)

Incorporating EpiVax immunogenicity analysis with polyspecificity reagent (PSR) developability scoring matrix, as described in Xu Y, et al., Protein Eng Des Sel. 2013 October;26(10):663-70 (which is hereby incorporated in its entirety by reference), SIRPAB-11 was identified as an exemplary anti-SIRPα clone, having potent affinity toward SIRPα and SIRPγ, cellular activity, and favorable cynomolgus cross reactivity profile (described further below). This clone was chosen for further Fc variant engineering to assess Fc effector function requirements and additional in vitro and in vivo testing.

5.1.2 Generation of Anti-SIRPα Antibodies with High SIRPα Haplotype Coverage Polymorphism analysis of the SIRPα IgV-domain, especially residues spanning the CD47 binding interface, has identified several haplotypes covering >95% of the polymorphisms in the CD47 binding interface in the human population (Takenaka K, et al., Nat Immunol. 2007 Dece, ber;8(12):1313-23). As part of the screening campaign, the most prevalent haplotype (SIRPα V1:DLN, FIG. 2) was utilized for the first round screen, with follow-up affinity maturation towards the top two polymorphisms (SIRPα V1:DLN and SIRPα V2:ESE, FIG. 2). As part of the in vitro assessment, binding $K_D$ for each antibody was performed across the top six haplotypes (FIG. 2), including SIRPα v1 comprising SEQ ID NO:149 in the IgV-domain, SIRPα v2 comprising SEQ ID NO:150 in the IgV-domain, SIRPα v3 comprising SEQ ID NO:151 in the IgV-domain, SIRPα v4 comprising SEQ ID NO:152 in the IgV-domain, SIRPα v5 comprising SEQ ID NO:153 in the IgV-domain, and SIRPα v6 comprising SEQ ID NO:154 in the IgV-domain (see further below for affinity measurements). As a result, the SIRPAB-11 has a profile of pan-binding coverage across >95% of SIRPα polymorphisms in the CD47 binding interface in human.

5.13 Generation of Variants of Anti-SIRPα Antibodies

For subsequent antibody studies, the anti-SIRPα antibody VH/VL pair was generated. To generate the anti-SIRPα antibody, the VL was fused to a WT human kappa constant region, the VH was fused to a human IgG1 Fc region. SIRPAB-11 IgG1 antibody (SIRPAB-11-IgG1 or SIRPAB-11), and the Fc modified variants such as IgG4PE antibody (SIRPAB-11-4PE) were generated. SIRPAB-11-4PE was designed to have significantly lower Fc-mediated effector function. The CH region, γ4 contains two non-standard amino acids substitutions, S228P and L235E (EU numbering systems, Kabat and Wu, J Immunol. 1991 September 1;147 (5):1709-19 Kabat et al., Sequences of Proteins of Immunological Interest (5th ed. 1991)). Serine 228, a common amino acid type in the hinge of IgG4, was changed to proline, a less commonly observed amino acid type in IgG4 and highly conserved amino acid in IgG1. This change significantly reduced the level of "half-antibody" that is commonly observed in the production of IgG4-subclass antibody. Leucine 235, one of the critical amino acids involved in heavy chain interactions with Fcγ receptors was changed to glutamic acid. The L235E substitution significantly reduced the interaction of γ4 chain to FcγR, eliminating ADCC and Fc-receptor-mediated elimination of SIRPα-expressing normal cells. In addition, inherent lack of complement binding by γ4 heavy chain renders the SIRPAB-11-4PE molecule devoid of CDC function.

Two other variants were generated to minimize binding affinity to C1q for reduced CDC. To generate SIRPAB-11-K322A, lysine 322 was substituted with alanine in SIRPAB-11-IgG1. The K322A substitution is reported to suppress C1q binding on rituximab, a chimeric antibody with a human IgG1 Fc (Idusogie et al., 2000, J. Immunol. 164(8): 4178-84). SIRPAB-11-4P was generated by converting the Fc-backbone of the SIRPAB-11-IgG1 to the Fc-backbone of IgG4 with S228P substitution. The S228P substitution significantly reduces the level of half-antibody that is frequently observed in the production of IgG4-subclass antibody. IgG4 antibody was reported to have attenuated ADCC and CDC function (Overdijk et al, 2012, J. Immunol. 189(7):3430-38). SIRPAB-11-4PE was generated by converting the Fc-backbone of the SIRPAB-11-IgG1 to the Fc-backbone of IgG4 with S228P and L235E substitutions. All changes were created in the CH region with no changes in the variable regions. The amino acid sequences of the light and heavy chains of SIRPAB-11-IgG1 are referred to as LC_SIRPAB-11-IgG1 and HC_SIRPAB-11-IgG1, respectively. The two heavy chain variants include HC_SIRPAB-11-IgG1-K322A and HC_SIRPAB-11-IgG4PE. The light chain LC_SIRPAB-11-IgG1 is paired with the three individual heavy chains to generate SIRPAB-11-IgG1 (SEQ ID NO:142), SIRPAB-11-K322A (SEQ ID NO:119), and SIRPAB-11-4PE (SEQ ID NO:120), respectively. Other antibodies and variants, such as the heavy chains of SIRPAB-11-4P (SEQ ID NO:112), SIRPAB-11-AAS (SEQ ID NO:98), SIRPAB-12 (SEQ ID NO:204), and corresponding variants of SIRPAB-12 were similarly generated.

All variants of SIRPAB-11 were generated by standard mutagenesis method (e.g., site-directed mutagenesis) or by fusing VH to a variant human IgG Fc. For example, the heavy chain of SIRPAB-11-K322A was also generated by fusing VH to a human IgG1 Fc with a lysine to alanine amino acid substitution at position 322 (SEQ ID NO:119, having K322A mutation, EU numbering systems; Kabat, et al., J Immunol. 1991 September 1;147(5):1709-19).

5.1.4 Generation of Anti-Mouse-SIRPα Antibodies

The anti-SIRPα antibodies generated in the above described campaign using recombinant human SIRPα as antigen did not bind to rodent (e.g. mouse) SIRPα (FIG. 3). Therefore, a sub-discovery campaign was performed to identify antibodies against WT C57/BL6 or NOD-SCID SIRPα. Initial rounds of mouse SIRPα selection identified two antibodies (SIRPAB-5 and SIRPAB-17) demonstrating NOD-SCID SIRPα binding (FIG. 3). Additional affinity maturation with SIRPAB-17 resulted in six progeny binders with significantly improved WT and NOD-SCID SIRPα binding affinity. Three exemplary clones, SIRPAB-19, SIRPAB-20, and SIRPAB-21 were further assessed for binding affinities and CD47-blocking activities (see below). Each was fused with mIgG2a Fc for in vitro and in vivo efficacy studies.

5.2 Example 2: Characterization of Anti-SIRPα Antibodies

5.2.1 Characterization of Binding Properties of Anti-Human-SIRPα Antibodies Initial characterizations for antibody binding to human or cyno SIRPα cell were performed with SIRPAB-11-4PE, an IgG4PE Fc variant designed to have attenuated FcγR effector function. CHO cells overexpressing either human or cyno SIRPα were obtained by stable transfection or transient transfection. Serially-diluted antibodies were added to cells, followed by washing and additional incubation with a secondary anti-human IgG-AF647 detection antibody. Levels of antibody binding were analyzed by determining the mean fluorescence intensity (MEI) by flow cytometry. SIRPAB-11-K322A binds to human SIRPα-CHO cells with an $EC_{50}$ of 2.06 nM and cyno SIRPα-CHO at an $EC_{50}$ of 1.9 nM, and does not bind to rat or mouse SIRPα-CHO (FIG. 4A-4D).

In other assays, purified SIRPAB-11-K322A antibody was analyzed on Biacore T200 for binding to SIRPα v1-DLN (e.g. SIRPα1), SIRPβ and SIRPγ antigens using capture method. To perform the binding assays, extracellular domain of SIRPα v1-DLN (e.g. SIRPα1) with the sequence of SEQ ID NO:101, SIRPβ with the sequence of MPVPASWPHLPSPFLLMTLLLGRLTGVAGEDELQVIQ-PEKSVSVAAGESATLCCAMTSLIPVGP IMWFR-GAGAGRELIYNQKEGHFPRVTTVSELTKRNNLDFSIS ISNITPADAGTYYCVKFRKGSP DDVEFKSGAG-TELSVRAKPSAPVVSGPAVAATPEHTVSFT-CESHGFSPRDITLKWFKNGNSLSD FQTNVDPAGDSV-SYSIHSTAPVVLTRGDVHSQVICEMAHITLQGDPLRG TANLSEAIRVPPTLE VTQQPMRAE-NQANVTCQVSNFYPRGLQLTWLENGNVSRTETAST-LIENKDGTYNWMSWLLVNTCC AHRDDVVLTCQVEHDGQQAVSKSYALEI-SAHQKEHGSDITHEPALAPTAPL (SEQ ID NO:108), and SIRPγ with the sequence of MPVPASWPHPPGP-FLLLTLLLGLTEVAGEEELQMIQPEKLLLVTVGK-TATLHCTVTSLLPVGPV LWFRGVGPGRELIYNQKEG-HFPRVTTVSDLTKRNNMDFSIRISSITPADVGTYYCVK FRKGSPE NVEFKSGPGTEMALGAKP-SAPVVLGPAARTTPEHTVSFT-CESHGFSPRDITLKWFKNGNELSDF QTNVDPTGQSVAYSIRSTAPVVLDPWDVRSQVICE-VAHVTLQGDPLRGTANLSEAIRVPPTLEV TQQPMRVGNQVNVTCQVRKFYPQSLQLTWSSNG-NVCQRETASTLTENKDGTYNWTSWFLVNISD QRDDVVLTCQVKHDGQLAVSKRLA-LEVTVHQKDQSSDATP (SEQ ID NO:114) were prepared.

A Protein A chip from GE Healthcare (catalog number 29127556) was used to capture antibody, purified SIRPAB-11-K322A antibody was captured on channel 2, and SIRP antigens were flowed over on both channel 1 and 2 using five-fold dilution series from 20 nM to 0.16 nM to determine kinetics of binding. Surface of the chip was regenerated between each antigen concentration using 10 mM glycine, pH 1.5. An example of $k_a$, $k_d$, and the calculated $K_D$ for SIRPAB-11-K322A antibody and SIRPα, SIRPβ, and SIRPγ are shown in Table 15 below.

TABLE 15

| Biacore measurements of binding parameters between SIRPAB-11-K322A and each of SIRPα, SIRPβ, and SIRPγ | | | |
|---|---|---|---|
| | SIRPAB-11-K322A binding to SIRPα | SIRPAB-11-K322A binding to SIRPβ | SIRPAB-11-K322A binding to SIRPγ |
| $k_a$ (association rate constant) | $7.75 \times 10^6$ (1/Ms) | $5.06 \times 10^4$ (1/Ms) | $1.71 \times 10^7$ (1/Ms) |
| $k_d$ (dissociation rate constant) | $1.18 \times 10^{-4}$ (1/s) | $6.14 \times 10^{-4}$ (1/s) | $1.88 \times 10^{-4}$ (1/s) |
| $K_D$ (equilibrium constant) | $1.52 \times 10^{-11}$ M | $1.21 \times 10^{-8}$ M | $1.01 \times 10^{-11}$ M |
| Rmax (RU = response unit) | 12.48 RU | 30.09 RU | 9.4 RU |

Additionally, affinities between the anti-SIRPα antibodies and six most prevalent human SIRPα haplotypes (including SIRPα v1 to v6 as described above, SEQ ID NOs:101, 103,105, 93, 95, 97), human SIRPβ (SEQ ID NO:108), human SIRPγ (SEQ ID NO:114), cyno SIRPα (SEQ ID NO:115), mouse SIRPα (SEQ ID NO:102), and NOD/SCID mouse SIRPα (SEQ ID NO:100) were determined and compared in Octet Systems (from Pall ForteBio). The various SIRPα, β, and γ constructs were fused via a GS (glycine-serine) linker to human IGHG1_Fc having the sequence of DKTHTCPPCPA-PELLGGPSVFLFPPKPKDTLMISRTPE-VTCVVVDVSHEDPEVKFNWYVDGVEV HNAKTKPRE- (SEQ ID NO:109). The resulting fusion proteins, including various human SIRPα-Fc, cyno SIRPα-Fc (SEQ ID NO:104), human SIRPβ-Fc (SEQ ED NO:92), human SIRPγ-Fc (SEQ ID NO:113), mouse SIRPα-Fc (SEQ ID NO:96), and NOD/SCID mouse SIRPα-Fc (SEQ ID NO:94) were prepared and used for affinity measurements in Octet. The measurements from Octet Systems are useful for studying interactions of a large number of binding pairs in a high-throughput format and comparing the interactions of the various binding pairs. Briefly, the antigens were captured on the biosensors and dipped into solutions containing the antibodies for high-throughput measurements. The results, including the $k_{on}$, $k_{off}$, and $K_D$, were summarized in Table 16.

TABLE 16

Summary Binding Profile of Anti-human SIRPα Antibodies

| Antibodies | Measurements | Binding of SIRPABs to Human SIRPα, SIRPβ, or SIRPγ | | | | | | | | Cross-Reactivity $K_D$ (nM) | |
|---|---|---|---|---|---|---|---|---|---|---|---|
| | | V1 (e.g. SIRPα1) | V2 (e.g. SIRPα2) | V3 (e.g. SIRPα3) | V4 (e.g. SIRPα4) | V5 (e.g. SIRPα5) | V6 (e.g. SIRPα6) | SIRPβ | SIRPγ | Cyno | Ms |
| SIRPAB-1 | Binding $K_D$ (nM) | 2.95 | 44.22 | 54.8 | N.B | 11.3 | 54.9 | 4.61 | 1.43 | P.F. | 29 |
| | $k_{on}$ (M$^{-1}$s$^{-1}$) (×10$^6$) | 0.98 | 0.13 | 0.085 | — | 1.17 | 0.11 | 0.89 | 1.04 | — | 0.41 |
| | $K_{off}$ (s$^{-1}$) (×10$^{-4}$) | 28.9 | 57.2 | 46.4 | — | 132 | 57.9 | 41.1 | 14.9 | — | 119 |
| SIRPAB-2 | Binding $K_D$ (nM) | 0.299 | 10.7 | 12.2 | 32.6 | 1.95 | 11.9 | 0.89 | 0.14 | 19.3 | P.F. |
| | $k_{on}$ (M$^{-1}$s$^{-1}$) (×10$^6$) | 1.39 | 0.69 | 0.61 | 0.922 | 1.43 | 0.75 | 1.24 | 1.46 | 0.811 | — |
| | $K_{off}$ (s$^{-1}$) (×10$^{-4}$) | 4.13 | 73.9 | 73.7 | 301 | 28 | 89.1 | 11.1 | 2 | 157 | — |
| SIRPAB-3 | Binding $K_D$ (nM) | 0.2 | P.F. | 10.5 | P.F. | 0.9 | 9.47 | 0.22 | 0.118 | 7.95 | 12.6 |
| | $k_{on}$ (M$^{-1}$s$^{-1}$) (×10$^6$) | 1.55 | | 0.64 | | 2.26 | 1.21 | 1.43 | 1.69 | 1.07 | 1.04 |
| | $K_{off}$ (s$^{-1}$) (×10$^{-4}$) | 3.1 | | 67.6 | | 20.3 | 114 | 3.19 | 2 | 85 | 131 |
| SIRPAB-4 | Binding $K_D$ (nM) | 0.45 | 18.2 | 19 | P.F. | 2.51 | 15.4 | 1.00 | 0.144 | 18 | 72.8 |
| | $k_{on}$ (M$^{-1}$s$^{-1}$) (×10$^6$) | 1.29 | 0.74 | 0.61 | | 1.52 | 0.88 | 1.21 | 1.39 | 0.82 | 0.13 |
| | $K_{off}$ (s$^{-1}$) (×10$^{-4}$) | 5.82 | 134 | 57 | | 38.1 | 136 | 12.1 | 2 | 149 | 95.3 |
| SIRPAB-5 | Binding $K_D$ (nM) | 0.165 | 27.5 | 9.34 | P.F. | 0.526 | 7.96 | 0.15 | 0.154 | 5.42 | 7.51 |
| | $k_{on}$ (M$^{-1}$s$^{-1}$) (×10$^6$) | 1.22 | 0.55 | 0.61 | | 1.6 | 0.837 | 1.33 | 1.3 | 0.775 | 0.628 |
| | $K_{off}$ (s$^{-1}$) (×10$^{-4}$) | 2.02 | 151 | 57 | | 8.43 | 66.6 | 2.00 | 2 | 42 | 47.2 |
| SIRPAB-6 | Binding $K_D$ (nM) | 6.07 | N.B. | 77.8 | 63.3 | 38.6 | N.B. | P.F. | 8.36 | P.F. | N.B. |
| | $k_{on}$ (M$^{-1}$s$^{-1}$) (×10$^6$) | 1.13 | | 0.161 | 0.60 | 0.985 | | | 1.14 | | |
| | $K_{off}$ (s$^{-1}$) (×10$^{-4}$) | 68.7 | | 125 | 378 | 381 | | | 95.3 | | |
| SIRPAB-7 | Binding $K_D$ (nM) | 0.15 | 13.2 | 10.2 | 0.95 | 0.66 | 12.2 | 2.56 | 0.1 | 4.59 | P.F. |
| | $k_{on}$ (M$^{-1}$s$^{-1}$) (×10$^6$) | 1.84 | 0.73 | 0.702 | 1.74 | 2.17 | 0.907 | 1.53 | 1.94 | 1.19 | |
| | $K_{off}$ (s$^{-1}$) (×10$^{-4}$) | 2.71 | 95.6 | 71.8 | 16.5 | 14.3 | 111 | 39.1 | 2 | 54.6 | |
| SIRPAB-8 | Binding $K_D$ (nM) | P.F. | N.B. | 22.3 | P.F. | P.F. | P.F. | P.F. | P.F. | N.B. | N.B. |
| | $k_{on}$ (M$^{-1}$s$^{-1}$) (×10$^6$) | | | 1.02 | | | | | | | |
| | $K_{off}$ (s$^{-1}$) (×10$^{-4}$) | | | 226 | | | | | | | |
| SIRPAB-9 | Binding $K_D$ (nM) | 0.714 | 23.0 | 0.53 | 7.69 | 4.75 | 1.56 | 2.79 | 1.37 | 18.8 | N.B. |
| | $k_{on}$ (M$^{-1}$s$^{-1}$) (×10$^6$) | 1.06 | 0.81 | 0.98 | 1.01 | 0.97 | 1.17 | 1.02 | 1.17 | 1.13 | |
| | $K_{off}$ (s$^{-1}$) (×10$^{-4}$) | 7.57 | 185 | 5.15 | 77.7 | 46.2 | 18.2 | 28.4 | 16.1 | 212 | |
| SIRPAB-10 | Binding $K_D$ (nM) | 0.25 | 1.06 | 0.21 | 1.93 | 1.58 | 0.38 | 0.34 | 0.85 | 4.89 | N.B. |
| | $k_{on}$ (M$^{-1}$s$^{-1}$) (×10$^6$) | 1.4 | 1.25 | 1.24 | 1.38 | 1.13 | 1.28 | 1.40 | 1.45 | 1.40 | |
| | $K_{off}$ (s$^{-1}$) (×10$^{-4}$) | 3.45 | 13.2 | 2.61 | 26.7 | 17.8 | 4.91 | 4.77 | 12.3 | 68.3 | |
| SIRPAB-11 | Binding $K_D$ (nM) | 0.13 | 4.4 | 0.145 | 1.52 | 0.611 | 0.183 | 0.32 | 0.13 | 4.9 | N.B. |
| | $k_{on}$ (M$^{-1}$s$^{-1}$) (×10$^6$) | 1.49 | 1.27 | 1.38 | 1.50 | 1.73 | 1.94 | 1.49 | 1.57 | 1.77 | |
| | $K_{off}$ (s$^{-1}$) (×10$^{-4}$) | 2 | 55.9 | 2 | 22.8 | 10.6 | 3.56 | 4.73 | 2.05 | 86.9 | |
| SIRPAB-12 | Binding $K_D$ (nM) | 0.81 | 15.4 | 0.53 | 8.13 | 4.87 | 1.58 | 3.35 | 1.49 | P.F. | N.B. |
| | $k_{on}$ (M$^{-1}$s$^{-1}$) (×10$^6$) | 1.31 | 0.98 | 1.31 | 1.35 | 1.43 | 1.63 | 1.33 | 1.46 | | |
| | $K_{off}$ (s$^{-1}$) (×10$^{-4}$) | 10.7 | 151 | 6.94 | 109 | 69.7 | 25.6 | 44.5 | 21.8 | | |
| SIRPAB-13 | Binding $K_D$ (nM) | 1.65 | 17.2 | 0.83 | 11.4 | 7.73 | 2.71 | 4.52 | 4.12 | 14.9 | N.B. |
| | $k_{on}$ (M$^{-1}$s$^{-1}$) (×10$^6$) | 1.24 | 1.00 | 1.17 | 1.2 | 1.16 | 1.35 | 1.21 | 1.35 | 1.32 | |
| | $K_{off}$ (s$^{-1}$) (×10$^{-4}$) | 20.5 | 172 | 9.65 | 137 | 892 | 36.4 | 54.4 | 55.8 | 197 | |

SIRPABs = anti-SIRPα antibodies;
Cyno = cynomolgus;
Ms = mouse;
N.B. = no binding;
P.F. = poor fit, indicating inaccurate measurements EQYASTYRVVSVLTVLHQDWLNGKEYKCKVSNKA-LPAPIEKTISKAKGQPREPQV YTLPPSRDELT-KNQVSLTCLVKGFYPSDIAVEWESNGQPENNYKTTPP VLDSDGSFFLYSKLTV DKSRWQQGNVFSCSVMHEALHNHYTQKSLSLSPGK Binding between certain SIRPα antibodies that capable of binding to mouse SIRPα and mouse SIRPα-Fc (SEQ ID NO:96) or NOD/SCID mouse SIRPα-Fc (SEQ ID NO:94), was also determined in Octet Systems (from Pall ForteBio) as described above. In additional experiments, the binding between certain SIRPα antibodies that capable of binding to mouse SIRPα and CHO-K1 cells expressing mouse SIRPα were also determined as fold increase over background at the concentration of 100 nM antibodies. The results from the Octet binding assays and CHO cell binding assays were summarized in Table 17 below.

Additionally, surface lymphoid and myeloid lineage markers were used to define primary human immune cell subsets: monocytes (CD14+CD19−); B cells (CD14−CD19+); T cells (CD14−CD19−CD56−CD3+); natural killer (NK) cells (CD14−CD19−CD56+CD3−). Cynomolgus macaque surface marker cross-reactive clones were

TABLE 17

Summary of Binding between Some Anti-SIRPα Antibodies and Mouse SIRPα

| Abs | Ms SIRPα-Fc | | | NOD/SCID Ms SIRPα-Fc | | | Ms SIRPα-CHO-K1 Cell Binding-Fold Increase Over Background (100 nM) |
|---|---|---|---|---|---|---|---|
| | Binding $K_D$ (nM) | $k_{on}$ ($M^{-1}s^{-1}$) (×10$^6$) | $K_{off}$ ($s^{-1}$) (×10$^{-4}$) | Binding $K_D$ (nM) | $k_{on}$ ($M^{-1}s^{-1}$) (×10$^6$) | $K_{off}$ ($s^{-1}$) (×10$^{-4}$) | |
| SIRPAB-17 | 17.3 | 0.22 | 37.3 | 152 | 0.15 | 228 | 448.7 |
| SIRPAB-18 | 2.2 | 0.29 | 6.45 | 28.1 | 0.16 | 45.8 | 2513 |
| SIRPAB-19 | 1.02 | 0.64 | 6.56 | 4.02 | 0.46 | 18.3 | 2737 |
| SIRPAB-20 | 0.39 | 0.76 | 2.92 | 3.84 | 0.53 | 20.2 | 4393 |
| SIRPAB-21 | 1.46 | 0.49 | 7.08 | 5.43 | 0.35 | 19.0 | 2439 |

Abs = antibodies;
Ms = mouse

Similarly, the binding between SIRPα antibodies and CHO-K1 cells expressing cyno or human SIRPα was also determined as fold increase over background at the concentration of 100 nM antibodies and shown in Table 18 below:

TABLE 18

Summary of Binding Between Anti-SIRPα Antibodies and CHO-K1 cells expressing cyno or human SIRPα.

| Antibodies | Hu SIRPα- CHO-K1 Cell Binding- Fold Increase Over Background (100 nM) | Cyno SIRPα-CHO-K1 Cell Binding- Fold Increase Over Background (100 nM) |
|---|---|---|
| SIRPAB-1 | 1762 | 1610 |
| SIRPAB-2 | 1982 | 2116 |
| SIRPAB-3 | 2048 | 2284 |
| SIRPAB-4 | 1582 | 1583 |
| SIRPAB-5 | 2259 | 2679 |
| SIRPAB-6 | 1981 | 1538 |
| SIRPAB-7 | 2100 | 2391 |
| SIRPAB-8 | 1310 | 1023 |
| SIRPAB-9 | 2649 | 2295 |
| SIRPAB-10 | 1168 | 1068 |
| SIRPAB-11 | 1894 | 1951 |
| SIRPAB-12 | 2347 | 2216 |
| SIRPAB-13 | 1940 | 1948 |

Hu = human.

Figure 5A:
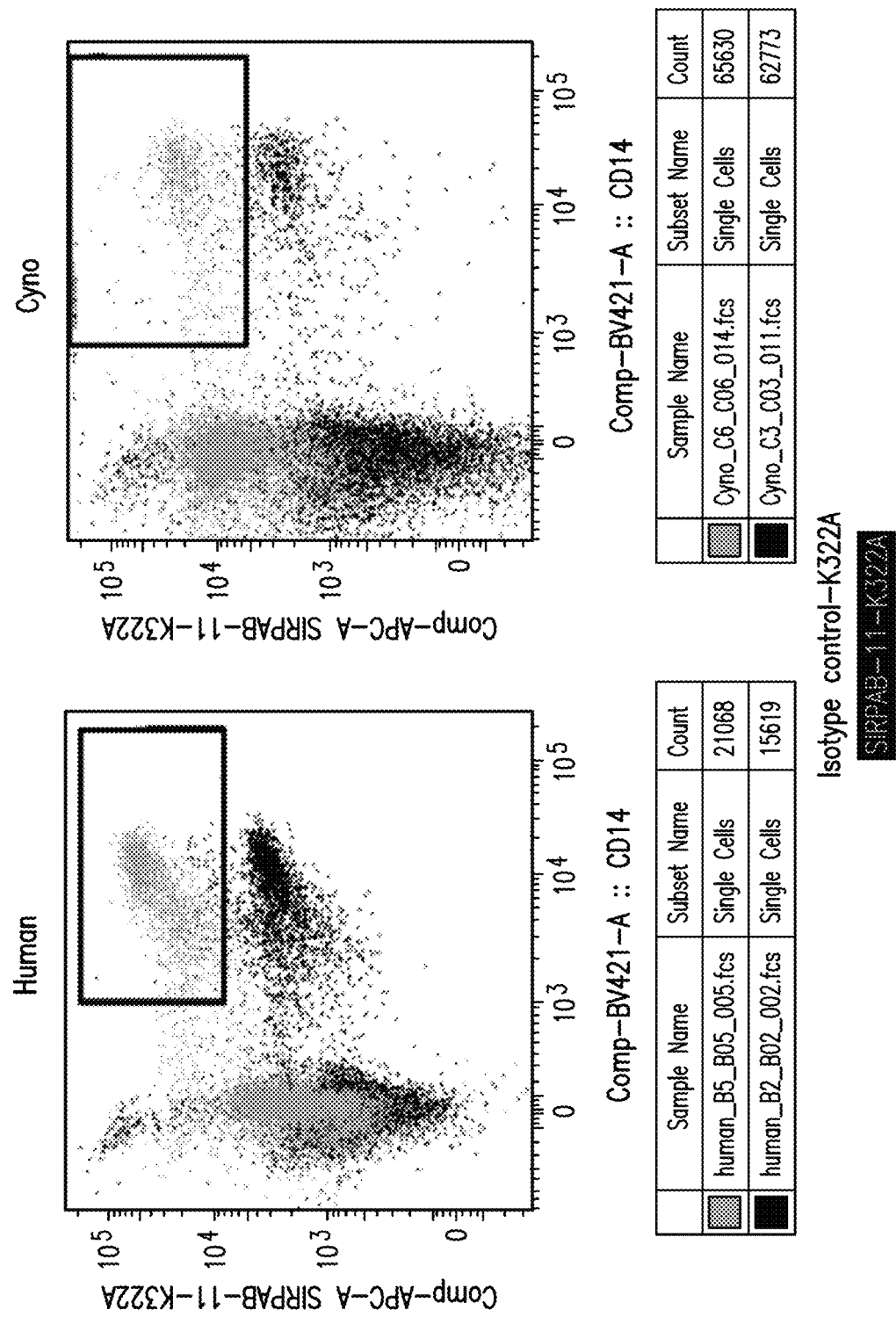
Figure 5D:
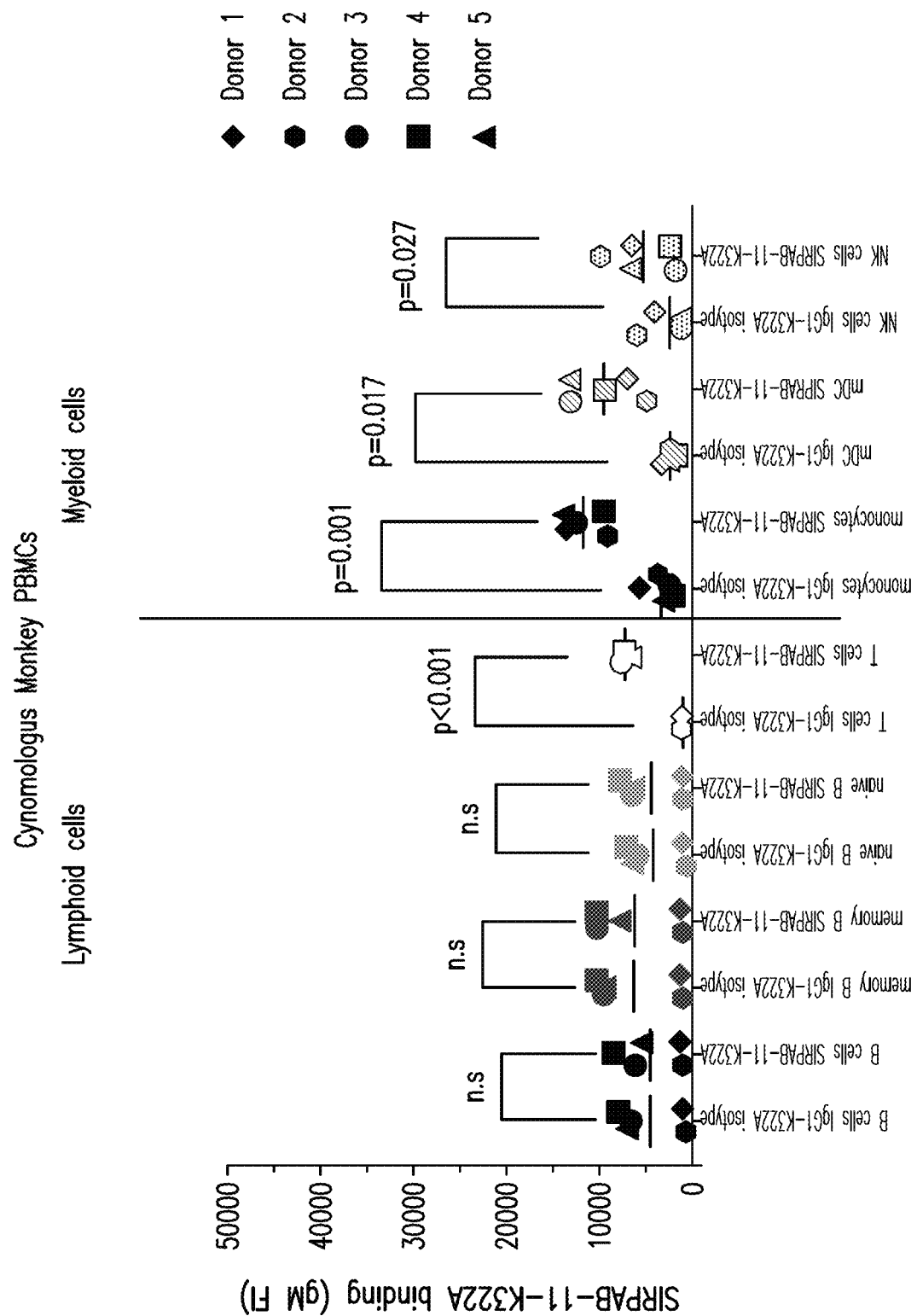

Primary cell binding with SIRPAB-11-K322A variant was performed to compare relative percentage of monocytes binding on both human and cyno peripheral blood mononuclear cells (PBMCs). Five human donor PBMCs were co-stained with SIRPAB-11-K322A-AlexaFluor647 and the monocytic marker CD14, followed by analysis by flow cytometry (FIG. 5A, left panel). Of the five human donors, an average of 22% of PBMCs stained positive CD14 (monocytes), of which the majority showed co-binding to SIRPAB-11-K322A (FIG. 5A; left panel). Similarly, five donor cyno PBMCs were co-stained with SIRPAB-11-K322A and the cross-reactive CD14 antibodies (FIG. 5A; right panel). Compared to human cells, a lower population of CD14 positive monocytes were present in cynos. However, similar to the human cells, the majority of CD14 positive cyno cells also bind SIRPAB-11-K322A (FIG. 5A; right panel).

selected for this flow cytometry panel. SIRPAB-11-K322A and negative control, IgG1 isotype control-K322A, were directly labeled with Alexa Fluor 647 (SIRPAB-11-K322A-AF647 and IgG1 isotype control-K322A-AF647, respectively).

SIRPAB-11-K322A bound to CD14+ monocytes, CD14−CD11b+HLA-DR+ myeloid dendritic cells, and CD3+ cells (FIG. 5B), SIRPAB-11-K322A did not bind to natural killer (NK) cells or B cells. Across 11 human donors tested, binding of SIRPAB-11-K322A was much higher on monocytes (geometric mean fluorescence intensity [gMFI]=8575.8±1843) than on T cells (gMFI=687.7±211.9). The majority of SIRPAB-11-K322A-bound cells in human PBMCs were CD14+ monocytes. The percentage of SIRPAB-11+CD14+ cells (17.0±5.7) was comparable to that of CD14+ monocytes (16.4±6.0) in human PBMCs.

To further compare binding of the anti-SIRPα antibodies with multiple species, a detailed immunophenotyping of immune subpopulations in cynomolgus PBMCs were performed and analyzed by multi-parameter flow cytometry. A panel of cross-reactive antibodies to human/primate surface markers were added to a set of five human or cynomolgus donor PBMCs along with SIRPAB-11-K322A or IgG isotype control-K322A. After properly defining and gating for B, T, NK, dendritic cells (DCs), and monocyte populations as described above, the amount of SIRPAB-11-K322A staining was compared between human and cynomolgus cells as summarized in FIGS. 5C-5D. Binding of SIRPAB-11-K322A to cynomolgus macaque immune cell subsets was comparable to human, and was restricted to CD14+ monocytes, myeloid dendritic cells, and T cells (FIGS. 5C-5D); cynomolgus monkey PBMCs: SIRPAB-11-K322A vs IgG isotype control-K322A for monocytes, p=0.001; myeloid dendritic cells, p=0.017; and T cells, p<0.001). Of five human and cynomolgus macaque donors tested, an average of 22% and 9%, respectively, of PBMCs stained positive for CD14. Similar to human PBMCs, the major immune subset recognized by SIRPAB-11-K322A was CD14+ monocytes in cynomolgus macaque PBMCs. The absolute number of SIRPAB-11-K322A antibody molecules bound to cynomolgus macaque CD14+ monocytes was lower than the number bound to human CD14+ monocytes (gMFI=7245±490 vs 32532±12672, respectively) due to lower SIRPα expression on cynomolgus macaque monocytes.

Figure 5E:
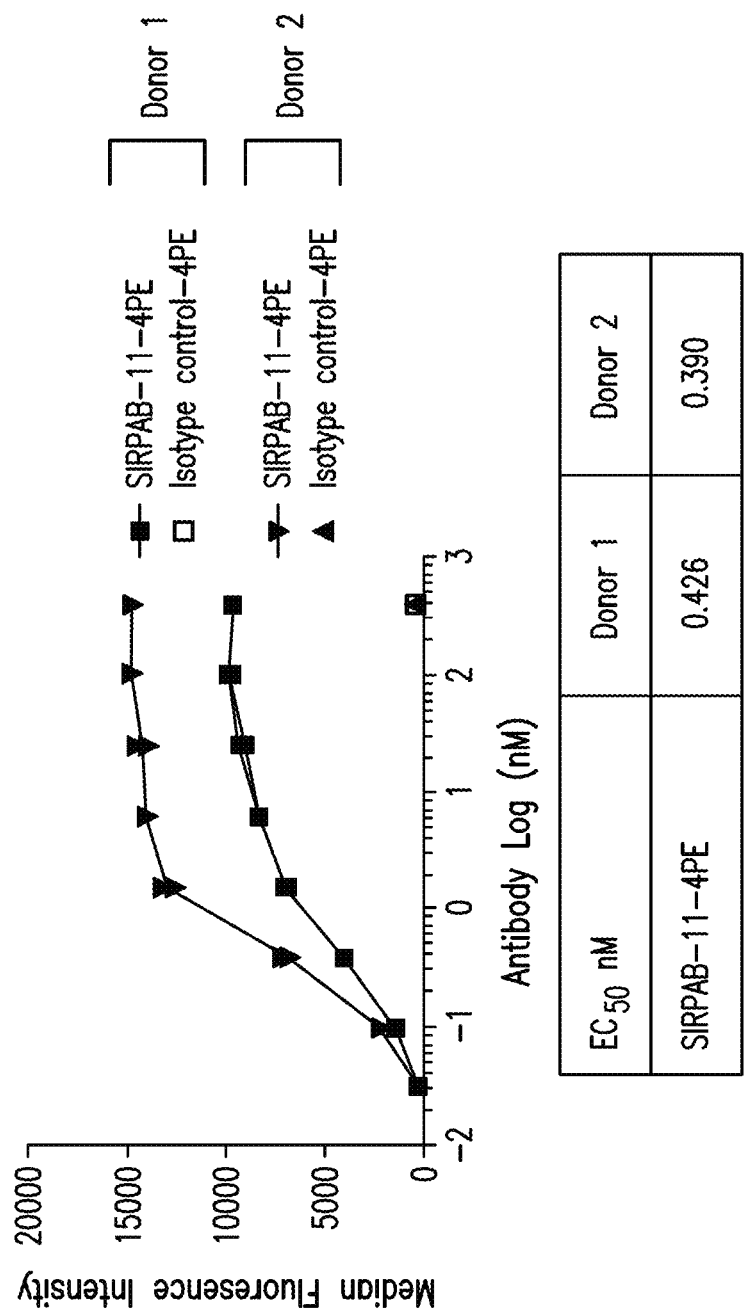

Additionally, SIRPAB-11-4PE binding to cyno whole blood was assessed. Fresh whole blood from two cynomolgus donors were Fc blocked prior to the addition of serially diluted, PE-conjugated SIRPAB-11 or IgG isotype control-4PE antibodies in duplicate wells. Anti-CD14-APC was also added to each sample to stain for the monocyte population. Flow cytometry was performed to detect antibody binding. Mean fluorescence intensity for each sample tested within the gated CD14+ population was plotted as shown in FIG. 5E. Across two cyno donors, SIRPAB-11-4PE demonstrated dose-dependent binding with a calculated $EC_{50}$ of 0.43 nM and 0.39 nM. The IgG isotype control-4PE, in both donors, showed minimal staining at the highest dose tested (400 nM).

Figure 5F:
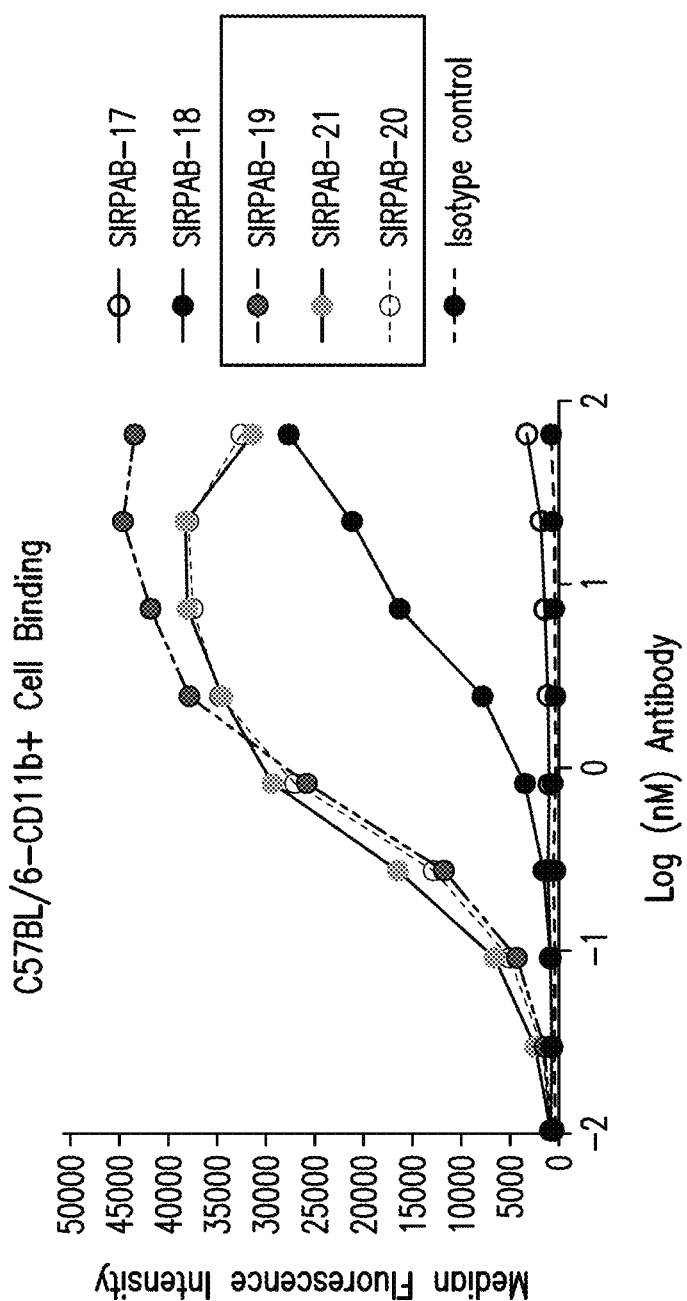

To test the binding between anti-mouse-SIRPα to mouse SIRPα, six exemplary anti-mouse-SIRPα antibodies with mouse IgG2a were dose-titrated and checked for binding to C57BL/6 mouse CD11b+ monocytes cells by flow cytometry (FIG. 5F). SIRPAB-19, SIRPAB-20, and SIRPAB-21 demonstrated the strongest binding, with $EC_{50}$ at 0.28 nM to 0.63 nM.

5.2.2 Characterization of Activity of Anti-SIRPα Antibodies in Blocking CD47-SIRPα Binding The ability of SIRPAB-11-K322A to block the interaction of SIRα to CD47 was analyzed using the Biacore T200 instrument. Recombinant human CD47-ECD was produced in HEK293 cells and recombinant SIRPα protein was purchased from Novoprotein (catalog number C385). The CD47-ECD has the sequence of SEQ ID NO:116. THE CD47-ECD was fused with an Avi-His tag having the sequence of RSGGGLNDIFEAQKIEWHEHHHHHH (SEQ ID NO:107), to generated the his-tagged CD47-ECD (SEQ ID NO:99). For the blocking assay, CD47-ECD was immobilized to a level of about 4022 RU on flow channel 2, and the assay was done by pre-incubating a fixed concentration of SIRPα at 20 nM and a 3-fold dilution series of SIRPAB-11-K322A from 100 nM to 0.4 nM. Pre-incubated SIRPα antigen and SIRPAB-11-K322A samples were flowed over channels 1 and 2, and data were analyzed using Affinity-in-Solution model on the Biacore T200. Representative data are shown in FIG. 6A. The calculated IC50 value was 12.59 nM. At the highest concentration tested, 100 nM SIRPAB-11-K322A, 97.43% of human recombinant SIRPα protein (20 nM) was inhibited from binding to immobilized CD47.

In addition, to test the CD47 blocking activity of anti-mouse-SIRPα antibodies, the anti-mouse-SIRPα antibodies were incubated against 6.7 nM of mCD47-hFc (previously determined mCD47-hFc binding $EC_{50}$) for binding with C57/BL6 macrophages. After washing, the remaining amount of bound mCD47-hFc was determined by flow cytometry with an anti-human Fc detection antibody. As shown in FIG. 6B, four anti-mouse-SIRPα antibodies, including SIRPAB-19, SIRPAB-20, SIRPAB-21, and SIRPAB-18 significantly inhibited CD47 binding to mouse macrophages, among which three anti-mouse-SIRPα antibodies (SIRPAB-19, SIRPAB-20, and SIRPAB-21) were effective in blocking >90% of mCD47 binding at a concentration equal to or higher than 0.5 nM.

5.3 Example 3: Epitope Mapping

The SIRPAB-11-K322A epitope was determined by solving the crystal structure of the SIRPAB-11 fragment antigen-binding (Fab) in complex with the human SIRPα extracellular domain 1 (also known as SIRPα IgV domain) at 2.2 Å resolution (FIG. 7A). The SIRPα:Fab interactions occur at the most distal portion of SIRPα region relative to the transmembrane domain. Overall, the SIRPα:Fab interaction site characterized overlaps with the CD47 binding site (FIG. 7B) and is consistent with the observation that SIRPAB-11-K322A can fully block binding of CD47. The HC CDR3 loop of SIRPAB-11-Fab mediates most of the SIRPα/Fab polar interactions and is partially inserted into a large SIRPα pocket formed predominantly by residues Phe74, Ile36, Leu30, Lys93, and Asn52 (FIG. 7A). This same pocket is also recognized by the CD47 F-G loop (FIG. 7B). Three important negatively-charged residues on the Fab HC (Glu57, Glu99, and Asp106) establish key electrostatic interactions with positively-charged SIRPα residues (Arg95, Lys96, and Arg69, respectively) (FIG. 7A). Additional hydrogen bonds in the complex interface are observed between the Fab HC Asn59 and SIRPα Ser98, Fab GC Ser102 and SIRPα Arg69, and Fab LC Asn53 and SIRPα Thr67 (FIG. 7A).

5.4 Example 4: Cell Lines for Antibody Expression and Antibody Production

5.4.1 Molecular Cloning of the Heavy and Light Chain

For expressing the anti-SIRPα antibodies, multiple versions of the mammalian expression vector pTT5 (National Research Council of Canada, Ottowa, Canada) were constructed with codon-optimized signal peptides, a VH or VL stuffer region configured for seamless cloning, and LC or HC constant regions (ATUM, Newark, Calif.). Specifically, the LC vector used was pDT5-SP6-Vk-kappa-Hs_257445, and the HC vector used was pDT5-SP1-VH-IgG1_K322A_KEMA_257440 (where KEMA represents amino acids composing the same mixed allotype used in Herceptin, and pDT5 indicates the pTT5 backbone reconfigured for seamless cloning). Variable regions were converted into codon-optimized synthesized DNAs and subcloned into stuffer regions of the described vectors using seamless cloning methods (ATUM). The HC vector is named pDT5-SP1-JDS-1462, and the LC vector is pDT5-JDS-SP6-1464_261066.

5.4.2 Transient Protein Production

The anti-SIRPα antibodies were manufactured, for example, at the laboratory scale in 3 L shake-flasks for in vitro and in vivo efficacy studies. The ExpiCHO expression system was used for transient transfection of ExpiCHO cells using a Life Technologies (ThermoFisher Scientific) standard protocol. A 1:1 ratio of LC versus HC was used for DNA mixture at 0.5 mg/L of culture during the transfection. Cells were seeded at $6 \times 10^6$ cells/mL in a 3 L shaker flask with 1 L working volume at 37° C. plus 5% CO2, cells then were transfected using Life Technologies standard protocols. On day 1 post-transfection, standard enhancers 1 and 2 were added. Cell viability and titer were monitored every day and supernatant was harvested on Day 8 post-transfection, a VICELL instrument was used for viability analysis, and Octet red equipped with Protein A sensor was used for titer analysis. Cells and supernatant were harvested using GE Lifesciences depth filtration and sterilization columns. ULTA Prime GF 5 µM capsules were used for depth filtration followed by ULTA Pure HC 0.6/0.2 μM sterilization capsules. Cell growth and viability, as well as titer, are shown in FIG. 8.

5.4. Purification of Anti-SIRPα Antibodies

Purification of the expressed anti-SIRPα antibodies was performed by a series of downstream purification steps including Protein A affinity chromatography and low pH virus inactivation, followed by IEX interaction (CAPTO Adhere and CAPTO SP ImpRes) chromatography steps.

Briefly, the Protein A affinity chromatography was carried out with MABSELECT SURE (GE Healthcare Life Sciences), designed to capture the product and to remove process-related impurities. The subsequent virus inactivation step was performed under acidic conditions (pH 3.4±0.1) followed by conditioning of the inactivation pool to pH 5.5±0.1. After virus inactivation, an anion exchanger was used in a flow through mode for the intermediate polishing step using CAPTO Adhere to remove impurities such as aggregates, DNA, host cell protein, and endotoxins. The product pool was pH adjusted to 6.5±0.1 and the conductivity was reduced to 2 mS/cm prior to the next process step. Cation exchanger CAPTO SP ImpRes was used as a polishing step and the product was resolved at 10 mS/cm. The antibody was then buffer exchanged in stock solution (10 mM succinate, 9% sucrose, 0.05% PS 20, pH 5.5) and concentrated to 18.6 mg/mL. The product pool was then filtered through a 0.2 μM filter and aliquoted.

For expression and purification of SIRPα and Fab from SIRPAB-11-K322A for crystallographic studies, the gene of the WT SIRPα domain 1 (SHPS1, residues 31-149, UNIPROT identifier P78324-1 isoform 1) was synthesized by GENSCRIPT with codon optimization for expression in *S. frugiperda*, and cloned into a pFastBac1 vector (Invitrogen) between the BamH1 and Xho1 sites. The signal peptide sequence of GP67 (MLLVNQSHQGFNKEHTSKMV-SAIVLYVLLAAAAHSAFA (SEQ ID NO:206)) was used for secretion of SIRPα. A thrombin cleavage site and a 6× histidine tag was added to the C-terminal of the protein to facilitate purification. Recombinant baculoviruses were generated using the BAC-TO-BAC system (Invitrogen), and were used to infect cells. Infected cells were grown at 27° C. for 48 hours in the presence of kifunesin to limit protein glycosylation; culture supernatants were kept for purification of the overexpressed protein. Supernatants were subjected to affinity purification using a 5 mL Ni-NTA column (COMPLETE His-Tag purification resin, Roche) at a flow rate of 5 mL/minute in an Äcta Pure chromatography system. Fractions containing the protein of interest were deglycosylated using ENDO-H enzyme, and further purified through a size exclusion chromatography step followed by anion exchange chromatography step. Fragment antigen binding from SIRPAB-11-K322A IgG1 was prepared using the Pierce Fab Preparation Kit. For crystallization experiments, SIRPα and Fab were mixed at equal stoichiometric ratios and concentrated to 18 mg/mL. SIRPα/Fab SIRPAB-11-K322A crystal were obtained in 0.1 M 4-morpholineethanesulfonic acid pH 6.5, 25% w/v polyethylene glycol methyl ether 550, and 0.01 M zinc sulfate.

5.5 Example 5: Characterization of Antibody Binding to Fragment Crystallizable Gamma Receptor The Fc region of an IgG can interact with high- and low-affinity FcγR, mediating immune effector functions including antibody-dependent cellular cytotoxicity (ADCC) and antibody-dependent cellular phagocytosis (ADCP) (Nimmerjahn F, et al., Immunity. 2006 January;24(1):19-28; Abés R, et al., Expert Rev Clin Immunol. 2009 November; 5(6):735-47; Desjarlais J R, et al., Exp Cell Res. 2011 May 15;317(9):1278-85).

The binding ability of SIRPAB-11 and its variants with different Fc backbones was assessed on different FcγR engineered HEK293 cells. Shown summarized in Table 19, SIRPAB-11-K322A demonstrated binding to human FcγR1-3 with comparable $EC_{50}$s to a wild type (WT) isotype control-IgG1 antibody and another commercially available IgG1.

TABLE 19

Summary of Cellular Binding $EC_{50}$ Determination of SIRPAB-11-K322A versus Control

| $EC_{50}$ nM | Isotype Control-IgG1 | SIRPAB-11-K322A | Commercially Available IgG1 |
|---|---|---|---|
| FcγR1 (CD64) | 1.18 | 0.79 | 0.83 |
| FcγR2A (CD32aH131) | 137 | 200 | 361 |
| FcγR2A (CD32aR131) | 90.2 | 194 | 188 |
| FcγR2B | 1200 | 2478 | 1325 |
| FcγR3A (CD16aV158) | 448.6 | 795.1 | 574.6 |
| FcγR3A (CD16aF158) | 311.3 | 1200 | 1270 |

FcγR = fragment crystallizable gamma receptor.

The binding ability of SIRPAB-11 with an IgG1K322A, IgG1AAS, or an IgG4PE variant was additionally assessed on different FcγR engineered HEK293 cells. As shown in Table 20, SIRPAB-11-K322A showed binding to human FcγR1-3 with comparable $EC_{50}$s as an isotype control-IgG1 antibody. As expected, the SIRPAB-11-4PE or SIRPAB-11-AAS variants having attenuated Fc regions demonstrated significantly lower binding against all FcγR lines Table 20.

TABLE 20

Summary Fragment Crystallizable Gamma Receptor Cell Line Binding $EC_{50}$ nM of SIRPAB-11 Variants

| | Isotype | SIRPAB-11 | | |
|---|---|---|---|---|
| $EC_{50}$ nM | Control-IgG1 | K322A | AAS | 4PE |
| FcγR1 (CD64) | 0.98 | 0.79 | 3175 | 756 |
| FcγR2B | 2245 | 2709 | >20000 | 5178 |
| FcγR3A (CD16aV158) | 127 | 142 | 15100 | 2061 |

FcγR = fragment crystallizable gamma receptor; IgG1 = immunoglobulin G1.

5.6 Example 6: Characterization of the ADCC, CDC, and ADCP of the Anti-SIRPα Antibodies ADCC is a known immune mechanism in which avidity binding interactions triggered through FcγR3 (low-affinity) activates NK cells to lyse antibody-bound target cells. Because SIRPAB-11 was demonstrated to bind FcγRs (see Table 19 and 20 above), the ability of SIRPAB-11 to induce ADCC of cells expressing SIRPα was examined. Induction of SIRPAB-11-mediated ADCC targeting the human cell line MOLM-13 was tested in vitro by 3-hour co-culture assays using IL-2-activated human PBMCs from five donors as effector cells. Effector cells treated with three different anti-CD33 antibodies were used as positive controls; cells treated with IgG1 isotype control-K322A and an isotype control-IgG1 were used as negative controls. The cells were incubated with antibodies at an effector-to-target (E:T) cell ratio of 80:1. Cell lysis was determined by fluorescent cytometry using the Mirrorball fluorescence cytometer.

Expression of SIRPα and CD33 at robust levels on MOLM-13 cells was confirmed by flow cytometry using directly fluorescent dye conjugated SIRPAB-11-IgG4PE-AF647 and anti-CD33-phycoerythrin (PE) antibodies. Using PBMCs from three donors, the average percent ADCC level was 0.5±2 at 200 nM SIRPAB-11-K322A, the highest concentration tested (see FIG. 9A for example). This level was similar to the percent ADCC baseline levels defined by the isotype control-IgG1 antibody (−1.0±1.2) and the IgG1 isotype control-K322A antibody (−1.0±2.2). In assays using PBMCs from two additional donors, treatment with 133 nM SIRPAB-11-K322A, the highest concentration tested, demonstrated an average percent ADCC level of −1.2±3.1, which was the same as the baseline level for an isotype control-IgG1 antibody (−1.3±1.8), and similar to the IgG1 isotype control-K322A antibody (2.3±3.2) (see FIG. 9A for example). The three positive control anti-CD33 antibodies (two with an IgG1 format and one with an IgG4 format) demonstrated ADCC with a range of 14.4% to 22.1% ADCC at the highest concentration tested across the 5 donors. These assays demonstrated that SIRPAB-11-K322A does not induce ADCC directed toward MOLM-13 cells.

Additionally, SIRPAB-11-K322A-mediated ADCC, targeting autologous SIRPγ-expressing CD4+ and CD8+ T cells and autologous SIRPα-positive monocytes, was assessed using IL-2-activated NK cells as effectors. Effector cells were incubated with target cells (monocytes, non-activated T cells, or staphylococcal enterotoxin B [SEB]-activated T cells) at a 10:1 ratio for 3 hours before cell lysis was measured by either flow cytometry or fluorescent cytometry. Target T cells preincubated with anti-CD3 IgG1 and anti-CD4 IgG1 were used as positive controls, and IgG1 isotype control-K322A, an isotype control-IgG1, or anti-CD3 Fc null were used as negative controls. For assays with monocytes as the target cell, preincubation of the target cells with anti-CD33 IgG1 was tested, and IgG1 isotype control-K322A and an isotype control-IgG1 were used as negative controls.

To determine whether SIRPγ expression was changed based on the activation state of CD4+ and CD8+ T cells, the SIRPAB-11-IgG4PE directly conjugated to Alexa647 was used for flow cytometry analysis, along with an anti-CD69-APC/Fire 750 antibody which binds to activated T cells. The average gMFI of non-activated and activated SIRPAB-11-IgG4PE+CD4+ T cells, across three individual donors, was 412±90.2 and 445±109.7, respectively, indicating no change in SIRPγ expression in the absence or presence of SEB stimulation. Similar SIRPAB-11-IgG4PE binding data was generated in non-activated and activated CD8+ T cells from two individual donors (average gMFIs: 267±202 and 301±223, respectively).

Figure 9A:
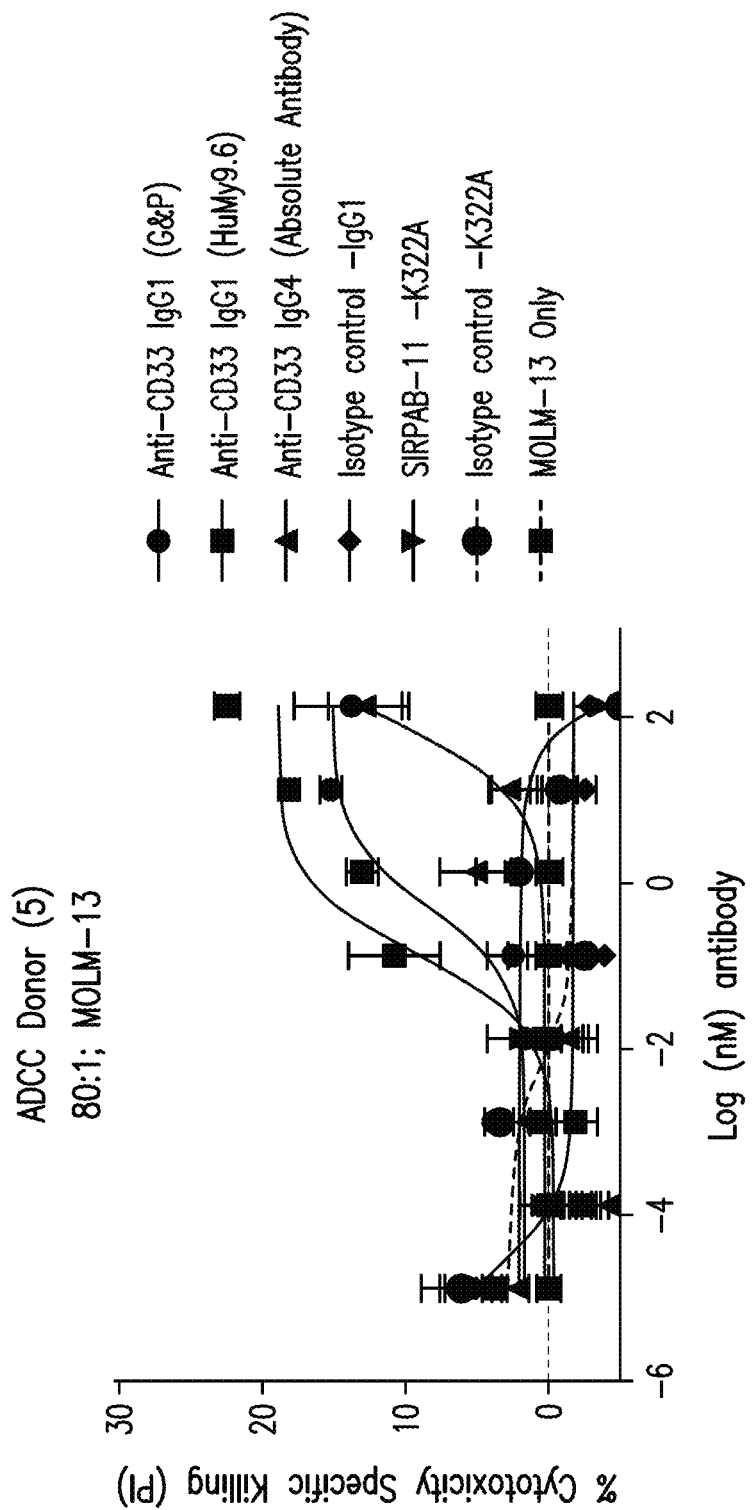
Figure 9B:
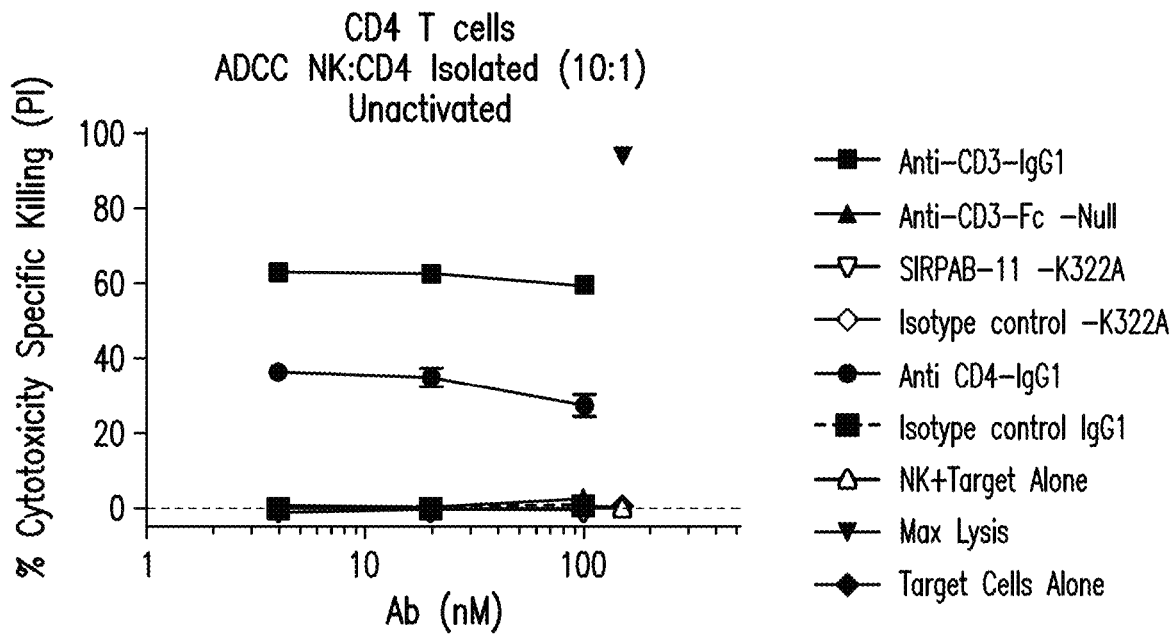
Figure 9C:
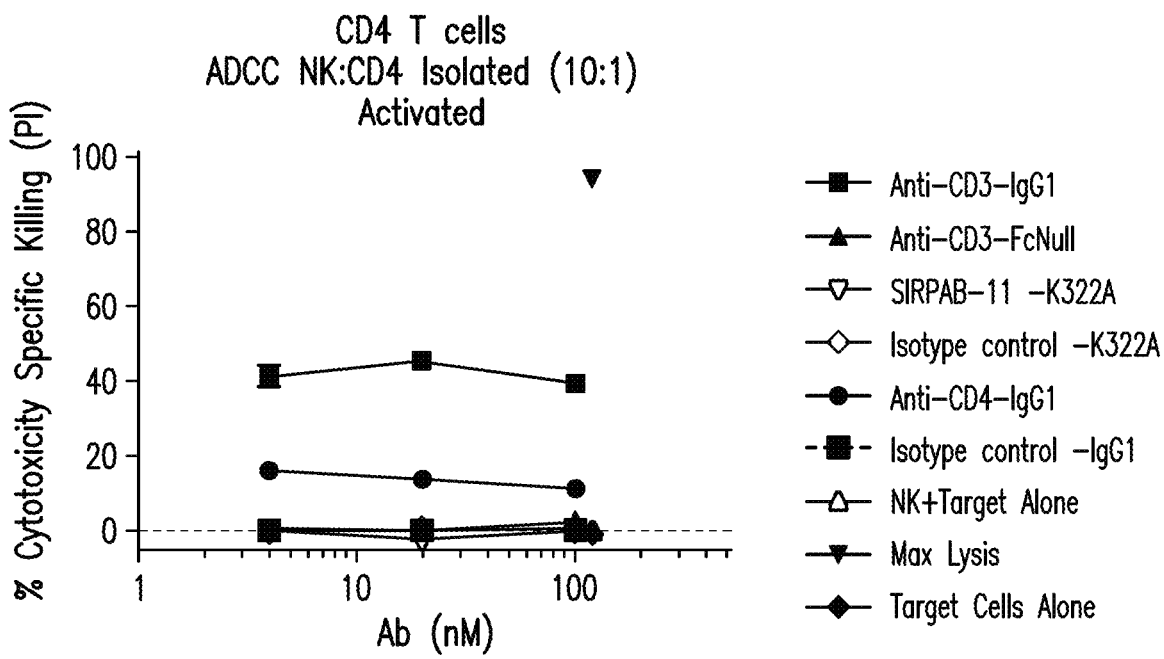

Cytotoxicity assays using co-cultures of autologous NK effector cells and target CD4+ T cells from three donors demonstrated that SIRPAB-11-K322A treatment did not induce ADCC of autologous CD4+ T cells in non-activated or SEB-activated states (for example see FIGS. 9B-9C). Natural killer cells co-cultured with CD4+ T cells preincubated with SIRPAB-11-K322A (20 nM) displayed low percentages of cytotoxicity specific killing in wells with (1.2±5.8) or without (2.2±4.2) SEB activation (n=3). Similar data was generated with 100 nM SIRPAB-11-K322A in two of the three donors (see FIG. 9A). This level of cytotoxicity was comparable to that observed with the negative isotype control, IgG1 isotype control-K322A, and baseline wells containing target and effector cells without antibody. Both positive controls, anti-CD3 IgG1 and anti-CD4 IgG1, induced higher cytotoxicity levels at 20 nM. With anti-CD3-IgG1 antibody treatment, average percentages of ADCC across all three donors were 37.3±10.3 and 44.5±18.4, with and without SEB activation, respectively. With anti-CD4-IgG1 antibody treatment, average percentages of ADCC across all three donors were 26.0±8.2 without SEB, and 17.1±3.0 with SEB activation.

Figure 9D:
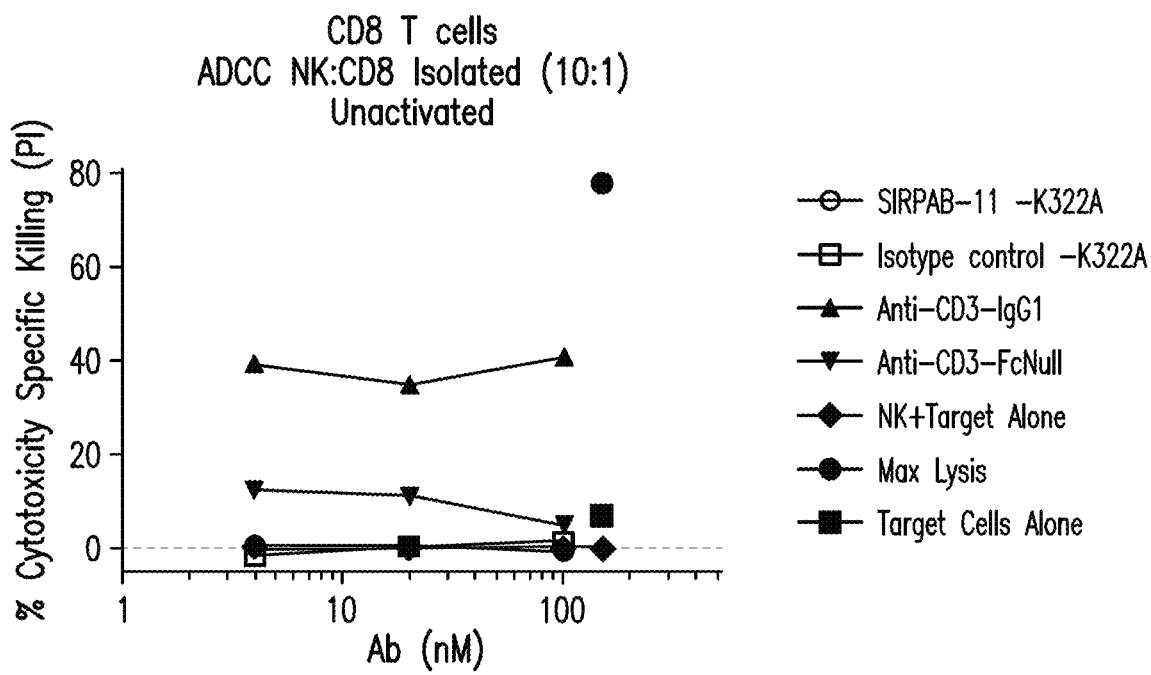
Figure 9E:
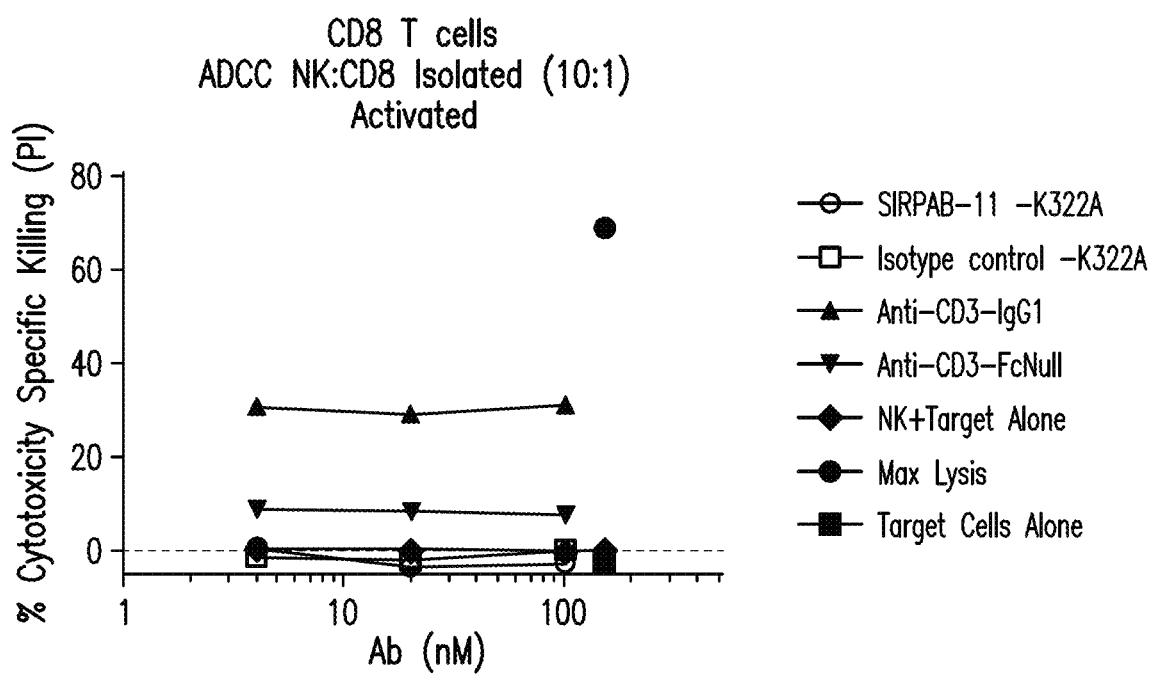

Cytotoxicity assays using co-cultures of autologous NK effector cells and target CD8 + T cells from two donors demonstrated that SIRPAB-11-K322A treatment did not induce ADCC of autologous CD8+ T cells in non-activated or SEB-activated states (for example see FIGS. 9D-9E). Natural killer cells co-cultured with CD8+ T cells preincubated with SIRPAB-11-K322A (100 nM) displayed low levels of cytotoxicity with or without SEB activation (average percentages [n=2]; −1.7±1.1 and 0.3±0.5 cytotoxicity specific killing, respectively). This level of cytotoxicity was comparable to that observed with the negative isotype control, IgG1 isotype control-K322A. The positive control anti-CD3-IgG1 antibody induced higher cytotoxicity percentages at 100 nM, with (20.1±15.5, average n=2) or without (29.5±16.0, average n=2) SEB activation, compared to those observed with SIRPAB-11-K322A.

Figure 9F:
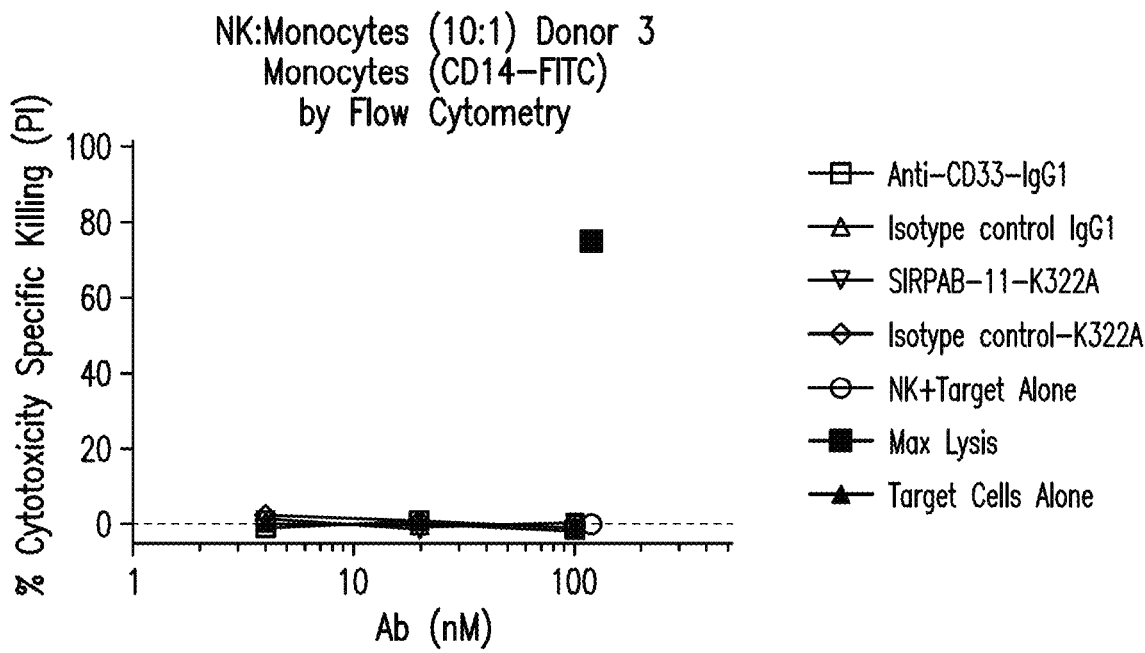
Figure 9G:
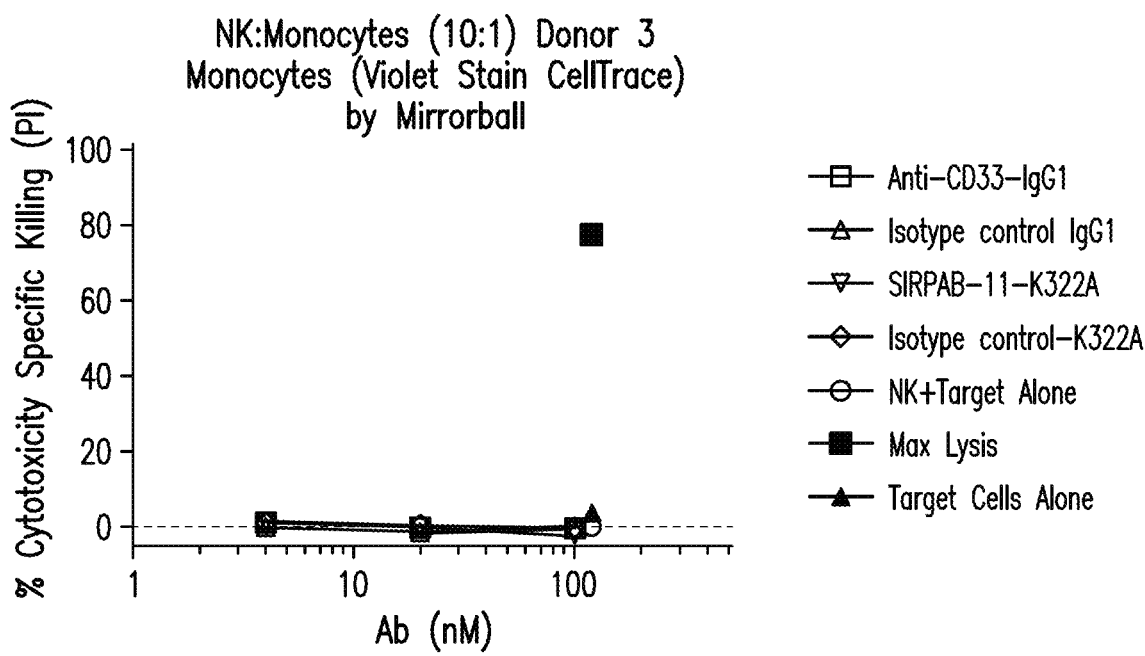

Similarly, cytotoxicity assays using co-cultures of autologous NK effector cells (previously used for the T cell ADCC experiments) and target monocytes from a single donor demonstrated that SIRPAB-11-K322A treatment did not induce ADCC of autologous monocytes under the assay conditions tested (FIGS. 9F-9G). Cytotoxicity measured by flow cytometry (FIG. 9F) and by Mirrorball fluorescent cytometry (FIG. 9G) yielded similar results. Natural killer cells co-cultured with monocytes preincubated with SIRPAB-11-K322A (100 nM) displayed low levels of cytotoxicity, and were comparable to the negative isotype control, anti-IgG1 isotype control-K322A (−0.5% SIRPAB-11-K322A vs −0.9% IgG1 isotype control-K322A cytotoxicity specific killing). Anti-CD33 IgG1 treatment was tested in this co-culture system since it induced ADCC against MOLM-13 tumor cells, but it did not demonstrate cell killing (−0.6% anti-CD33-IgG1 vs −0.8% isotype control-IgG1 cytotoxicity specific killing).

Complement-dependent cytotoxicity (CDC) has been identified as an immune mechanism in which antibody-opsonized targets (e.g., microbes and cells) are depleted by components of the complement cascade. The ability of SIRPAB-11 and its engineered Fc variants to induce CDC was evaluated using REC-1 lymphoma cell line, identified to express both SIRPα and CD20. To enable assessment of CDC, surface target expression of the non-Hodgkin lymphoma cell line REC-1 was determined. Cells were stained with SIRPAB-11-K322A or SIRPAB-11-IgG4PE. Binding was detected with an anti-human IgG Alexa Fluor 647 antibody. Human isotype control-IgG1 and IgG4 isotype control-4PE antibodies were used as negative isotype controls. An anti-CD20 antibody was used as a positive staining control. Complement-dependent cytotoxicity assays were performed by incubating REC-1 cells with SIRPAB-11-K322A, SIRPAB-11-IgG4PE, or an anti-CD20 antibody across a concentration range. Diluted rabbit serum was added as a source of complement before determination of cell viability by a luminescent cell viability assay. Isotype control-IgG1 and IgG4 isotype control-4PE antibodies were used as negative controls.

Binding to SIRPα-positive human non-Hodgkin lymphoma REC-1 cells by SIRPAB-11-K322A, SIRPAB-11-

IgG4PE, and anti-human CD20-mIgG2a antibody, at a fixed concentration of 66.7 nM, was confirmed by flow cytometry using fluorescently conjugated secondary antibodies. As described above, the SIRPAB-11-K322A Fc region was engineered with a lysine 322 to alanine (K322A) mutation to silence complement C1q interactions. The capacity of SIRPAB-11-K322A to fix complement was compared to SIRPAB-11-IgG4PE (which is not expected to bind complement due to the IgG4PE backbone) over a concentration range of 0.021 nM to 333.3 nM in the presence of 3- to 4 week old rabbit serum, using a luminescent cell viability assay. The positive control anti-CD20 human IgG1 (hIgG1) antibody, demonstrated concentration-dependent lysis of REC-1 target cells in the presence of rabbit complement serum, with an EC50 value of 0.012 nM. SIRPAB-11-K322A, SIRPAB-11-IgG4PE, and isotype control-IgG1 and IgG4 isotype control-4PE demonstrated no discernable CDC activity at concentrations up to 333.3 nM, the highest concentration tested (FIG. 9I).

Figure 9H:
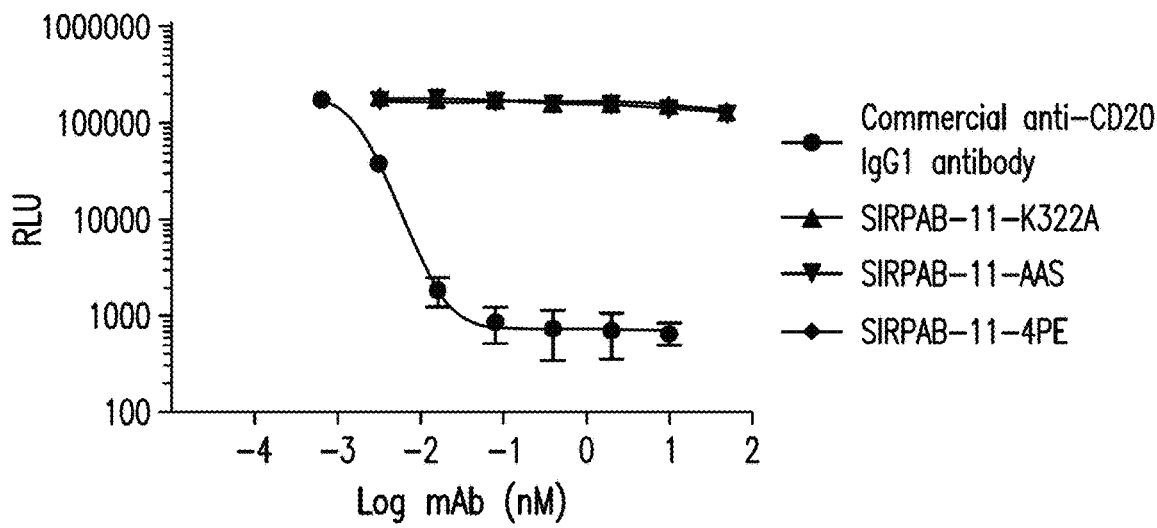
Figure 9I:
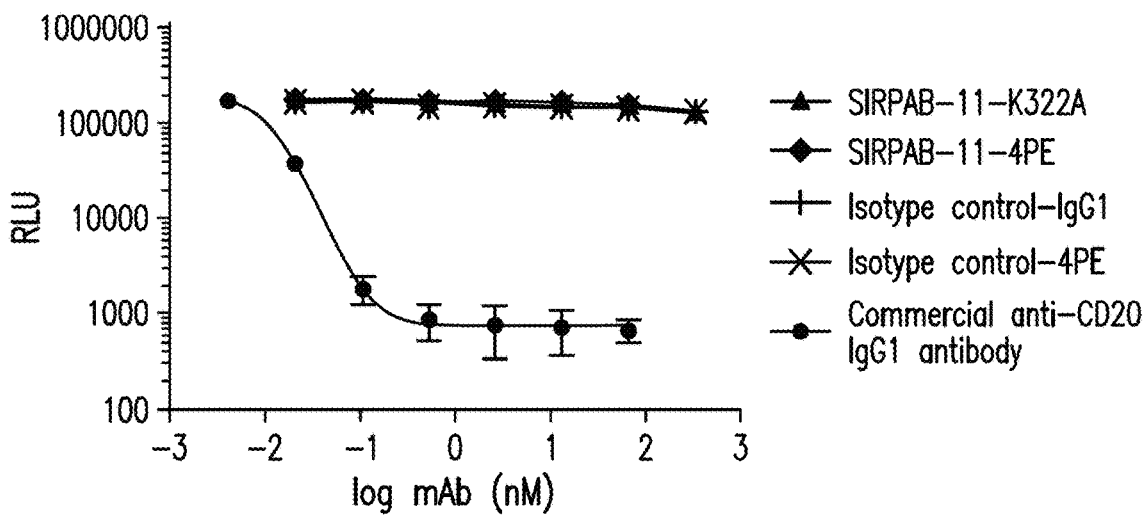

Additionally, another SIRPAB-11 Fc variant, SIRPAB-11-AAS, at the highest dose tested, demonstrated no CDC activity in the presence of 5% rabbit complement (FIG. 9H). By contrast, the positive control of a commercial anti-CD20 antibody showed potent CDC activity (FIG. 9H).

Antibody-mediated cellular phagocytosis (ADCP) is an immune effector mechanism mediated by Fc binding to FcγR1 expressed on macrophages. Since SIRPAB-11-K322A binds FcγR1 with comparable $EC_{50}$s to WT human IgG1 as described above, the capacity of autologous ADCP with SIRPAB-11-K322A was evaluated with human monocyte derived macrophages (effectors) and antibody opsonized autologous CD3+ immune cells and autologous monocytes (self-targets) that express SIRPγ and SIRPα, respectively.

The ability of SIRPAB-11-K322A to induce ADCP by macrophages targeting autologous T cells and monocytes was investigated using isolated effector and target cells from two donors. Antibody-dependent cellular phagocytosis was determined by co-detecting fluorescently labeled target cells within effector macrophages. The percentage level of phagocytosis was calculated as the number of double-positive cells divided by the total number of macrophages plated per well. Each assay was performed twice with cells from each donor over a 0.033 nM to 200 nM concentration range. To assess the contribution of Fc effector mediated phagocytosis, SIRPAB-11-K322A was tested along with the effector function detuned SIRPAB-11-IgG4PE antibody, which shares identical variable regions with SIRPAB-11-K322A, but has a different Fc backbone. A human anti-CD3 IgG1 antibody, previously known to mediate ADCC of autologous cells, was used as a control to assess ADCP of autologous T cells. A human anti-CD33 IgG1 antibody, previously used as a positive control to assess tumor-targeted ADCC, was included as a control to evaluate ADCP of autologous monocytes.

Figure 9J:
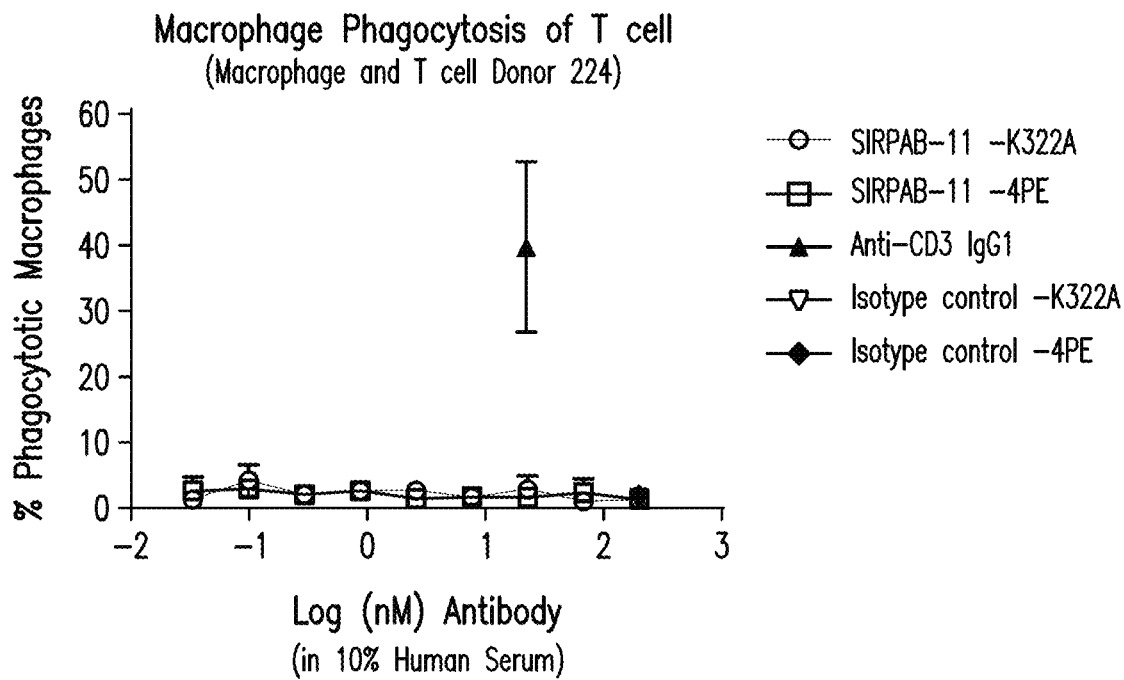

In co-culture assays assessing ADCP activity mediated by SIRPAB-11-K322A using autologous macrophages and target T cells, the percentage level of phagocytosis was 1.14 and 1.98 for Donor 224, and 2.06 and 1.38 for Donor 345 (n=2 for each donor) at 200 nM, the highest concentration tested (FIG. 9J and Table 21 for Donor 224). These levels were similar to 200 nM IgG1 isotype control-K322A antibody (range of 0.99% to 2.34 phagocytic macrophages across donors and replicates), as well as the SIRPAB-11-IgG4PE antibody and its respective control, IgG4 isotype control-4PE. Positive control anti-CD3 antibody induced phagocytosis levels ranging from 21.13% to 39.72% for the two donors.

TABLE 21

T Cell Phagocytosis Assay Results at Highest
Tested Concentrations for Donor 224

| Treatment | Concentration | Percent ADCP (average of 3 wells) |
|---|---|---|
| SIRPAB-11-K322A | 200 nM | 1.14 ± 0.24 |
| SIRPAB-11-IgG4PE | 200 nM | 0.91 ± 0.31 |
| IgG1 isotype control-K322A | 200 nM | 1.69 ± 0.27 |
| IgG4 isotype control-4PE | 200 nM | 2.2 ± 0.75 |
| Anti-CD3 | 20 nM | 39.72 ± 12.98 |

ADCP = antibody-dependent cellular phagocytosis; CD = cluster of differentiation.

Figure 9K:
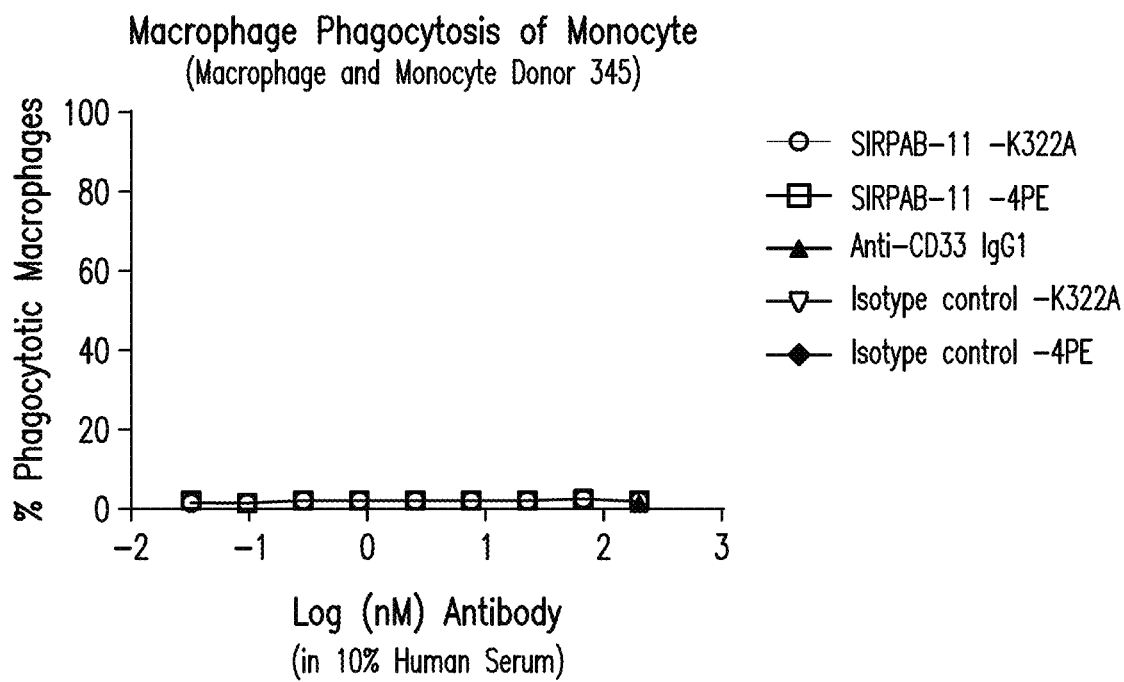

In assays using autologous monocytes as targets, the phagocytosis levels for co-cultures treated with SIRPAB-11-K322A were 1.99% and 2.09% for Donor 224, and 1.19% and 3.92% for Donor 345 (n=2 for each donor) at 200 nM, the highest concentration tested (FIG. 9K and Table 22 for Donor 345). These levels were similar to IgG1 isotype control-K322A antibody (range of 0.63% to 2.29% phagocytic macrophages across donors and replicates) as well as the SIRPAB-11-IgG4PE antibody and its respective control, IgG4 isotype control-4PE. The anti-CD33 IgG1 antibody displayed percent phagocytosis levels that were similar to isotype controls indicating that in this assay system it was not able to induce phagocytosis of autologous monocytes.

TABLE 22

Monocyte Phagocytosis Assay Results At Highest
Tested Concentrations for Donor 345

| Treatment | Highest Tested Concentration | Percent ADCP at Highest Tested Concentration |
|---|---|---|
| SIRPAB-11-K322A | 200 nM | 1.19 ± 1.24 |
| SIRPAB-11-IgG4PE | 200 nM | 1.07 ± 0.85 |
| IgG1 isotype control-K322A | 200 nM | 0.63 ± 0.62 |
| IgG4 isotype control-4PE | 200 nM | 0.63 ± 0.60 |
| Anti-CD33 | 200 nM | 0.72 ± 0.40 |

ADCP = antibody-dependent cellular phagocytosis; CD = cluster of differentiation.

5.7 Example 7: Immunogenicity Analysis of Anti-SIRPα Antibodies

There are various elements that contribute to immunogenicity of antibodies and proteins. It has been reported that T cell-dependent responses play an important role in the development of anti-drug antibody (ADA) responses to biologics (Java V, et al., Clin Immunol. 2013 December;149 (3):534-55). Interactive Screening and Protein Reengineering Interface (ISPRI) was employed as a tool for assessing potential immunogenicity. Interactive Screening and Protein Reengineering Interface was developed by EpiVax (Providence, R.I.) and is known to be a clinically well-established T cell-dependent in silico analysis tool. Using ISPRI, the immunogenic potential of the SIRPAB-11 mAb or its variant was uploaded into the EpiVax server, and analyzed.

First, entire heavy and light chains of SIRPAB-11-K322A were analyzed by EpiMatrix, which screens the entire primary amino acid sequences for the presence of putative effector T cell effectors (Teff) and regulatory T cell epitopes (Treg). More Teff increases the immunogenic potential, while more Treg decreases the immunogenic potential of each sequence on a normalized scale. Overall, a Treg adjusted score below −30 is considered to be acceptable (Table 23). Detailed analysis indicated that most CDRs, except for CDR L2, include very few putative effector T cell epitopes (data not shown).

TABLE 23

Immunogenicity Report

| Protein Sequence | Length | EpiMatrix Hits | EpiMatrix Score | tReg Adjusted Epx Score |
|---|---|---|---|---|
| SIRPAB-11_HC | 456 | 178 | −12.54 | −35.05 |
| SIRPAB-11_LC | 214 | 92 | 5.18 | −29.48 |
| SIRPAB-11_VH | 126 | 44 | −13.79 | −40.46 |
| SIRPAB-11_VL | 107 | 50 | 22.82 | −35.49 |

EpiMatrix Hits is the number of EpiMatrix Z-scores above 1.64 found within the sequence. The EpiMatrix Score is derived from the number and intensity of the EpiMatrix Hits normalized for the length of the protein. In other words the Score is the excess or shortfall in predicted aggregate immunogenicity relative to a random peptide standard. Alleles considered in protein analysis: DRB1*0101, DRB1*0301, DRB1*0401, DRB1*0701, DRB1*0801, DRB1*1101, DRB1*1301, DRB1*1501. These alleles at HLA class II loci were used for in silico screening for antibody sequences for potential peptide binding domains, resulting in putative T-cell epitopes that may result in immunogenicity. Jawa V, et al, Clinical Immunology 149; 534-555 (2013).

Second, ADA potential was predicted on the VH and VL domains by the EpiMatrix Antibody immunogenicity Prediction module. In evaluating the immunogenic potential of antibody sequences, EpiVax characterizes those antibodies according to two criteria, Treg content and Teff content. Antibodies with low Teff content and high Treg content are the least likely to be immunogenic (Optimal Antibodies). Antibodies with low Teff content and low Treg content are also frequently non-immunogenic (Low Risk Antibodies). Antibodies in this category frequently produce ADA response rates between 5% and 10%. Antibodies with high Teff content and high Treg content are the most difficult to characterize. In general, it is expected that antibodies in this category will be more immunogenic than the low risk antibodies (Mixed Antibodies). Antibodies with high Teff content and low Treg content tend to be the most immunogenic with immunogenicity rates frequently exceeding 10% (High Risk Antibodies). Most chimeric antibodies fall into this category. The SIRPAB-11-K322A antibody is categorized as an Optimal Antibody due to its low Teff and high Treg content (FIG. 10A and FIG. 10B). The SIRPAB-11-K322A antibody has superior EpiMatrix Antibody Immunogenicity score of 0.17%, which is only less than 1/20 of the immunogenicity score (3.66%) of the SIRPα reference antibody that has a light chain of an amino acid sequence of SEQ ID NO:224 and a heavy chain of an amino acid sequence of SEQ ID NO:225.

5.8 Example 8: Cytokine Release Assays

Antibodies that induce target crosslinking of human T, NK, or monocytic lineages have the potential of initiating a cascade of systemic release of proinflammatory cytokines, resulting in potential fatal systemic immune reaction. To determine whether SIRPAB-11-K322A binding can mediate the trigger of a "cytokine storm," a panel of cytokines was measured on human PBMCs from ten normal donors to assess for systemic cytokine release. Briefly, Human PBMCs were isolated from whole-blood using Ficoll-Paque, and following an overnight resting period, were added to antibody pre-coated plates. After 48 hours, supernatants were collected for multi-cytokine determination and analysis using a Mesoscale proinflammatory 9-plex (from Meso Scale Diagnostics, LLC). Data for a total of ten donors were collected and analyzed against isotype or positive controls (FIG. 11A to 11J). The following cytokines were evaluated: interleukin (IL)-1beta (β), IL-2, IL-6, IL-8, IL-10, IL-12 p70, tumor necrosis factor-alpha (TNF α), interferon-gamma (IFN-γ) and granulocyte macrophage-colony stimulating factor (GM-CSF). A SIRPAB-11-K322A concentration titration from 30 μg/mL to 0.001 μg/mL (3 μg/well to 0.0001 μg/well) was used. Anti-CD3 antibody (clone OKT-3) and lipopolysaccharide (LPS) were used as positive controls; human IgG1 isotype control-K322A and a commercial human IgG1 antibody was used as isotype negative controls. Representative data of cytokine release profiles are presented for IL-1β, IL-2, IL-6, IL-8, IL-10, IL-12p70, TNFα, IFN-gamma, and granulocyte macrophage colony-stimulating factor in FIG. 11A to 11I, with complete dataset and statistical analysis shown in FIG. 11J. Positive controls anti-CD3 antibody clone OKT-3 and/or LPS induced release of eight cytokines (IL-1β, IL-2, IL-6, IL-10, IL-12p70, TNF-α, IFN-γ, and GM-CSF) in PBMCs from all 10 donors. Little to no IL-8 was induced by the positive controls. SIRPAB-11-K322A induced minimal levels of cytokine release or levels comparable to the negative controls (IgG1 isotype control-K322A and IgG1 isotype control).

The ability of SIRPAB-11-K322A to induce cytokine release from LPS- and SEB-activated human PBMCs in vitro was also examined. The following cytokines were evaluated: IL-1β, IL-2, IL-6, IL-8, IL-10, IL-12p70, TNF-α, IFNγ, and GM-CSF. SIRPAB-11-K322A concentrations of 0.03, 3, and 30 μg/mL or 0.03, 3 and 30 μg/well were used in soluble and plate-bound (immobilized) formats, respectively. Peripheral blood mononuclear cells were isolated from whole-blood using Ficoll-Paque. For LPS stimulation, the PBMCs were divided equally into tubes with or without 100 ng/mL LPS, and added to antibody pre-coated plates or incubated with soluble antibody in wells. For SEB stimulation, PBMCs were incubated with 0, 1, or 100 ng/mL SEB for 24 hours, washed, and then 0, 1, or 100 ng/mL SEB was added to the cells prior to plating on antibody pre-coated plates, or incubating with soluble antibody in wells. Cultured supernatants were collected for cytokine analysis 48 hours post-plating.

Figure 12B:
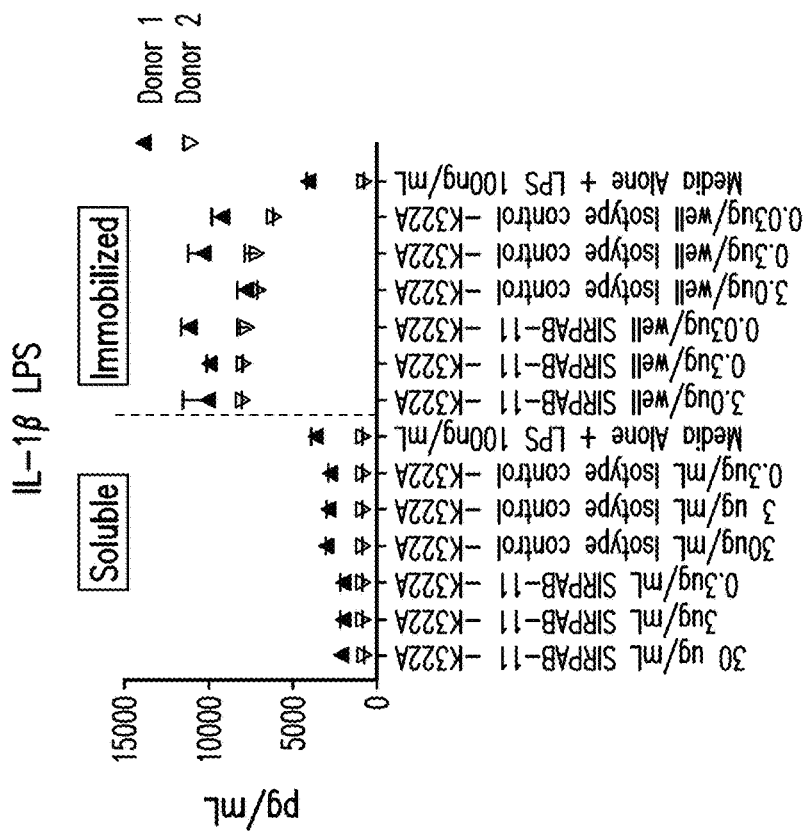
Figure 12A:
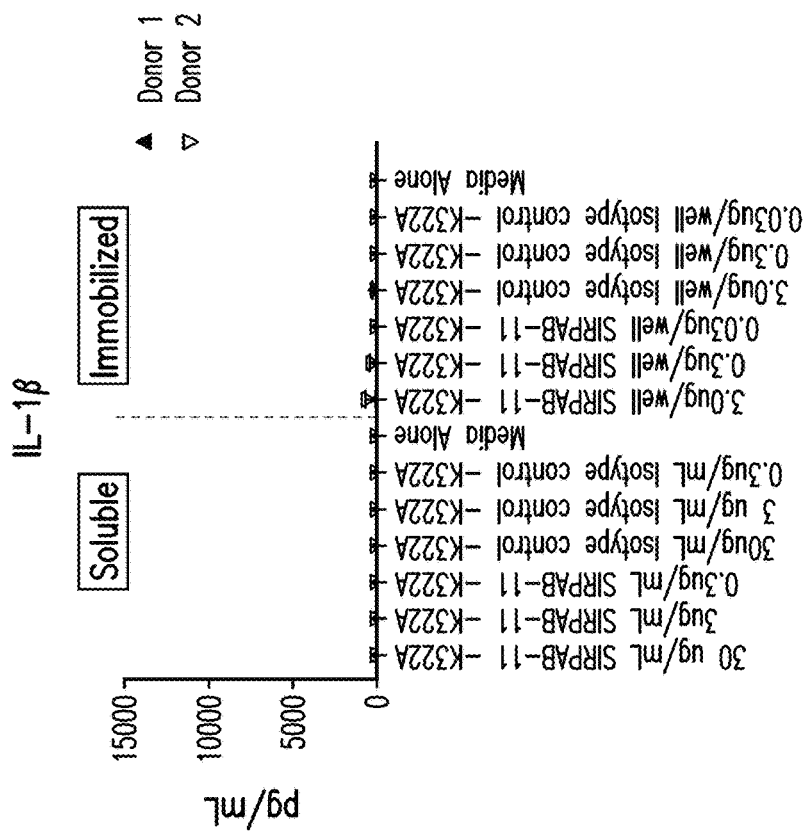

To determine if SIRPAB-11-K322A altered the function of activated myeloid cells, cytokine release of LPS-stimulated PBMCs treated with soluble and immobilized SIRPAB-11-K322A was assessed. In unstimulated PBMCs, overall levels of GM-CSF, IFN-γ, IL-2, IL-12p70, IL-10, and IL-1β were low. Stimulation with LPS elevated IFN-γ, IL-10, IL-1β, and IL-6 production. The data for IL-1β release from unstimulated and LPS-stimulated PBMCs are shown in FIG. 12A and FIG. 12B, respectively. Unstimulated PBMCs demonstrated absolute levels of IL-1β that were low and not biologically relevant (FIG. 12A). In PBMCs stimulated with LPS, treatment with SIRPAB-11-K322A did not change the level of IL-1β compared to IgG1 isotype control-K332A, regardless of whether the antibodies were soluble or immobilized (FIG. 12B). Treatment with soluble or immobilized. SIRPAB-11-K322A induced levels of IL-2, IL-6, IL-8, IL-10, IL-12p70, GM-CSF, TNF-α, and IFN-γ similar to those induced by negative control, IgG1 isotype control-K322A, regardless of whether the PBMCs had been activated with LPS. The data were further summarized in FIG. 12C.

Figure 12E:
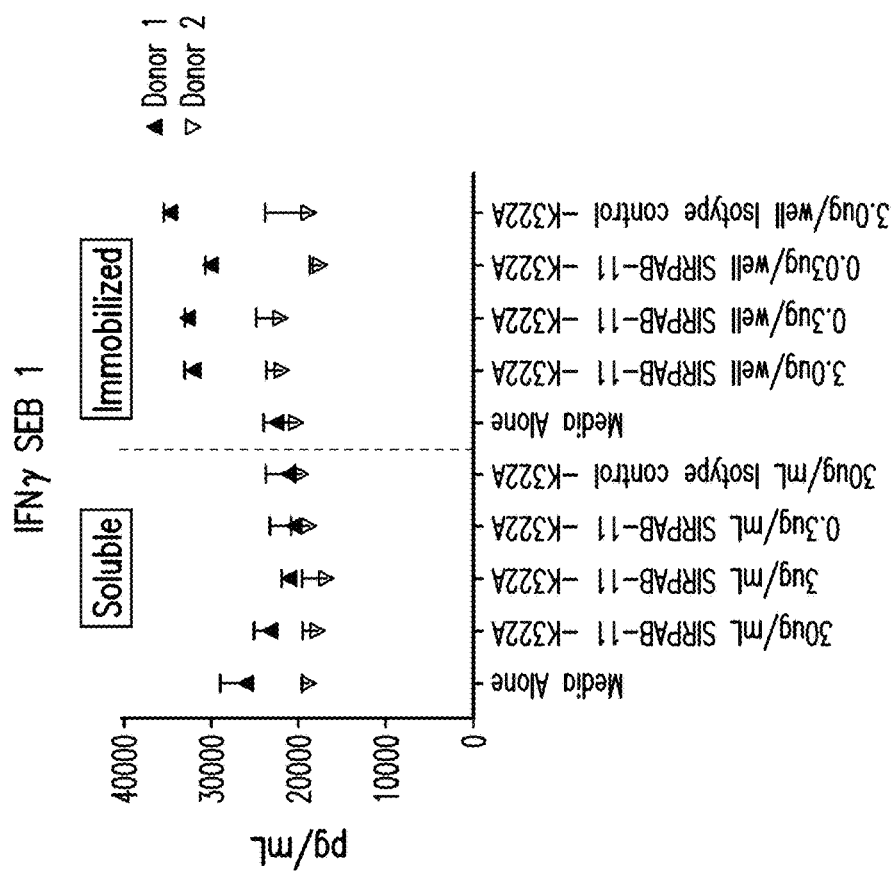
Figure 12D:
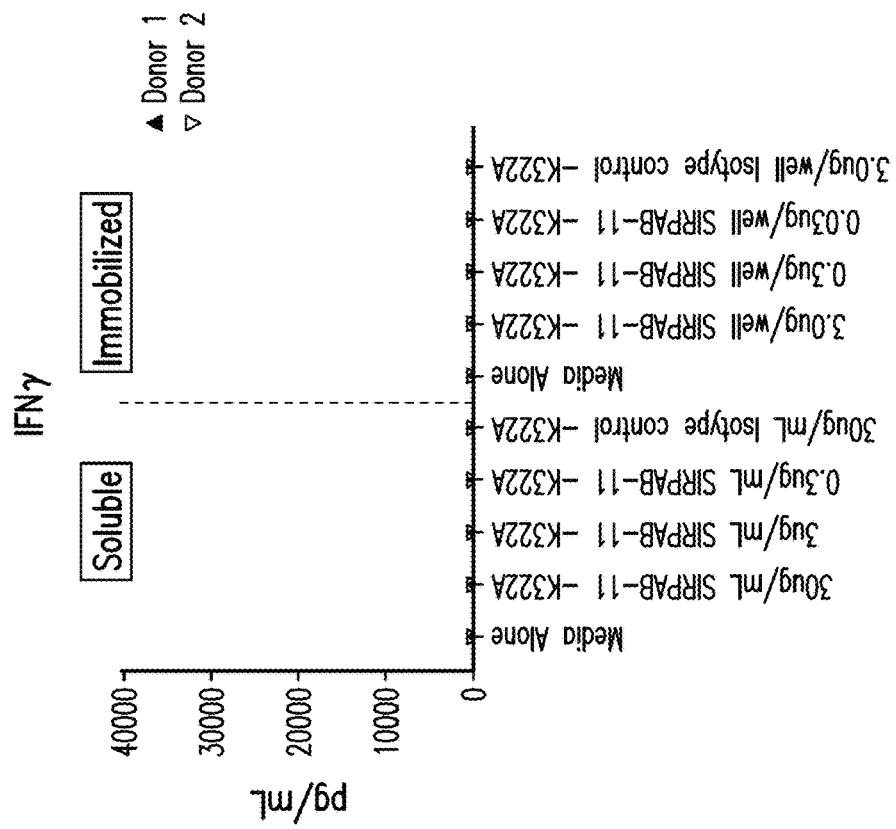
Figure 12F:
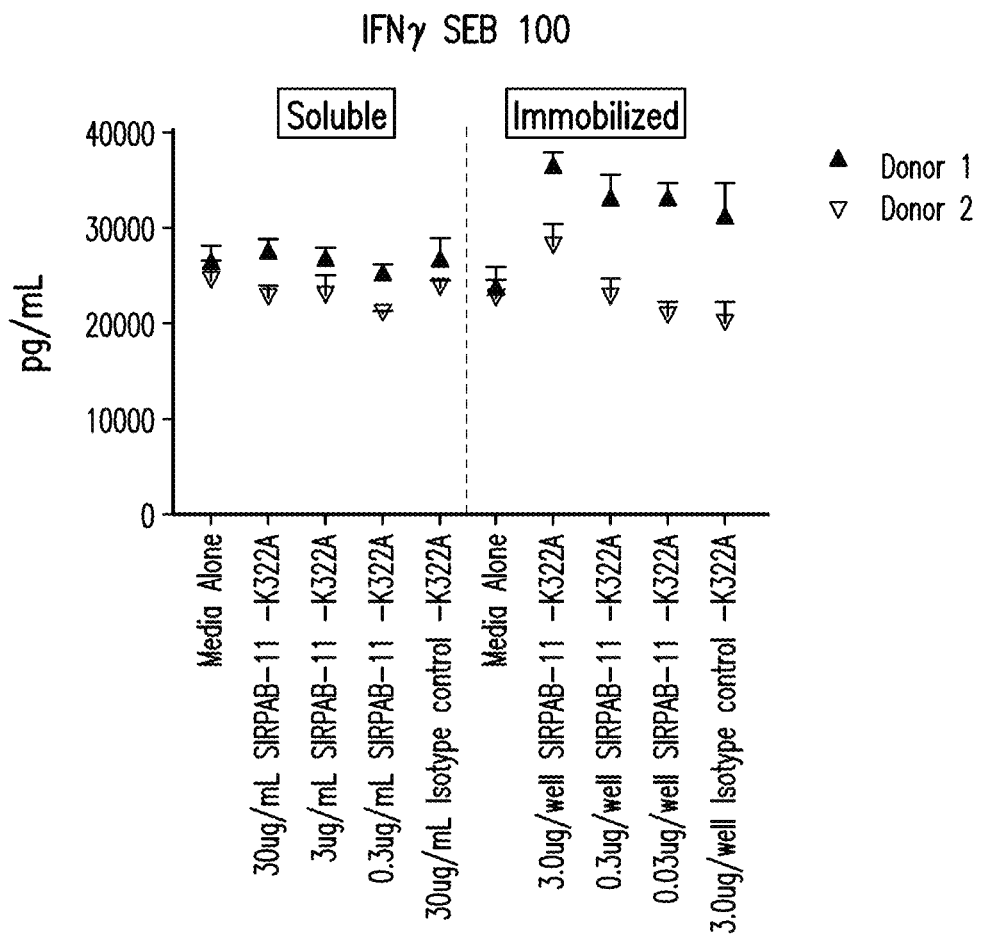

To determine if SIRPAB-11-K322A altered the function of pre-activated T cells, cytokine release by SEB-stimulated PBMCs treated with soluble and immobilized SIRPAB-11-K322A was assessed. In unstimulated PBMCs, cytokine levels of GM-CSF, IFN-γ, IL-2, Il-12p70, IL-10, and IL-1β were low. Stimulation with SEB elevated IFN-γ, IL-10, IL-1β, and IL-6 production in PBMCs. The data for IFN-γ release from unstimulated and SEB-stimulated PBMCs are shown in FIGS. 12D, 12E, and 12F. Stimulation with 1 and 100 ng/mL SEB did not change the IFN-γ levels as compared to those of unstimulated PBMCs. Treatment with soluble or immobilized SIRPAB-11-K322A did not change the levels of IFN-γ release from either unstimulated (FIG. 12D) or stimulated (FIGS. 12E and 12F) PBMCs as compared to IgG1 isotype control-K322A treatment. Treatment with soluble or immobilized SIRPAB-11-K322A resulted in levels of IL-1β, IL-2, IL-6, IL-8, IL-10, IL-12p70, GM-CSF, and TNF-α similar to levels observed with the negative control, IgG1 isotype control-K322A, regardless of whether the PBMCs had been activated with either concentration of SEB. The data were further summarized in FIGS. 12G and 12H.

5.9 Example 9: Phagocytosis Assays 5.9.1 Methods of Phagocytosis Assays

The activity of SIRPAB-11-K322A to promote phagocytosis of tumor cells by human macrophages as a single agent or in combination with either cetuximab or rituximab was assessed in vitro by co-culture assays. Five solid tumor cell lines were assayed for the effect of SIRPAB-11-K322A., both with cetuximab and as a single agent; one DLBCL line was used to examine the combination effect with rituxitnab. The single agent effect of SIRPAB-11-K322A was assessed utilizing three Acute Myeloid Leukemia (AML) cell lines and two PDX cultures. The presence of SIRPα, epidermal growth factor receptor (EGFR), and CD47 on tumor cells was confirmed by flow cytometry using fluorescently labeled monoclonal antibodies (e.g. SIRPAB-11-IgG4PE-AF647 for SIRPα staining).

Titrated doses of SIRPAB-11-K322A (0.001 nM to 20 nM), combined with cetuximab (0.2 mM or 1 nM), were tested using several cell lines, including the colorectal cancer (CRC) cell lines, GP2d, GP5d, SW480, and the head and neck squamous cell carcinoma. (HNSCC) cell line, FaDu, as target cells. The combination studies with rituximab (0.1 nM) utilized OCI-LY3 cells as the target cell line. Cells receiving cetuximab or rituximab treatment alone or in combination with isotype control antibodies were treated with the same concentration of antibody used in the SIRPAB-11-K322A combination wells. Tumor cells were labeled with carboxyfluorescein succinimidyl ester (CSFE), opsonized with cetuximab or rituximab, and added to wells containing 40,000 macrophages differentiated from human donor monocytes (n=2). The cells were then incubated with SIRPAB-11-K322A or control antibodies for 3 hours before the macrophages were labeled with anti-CD14-APC and quantitated using high content imaging. The percentage level of phagocytosis was calculated as the number of macrophages that were positive for both dyes divided by the total number of macrophages. Anti-CD47 IgG1 treatment alone at 20 nM was used as a positive control and the IgG1 isotype control-K322A antibody (20 nM) was used as a negative control.

To assess for single agent activity, AML cell lines OCI-AML2, MV-4-1, MOLM-13, and AML PDX cultures, AML PDX P1202 and AML PDX P5378, were used as target cells. Tumor cells opsonized with SIRPAB-11-K322A, SIRPAB-11-IgG4PE, or control antibodies were added to co-culture wells with 40,000 monocyte-derived macrophages and the same titrated doses of SIRPAB-11-K322A, SIRPAB-11-IgG4PE, IgG1 isotype control-K322A or IgG4 isotype control-4PE. The methods are the same as for the combination experiments described in this section.

5.9.2 Activity of Anti-SIRPα Antibodies Alone or in Combination with Cetuximab

The phagocytic activity of SIRPAB-11-K322A in combination with cetuximab was assessed in four cetuximab-resistant colorectal cancer (CRC) cell lines with identified KRAS alterations (Medico E, et al, Nat Cornmun. 2015 Apr. 30;6:7002). The combination of SIRPAB-11-K322A and cetuximab was effective in promoting phagocytosis in three of the four CRC cell lines tested. These were GP2d and GP5d, both containing the KRASG12D mutation; SW480, containing the KRASG12V mutation. In the fourth cell line where no increase in phagocytosis was observed with treatment by SIRPAB-11-K322A and cetuximab, the positive control antibody, anti-CD47 IgG1, had only a marginal effect on the phagocytosis of the cell line in comparison with the other three CRC cell lines, indicating that this fourth cell line is less responsive to modulation of the CD47/SIRPα pathway (data not shown).

Figures 13A, 13B, 13C:
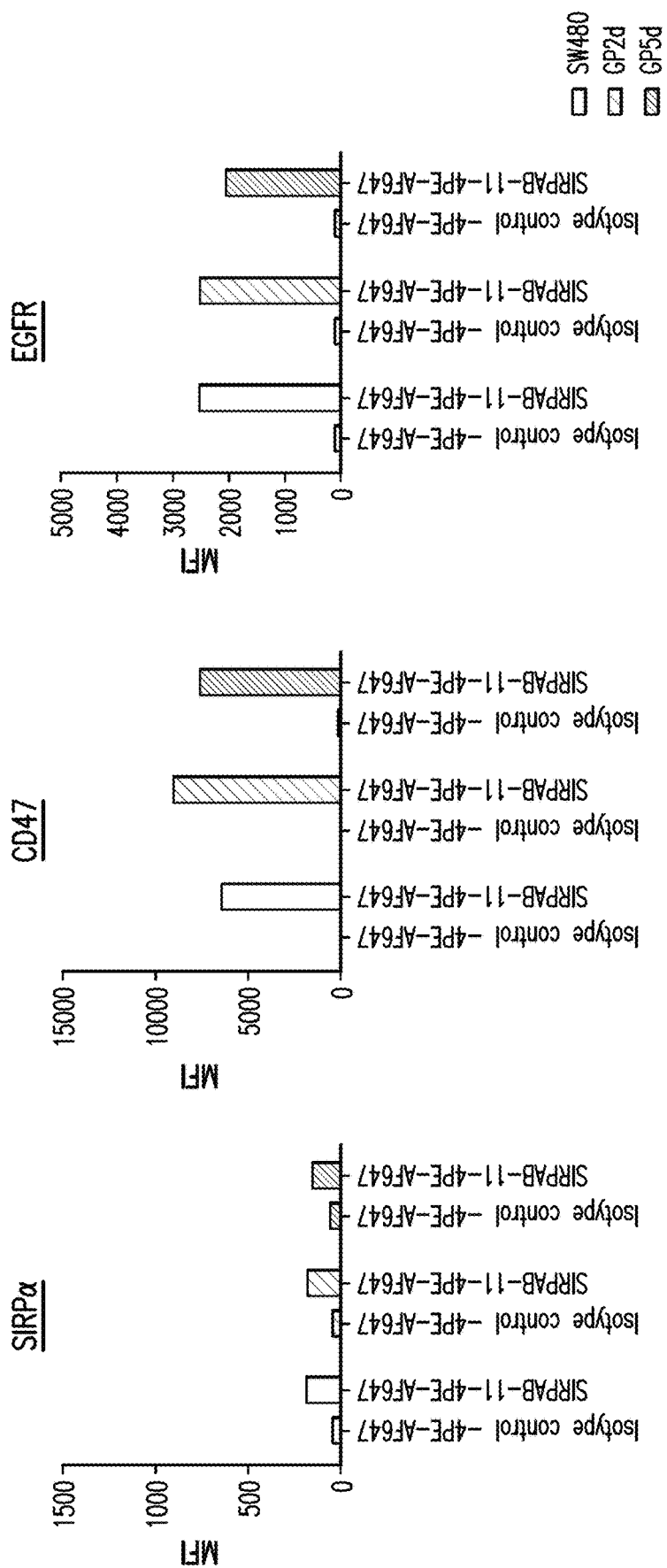

To demonstrate target and pathway expression, cell surface staining of SIRPα, EGFR, and CD47 on GP2d, GP5d and SW480 cells was evaluated by flow cytometry (FIGS. 13A-13C). All three cell lines displayed comparable high levels of CD47 and EGFR expression. Low but positive cell surface binding was demonstrated with SIRPAB-11-IgG4PE-AF647 compared to the isotype control.

Figure 13D:
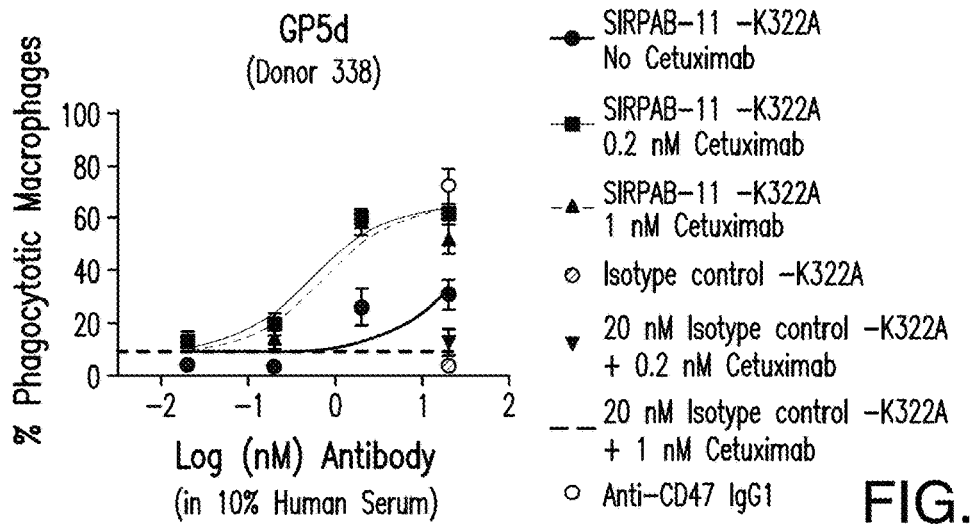
Figure 13E:
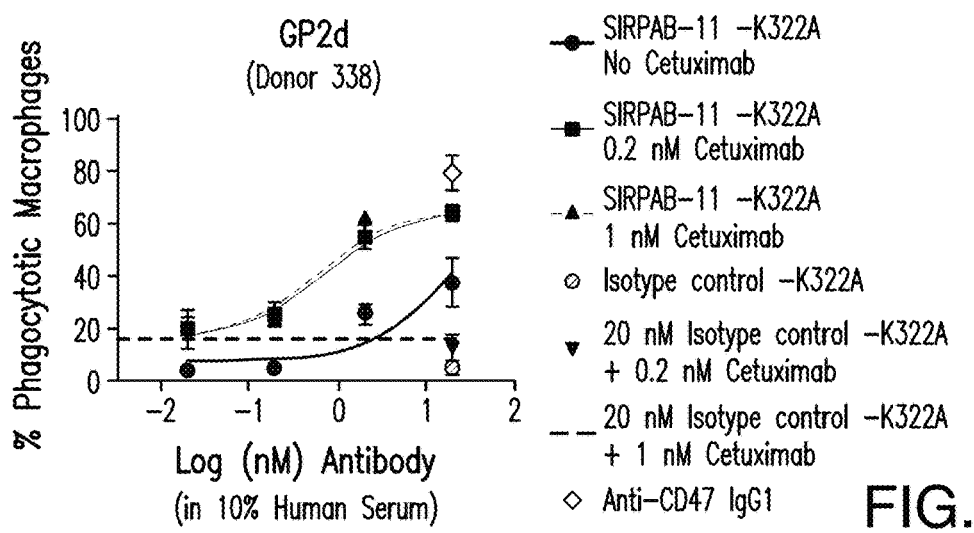
Figure 13F:
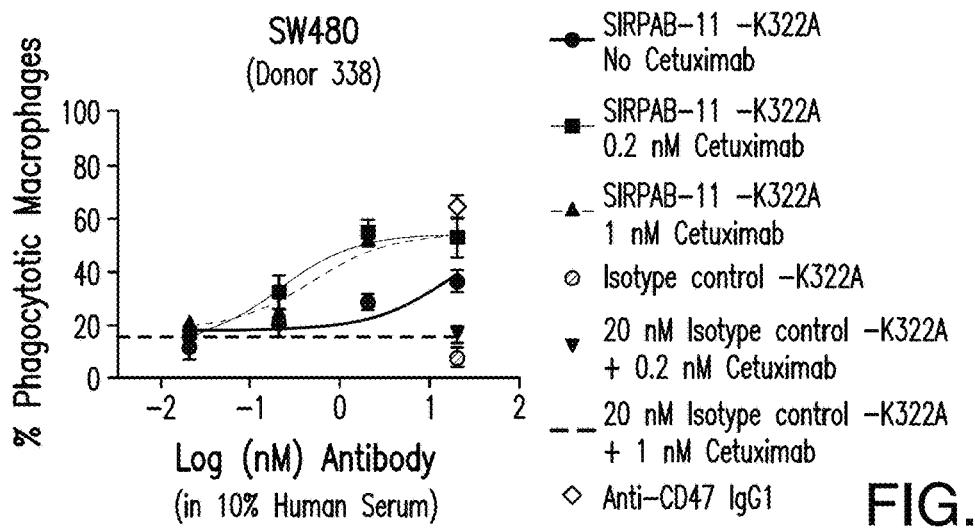

Macrophage-mediated phagocytosis of CRC tumor cells with SIRPAB-11-K322A treatment alone or in combination with cetuximab is shown in FIGS. 13D-13F. Co-cultures of monocyte-derived macrophages and target tumor cells, opsonized with 0.2 nM or 1 nM cetuximab and treated with SIRPAB-11-K322A, or treated with SIRPAB-11-K322A alone, demonstrated concentration-dependent increases in phagocytosis (FIGS. 13D-13F). SIRPAB-11-K322A treatment increased phagocytosis of the GP2d, GP5d, and SW480 CRC cell lines in combination with cetuximab over SIRPAB-11-K322A treatment alone. The mean EC50 values for percent phagocytic macrophages treated with the combination of 1 nM cetuximab and SIRPAB-11-K322A ranged between 0.28 nM and 0.44 nM for these three cells lines, compared to 8.79 nM to >20 nM for SIRPAB-11-K322A treatment alone, which calculated to an ~40-fold lower EC50 value for the combination (Table 24). Lower mean EC50 values were also observed with the combination of 0.2 nM cetuximab and SIRPAB-11-K322A compared to SIRPAB-11-K322A alone, but there was more variability across donors noted at this concentration of cetuximab. Cetuximab treatment alone (1 nM) or in combination with IgG1 isotype control-K322A (20 nM) demonstrated mean percent phagocytic macrophage levels (n=2 donors) of 24, 10.5, and 21 for the GP2d, GP5d, and SW480 CRC cell lines, respectively. This level of phagocytosis is lower than the mean percent phagocytic macrophage levels for the combination of 1 nM cetuximab and SIRPAB-11-K322A (20 nM, the highest concentration tested) in the same cell lines (62, 42.5, and 57 for GP2d, GP5d, and SW480 CRC cell lines, respectively, n=2 donors) indicating an enhancement of phagocytosis with SIRPAB-11-K322A treatment.

isotype control-K322A (20 nM) demonstrated percent phagocytic macrophage levels which were lower than that observed with the combination of cetuximab and SIRPAB-11-K322A (20 nM) indicating an enhancement of phagocytosis with SIRPAB-11-K322A treatment (percent phagocytic

TABLE 24

Half Maximal Effective Concentrations of SIRPAB-11-K322A in Cetuximab Combination Phagocytosis Assays

| | $EC_{50}$ Values (nM) | | | | | | | | | | |
|---|---|---|---|---|---|---|---|---|---|---|---|
| | GP2d | | | GP5d | | | SW480 | | | FaDu | |
| Donor | 338 | 358 | Mean | 338 | 358 | Mean | 338 | 358 | Mean | 358 | 224 |
| No Cetuximab | 13.110 | >20 | >16.56 | >20 | >20 | >20 | 14.19 | 3.393 | 8.79 | >20 | NC |
| 0.2 nM Cetuximab | 0.657 | 16.210 | 8.434 | 0.543 | 0.886 | 0.715 | 0.200 | 2.061 | 1.130 | 0.075 | NC |
| 1 nM Cetuximab | 0.495 | 0.247 | 0.371 | 0.714 | 0.162 | 0.438 | 0.461 | 0.102 | 0.282 | 0.049 | NC |

$EC_{50}$ = half-maximal effective concentration; FaDu = head and neck squamous cell carcinoma cell line; GP2d, GP5d, SW480 = colorectal cancer cell lines; NC = not calculated; nM = nanomolar.

In all cases, co-cultures treated with IgG1 isotype control-K322A alone exhibited low levels of phagocytosis.

Figure 13G:
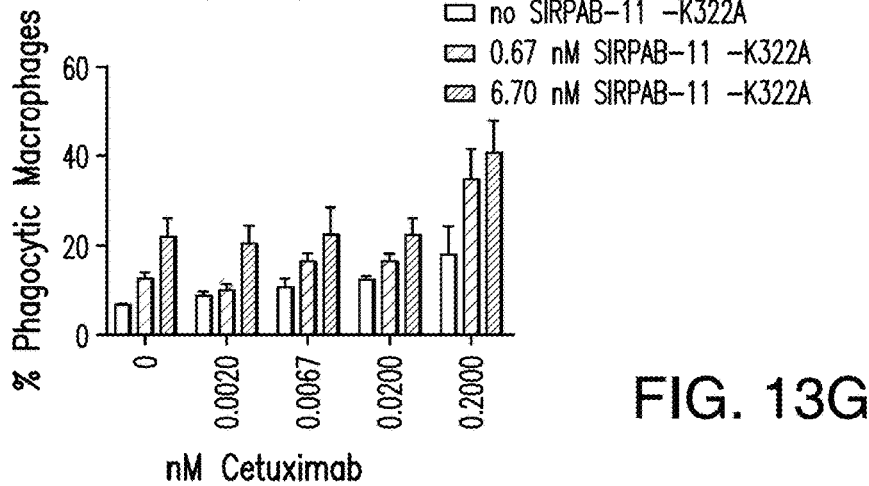
Figure 13H:
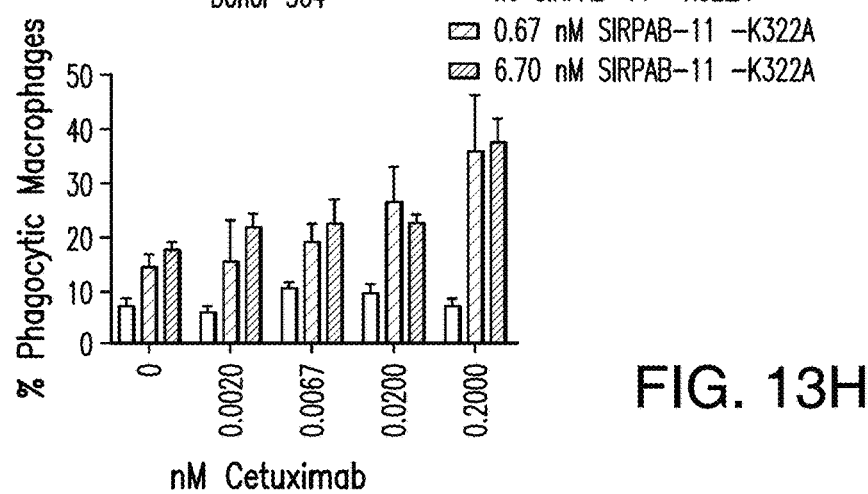

To determine the saturating concentrations of cetuxiinab on CRC tumor cells, flow cytometric binding assays were performed using GP2d and GP5d cells. Based on their EC10, EC50, and EC90 calculations, GP2d and GP5d phagocytosis assays were performed at or near cetuximab staining saturation, with EC50 and EC90 values well below 0.2 nM used in the phagocytosis assays. In vitro combination treatment assays were performed to evaluate the effect of cetuximab at concentrations below 0.2 nM on phagocytosis of GP2d and GP5d tumor cells (FIGS. 13G and 13H). A marked reduction in tumor phagocytosis was detected with cetuximab at the EC90, EC50, and EC10 concentrations compared to 0.2 nM and 1 nM, which were used in phagocytosis assays measuring the concentration-dependent effects of SIRPAB-11-K322A.

Additionally, FIG. 13H demonstrates that SIRPAB-11-K322A synergizes with cetuximab in promoting macrophage phagocytosis. For example, 0.67 nM of SIRPAB-11-K322A induced an increase in the percentage of phagocytic macrophages; however, the increase seen with both 0.67 nM of SIRPAB-11-K322A and 0.2 nM of cetuximab is greater than the summation of the increases induced by 0.67 nM of SIRPAB-11-K322A or 0.2 nM of cetuxiinab individually (compare the second bar from the left, the third bar from the right, and the second bar from the right in FIG. 13H).

Figure 13I:
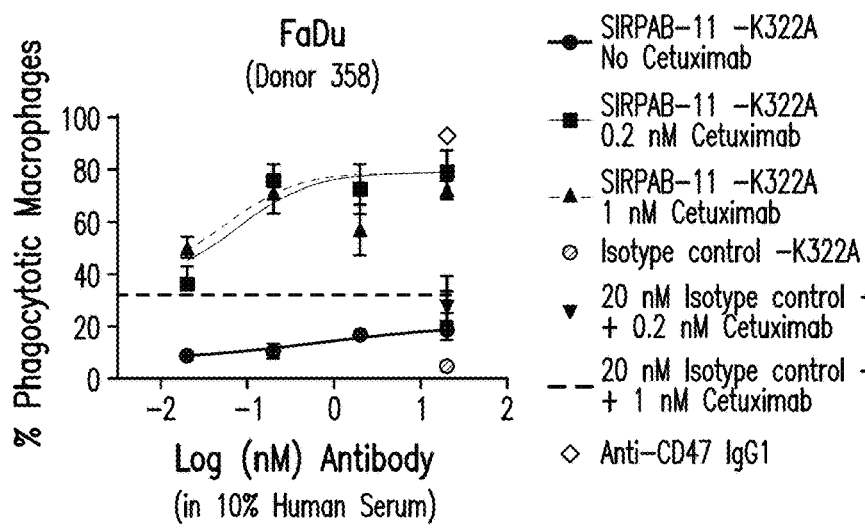

The phagocytic potential of SIRPAB-11-K322A combined with cetuximab was also evaluated in the HNSCC cell line FaDu (FIG. 13I). In combination co-culture assays, monocyte-derived macrophages demonstrated a robust increase in phagocytosis over SIRPAB-11-K322A treatment alone, reaching a plateau of approximately 70% phagocytic macrophages at SIRPAB-11-K322A concentrations ≥0.02 nM (for both 0.2 nM and 1 nM cetuximab). The mean EC50 values for percent phagocytic macrophages treated with 0.2 nM or 1 nM cetuximab and SIRPAB-11-K322A were 0.08 nM and 0.05 nM, respectively, compared to >20 nM for SIRPAB-11-K322A treatment alone (Table 24). Data from a second donor demonstrated a similar enhancement of phagocytosis with SIRPAB-11-K322A treatment in combination with 0.2 nM cetuximab (percent phagocytic macrophages: 34.8 for 20 nM SIRPAB-11-K322A in combination with 0.2 nM cetuximab vs 1.84 for SIRPAB-11-K322A alone), but did not reach the same maximum levels of phagocytosis as observed for the first donor making an EC50 value not calculable. Cetuximab treatment in combination with IgG1 macrophages for Donor 358: 1 nM cetuximab in combination with SIRPAB-11-K322A was 72.1 vs 31.8 for 1 nM cetuximab in combination with IgG1 isotype control-K322A).

5.9.3 Activity of Anti-SIRPα Antibodies in Combination with Rituximab

To assess the combination activity of SIRPAB-11-K322A in hematological malignancies, cells from the DLBCL cell line OCI-LY3 were opsonized with rituximab, and then co-cultured with macrophages in medium containing either concentration-titrated SIRPAB-11-K322A or the SIRPAB-11-IgG4PE variant antibody; isotype and Fc matched negative control antibodies were used. SIRPAB-11-K322A treatment increased phagocytosis of the OCI-LY3 cell line in combination with rituximab, over rituximab treatment alone (FIG. 14). The mean EC50 values (n=2 donors) for percent phagocytic macrophages treated with SIRPAB-11-K322A in combination with 0.1 nM rituximab was 0.11 nM compared to 1.46 nM for rituximab alone; the SIRPAB-11-K322A single agent EC50 values could not be calculated. Similar combination results were observed for SIRPAB-11-IgG4PE which has the same variable region as SIRPAB-11-K322A. Rituximab treatment at 0.082 nM (~0.1 nM) exhibited minimal phagocytosis as a single agent (11.9% and 11.5% phagocytic macrophages, n=2 donors) as did SIRPAB-11-K322A over the concentration range tested (<5% phagocytic macrophages for all concentrations, n=2 donors). In contrast, robust increases in phagocytosis (up to a maximum 63.1% and 75.3% phagocytic macrophages for 20 nM SIRPAB-11-K322A and 0.1 nM rituximab, n=2 donors) were observed with the combination of SIRPAB-11-K322A and 0.1 nM rituximab starting at low SIRPAB-11-K322A concentrations. Minimal increases in the percentage of phagocytic macrophages were seen for rituximab in combination with the IgG1 isotype control-K322A (% phagocytic macrophages, n=2 donors: 20.7 and 18.6 for 0.1 nM rituximab in combination with 20 nM IgG1 isotype control-K322A compared to 11.9 and 11.5 for 0.082 nM [~0.1 nM] rituximab alone and 2 for 20 nM IgG1 isotype control-K322A alone)

Additionally, FIG. 14 demonstrates that SIRPAB-11-K322A synergizes with rituximab in promoting macrophage phagocytosis. For example, the increase of macrophage phagocytosis seen with both 0.1 nM of SIRPAB-11-K322A and 0.1 nM of rituximab is greater than the summation of the increases induced by 0.1 nM of SIRPAB-11-K322A or 0.1 nM of rituximab individually (compare the data points right above "−1" on the x-axis of in FIG. 14). Similar synergy was also observed between SIRPAB-11-Ig4PE and rituximab, indicating that the synergy is not unique to a particular Fc variant.

As shown above, SIRPAB-11-K322A in combination with cetuximab or rituximab, promoted phagocytosis of HNSCC cell line, DLBCL cell line or CRC cell line in co-culture assays with human monocyte-derived macrophages. The mechanism underlying the combination effect against the tested cells can be that through the blockade of the CD47/SIRPα interaction, which allows the unblocking of the "don't eat me" signal (Jaiswal S, Cell. 2009 Jul. 23;138(2):271-85; Majeti R, et al., Cell. 2009 Jul. 23;138(2):286-99). the effector-competent partner antibody provides a positive signal to the macrophages through FcγR1 binding and activation. In contrast, the autologous T-cell and monocyte aberrant phagocytosis (antibody-dependent cellular phagocytosis (ADCP)) of self cell targets by autologous macrophages does not occur with SIRPAB-11-K322A treatment, as described above. The absence of ADCP with SIRPAB-11-K322A treatment, which is desirable, is likely due to the presence of other mechanisms that inhibit the phagocytosis of self cell targets.

5.9.4 Single Agent Activity

The effect of SIRPAB-11-K322A alone in promoting macrophage-mediated phagocytosis was further evaluated in three AML tumor lines and cultures from two AML PDX models. Surface expression of SIRPα on these cells was confirmed by flow cytometric binding analysis using the SIRPAB-11-IgG4PE antibody.

Figure 15A:
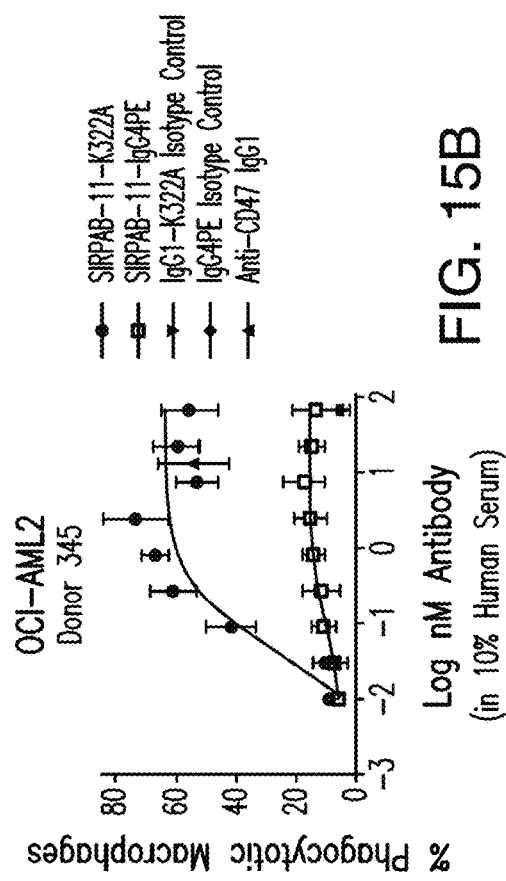
Figure 15B:
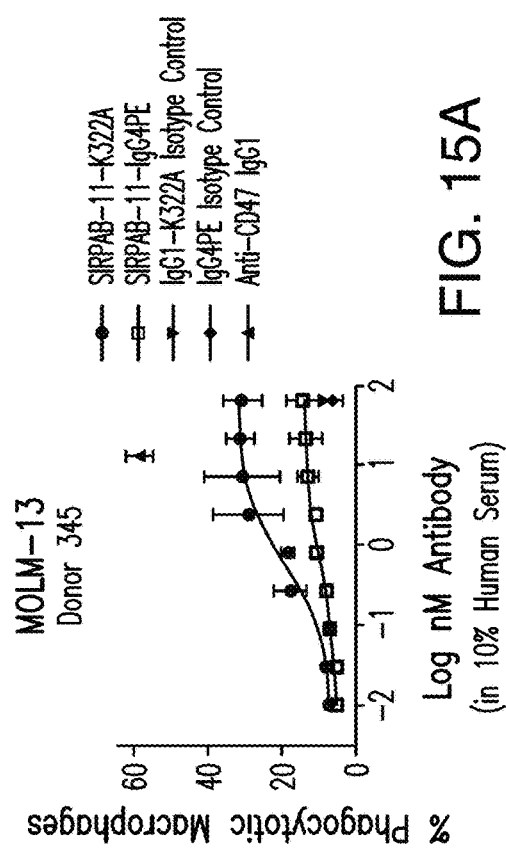
Figure 15C:
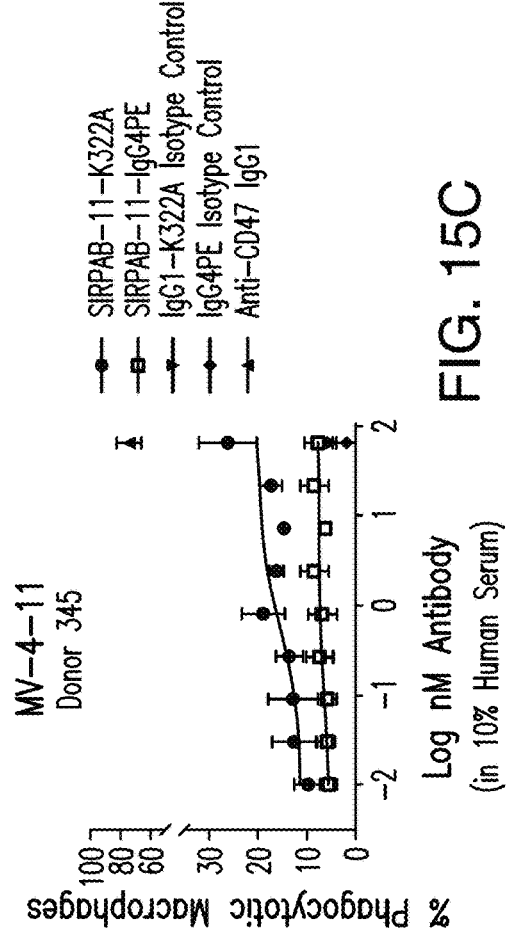

In single agent phagocytosis assays, SIRPAB-11-K322A treatment demonstrated concentration-dependent increases in percentages of phagocytic macrophages with maximum percent ranges: for MOLM 13, 28 to 31, n=3 donor macrophages (FIG. 15A, Donor 345); for OCI-AML2, 45 to 74, n=3 donor macrophages (FIG. 15B, Donor 345); for MV-4-11, 26 to 48, n=3 donor macrophages (FIG. 15C, Donor 345). Mean EC50 values for single agent phagocytosis were 0.24 nM, 0.03 nM, and 0.41 nM for the MOLM-13, OCI-AML-2, and MV-4-11 AML cell lines, respectively (Table 25). Single agent treatment with SIRPAB-11-IgG4PE antibody demonstrated less phagocytosis with the three AML cells lines compared to SIRPAB-11-K322A, when tested over a 0.01 nM to 66.67 nM concentration range. However, when tested at a single high concentration, the difference between treatment with SIRPAB-11-K322A and the SIRPAB-11-IgG4PE antibody was less clear.

In all cases, co-cultures of AML cell lines and macrophages treated with anti-IgG1 isotype control-K322A and IgG4 isotype control-4PE exhibited low levels of phagocytosis.

Figure 15D:
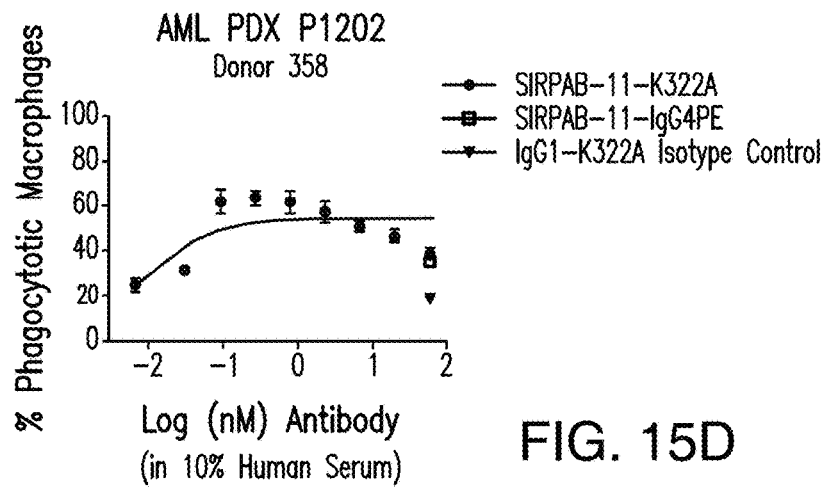
Figure 15E:
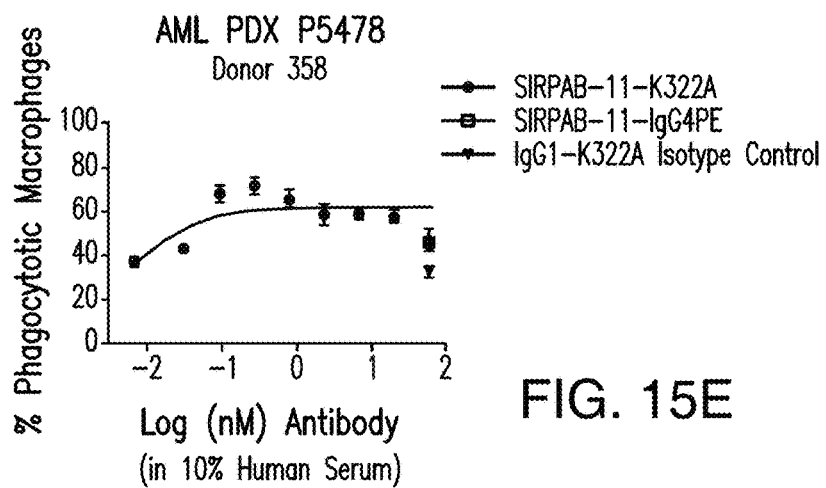

Additional single agent phagocytosis data was generated with cultures of 2 AML patient samples derived from PDX models (FIGS. 15D and 15E). SIRPAB-11-K322A treatment demonstrated enhancement of phagocytic macrophages with maximum values of 63.35% and 71.54% for AML PDX models P1202 and P5478, respectively. Similar to the AML cell lines, single agent treatment with the SIRPAB-11-IgG4PE antibody exhibited less phagocytosis compared to the SIRPAB-11-K322A maximum values (35.38% and 45.08% phagocytic macrophages for PDX models P1202 and P5478, respectively, treated with the SIRPAB-11-IgG4PE antibody). These levels were still above the IgG1 isotype control-K322A control in both cases.

5.9.5 Cynomolgus Phagocytosis Assay

The functional relevance of SIRPAB-11-K322A binding to cynomolgus SIRPα was determined by assessing the phagocytic activity of SIRPAB-11-K322A-treated cynomolgus monocyte-derived macrophages against the human tumor cell line, OCI-AML2. Cynomolgus PBMC-derived monocytes were differentiated into macrophages and used in co-culture assays (n=2). Tumor cells were labeled with carboxyfluorescein diacetate succinimidyl ester (CFSE), opsonized with SIRPAB-11-K322A (0.067 nM to 66.7 nM) or control antibodies (0.067 to 66.7 nM), and added to co-culture assays with 40,000 cynomolgus macrophages and the same concentrations of SIRPAB-11-K322A, IgG1 isotype control-K322A, or CD47 IgG1, for 1 or 3 hours. At the end of the incubation period, macrophages were labeled with anti-CD14-allophycocyanin (APC), and quantitated using high content imaging. The percentage of phagocytic macrophages was calculated as the number of macrophages that were positive for both dyes divided by the total number of macrophages.

Figure 15F:
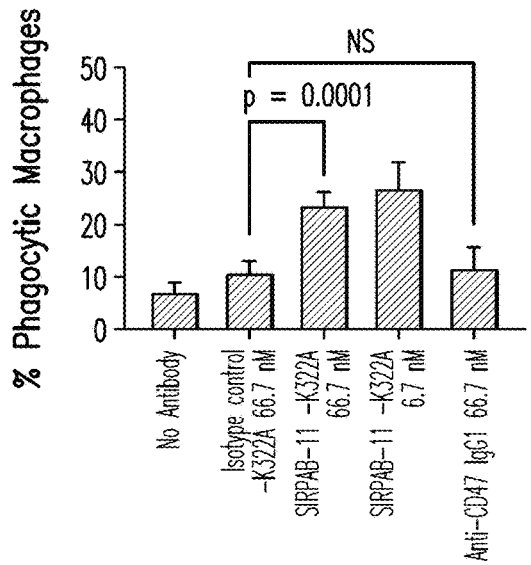

Treatment of cynomolgus macaque macrophages with SIRPAB-11-K322A significantly increased phagocytosis of OCI-AML2 human tumor cells compared to that observed with the negative control, IgG1 isotype control-K322A (p<0.0001, 1 hour incubation; FIG. 15F). There was no difference in the percent phagocytic macrophages between the two SIRPAB-11-K322A concentrations tested. A repeat of the assay with macrophages from a different cynomolgus macaque donor yielded similar results (p<0.0001 for 0.067 nM, 0.67 nM, 6.67 nM, or 66.7 nM SIRPAB-11-K322A compared to concentration-matched isotype control, IgG1 isotype control-K322A at 1 hour incubation). These data

TABLE 25

Half Maximal Effective Concentrations for Single Agent Phagocytosis Assays

| | $EC_{50}$ SIRPAB-11-K322A (nM) | | | | | | | | | | | |
|---|---|---|---|---|---|---|---|---|---|---|---|---|
| | MOLM-13 | | | | OCI-AML2 | | | | MV-4-11 | | | |
| Donor | 345 | 226 | 358 | M | 345 | 226 | 358 | M | 345 | 226 | 358 | M |
| $EC_{50}$ | 0.57 | 0.10 | 0.04 | 0.24 | 0.04 | 0.02 | 0.02 | 0.03 | 0.55 | 0.13 | 0.56 | 0.41 |

$EC_{50}$ = half maximal concentration; M = mean; MOLM-13, MV-4-11, and OCI-AML2 = acute myeloid leukemia (AML) cell lines.

indicate that SIRPAB-11-K322A binding to cynomolgus macaque SIRPα has a functional effect in promoting the phagocytotic activities of macrophages co-cultured with tumor cells.

5.10 Example 10: A Phase 1, Open-Label, Dose Finding Study of SIRPAB-11-K322A, A Monoclonal Antibody Directed Against SIRPα, Alone and in Combination with Cetuximab in Subjects with Advanced Solid Cancers The antibody SIRPAB-11-K322A is to be studied in advanced solid cancers (Part A, Stage 1 and Part B), and in advanced colorectal cancer (CRC) and/or advanced squamous cell carcinoma of the head and neck (SCCHN) (Part A, Stage 2 and Part B).

5.10.1 Objectives

Primary Objectives:
To determine the safety and tolerability of SIRPAB-11-K322A alone and in combination with cetuximab.
To define the non-tolerated dose (NTD), the maximum tolerated dose (MTD) and/or the recommended Phase 2 dose (RP2D) of SIRPAB-11-K322A alone and in combination with cetuximab.
Secondary Objectives:
To provide information on the preliminary efficacy of SIRPAB-11-K322A alone and in combination with cetuximab.
To characterize the pharmacokinetics (PK) of SIRPAB-11-K322A.
To evaluate the presence, frequency, and functional impact of anti-SIRPAB-11-K322A antibodies (ADAs).

5.10.2 Study Design

This study is an open-label, Phase 1, dose escalation (Part A) and expansion (Part B), first-in-human clinical study of SIRPAB-11-K322A in subjects with advanced solid cancers. The dose escalation part (Part A) of the study will be conducted in two stages using Bayesian methodology. Stage 1 will evaluate the safety and tolerability of escalating doses of SIRPAB-11-K322A, administered intravenously (IV), to determine MTD, NTD, and/or RP2D of SIRPAB-11-K322A in subjects with advanced unresectable solid cancers. Stage 2 will evaluate the safety and tolerability of escalating doses of SIRPAB-11-K322A, in combination with weekly cetuximab, both administered IV, to determine the NTD, MTD, and/or RP2D of SIRPAB-11-K322A plus cetuximab in subjects with advanced CRC and/or SCCHN.

The dose expansion part (Part B) will further evaluate the safety and efficacy of SIRPAB-11-K322A administered at or below the Stage 2 MTD in combination with cetuximab in selected expansion cohorts of up to approximately 20 evaluable subjects each, in order to determine the RP2D. Part B expansion cohorts may test different doses and/or schedules of SIRPAB-11-K322A based on the safety and tolerability determined in Part A. Part B expansion cohorts may include subjects with advanced CRC (KRAS/NRAS/BRAF wild-type), CRC (KRAS/NRAS/BRAF mutant), SCCHN, and/or other advanced solid cancers. Additional cohorts of subjects with advanced solid tumors may be considered in Part B. All treatments will be administered in 28-day cycles until clinically-significant disease progression, unacceptable toxicity, or decision to withdraw.

In Stage 1 (Part A), each subject will receive the assigned dose of SIRPAB-11-K322A on Cycle 1 Day 1 and weekly (QW) thereafter. The starting dose (Stage 1, Cohort 1) of SIRPAB-11-K322A will be 0.3 mg/kg. If the starting dose of SIRPAB-11-K322A is not tolerated, a lower dose level may be explored. The initial dose escalation increment in each cohort will be approximately 3-fold.

The decision to proceed to Stage 2 will be made based on the safety, tolerability, PK, PD, and ADA observed in at least 1 cohort of Stage 1. Stage 2 will begin after at least one dose cohort in Stage 1 is determined to be tolerated, and may therefore begin prior to establishing the MTD or NTD in Stage 1. The starting dose (Stage 2, Cohort 1) of SIRPAB-11-K322A must be determined to be tolerated in Stage 1. The starting dose of SIRPAB-11-K322A plus cetuximab is not tolerated, a lower dose level of SIRPAB-11-K322A may be explored. Subsequent cohorts in Stage 2 will only open to enrollment only after the corresponding dosing cohorts in Stage 1 are determined to be tolerated. In Stage 2, cetuximab dosing will be fixed and will be administered on Cycle 1 Day 1 (400 mg/m$^2$ IV) and weekly thereafter (250 mg/m$^2$ IV QW).

During dose escalation, the decision to evaluate additional subjects within a dose cohort, the next higher dose level, intermediate dose levels, an alternate dosing interval, or declare an MTD will be determined, based on the Bayesian logistic regression model, clinical and laboratory safety data (both Dose Limiting Toxicity [DLT] and non-DLT safety data), PK, and ADA for a given dose level, The frequency of SIRPAB-11-K322A dosing may be reduced based on review of PK and/or PD from a given dose level. If the dose frequency is reduced, the total dose intensity of the subsequent cohort will not exceed 3-fold.

In Part A, after the first dose is administered in any cohort, subjects in each cohort are to be observed for at least 28 days (Cycle 1, Days 1 to 28, DLT window) before the next higher, protocol-specified dose cohort can begin. For the first two subjects, a one-week interval between the initial and subsequently enrolled dosing subject will be employed to observe for acute toxicities. After the first two subjects, there will be 1 day between initial dosing of new subjects in a given cohort.

In subjects receiving SIRPAB-11-K322A monotherapy (Part A, Stage 1), a subject evaluable for DLT is defined as one who:
Has received at least 3 of 4 complete doses of SIRPAB-11-K322A during Cycle 1, Days 1 to 28 (QW dosing) (or at least 75% of the total planned Cycle 1 dose intensity) without experiencing a DLT,
or
Experienced a DLT after receiving at least one dose of SIRPAB-11-K322A or fraction thereof during Cycle 1, Days 1 to 28.

In subjects receiving SIRPAB-11-K322A in combination with cetuximab (Part A, Stage 2), a subject evaluable for DLT is defined as one who:
Has received at least 3 of 4 complete doses of cetuximab and at least 3 of 4 complete doses of SIRPAB-11-K322A during Cycle 1, Days 1 to 28 (or at least 75% of the total planned Cycle 1 dose intensity of cetuximab and SIRPAB-11-K322A) without experiencing a DLT,
or
Experienced a DLT after receiving at least one dose or fraction thereof SIRPAB-11-K322A during Cycle 1, Days 1 to 28.

Subjects non-evaluable for DLT will be replaced. Additional subjects within any cohort may be enrolled to better characterize PK, PD, or the MTD in accordance with the BLRM.

Following completion of dose escalation (Part A), selected cohorts of up to approximately 20 efficacy evaluable subjects per cohort will receive SIRPAB-11-K322A in combination with cetuximab. Expansion may occur at the MTD established in the cetuximab combination dose escalation phase and/or at a lower dose, or an alternative tolerable dosing schedule, based on review of safety, PK, PD, and ADA data. Cohorts may include subjects with advanced, unresectable CRC (KR4S, NRAS, or BRAF mutant), CRC (KRAS, NRAS, or BRAF wild-type), SCCHN, and/or advanced solid tumors. All CRC subjects should have determination of tumor gene status for RAS (KRAS and NRAS) and BRAF (V600E) mutations (individually or as part of next-generation sequencing panel). RAS mutations are defined as somatic mutations in exon 2 (codons 12 and 13), exon 3 (codons 59 and 61), and exon 4 (codons 117 and 146) of either KRAS or NR4S. Testing for KRAS, NRAS, and BRAF mutations in the United States should be performed only in laboratories that are certified under the clinical laboratory improvement amendments of 1988 (CLIA-88), as qualified to perform high-complexity clinical laboratory (molecular pathology) testing. Mutation status will be confirmed after subject enrollment by central laboratory testing.

The study will be conducted in compliance with International Conference on Harmonisation (ICH) Good Clinical Practices (GCPs).

5.10.3 Study Population

Subjects (male or female) ≥18 years of age, with advanced solid cancers, including advanced CRC and advanced SCCHN, who have progressed on (or not been able to tolerate due to medical comorbidities or unacceptable toxicity) standard anticancer therapy, or for whom no other approved conventional therapy exists, will be enrolled in the study.

The study will enroll approximately 140 subjects with advanced solid cancers. In Part A, approximately 60 subjects (including dose escalation cohorts in Stage 1 and Stage 2 of approximately 3 to 6 evaluable subjects each will be enrolled. In the Part B expansion phase, up to 20 subjects in up to 4 cohorts may be enrolled (up to approximately 80 total subjects).

5.10.4 Length of Study

Full enrollment is expected to take approximately 30 months to complete (18 months for Part A and 12 months for Part B). Completion of active treatment and post-treatment follow-up is expected to take an additional 6 to 12 months. The entire study is expected to continue for approximately 42 months.

The End of Trial is defined as either the date of the last visit of the last subject to complete the post-treatment follow-up, or the date of receipt of the last data point from the last subject that is required for primary, secondary and/or exploratory analysis, as prespecified in the protocol, whichever is the later date.

5.10.5 Study Treatments

The investigational product (IP), SIRPAB-11-K322A, will be supplied for IV administration.

To reduce the risk of infusion-related reactions (IRR), premedication with an antipyretic and an antihistamine are required in Cycle 1. If a subject does not experience an IRR during Cycle 1, then premedication can be stopped for subsequent treatment cycles. For subjects receiving cetuximab, premedications do not need to be repeated prior to SIRPAB-11-K322A dosing. SIRPAB-11-K322A treatment will continue until clinically significant disease progression, unacceptable toxicity, or subject/Investigator decision to withdraw.

For subjects receiving cetuximab in combination with SIRPAB-11-K322A, cetuximab will be administered (per package insert and institutional standard practice) on Cycle 1 Day 1 (400 mg/m$^2$ IV as a 120-minute infusion) and weekly thereafter (250 mg/m$^2$ IV QW infused over 60 minutes). Subjects will receive cetuximab infusion prior to starting the SIRPAB-11-K322A infusion on days receiving both treatments. Subjects receiving cetuximab should receive premedication with an H1 antagonist (such as 50 mg of diphenhydramine IV) 30 to 60 minutes prior to the first dose. Additional premedication such as a corticosteroid may be given according to institutional standard of care and country cetuximab product information. For subjects with a history of Grade 2 IRR with a prior cetuximab infusion, premedication with corticosteroids is recommended (eg, dexamethasone 10 mg or equivalent). Premedication should be administered for subsequent cetuximab infusions based upon clinical judgment and presence/severity of prior IRRs. For subjects who experience Grade 1 or Grade 2 IRRs and non-serious Grade 3 IRRs, the cetuximab infusion rate should be reduced by 50%. For serious infusion reactions, requiring medical intervention and/or hospitalization, cetuximab should be immediately and permanently discontinued. Dose reductions for Grade 3 or 4 acneiform rash are permitted per the cetuximab package insert. See Erbitux label approved by FDA, reference ID 4258364, revised May 2018, Section 2.4, at accessdatafda.gov/drugsatfda_docs/label/2018/1250840rig1s2681b1.pdf.

In the Part B expansion, based on the safety, PK, PD and ADA evaluations from the SIRPAB-11-K322A single-agent and cetuximab combination dose escalation, subjects may receive SIRPAB-11-K322A at the MTD and/or at a lower dose, and on a QW, Q2W, or alternate dose schedule.

5.10.6 Overview of Key Efficacy Assessments

The primary efficacy variable is tumor response rate. Subjects will be evaluated for efficacy after Cycles 2, 4, and 6; and then every 3 cycles thereafter. All treated subjects will be included in the efficacy analyses. For solid tumors, assessment will be based on Response Evaluation Criteria in Solid Tumors (RECIST 1.1) (Eisenhauer E A, et al. Eur J Cancer 2009;45(2):228-247) as the primary method as well as modified RECIST 1.1 for immune-based therapeutics (iRECIST) (Seymour L, et al. Lancet Oncol. 2017;18:e143-e152) as a supplementary exploratory method.

A descriptive analysis of evidence of antitumor activity will be provided based on clinical, laboratory, and radiographic assessments, which includes assessment of target lesion, non-target lesion, new lesion and overall response. Both confirmed and unconfirmed responses by RECIST 1.1 will be assessed.

The efficacy variable of focus for Part A will be objective response rate (ORR). Additional efficacy variables to be analyzed include time to response and duration of response.

For Part B, efficacy variables to be analyzed include ORR, time to response, duration of response, progression-free survival (PFS) and overall survival (OS).

If treatment is discontinued for reasons other than disease progression, start of a new anticancer therapy, or withdrawal of consent from the entire study, subjects will be requested to continue tumor assessments according to the specified tumor assessment schedule until disease progression and/or initiation of new systemic anticancer therapies. Survival status will be determined following disease progression, approximately every 12 weeks for up to 1 year. In addition, anticancer therapies will be collected after disease progression.

Efficacy variables will mature when the last subject in each cohort has withdrawn from the study or completed 6 cycles.

The primary efficacy variable for Part A is ORR. For Part B, efficacy variables to be analyzed include ORR, time to response, duration of response, PFS, and OS. Point estimates and 2-sided 95% confidence intervals of ORR will be reported. For time to event endpoints, Kaplan-Meier survival analyses will be performed.

5.10.7 Inclusion Criteria

Subjects must satisfy the following criteria to be enrolled in the study:

1. Subject must understand and voluntarily sign an informed consent form (ICF) prior to any study-related assessments/procedures being conducted.
2. Subject (male or female) is ≥18 years of age at the time of signing the ICF.
3. Subject must have progressed on (or not been able to tolerate due to medical comorbidities or unacceptable toxicity) standard anticancer therapy or for whom no other approved conventional therapy exists and have histological or cytological confirmation of:
   In Part A, Stage 1, advanced unresectable solid tumors.
   In Part A, Stage 2, advanced unresectable colorectal cancer or squamous cell carcinoma of the head and neck.
   In Part B,
   Cohort 1: advanced unresectable colorectal cancer with molecular documentation of a mutation in RAS (KRAS or NRAS) or BRAF (V600E). RAS mutations are defined as somatic mutations in exon 2 (codons 12 and 13), exon 3 (codons 59 and 61), and exon 4 (codons 117 and 146) of either KRAS or NRAS.
   Cohort 2: advanced unresectable colorectal cancer with wild-type RAS (without somatic mutations in exons 2, 3, and 4 of either KRAS or NRAS), and BRAF WT for V600E.
   Cohort 3: advanced unresectable squamous cell carcinoma of the head and neck.
   Cohort 4: advanced unresectable solid tumors.
4. Subject consents to retrieve formalin-fixed paraffin-embedded (FFPE) archival tumor tissue, either in tumor blocks or sectioned/mounted specimens.
5. For subjects participating in the Part A intensive PD cohorts and Part B only, subject consents and has tumor accessible for paired tumor biopsies during Screening and Cycle 1.
6. Subject must have at least one site of measurable disease as determined by RECIST v1.1.
7. Subject has an ECOG PS of 0 or 1.
8. Subjects must have the following laboratory values:
   Absolute neutrophil count (ANC)≥$1.5 \times 10^9$/L without growth factor support for 7 days (14 days if pegfilgrastim).
   Hemoglobin (Hgb)≥8 g/dL.
   Platelets (plt)≥$75 \times 10^9$/L without transfusion for 7 days.
   Aspartate aminotransferase (AST/SGOT) and alanine aminotransferase (ALT/SGPT)≤2.5×Upper Limit of Normal (ULN) or ≤5.0×ULN if liver tumor is present.
   Serum bilirubin ≤1.5×ULN.
   Estimated serum creatinine clearance of ≥45 mL/min using the Cockcroft-Gault equation or measured creatinine clearance using 24 hour urine collection.
   International normalized ratio (INR)<1.5×ULN and partial thromboplastin time (PTT)<1.5×ULN.
9. Females of childbearing potential (FCBP) must:
   Either commit to true abstinence from heterosexual contact (which must be reviewed on a monthly basis and source documented) or agree to use, and be able to comply with, at least two effective contraceptive methods (oral, injectable, or implantable hormonal contraceptive; tubal ligation; intra-uterine device; barrier contraceptive with spermicide; or vasectomized partner), one of which must be barrier, from signing the ICF, while participating in the study, during dose interruptions, and for up to 56 days following the last dose of SIRPAB-11-K322A; and
   Have two negative pregnancy tests prior to starting SIRPAB-11-K322A. She must agree to ongoing pregnancy testing during the course of the study, and 56 days after end of study treatment. This applies even if the subject practices true abstinence from heterosexual contact. The subject may not receive SIRPAB-11-K322A until the result of the pregnancy test is negative; and
   Have a negative serum pregnancy test (sensitivity of at least 25 mIU/mL) at Screening.
   Have a negative serum or urine pregnancy test within 72 hours prior to Cycle 1 Day-1 of study treatment, and within 72 hours prior to Day-1 of every subsequent cycle (note that the Screening serum pregnancy test can be used as the test prior to Day-1 study treatment if it is performed within the prior 72 hours). A serum or urine pregnancy test must also be performed at the end of study for each FCBP; and
   Avoid conceiving for 56 days after the last dose of SIRPAB-11-K322A.
   Females of childbearing potential receiving cetuximab should use effective contraception during treatment with cetuximab and for 2 months after the last dose of cetuximab.

10. Males must practice true abstinence (which must be reviewed on a monthly basis and source documented) or agree to use a condom (a latex condom is recommended) during sexual contact with a pregnant female or a FCBP and will avoid conceiving from signing the ICF, while participating in the study, during dose interruptions, and for at least 56 days following SIRPAB-11-K322A discontinuation, even if he has undergone a successful vasectomy.
11. Subject is willing and able to adhere to the study visit schedule and other protocol requirements.

5.10.8 Exclusion Criteria

The presence of any of the following will exclude a subject from enrollment:
1. Subject has received prior investigational therapy directed at CD47 or SIRPα.
2. Subject has cancer with symptomatic central nervous system involvement.
3. Subject is on chronic systemic immunosuppressive therapy or corticosteroids (eg, prednisone or equivalent exceeding a total dose of 140 mg over the last 14 days). Intranasal, inhaled, topical, or local corticosteroid injections (eg, intra-articular injection), or steroids as premedication for hypersensitivity reactions (eg, computed tomography [CT] scan premedication) are exceptions to this criterion.
4. Subjects with a history of class III or IV congestive heart failure (CHF) or severe non-ischemic cardiomyopathy, unstable angina, myocardial infarction, or ventricular arrhythmia within the previous 6 months.
5. Subject had a prior systemic cancer-directed treatments or investigational modalities ≤5 half-lives or 4 weeks prior to starting SIRPAB-11-K322A, whichever is shorter.
6. Subject had major surgery ≤2 weeks prior to starting SIRPAB-11-K322A. Subjects must have recovered from any clinically significant effects of recent surgery.
7. Subject is a pregnant or lactating female.
8. Subject has known human immunodeficiency virus (HIV) infection.
9. Subject has known chronic, active hepatitis B or C (HBV/HCV) infection.
10. Ongoing treatment with chronic, therapeutic dosing of anti-coagulants (eg. warfarin, low molecular weight heparin, Factor Xa inhibitors)
11. History of autoimmune hemolytic anemia or autoimmune thrombocytopenia.
12. History of concurrent second cancers requiring active, ongoing systemic treatment.
13. Subject has any significant medical condition, laboratory abnormality, or psychiatric illness that would prevent the subject from participating in the study.
14. Subject has any condition including the presence of laboratory abnormalities, which places the subject at unacceptable risk if he/she were to participate in the study.
15. Subject has any condition that confounds the ability to interpret data from the study.
16. For subjects receiving cetuximab, known history of cetuximab intolerance including Grade 3 or 4 infusion reactions; severe, persistent acneiform rash requiring cetuximab discontinuation; or interstitial lung disease.
17. For subjects participating in ferumoxytol MRI assessments in the Part A intensive PD cohorts:
    History of allergic reaction to any intravenous iron product.
    Known hypersensitivity to ferumoxytol or any of its components (eg, iron, dextran or polysaccharides of molecular weight ≥1000 daltons).
    Any contraindication to MRI examination, eg, imbedded metallic material/devices.
    Known history of hemochromatosis with iron overload.

5.11 Example 11: A Phase 1, Open-Label, Dose Finding Study of SIRPAB-11-K322A, A Monoclonal Antibody Directed Against SIRPα, Alone and in Combination with Cetuxiinab or Rituximab in Subjects with Advanced Solid and Hematologic Cancers The antibody SIRPAB-11-K322A is to be studied in advanced solid cancers (Part A, Stage 1 and Part B), in advanced colorectal cancer (CRC) and/or advanced squamous cell carcinoma of the head and neck (SCCHN) (Part A, Stage 2 and Part B), and in CD20-positive NHL such as such as DLBCL (including relapsed DLBCL and refractory DLBCL), follicular lymphoma (including Grade 1, Grade 2, Grade 3a, Grade 3b, relapsed, and refractory follicular lymphoma), marginal zone lymphoma, and mantle cell lymphoma. (Part A, Stage 3 and Part C).

5.11.1 Objectives

Primary Objectives:
To determine the safety and tolerability of SIRPAB-11-K322A alone and in combination with cetuximab or rituximab.
To define the non-tolerated dose (NTD), the maximum tolerated dose (MTD) and/or the recommended Phase 2 dose (RP2D) of SIRPAB-11-K322A alone and in combination with cetuximab or rituximab.
Secondary Objectives:
To provide information on the preliminary efficacy of SIRPAB-11-K322A alone and in combination with cetuximab or rituximab.
To characterize the pharmacokinetics (PK) of SIRPAB-11-K322A.
To evaluate the presence, frequency, and functional impact of anti-SIRPAB-11-K322A antibodies (ADAs).

5.11.2 Study Design

This study is an open-label, Phase 1, dose escalation (Part A) and expansion (Parts B and C), first-in-human clinical study of SIRPAB-11-K322A in subjects with advanced solid and hematologic cancers. The dose escalation part (Part A) of the study will be conducted in three stages using Bayesian methodology. Stage 1 will evaluate the safety and tolerability of escalating doses of SIRPAB-11-K322A, administered intravenously (IV), to determine MIT, NTD, and/or RP2D of SIRPAB-11-K322A in subjects with advanced unresectable solid cancers. Stage 2 will evaluate the safety and tolerability of escalating doses of SIRPAB-11-K322A, in combination with weekly cetuximab, both administered IV, to determine the NTD, MTD, and/or RP2D of SIRPAB-11-K322A plus cetuximab in subjects with advanced CRC and/or SCCHN. Stage 3 will evaluate the safety and tolerability of escalating doses of SIRPAB-11-K322A in combination with rituximab, both administered IV, to establish the MTD, NTD, and/or RP2D of SIRPAB-11-K322A plus rituximab in subjects with CD20-positive NHL including DLBCL, Grade 1, 2, and 3a follicular lymphoma, marginal zone lymphoma, and mantle cell lymphoma.

The dose expansion part (Part B) will further evaluate the safety and efficacy of SIRPAB-11-K322A administered at or below the Stage 2 MTD in combination with cetuximab in selected expansion cohorts of up to approximately 20 evaluable subjects each, in order to determine the RP2D.

Part B expansion cohorts may test different doses and/or schedules of SIRPAB-11-K322A based on the safety and tolerability determined in Part A. Part B expansion cohorts may include subjects with advanced CRC (KRAS/NRAS/BRAF wild-type), CRC (KRAS/NRAS/BRAF mutant), SCCHN, and/or other advanced solid cancers. Additional cohorts of subjects with advanced solid tumors may be considered in Part B.

The Part C dose expansion will further evaluate the safety and efficacy of SIRPAB-11-K322A administered at or below the Stage 3 MTD of SIRPAB-11-K322A in combination with rituximab in selected expansion cohorts of up to approximately 20 (follicular lymphoma) or 30 (DLBCL) evaluable subjects each, in order to determine the RP2D for the SIRPAB-11-K322A and rituximab combination.

Part C expansion cohorts may also test different doses and/or schedules of SIRPAB-11-K322A based on the safety and tolerability determined in Part A. Part C expansion cohorts may include relapsed and/or refractory DLBCL and/or Grade 1, 2 and 3a follicular lymphoma (FL).

All treatments will be administered in 28-day cycles until clinically-significant disease progression, unacceptable toxicity, or decision to withdraw.

In Stage 1 (Part A), each subject will receive the assigned dose of SIRPAB-11-K322A on Cycle 1 Day 1 and weekly (QW) thereafter. The starting dose (Stage 1, Cohort 1) of SIRPAB-11-K322A will be 0.3 mg/kg. If the starting dose of SIRPAB-11-K322A is not tolerated, a lower dose level may be explored. The initial dose escalation increment in each cohort will be approximately 3-fold.

The decision to proceed to Stage 2 will be made based on the safety, tolerability, PK, PD, and ADA observed in at least two stages of Stage 1. Stage 2 or 3 may begin prior to establishing the MTD or NTD in Stage 1. The starting dose (Stage 2, Cohort 1) of SIRPAB-11-K322A in Stage 2 will be at least one dose level below the dose that has been determined to be tolerated in Stage 1. Stage 3 will start after at least two dose levels in Stage 1 have been completed. The starting dose (Stage 3, Cohort 1) of SIRPAB-11-K322A in Stage 3 will be no higher than the highest dose that has been determined to be tolerated in Stage 1.

If the starting dose of SIRPAB-11-K322A in combination with cetuximab or rituximab is not tolerated, a lower dose level of SIRPAB-11-K322A may be explored. Subsequent cohorts in Stages 2 and 3 will open to enrollment only after the corresponding dosing cohorts in Stage 1 are determined to be tolerated.

In Stage 2, the cetuximab starting dose (Stage 2, Cohort 1a) will be 250 mg/m$^2$ IV on Cycle 1 Day 1 followed by 150 mg/m$^2$ IV weekly in Cycle 1. If this reduced dose of cetuximab is tolerated for one cycle, intra-patient dose escalation to 250 mg/m$^2$ IV weekly may occur. If the dose level of cetuximab in Stage 2, Cohort 1a is deemed tolerable, the second cohort of Stage 2 (Stage 2, Cohort 1b) will treat subjects at the same dose of SIRPAB-11-K322A with cetuximab at 400 mg/m$^2$ IV on Cycle 1 Day 1 followed by 250 mg/m$^2$ IV weekly thereafter (400/250 mg/m$^2$). If Cohort 1b is tolerated, subsequent cohorts will receive cetuximab (400/250 mg/m$^2$) with escalating doses of SIRPAB-11-K322A.

In Stage 3, rituximab dosing will be fixed at 375 mg/m2 IV. Rituximab will be administered weekly for 4 doses (Days 1, 8, 15, and 22 of Cycle 1), on Day 1 of Cycles 2 through 5 and on Day 1 of every other cycle from Cycle 6 through 24.

During dose escalation, the decision to evaluate additional subjects within a dose cohort, the next higher dose level, intermediate dose levels, an alternate dosing interval, or declare an MTD will be determined, based on the Bayesian logistic regression model, clinical and laboratory safety data (both Dose Limiting Toxicity [DLT] and non-DLT safety data), PK, PD, and ADA for a given dose level. The frequency of SIRPA-11-K322A dosing may be reduced based on review of PK and/or PD from a given dose level. If the dose frequency is reduced, the total dose intensity of the subsequent cohort will not exceed 3-fold.

In Part A, after the first dose is administered in any cohort, subjects in each cohort are to be observed for at least 28 days (Cycle 1, Days 1 to 28, DLT window) before the next higher, protocol-specified dose cohort can begin. For the first two subjects, a one-week interval between the initial and subsequently enrolled dosing subject will be employed to observe for acute toxicities. After the first two subjects, no more than one subject per day will be enrolled in a given dose escalation cohort.

In subjects receiving SIRPAB-11-K322A monotherapy (Part A, Stage 1), a subject evaluable for DLT is defined as one who:

Has received at least 3 of 4 complete doses of SIRPAB-11-K322A during Cycle 1, Days 1 to 28 (QW dosing) (or at least 75% of the total planned Cycle 1 dose intensity) without experiencing a DLT, or Experienced a DLT after receiving at least one dose of SIRPAB-11-K322A or fraction thereof during Cycle 1, Days 1 to 28.

In subjects receiving SIRPAB-11-K322A in combination with cetuximab (Part A, Stage 2) or rituximab (Part A, Stage 3), a subject evaluable for DLT is defined as one who:

Has received at least 3 of 4 complete doses of cetuximab or rituximab and at least 3 of 4 complete doses of SIRPAB-11-K322A during Cycle 1, Days 1 to 28 (or at least 75% of the total planned Cycle 1 dose intensity of cetuximab, rituximab, and SIRPAB-11-K322A) without experiencing a DLT, or Experienced a DLT after receiving at least one dose or fraction thereof SIRPAB-11-K322A during Cycle 1, Days 1 to 28.

Subjects non-evaluable for DLT will be replaced. Additional subjects within any cohort may be enrolled to better characterize PK, PD, or the MTD in accordance with the BLRM.

Following completion of dose escalation (Part A), selected cohorts of up to approximately 20 (solid tumors, follicular lymphoma) or 30 (DLBCL) efficacy evaluable subjects per cohort will receive SIRPAB-11-K322A in combination with either cetuximab (Part B) or rituximab (Part C). Expansion may occur at the MTDs established in the combination dose escalations (Part A, Stages 2 and 3) and/or at lower doses, or on an alternative tolerable dosing schedule, based on review of safety, PK, PD, and ADA data.

Part B cohorts may include subjects wih advanced, unresectable CRC (KRAS, NRAS, or BRAF mutant), CRC (KRAS, NRAS, or BRAF wild-type), SCCHN, and/or advanced solid tumors. All CRC subjects should have determination of tumor gene status for RAS (KRAS and NRAS) and BRAF (V600E) mutations (individually or as part of next-generation sequencing panel). The NRAS and KRAS mutations refer to certain somatic point mutations. Testing for KRAS, NRAS, and BRAF mutations in the United States should be performed only in laboratories that are certified under the clinical laboratory improvement amendments of 1988 (CLIA-88), as qualified to perform high-complexity clinical laboratory (molecular pathology) testing. Mutation status will be confirmed after subject enrollment by central laboratory testing.

Part C expansion cohorts may include relapsed and/or refractory DLBCL, not otherwise specified (NOS) and relapsed and/or refractory follicular lymphoma.

The study will be conducted in compliance with International Conference on Harmonisation (ICH) Good Clinical Practices (GCPs).

5.11.3 Study Population

Subjects (male or female) ≥18 years of age, with advanced solid cancers, including advanced CRC, advanced SCCHN, and CD20-positive NHL who have progressed on (or not been able to tolerate due to medical comorbidities or unacceptable toxicity) standard anticancer therapy, or for whom no other approved conventional therapy exists, will be enrolled in the study.

The study will enroll up to 230 subjects with advanced solid and hematologic cancers. In Part A, approximately 100 subjects (including dose escalation cohorts in Stages 1, 2, and 3 of approximately 3 to 6 evaluable subjects each will be enrolled. In the Part B expansion phase, up to 20 subjects in up to 4 cohorts may be enrolled (up to approximately 80 total subjects). In the Part C expansion phase, cohorts of up to 20 subjects with FL and up to 30 subjects with DLBCL may be enrolled (up to approximately 50 total subjects).

5.11.4 Length of Study

Full enrollment is expected to take approximately 30 months to complete (18 months for Part A and 12 months for Parts B and C). Completion of active treatment and post-treatment follow-up is expected to take an additional 30 to 36 months. The entire study is expected to continue for approximately 66 months.

The End of Trial is defined as either the date of the last visit of the last subject to complete the post-treatment follow-up, or the date of receipt of the last data point from the last subject that is required for primary, secondary and/or exploratory analysis, as prespecified in the protocol, whichever is the later date.

5.11.5 Study Treatments

The investigational product (IP), SIRPAB-11-K322A, will be supplied for IV administration.

For subjects who have infusion-related reactions (IRR) with SIRPAB-11-K322A, treatment, premedications (e.g. an antipyretic, an antihistamine, or a corticosteroid) will be required with subsequent dosing. For subjects receiving cetuximab or rituximab, premedications do not need to be repeated prior to SIRPAB-11-K322A. dosing. SIRPAB-11-K322A treatment will continue until clinically significant disease progression, unacceptable toxicity, or subject/Investigator decision to withdraw.

For subjects receiving cetuximab in combination with SIRPAB-11-K322A, cetuximab will be administered on Cycle 1 Day 1 (250 or 400 mg/m$^2$ IV as a 120-minute infusion) and weekly thereafter (150 or 250 mg/m$^2$ IV QW infused over 60 minutes). Subjects will receive cetuximab infusion prior to starting the SIRPAB-11-K322A infusion on days receiving both treatments. Subjects receiving cetuximab should receive premedication with an H1 antagonist (such as 50 mg of diphenhydramine IV) 30 to 60 minutes prior to the first dose. Additional premedication such as a corticosteroid may be given according to institutional standard of care and country cetuximab product information. For subjects with a history of Grade 2 IRR with a prior cetuximab infusion, premedication with corticosteroids is recommended (eg, dexametha.sone 10 mg or equivalent). Premedication should be administered for subsequent cetuximab infusions based upon clinical judgment and presence/severity of prior IRRs. For subjects who experience Grade 1 or Grade 2 IRRs and non-serious Grade 3 IRRs, the cetuximab infusion rate should be reduced by 50%. For serious infusion reactions, requiring medical intervention and/or hospitalization, cetuximab should be immediately and permanently discontinued. Dose reductions for Grade 3 or 4 acneiform rash are permitted per the cetuximab package insert. See Erbitux label approved by FDA, reference ID 4258364, revised May 2018, Section 2.4, at accessdata.fda.gov/drugsatfda_docs/label/2018/125084Orig1s2681b1.pdf.

For subjects receiving rituximab in combination with SIRPAB-11-K322A, rituximab will be administered (per Rituximab Package Insert (See Rituxan label approved by FDA, reference ID 4274293, revised June, 2018, at accessdata.fda.gov/drugsatfda_docs/label/2018/103705s54501b1.pdf) and institutional standard practice) at a fixed dose of 375 mg/m2 IV on Days 1, 8, 15 and 22 of Cycle 1, Day 1 of Cycles 2 to 5, and Day 1 of Cycles 6, 8, 10, 12, 14, 16, 18, 20, 22 and 24. Subjects will receive rituximab infusion prior to starting the SIRPAB-11-K322A infusion on days receiving both treatments. Subjects receiving rituximab should be premedicated with an anti-pyretic (e.g., acetaminophen 650-1000 mg) and an antihistamine (e.g., diphenhydramine 25-50 mg or equivalent non-sedating antihistamine such as loratadine or cetirizine 10 mg) before rituximab infusions.

In the Part B and C expansions, based on the safety, PK, PD and ADA evaluations from the SIRPAB-11-K322A single-agent and combination dose escalations, subjects may receive SIRPAB-11-K322A at the MTD and/or at a lower dose, and on a QW, Q2W, or alternate dose schedule.

5.11.6 Overview of Key Efficacy Assessments

The primary efficacy variable is tumor response rate. Subjects will be evaluated for efficacy after Cycles 2, 4, and 6; and then every 3 cycles thereafter. All treated subjects will be included in the efficacy analyses. For solid tumors, assessment will be based on Response Evaluation Criteria in Solid Tumors (RECIST 1.1) (Eisenhauer E A, et al. Eur J Cancer 2009;45(2):228-247) as the primary method as well as modified RECIST 1.1 for immune-based therapeutics (iRECIST) (Seymour L, et al. Lancet Oncol. 2017;18:e143-e152) as a supplementary method. For NHL, the "Lugano Criteria", which incorporate International Working Group (IWG) Response Criteria for NHL (Cheson B D, et al. J Clin Oncol. 2014;32(27):3059-3068) and Deauville Criteria for fluorodeoxyglucose-positron emission tomography (FDG PET) scan interpretation (Itti F, et al. Eur J Nucl Med Mol Imaging. 2013 September;40(9):1312-20; Meignan M, et al. Leuk Lymphoma. 2014 January;55(1):31-7) will be utilized for efficacy assessments.

A descriptive analysis of evidence of antitumor activity will be provided based on clinical, laboratory, and radiographic assessments, which includes assessment of target lesion, non-target lesion, new lesion and overall response. Both confirmed and unconfirmed responses by RECIST 1.1 and Lugano Criteria will be assessed.

The efficacy variable of focus for Part A will be objective response rate (ORR). Additional efficacy variables to be analyzed include time to response and duration of response.

For Part B and Part C, efficacy variables to he analyzed include ORR, time to response, duration of response, progression-free survival (PFS) and overall survival (OS).

If treatment is discontinued for reasons other than disease progression, start of a new anticancer therapy, or withdrawal of consent from the entire study, subjects will be requested to continue tumor assessments according to the specified tumor assessment schedule until disease progression and/or initiation of new systemic anticancer therapies. Survival status will be determined following disease progression, approximately every 12 weeks for up to 1 year in Part B and up to 2 years in Part C. In addition, the use of subsequent anticancer therapies including stem cell transplant will be collected after disease progression.

Efficacy variables will mature when the last subject in each cohort has withdrawn from the study or completed 6 cycles.

The primary efficacy variable for Part A is ORR. For Part B and Part C, efficacy variables to be analyzed include ORR, time to response, duration of response, PFS, and OS. Point estimates and 2-sided 95% confidence intervals of ORR will be reported. For time to event endpoints, Kaplan-Meier survival analyses will be performed.

5.11.7 Inclusion Criteria

Subjects must satisfy the following criteria to be enrolled in the study:
1. Subject must understand and voluntarily sign an informed consent form (ICF) prior to any study-related assessments/procedures being conducted.
2. Subject (male or female) is ≥18 years of age at the time of signing the ICF.
3. Subject must have progressed on (or not been able to tolerate due to medical comorbidities or unacceptable toxicity) standard anticancer therapy or for whom no other approved conventional therapy exists and have histological or cytological confirmation of:
   In Part A, Stage 1, advanced unresectable solid tumors.
   In Part A, Stage 2, advanced unresectable colorectal cancer or squamous cell carcinoma of the head and neck.
   In Part A, Stage 3, CD20-positive non-Hodgkin's lymphoma (including DLBCL, Grade 1, 2, and 3a follicular lymphoma, marginal zone lymphoma, and mantle cell lymphoma)
   In Part B,
      Cohort 1: advanced unresectable colorectal cancer with molecular documentation of a mutation in RAS ((KRAS or NRAS) or BRAF (V600E). The NRAS and KRAS mutations refer to certain somatic point mutations.
      Cohort 2: advanced unresectable colorectal cancer with wild-type RAS (without the same NRAS somatic point mutations as those included in cohort 1 and without the same KRAS somatic point mutations as those included in cohort 1) and BRAF WT for V600E.
      Cohort 3: advanced unresectable squamous cell carcinoma of the head and neck.
      Cohort 4: advanced unresectable solid tumors.
   in Part C
      Cohort 1: DLBCL, not otherwise specified (NOS; includes transformed DLBCL from indolent histology, high grade B-cell lymphoma with DLBCL histology, primary mediastinal B-cell lymphoma, and follicular lymphoma Grade 3b)
      Cohort 2: Follicular lymphoma (Grade 1, 2, and 3a)
4. Subject consents to retrieve formalin-fixed paraffin-embedded (FFPE) archival tumor tissue, either in tumor blocks or sectioned/mounted specimens.
5. For subjects participating in the Part A intensive PD cohorts, Part B and Part C, subject consents and has tumor accessible for paired tumor biopsies during Screening and Cycle 1.
6. Subjects with solid tumors must have at least one site of measurable disease as determined by RECIST v1.1. NHL subjects must have bi-dimensionally measurable disease on cross sectional imaging by CT or MRI as defined by Lugano/IWG criteria (Cheson B D, et al. J Clin Oncol. 2014;32(27):3059-3068).
7. Subject has an ECOG PS of 0 or 1.
7. Subjects must have the following laboratory values:
   Absolute neutrophil count (ANC)≥1.5×10$^9$/L without growth factor support for 7 days (14 days if pegfilgrastim).
   Hemoglobin (Hgb)≥8 g/dL.
   Platelets (plt)≥75×10$^9$/L without transfusion for 7 days.
   Aspartate aminotransferase (AST/SGOT) and alanine aminotransferase (ALT/SGPT)≥2.5×Upper Limit of Normal (ULN) or ≤5.0×ULN if liver tumor is present.
   Serum bilirubin≤1.5×ULN.
   Estimated serum creatinine clearance of ≥45 ml/min using the Cockcroft-Gault equation or measured creatinine clearance using 24 hour urine collection.
   International normalized ratio (INR)<1.5×ULN and partial thromboplastin time (PTT)<1.5×ULN.
9. Females of childbearing potential (FCBP) must:
   Either commit to true abstinence from heterosexual contact (which must be reviewed on a monthly basis and source documented) or agree to use, and be able to comply with, at least two effective contraceptive methods (oral, injectable, or implantable hormonal contraceptive; tubal ligation; intra-uterine device; barrier contraceptive with spermicide; or vasectomized partner), one of which must be barrier, from signing the ICF, while participating in the study, during dose interruptions, and for up to 56 days following the last dose of SIRPAB-11-K322A; and
   Have two negative quantitative serum or urine pregnancy tests prior to starting SIRPAB-11-K322A. She must agree to ongoing pregnancy testing during the course of the study, and 56 days after end of study treatment. This applies even if the subject practices true abstinence from heterosexual contact. The subject may not receive SIRPAB-11-K322A until the result of the pregnancy test is negative; and
   Have a negative quantitative serum pregnancy test (sensitivity of at least 25 mIU/mL at Screening.
   Have a negative serum or urine pregnancy test within 72 hours prior to Cycle 1 Day-1 of study treatment, and within 72 hours prior to Day-1 of every subsequent cycle (note that the Screening serum pregnancy test can be used as the test prior to Day-1 study treatment if it is performed within the prior 72 hours). A serum or urine pregnancy test must also be performed at the end of study for each FCBP; and
Avoid conceiving for 56 days after the last dose of SIRPAB-11-K-322A.
Females of childbearing potential receiving cetuximab (Part A, Stage 2 and Part B) should use effective contraception during treatment with cetuximab and for 2 months after the last dose of cetuximab.
Females of childbearing potential receiving rituximab (Part A, Stage 3 and Part C) should use effective contraception during treatment with rituximab and for 12 months after the last dose of rituximab.
10. Males must practice true abstinence (which must be reviewed on a monthly basis and source documented) or agree to use a condom (a latex condom is recommended) during sexual contact with a pregnant female or a FCBP and will avoid conceiving from signing the ICF, while participating in the study, during dose interruptions, and for at least 56 days following SIRPAB-11-K322A discontinuation, even if he has undergone a successful vasectomy.
11. Subject is willing and able to adhere to the study visit schedule and other protocol requirements.

5.11.8 Exclusion Criteria

The presence of any of the following will exclude a subject from enrollment:
1. Subject has received prior investigational therapy directed at CD47 or SIRPα.
2. High-grade lymphomas (Burkitt's or lymphoblastic).
3. Subject has cancer with symptomatic central nervous system (CNS) involvemen
4. Subject is on chronic systemic immunosuppressive therapy or corticosteroids (eg, prednisone or equivalent exceeding a total dose of 140 mg over the last 14 days). Intranasal, inhaled, topical, or local corticosteroid injections (eg, intra-articular injection), or steroids as premedication for hypersensitivity reactions (eg, computed tomography [CT] scan premedication) are exceptions to this criterion.
5. Subjects with a history of class III or IV congestive heart failure (CHF) or severe non-ischemic cardiomyopathy, unstable angina, myocardial infarction, or ventricular arrhythmia within the previous 6 months.
6. Subject had a prior systemic cancer-directed treatments or investigational modalities ≤5 half-lives or 4 weeks prior to starting SIRPAB-11-K322A, whichever is shorter.
7. Subject had treatment with CAR-T therapy ≤4 weeks prior to starting SIRPAB-11-K322A.
8. Subject had major surgery ≤2 weeks prior to starting SIRPAB-11-K322A. Subjects must have recovered from any clinically significant effects of recent surgery.
9. Subject is a pregnant or lactating female.
10. Subject has known human immunodeficiency virus (HIV) infection.
11. Subject has known chronic, active hepatitis B or C (HBV/HCV) infection.
  a. NHL subjects receiving rituximab with no active hepatitis B infection (eg, HBsAg negative, anti-HBc positive) who are under adequate prophylaxis against HBV re-activation are eligible.
12. Prior autologous stem cell transplant ≤3 months prior to starting SIRPAB-11-K322A.
13. Prior allogeneic stem cell transplant with either standard or reduced intensity conditioning 6 months prior to starting SIRPAB-11-K322A.
14. Ongoing treatment with chronic, therapeutic dosing of anti-coagulants (eg, warfarin, low molecular weight heparin, Factor Xa inhibitors)
15. History of autoimmune hemolytic anemia or autoimmune thrombocytopenia.
16. History of concurrent second cancers requiring active, ongoing systemic treatment.
17. Subject has any significant medical condition, laboratory abnormality, or psychiatric illness that would prevent the subject from participating in the study.
18. Subject has any condition including the presence of laboratory abnormalities, which places the subject at unacceptable risk if he/she were to participate in the study.
19. Subject has any condition that confounds the ability to interpret data from the study.
20. For subjects receiving cetuximab, known history of cetuximab intolerance including Grade 3 or 4 infusion reactions; severe, persistent acneiform rash requiring cetuximab discontinuation; or interstitial lung disease.
21. For subjects with solid tumors participating in ferumoxytol MRI assessments in the Part A intensive PD cohorts:
  History of allergic reaction to any intravenous iron product,
  Known hypersensitivity to ferumoxytol or any of its components (eg, iron, dextran or polysaccharides of molecular weight 1000 daltons).
  Any contraindication to MRI examination, eg, imbedded metallic material/devices.
  Known history of hemochromatosis with iron overload.

5.12 Example 12: Additional Studies on the Activity of Anti-SIRPα Antibodies in Combination with Rituximab In a second study similar to that described in Section 5.9.3, the phagocytic effects of SIRPAB-11-K322A (0.001 nM through 20 nM) with or without rituximab (0.67 nM or 0.1 nM) were assessed using 4 NHL DLBCL cell lines: OCI-LY3 (from German Collection of Microorganisms and Cell Cultures (DSMZ)), RIVA (from DSMZ), Karpas 422 (from DSMZ), and Pfeiffer (from American Type Culture Collection (ATCC)). Two of the lines, OCI-LY3 and RIVA are activated B cell-like; the other two lines, Pfeiffer and Karpas 422 are germinal center B cell-like.

Briefly, surface expression of SIRPα, CD47, and CD20 were measured by flow cytometry in all cell lines with Alexa Fluor 647 labeled SIRPAB-11-IgG4PE, rituximab, and anti-CD47 hIgG1 (TPP-23) antibody. Alexa Fluor 647 labeled anti-RSV IgG4PE was used as a negative control. Pfeiffer cells were positive for SIRPα; OCI-LY3, RIVA, and Karpas 422 cells did not display SIRPα staining (FIG. 16A). All four lines were positive for CD20 and CD47 with RIVA showing the highest levels of staining (FIG. 16B and 16C).

For the phagocytosis assay, tumor cells labeled with carboxyfluorescein diacetate succinimidyl ester were opsonized with rituximab or left untreated, added to wells containing macrophages differentiated from human donor monocytes (n=4), incubated with SIRPAB-11-K322A or control antibodies for 3 hours, labeled with anti-CD14-allophycocyanin, and quantitated using high content imaging. Levels of phagocytosis were measured and compared to SIRPAB-11-K322A or rituximab treatment alone across 4 normal donor macrophages. Anti-RSV IgG1K322A was used as a negative control.

Macrophage phagocytosis was greater when SIRPAB-11-K322A was added in combination with rituximab (predetermined suboptimal rituximab concentration of 0.1 nM for OCI-LY3 and RIVA or 0.67 nM for Pfeiffer and Karpas 422) compared to single-agent SIRPAB-11-K322A for all tested cell lines (FIGS. 17A-17C and FIGS. 18A-18D). When tested against OCI-LY3 or RIMA cells, SIRPAB-11-K322A in combination with 0.1 nM rituximab enhanced phagocytosis across all 4 donor macrophages compared to SIRPAB-11-K322A treatment alone (FIG. 17A-17B, exemplary data from one donor shown). When tested in combination on Karpas 422 cells, SIRPAB-11-K322A with 0.67 nM rituximab enhanced phagocytosis in 3 of 4 donors (FIG. 17C, exemplary data from one donor shown). When tested against Pfeiffer cells, SIRPAB-11-K322A alone demonstrated macrophage phagocytic activity for at least 3 donors, with the calculated EC50 ranging from 0.60 nM to 2.90 nM (FIGS. 18A-18D). In this cell line, the combination of SIRPAB-11-K322A with 0.67 nM rituximab enhanced phagocytosis in 3 of 4 donor macrophages (FIGS. 18A-18D). Combination activity was not statistically significant over SIRPAB-11-K322A treatment alone for one donor where single agent activity was observed (FIG. 18A).

Across all cell lines and donors tested, the macrophage phagocytosis EC50 values for SIRPAB-11-K322A in combination with rituximab (0.1 nM or 0.67 nM) ranged from 0.0208 nM to 1.17 nM, and were consistently lower than the EC50 values for SIRPAB-11-K322A alone (p<0.0001 through 0.234). These results demonstrate the combinational effect of SIRPAB-11-K322A and rituximab in mediating the enhancement of macrophage phagocytosis activity compared to SIRPAB-11-K322A.

5.13 Example 13: Receptor Occupancy of SIRPAB-11-K322A from Phase 1 Clinical Trial SIRPAB-11-K322A binds to SIRPα on circulating monocytes, neutrophils, and dendritic cells, and some tumor cells. One clinical evaluation of biologic agents targeting cellular antigens is receptor occupancy (RO), to demonstrate that the drug is binding the appropriate target. Receptor occupancy assays can provide valuable data that can be used to generate mathematical models of the level of occupancy predicted to lead to a biological effect. An RO assay was validated for SIRPα to allow accurate determination of the binding of SIRPAB-11-K322A to SIRPα on monocytes, neutrophils and dendritic cells in whole blood taken from patients. This assay utilizes a non-competing anti-SIRPα antibody that can be used to identify SIRPα molecules both bound and unbound by SIRPAB-11-K322A on SIRPα expressing cells (FIG. 19A). The objective is to quantify target engagement and saturation for each SIRPAB-11-K322A dose group.

Briefly, whole blood was incubated with fluorescently labeled antibodies to identify key leukocyte subsets, as well as two antibodies specific for SIRPα, one which binds in the presence of SIRPAB-11-K322A (non-competitive) labeled with alexa fluor 488, and one that only binds in the absence of SIRPAB-11-K322A (competitive) labeled with alexa fluor 647. The levels of staining of the two SIRPα antibodies is calculated for leukocyte subgroups, and from this, the levels of receptor occupany by SIRPAB-11-K322A can be calculated using this equation: % SIRPα RO=100%*((1−(competitive AF647 actual/competitive AF647 pre-dose) (non-competitive AF488 actual/non-competitive AF488 pre-dose)) (FIGS. 19A-19B). Nearly complete receptor occupancy was achieved in monocytes, neutrophils and dendritic cells 24 hrs and 48 hrs post dose at 0.3 mg/kg and 1 mg/kg doses, as shown in Table 26 and Table 27.

TABLE 26

Representative percent receptor occupancy was measured 24 hours post dose with SIRPAB-11-K322A from patients dosed with 0.3 mg/kg and 1 mg/kg dose cohorts for the phase 1 clinical study.

| Patient | Dose (mg/kg) | Monocytes | Neutrophils | Dendritic cells |
|---|---|---|---|---|
| 1 | 0.3 | 98 | 94 | 96 |
| 2 | 0.3 | 99 | 97 | 100 |
| 3 | 1 | 100 | 98 | 100 |
| 4 | 1 | 100 | 95 | 90 |
| 5 | 1 | 98 | 85 | 98 |

TABLE 27

Representative percent receptor occupancy was measured 48 hours post dose with SIRPAB-11-K322A from patients dosed with 0.3 mg/kg and 1 mg/kg dose cohorts for the phase 1 clinical study.

| Patient | Dose (mg/kg) | Monocytes | Neutrophils | Dendritic cells |
|---|---|---|---|---|
| 1 | 0.3 | 87 | 83 | 79 |
| 2 | 0.3 | 93 | 93 | 94 |
| 3 | 1 | 99 | 95 | 99 |
| 4 | 1 | 100 | 82 | 87 |

(Note: data at 48 hours for patient 5 is unavailable)

5.14 Example 14: Percentage of T-cells, B-cells, Monocytes and Natural Killer Cells Post Dose with SIRPAB-11-K322A from Phase 1 Clinical Trial Human leukocytes can be divided into four major subset populations based on their biologic function and cell-surface antigen expression: T lymphocytes (CD3+), B lymphocytes (CD19+), monocytes (CD14) and NK lymphocytes (CD16+CD56+). The BD Multitest TBNK reagent (BD Biosciences, San Jose, Calif. USA), which was validated to also quantify monocytes, was used to determine the percentage of these cell subsets post dose with SIRPAB-11-K322A. SIRPAB-11-K322A was dosed QW (weekly).

Representative percentages of leukocyte subsets in patients treated with SIRPAB-11-K322A at Day 1 pre-dose and Day 29 post dose of 0.3mg/kg are shown in Table 28 below.

TABLE 28

Representative percentages of leukocyte subsets in patients treated with SIRPAB-11-K322A at a dose of 0.3 mg/ml (percentage of CD45+ cells (lymphocytes)).

|  | CD3+ T cells | CD19+ B cells | CD3−(CD16+CD56)+ Natural Killer cells | CD14+ Monocytes |
|---|---|---|---|---|
| Day 1 pre-dose | 65.9 | 21.4 | 10.1 | 7.6 |
| Day 29 post-dose | 64.9 | 19.4 | 13.9 | 9.3 |

Representative percentages of leukocyte subsets in patients treated with SIRPAB-11-K322A at Day 1 pre-dose and Day 29 post dose of 1 mg/kg are shown in Table 29.

TABLE 29

Representative percentages of leukocyte subsets in
patients treated with SIRPAB-11-K322A at a dose of
1 mg/kg (percentage of CD45+ cells (lymphocytes)).

| | CD3+<br>T cells | CD19+<br>B cells | CD3−(CD16+CD56)+<br>Natural Killer cells | CD14+<br>Monocytes |
|---|---|---|---|---|
| Day 1 pre-dose | 66.7 | 9.3 | 20.6 | 8.0 |
| Day 29 post-dose | 59.0 | 14.2 | 26.0 | 6.5 |

No significant change in the percentages of cell subsets was observed after SIRPAB-11-K322A QW dosing out to one month in patients treated at a dose of 0.3 mg/kg or 1 mg/kg. The changes seen were within the drift of the assay and within normal range for healthy subjects. These clinical data demonstrate the superior safety profile of SIRPAB-11-K322A..

5.15 Example 15: Comparason of Anti-SIRPα Antibodies Provided Herein and Reference Anti-SIRPα Antibodies in Their Binding for SIRPα, SIRPβ and SIRPγ

The binding of anti-SIRPα and control antibodies to human SIRPα, SIRPβ and SIRPγ antigens was determined and compared by surface plasmon resonance using Biacore T200 instrument. The antibodies compared in this study include SIRPAB-11-K322A, SIRPAB-12-K322A, a SIRPα reference antibody that has a light chain of an amino acid sequence of SEQ ID NO:224 and a heavy chain of an amino acid sequence of SEQ ID NO:225 (as REFERENCE ANTIBODY in this Example), and isotype control-K322A antibody. Briefly, SIRPAB-11-K322A, SIRPAB-11-K322A, REFERENCE ANTIBODY, and isotype control-K322A antibodies were captured onto the channel 2 of the Protein A Series S chip from GE Healthcare (Cat #: 29127556) at 0.5 ug/mL. Human SIRα, SIRPβ and SIRγ antigens were then injected via microfluidics at a rate of 30 µL per minute into channels 1 and 2. The resonance signal over a span of 300 seconds for antigen association time and 300 seconds for antigen dissociation time at each antigen concentration was captured, analyzed, and fitted with a 1:1 Langmuir model using the Biacore BIAevaluation software. The binding affinities determined from the fitted curves are listed in Table 30 below. As shown in Table 30, SIRPAB-11-K322A and SIRPAB-12-K322A have superior binding affinities over the REFERENCE ANTIBODY in binding to human SIRPα, SIRPβ and SIRPγ antigens.

TABLE 30

Binding affinities (equilibrium constant, $K_D$, in M) determined from the comparative studies.

| | hSIRPα - ECD (v1) | hSIRPβ - ECD | hSIRPγ - ECD |
|---|---|---|---|
| SIRPAB-11 -K322A | $9.23 \times 10^{-11}$ | $3.80 \times 10^{-10}$ | $6.32 \times 10^{-11}$ |
| SIRPAB-12 -K322A | $4.24 \times 10^{-10}$ | $2.08 \times 10^{-09}$ | $3.51 \times 10^{-10}$ |
| REFERENCE ANTIBODY | $3.65 \times 10^{-09}$ | $2.98 \times 10^{-09}$ | $1.47 \times 10^{-09}$ |

ECD = extracellular domain
REFERENCE ANTIBODY = the reference anti-SIRPα antibody that has a light chain of an amino acid sequence of SEQ ID NO: 224 and a heavy chain of an amino acid sequence of SEQ ID NO: 225

6. SEQUENCE LISTING

The present specification is being filed with a computer readable form (CRF) copy of the Sequence Listing. The CRF entitled 10624-442-999_SEQ_LISTING.txt, which was created on Sep. 25, 2019 and is 298,101 bytes in size, is identical to the paper copy of the Sequence Listing and is incorporated herein by reference in its entirety.

What is claimed:

1. An antibody or antigen-binding fragment thereof that binds to human SIRPα, wherein the antibody or the antigen-binding fragment thereof comprises:
   (i) a VL comprising a VL CDR1, a VL CDR2, and a VL CDR3 having an amino acid sequence of a VL CDR1, a VL CDR2, and a VL CDR3, respectively, of a VL having the amino acid sequence of SEQ ID NO:67; and
   (ii) a VH comprising a VH CDR1, a VH CDR2, and a VH CDR3 having an amino acid sequence of a VH CDR1, a VH CDR2, and a VH CDR3, respectively, of a VH having the amino acid sequence of SEQ ID NO:80.

2. The antibody or the antigen-binding fragment thereof of claim 1, wherein the antibody or the antigen-binding fragment thereof comprises:
   (a) a VL comprising: a VL CDR1 comprising the amino acid sequence of SEQ ID NO:62, a VL CDR2 comprising the amino acid sequence of SEQ ID NO:63, and a VL CDR3 comprising the amino acid sequence of SEQ ID NO:65; and
   (b) a VH comprising: a VH CDR1 comprising the amino acid sequence of SEQ ID NO:78, a VH CDR2 comprising the amino acid sequence of SEQ ID NO:69, and a VH CDR3 comprising the amino acid sequence of SEQ ID NO:57.

3. The antibody or the antigen-binding fragment thereof of claim 1, wherein the antibody or the antigen-binding fragment thereof comprises a VL comprising an amino acid sequence having at least 95% identity to the amino acid sequence of SEQ ID NO:67.

4. The antibody or the antigen-binding fragment thereof of claim 1, wherein the antibody or the antigen-binding fragment thereof comprises a VL comprising the amino acid sequence of SEQ ID NO:67.

5. The antibody or the antigen-binding fragment thereof of claim 1, wherein the antibody or the antigen-binding fragment thereof comprises a VH comprising an amino acid sequence having at least 95% identity to the amino acid sequence of SEQ ID NO:80.

6. The antibody or the antigen-binding fragment thereof of claim 1, wherein the antibody or the antigen-binding fragment thereof comprises a VH comprising the amino acid sequence of SEQ ID NO:80.

7. The antibody or the antigen-binding fragment thereof of claim 1, wherein the antibody or the antigen-binding fragment thereof comprises a VL comprising an amino acid sequence having at least 95% identity to the amino acid sequence of SEQ ID NO:67; and a VH comprising an amino acid sequence having at least 95% identity to the amino acid sequence of SEQ ID NO:80.

8. An antibody or antigen-binding fragment thereof that binds to human SIRPα, wherein the antibody or the antigen-binding fragment thereof comprises a VL comprising the amino acid sequence of SEQ ID NO:67; and a VH comprising the amino acid sequence of SEQ ID NO:80.

9. The antibody or the antigen-binding fragment thereof of claim 1, wherein the antibody or the antigen-binding fragment thereof comprises a light chain comprising an amino acid sequence having at least 95% identity to the amino acid sequence of SEQ ID NO:143.

10. The antibody or the antigen-binding fragment thereof of claim 1, wherein the antibody or the antigen-binding fragment thereof comprises a light chain comprising the amino acid sequence of SEQ ID NO:143.

11. The antibody or the antigen-binding fragment thereof of claim 1, wherein the antibody or the antigen-binding fragment thereof comprises a heavy chain comprising an amino acid sequence having at least 95% identity to the amino acid sequence of SEQ ID NO:119.

12. The antibody or the antigen-binding fragment thereof of claim 1, wherein the antibody or the antigen-binding fragment thereof comprises a heavy chain comprising the amino acid sequence of SEQ ID NO:119.

13. The antibody or the antigen-binding fragment thereof of claim 1, wherein the antibody or the antigen-binding fragment thereof comprises a light chain comprising an amino acid sequence having at least 95% identity to the amino acid sequence of SEQ ID NO:143, and a heavy chain comprising an amino acid sequence having at least 95% identity to the amino acid sequence of SEQ ID NO:119.

14. An antibody that binds to human SIRPα, wherein the antibody comprises a light chain comprising the amino acid sequence of SEQ ID NO:143, and a heavy chain comprising the amino acid sequence of SEQ ID NO:119.

15. The antibody or the antigen-binding fragment thereof of claim 1, wherein the antigen-binding fragment is a Fab, Fab', (Fab')$_2$, Fv, or scFv fragment.

16. The antibody or the antigen-binding fragment of claim 8, wherein the antigen-binding fragment is a Fab, Fab', (Fab')$_2$, Fv, or scFv fragment.

17. The antibody or the antigen-binding fragment thereof of claim 1, wherein the antibody or the antigen-binding fragment thereof comprises a human IgG1 Fc region or a mutant thereof.

18. The antibody or the antigen-binding fragment thereof of claim 1, wherein the antibody or the antigen-binding fragment thereof comprises a heavy chain Fc region comprising the amino acid sequence selected from the group consisting of SEQ ID NOS:144 and 155-159.

19. The antibody or the antigen-binding fragment thereof of claim 1, wherein the antibody or the antigen-binding fragment thereof further comprises a light chain constant region comprising the amino acid sequence of SEQ ID NO:211.

20. The antibody or the antigen-binding fragment thereof of claim 1, wherein the antibody or the antigen-binding fragment thereof comprises: a light chain constant region comprising the amino acid sequence of SEQ ID NO:211; and a heavy chain Fc region comprising the amino acid sequence selected from the group consisting of SEQ ID NOS:144 and 155-159.

21. The antibody or the antigen-binding fragment thereof of claim 1, wherein the antibody is a monoclonal antibody.

22. The antibody or the antigen-binding fragment thereof of claim 1, wherein the antibody is a humanized, human, or chimeric antibody.

23. The antibody or the antigen-binding fragment thereof of claim 1, wherein the antibody or the antigen-binding fragment thereof is conjugated to an agent.

24. The antibody or the antigen-binding fragment thereof of claim 23, wherein the agent is selected from the group consisting of a radioisotope, a metal chelator, an enzyme, a fluorescent compound, a bioluminescent compound, and a chemiluminescent compound.

* * * * *